(12) United States Patent
Matsumoto et al.

(10) Patent No.: US 7,517,875 B2
(45) Date of Patent: *Apr. 14, 2009

(54) PIPERIDINE DERIVATIVES HAVING CCR3 ANTAGONISM

(75) Inventors: Yoshiyuki Matsumoto, Tokyo (JP); Minoru Imai, Tokyo (JP); Yoshiyuki Sawai, Tokyo (JP); Susumu Takeuchi, Tokyo (JP); Akinobu Nakanishi, Tokyo (JP); Kunio Minamizono, Tokyo (JP); Tomonori Yokoyama, Tokyo (JP)

(73) Assignee: Teijin Limited, Osaka (JP)

( * ) Notice: Subject to any disclaimer, the term of this patent is extended or adjusted under 35 U.S.C. 154(b) by 723 days.

This patent is subject to a terminal disclaimer.

(21) Appl. No.: 10/511,174

(22) PCT Filed: Apr. 16, 2003

(86) PCT No.: PCT/JP03/04841

§ 371 (c)(1), (2), (4) Date: Oct. 15, 2004

(87) PCT Pub. No.: WO03/087089

PCT Pub. Date: Oct. 23, 2003

(65) Prior Publication Data

US 2007/0032525 A1    Feb. 8, 2007

(30) Foreign Application Priority Data

Apr. 16, 2002 (JP) ............................ 2002-113220
Aug. 21, 2002 (JP) ............................ 2002-240509

(51) Int. Cl.
C07D 487/04 (2006.01)
C07D 403/12 (2006.01)
C07D 403/14 (2006.01)
A61K 31/4523 (2006.01)
A61K 31/454 (2006.01)
A61P 11/06 (2006.01)

(52) U.S. Cl. ..................... 514/223.2; 544/12; 544/287; 546/199; 546/201; 546/202; 514/266.21; 514/322; 514/323; 514/324

(58) Field of Classification Search ............ 544/12, 544/287; 546/199, 201, 202; 514/223.2, 514/266.21, 322, 323, 324

See application file for complete search history.

(56) References Cited

FOREIGN PATENT DOCUMENTS

| | | | |
|---|---|---|---|
| AU | 9913741 A | 6/1999 |
| AU | 2000029420 A | 9/2000 |
| AU | 200063193 A | 3/2001 |
| BR | 9814645 A | 7/2001 |
| CN | 1279668 A | 1/2001 |
| CN | 1376063 A | 10/2002 |
| CZ | 200001434 A | 9/2000 |
| EP | 1030840 A1 | 8/2000 |
| EP | 1201239 A1 | 5/2002 |
| HU | 200004200 A | 3/2000 |
| JP | 2001-523661 A | 11/2001 |
| KR | 2001032213 A | 4/2001 |
| KR | 2001032253 A | 4/2001 |
| KR | 2002015722 A | 2/2002 |
| NO | 200002486 A | 7/2000 |
| NZ | 503782 A | 3/2002 |
| SK | 200000553 A | 2/2001 |
| WO | WO 99/25686 A1 | 5/1999 |
| WO | WO 99/37304 A1 | 7/1999 |
| WO | WO 00/53600 A1 | 9/2000 |
| WO | WO 01/07436 A2 | 2/2001 |
| WO | WO 01/10439 A1 | 2/2001 |
| WO | WO 01/32615 A1 | 5/2001 |
| WO | WO 02/068409 A1 | 9/2002 |
| WO | WO 03/028641 A2 | 4/2003 |

OTHER PUBLICATIONS

International Search Report dated Jul. 1, 2003.

*Primary Examiner*—Kahsay Habte
(74) *Attorney, Agent, or Firm*—Sughrue Mion Pllc.

(57) ABSTRACT

The invention provides low molecular compounds having activity which inhibits binding of CCR3 ligands to CCR3 on target cells, i.e. CCR3 antagonists. The invention also provides compounds represented by formula (I) below, pharmaceutically acceptable acid adducts thereof, or pharmaceutically acceptable $C_1$-$C_6$ alkyl adducts thereof, as well as pharmaceutical compositions comprising them as effective ingredients, which are useful for treatment or prevention of diseases associated with CCR3, such as asthma and allergic rhinitis.

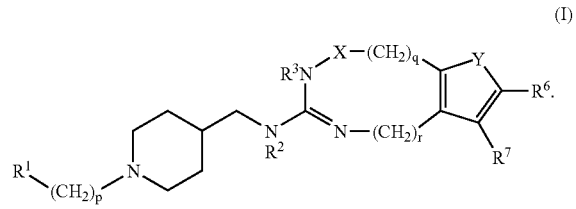

(I)

25 Claims, No Drawings

PIPERIDINE DERIVATIVES HAVING CCR3 ANTAGONISM

This is a National Stage of Application No. PCT/JP03/04841 filed April 16, 2003.

TECHNICAL FIELD

The present invention relates to piperidine derivatives with CCR3 (C—C Chemokine Receptor 3) antagonism. More specifically, the invention relates to CCR3 antagonists with anticipated effects as therapeutic and/or prophylactic agents for allergic conditions such as bronchial asthma, allergic rhinitis, atopic dermatitis, urticaria, contact dermatitis or allergic conjunctivitis, inflammatory bowel diseases such as ulcerative colitis or Crohn's disease, diseases whose major factor is accelerated or sustained increase or tissue infiltration of eosinophils, basophils or activated T cells, such as eosinophilia, eosinophilic gastroenteritis, eosinophilic enteropathy, eosinophilic fasciitis, eosinophilic granuloma, eosinophilic pustular folliculitis, eosinophilic pneumonia or eosinophilic leukemia, or AIDS (Acquired Immune Deficiency Syndrome) caused by infection with HIV (Human Immunodeficiency Virus).

BACKGROUND ART

In recent years, the concept that allergic conditions such as bronchial asthma are fundamentally diseases of chronic inflammation has been established, and accumulation of eosinophils at local sites of inflammation is considered to be a major feature thereof (for example, see Busse, W. W. J. Allergy Clin. Immunol. 1998, 102, S17-S22; Fujisawa, T. Gendai Iryou 1999, 31, 1297). For example, administration of anti-adhesion molecule (ICAM-1) antibodies in monkey asthma models inhibits accumulation of eosinophils and suppresses late asthmatic symptoms, suggesting the importance of eosinophils in allergic conditions (Wegner, C. D. et al. Science, 1990, 247, 456).

Eotaxins have been identified as specific chemotactic factors inducing accumulation and/or migration of eosinophils (eosinophil-specific chemokines) (for example, see Jose, P. J., et al. J. Exp. Med. 1994, 179, 881; Garcia-Zepda, E. A. et al. Nature Med. 1996, 2, 449; Ponath, P. D. et al. J. Clin. Invest. 1996, 97, 604; Kitaura, M. et al. J. Biol. Chem. 1996, 271, 7725). It has also been demonstrated that eotaxins bind to CCR3 expressed on eosinophils, exhibiting an effect of promoting accumulation and/or migration of eosinophils. In addition, chemotactic factors such as eotaxin-2, RANTES (abbreviation for Regulated on Activation, Normal T-cell Expressed and Secreted) antibodies, MCP-2 (abbreviation for Monocyte Chemoattractant Protein-2), MCP-3 (abbreviation for Monocyte Chemoattractant Protein-3), MCP-4 (abbreviation for Monocyte Chemoattractant Protein-4) and the like are also known to exhibit effects similar to those of eotaxins via CCR3, although their potency is weaker than that of eotaxins (for example, see Kitaura, M. et al. J. Biol. Chem. 1996, 271, 7725; Daugherty, B. L. et al. J. Exp. Med. 1996, 183, 2349; Ponath, P. D. et al. J. Exp. Med. 1996, 183, 2437; Hiath, H. et al. J. Clin. Invest. 1997, 99, 178; Patel, V. P. et al. J. Exp. Med. 1997, 185, 1163; Forssmann, U. et al. J. Exp. Med. 185, 2171, 1997).

The reported effects of eotaxins on eosinophils include not only inducing migration of eosinophils, but also effects related to eosinophil activation, such as augmenting expression of adhesion molecule receptor (CD11b) (for example, see Tenscher, K. et al. Blood, 1996, 88, 3195), accelerating production of active oxygen (for example, see Elsner, J. et al. Eur. J. Immunol. 1996, 26, 1919), and promoting release of EDN (Eosinophil-Derived Neurotoxin) (see El-Shazly, et al. Int. Arch. Allergy Immunol. 1998, 117 (suppl. 1), 55). Eotaxins have also been reported to accelerate liberation of eosinophils and their precursors from the bone marrow into the blood (for example, see Palframan, R. T. et al. Blood 1998, 91, 2240).

Numerous reports indicate that eotaxins and CCR3 play important roles in allergic conditions such as bronchial asthma. For example, it has been reported that infiltration of eosinophils is suppressed by anti-eotaxin antibodies in mouse asthma models (Gonzalo, J.-A. et al. J. Clin. Invest. 1996, 98, 2332), that infiltration of eosinophils is suppressed by anti-eotaxin antiserum in mouse cutaneous allergy models (Teixeira, M. M. et al. J. Clin. Invest. 1997, 100, 1657), that formation of pulmonary granulomas is suppressed by anti-eotaxin antibodies in mouse models (see Ruth, J. H. et al. J. Immunol. 1998, 161, 4276), that infiltration of eosinophils is suppressed in eotaxin gene-deficient mouse asthma models and interstitial keratitis models (see Rothenberg, M. E. et al. J. Exp. Med. 1997, 185, 785), that expression of eotaxins and CCR3 is augmented on both the genetic and protein level in asthmatic bronchi compared to healthy controls (see Ying, S. et al. Eur. J. Immunol. 1997, 27, 3507), and that eotaxin expression is augmented in nasal subepithelial tissue of chronic sinusitis patients (Am. J. Respir. Cell Mol. Biol. 1997, 17, 683).

Also, based on reports that eotaxins are abundantly expressed at sites of inflammation in the inflammatory bowel diseases of ulcerative colitis and Crohn's disease (see Garcia-Zepda, E. A. et al. Nature Med. 1996, 2, 449), it is believed that eotaxins also play an important role in such inflammatory bowel diseases.

These data strongly suggest that eotaxins, via CCR3-mediated accumulation and activation of eosinophils at lesion sites, are intimately involved in the onset, progression or sustaining of diseases wherein eosinophils are closely associated with developing lesions, including, for example, allergic conditions such as bronchial asthma, allergic rhinitis, atopic dermatitis, urticaria, contact dermatitis or allergic conjunctivitis, inflammatory bowel diseases such as ulcerative colitis or Crohn's disease, and eosinophilia, eosinophilic gastroenteritis, eosinophilic enteropathy, eosinophilic fasciitis, eosinophilic granuloma, eosinophilic pustular folliculitis, eosinophilic pneumonia or eosinophilic leukemia. In addition, since CCR3 is expressed not only on eosinophils but also on basophils and Th2 lymphocytes, and eotaxins induce intracellular calcium ion concentration increase and migration of these cells, it is believed that eotaxins and CCR3 are involved in the onset, progression and sustaining of diseases associated with these cells, such as allergic conditions, also via accumulation and activation of basophils and Th2 lymphocytes (for example, see Sallusto, F. et al. Science 1997, 277, 2005; Gerber, B. O. et al. Current Biol. 1997, 7, 836; Sallusto, F. et al. J. Exp. Med. 1998, 187, 875; Uguccioni, M. et al. J. Clin. Invest. 1997, 100, 1137; Yamada, H. et al. Biochem Biophys. Res. Commun. 1997, 231, 365).

Consequently, compounds which inhibit binding of CCR3 to CCR3 ligands such as eotaxins, or in other words CCR3 antagonists, should inhibit the effects of the CCR3 ligands on target cells and are therefore expected be useful as therapeutic and/or prophylactic agents for allergic conditions and inflammatory bowel disease. Yet, no agents having such activity have been known.

Moreover, it has also been reported that HIV-1 (Human Immunodeficiency Virus-1) may utilize CCR3 to infect host cells, and therefore CCR3 antagonists are also expected to be useful as therapeutic or prophylactic agents for AIDS (Acquired Immune Deficiency Syndrome) caused by HIV infection (for example, see Choe, H. et al. Cell 1996, 85, 1135; Doranz, B. J. et al. Cell 1996, 85, 1149).

Recently, piperidine derivatives (see Patent Specification No. WO9802151, Patent Specification No. WO9804554, Patent Specification No. WO0029377, Patent Specification No. WO0031033, Patent Specification No. WO0035449, Patent Specification No. WO0035451, Patent Specification No. WO0035452, Patent Specification No. WO0035453, Patent Specification No. WO0035454, Patent Specification No. WO0035876, Patent Specification No. WO0035877, Patent Specification No. WO0051607, Patent Specification No. WO0051608, Patent Specification No. WO0051609, Patent Specification No. WO0051610, Patent Specification No. WO0053600, Patent Specification No. WO0058305, Patent Specification No. WO0059497, Patent Specification No. WO0059498, Patent Specification No. WO0059502, Patent Specification No. WO0059503, Patent Specification No. WO0076511, Patent Specification No. WO0076512, Patent Specification No. WO0076513, Patent Specification No. WO0076514, Patent Specification No. WO0076972, Patent Specification No. WO0076973, Patent Specification No. WO0105782, Patent Specification No. WO0114333, Patent Specification No. WO0164216, Patent Specification No. WO0177101, Patent Specification No. WO0192227, Patent Specification No. WO0198268, Patent Specification No. WO0198269, Patent Specification No. WO0198270, Patent Specification No. WO0202525, Patent Specification No. WO0204420), piperazine derivatives (see Patent Specification No. EP0903349, Patent Specification No. WO0034278, Patent Specification No. WO0102381) and other low molecular compounds (see Patent Specification No. WO9955324, Patent Specification No. WO9955330, Patent Specification No. WO0004003, Patent Specification No. WO0027800, Patent Specification No. WO0027835, Patent Specification No. WO0027843, Patent Specification No. WO0031032, Patent Specification No. WO0041685, Patent Specification No. WO0053172, Patent Specification No. WO0109088, Patent Specification No. WO0128987, Patent Specification No. WO0129000), have been reported to exhibit antagonism against CCR3. However, these compounds differ from the compounds of the invention.

Patent Specification No. WO0107436 and Patent Specification No. WO9937304 describe oxopiperazine derivatives having inhibiting activity on Factor Xa, but they do not specifically mention the piperidine derivatives of the invention, nor is it known whether these oxopiperazine derivatives exhibit competitive inhibition for CCR3. Patent Specification No. WO0132615 and Patent Specification No. WO0268409 describe N-substituted piperidine derivatives having NMDA/NR2B antagonism, but they do not specifically mention the piperidine derivatives of the invention, nor is it known whether these N-substituted piperidine derivatives exhibit competitive inhibition for CCR3.

It is an object of the present invention to provide low molecular compounds having activity which inhibits binding of CCR3 ligands to CCR3 on target cells, i.e. CCR3 antagonists.

It is another object of the invention to provide therapeutic and/or prophylactic agents for diseases of which a causal factor is binding of a CCR3 ligand to CCR3 on target cells.

DISCLOSURE OF THE INVENTION

The present invention provides the following:
(1) Compounds represented by the following formula (I):

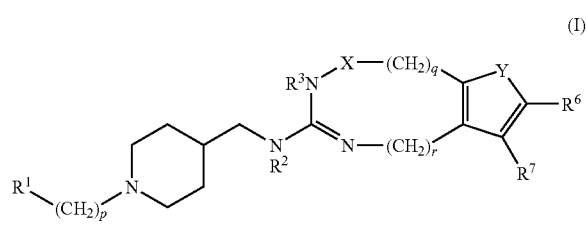

[wherein $R^1$ represents phenyl, $C_3$-$C_8$ cycloalkyl or an aromatic heterocyclic group (having 1-3 atoms selected from the group consisting of oxygen, sulfur and nitrogen as hetero atoms), the phenyl or aromatic heterocyclic group of $R^1$ may optionally fuse with a benzene ring or aromatic heterocyclic group (having 1-3 atoms selected from the group consisting of oxygen, sulfur and nitrogen as hetero atoms) to form a fused ring, the phenyl, $C_3$-$C_8$ cycloalkyl or aromatic heterocyclic group, or fused ring, in $R^1$ may be unsubstituted, or substituted with one or more substituents selected from the group consisting of halogens, hydroxy, cyano, nitro, carboxyl, $C_1$-$C_6$ alkyl, $C_3$-$C_8$ cycloalkyl, $C_2$-$C_6$ alkenyl, $C_1$-$C_6$ alkoxy, $C_1$-$C_6$ alkylthio, $C_3$-$C_5$ alkylene, $C_2$-$C_4$ alkyleneoxy, $C_1$-$C_3$ alkylenedioxy, phenyl, phenoxy, phenylthio, benzyl, benzyloxy, benzoylamino, formyl, $C_2$-$C_7$ alkanoyl, $C_2$-$C_7$ alkoxycarbonyl, $C_2$-$C_7$ alkanoyloxy, $C_2$-$C_7$ alkanoylamino, $C_1$-$C_6$ alkylsulfonyl, $C_3$-$C_8$ (alkoxycarbonyl)methyl, amino, mono($C_1$-$C_6$ alkyl)amino, di($C_1$-$C_6$ alkyl)amino, carbamoyl, $C_2$-$C_7$ N-alkylcarbamoyl, $C_4$-$C_9$ N-cycloalkylcarbamoyl, N-phenylcarbamoyl, piperidylcarbonyl, morpholinylcarbonyl, pyrrolidinylcarbonyl, piperazinylcarbonyl, N-methoxycarbamoyl, (formyl)amino and ureido, and the substituent of the phenyl, $C_3$-$C_8$ cycloalkyl or aromatic heterocyclic group, or fused ring, of $R^1$ may be unsubstituted, or substituted with one or more substituents selected from the group consisting of $C_1$-$C_6$ alkyl, $C_2$-$C_6$ alkenyl, $C_2$-$C_6$ alkynyl, phenyl, $C_3$-$C_5$ alkylene, $C_3$-$C_8$ cycloalkyl, $C_3$-$C_8$ cycloalkenyl, $C_1$-$C_6$ alkoxy, $C_1$-$C_6$ alkylthio, amino, mono($C_1$-$C_6$ alkyl)amino, di($C_1$-$C_6$ alkyl)amino, pyrrolidinyl, piperidyl, $C_3$-$C_7$ lactam, carbamoyl, $C_2$-$C_7$ N-alkylcarbamoyl, $C_2$-$C_7$ alkoxycarbonyl, carboxyl, hydroxy, benzoyl, cyano, trifluoromethyl, halogen and tert-butoxycarbonylamino, provided that when $R^1$ is $C_3$-$C_8$ cycloalkyl, the substituent does not include amino, mono($C_1$-$C_6$ alkyl)amino or di($C_1$-$C_6$ alkyl)amino;

p represents an integer of 1-6;

$R^2$ and $R^3$ may be the same or different and each independently represents hydrogen, $C_1$-$C_6$ alkyl or phenyl, where the $C_1$-$C_6$ alkyl or phenyl group of $R^2$ and $R^3$ may be unsubstituted, or substituted with one or more substituents selected from the group consisting of halogens, hydroxy, $C_1$-$C_6$ alkyl, $C_2$-$C_7$ alkoxycarbohyl, amino, carbamoyl, carboxyl, cyano and $C_1$-$C_6$ alkoxy;

X represents —CO—, —SO$_2$—, —CH$_2$—, —CS— or a single bond;

q represents 0 or 1;

r represents 0 or 1;

Y represents —$(R^4)C$=$C(R^5)$—, —S— or —$NR^8$—;

$R^4$, $R^5$, $R^6$ and $R^7$ may be the same or different, and each independently represents hydrogen, a halogen, hydroxy, cyano, nitro, carboxyl, $C_1$-$C_6$ alkyl, $C_3$-$C_8$ cycloalkyl, $C_2$-$C_6$ alkenyl, $C_1$-$C_6$ alkoxy, $C_1$-$C_6$ alkylthio, $C_3$-$C_5$ alkylene, $C_2$-$C_4$ alkyleneoxy, $C_1$-$C_3$ alkylenedioxy, phenyl, phenoxy, phenylthio, phenylsulfonyl, benzyl, benzyloxy, benzoylamino, formyl, $C_2$-$C_7$ alkanoyl, $C_2$-$C_7$ alkoxycarbonyl, $C_2$-$C_7$ alkanoyloxy, $C_2$-$C_7$ alkanoylamino, $C_4$-$C_{10}$ cycloalkanoylamino, $C_3$-$C_7$ alkenoylamino, $C_1$-$C_6$ alkylsulfonyl, $C_1$-$C_6$ alkylsulfonylamino, $C_3$-$C_8$ (alkoxycarbonyl)methyl, amino, mono($C_1$-$C_6$ alkyl)amino, di($C_1$-$C_6$ alkyl)amino, carbamoyl, $C_2$-$C_7$ N-alkylcarbamoyl, $C_4$-$C_9$ N-cycloalkylcarbamoyl, N-phenylcarbamoyl, N—($C_7$-$C_{12}$ phenylalkyl)carbamoyl, piperidylcarbonyl, morpholinylcarbonyl, pyrrolidinylcarbonyl, piperazinylcarbonyl, N-methoxycarbamoyl, sulfamoyl, $C_1$-$C_6$ N-alkylsulfamoyl, (formyl)amino, (thioformyl)amino, ureido or thioureido, where the aforementioned groups of $R^4$, $R^5$, $R^6$ and $R^7$ each may be independently unsubstituted, or substituted with one or more substituents selected from the group consisting of $C_1$-$C_6$ alkyl, $C_2$-$C_6$ alkenyl, $C_2$-$C_6$ alkynyl, phenyl, $C_3$-$C_5$ alkylene, $C_3$-$C_8$ cycloalkyl, $C_3$-$C_8$ cycloalkenyl, $C_1$-$C_6$ alkoxy, ($C_1$-$C_6$ alkoxy) ($C_1$-$C_6$ alkoxy), phenyl($C_1$-$C_6$ alkoxy), $C_1$-$C_6$ alkylthio, amino, mono($C_1$-$C_6$ alkyl)amino, di($C_1$-$C_6$ alkyl)amino, pyrrolidinyl, piperidyl, ($C_2$-$C_7$ alkanoyl)piperidyl, $C_3$-$C_7$ lactam, carbamoyl, $C_2$-$C_7$ N-alkylcarbamoyl, $C_4$-$C_9$ N-cycloalkylcarbamoyl, N-phenylcarbamoyl, N—($C_7$-$C_{12}$ phenylalkyl)carbamoyl, $C_2$-$C_7$ alkanoylamino, $C_2$-$C_7$ alkoxycarbonyl, carboxyl, hydroxy, benzoyl, cyano, trifluoromethyl, halogens, tert-butoxycarbonylamino, $C_1$-$C_6$ alkylsulfonyl and heterocycles or aromatic heterocycles (where a heterocycle or aromatic heterocycle has 1-3 atoms selected from the group consisting of oxygen, sulfur and nitrogen as hetero atoms, and may be substituted with $C_1$-$C_6$ alkyl); and $R^8$ represents hydrogen or $C_1$-$C_6$ alkyl, where the $C_1$-$C_6$ alkyl group of $R^8$ may be unsubstituted, or substituted with one or more substituents selected from the group consisting of halogens, hydroxy, cyano, nitro, carboxyl, carbamoyl, mercapto, guanidino, $C_3$-$C_8$ cycloalkyl, $C_1$-$C_6$ alkoxy, $C_1$-$C_6$ alkylthio, phenyl (where phenyl may be substituted, or substituted with one or more substituents selected from the group consisting of halogens, hydroxy, $C_1$-$C_6$ alkyl, $C_1$-$C_6$ alkoxy and benzyloxy), phenoxy, benzyloxy, benzyloxycarbonyl, $C_2$-$C_7$ alkanoyl, $C_2$-$C_7$ alkoxycarbonyl, $C_2$-$C_7$ alkanoyloxy, $C_2$-$C_7$ alkanoylamino, $C_2$-$C_7$ N-alkylcarbamoyl, $C_2$-$C_6$ alkylsulfonyl, amino, mono($C_1$-$C_6$ alkyl)amino, di($C_1$-$C_6$ alkyl)amino and ureido], pharmaceutically acceptable acid adducts thereof, or pharmaceutically acceptable $C_1$-$C_6$ alkyl adducts thereof;

(2) Compounds according to (1), pharmaceutically acceptable acid adducts thereof, or pharmaceutically acceptable $C_1$-$C_6$ alkyl adducts thereof, wherein X in formula (I) is —$SO_2$—;

(3) Compounds according to (1), pharmaceutically acceptable acid adducts thereof, or pharmaceutically acceptable $C_1$-$C_6$ alkyl adducts thereof, wherein X in formula (I) is —CO—;

(4) Compounds according to (1), pharmaceutically acceptable acid adducts thereof, or pharmaceutically acceptable $C_1$-$C_6$ alkyl adducts thereof, wherein X in formula (I) is —$CH_2$—;

(5) Compounds according to (1), pharmaceutically acceptable acid adducts thereof, or pharmaceutically acceptable $C_1$-$C_6$ alkyl adducts thereof, wherein X in formula (I) is —CS—;

(6) Compounds according to (1), pharmaceutically acceptable acid adducts thereof, or pharmaceutically acceptable $C_1$-$C_6$ alkyl adducts thereof, wherein X in formula (I) is a single bond;

(7) Compounds according to any one of (1) to (6), pharmaceutically acceptable acid adducts thereof, or pharmaceutically acceptable $C_1$-$C_6$ alkyl adducts thereof, wherein Y in formula (I) is —$(R^4)C$=$C(R^5)$—;

(8) Compounds according to any one of (1) to (6), pharmaceutically acceptable acid adducts thereof, or pharmaceutically acceptable $C_1$-$C_6$ alkyl adducts thereof, wherein Y in formula (I) is —S—;

(9) Compounds according to any one of (1) to (6), pharmaceutically acceptable acid adducts thereof, or pharmaceutically acceptable $C_1$-$C_6$ alkyl adducts thereof, wherein Y in formula (I) is —$NR^8$—;

(10) Compounds according to any one of (1) to (9), pharmaceutically acceptable acid adducts thereof, or pharmaceutically acceptable $C_1$-$C_6$ alkyl adducts thereof, wherein $R^1$ in formula (I) is substituted or unsubstituted phenyl;

(11) Compounds according to any one of (1) to (10), pharmaceutically acceptable acid adducts thereof, or pharmaceutically acceptable $C_1$-$C_6$ alkyl adducts thereof, wherein $R^2$ in formula (I) is hydrogen;

(12) Compounds according to any one of (1) to (11), pharmaceutically acceptable acid adducts thereof, or pharmaceutically acceptable $C_1$-$C_6$ alkyl adducts thereof, wherein $R^3$ in formula (I) is hydrogen;

(13) Compounds according to any one of (1) to (12), pharmaceutically acceptable acid adducts thereof, or pharmaceutically acceptable $C_1$-$C_6$ alkyl adducts thereof, wherein q=0 and r=0 in formula (I);

(14) Compounds according to any one of (1) to (12), pharmaceutically acceptable acid adducts thereof, or pharmaceutically acceptable $C_1$-$C_6$ alkyl adducts thereof, wherein q=1 and r=0 in formula (I);

(15) Compounds according to any one of (1) to (12), pharmaceutically acceptable acid adducts thereof, or pharmaceutically acceptable $C_1$-$C_6$ alkyl adducts thereof, wherein q=0 and r=1 in formula (I);

(16) Compounds according to any one of (1) to (15), pharmaceutically acceptable acid adducts thereof, or pharmaceutically acceptable $C_1$-$C_6$ alkyl adducts thereof, wherein p=1 in formula (I);

(17) Compounds according to (2), pharmaceutically acceptable acid adducts thereof, or pharmaceutically acceptable $C_1$-$C_6$ alkyl adducts thereof, wherein Y is $(R^4)C$=$C(R^5)$—, $R^1$ is substituted or unsubstituted phenyl, $R^2$ is hydrogen, $R^3$ is hydrogen, q=0, r=0 and p=1 in formula (I);

(18) Compounds according to (3), pharmaceutically acceptable acid adducts thereof, or pharmaceutically acceptable $C_1$-$C_6$ alkyl adducts thereof, wherein Y is —$(R^4)C$=$C(R^5)$—, $R^1$ is substituted or unsubstituted phenyl, $R^2$ is hydrogen, $R^3$ is hydrogen, q=0, r=0 and p=1 in formula (I);

(19) Compounds according to (4), pharmaceutically acceptable acid adducts thereof, or pharmaceutically acceptable $C_1$-$C_6$ alkyl adducts thereof, wherein Y is —$(R^4)C=C(R^5)$—, $R^1$ is substituted or unsubstituted phenyl, $R^2$ is hydrogen, $R^3$ is hydrogen, q=0, r=0 and p=1 in formula (I);

(20) Compounds according to (6), pharmaceutically acceptable acid adducts thereof, or pharmaceutically acceptable $C_1$-$C_6$ alkyl adducts thereof, wherein Y is —$(R^4)C=C(R^5)$—, $R^1$ is substituted or unsubstituted phenyl, $R^2$ is hydrogen, $R^3$ is hydrogen, q=0, r=0 and p=1 in formula (I);

(21) Compounds according to any one of (17) to (20), pharmaceutically acceptable acid adducts thereof or pharmaceutically acceptable $C_1$-$C_6$ alkyl adducts thereof, wherein $R^4$ and $R^5$ in formula (I) may be the same or different and each is independently hydrogen, a halogen, hydroxy, cyano, nitro, carboxyl, $C_1$-$C_6$ alkyl, $C_1$-$C_6$ alkoxy, $C_2$-$C_7$ alkoxycarbonyl, $C_2$-$C_7$ alkanoylamino, $C_1$-$C_6$ alkylsulfonyl, amino, carbamoyl, $C_2$-$C_7$ N-alkylcarbamoyl, sulfamoyl or $C_1$-$C_6$ N-alkylsulfamoyl;

(22) Compounds according to any one of (17) to (20), pharmaceutically acceptable acid adducts thereof or pharmaceutically acceptable $C_1$-$C_6$ alkyl adducts thereof, wherein $R^4$ and $R^5$ in formula (I) may be the same or different and each is independently a halogen, hydroxy, cyano, nitro, $C_1$-$C_6$ alkyl, $C_1$-$C_6$ alkoxy, $C_2$-$C_7$ alkoxycarbonyl, $C_1$-$C_6$ alkylsulfonyl or $C_1$-$C_6$ N-alkylsulfonyl;

(23) Compounds according to any one of (17) to (22), pharmaceutically acceptable acid adducts thereof or pharmaceutically acceptable $C_1$-$C_6$ alkyl adducts thereof, wherein each $R^1$ in formula (I) above may be the same or different and is independently hydrogen, a halogen, hydroxy, cyano, nitro, $C_1$-$C_6$ alkyl or $C_1$-$C_6$ alkoxy;

(24) Pharmaceutical compositions with CCR3 antagonism which comprise as effective ingredients thereof compounds represented by formula (I) according to any one of (1) to (23), pharmaceutically acceptable acid adducts thereof or pharmaceutically acceptable $C_1$-$C_6$ alkyl adducts thereof;

(25) Prophylactic and/or therapeutic compositions for any disease associated with CCR3, which comprise as effective ingredients thereof compounds represented by formula (I) according to any one of (1) to (23), pharmaceutically acceptable acid adducts thereof or a pharmaceutically acceptable $C_1$-$C_6$ alkyl adducts thereof;

(26) Prophylactic and/or therapeutic compositions according to (25), wherein the disease is an allergic condition;

(27) Prophylactic and/or therapeutic compositions according to (26), wherein the allergic condition is bronchial asthma, allergic rhinitis, atopic dermatitis, urticaria, contact dermatitis or allergic conjunctivitis;

(28) Prophylactic and/or therapeutic compositions according to (25), wherein the disease is an inflammatory bowel disease;

(29) Prophylactic and/or therapeutic compositions according to (25), wherein the disease is AIDS (Acquired Immune Deficiency Syndrome);

(30) Prophylactic and/or therapeutic compositions according to (25), wherein the disease is eosinophilia, eosinophilic gastroenteritis, eosinophilic enteropathy, eosinophilic fasciitis, eosinophilic granuloma, eosinophilic pustular folliculitis, eosinophilic pneumonia or eosinophilic leukemia.

BEST MODE FOR CARRYING OUT THE INVENTION

The number of substituents on the phenyl, $C_3$-$C_8$ cycloalkyl or aromatic heterocyclic group, or fused ring, of $R^1$, and the number of substituents on the substituents of the phenyl, $C_3$-$C_8$ cycloalkyl or aromatic heterocyclic group, or fused ring, of $R^1$ may be any chemically possible number, but it is preferably 0-15, more preferably 0-10 and more preferably 0-7.

The term "$C_3$-$C_8$ cycloalkyl" for $R^1$ means a cyclic alkyl group such as, for example, cyclopropyl, cyclobutyl, cyclopentyl, cyclohexyl, cycloheptyl or cyclooctyl, and as preferred examples there may be mentioned cyclopropyl, cyclopentyl and cyclohexyl.

The term "aromatic heterocyclic group (having 1-3 atoms selected from the group consisting of oxygen, sulfur and nitrogen as hetero atoms)" for $R^1$ means an aromatic heterocyclic group such as, for example, thienyl, furyl, pyrrolyl, imidazolyl, pyrazolyl, oxazolyl, isooxazolyl, thiazolyl, isothiazolyl, pyridyl, pyrimidinyl, triazinyl, triazolyl, oxadiazolyl(furazanyl) or thiadiazolyl, and as preferred examples there may be mentioned thienyl, furyl, pyrrolyl and pyridyl.

The term "fused ring" for $R^1$ means a bicyclic aromatic heterocyclic group formed by fusing the phenyl or aromatic heterocyclic group with a benzene ring or an aromatic heterocyclic group (having 1-3 atoms selected from the group consisting of oxygen, sulfur and nitrogen as hetero atoms) at any possible position, and as preferred examples there may be mentioned naphthyl, indolyl, benzofuranyl, benzothienyl, quinolyl and benzoimidazolyl.

$R^1$ according to the invention is most preferably phenyl, thienyl, furanyl, pyrrolyl, naphthyl, benzothienyl, benzofuranyl or indolyl.

The term "halogen" as a substituent on the phenyl, $C_3$-$C_8$ cycloalkyl or aromatic heterocyclic group, or fused ring, of $R^1$ means fluorine, chlorine, bromine and iodine or the like, and as preferred examples there may be mentioned fluorine, chlorine, bromine or iodine.

The term "$C_1$-$C_6$ alkyl" as a substituent on $R^1$ means a $C_1$-$C_6$ straight-chain or branched alkyl group such as, for example, methyl, ethyl, n-propyl, n-butyl, n-pentyl, n-hexyl, n-heptyl, n-octyl, isopropyl, isobutyl, sec-butyl, tert-butyl, isopentyl, neopentyl, tert-pentyl, isohexyl, 2-methylpentyl or 1-ethylbutyl, and as preferred examples there may be mentioned methyl, ethyl, propyl and isopropyl.

The term "$C_3$-$C_8$ cycloalkyl" as a substituent on $R^1$ has the same meaning as "$C_3$-$C_8$ cycloalkyl" for $R^1$ itself, and the same preferred examples may be mentioned.

The term "$C_2$-$C_6$ alkenyl" as a substituent on $R^1$ means a $C_2$-$C_6$ straight-chain or branched alkenyl group such as, for example, vinyl, allyl, 1-propenyl, 2-butenyl, 3-butenyl, 2-methyl-1-propenyl, 4-pentenyl, 5-hexenyl or 4-methyl-3-pentenyl, and as preferred examples there may be mentioned vinyl and 2-methyl-1-propenyl.

The term "$C_1$-$C_6$ alkoxy" as a substituent on $R^1$ means a group comprising a $C_1$-$C_6$ alkyl group and an oxy group, and as preferred examples there may be mentioned methoxy and ethoxy.

The term "$C_1$-$C_6$ alkylthio" as a substituent on $R^1$ means a group comprising a $C_1$-$C_6$ alkyl group and a thio group, and as preferred examples there may be mentioned methylthio and ethylthio.

The term "$C_3$-$C_5$ alkylene" as a substituent on $R^1$ means a $C_3$-$C_5$ divalent alkylene group such as, for example, trimethylene, tetramethylene, pentamethylene or 1-methyltrimethylene, and as preferred examples there may be mentioned trimethylene and tetramethylene.

The term "$C_2$-$C_4$ alkyleneoxy" as a substituent on $R^1$ means a group comprising a $C_2$-$C_4$ divalent alkylene group and an oxy group, such as, for example, ethyleneoxy(—$CH_2CH_2O$—), trimethyleneoxy(—$CH_2CH_2CH_2O$—), tetramethyleneoxy (—$CH_2CH_2CH_2CH_2O$—) or 1,1-dimethylethyleneoxy(—$CH_2C(CH_3)_2O$—), and as preferred examples there may be mentioned ethyleneoxy and trimethyleneoxy.

The term "$C_1$-$C_3$ alkylenedioxy" as a substituent on $R^1$ means a group comprising a $C_1$-$C_3$ divalent alkylene group and two oxy groups, such as, for example, methylenedioxy (—$OCH_2O$—), ethylenedioxy(—$OCH_2CH_2O$—), trimethylenedioxy(—$OCH_2CH_2CH_2O$—) or propylenedioxy(—$OCH_2CH(CH_3)O$—), and as preferred examples there may be mentioned methylenedioxy and ethylenedioxy.

The term "$C_2$-$C_7$ alkanoyl" as a substituent on $R^1$ means a $C_2$-$C_7$ straight-chain or branched alkanoyl group such as, for example, acetyl, propanoyl, butanoyl, pentanoyl, hexanoyl, heptanoyl, isobutyryl, 3-methylbutanoyl, 2-methylbutanoyl, pivaloyl, 4-methylpentanoyl, 3,3-dimethylbutanoyl or 5-methylhexanoyl, and as a preferred example there may be mentioned acetyl.

The term "$C_2$-$C_7$ alkoxycarbonyl" as a substituent on $R^1$ means a group comprising the aforementioned $C_1$-$C_6$ alkoxy group and a carbonyl group, and as preferred examples there may be mentioned methoxycarbonyl and ethoxycarbonyl.

The term "$C_2$-$C_7$ alkanoyloxy" as a substituent on $R^1$ means a group comprising the aforementioned $C_2$-$C_7$ alkanoyl and an oxy group, and as a preferred example there may be mentioned acetyloxy.

The term "$C_2$-$C_7$ alkanoylamino" as a substituent on $R^1$ means a group comprising the aforementioned $C_2$-$C_7$ alkanoyl group and an amino group, and as a preferred example there may be mentioned acetylamino.

The term "$C_1$-$C_6$ alkylsulfonyl" as a substituent on $R^1$ means a group comprising the aforementioned $C_1$-$C_6$ alkyl group and a sulfonyl group, and as a preferred example there may be mentioned methylsulfonyl.

The term "$C_3$-$C_8$ (alkoxycarbonyl)methyl" as a substituent on $R^1$ means a group comprising the aforementioned $C_2$-$C_7$ alkoxycarbonyl group and a methyl group, and as preferred examples there may be mentioned (methoxycarbonyl)methyl and (ethoxycarbonyl)methyl.

The term "mono($C_1$-$C_6$ alkyl)amino as a substituent on $R^1$ means an amino group substituted with the aforementioned $C_1$-$C_6$ alkyl group, and as preferred examples there may be mentioned methylamino and ethylamino.

The term "di($C_1$-$C_6$ alkyl)amino" as a substituent on $R^1$ means an amino group substituted with two identical or different $C_1$-$C_6$ alkyl groups, and as preferred examples there may be mentioned dimethylamino, diethylamino and N-ethyl-N-methylamino.

The term "$C_2$-$C_7$ N-alkylcarbamoyl" as a substituent on $R^1$ means a group comprising the aforementioned $C_1$-$C_6$ alkyl group and a carbamoyl group, and as preferred examples there may be mentioned N-methylcarbamoyl and N-ethylcarbamoyl.

The term "$C_4$-$C_9$ N-cycloalkylcarbamoyl" as a substituent on $R^1$ means a group comprising the aforementioned $C_3$-$C_8$ cycloalkyl group and a carbamoyl group, and as preferred examples there may be mentioned N-cyclopentylcarbamoyl and N-cyclohexylcarbamoyl.

The term "piperidylcarbonyl" as a substituent on $R^1$ means a group resulting from bonding a piperidine group and a carbonyl group, and as a preferred example there may be mentioned (1-piperidyl)carbonyl.

The term "morpholinylcarbonyl" as a substituent on $R^1$ means a group resulting from bonding a morpholine group and a carbonyl group, and as a preferred example there may be mentioned (1-morpholinyl)carbonyl.

The term "pyrrolidinylcarbonyl" as a substituent on $R^1$ means a group resulting from bonding a pyrrolidine group and a carbonyl group, and as a preferred example there may be mentioned (1-pyrrolidinyl)carbonyl.

The term "piperazinylcarbonyl" as a substituent on $R^1$ means a group resulting from bonding a piperazine group and a carbonyl group, and as a preferred example there may be mentioned (1-piperazinyl)carbonyl.

As particularly preferred substituents on $R^1$ there may be mentioned halogens, hydroxy, cyano, nitro, $C_1$-$C_6$ alkyl and $C_1$-$C_6$ alkoxy.

The term "$C_2$-$C_6$ alkynyl" as a substituent further substituting the substituent on the phenyl, $C_3$-$C_8$ cycloalkyl or aromatic heterocyclic group, or fused ring, of $R^1$, means a $C_2$-$C_6$ alkynyl group such as, for example, ethynyl, methylethynyl and ethylethynyl, and as a preferred example there may be mentioned ethynyl.

The term "$C_3$-$C_8$ cycloalkenyl" as a substituent further substituting the substituent on $R^1$ means a $C_3$-$C_8$ cyclic alkenyl group such as, for example, cyclopentenyl, cyclohexenyl or 1,3-cyclohexadienyl, and as a preferred example there may be mentioned cyclohexenyl.

The term "$C_3$-$C_7$ lactam" as a substituent further substituting the substituent on $R^1$ means a group derived by removing one hydrogen from a cyclic amide group such as, for example, 3-propanelactam, 4-butanelactam, 5-pentanelactam or 6-hexanelactam, and as a preferred example there may be mentioned "a group derived by removing one hydrogen from 4-butanelactam".

The $C_1$-$C_6$ alkyl, $C_2$-$C_6$ alkenyl, $C_1$-$C_6$ alkoxy, $C_1$-$C_6$ alkylthio, $C_3$-$C_5$ alkylene, $C_3$-$C_8$ cycloalkyl, mono($C_1$-$C_6$ alkyl)amino, di($C_1$-$C_6$ alkyl)amino, $C_2$-$C_7$ alkoxycarbonyl or $C_2$-$C_7$ N-alkylcarbamoyl groups as substituents further substituting the substituent on $R^1$ have the same definitions as the substituents on $R^1$, and the same preferred examples may be mentioned.

In formula (I), p represents an integer of 1-6, and preferably 1 or 3.

The number of substituents on the $C_1$-$C_6$ alkyl or phenyl group of $R^2$ and $R^3$ according to the invention may be any chemically possible number, but it is preferably 0-13, more preferably 0-10 and more preferably 0-7.

The $C_1$-$C_6$ alkyl group of $R^2$ and $R^3$ has the same definition as the substituent on $R^1$, and the same preferred examples may be mentioned.

The halogen, $C_1$-$C_6$ alkyl, $C_2$-$C_7$ alkoxycarbonyl and $C_1$-$C_6$ alkoxy groups as substituents on the $C_1$-$C_6$ alkyl or phenyl group of $R^2$ and $R^3$ have the same definitions as the substituents on $R^1$, and the same preferred examples may be mentioned.

Either $R^2$ and $R^3$ of formula (I) preferably represents hydrogen, and most preferably both represent hydrogen.

In formula (I), X represents —CO—, —$SO_2$—, —$CH_2$—, —CS— or a single bond, all of which may be mentioned as preferred examples. Here, —CO— represents carbonyl, —$SO_2$— represents sulfonyl and —CS— represents thiocarbonyl.

In formula (I), q represents 0 or 1, and r represents 0 or 1. The cases where q=0 and r=0, q=1 and r=0, and q=0 and r=1 may be mentioned as preferred examples.

In formula (I), Y represents —($R^4$)C=C($R^5$)—, —S— or —$NR^8$—, all of which may be mentioned as preferred examples.

The number of substituents on the groups for $R^4$, $R^5$, $R^6$ and $R^7$ according to the invention may be any chemically possible number, but it is preferably 0-15, more preferably 0-10 and more preferably 0-7.

The $C_1$-$C_6$ alkyl, $C_3$-$C_8$ cycloalkyl, $C_2$-$C_6$ alkenyl, $C_1$-$C_6$ alkoxy, $C_1$-$C_6$ alkylthio, $C_3$-$C_5$ alkylene, $C_2$-$C_4$ alkyleneoxy, $C_1$-$C_3$ alkylenedioxy, $C_2$-$C_7$ alkanoyl, $C_2$-$C_7$ alkoxycarbonyl, piperidylcarbonyl, morpholinylcarbonyl, pyrrolidinylcarbonyl, piperazinylcarbonyl, $C_2$-$C_7$ alkanoyloxy, $C_2$-$C_7$ alkanoylamino, $C_1$-$C_6$ alkylsulfonyl; $C_3$-$C_8$ (alkoxycarbonyl)methyl, mono($C_1$-$C_6$ alkyl)amino, di($C_1$-$C_6$ alkyl)amino, carbamoyl, $C_2$-$C_7$ N-alkylcarbamoyl or $C_4$-$C_9$N-cycloalkylcarbamoyl groups for $R^4$, $R^5$, $R^6$ and $R^7$ have the same respective definitions as the substituents on $R^1$ or the substituents further substituting those substituents, and the same preferred examples may be mentioned.

The term "$C_4$-$C_{10}$ cycloalkanoylamino" for $R^4$, $R^5$, $R^6$ and $R^7$ means a group comprising a $C_4$-$C_{10}$ cycloalkanoyl group and an amino group, and as preferred examples there may be mentioned cyclopropanoylamino, cyclobutanoylamino, cyclopentanoylamino and cyclohexanoylamino.

The term "$C_3$-$C_7$ alkenoylamino" for $R^4$, $R^5$, $R^6$ and $R^7$ means a group comprising a $C_3$-$C_7$ alkenoyl group and an amino group, and as a preferred example there may be mentioned acryloyl.

The term "$C_1$-$C_6$ alkylsulfonylamino" for $R^4$, $R^5$, $R^6$ and $R^7$ means a group comprising a $C_1$-$C_6$ alkylsulfonyl group and an amino group, and as preferred examples there may be mentioned methylsulfonylamino, ethylsulfonylamino, propylsulfonylamino and butylsulfonylamino.

The term "N—($C_7$-$C_{12}$ phenylalkyl)carbamoyl" for $R^4$, $R^5$, $R^6$ and $R^7$ means a group comprising a carbamoyl group and a $C_7$-$C_{12}$ phenylalkyl group, and as preferred examples there may be mentioned phenylmethylcarbamoyl and phenylethylcarbamoyl.

The term "$C_1$-$C_6$ N-alkylsulfamoyl" for $R^4$, $R^5$, $R^6$ and $R^7$ means a group comprising a $C_1$-$C_6$ alkyl group having the same definition as "$C_1$-$C_6$ alkyl" as a substituent on $R^1$, and a sulfamoyl group, and as preferred examples there may be mentioned N-methylsulfamoyl and N,N-dimethylsulfamoyl.

As particularly preferred groups for $R^4$, $R^5$, $R^6$ and $R^7$ there may be mentioned halogens, hydroxy, cyano, nitro, $C_1$-$C_6$ alkyl, $C_1$-$C_6$ alkoxy, $C_2$-$C_7$ alkoxycarbonyl, $C_1$-$C_6$ alkylsulfonyl and $C_1$-$C_6$ N-alkylsulfamoyl.

The $C_1$-$C_6$ alkyl, $C_2$-$C_6$ alkenyl, $C_2$-$C_6$ alkynyl, $C_3$-$C_5$ alkylene, $C_3$-$C_8$ cycloalkyl, $C_3$-$C_8$ cycloalkenyl, $C_1$-$C_6$ alkoxy, $C_1$-$C_6$ alkylthio, mono($C_1$-$C_6$ alkyl)amino, di($C_1$-$C_6$ alkyl)amino, $C_3$-$C_7$ lactam, $C_2$-$C_7$ N-alkylcarbamoyl, $C_4$-$C_9$ N-cycloalkylcarbamoyl, N—($C_7$-$C_{12}$ phenylalkyl)carbamoyl or $C_2$-$C_7$ alkoxycarbonyl groups as substituents on $R^4$, $R^5$, $R^6$ and $R^7$ have the same respective definitions as the substituents on $R^1$, as the substituents further substituting those substituents on $R^1$, as the substituents further substituting those substituents or as $R^4$, $R^5$, $R^6$ and $R^7$ themselves, and the same preferred examples may be mentioned.

The term "($C_1$-$C_6$ alkoxy) ($C_1$-$C_6$ alkoxy)" as a substituent on $R^4$, $R^5$, $R^6$ and $R^7$ means a group comprising a $C_1$-$C_6$ alkoxy group and a $C_1$-$C_6$ alkoxy group, and as preferred examples there may be mentioned methoxymethoxy, methoxyethoxy and ethoxyethoxy.

The term "phenyl($C_1$-$C_6$ alkoxy)" as a substituent on $R^4$, $R^5$, $R^6$ and $R^7$ means a group comprising a phenyl group and a $C_1$-$C_6$ alkoxy group, and as preferred examples there may be mentioned benzyloxy, phenylethoxy and phenylpropoxy.

The term "($C_2$-$C_7$ alkanoyl)piperidyl" as a substituent on $R^4$, $R^5$, $R^6$ and $R^7$ means a group comprising a $C_2$-$C_7$ alkanoyl group and a piperidyl group, and as a preferred example there may be mentioned 1-(acetyl)-4-piperidyl.

The number of substituents on the $C_1$-$C_6$ alkyl group for $R^8$ and the number of substituents on the phenyl group as a substituent on the $C_1$-$C_6$ alkyl group for $R^8$ according to the invention may be any chemically possible number, but it is preferably 0-15, more preferably 0-10 and more preferably 0-7.

The $C_1$-$C_6$ alkyl group for $R^8$ has the same definition as the substituent on $R^1$, and the same preferred examples may be mentioned.

The halogen, $C_3$-$C_8$ cycloalkyl, $C_1$-$C_6$ alkoxy, $C_1$-$C_6$ alkylthio, $C_2$-$C_7$ alkanoyl, $C_2$-$C_7$ alkoxycarbonyl, $C_2$-$C_7$ alkanoyloxy, $C_2$-$C_7$ alkanoylamino, $C_2$-$C_7$ N-alkylcarbamoyl, $C_2$-$C_6$ alkylsulfonyl, mono($C_1$-$C_6$ alkyl)amino and di($C_1$-$C_6$ alkyl)amino groups as substituents on the $C_1$-$C_6$ alkyl group for $R^8$ have the same respective definitions as the substituents of $R^1$, and the same preferred examples may be mentioned.

The terms "halogen", "$C_1$-$C_6$ alkyl" and "$C_1$-$C_6$ alkoxy" as substituents on the phenyl group substituting the $C_1$-$C_6$ alkyl group of $R^8$ have the same definitions as the substituents on $R^1$, and the same preferred examples may be mentioned.

As preferred examples of piperidine derivatives of formula (I) there may be mentioned compounds containing the substituents listed in Tables 1 to 8 below. The compound numbers are listed in the columns titled "Compnd. No." in Tables 1 to 8.

Tables 1-1 to 1-6 list preferred examples of compounds wherein X=single bond, q=0, r=0 and Y=—($R^4$)C=C($R^5$)—. Table 2 lists preferred examples of compounds wherein X=—CO—, q=0, r=0 and Y=—($R^4$)C=C($R^5$)—. Table 3 lists preferred examples of compounds wherein X=—$SO_2$—, q=0, r=0 and Y=—($R^4$)C=C($R^5$)—. Table 4 lists preferred examples of compounds wherein X=—$CH_2$—, q=0, r=0 and Y=—($R^4$)C=C($R^5$)—. Table 5 lists preferred examples of compounds wherein X=—CO—, q=0, r=0 and Y=—S—. Table 6 lists preferred examples of compounds wherein X=—CO—, q=0, r=0 and Y=—N($R^8$)—. Table 7 lists preferred examples of compounds wherein X=—CO—, q=1, r=0 and Y=—($R^4$)C=C($R^5$)—. Table 8 lists preferred examples of compounds wherein X=—CS—, q=0, r=0 and Y=—($R^4$)C=C($R^5$)—.

TABLE 1-1

X = Single Bond, q = 0, r = 0, Y = —(R4)C=C(R5)—

| Compound No. | R1—(CH2)p— | R2 | R3 | R4 | R5 | R6 | R7 |
|---|---|---|---|---|---|---|---|
| 1-1-1 | 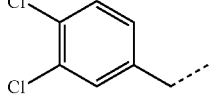 | H | H | H | H | H | H |

TABLE 1-1-continued

X = Single Bond, q = 0, r = 0, Y = —(R4)C=C(R5)—

| Compound No. | R1—(CH2)p— | R2 | R3 | R4 | R5 | R6 | R7 |
|---|---|---|---|---|---|---|---|
| 1-1-2 | 3,4-diCl-phenyl-CH2 | H | H | H | H | NO2 | H |
| 1-1-3 | 3,4-diCl-phenyl-CH2 | H | H | H | H | Me | H |
| 1-1-4 | 3,4-diCl-phenyl-CH2 | H | H | H | H | Cl | H |
| 1-1-5 | 3,4-diCl-phenyl-CH2 | H | H | H | H | F | H |
| 1-1-6 | 3,4-diCl-phenyl-CH2 | H | H | H | H | CF3 | H |
| 1-1-7 | 3,4-diCl-phenyl-CH2 | H | H | H | H | COOH | H |
| 1-1-8 | 3,4-diCl-phenyl-CH2 | H | H | H | Cl | Cl | H |
| 1-1-9 | 3,4-diCl-phenyl-CH2 | H | H | H | H | H | Me |
| 1-1-10 | 3,4-diCl-phenyl-CH2 | H | H | H | H | MeO | H |
| 1-1-11 | 3,4-diCl-phenyl-CH2 | H | H | H | H | H | NO2 |
| 1-1-12 | 3,4-diCl-phenyl-CH2 | H | H | H | H | H | MeO |
| 1-1-13 | 3,4-diCl-phenyl-CH2 | H | H | H | H | H | F |

TABLE 1-1-continued
X = Single Bond, q = 0, r = 0, Y = —(R4)C=C(R5)—
| Compound No. | R1—(CH2)p— | R2 | R3 | R4 | R5 | R6 | R7 |
|---|---|---|---|---|---|---|---|
| 1-1-14 | 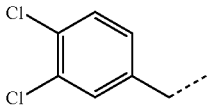 | H | H | H | H | H | Cl |
| 1-1-15 | 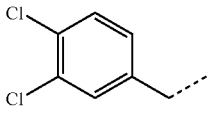 | H | H | H | H | OCF3 | H |
| 1-1-16 | 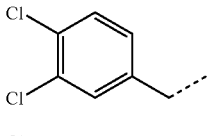 | H | H | H | H | CN | H |
| 1-1-17 |  | H | H | H | H | H | CN |
| 1-1-18 | 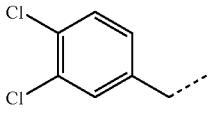 | H | H | H | H | H | COOH |
| 1-1-19 |  | H | H | H | H | OH | H |
| 1-1-20 |  | H | H | H | H | H | OH |
| 1-1-21 | 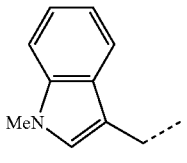 | H | H | H | H | NO2 | H |
| 1-1-22 | 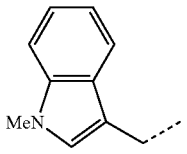 | H | H | H | H | Me | H |
| 1-1-23 | 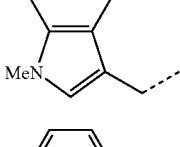 | H | H | H | H | Cl | H |
| 1-1-24 | 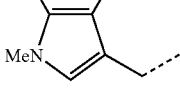 | H | H | H | H | F | H |

TABLE 1-1-continued
X = Single Bond, q = 0, r = 0, Y = —(R4)C=C(R5)—
| Compound No. | R1—(CH2)p— | R2 | R3 | R4 | R5 | R6 | R7 |
|---|---|---|---|---|---|---|---|
| 1-1-25 | 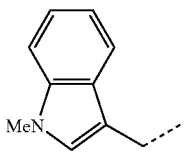 | H | H | H | H | CF3 | H |
| 1-1-26 | 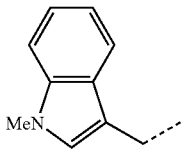 | H | H | H | H | COOH | H |
| 1-1-27 | 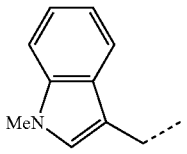 | H | H | H | Cl | Cl | H |
| 1-1-28 | 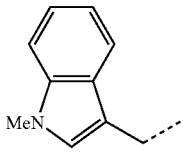 | H | H | H | H | H | Me |
| 1-1-29 | 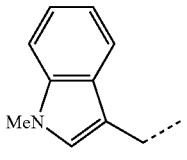 | H | H | H | H | MeO | H |
| 1-1-30 | 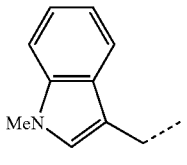 | H | H | H | H | H | NO2 |
| 1-1-31 | 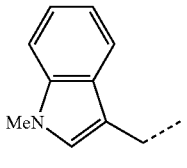 | H | H | H | H | H | MeO |
| 1-1-32 | 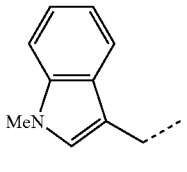 | H | H | H | H | H | F |
| 1-1-33 | 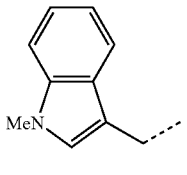 | H | H | H | H | H | Cl |

TABLE 1-1-continued

X = Single Bond, q = 0, r = 0, Y = —(R4)C=C(R5)—

| Compound No. | R1—(CH2)p— | R2 | R3 | R4 | R5 | R6 | R7 |
|---|---|---|---|---|---|---|---|
| 1-1-34 | 1-methylindol-3-ylmethyl | H | H | H | H | OCF3 | H |
| 1-1-35 | 1-methylindol-3-ylmethyl | H | H | H | H | CN | H |
| 1-1-36 | 1-methylindol-3-ylmethyl | H | H | H | H | H | CN |
| 1-1-37 | 1-methylindol-3-ylmethyl | H | H | H | H | H | COOH |
| 1-1-38 | 1-methylindol-3-ylmethyl | H | H | H | H | OH | H |
| 1-1-39 | 1-methylindol-3-ylmethyl | H | H | H | H | H | OH |
| 1-1-40 | naphth-1-ylmethyl | H | H | H | H | NO2 | H |
| 1-1-41 | naphth-1-ylmethyl | H | H | H | H | Me | H |
| 1-1-42 | naphth-1-ylmethyl | H | H | H | H | Cl | H |

TABLE 1-1-continued

X = Single Bond, q = 0, r = 0, Y = —(R4)C═C(R5)—

| Compound No. | R1—(CH2)p— | R2 | R3 | R4 | R5 | R6 | R7 |
|---|---|---|---|---|---|---|---|
| 1-1-43 | naphthyl-CH2 | H | H | H | H | F | H |
| 1-1-44 | naphthyl-CH2 | H | H | H | H | CF3 | H |
| 1-1-45 | naphthyl-CH2 | H | H | H | H | COOH | H |
| 1-1-46 | naphthyl-CH2 | H | H | H | Cl | Cl | H |
| 1-1-47 | naphthyl-CH2 | H | H | H | H | H | Me |
| 1-1-48 | naphthyl-CH2 | H | H | H | H | MeO | H |
| 1-1-49 | naphthyl-CH2 | H | H | H | H | H | NO2 |
| 1-1-50 | naphthyl-CH2 | H | H | H | H | H | MeO |
| 1-1-51 | naphthyl-CH2 | H | H | H | H | H | F |

TABLE 1-1-continued

| | X = Single Bond, q = 0, r = 0, Y = —(R4)C=C(R5)— | | | | | | |
|---|---|---|---|---|---|---|---|
| Compound No. | R1—(CH2)p— | R2 | R3 | R4 | R5 | R6 | R7 |
| 1-1-52 | 1-naphthylmethyl | H | H | H | H | H | Cl |
| 1-1-53 | 1-naphthylmethyl | H | H | H | H | OCF3 | H |
| 1-1-54 | 1-naphthylmethyl | H | H | H | H | CN | H |
| 1-1-55 | 1-naphthylmethyl | H | H | H | H | H | CN |
| 1-1-56 | 1-naphthylmethyl | H | H | H | H | H | COOH |
| 1-1-57 | 1-naphthylmethyl | H | H | H | H | OH | H |
| 1-1-58 | 1-naphthylmethyl | H | H | H | H | H | OH |
| 1-1-59 | phenylpropyl | H | H | H | H | NO2 | H |
| 1-1-60 | phenylpropyl | H | H | H | H | Me | H |

TABLE 1-1-continued
X = Single Bond, q = 0, r = 0, Y = —(R4)C=C(R5)—
| Compound No. | R1—(CH2)p— | R2 | R3 | R4 | R5 | R6 | R7 |
|---|---|---|---|---|---|---|---|
| 1-1-61 | 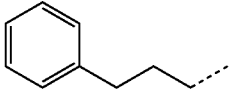 | H | H | H | H | Cl | H |
| 1-1-62 | 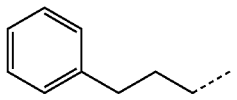 | H | H | H | H | F | H |
| 1-1-63 | 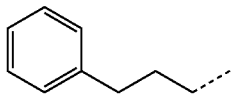 | H | H | H | H | CF3 | H |
| 1-1-64 | 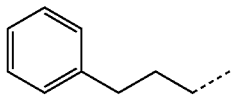 | H | H | H | H | COOH | H |
| 1-1-65 | 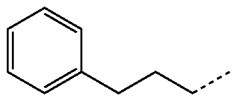 | H | H | H | Cl | Cl | H |
| 1-1-66 | 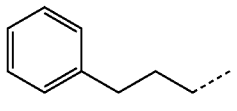 | H | H | H | H | H | Me |
| 1-1-67 | 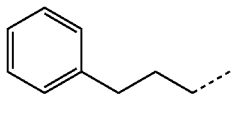 | H | H | H | H | MeO | H |
| 1-1-68 | 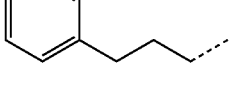 | H | H | H | H | H | NO2 |
| 1-1-69 | 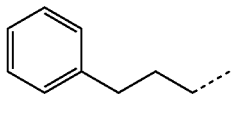 | H | H | H | H | H | MeO |
| 1-1-70 | 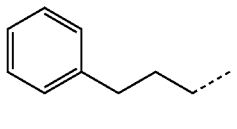 | H | H | H | H | H | F |
| 1-1-71 | 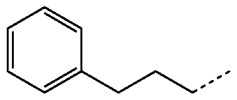 | H | H | H | H | H | Cl |
| 1-1-72 | 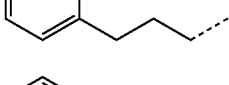 | H | H | H | H | OCF3 | H |
| 1-1-73 | 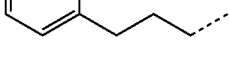 | H | H | H | H | CN | H |

TABLE 1-1-continued
X = Single Bond, q = 0, r = 0, Y = —(R4)C=C(R5)—
| Compound No. | R1—(CH2)p— | R2 | R3 | R4 | R5 | R6 | R7 |
|---|---|---|---|---|---|---|---|
| 1-1-74 | 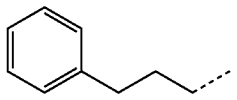 | H | H | H | H | H | CN |
| 1-1-75 | 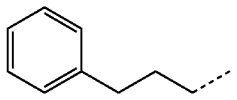 | H | H | H | H | H | COOH |
| 1-1-76 | 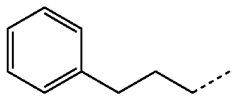 | H | H | H | H | OH | H |
| 1-1-77 | 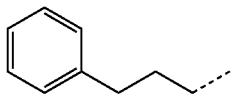 | H | H | H | H | H | OH |
| 1-1-78 | 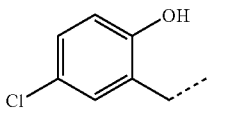 | H | H | H | H | NO2 | H |
| 1-1-79 | 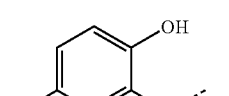 | H | H | H | H | Me | H |
| 1-1-80 |  | H | H | H | H | Cl | H |
| 1-1-81 |  | H | H | H | H | F | H |
| 1-1-82 |  | H | H | H | H | CF3 | H |
| 1-1-83 |  | H | H | H | H | COOH | H |
| 1-1-84 |  | H | H | H | Cl | Cl | H |
| 1-1-85 | 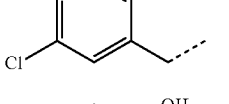 | H | H | H | H | H | Me |
| 1-1-86 | 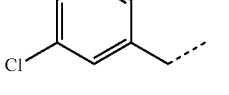 | H | H | H | H | MeO | H |

TABLE 1-1-continued
X = Single Bond, q = 0, r = 0, Y = —(R4)C=C(R5)—
| Compound No. | R1—(CH2)p— | R2 | R3 | R4 | R5 | R6 | R7 |
|---|---|---|---|---|---|---|---|
| 1-1-87 | 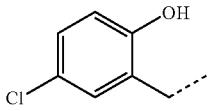 | H | H | H | H | H | NO2 |
| 1-1-88 | 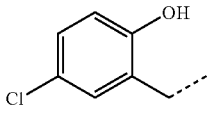 | H | H | H | H | H | MeO |
| 1-1-89 | 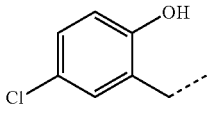 | H | H | H | H | H | F |
| 1-1-90 | 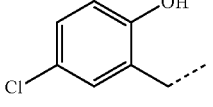 | H | H | H | H | H | Cl |
| 1-1-91 | 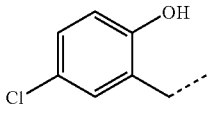 | H | H | H | H | OCF3 | H |
| 1-1-92 | 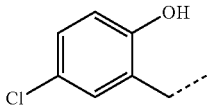 | H | H | H | H | CN | H |
| 1-1-93 | 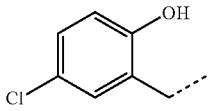 | H | H | H | H | H | CN |
| 1-1-94 | 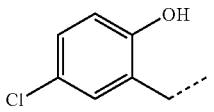 | H | H | H | H | H | COOH |
| 1-1-95 | 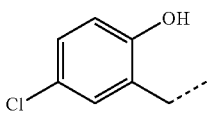 | H | H | H | H | OH | H |
| 1-1-96 | 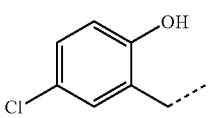 | H | H | H | H | H | OH |
| 1-1-97 | 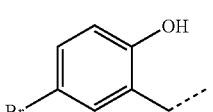 | H | H | H | H | NO2 | H |
| 1-1-98 | 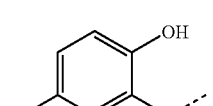 | H | H | H | H | Me | H |

TABLE 1-1-continued

X = Single Bond, q = 0, r = 0, Y = —(R4)C═C(R5)—

| Compound No. | R1—(CH2)p— | R2 | R3 | R4 | R5 | R6 | R7 |
|---|---|---|---|---|---|---|---|
| 1-1-99 | 4-Br, 2-OH-phenyl-CH2- | H | H | H | H | Cl | H |
| 1-1-100 | 4-Br, 2-OH-phenyl-CH2- | H | H | H | H | F | H |
| 1-1-101 | 4-Br, 2-OH-phenyl-CH2- | H | H | H | H | CF3 | H |
| 1-1-102 | 4-Br, 2-OH-phenyl-CH2- | H | H | H | H | COOH | H |
| 1-1-103 | 4-Br, 2-OH-phenyl-CH2- | H | H | H | Cl | Cl | H |
| 1-1-104 | 4-Br, 2-OH-phenyl-CH2- | H | H | H | H | H | Me |
| 1-1-105 | 4-Br, 2-OH-phenyl-CH2- | H | H | H | H | MeO | H |
| 1-1-106 | 4-Br, 2-OH-phenyl-CH2- | H | H | H | H | H | NO2 |
| 1-1-107 | 4-Br, 2-OH-phenyl-CH2- | H | H | H | H | H | MeO |
| 1-1-108 | 4-Br, 2-OH-phenyl-CH2- | H | H | H | H | H | F |
| 1-1-109 | 4-Br, 2-OH-phenyl-CH2- | H | H | H | H | H | Cl |
| 1-1-110 | 4-Br, 2-OH-phenyl-CH2- | H | H | H | H | OCF3 | H |

TABLE 1-1-continued
X = Single Bond, q = 0, r = 0, Y = —(R4)C═C(R5)—
| Compound No. | R1—(CH2)p— | R2 | R3 | R4 | R5 | R6 | R7 |
|---|---|---|---|---|---|---|---|
| 1-1-111 | 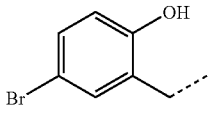 | H | H | H | H | CN | H |
| 1-1-112 | 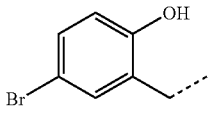 | H | H | H | H | H | CN |
| 1-1-113 | 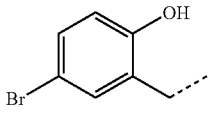 | H | H | H | H | H | COOH |
| 1-1-114 | 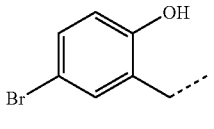 | H | H | H | H | OH | H |
| 1-1-115 | 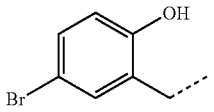 | H | H | H | H | H | OH |
| 1-1-116 | 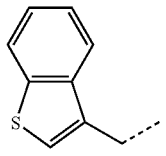 | H | H | H | H | NO2 | H |
| 1-1-117 | 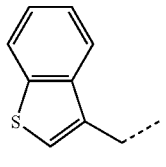 | H | H | H | H | Me | H |
| 1-1-118 | 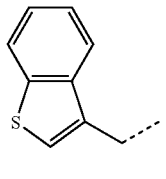 | H | H | H | H | Cl | H |
| 1-1-119 | 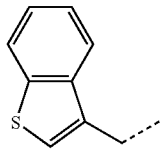 | H | H | H | H | F | H |
| 1-1-120 | 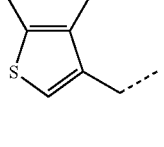 | H | H | H | H | CF3 | H |

TABLE 1-1-continued

X = Single Bond, q = 0, r = 0, Y = —(R4)C═C(R5)—

| Compound No. | R1—(CH2)p— | R2 | R3 | R4 | R5 | R6 | R7 |
|---|---|---|---|---|---|---|---|
| 1-1-121 | benzothiophen-3-ylmethyl | H | H | H | H | COOH | H |
| 1-1-122 | benzothiophen-3-ylmethyl | H | H | H | Cl | Cl | H |
| 1-1-123 | benzothiophen-3-ylmethyl | H | H | H | H | H | Me |
| 1-1-124 | benzothiophen-3-ylmethyl | H | H | H | H | MeO | H |
| 1-1-125 | benzothiophen-3-ylmethyl | H | H | H | H | H | NO2 |
| 1-1-126 | benzothiophen-3-ylmethyl | H | H | H | H | H | MeO |
| 1-1-127 | benzothiophen-3-ylmethyl | H | H | H | H | H | F |
| 1-1-128 | benzothiophen-3-ylmethyl | H | H | H | H | H | Cl |
| 1-1-129 | benzothiophen-3-ylmethyl | H | H | H | H | OCF3 | H |

TABLE 1-1-continued
X = Single Bond, q = 0, r = 0, Y = —(R4)C=C(R5)—
| Compound No. | R1—(CH2)p— | R2 | R3 | R4 | R5 | R6 | R7 |
|---|---|---|---|---|---|---|---|
| 1-1-130 | 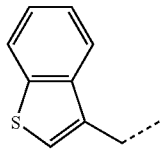 | H | H | H | H | CN | H |
| 1-1-131 | 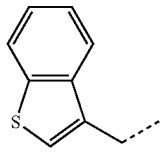 | H | H | H | H | H | CN |
| 1-1-132 | 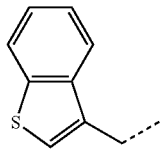 | H | H | H | H | H | COOH |
| 1-1-133 | 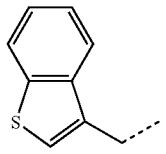 | H | H | H | H | OH | H |
| 1-1-134 | 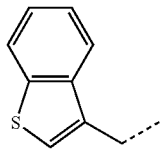 | H | H | H | H | H | OH |
| 1-1-135 | 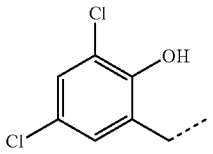 | H | H | H | H | NO2 | H |
| 1-1-136 | 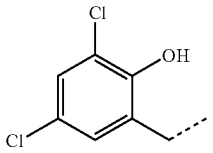 | H | H | H | H | Me | H |
| 1-1-137 | 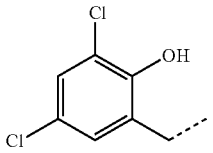 | H | H | H | H | Cl | H |
| 1-1-138 | 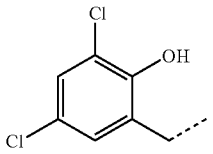 | H | H | H | H | F | H |

TABLE 1-1-continued
X = Single Bond, q = 0, r = 0, Y = —(R4)C═C(R5)—
| Compound No. | R1—(CH2)p— | R2 | R3 | R4 | R5 | R6 | R7 |
|---|---|---|---|---|---|---|---|
| 1-1-139 | 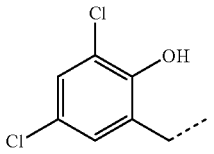 | H | H | H | H | CF3 | H |
| 1-1-140 | 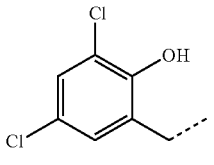 | H | H | H | H | COOH | H |
| 1-1-141 | 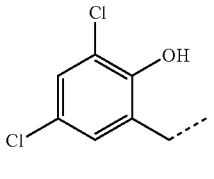 | H | H | H | Cl | Cl | H |
| 1-1-142 | 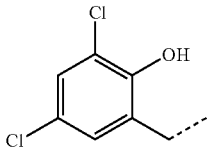 | H | H | H | H | H | Me |
| 1-1-143 | 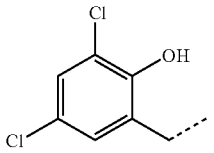 | H | H | H | H | MeO | H |
| 1-1-144 | 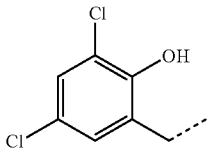 | H | H | H | H | H | NO2 |
| 1-1-145 |  | H | H | H | H | H | MeO |
| 1-1-146 |  | H | H | H | H | H | F |
| 1-1-147 | 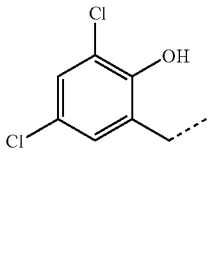 | H | H | H | H | H | Cl |

TABLE 1-1-continued
X = Single Bond, q = 0, r = 0, Y = —(R4)C=C(R5)—
| Compound No. | R1—(CH2)p— | R2 | R3 | R4 | R5 | R6 | R7 |
|---|---|---|---|---|---|---|---|
| 1-1-148 | 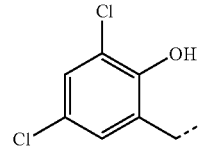 | H | H | H | H | OCF3 | H |
| 1-1-149 | 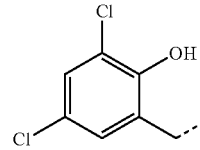 | H | H | H | H | CN | H |
| 1-1-150 | 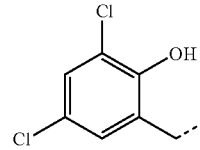 | H | H | H | H | H | CN |
| 1-1-151 | 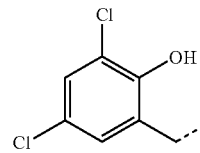 | H | H | H | H | H | COOH |
| 1-1-152 | 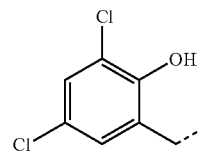 | H | H | H | H | OH | H |
| 1-1-153 | 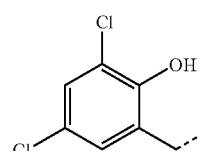 | H | H | H | H | H | OH |
TABLE 1-2
X = Single Bond, q = 0, r = 0, Y = —(R4)C=C(R5)—
| Compound No. | R1—(CH2)p— | R2 | R3 | R4 | R5 | R6 | R7 |
|---|---|---|---|---|---|---|---|
| 1-2-1 | 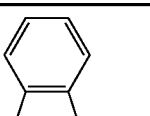 | H | H | H | H | H | H |
| 1-2-2 | 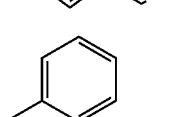 | H | H | H | H | H | H |

TABLE 1-2-continued
| | X = Single Bond, q = 0, r = 0, Y = —(R4)C=C(R5)— | | | | | | |
|---|---|---|---|---|---|---|---|
| Compound No. | R1—(CH2)p— | R2 | R3 | R4 | R5 | R6 | R7 |
| 1-2-3 | 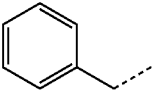 | H | H | H | H | H | H |
| 1-2-4 | 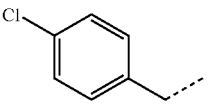 | H | H | H | H | H | H |
| 1-2-5 | 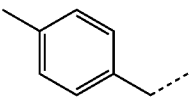 | H | H | H | H | H | H |
| 1-2-6 | 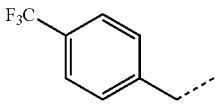 | H | H | H | H | H | H |
| 1-2-7 | 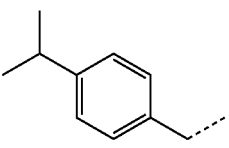 | H | H | H | H | H | H |
| 1-2-8 | 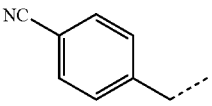 | H | H | H | H | H | H |
| 1-2-9 | 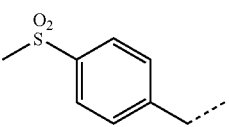 | H | H | H | H | H | H |
| 1-2-10 | 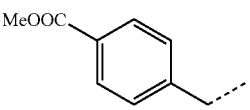 | H | H | H | H | H | H |
| 1-2-11 | 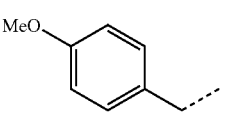 | H | H | H | H | H | H |
| 1-2-12 | 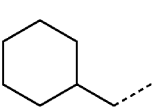 | H | H | H | H | H | H |
| 1-2-13 | 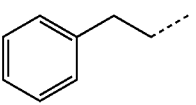 | H | H | H | H | H | H |
| 1-2-14 |  | H | H | H | H | H | H |

TABLE 1-2-continued

X = Single Bond, q = 0, r = 0, Y = —(R4)C═C(R5)—

| Compound No. | R1—(CH2)p— | R2 | R3 | R4 | R5 | R6 | R7 |
|---|---|---|---|---|---|---|---|
| 1-2-15 | 1H-indol-3-ylmethyl | H | H | H | H | H | H |
| 1-2-16 | 1-methyl-1H-indol-2-ylmethyl | H | H | H | H | H | H |
| 1-2-17 | furan-2-ylmethyl | H | H | H | H | H | H |
| 1-2-18 | thiophen-2-ylmethyl | H | H | H | H | H | H |
| 1-2-19 | 3-methylbenzothiophen-2-ylmethyl | H | H | H | H | H | H |
| 1-2-20 | pyridin-2-ylmethyl | H | H | H | H | H | H |
| 1-2-21 | pyridin-4-ylmethyl | H | H | H | H | H | H |
| 1-2-22 | quinolin-2-ylmethyl | H | H | H | H | H | H |
| 1-2-23 | quinolin-4-ylmethyl | H | H | H | H | H | H |
| 1-2-24 | thiazol-2-ylmethyl | H | H | H | H | H | H |
| 1-2-25 | 1H-imidazol-2-ylmethyl | H | H | H | H | H | H |
| 1-2-26 | 1H-pyrazol-3-ylmethyl | H | H | H | H | H | H |

TABLE 1-2-continued

X = Single Bond, q = 0, r = 0, Y = —(R4)C═C(R5)—

| Compound No. | R1—(CH2)p— | R2 | R3 | R4 | R5 | R6 | R7 |
|---|---|---|---|---|---|---|---|
| 1-2-27 | 1,5-dimethyl-2-phenyl-pyrazol-4-yl-methyl | H | H | H | H | H | H |
| 1-2-28 | 2,5-dimethyl-1-phenyl-pyrrol-3-yl-methyl | H | H | H | H | H | H |
| 1-2-29 | 1-methyl-benzimidazol-2-yl-methyl | H | H | H | H | H | H |
| 1-2-30 | 2-methylbenzyl | H | H | H | H | H | H |
| 1-2-31 | 2-cyanobenzyl | H | H | H | H | H | H |
| 1-2-32 | 4-biphenylmethyl | H | H | H | H | H | H |
| 1-2-33 | 2-methoxybenzyl | H | H | H | H | H | H |
| 1-2-34 | 2-chlorobenzyl | H | H | H | H | H | H |
| 1-2-35 | 2,4-dichlorobenzyl | H | H | H | H | H | H |

TABLE 1-2-continued

| | X = Single Bond, q = 0, r = 0, Y = —(R4)C═C(R5)— | | | | | | |
|---|---|---|---|---|---|---|---|
| Compound No. | R1—(CH2)p— | R2 | R3 | R4 | R5 | R6 | R7 |
| 1-2-36 | 3-chlorobenzyl | H | H | H | H | H | H |
| 1-2-37 | 3-nitrobenzyl | H | H | H | H | H | H |
| 1-2-38 | 3-trifluoromethylbenzyl | H | H | H | H | H | H |
| 1-2-39 | 4-bromobenzyl | H | H | H | H | H | H |
| 1-2-40 | 3-methylbenzyl | H | H | H | H | H | H |
| 1-2-41 | 4-hydroxybenzyl | H | H | H | H | H | H |
| 1-2-42 | 3-hydroxybenzyl | H | H | H | H | H | H |
| 1-2-43 | 4-dimethylaminobenzyl | H | H | H | H | H | H |
| 1-2-44 | 4-acetamidobenzyl | H | H | H | H | H | H |
| 1-2-45 | 4-ethoxybenzyl | H | H | H | H | H | H |
| 1-2-46 | 4-propoxybenzyl | H | H | H | H | H | H |

TABLE 1-2-continued

| | X = Single Bond, q = 0, r = 0, Y = —(R4)C=C(R5)— | | | | | | |
|---|---|---|---|---|---|---|---|
| Compound No. | R1—(CH2)p— | R2 | R3 | R4 | R5 | R6 | R7 |
| 1-2-47 | 2-propoxyphenylmethyl | H | H | H | H | H | H |
| 1-2-48 | 4-benzyloxyphenylmethyl | H | H | H | H | H | H |
| 1-2-49 | 2-benzyloxyphenylmethyl | H | H | H | H | H | H |
| 1-2-50 | 2-naphthylmethyl | H | H | H | H | H | H |
| 1-2-51 | 2-ethoxyphenylmethyl | H | H | H | H | H | H |
| 1-2-52 | benzofuran-2-ylmethyl | H | H | H | H | H | H |
| 1-2-53 | 5-(4-chlorophenyl)furan-2-ylmethyl | H | H | H | H | H | H |
| 1-2-54 | 2-phenylphenylmethyl | H | H | H | H | H | H |

TABLE 1-2-continued

X = Single Bond, q = 0, r = 0, Y = —(R4)C═C(R5)—

| Compound No. | R1—(CH2)p— | R2 | R3 | R4 | R5 | R6 | R7 |
|---|---|---|---|---|---|---|---|
| 1-2-55 | 4H-chromen-4-one-3-yl | H | H | H | H | H | H |
| 1-2-56 | 5-OMe-1-Me-indol-3-yl | H | H | H | H | H | H |
| 1-2-57 | 5-Me-1-Me-indol-3-yl | H | H | H | H | H | H |
| 1-2-58 | 4-F-phenyl | H | H | H | H | H | H |
| 1-2-59 | pyridin-3-yl | H | H | H | H | H | H |
| 1-2-60 | 3-F-phenyl | H | H | H | H | H | H |
| 1-2-61 | 3-MeO-phenyl | H | H | H | H | H | H |
| 1-2-62 | 4-iPrO-phenyl | H | H | H | H | H | H |
| 1-2-63 | 4-PhO-phenyl | H | H | H | H | H | H |
| 1-2-64 | 3-F3CO-phenyl | H | H | H | H | H | H |

TABLE 1-2-continued
X = Single Bond, q = 0, r = 0, Y = —(R4)C═C(R5)—
| Compound No. | R1—(CH2)p— | R2 | R3 | R4 | R5 | R6 | R7 |
|---|---|---|---|---|---|---|---|
| 1-2-65 | 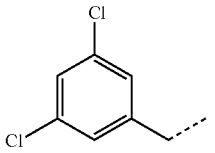 | H | H | H | H | H | H |
| 1-2-66 | 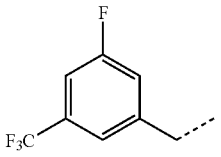 | H | H | H | H | H | H |
| 1-2-67 | 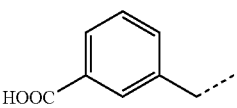 | H | H | H | H | H | H |
| 1-2-68 | 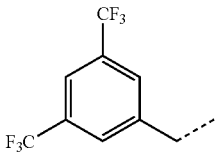 | H | H | H | H | H | H |
| 1-2-69 | 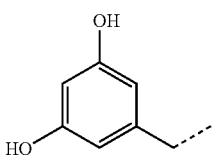 | H | H | H | H | H | H |
| 1-2-70 | 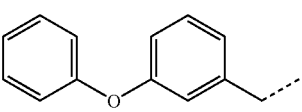 | H | H | H | H | H | H |
| 1-2-71 | 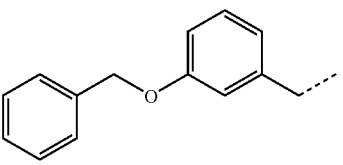 | H | H | H | H | H | H |
| 1-2-72 | 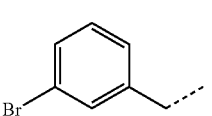 | H | H | H | H | H | H |
| 1-2-73 | 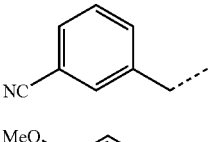 | H | H | H | H | H | H |
| 1-2-74 | 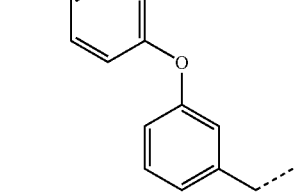 | H | H | H | H | H | H |

TABLE 1-2-continued

X = Single Bond, q = 0, r = 0, Y = —(R4)C═C(R5)—

| Compound No. | R1—(CH2)p— | R2 | R3 | R4 | R5 | R6 | R7 |
|---|---|---|---|---|---|---|---|
| 1-2-75 | 3-nitrobenzyl (O₂N-C₆H₄-CH₂-) | H | H | H | H | H | H |
| 1-2-76 | 3-(4-methylphenoxy)benzyl | H | H | H | H | H | H |
| 1-2-77 | 3-(4-chlorophenoxy)benzyl | H | H | H | H | H | H |
| 1-2-78 | 2,3-dimethoxybenzyl | H | H | H | H | H | H |
| 1-2-79 | 3-ethoxy-2-hydroxybenzyl | H | H | H | H | H | H |
| 1-2-80 | 2,3-dihydrobenzofuran-5-ylmethyl | H | H | H | H | H | H |
| 1-2-81 | 3-chloro-4-hydroxybenzyl | H | H | H | H | H | H |
| 1-2-81 | 3-chloro-4-fluorobenzyl | H | H | H | H | H | H |
| 1-2-83 | 3-benzyloxy-4-methoxybenzyl | H | H | H | H | H | H |

TABLE 1-2-continued
X = Single Bond, q = 0, r = 0, Y = —(R4)C=C(R5)—
| Compound No. | R1—(CH2)p— | R2 | R3 | R4 | R5 | R6 | R7 |
|---|---|---|---|---|---|---|---|
| 1-2-84 | 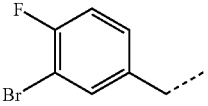 | H | H | H | H | H | H |
| 1-2-85 | 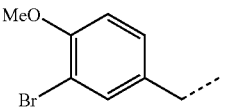 | H | H | H | H | H | H |
| 1-2-86 | 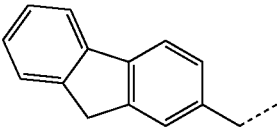 | H | H | H | H | H | H |
| 1-2-87 | 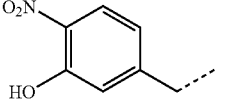 | H | H | H | H | H | H |
| 1-2-88 | 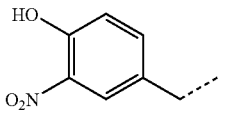 | H | H | H | H | H | H |
| 1-2-89 | 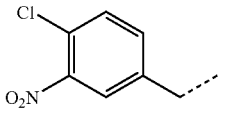 | H | H | H | H | H | H |
| 1-2-90 | 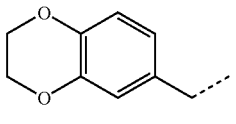 | H | H | H | H | H | H |
| 1-2-91 | 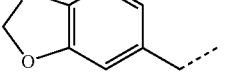 | H | H | H | H | H | H |
| 1-2-92 | 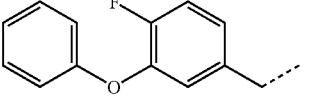 | H | H | H | H | H | H |
| 1-2-93 | 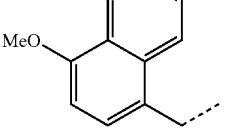 | H | H | H | H | H | H |
| 1-2-94 | 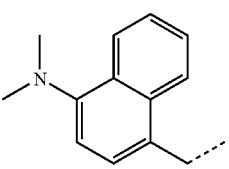 | H | H | H | H | H | H |

TABLE 1-2-continued

X = Single Bond, q = 0, r = 0, Y = —(R4)C=C(R5)—

| Compound No. | R1—(CH2)p— | R2 | R3 | R4 | R5 | R6 | R7 |
|---|---|---|---|---|---|---|---|
| 1-2-95 | 7-methoxy-naphthalen-1-ylmethyl | H | H | H | H | H | H |
| 1-2-96 | 7-ethoxy-naphthalen-1-ylmethyl | H | H | H | H | H | H |
| 1-2-97 | 3,4-diethoxybenzyl | H | H | H | H | H | H |
| 1-2-98 | 2-hydroxy-3-methylbenzyl | H | H | H | H | H | H |
| 1-2-99 | 3-carboxy-2-hydroxybenzyl | H | H | H | H | H | H |
| 1-2-100 | 2-hydroxy-3-methoxybenzyl | H | H | H | H | H | H |
| 1-2-101 | 2-benzyloxy-3-methoxybenzyl | H | H | H | H | H | H |
| 1-2-102 | 2,3-dihydroxybenzyl | H | H | H | H | H | H |

TABLE 1-2-continued

X = Single Bond, q = 0, r = 0, Y = —(R4)C=C(R5)—

| Compound No. | R1—(CH2)p— | R2 | R3 | R4 | R5 | R6 | R7 |
|---|---|---|---|---|---|---|---|
| 1-2-103 | MeO, HO-substituted benzyl | H | H | H | H | H | H |
| 1-2-104 | 1-bromonaphthalen-2-ylmethyl | H | H | H | H | H | H |
| 1-2-105 | 2,3,4-trimethoxybenzyl (OMe, OMe, MeO) | H | H | H | H | H | H |
| 1-2-106 | 2,3-dichlorobenzyl | H | H | H | H | H | H |
| 1-2-107 | 2,3-difluorobenzyl | H | H | H | H | H | H |
| 1-2-108 | 2-chloro-3-(trifluoromethyl)benzyl | H | H | H | H | H | H |
| 1-2-109 | 2-fluoro-3-(trifluoromethyl)benzyl (F₃C, F) | H | H | H | H | H | H |
| 1-2-110 | 2-tert-butyl-6-hydroxybenzyl | H | H | H | H | H | H |
| 1-2-111 | 2-methoxy-3-nitrobenzyl (OMe, NO₂) | H | H | H | H | H | H |

TABLE 1-2-continued
X = Single Bond, q = 0, r = 0, Y = —(R4)C=C(R5)—
| Compound No. | R1—(CH2)p— | R2 | R3 | R4 | R5 | R6 | R7 |
|---|---|---|---|---|---|---|---|
| 1-2-112 | 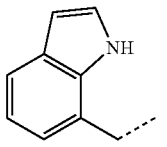 | H | H | H | H | H | H |
| 1-2-113 | 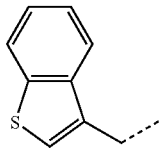 | H | H | H | H | H | H |
| 1-2-114 | 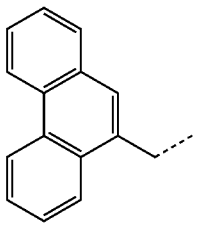 | H | H | H | H | H | H |
| 1-2-115 | 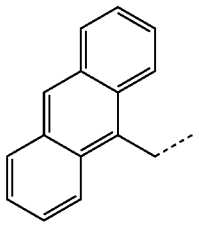 | H | H | H | H | H | H |
| 1-2-116 | 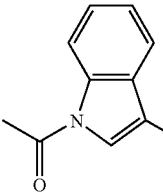 | H | H | H | H | H | H |
| 1-2-117 | 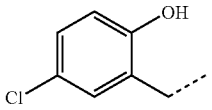 | H | H | H | H | H | H |
| 1-2-118 |  | H | H | H | H | H | H |
| 1-2-119 | 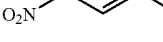 | H | H | H | H | H | H |
| 1-2-120 | 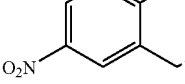 | H | H | H | H | H | H |

TABLE 1-2-continued

X = Single Bond, q = 0, r = 0, Y = —(R4)C=C(R5)—

| Compound No. | R1—(CH2)p— | R2 | R3 | R4 | R5 | R6 | R7 |
|---|---|---|---|---|---|---|---|
| 1-2-121 | 4-fluoro-2-hydroxybenzyl (F, OH on phenyl) | H | H | H | H | H | H |
| 1-2-122 | 4-tert-butyl-2-hydroxybenzyl | H | H | H | H | H | H |
| 1-2-123 | 2-fluoro-5-methoxybenzyl (F, MeO on phenyl) | H | H | H | H | H | H |
| 1-2-124 | 5-bromo-2-fluorobenzyl | H | H | H | H | H | H |
| 1-2-125 | 5-bromo-2-methoxybenzyl | H | H | H | H | H | H |
| 1-2-126 | 2-hydroxy-4-methoxybenzyl | H | H | H | H | H | H |
| 1-2-127 | 5-bromo-2-ethoxybenzyl | H | H | H | H | H | H |
| 1-2-128 | 2-chloro-5-nitrobenzyl | H | H | H | H | H | H |
| 1-2-129 | 2-ethoxy-3-methoxybenzyl | H | H | H | H | H | H |
| 1-2-130 | 2,3-difluoro-4-methylbenzyl | H | H | H | H | H | H |
| 1-2-131 | 3-chloro-2-fluorobenzyl | H | H | H | H | H | H |

TABLE 1-2-continued

X = Single Bond, q = 0, r = 0, Y = —(R4)C═C(R5)—

| Compound No. | R1—(CH2)p— | R2 | R3 | R4 | R5 | R6 | R7 |
|---|---|---|---|---|---|---|---|
| 1-2-132 | 2-EtO, 3-Me, 4-OEt-phenyl | H | H | H | H | H | H |
| 1-2-133 | 3-EtO-phenyl | H | H | H | H | H | H |
| 1-2-134 | 3-F, 2-Me-phenyl | H | H | H | H | H | H |
| 1-2-135 | 2-NO2, 4-Cl-phenyl | H | H | H | H | H | H |
| 1-2-136 | 4-MeO, 2,3-diMe-phenyl | H | H | H | H | H | H |
| 1-2-137 | 2-OH, 4-F3CO-phenyl | H | H | H | H | H | H |
| 1-2-138 | 2,3-diMe-phenyl | H | H | H | H | H | H |
| 1-2-139 | 2-OMe, 3-MeO, 6-COOH-phenyl | H | H | H | H | H | H |
| 1-2-140 | 3-(HOCH2CH2O)-phenyl | H | H | H | H | H | H |
| 1-2-141 | 10-methyl-phenothiazin-3-yl | H | H | H | H | H | H |
| 1-2-142 | 2,2-dimethyl-chroman-6-yl | H | H | H | H | H | H |

TABLE 1-2-continued
| | X = Single Bond, q = 0, r = 0, Y = —(R4)C=C(R5)— | | | | | | |
|---|---|---|---|---|---|---|---|
| Compound No. | R1—(CH2)p— | R2 | R3 | R4 | R5 | R6 | R7 |
| 1-2-143 | 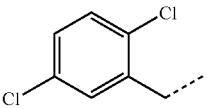 | H | H | H | H | H | H |
| 1-2-144 | 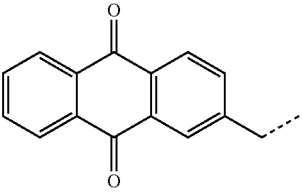 | H | H | H | H | H | H |
| 1-2-145 | 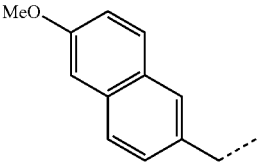 | H | H | H | H | H | H |
| 1-2-146 | 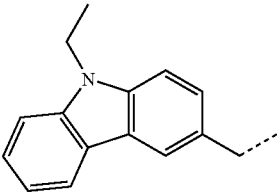 | H | H | H | H | H | H |
| 1-2-147 | 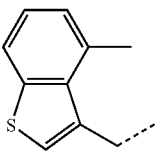 | H | H | H | H | H | H |
| 1-2-148 | 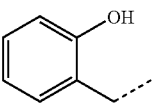 | H | H | H | H | H | H |
| 1-2-149 | 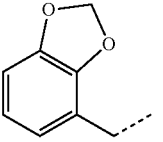 | H | H | H | H | H | H |
| 1-2-150 | 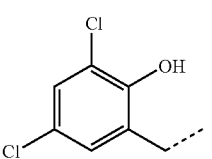 | H | H | H | H | H | H |

TABLE 1-2-continued
X = Single Bond, q = 0, r = 0, Y = —(R4)C=C(R5)—
| Compound No. | R1—(CH2)p— | R2 | R3 | R4 | R5 | R6 | R7 |
|---|---|---|---|---|---|---|---|
| 1-2-151 | 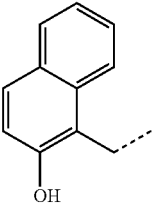 | H | H | H | H | H | H |
| 1-2-152 | 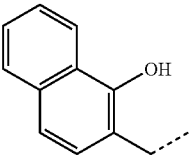 | H | H | H | H | H | H |
| 1-2-153 | 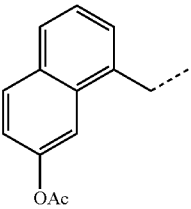 | H | H | H | H | H | H |
| 1-2-154 | 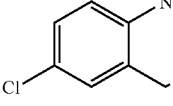 | H | H | H | H | H | H |
| 1-2-155 | 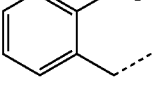 | H | H | H | H | H | H |
| 1-2-156 | 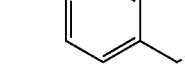 | H | H | H | H | H | H |
| 1-2-157 | 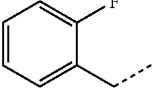 | H | H | H | H | H | H |
| 1-2-158 | 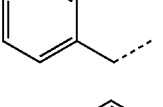 | H | H | H | H | H | H |
| 1-2-159 | 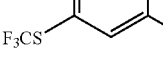 | H | H | H | H | H | H |
| 1-2-160 | 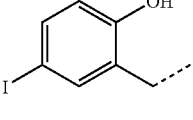 | H | H | H | H | H | H |

TABLE 1-2-continued
X = Single Bond, q = 0, r = 0, Y = —(R4)C=C(R5)—
| Compound No. | R1—(CH2)p— | R2 | R3 | R4 | R5 | R6 | R7 |
|---|---|---|---|---|---|---|---|
| 1-2-161 | 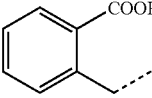 | H | H | H | H | H | H |
| 1-2-162 | 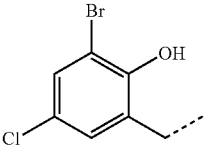 | H | H | H | H | H | H |
| 1-2-163 | 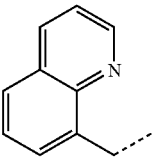 | H | H | H | H | H | H |
| 1-2-164 | 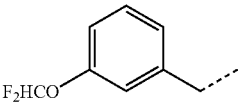 | H | H | H | H | H | H |
| 1-2-165 | 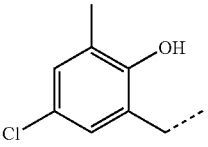 | H | H | H | H | H | H |
| 1-2-166 | 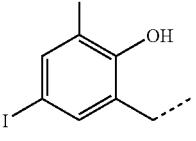 | H | H | H | H | H | H |
| 1-2-167 | 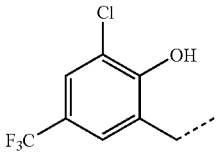 | H | H | H | H | H | H |
| 1-2-168 | 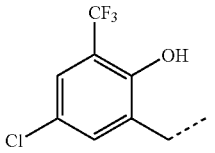 | H | H | H | H | H | H |
| 1-2-169 | 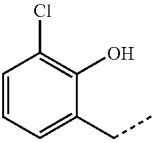 | H | H | H | H | H | H |
| 1-2-170 | 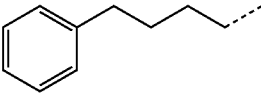 | H | H | H | H | H | H |

TABLE 1-2-continued
X = Single Bond, q = 0, r = 0, Y = —(R4)C=C(R5)—
| Compound No. | R1—(CH2)p— | R2 | R3 | R4 | R5 | R6 | R7 |
|---|---|---|---|---|---|---|---|
| 1-2-171 | 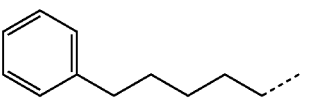 | H | H | H | H | H | H |
| 1-2-172 | 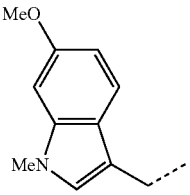 | H | H | H | H | H | H |
| 1-2-173 | 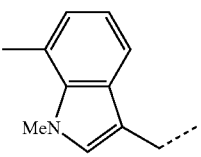 | H | H | H | H | H | H |
| 1-2-174 | 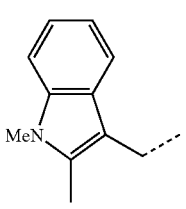 | H | H | H | H | H | H |
| 1-2-175 | 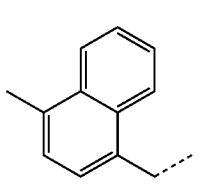 | H | H | H | H | H | H |
| 1-2-176 | 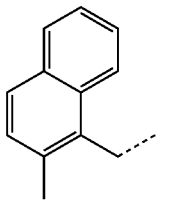 | H | H | H | H | H | H |
| 1-2-177 | 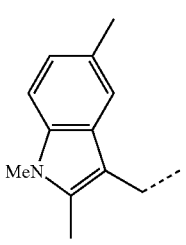 | H | H | H | H | H | H |
| 1-2-178 | 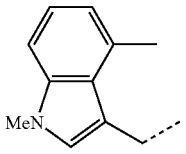 | H | H | H | H | H | H |

TABLE 1-2-continued

X = Single Bond, q = 0, r = 0, Y = —(R4)C=C(R5)—

| Compound No. | R1—(CH2)p— | R2 | R3 | R4 | R5 | R6 | R7 |
|---|---|---|---|---|---|---|---|
| 1-2-179 | 6-methyl-1-methylindol-3-yl-CH2- | H | H | H | H | H | H |
| 1-2-180 | 1-methyl-2-phenylindol-3-yl-CH2- | H | H | H | H | H | H |

TABLE 1-3

X = Single Bond, q = 0, r = 0, Y = —(R4)C=C(R5)—

| Compound No. | (R1—(CH2)p— | R2 | R3 | R4 | R5 | R6 | R7 |
|---|---|---|---|---|---|---|---|
| 1-3-1 | naphthalen-1-yl-CH2- | H | H | H | H | H | -NH-C(=O)-CH2CH2-NH-C(=O)-CH3 |
| 1-3-2 | 3,4-dichlorophenyl-CH2- | H | H | H | H | H | -NH-C(=O)-CH2CH2-O-CH3 |
| 1-3-3 | phenyl-CH2CH2CH2- | H | H | H | H | H | -NH-C(=O)-CH2-NH-C(=O)-CH3 |
| 1-3-4 | phenyl-CH2CH2CH2- | H | H | H | H | H | -NH-C(=O)-CH2CH2-NH-C(=O)-CH3 |
| 1-3-5 | naphthalen-1-yl-CH2- | H | H | H | H | H | -NH-C(=O)-CH2-NH-C(=O)-CH3 |
| 1-3-6 | 4-chloro-2-hydroxyphenyl-CH2- | H | H | H | H | H | -NH-C(=O)-CH2CH2-NH-C(=O)-CH3 |

TABLE 1-3-continued
X = Single Bond, q = 0, r = 0, Y = —(R4)C═C(R5)—
| Compound No. | (R1—(CH2)p— | R2 | R3 | R4 | R5 | R6 | R7 |
|---|---|---|---|---|---|---|---|
| 1-3-7 | 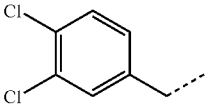 | H | H | H | H | 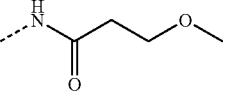 | H |
| 1-3-8 | 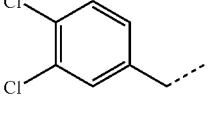 | H | H | H | H | 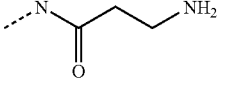 | H |
| 1-3-8 | 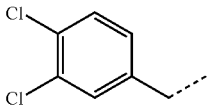 | H | H | H | H | H | 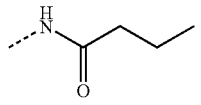 |
| 1-3-10 | 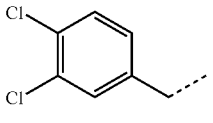 | H | H | H | H | H | 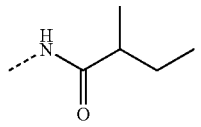 |
| 1-3-11 | 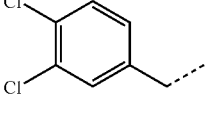 | H | H | H | H | H | 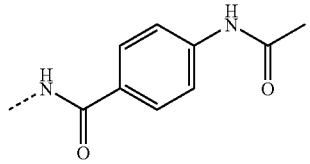 |
| 1-3-12 | 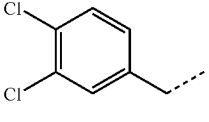 | H | H | H | H | H | 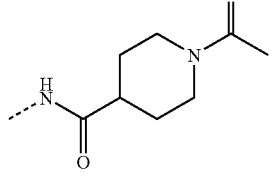 |
| 1-3-13 | 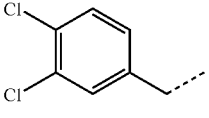 | H | H | H | H | H | 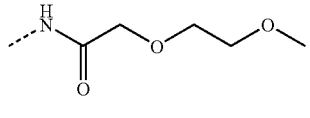 |
| 1-3-14 | 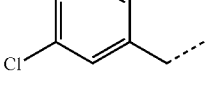 | H | H | H | H | H | 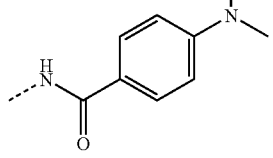 |
| 1-3-15 | 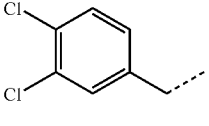 | H | H | H | H | H | 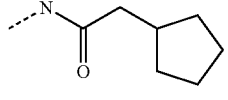 |
| 1-3-16 | 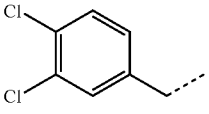 | H | H | H | H | H | 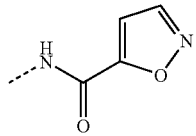 |

TABLE 1-3-continued
X = Single Bond, q = 0, r = 0, Y = —(R4)C═C(R5)—
| Compound No. | (R1—(CH2)p— | R2 | R3 | R4 | R5 | R6 | R7 |
|---|---|---|---|---|---|---|---|
| 1-3-17 | 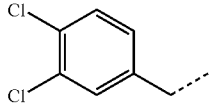 | H | H | H | H | H | 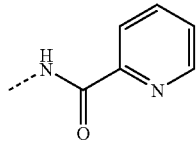 |
| 1-3-18 | 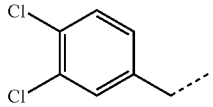 | H | H | H | H | H | 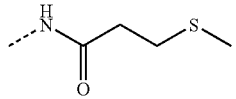 |
| 1-3-19 | 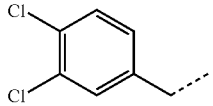 | H | H | H | H | H | 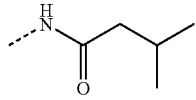 |
| 1-3-20 | 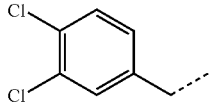 | H | H | H | H | H | 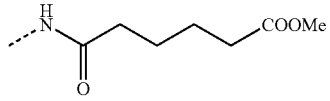 |
| 1-3-21 | 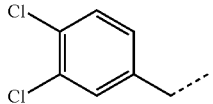 | H | H | H | H | H | 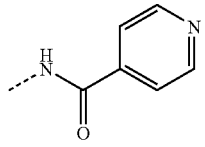 |
| 1-3-22 | 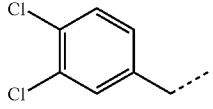 | H | H | H | H | H | 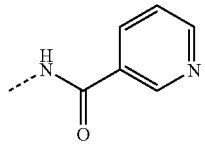 |
| 1-3-23 | 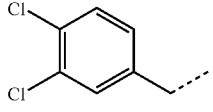 | H | H | H | H | H | 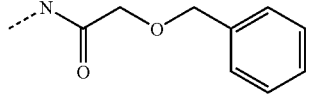 |
| 1-3-24 | 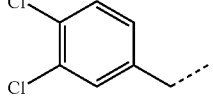 | H | H | H | H | H | 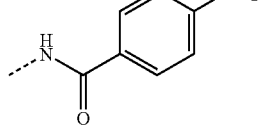 |
| 1-3-25 | 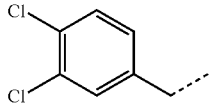 | H | H | H | H | H | 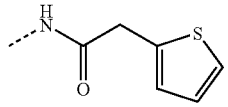 |
| 1-3-26 | 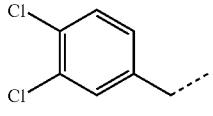 | H | H | H | H | H | 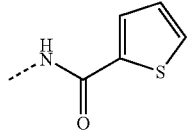 |

TABLE 1-3-continued

X = Single Bond, q = 0, r = 0, Y = —(R4)C═C(R5)—

| Compound No. | (R1—(CH2)p— | R2 | R3 | R4 | R5 | R6 | R7 |
|---|---|---|---|---|---|---|---|
| 1-3-27 | 3,4-diClC6H3CH2— | H | H | H | H | H | —NHC(O)-2-furyl |
| 1-3-28 | 3,4-diClC6H3CH2— | H | H | H | H | H | —NHC(O)-cyclohexyl |
| 1-3-29 | 3,4-diClC6H3CH2— | H | H | H | H | H | —NHC(O)CH2CH2-cyclopentyl |
| 1-3-30 | 3,4-diClC6H3CH2— | H | H | H | H | H | —NHC(O)-cyclopentyl |
| 1-3-31 | 3,4-diClC6H3CH2— | H | H | H | H | H | —NHC(O)-cyclobutyl |
| 1-3-32 | 3,4-diClC6H3CH2— | H | H | H | H | H | —NHC(O)-cyclopropyl |
| 1-3-33 | 3,4-diClC6H3CH2— | H | H | H | H | H | —NHC(O)CH2CH3 |
| 1-3-34 | 3,4-diClC6H3CH2— | H | H | H | H | H | —NHC(O)CH═CH2 |
| 1-3-35 | 3,4-diClC6H3CH2— | H | H | H | H | H | —NHC(O)CH2OCH3 |
| 1-3-36 | 3,4-diClC6H3CH2— | H | H | H | H | H | —NHC(O)CH2CH2OC6H5 |
| 1-3-37 | 3,4-diClC6H3CH2— | H | H | H | H | H | —NHC(O)CH(CH3)2 |

TABLE 1-3-continued
X = Single Bond, q = 0, r = 0, Y = —(R4)C=C(R5)—
| Compound No. | (R1—(CH2)p— | R2 | R3 | R4 | R5 | R6 | R7 |
|---|---|---|---|---|---|---|---|
| 1-3-38 | 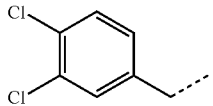 | H | H | H | H | H | 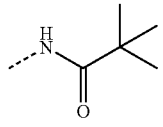 |
| 1-3-39 | 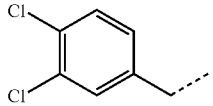 | H | H | H | H | H | 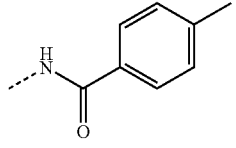 |
| 1-3-40 | 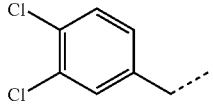 | H | H | H | H | H | 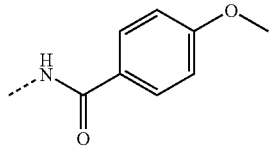 |
| 1-3-41 | 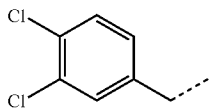 | H | H | H | H | H | 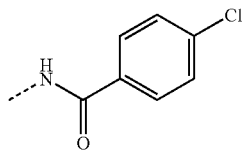 |
| 1-3-42 | 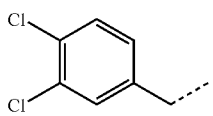 | H | H | H | H | H | 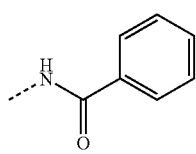 |
| 1-3-43 | 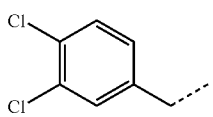 | H | H | H | H | H | 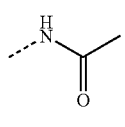 |
| 1-3-44 | 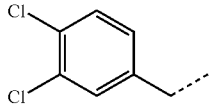 | H | H | H | H | H | 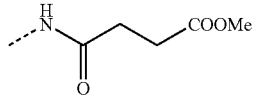 |
| 1-3-45 | 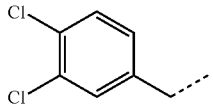 | H | H | H | H | H | 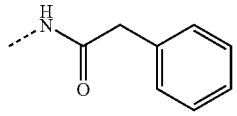 |
| 1-3-46 | 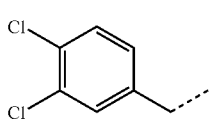 | H | H | H | H | H | 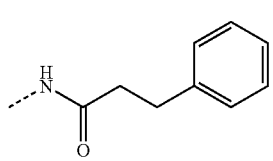 |
| 1-3-47 | 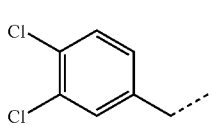 | H | H | H | H | H | 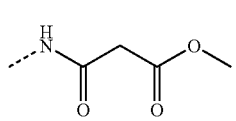 |

TABLE 1-3-continued

X = Single Bond, q = 0, r = 0, Y = —(R4)C=C(R5)—

| Compound No. | (R1—(CH2)p— | R2 | R3 | R4 | R5 | R6 | R7 |
|---|---|---|---|---|---|---|---|
| 1-3-48 | 3,4-dichlorobenzyl | H | H | H | H | H | —NH-C(O)-CH2-NH-C(O)-CH3 |
| 1-3-49 | 3,4-dichlorobenzyl | H | H | H | H | H | —NH-C(O)-CH2-CH2-OH |
| 1-3-50 | 3,4-dichlorobenzyl | H | H | H | H | H | —NH-C(O)-CH2-CH2-NH2 |
| 1-3-51 | 3,4-dichlorobenzyl | H | H | H | H | H | —NH-C(O)-CH2-CH2-NH-C(O)-CH3 |
| 1-3-52 | 3,4-dichlorobenzyl | H | H | H | H | —NH-C(O)-CH2-CH3 | H |
| 1-3-53 | 3,4-dichlorobenzyl | H | H | H | H | —NH-C(O)-CH2-CH2-Ph | H |
| 1-3-54 | 3,4-dichlorobenzyl | H | H | H | H | —NH-C(O)-CH2-CH2-CH3 | H |
| 1-3-55 | 3,4-dichlorobenzyl | H | H | H | H | —NH-C(O)-CH2-Ph | H |
| 1-3-56 | 3,4-dichlorobenzyl | H | H | H | H | —NH-C(O)-CH2-C(O)-OCH3 | H |
| 1-3-57 | 3,4-dichlorobenzyl | H | H | H | H | H | —NH-SO2-CH2-CH3 |
| 1-3-58 | 3,4-dichlorobenzyl | H | H | H | H | —NH-SO2-CH2-CH3 | H |

TABLE 1-3-continued
X = Single Bond, q = 0, r = 0, Y = —(R4)C=C(R5)—
| Compound No. | (R1—(CH2)p— | R2 | R3 | R4 | R5 | R6 | R7 |
|---|---|---|---|---|---|---|---|
| 1-3-59 | 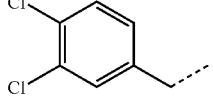 | H | H | H | H | H | 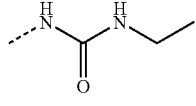 |
| 1-3-60 | 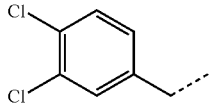 | H | H | H | H | 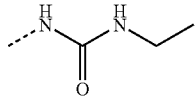 | H |
| 1-3-61 | 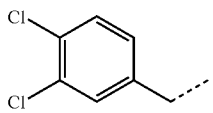 | H | H | H | H | H | NH2 |
| 1-3-62 | 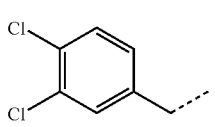 | H | H | H | H | NH2 | H |
| 1-3-63 | 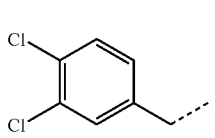 | H | H | H | H | H | 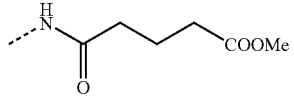 |
| 1-3-64 | 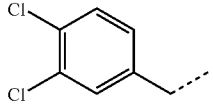 | H | H | H | H | H | 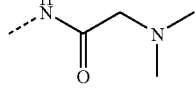 |
| 1-3-65 | 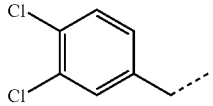 | H | H | H | H | H | 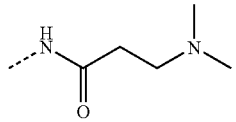 |
| 1-3-66 | 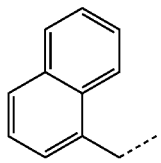 | H | H | H | H | H | 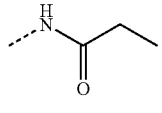 |
| 1-3-67 | 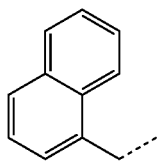 | H | H | H | H | H | 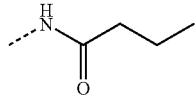 |
| 1-3-68 | 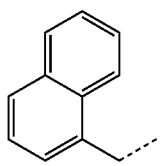 | H | H | H | H | H | 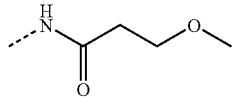 |

TABLE 1-3-continued
X = Single Bond, q = 0, r = 0, Y = —(R4)C═C(R5)—
| Compound No. | (R1—(CH2)p— | R2 | R3 | R4 | R5 | R6 | R7 |
|---|---|---|---|---|---|---|---|
| 1-3-69 | 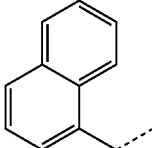 | H | H | H | H | H | 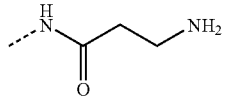 |
| 1-3-70 | 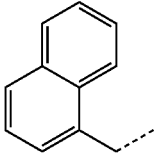 | H | H | H | H | H | 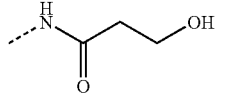 |
| 1-3-71 | 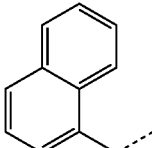 | H | H | H | H | H | 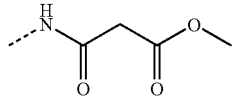 |
| 1-3-72 | 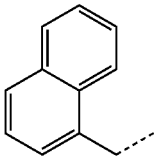 | H | H | H | H | H | 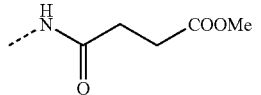 |
| 1-3-73 | 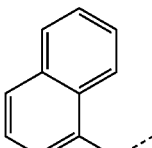 | H | H | H | H | H | 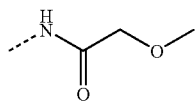 |
| 1-3-74 | 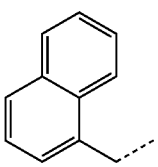 | H | H | H | H | H | 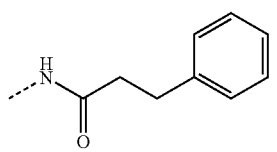 |
| 1-3-75 | 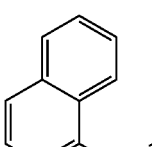 | H | H | H | H | H | 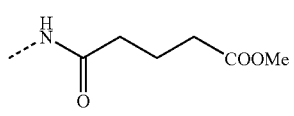 |
| 1-3-76 | 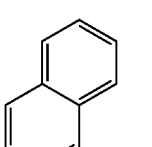 | H | H | H | H | H | 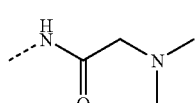 |

TABLE 1-3-continued

X = Single Bond, q = 0, r = 0, Y = —(R4)C=C(R5)—

| Compound No. | (R1—(CH2)p—) | R2 | R3 | R4 | R5 | R6 | R7 |
|---|---|---|---|---|---|---|---|
| 1-3-77 | naphthyl-CH2- | H | H | H | H | H | —NH—C(=O)—CH2CH2—N(CH3)2 |
| 1-3-78 | naphthyl-CH2- | H | H | H | H | H | —NH—C(=O)—NH—Et |
| 1-3-79 | naphthyl-CH2- | H | H | H | H | H | —NH—S(O2)—CH2CH3 |
| 1-3-80 | Ph-(CH2)3- | H | H | H | H | H | —NH—C(=O)—CH2CH3 |
| 1-3-81 | Ph-(CH2)3- | H | H | H | H | H | —NH—C(=O)—CH2CH2CH3 |
| 1-3-82 | Ph-(CH2)3- | H | H | H | H | H | —NH—C(=O)—CH2CH2—OCH3 |
| 1-3-83 | Ph-(CH2)3- | H | H | H | H | H | —NH—C(=O)—CH2CH2—NH2 |
| 1-3-84 | Ph-(CH2)3- | H | H | H | H | H | —NH—C(=O)—CH2CH2—OH |
| 1-3-85 | Ph-(CH2)3- | H | H | H | H | H | —NH—C(=O)—CH2—C(=O)—OCH3 |
| 1-3-86 | Ph-(CH2)3- | H | H | H | H | H | —NH—C(=O)—CH2CH2—COOMe |
| 1-3-87 | Ph-(CH2)3- | H | H | H | H | H | —NH—C(=O)—CH2—Ph |

TABLE 1-3-continued

X = Single Bond, q = 0, r = 0, Y = —(R4)C=C(R5)—

| Compound No. | (R1—(CH2)p—) | R2 | R3 | R4 | R5 | R6 | R7 |
|---|---|---|---|---|---|---|---|
| 1-3-88 | phenyl-(CH2)2- | H | H | H | H | H | -NHC(O)CH2CH2-phenyl |
| 1-3-89 | phenyl-(CH2)2- | H | H | H | H | H | -NHC(O)(CH2)3COOMe |
| 1-3-90 | phenyl-(CH2)2- | H | H | H | H | H | -NHC(O)CH2N(CH3)2 |
| 1-3-91 | phenyl-(CH2)2- | H | H | H | H | H | -NHC(O)CH2CH2N(CH3)2 |
| 1-3-92 | phenyl-(CH2)2- | H | H | H | H | H | -NHC(O)NHCH2CH3 |
| 1-3-93 | phenyl-(CH2)2- | H | H | H | H | H | -NHS(O)2CH2CH3 |
| 1-3-94 | 4-Cl-2-(OH)-phenyl-CH2- | H | H | H | H | H | -NHC(O)CH2NHC(O)CH3 |
| 1-3-95 | 4-Cl-2-(OH)-phenyl-CH2- | H | H | H | H | H | -NHC(O)CH2CH3 |
| 1-3-96 | 4-Cl-2-(OH)-phenyl-CH2- | H | H | H | H | H | -NHC(O)CH2CH2CH3 |
| 1-3-97 | 4-Cl-2-(OH)-phenyl-CH2- | H | H | H | H | H | -NHC(O)CH2CH2OCH3 |
| 1-3-98 | 4-Cl-2-(OH)-phenyl-CH2- | H | H | H | H | H | -NHC(O)CH2CH2NH2 |
| 1-3-99 | 4-Cl-2-(OH)-phenyl-CH2- | H | H | H | H | H | -NHC(O)CH2CH2OH |

TABLE 1-3-continued

X = Single Bond, q = 0, r = 0, Y = —(R4)C═C(R5)—

| Compound No. | (R1—(CH2)p— | R2 | R3 | R4 | R5 | R6 | R7 |
|---|---|---|---|---|---|---|---|
| 1-3-100 | 4-Cl-2-(OH)-C6H3-CH2- | H | H | H | H | H | —NH-C(O)-CH2-C(O)-OMe |
| 1-3-101 | 4-Cl-2-(OH)-C6H3-CH2- | H | H | H | H | H | —NH-C(O)-CH2CH2-COOMe |
| 1-3-102 | 4-Cl-2-(OH)-C6H3-CH2- | H | H | H | H | H | —NH-C(O)-CH2-C6H5 |
| 1-3-103 | 4-Cl-2-(OH)-C6H3-CH2- | H | H | H | H | H | —NH-C(O)-CH2CH2-C6H5 |
| 1-3-104 | 4-Cl-2-(OH)-C6H3-CH2- | H | H | H | H | H | —NH-C(O)-CH2CH2CH2-COOMe |
| 1-3-105 | 4-Cl-2-(OH)-C6H3-CH2- | H | H | H | H | H | —NH-C(O)-CH2-N(CH3)2 |
| 1-3-106 | 4-Cl-2-(OH)-C6H3-CH2- | H | H | H | H | H | —NH-C(O)-CH2CH2-N(CH3)2 |
| 1-3-107 | 4-Cl-2-(OH)-C6H3-CH2- | H | H | H | H | H | —NH-C(O)-NH-CH2CH3 |
| 1-3-108 | 4-Cl-2-(OH)-C6H3-CH2- | H | H | H | H | H | —NH-S(O2)-CH2CH3 |
| 1-3-109 | 2,4-di-Cl-6-(OH)-C6H2-CH2- | H | H | H | H | H | —NH-C(O)-CH2-NH-C(O)-CH3 |
| 1-3-110 | 2,4-di-Cl-6-(OH)-C6H2-CH2- | H | H | H | H | H | —NH-C(O)-CH2CH2-NH-C(O)-CH3 |

TABLE 1-3-continued

X = Single Bond, q = 0, r = 0, Y = —(R4)C=C(R5)—

| Compound No. | (R1—(CH2)p— | R2 | R3 | R4 | R5 | R6 | R7 |
|---|---|---|---|---|---|---|---|
| 1-3-111 | 2,4-dichloro-6-hydroxybenzyl | H | H | H | H | H | —NHC(O)CH2CH3 |
| 1-3-112 | 2,4-dichloro-6-hydroxybenzyl | H | H | H | H | H | —NHC(O)CH2CH2CH3 |
| 1-3-113 | 2,4-dichloro-6-hydroxybenzyl | H | H | H | H | H | —NHC(O)CH2CH2OMe |
| 1-3-114 | 2,4-dichloro-6-hydroxybenzyl | H | H | H | H | H | —NHC(O)CH2CH2NH2 |
| 1-3-115 | 2,4-dichloro-6-hydroxybenzyl | H | H | H | H | H | —NHC(O)CH2CH2OH |
| 1-3-116 | 2,4-dichloro-6-hydroxybenzyl | H | H | H | H | H | —NHC(O)CH2C(O)OMe |
| 1-3-117 | 2,4-dichloro-6-hydroxybenzyl | H | H | H | H | H | —NHC(O)CH2CH2COOMe |
| 1-3-118 | 2,4-dichloro-6-hydroxybenzyl | H | H | H | H | H | —NHC(O)CH2Ph |
| 1-3-119 | 2,4-dichloro-6-hydroxybenzyl | H | H | H | H | H | —NHC(O)CH2CH2Ph |

TABLE 1-3-continued
X = Single Bond, q = 0, r = 0, Y = —(R4)C=C(R5)—
| Compound No. | (R1—(CH2)p— | R2 | R3 | R4 | R5 | R6 | R7 |
|---|---|---|---|---|---|---|---|
| 1-3-120 | 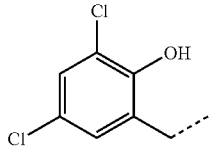 | H | H | H | H | H | 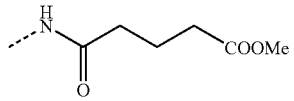 |
| 1-3-121 | 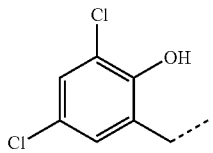 | H | H | H | H | H | 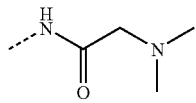 |
| 1-3-122 | 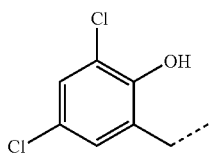 | H | H | H | H | H | 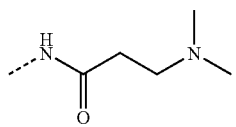 |
| 1-3-123 | 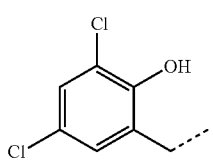 | H | H | H | H | H | 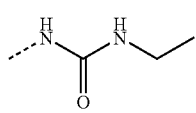 |
| 1-3-124 | 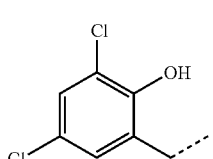 | H | H | H | H | H | 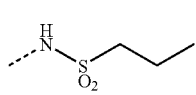 |
| 1-3-125 | 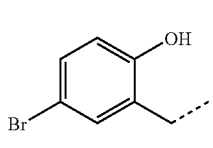 | H | H | H | H | H | 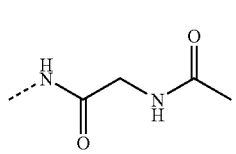 |
| 1-3-126 | 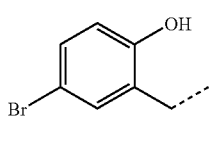 | H | H | H | H | H | 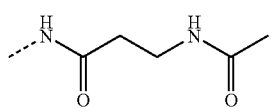 |
| 1-3-127 | 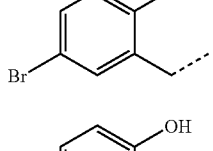 | H | H | H | H | H | 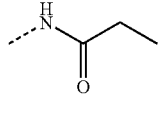 |
| 1-3-128 | 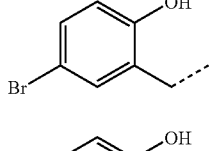 | H | H | H | H | H | 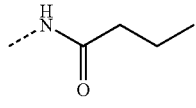 |
| 1-3-129 | 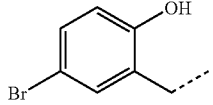 | H | H | H | H | H | 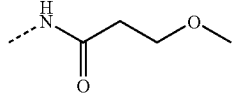 |

TABLE 1-3-continued
X = Single Bond, q = 0, r = 0, Y = —(R4)C═C(R5)—
| Compound No. | (R1—(CH2)p— | R2 | R3 | R4 | R5 | R6 | R7 |
|---|---|---|---|---|---|---|---|
| 1-3-130 | 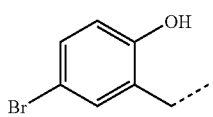 | H | H | H | H | H | 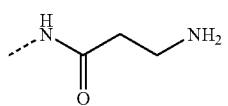 |
| 1-3-131 | 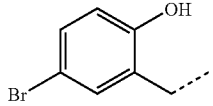 | H | H | H | H | H | 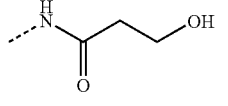 |
| 1-3-132 | 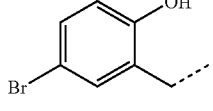 | H | H | H | H | H | 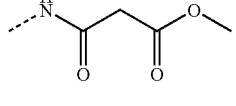 |
| 1-3-133 | 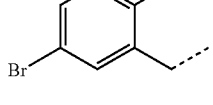 | H | H | H | H | H | 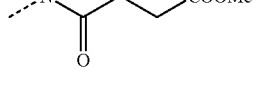 |
| 1-3-134 | 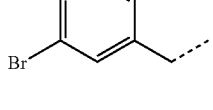 | H | H | H | H | H | 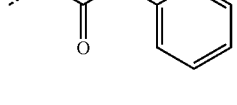 |
| 1-3-135 | 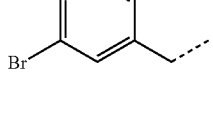 | H | H | H | H | H | 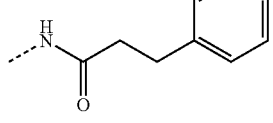 |
| 1-3-136 | 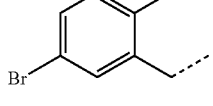 | H | H | H | H | H | 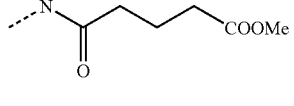 |
| 1-3-137 | 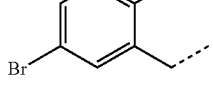 | H | H | H | H | H | 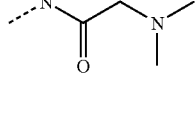 |
| 1-3-138 | 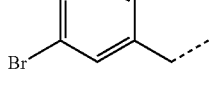 | H | H | H | H | H | 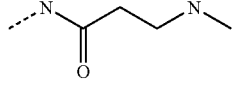 |
| 1-3-139 | 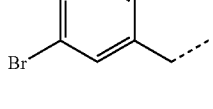 | H | H | H | H | H | 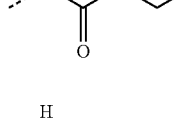 |
| 1-3-140 | 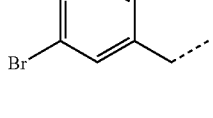 | H | H | H | H | H | 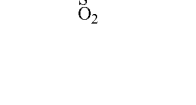 |

TABLE 1-3-continued

X = Single Bond, q = 0, r = 0, Y = —(R4)C═C(R5)—

| Compound No. | (R1—(CH2)p— | R2 | R3 | R4 | R5 | R6 | R7 |
|---|---|---|---|---|---|---|---|
| 1-3-141 | 1-Me-indol-3-ylmethyl | H | H | H | H | H | —NH—C(O)—CH2—NH—C(O)—CH3 |
| 1-3-142 | 1-Me-indol-3-ylmethyl | H | H | H | H | H | —NH—C(O)—CH2CH2—NH—C(O)—CH3 |
| 1-3-143 | 1-Me-indol-3-ylmethyl | H | H | H | H | H | —NH—C(O)—CH2CH3 |
| 1-3-144 | 1-Me-indol-3-ylmethyl | H | H | H | H | H | —NH—C(O)—CH2CH2CH3 |
| 1-3-145 | 1-Me-indol-3-ylmethyl | H | H | H | H | H | —NH—C(O)—CH2CH2—OMe |
| 1-3-146 | 1-Me-indol-3-ylmethyl | H | H | H | H | H | —NH—C(O)—CH2CH2—NH2 |
| 1-3-147 | 1-Me-indol-3-ylmethyl | H | H | H | H | H | —NH—C(O)—CH2CH2—OH |
| 1-3-148 | 1-Me-indol-3-ylmethyl | H | H | H | H | H | —NH—C(O)—CH2—C(O)—OMe |
| 1-3-149 | 1-Me-indol-3-ylmethyl | H | H | H | H | H | —NH—C(O)—CH2CH2—COOMe |

TABLE 1-3-continued

X = Single Bond, q = 0, r = 0, Y = —(R4)C=C(R5)—

| Compound No. | (R1—(CH2)p— | R2 | R3 | R4 | R5 | R6 | R7 |
|---|---|---|---|---|---|---|---|
| 1-3-150 | N-methylindol-3-ylmethyl | H | H | H | H | H | —NHC(O)CH2Ph |
| 1-3-151 | N-methylindol-3-ylmethyl | H | H | H | H | H | —NHC(O)CH2CH2Ph |
| 1-3-152 | N-methylindol-3-ylmethyl | H | H | H | H | H | —NHC(O)(CH2)3COOMe |
| 1-3-153 | N-methylindol-3-ylmethyl | H | H | H | H | H | —NHC(O)CH2N(Me)2 |
| 1-3-154 | N-methylindol-3-ylmethyl | H | H | H | H | H | —NHC(O)CH2CH2N(Me)2 |
| 1-3-155 | N-methylindol-3-ylmethyl | H | H | H | H | H | —NHC(O)NHEt |
| 1-3-156 | N-methylindol-3-ylmethyl | H | H | H | H | H | —NHS(O)2CH2CH2CH3 |
| 1-3-157 | benzothiophen-3-ylmethyl | H | H | H | H | H | —NHC(O)CH2NHC(O)CH3 |
| 1-3-158 | benzothiophen-3-ylmethyl | H | H | H | H | H | —NHC(O)CH2CH2NHC(O)CH3 |

TABLE 1-3-continued

X = Single Bond, q = 0, r = 0, Y = —(R4)C═C(R5)—

| Compound No. | (R1—(CH2)p— | R2 | R3 | R4 | R5 | R6 | R7 |
|---|---|---|---|---|---|---|---|
| 1-3-159 | benzothiophen-3-ylmethyl | H | H | H | H | H | —NHC(O)CH2CH3 |
| 1-3-160 | benzothiophen-3-ylmethyl | H | H | H | H | H | —NHC(O)CH2CH2CH3 |
| 1-3-161 | benzothiophen-3-ylmethyl | H | H | H | H | H | —NHC(O)CH2CH2OCH3 |
| 1-3-162 | benzothiophen-3-ylmethyl | H | H | H | H | H | —NHC(O)CH2CH2NH2 |
| 1-3-163 | benzothiophen-3-ylmethyl | H | H | H | H | H | —NHC(O)CH2CH2OH |
| 1-3-164 | benzothiophen-3-ylmethyl | H | H | H | H | H | —NHC(O)CH2C(O)OMe |
| 1-3-165 | benzothiophen-3-ylmethyl | H | H | H | H | H | —NHC(O)CH2CH2COOMe |
| 1-3-166 | benzothiophen-3-ylmethyl | H | H | H | H | H | —NHC(O)CH2Ph |
| 1-3-167 | benzothiophen-3-ylmethyl | H | H | H | H | H | —NHC(O)CH2CH2Ph |

TABLE 1-3-continued

X = Single Bond, q = 0, r = 0, Y = —(R4)C=C(R5)—

| Compound No. | (R1—(CH2)p— | R2 | R3 | R4 | R5 | R6 | R7 |
|---|---|---|---|---|---|---|---|
| 1-3-168 | benzothiophen-3-ylmethyl | H | H | H | H | H | —NH-C(O)-CH2CH2CH2-COOMe |
| 1-3-169 | benzothiophen-3-ylmethyl | H | H | H | H | H | —NH-C(O)-CH2-N(CH3)2 |
| 1-3-170 | benzothiophen-3-ylmethyl | H | H | H | H | H | —NH-C(O)-CH2CH2-N(CH3)2 |
| 1-3-171 | benzothiophen-3-ylmethyl | H | H | H | H | H | —NH-C(O)-NH-CH2CH3 |
| 1-3-172 | benzothiophen-3-ylmethyl | H | H | H | H | H | —NH-SO2-CH2CH3 |
| 1-3-173 | 3,4-dichlorobenzyl | H | H | H | H | —NH-C(O)-CH2-NH-C(O)-CH3 | H |
| 1-3-174 | 3,4-dichlorobenzyl | H | H | H | H | —NH-C(O)-CH2CH2-NH-C(O)-CH3 | H |
| 1-3-175 | 3,4-dichlorobenzyl | H | H | H | H | —NH-C(O)-CH2CH2-OH | H |
| 1-3-176 | 3,4-dichlorobenzyl | H | H | H | H | —NH-C(O)-CH2CH2-COOMe | H |
| 1-3-177 | 3,4-dichlorobenzyl | H | H | H | H | —NH-C(O)-CH2CH2CH2-COOMe | H |

TABLE 1-3-continued

X = Single Bond, q = 0, r = 0, Y = —(R4)C═C(R5)—

| Compound No. | (R1—(CH2)p—) | R2 | R3 | R4 | R5 | R6 | R7 |
|---|---|---|---|---|---|---|---|
| 1-3-178 | 3,4-dichlorobenzyl | H | H | H | H | —NHC(O)CH$_2$N(CH$_3$)$_2$ | H |
| 1-3-179 | 3,4-dichlorobenzyl | H | H | H | H | —NHC(O)CH$_2$CH$_2$N(CH$_3$)$_2$ | H |
| 1-3-180 | 3,4-dichlorobenzyl | H | H | H | H | —NHC(O)CH$_2$Ph | H |
| 1-3-181 | 3,4-dichlorobenzyl | H | H | H | H | —NHC(O)CH$_2$CH$_2$Ph | H |
| 1-3-182 | 3,4-dichlorobenzyl | H | H | H | H | —NHC(O)CH$_2$N(CH$_3$)$_2$ | H |
| 1-3-183 | 3,4-dichlorobenzyl | H | H | H | H | —NHS(O)$_2$CH$_2$CH$_3$ | H |
| 1-3-184 | 1-naphthylmethyl | H | H | H | H | —NHC(O)CH$_2$NHC(O)CH$_3$ | H |
| 1-3-185 | 1-naphthylmethyl | H | H | H | H | —NHC(O)CH$_2$CH$_2$NHC(O)CH$_3$ | H |
| 1-3-186 | 1-naphthylmethyl | H | H | H | H | —NHC(O)CH$_2$CH$_3$ | H |
| 1-3-187 | 1-naphthylmethyl | H | H | H | H | —NHC(O)CH$_2$CH$_2$CH$_3$ | H |

TABLE 1-3-continued
X = Single Bond, q = 0, r = 0, Y = —(R4)C=C(R5)—
| Compound No. | (R1—(CH2)p—) | R2 | R3 | R4 | R5 | R6 | R7 |
|---|---|---|---|---|---|---|---|
| 1-3-188 | 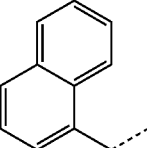 | H | H | H | H | 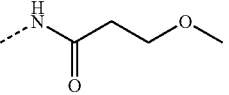 | H |
| 1-3-189 | 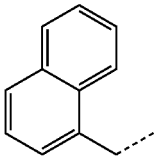 | H | H | H | H | 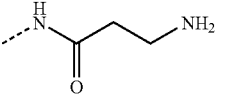 | H |
| 1-3-190 | 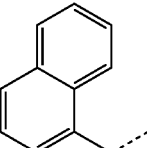 | H | H | H | H | 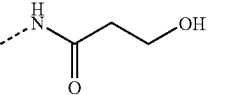 | H |
| 1-3-191 | 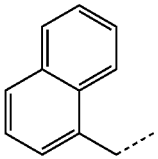 | H | H | H | H | 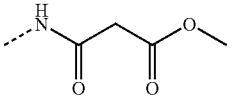 | H |
| 1-3-192 | 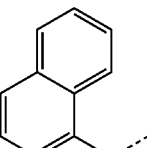 | H | H | H | H | 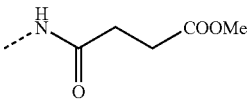 | H |
| 1-3-193 | 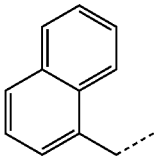 | H | H | H | H | 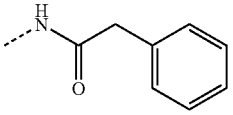 | H |
| 1-3-194 | 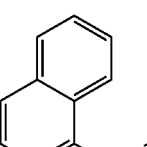 | H | H | H | H | 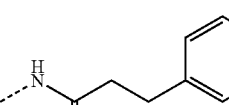 | H |
| 1-3-195 | 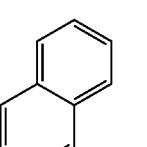 | H | H | H | H | 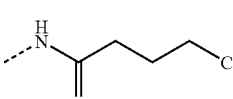 | H |

TABLE 1-3-continued

X = Single Bond, q = 0, r = 0, Y = —(R4)C=C(R5)—

| Compound No. | (R1—(CH2)p— | R2 | R3 | R4 | R5 | R6 | R7 |
|---|---|---|---|---|---|---|---|
| 1-3-196 | naphthalen-1-ylmethyl | H | H | H | H | —NHC(O)CH2N(CH3)2 | H |
| 1-3-197 | naphthalen-1-ylmethyl | H | H | H | H | —NHC(O)CH2CH2N(CH3)2 | H |
| 1-3-198 | naphthalen-1-ylmethyl | H | H | H | H | —NHC(O)NHCH2CH3 | H |
| 1-3-199 | naphthalen-1-ylmethyl | H | H | H | H | —NHS(O)2CH2CH3 | H |
| 1-3-200 | 3-phenylpropyl | H | H | H | H | —NHC(O)CH2NHC(O)CH3 | H |
| 1-3-201 | 3-phenylpropyl | H | H | H | H | —NHC(O)CH2CH2NHC(O)CH3 | H |
| 1-3-202 | 3-phenylpropyl | H | H | H | H | —NHC(O)CH2CH3 | H |
| 1-3-203 | 3-phenylpropyl | H | H | H | H | —NHC(O)CH2CH2CH3 | H |
| 1-3-204 | 3-phenylpropyl | H | H | H | H | —NHC(O)CH2CH2OCH3 | H |
| 1-3-205 | 3-phenylpropyl | H | H | H | H | —NHC(O)CH2CH2NH2 | H |

TABLE 1-3-continued

X = Single Bond, q = 0, r = 0, Y = —(R4)C═C(R5)—

| Compound No. | (R1—(CH2)p— | R2 | R3 | R4 | R5 | R6 | R7 |
|---|---|---|---|---|---|---|---|
| 1-3-206 | phenyl-(CH2)3- | H | H | H | H | —NH—C(O)—CH2CH2—OH | H |
| 1-3-207 | phenyl-(CH2)3- | H | H | H | H | —NH—C(O)—CH2—C(O)—OMe | H |
| 1-3-208 | phenyl-(CH2)3- | H | H | H | H | —NH—C(O)—CH2CH2—COOMe | H |
| 1-3-209 | phenyl-(CH2)3- | H | H | H | H | —NH—C(O)—CH2—phenyl | H |
| 1-3-210 | phenyl-(CH2)3- | H | H | H | H | —NH—C(O)—CH2CH2—phenyl | H |
| 1-3-211 | phenyl-(CH2)3- | H | H | H | H | —NH—C(O)—CH2CH2CH2—COOMe | H |
| 1-3-212 | phenyl-(CH2)3- | H | H | H | H | —NH—C(O)—CH2—N(CH3)2 | H |
| 1-3-213 | phenyl-(CH2)3- | H | H | H | H | —NH—C(O)—CH2CH2—N(CH3)2 | H |
| 1-3-214 | phenyl-(CH2)3- | H | H | H | H | —NH—C(O)—NH—Et | H |
| 1-3-215 | phenyl-(CH2)3- | H | H | H | H | —NH—C(O)—CH2—NH—C(O)—CH3 | H |
| 1-3-216 | phenyl-(CH2)3- | H | H | H | H | —NH—S(O2)—CH2CH2CH3 | H |
| 1-3-217 | 4-Cl-2-(CH2)-phenol | H | H | H | H | —NH—C(O)—CH2—NH—C(O)—CH3 | H |

TABLE 1-3-continued

X = Single Bond, q = 0, r = 0, Y = —(R4)C=C(R5)—

| Compound No. | (R1—(CH2)p—) | R2 | R3 | R4 | R5 | R6 | R7 |
|---|---|---|---|---|---|---|---|
| 1-3-218 | 4-Cl, 2-(CH2-), phenol (OH) | H | H | H | H | —NH-C(O)-CH2-CH2-NH-C(O)-CH3 | H |
| 1-3-219 | 4-Cl, 2-(CH2-), phenol (OH) | H | H | H | H | —NH-C(O)-CH2-CH3 | H |
| 1-3-219 | 4-Cl, 2-(CH2-), phenol (OH) | H | H | H | H | —NH-C(O)-CH2-CH2-CH3 | H |
| 1-3-220 | 4-Cl, 2-(CH2-), phenol (OH) | H | H | H | H | —NH-C(O)-CH2-CH2-OCH3 | H |
| 1-3-221 | 4-Cl, 2-(CH2-), phenol (OH) | H | H | H | H | —NH-C(O)-CH2-CH2-NH2 | H |
| 1-3-222 | 4-Cl, 2-(CH2-), phenol (OH) | H | H | H | H | —NH-C(O)-CH2-CH2-OH | H |
| 1-3-223 | 4-Cl, 2-(CH2-), phenol (OH) | H | H | H | H | —NH-C(O)-CH2-C(O)-OCH3 | H |
| 1-3-224 | 4-Cl, 2-(CH2-), phenol (OH) | H | H | H | H | —NH-C(O)-CH2-CH2-COOMe | H |
| 1-3-225 | 4-Cl, 2-(CH2-), phenol (OH) | H | H | H | H | —NH-C(O)-CH2-phenyl | H |
| 1-3-226 | 4-Cl, 2-(CH2-), phenol (OH) | H | H | H | H | —NH-C(O)-CH2-CH2-phenyl | H |
| 1-3-227 | 4-Cl, 2-(CH2-), phenol (OH) | H | H | H | H | —NH-C(O)-CH2-CH2-CH2-COOMe | H |

TABLE 1-3-continued

X = Single Bond, q = 0, r = 0, Y = —(R4)C═C(R5)—

| Compound No. | (R1—(CH2)p—) | R2 | R3 | R4 | R5 | R6 | R7 |
|---|---|---|---|---|---|---|---|
| 1-3-228 | 4-Cl, 2-(CH2—), phenol (OH) | H | H | H | H | —NH—C(O)—CH2—N(CH3)2 | H |
| 1-3-229 | 4-Cl, 2-(CH2—), phenol (OH) | H | H | H | H | —NH—C(O)—CH2CH2—N(CH3)2 | H |
| 1-3-230 | 4-Cl, 2-(CH2—), phenol (OH) | H | H | H | H | —NH—C(O)—NH—CH2CH3 | H |
| 1-3-231 | 4-Cl, 2-(CH2—), phenol (OH) | H | H | H | H | —NH—S(O)2—CH2CH2CH3 | H |
| 1-3-232 | 2,4-diCl, 6-(CH2—), phenol (OH) | H | H | H | H | —NH—C(O)—CH2—NH—C(O)—CH3 | H |
| 1-3-233 | 2,4-diCl, 6-(CH2—), phenol (OH) | H | H | H | H | —NH—C(O)—CH2CH2—NH—C(O)—CH3 | H |
| 1-3-234 | 2,4-diCl, 6-(CH2—), phenol (OH) | H | H | H | H | —NH—C(O)—CH2CH3 | H |
| 1-3-235 | 2,4-diCl, 6-(CH2—), phenol (OH) | H | H | H | H | —NH—C(O)—CH2CH2CH3 | H |
| 1-3-236 | 2,4-diCl, 6-(CH2—), phenol (OH) | H | H | H | H | —NH—C(O)—CH2CH2—O—CH3 | H |
| 1-3-237 | 2,4-diCl, 6-(CH2—), phenol (OH) | H | H | H | H | —NH—C(O)—CH2CH2—NH2 | H |

TABLE 1-3-continued

X = Single Bond, q = 0, r = 0, Y = —(R4)C=C(R5)—

| Compound No. | (R1—(CH2)p—) | R2 | R3 | R4 | R5 | R6 | R7 |
|---|---|---|---|---|---|---|---|
| 1-3-238 | 2,4-dichloro-6-hydroxyphenyl-CH< | H | H | H | H | —NH-C(O)-CH2CH2-OH | H |
| 1-3-239 | 2,4-dichloro-6-hydroxyphenyl-CH< | H | H | H | H | —NH-C(O)-CH2-COOMe | H |
| 1-3-240 | 2,4-dichloro-6-hydroxyphenyl-CH< | H | H | H | H | —NH-C(O)-CH2CH2-COOMe | H |
| 1-3-241 | 2,4-dichloro-6-hydroxyphenyl-CH< | H | H | H | H | —NH-C(O)-CH2-Ph | H |
| 1-3-242 | 2,4-dichloro-6-hydroxyphenyl-CH< | H | H | H | H | —NH-C(O)-CH2CH2-Ph | H |
| 1-3-243 | 2,4-dichloro-6-hydroxyphenyl-CH< | H | H | H | H | —NH-C(O)-CH2CH2CH2-COOMe | H |
| 1-3-244 | 2,4-dichloro-6-hydroxyphenyl-CH< | H | H | H | H | —NH-C(O)-CH2-N(Me)2 | H |
| 1-3-245 | 2,4-dichloro-6-hydroxyphenyl-CH< | H | H | H | H | —NH-C(O)-CH2CH2-N(Me)2 | H |
| 1-3-246 | 2,4-dichloro-6-hydroxyphenyl-CH< | H | H | H | H | —NH-C(O)-NH-Et | H |

TABLE 1-3-continued

X = Single Bond, q = 0, r = 0, Y = —(R4)C═C(R5)—

| Compound No. | (R1—(CH2)p— | R2 | R3 | R4 | R5 | R6 | R7 |
|---|---|---|---|---|---|---|---|
| 1-3-247 | 2,4-dichloro-6-hydroxyphenyl-CH2 | H | H | H | H | —NH-SO2-propyl | H |
| 1-3-248 | 4-bromo-2-hydroxyphenyl-CH2 | H | H | H | H | —NH-C(O)-CH2-NH-C(O)-CH3 | H |
| 1-3-249 | 4-bromo-2-hydroxyphenyl-CH2 | H | H | H | H | —NH-C(O)-CH2CH2-NH-C(O)-CH3 | H |
| 1-3-250 | 4-bromo-2-hydroxyphenyl-CH2 | H | H | H | H | —NH-C(O)-CH2CH3 | H |
| 1-3-251 | 4-bromo-2-hydroxyphenyl-CH2 | H | H | H | H | —NH-C(O)-CH2CH2CH3 | H |
| 1-3-252 | 4-bromo-2-hydroxyphenyl-CH2 | H | H | H | H | —NH-C(O)-CH2CH2-OCH3 | H |
| 1-3-253 | 4-bromo-2-hydroxyphenyl-CH2 | H | H | H | H | —NH-C(O)-CH2CH2-NH2 | H |
| 1-3-254 | 4-bromo-2-hydroxyphenyl-CH2 | H | H | H | H | —NH-C(O)-CH2CH2-OH | H |
| 1-3-255 | 4-bromo-2-hydroxyphenyl-CH2 | H | H | H | H | —NH-C(O)-CH2-C(O)-OCH3 | H |
| 1-3-256 | 4-bromo-2-hydroxyphenyl-CH2 | H | H | H | H | —NH-C(O)-CH2CH2-COOMe | H |
| 1-3-257 | 4-bromo-2-hydroxyphenyl-CH2 | H | H | H | H | —NH-C(O)-CH2-phenyl | H |

TABLE 1-3-continued
X = Single Bond, q = 0, r = 0, Y = —(R4)C=C(R5)—
| Compound No. | (R1—(CH2)p— | R2 | R3 | R4 | R5 | R6 | R7 |
|---|---|---|---|---|---|---|---|
| 1-3-258 | 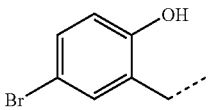 | H | H | H | H | 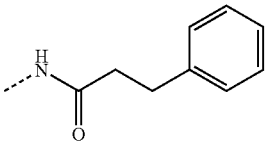 | H |
| 1-3-259 | 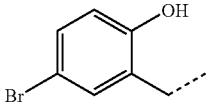 | H | H | H | H | 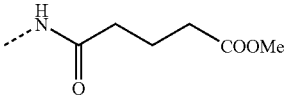 | H |
| 1-3-260 | 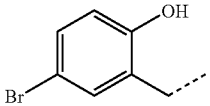 | H | H | H | H | 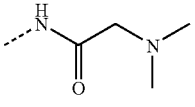 | H |
| 1-3-261 | 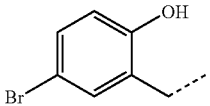 | H | H | H | H | 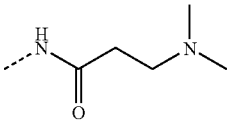 | H |
| 1-3-262 | 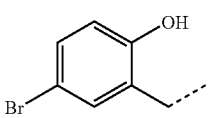 | H | H | H | H | 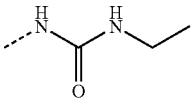 | H |
| 1-3-263 | 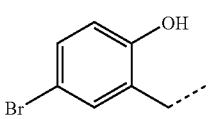 | H | H | H | H | 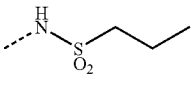 | H |
| 1-3-264 | 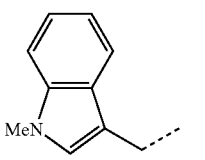 | H | H | H | H | 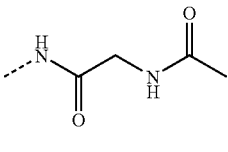 | H |
| 1-3-266 | 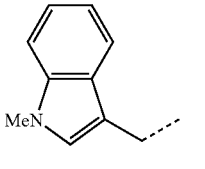 | H | H | H | H | 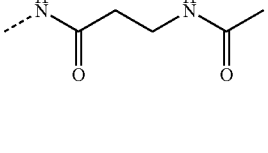 | H |
| 1-3-267 | 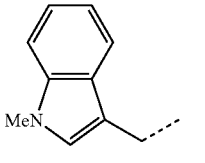 | H | H | H | H | 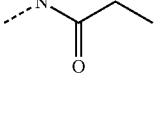 | H |
| 1-3-268 | 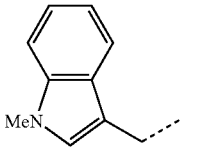 | H | H | H | H | 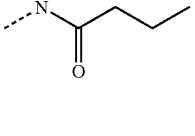 | H |

TABLE 1-3-continued

X = Single Bond, q = 0, r = 0, Y = —(R4)C=C(R5)—

| Compound No. | (R1—(CH2)p—) | R2 | R3 | R4 | R5 | R6 | R7 |
|---|---|---|---|---|---|---|---|
| 1-3-269 | 3-(1-methylindolyl)methyl | H | H | H | H | —NHC(O)CH2CH2OMe | H |
| 1-3-270 | 3-(1-methylindolyl)methyl | H | H | H | H | —NHC(O)CH2CH2NH2 | H |
| 1-3-271 | 3-(1-methylindolyl)methyl | H | H | H | H | —NHC(O)CH2CH2OH | H |
| 1-3-272 | 3-(1-methylindolyl)methyl | H | H | H | H | —NHC(O)CH2COOMe | H |
| 1-3-273 | 3-(1-methylindolyl)methyl | H | H | H | H | —NHC(O)CH2CH2COOMe | H |
| 1-3-274 | 3-(1-methylindolyl)methyl | H | H | H | H | —NHC(O)CH2Ph | H |
| 1-3-275 | 3-(1-methylindolyl)methyl | H | H | H | H | —NHC(O)CH2CH2Ph | H |
| 1-3-276 | 3-(1-methylindolyl)methyl | H | H | H | H | —NHC(O)CH2CH2CH2COOMe | H |
| 1-3-277 | 3-(1-methylindolyl)methyl | H | H | H | H | —NHC(O)CH2N(Me)2 | H |

TABLE 1-3-continued

X = Single Bond, q = 0, r = 0, Y = —(R4)C═C(R5)—

| Compound No. | (R1—(CH2)p— | R2 | R3 | R4 | R5 | R6 | R7 |
|---|---|---|---|---|---|---|---|
| 1-3-278 | 3-(N-methylindolyl)methyl | H | H | H | H | —NHC(O)CH₂CH₂N(CH₃)₂ | H |
| 1-3-279 | 3-(N-methylindolyl)methyl | H | H | H | H | —NHC(O)NHEt | H |
| 1-3-280 | 3-(N-methylindolyl)methyl | H | H | H | H | —NHSO₂CH₂CH₂CH₃ | H |
| 1-3-281 | 3-benzothienylmethyl | H | H | H | H | —NHC(O)CH₂NHC(O)CH₃ | H |
| 1-3-282 | 3-benzothienylmethyl | H | H | H | H | —NHC(O)CH₂CH₂NHC(O)CH₃ | H |
| 1-3-283 | 3-benzothienylmethyl | H | H | H | H | —NHC(O)CH₂CH₃ | H |
| 1-3-284 | 3-benzothienylmethyl | H | H | H | H | —NHC(O)CH₂CH₂CH₃ | H |
| 1-3-285 | 3-benzothienylmethyl | H | H | H | H | —NHC(O)CH₂CH₂OCH₃ | H |
| 1-3-286 | 3-benzothienylmethyl | H | H | H | H | —NHC(O)CH₂CH₂NH₂ | H |

TABLE 1-3-continued
X = Single Bond, q = 0, r = 0, Y = —(R4)C═C(R5)—
| Compound No. | (R1—(CH2)p— | R2 | R3 | R4 | R5 | R6 | R7 |
|---|---|---|---|---|---|---|---|
| 1-3-287 | 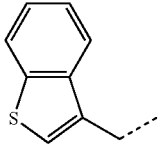 | H | H | H | H | 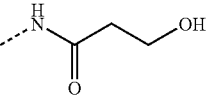 | H |
| 1-3-288 | 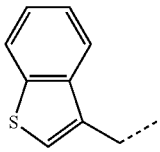 | H | H | H | H | 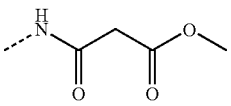 | H |
| 1-3-289 | 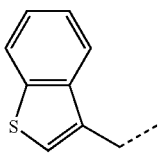 | H | H | H | H | 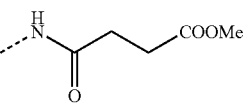 | H |
| 1-3-290 | 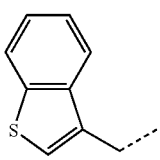 | H | H | H | H | 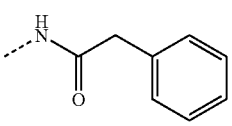 | H |
| 1-3-291 | 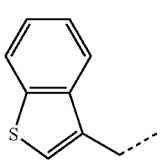 | H | H | H | H | 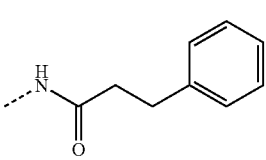 | H |
| 1-3-292 | 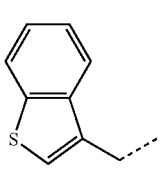 | H | H | H | H | 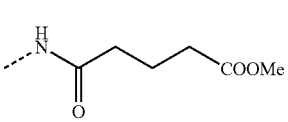 | H |
| 1-3-293 | 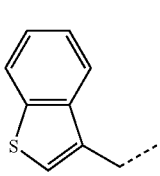 | H | H | H | H | 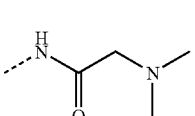 | H |
| 1-3-294 | 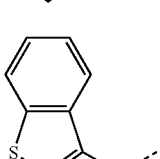 | H | H | H | H | 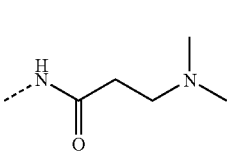 | H |
| 1-3-295 | 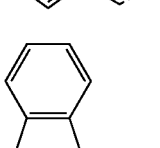 | H | H | H | H | 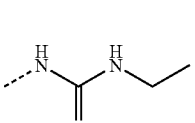 | H |

TABLE 1-3-continued
X = Single Bond, q = 0, r = 0, Y = —(R4)C=C(R5)—
| Compound No. | (R1—(CH2)p— | R2 | R3 | R4 | R5 | R6 | R7 |
|---|---|---|---|---|---|---|---|
| 1-3-296 | 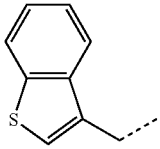 | H | H | H | H | 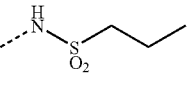 | H |
TABLE 1-4
X = Single Bond, q = 0, r = 0, Y = —(R4)C=C(R5)—
| Compound No. | R1—(CH2)p— | R2 | R3 | R4 | R5 | R6 | R7 |
|---|---|---|---|---|---|---|---|
| 1-4-1 | 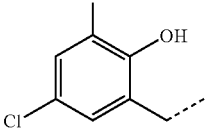 | H | H | H | H | H | 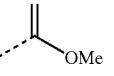 |
| 1-4-2 | 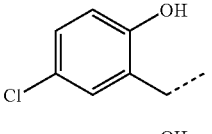 | H | H | H | H | H | 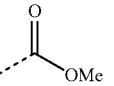 |
| 1-4-3 | 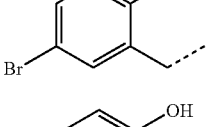 | H | H | H | H | H | 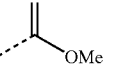 |
| 1-4-4 | 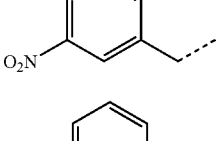 | H | H | H | H | H | 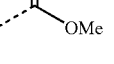 |
| 1-4-5 | 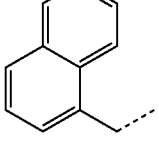 | H | H | H | H | H | 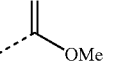 |
| 1-4-6 | 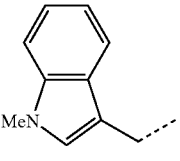 | H | H | H | H | H | 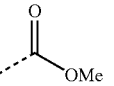 |
| 1-4-7 | 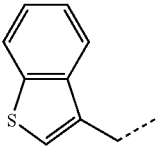 | H | H | H | H | H | 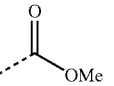 |
| 1-4-8 | 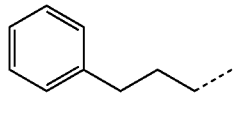 | H | H | H | H | H | 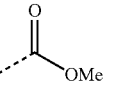 |

TABLE 1-4-continued

X = Single Bond, q = 0, r = 0, Y = —(R4)C=C(R5)—

| Compound No. | R1—(CH2)p— | R2 | R3 | R4 | R5 | R6 | R7 |
|---|---|---|---|---|---|---|---|
| 1-4-9 | 3,4-dichlorobenzyl | H | H | H | H | H | —C(O)OMe |
| 1-4-10 | 2-hydroxy-5-chlorobenzyl | H | H | H | H | H | —C(O)NH-CH2CH2-OMe |
| 1-4-11 | 2-hydroxy-5-bromobenzyl | H | H | H | H | H | —C(O)NH-CH2CH2-OMe |
| 1-4-12 | 2-hydroxy-5-nitrobenzyl | H | H | H | H | H | —C(O)NH-CH2CH2-OMe |
| 1-4-13 | 2-hydroxy-3,5-dichlorobenzyl | H | H | H | H | H | —C(O)NH-CH2CH2-OMe |
| 1-4-14 | 1-naphthylmethyl | H | H | H | H | H | —C(O)NH-CH2CH2-OMe |
| 1-4-15 | (1-methylindol-3-yl)methyl | H | H | H | H | H | —C(O)NH-CH2CH2-OMe |
| 1-4-16 | (benzothiophen-3-yl)methyl | H | H | H | H | H | —C(O)NH-CH2CH2-OMe |
| 1-4-17 | 3-phenylpropyl | H | H | H | H | H | —C(O)NH-CH2CH2-OMe |
| 1-4-18 | 2-hydroxy-3,5-dichlorobenzyl | H | H | H | H | H | —C(O)NH-iPr |

TABLE 1-4-continued

X = Single Bond, q = 0, r = 0, Y = —(R4)C=C(R5)—

| Compound No. | R1—(CH2)p— | R2 | R3 | R4 | R5 | R6 | R7 |
|---|---|---|---|---|---|---|---|
| 1-4-19 | 2,4-dichloro-6-hydroxybenzyl | H | H | H | H | H | C(=O)N(CH3)2 |
| 1-4-20 | 2,4-dichloro-6-hydroxybenzyl | H | H | H | H | H | C(=O)N(CH3)CH2CH2OCH3 |
| 1-4-21 | 2,4-dichloro-6-hydroxybenzyl | H | H | H | H | H | C(=O)-morpholinyl |
| 1-4-22 | 3,4-dichlorobenzyl | H | H | H | H | H | C(=O)NHCH2CH2NHC(=O)CH3 |
| 1-4-23 | 3,4-dichlorobenzyl | H | H | H | H | H | C(=O)NHCH2CH2N(CH3)2 |
| 1-4-24 | 3,4-dichlorobenzyl | H | H | H | H | H | C(=O)NHCH2CH2NHC(=O)OC(CH3)3 |
| 1-4-25 | 3,4-dichlorobenzyl | H | H | H | H | H | C(=O)NHCH2COOEt |
| 1-4-26 | 3,4-dichlorobenzyl | H | H | H | H | H | C(=O)NHCH2CH2COOMe |
| 1-4-27 | 3,4-dichlorobenzyl | H | H | H | H | H | C(=O)NHCH2CH2OCH3 |
| 1-4-28 | 3,4-dichlorobenzyl | H | H | H | H | H | C(=O)NHCH2-phenyl |

TABLE 1-4-continued
X = Single Bond, q = 0, r = 0, Y = —(R4)C=C(R5)—
| Compound No. | R1—(CH2)p— | R2 | R3 | R4 | R5 | R6 | R7 |
|---|---|---|---|---|---|---|---|
| 1-4-29 | 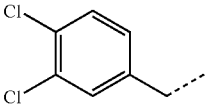 | H | H | H | H | H | 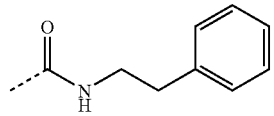 |
| 1-4-30 | 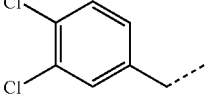 | H | H | H | H | H | 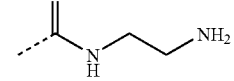 |
| 1-4-31 | 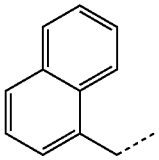 | H | H | H | H | H | 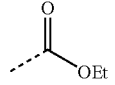 |
| 1-4-32 | 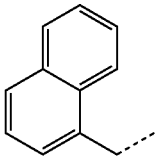 | H | H | H | H | H | 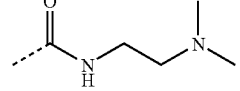 |
| 1-4-33 | 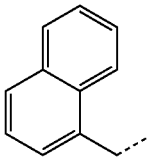 | H | H | H | H | H | 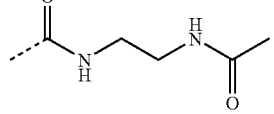 |
| 1-4-34 | 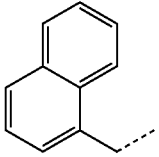 | H | H | H | H | H | 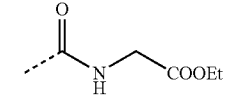 |
| 1-4-35 | 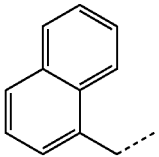 | H | H | H | H | H | 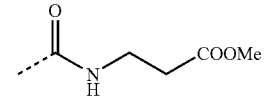 |
| 1-4-36 | 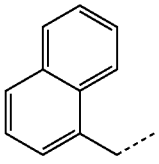 | H | H | H | H | H | 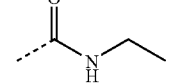 |
| 1-4-37 | 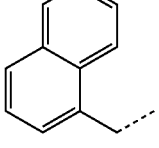 | H | H | H | H | H | 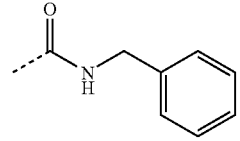 |

TABLE 1-4-continued

X = Single Bond, q = 0, r = 0, Y = —(R4)C=C(R5)—

| Compound No. | R1—(CH2)p— | R2 | R3 | R4 | R5 | R6 | R7 |
|---|---|---|---|---|---|---|---|
| 1-4-38 | phenyl-(CH2)2- | H | H | H | H | H | -C(=O)OEt |
| 1-4-39 | phenyl-(CH2)2- | H | H | H | H | H | -C(=O)NH-CH2CH2-N(CH3)2 |
| 1-4-40 | phenyl-(CH2)2- | H | H | H | H | H | -C(=O)NH-CH2CH2-NH-C(=O)CH3 |
| 1-4-41 | phenyl-(CH2)2- | H | H | H | H | H | -C(=O)NH-CH2-COOEt |
| 1-4-42 | phenyl-(CH2)2- | H | H | H | H | H | -C(=O)NH-CH2CH2-COOMe |
| 1-4-43 | phenyl-(CH2)2- | H | H | H | H | H | -C(=O)NH-iPr |
| 1-4-44 | phenyl-(CH2)2- | H | H | H | H | H | -C(=O)NH-CH2-phenyl |
| 1-4-45 | 4-Cl-2-OH-C6H3-CH2- | H | H | H | H | H | -C(=O)OEt |
| 1-4-46 | 4-Cl-2-OH-C6H3-CH2- | H | H | H | H | H | -C(=O)NH-CH2CH2-N(CH3)2 |
| 1-4-47 | 4-Cl-2-OH-C6H3-CH2- | H | H | H | H | H | -C(=O)NH-CH2CH2-NH-C(=O)CH3 |
| 1-4-48 | 4-Cl-2-OH-C6H3-CH2- | H | H | H | H | H | -C(=O)NH-CH2-COOEt |
| 1-4-49 | 4-Cl-2-OH-C6H3-CH2- | H | H | H | H | H | -C(=O)NH-CH2CH2-COOMe |

TABLE 1-4-continued

X = Single Bond, q = 0, r = 0, Y = —(R4)C=C(R5)—

| Compound No. | R1—(CH2)p— | R2 | R3 | R4 | R5 | R6 | R7 |
|---|---|---|---|---|---|---|---|
| 1-4-50 | 4-Cl, 2-(CH2)— phenol | H | H | H | H | H | —C(=O)NH-Et |
| 1-4-51 | 4-Cl, 2-(CH2)— phenol | H | H | H | H | H | —C(=O)NH-CH2-Ph |
| 1-4-52 | 3,5-diCl, 2-(CH2)— phenol | H | H | H | H | H | —C(=O)OEt |
| 1-4-53 | 3,5-diCl, 2-(CH2)— phenol | H | H | H | H | H | —C(=O)NH-CH2CH2-N(Me)2 |
| 1-4-54 | 3,5-diCl, 2-(CH2)— phenol | H | H | H | H | H | —C(=O)NH-CH2CH2-NHC(=O)Me |
| 1-4-55 | 3,5-diCl, 2-(CH2)— phenol | H | H | H | H | H | —C(=O)NH-CH2-COOEt |
| 1-4-56 | 3,5-diCl, 2-(CH2)— phenol | H | H | H | H | H | —C(=O)NH-CH2CH2-COOMe |
| 1-4-57 | 3,5-diCl, 2-(CH2)— phenol | H | H | H | H | H | —C(=O)NH-Et |
| 1-4-58 | 3,5-diCl, 2-(CH2)— phenol | H | H | H | H | H | —C(=O)NH-CH2-Ph |

TABLE 1-4-continued

X = Single Bond, q = 0, r = 0, Y = —(R4)C=C(R5)—

| Compound No. | R1—(CH2)p— | R2 | R3 | R4 | R5 | R6 | R7 |
|---|---|---|---|---|---|---|---|
| 1-4-59 | 4-Br, 2-(CH2)-, phenol | H | H | H | H | H | -C(=O)OEt |
| 1-4-60 | 4-Br, 2-(CH2)-, phenol | H | H | H | H | H | -C(=O)NH-CH2CH2-N(Me)2 |
| 1-4-61 | 4-Br, 2-(CH2)-, phenol | H | H | H | H | H | -C(=O)NH-CH2CH2-NH-C(=O)Me |
| 1-4-62 | 4-Br, 2-(CH2)-, phenol | H | H | H | H | H | -C(=O)NH-CH2-COOEt |
| 1-4-63 | 4-Br, 2-(CH2)-, phenol | H | H | H | H | H | -C(=O)NH-CH2CH2-COOMe |
| 1-4-64 | 4-Br, 2-(CH2)-, phenol | H | H | H | H | H | -C(=O)NH-Et |
| 1-4-65 | 4-Br, 2-(CH2)-, phenol | H | H | H | H | H | -C(=O)NH-CH2-phenyl |
| 1-4-66 | 1-Me-indol-3-yl-CH2- | H | H | H | H | H | -C(=O)OEt |
| 1-4-67 | 1-Me-indol-3-yl-CH2- | H | H | H | H | H | -C(=O)NH-CH2CH2-N(Me)2 |
| 1-4-68 | 1-Me-indol-3-yl-CH2- | H | H | H | H | H | -C(=O)NH-CH2CH2-NH-C(=O)Me |

TABLE 1-4-continued

X = Single Bond, q = 0, r = 0, Y = —(R4)C=C(R5)—

| Compound No. | R1—(CH2)p— | R2 | R3 | R4 | R5 | R6 | R7 |
|---|---|---|---|---|---|---|---|
| 1-4-69 | 3-(1-methylindolyl)- | H | H | H | H | H | —C(=O)NH-CH2-COOEt |
| 1-4-70 | 3-(1-methylindolyl)- | H | H | H | H | H | —C(=O)NH-CH2CH2-COOMe |
| 1-4-71 | 3-(1-methylindolyl)- | H | H | H | H | H | —C(=O)NH-Et |
| 1-4-72 | 3-(1-methylindolyl)- | H | H | H | H | H | —C(=O)NH-CH2-Ph |
| 1-4-73 | 3-benzothienyl- | H | H | H | H | H | —C(=O)-OEt |
| 1-4-74 | 3-benzothienyl- | H | H | H | H | H | —C(=O)NH-CH2CH2-N(Me)2 |
| 1-4-75 | 3-benzothienyl- | H | H | H | H | H | —C(=O)NH-CH2CH2-NH-C(=O)Me |
| 1-4-76 | 3-benzothienyl- | H | H | H | H | H | —C(=O)NH-CH2-COOEt |
| 1-4-77 | 3-benzothienyl- | H | H | H | H | H | —C(=O)NH-CH2CH2-COOMe |

TABLE 1-4-continued
X = Single Bond, q = 0, r = 0, Y = —(R4)C═C(R5)—
| Compound No. | R1—(CH2)p— | R2 | R3 | R4 | R5 | R6 | R7 |
|---|---|---|---|---|---|---|---|
| 1-4-78 | 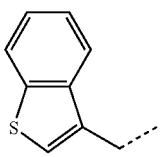 | H | H | H | H | H | 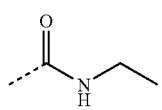 |
| 1-4-79 | 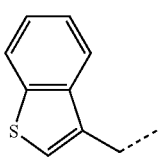 | H | H | H | H | H | 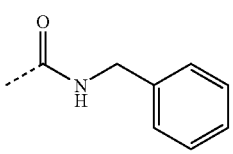 |
TABLE 1-5
X = Single Bond, q = 0, r = 0, Y = —(R4)═C(R5)—
| Compound No. | R1—(CH2)p— | R2 | R3 | R4 | R5 | R6 | R7 |
|---|---|---|---|---|---|---|---|
| 1-5-1 | 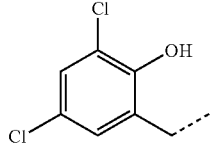 | H | H | H | H | COOEt | H |
| 1-5-2 | 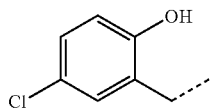 | H | H | H | H | COOEt | H |
| 1-5-3 | 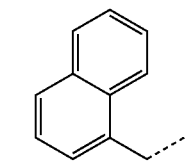 | H | H | H | H | COOEt | H |
| 1-5-4 | 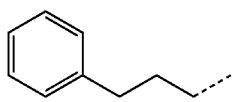 | H | H | H | H | COOEt | H |
| 1-5-5 | 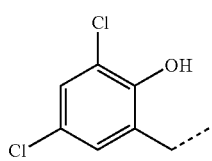 | H | H | H | H | COOCH(Me)2 | H |
| 1-5-6 | 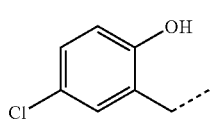 | H | H | H | H | COOCH(Me)2 | H |

TABLE 1-5-continued

X = Single Bond, q = 0, r = 0, Y = —(R4)═C(R5)—

| Compound No. | R1—(CH2)p— | R2 | R3 | R4 | R5 | R6 | R7 |
|---|---|---|---|---|---|---|---|
| 1-5-7 | 1-naphthylmethyl | H | H | H | H | COOCH(Me)2 | H |
| 1-5-8 | phenylpropyl | H | H | H | H | COOCH(Me)2 | H |
| 1-5-9 | 1-naphthylmethyl | H | H | H | H | COOMe | H |
| 1-5-10 | phenylpropyl | H | H | H | H | COOMe | H |
| 1-5-11 | 3,5-dichloro-2-hydroxybenzyl | H | H | H | H | COOMe | H |
| 1-5-12 | 4-nitro-2-hydroxybenzyl | H | H | H | H | COOMe | H |
| 1-5-13 | benzothiophen-3-ylmethyl | H | H | H | H | COOMe | H |
| 1-5-14 | 3,5-dichloro-2-hydroxybenzyl | H | Me | H | H | COOMe | H |
| 1-5-15 | 1-naphthylmethyl | H | Me | H | H | COOMe | H |
| 1-5-16 | phenylpropyl | H | Me | H | H | COOMe | H |

TABLE 1-5-continued
X = Single Bond, q = 0, r = 0, Y = —(R4)=C(R5)—
| Compound No. | R1—(CH2)p— | R2 | R3 | R4 | R5 | R6 | R7 |
|---|---|---|---|---|---|---|---|
| 1-5-17 | 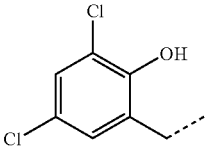 | H | Me | H | COOMeH | H | H |
| 1-5-18 | 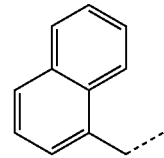 | H | Me | H | COOMe | H | H |
| 1-5-19 | 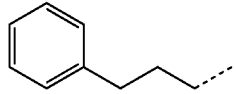 | H | Me | H | COOMe | H | H |
| 1-5-20 | 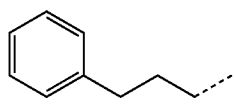 | H | H | H | H | COOH | H |
| 1-5-21 | 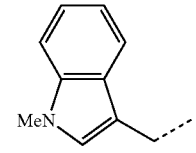 | H | H | H | H | COOH | H |
| 1-5-22 | 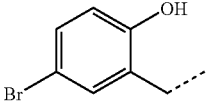 | H | H | H | H | COOH | H |
| 1-5-23 | 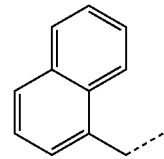 | H | H | H | H | 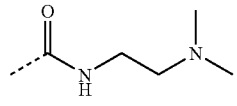 | H |
| 1-5-24 | 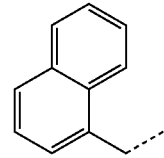 | H | H | H | H | 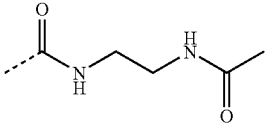 | H |
| 1-5-25 | 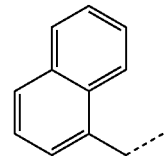 | H | H | H | H | 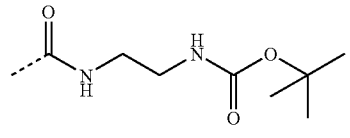 | H |
| 1-5-26 | 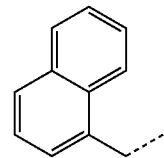 | H | H | H | H | 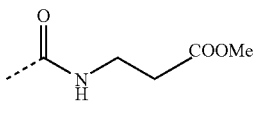 | H |

TABLE 1-5-continued

X = Single Bond, q = 0, r = 0, Y = —(R4)=C(R5)—

| Compound No. | R1—(CH2)p— | R2 | R3 | R4 | R5 | R6 | R7 |
|---|---|---|---|---|---|---|---|
| 1-5-27 | naphthyl-CH2- | H | H | H | H | -C(=O)NH-CH2CH2-O-CH3 | H |
| 1-5-28 | naphthyl-CH2- | H | H | H | H | -C(=O)NH-CH2-phenyl | H |
| 1-5-29 | naphthyl-CH2- | H | H | H | H | -C(=O)NH-CH2CH2-phenyl | H |
| 1-5-30 | naphthyl-CH2- | H | H | H | H | -C(=O)NH-propyl | H |
| 1-5-31 | naphthyl-CH2- | H | H | H | H | -C(=O)NH-butyl | H |
| 1-5-32 | naphthyl-CH2- | H | H | H | H | -C(=O)NH-CH(Et)2 | H |
| 1-5-33 | naphthyl-CH2- | H | H | H | H | -C(=O)NH-CH(CH3)CH2CH3 | H |
| 1-5-34 | naphthyl-CH2- | H | H | H | H | -C(=O)NH-CH2-COOEt | H |

TABLE 1-5-continued

X = Single Bond, q = 0, r = 0, Y = —(R4)=C(R5)—

| Compound No. | R1—(CH2)p— | R2 | R3 | R4 | R5 | R6 | R7 |
|---|---|---|---|---|---|---|---|
| 1-5-35 | naphthalen-1-ylmethyl | H | H | H | H | —C(=O)NH-CH2CH2-OH | H |
| 1-5-36 | naphthalen-1-ylmethyl | H | H | H | H | —C(=O)NH-CH2-COOH | H |
| 1-5-37 | naphthalen-1-ylmethyl | H | H | H | H | —C(=O)NH-CH2CH2-NH2 | H |
| 1-5-38 | 3-phenylpropyl | H | H | H | H | —C(=O)NH-propyl | H |
| 1-5-39 | 3-phenylpropyl | H | H | H | H | —C(=O)NH-CH2CH2-N(CH3)2 | H |
| 1-5-40 | 3-phenylpropyl | H | H | H | H | —C(=O)NH-CH2CH2-NH-C(=O)CH3 | H |
| 1-5-41 | 3-phenylpropyl | H | H | H | H | —C(=O)NH-CH2CH2-NH-C(=O)O-tBu | H |
| 1-5-42 | 3-phenylpropyl | H | H | H | H | —C(=O)NH-CH2-COOEt | H |
| 1-5-43 | 3-phenylpropyl | H | H | H | H | —C(=O)NH-CH2CH2-OH | H |
| 1-5-44 | 3-phenylpropyl | H | H | H | H | —C(=O)NH-CH2CH2-COOMe | H |
| 1-5-45 | 3-phenylpropyl | H | H | H | H | —C(=O)NH-CH2CH2-OMe | H |

TABLE 1-5-continued
X = Single Bond, q = 0, r = 0, Y = —(R4)═C(R5)—
| Compound No. | R1—(CH2)p— | R2 | R3 | R4 | R5 | R6 | R7 |
|---|---|---|---|---|---|---|---|
| 1-5-46 | 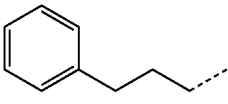 | H | H | H | H | 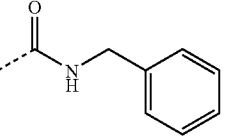 | H |
| 1-5-47 | 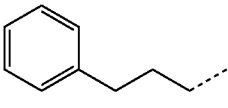 | H | H | H | H | 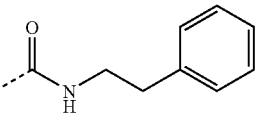 | H |
| 1-5-48 |  | H | H | H | H | 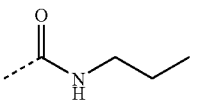 | H |
| 1-5-49 | 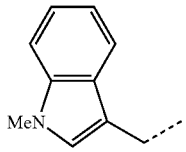 | H | H | H | H | 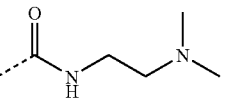 | H |
| 1-5-50 | 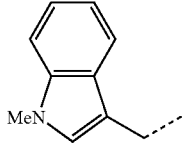 | H | H | H | H | 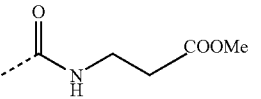 | H |
| 1-5-51 | 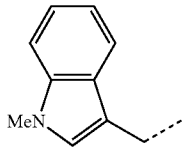 | H | H | H | H | 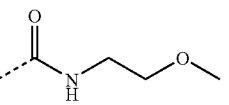 | H |
| 1-5-52 | 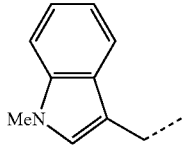 | H | H | H | H | 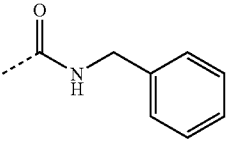 | H |
| 1-5-53 | 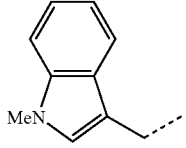 | H | H | H | H | 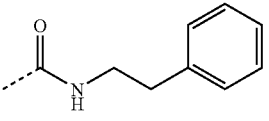 | H |
| 1-5-54 | 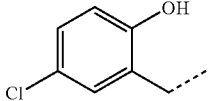 | H | H | H | H | 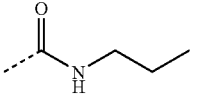 | H |
| 1-5-55 | 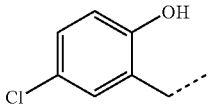 | H | H | H | H | 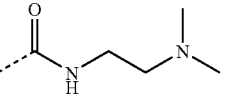 | H |

TABLE 1-5-continued

X = Single Bond, q = 0, r = 0, Y = —(R4)=C(R5)—

| Compound No. | R1—(CH2)p— | R2 | R3 | R4 | R5 | R6 | R7 |
|---|---|---|---|---|---|---|---|
| 1-5-56 | 4-Cl, 2-(CH2)-phenol | H | H | H | H | —C(O)NH-CH2CH2-NHC(O)CH3 | H |
| 1-5-57 | 4-Cl, 2-(CH2)-phenol | H | H | H | H | —C(O)NH-CH2CH2-NHC(O)O-tBu | H |
| 1-5-58 | 4-Cl, 2-(CH2)-phenol | H | H | H | H | —C(O)NH-CH2-COOEt | H |
| 1-5-59 | 4-Cl, 2-(CH2)-phenol | H | H | H | H | —C(O)NH-CH2CH2-COOMe | H |
| 1-5-60 | 4-Cl, 2-(CH2)-phenol | H | H | H | H | —C(O)NH-CH2CH2-OMe | H |
| 1-5-61 | 4-Cl, 2-(CH2)-phenol | H | H | H | H | —C(O)NH-CH2-Ph | H |
| 1-5-62 | 4-Cl, 2-(CH2)-phenol | H | H | H | H | —C(O)NH-CH2CH2-Ph | H |
| 1-5-63 | 3-Cl-benzyl | H | H | H | H | —C(O)NH-CH2CH2CH3 | H |
| 1-5-64 | 3-Cl-benzyl | H | H | H | H | —C(O)NH-CH2CH2-N(CH3)2 | H |
| 1-5-65 | 3-Cl-benzyl | H | H | H | H | —C(O)NH-CH2CH2-NHC(O)CH3 | H |
| 1-5-66 | 3-Cl-benzyl | H | H | H | H | —C(O)NH-CH2CH2-NHC(O)O-tBu | H |

TABLE 1-5-continued

X = Single Bond, q = 0, r = 0, Y = —(R4)=C(R5)—

| Compound No. | R1—(CH2)p— | R2 | R3 | R4 | R5 | R6 | R7 |
|---|---|---|---|---|---|---|---|
| 1-5-67 | 3-chlorobenzyl | H | H | H | H | —C(O)NH-CH2-COOEt | H |
| 1-5-68 | 3-chlorobenzyl | H | H | H | H | —C(O)NH-CH2CH2-OH | H |
| 1-5-69 | 3-chlorobenzyl | H | H | H | H | —C(O)NH-CH2CH2-COOMe | H |
| 1-5-70 | 3-chlorobenzyl | H | H | H | H | —C(O)NH-CH2-Ph | H |
| 1-5-71 | 3-chlorobenzyl | H | H | H | H | —C(O)NH-CH2CH2-Ph | H |
| 1-5-72 | 3-chlorobenzyl | H | H | H | H | —C(O)NH-CH2CH2-OMe | H |
| 1-5-73 | 1-naphthylmethyl | H | H | H | H | —C(O)N(Me)(OMe) | H |
| 1-5-74 | 3-phenylpropyl | H | H | H | H | —C(O)N(Me)(OMe) | H |
| 1-5-75 | (1-methylindol-3-yl)methyl | H | H | H | H | —C(O)N(Me)(OMe) | H |
| 1-5-76 | 4-chloro-2-hydroxybenzyl | H | H | H | H | —C(O)N(Me)(OMe) | H |
| 1-5-77 | 3-chlorobenzyl | H | H | H | H | —C(O)N(Me)(OMe) | H |

TABLE 1-5-continued
X = Single Bond, q = 0, r = 0, Y = —(R4)=C(R5)—
| Compound No. | R1—(CH2)p— | R2 | R3 | R4 | R5 | R6 | R7 |
|---|---|---|---|---|---|---|---|
| 1-5-78 | 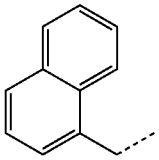 | H | H | H | H | 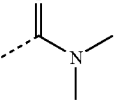 | H |
| 1-5-79 | 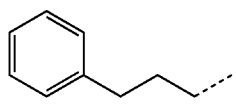 | H | H | H | H | 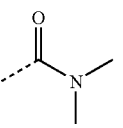 | H |
| 1-5-80 | 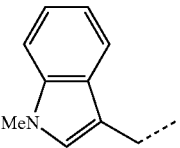 | H | H | H | H | 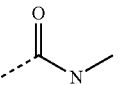 | H |
| 1-5-81 | 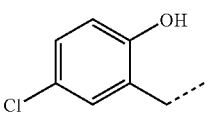 | H | H | H | H | 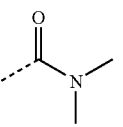 | H |
| 1-5-82 | 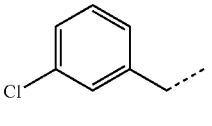 | H | H | H | H | 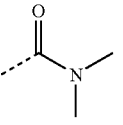 | H |
| 1-5-83 | 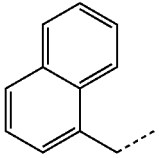 | H | H | H | H | 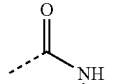 | H |
| 1-5-84 | 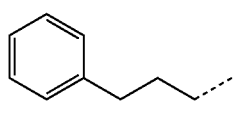 | H | H | H | H | 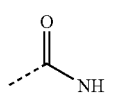 | H |
| 1-5-85 | 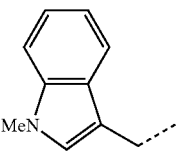 | H | H | H | H | 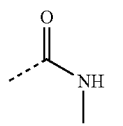 | H |
| 1-5-86 | 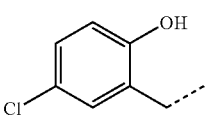 | H | H | H | H | 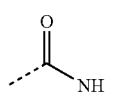 | H |
| 1-5-87 | 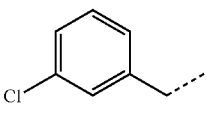 | H | H | H | H | 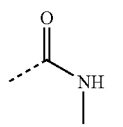 | H |

TABLE 1-5-continued

X = Single Bond, q = 0, r = 0, Y = —(R4)=C(R5)—

| Compound No. | R1—(CH2)p— | R2 | R3 | R4 | R5 | R6 | R7 |
|---|---|---|---|---|---|---|---|
| 1-5-88 | 3,4-diCl-benzyl | H | H | H | H | —C(O)NH-CH2-Ph | H |
| 1-5-89 | 3,4-diCl-benzyl | H | H | H | H | —C(O)NH-CH2-COOEt | H |
| 1-5-90 | 3,4-diCl-benzyl | H | H | H | H | —C(O)NH-propyl | H |
| 1-5-91 | 3,4-diCl-benzyl | H | H | H | H | —C(O)NH-CH2CH2-N(CH3)2 | H |
| 1-5-92 | 3,4-diCl-benzyl | H | H | H | H | —C(O)NH-CH2CH2-NHC(O)CH3 | H |
| 1-5-93 | 3,4-diCl-benzyl | H | H | H | H | —C(O)NH-CH2CH2-COOMe | H |
| 1-5-94 | 3,4-diCl-benzyl | H | H | H | H | —C(O)NH-CH2CH2-OCH3 | H |
| 1-5-95 | 3,4-diCl-benzyl | H | H | H | H | —C(O)NH-CH2CH2-NHC(O)OC(CH3)3 | H |
| 1-5-96 | 3,4-diCl-benzyl | H | H | H | H | —C(O)NH-CH2CH2-Ph | H |
| 1-5-97 | 3,4-diCl-benzyl | H | H | H | H | —C(O)NH-CH2CH2-NH2 | H |
| 1-5-98 | 3,4-diCl-benzyl | H | H | H | H | —C(O)NH-CH2-COOH | H |

TABLE 1-5-continued

X = Single Bond, q = 0, r = 0, Y = —(R4)=C(R5)—

| Compound No. | R1—(CH2)p— | R2 | R3 | R4 | R5 | R6 | R7 |
|---|---|---|---|---|---|---|---|
| 1-5-99 | 3,4-dichlorobenzyl | H | H | H | H | —C(=O)NH-CH2CH2-OH | H |
| 1-5-100 | 3,4-dichlorobenzyl | H | H | H | H | —C(=O)NH-(CH2)3-(2-oxopyrrolidin-1-yl) | H |
| 1-5-101 | 3,4-dichlorobenzyl | H | H | H | H | —C(=O)NH-CH2CH2-(1-methylpyrrolidin-2-yl) | H |
| 1-5-102 | 3,4-dichlorobenzyl | H | H | H | H | —C(=O)NH-C(Et)(Et)(C≡CH) | H |
| 1-5-103 | 3,4-dichlorobenzyl | H | H | H | H | —C(=O)NH-(1-ethynylcyclohexyl) | H |
| 1-5-104 | 3,4-dichlorobenzyl | H | H | H | H | —C(=O)NH-CH2CH2-C(CH3)3 | H |
| 1-5-105 | 3,4-dichlorobenzyl | H | H | H | H | —C(=O)NH-(2,3-dimethylcyclohexyl) | H |
| 1-5-106 | 3,4-dichlorobenzyl | H | H | H | H | —C(=O)NH-CH2-CF3 | H |
| 1-5-107 | 3,4-dichlorobenzyl | H | H | H | H | —C(=O)NH-CH2-cyclopropyl | H |
| 1-5-108 | 3,4-dichlorobenzyl | H | H | H | H | —C(=O)NH-CH2CH2-F | H |
| 1-5-109 | 3,4-dichlorobenzyl | H | H | H | H | —C(=O)NH-CH2CH2-O-C(=O)-C(CH3)=CH2 | H |

TABLE 1-5-continued

X = Single Bond, q = 0, r = 0, Y = —(R4)=C(R5)—

| Compound No. | R1—(CH2)p— | R2 | R3 | R4 | R5 | R6 | R7 |
|---|---|---|---|---|---|---|---|
| 1-5-110 | 3,4-diCl-benzyl | H | H | H | H | —C(O)NH-CH(CH3)-CH2-COOEt | H |
| 1-5-111 | 3,4-diCl-benzyl | H | H | H | H | —C(O)NH-(CH2)4-C(O)OMe | H |
| 1-5-112 | 3,4-diCl-benzyl | H | H | H | H | —C(O)NH-CH(CH3)-CH2-N(CH3)2 | H |
| 1-5-113 | 3,4-diCl-benzyl | H | H | H | H | —C(O)NH-CH(CH3)-CH2-CH2-CH(CH3)2 | H |
| 1-5-114 | 3,4-diCl-benzyl | H | H | H | H | —C(O)NH-CH2-CN | H |
| 1-5-115 | 3,4-diCl-benzyl | H | H | H | H | —C(O)NH-(CH2)3-C(O)OMe | H |
| 1-5-116 | 3,4-diCl-benzyl | H | H | H | H | —C(O)NH-CH2-CH=CH2 | H |
| 1-5-117 | 3,4-diCl-benzyl | H | H | H | H | —C(O)NH-CH(CH3)-C(CH3)3 | H |
| 1-5-118 | 3,4-diCl-benzyl | H | H | H | H | —C(O)NH-C(CH3)2-CH2CH3 | H |
| 1-5-119 | 3,4-diCl-benzyl | H | H | H | H | —C(O)NH-(CH2)2-piperidin-1-yl | H |
| 1-5-120 | 3,4-diCl-benzyl | H | H | H | H | —C(O)NH-cyclobutyl | H |

TABLE 1-5-continued
X = Single Bond, q = 0, r = 0, Y = —(R4)=C(R5)—
| Compound No. | R1—(CH2)p— | R2 | R3 | R4 | R5 | R6 | R7 |
|---|---|---|---|---|---|---|---|
| 1-5-121 | 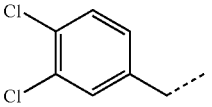 | H | H | H | H | 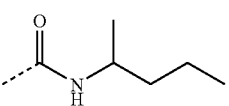 | H |
| 1-5-122 | 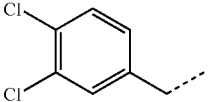 | H | H | H | H | 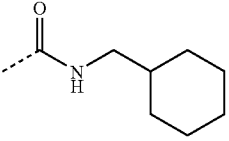 | H |
| 1-5-123 | 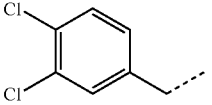 | H | H | H | H | 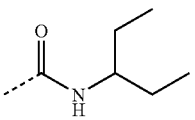 | H |
| 1-5-124 | 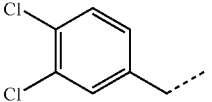 | H | H | H | H | 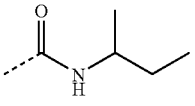 | H |
| 1-5-125 | 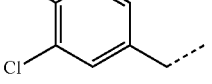 | H | H | H | H | 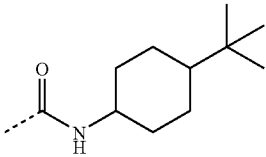 | H |
| 1-5-126 | 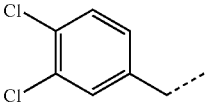 | H | H | H | H | 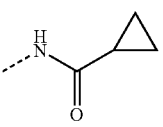 | H |
| 1-5-127 | 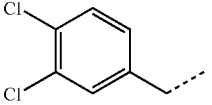 | H | H | H | H | 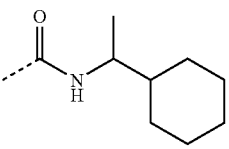 | H |
| 1-5-128 | 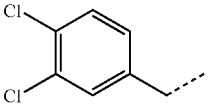 | H | H | H | H | 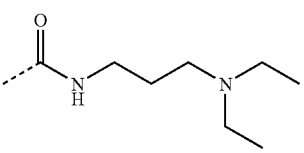 | H |
| 1-5-129 | 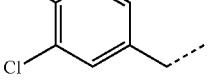 | H | H | H | H | 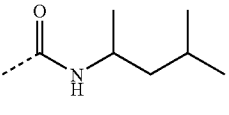 | H |
| 1-5-130 | 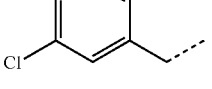 | H | H | H | H | 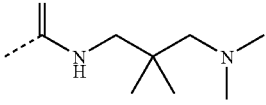 | H |

TABLE 1-5-continued

X = Single Bond, q = 0, r = 0, Y = —(R4)=C(R5)—

| Compound No. | R1—(CH2)p— | R2 | R3 | R4 | R5 | R6 | R7 |
|---|---|---|---|---|---|---|---|
| 1-5-131 | 3,4-diCl-benzyl | H | H | H | H | —C(=O)NH-CH(CH3)CH(CH3)2 | H |
| 1-5-132 | 3,4-diCl-benzyl | H | H | H | H | —C(=O)NH-Et | H |
| 1-5-133 | 3,4-diCl-benzyl | H | H | H | H | —C(=O)NH-(CH2)3-O-Et | H |
| 1-5-134 | 3,4-diCl-benzyl | H | H | H | H | —C(=O)NH-CH(CH2CH2CH3)2 | H |
| 1-5-135 | 3,4-diCl-benzyl | H | H | H | H | —C(=O)NH-CH2CH2CH(CH3)2 | H |
| 1-5-136 | 3,4-diCl-benzyl | H | H | H | H | —C(=O)NH-CH(Et)-CH2-O-Me | H |
| 1-5-137 | 3,4-diCl-benzyl | H | H | H | H | —C(=O)NH-(CH2)3-S-Me | H |
| 1-5-138 | 3,4-diCl-benzyl | H | H | H | H | —C(=O)NH-(2-methylcyclohexyl) | H |
| 1-5-139 | 3,4-diCl-benzyl | H | H | H | H | —C(=O)NH-(4-methylcyclohexyl) | H |
| 1-5-140 | 3,4-diCl-benzyl | H | H | H | H | —C(=O)NH-CH2-C≡CH | H |
| 1-5-141 | 3,4-diCl-benzyl | H | H | H | H | —C(=O)NH-(3,3,5-trimethylcyclohexyl) | H |

TABLE 1-5-continued

X = Single Bond, q = 0, r = 0, Y = —(R4)=C(R5)—

| Compound No. | R1—(CH2)p— | R2 | R3 | R4 | R5 | R6 | R7 |
|---|---|---|---|---|---|---|---|
| 1-5-142 | 3,4-dichlorobenzyl | H | H | H | H | —C(O)NH-CH2CH2CH2-N(CH3)2 | H |
| 1-5-143 | 3,4-dichlorobenzyl | H | H | H | H | —C(O)NH-C(CH3)3 | H |
| 1-5-144 | 3,4-dichlorobenzyl | H | H | H | H | —C(O)NH-CH2CH(CH3)2 | H |
| 1-5-145 | 3,4-dichlorobenzyl | H | H | H | H | —C(O)NH-CH2CH2CH2CH3 | H |
| 1-5-146 | 3,4-dichlorobenzyl | H | H | H | H | —C(O)NH-CH2-(tetrahydrofuran-2-yl) | H |
| 1-5-147 | 3,4-dichlorobenzyl | H | H | H | H | —C(O)NH-CH2CH2-N(CH2CH3)2 | H |
| 1-5-148 | 3,4-dichlorobenzyl | H | H | H | H | —C(O)NH-CH2CH2CH2-(morpholin-4-yl) | H |
| 1-5-149 | 3,4-dichlorobenzyl | H | H | H | H | —C(O)NH-CH(CH3)2 | H |
| 1-5-150 | 3,4-dichlorobenzyl | H | H | H | H | —C(O)NH-cyclopentyl | H |
| 1-5-151 | 3,4-dichlorobenzyl | H | H | H | H | —C(O)NH-cyclohexyl | H |
| 1-5-152 | 3,4-dichlorobenzyl | H | H | H | H | —C(O)NH-CH2CH2CH2-OCH3 | H |

TABLE 1-5-continued
X = Single Bond, q = 0, r = 0, Y = —(R4)=C(R5)—
| Compound No. | R1—(CH2)p— | R2 | R3 | R4 | R5 | R6 | R7 |
|---|---|---|---|---|---|---|---|
| 1-5-153 | 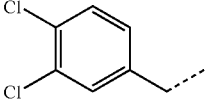 | H | H | H | H | 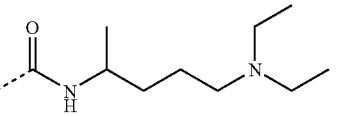 | H |
| 1-5-154 | 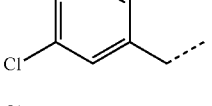 | H | H | H | H | 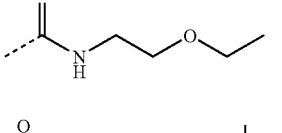 | H |
| 1-5-155 | 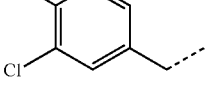 | H | H | H | H | 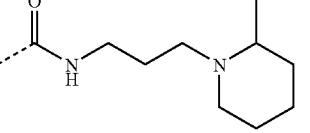 | H |
| 1-5-156 | 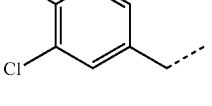 | H | H | H | H | 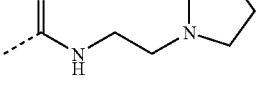 | H |
| 1-5-157 | 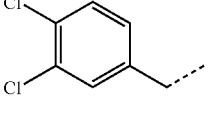 | H | H | H | H | 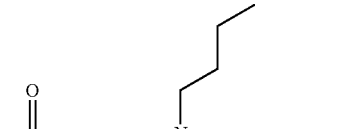 | H |
| 1-5-158 | 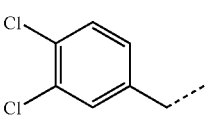 | H | H | H | H | 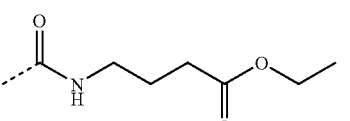 | H |
| 1-5-159 | 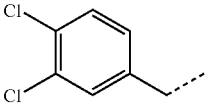 | H | H | H | H | 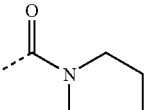 | H |
| 1-5-160 | 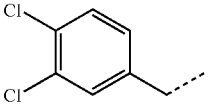 | H | H | H | H | 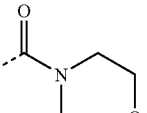 | H |
| 1-5-161 | 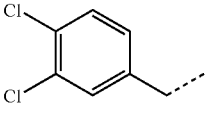 | H | H | H | H | 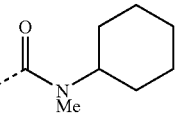 | H |
| 1-5-162 | 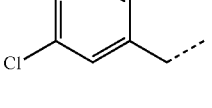 | H | H | H | H | 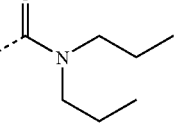 | H |

TABLE 1-5-continued
X = Single Bond, q = 0, r = 0, Y = —(R4)=C(R5)—
| Compound No. | R1—(CH2)p— | R2 | R3 | R4 | R5 | R6 | R7 |
|---|---|---|---|---|---|---|---|
| 1-5-163 | 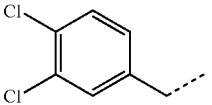 | H | H | H | H | 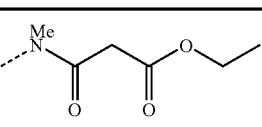 | H |
| 1-5-164 | 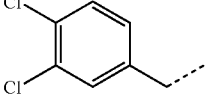 | H | H | H | H | 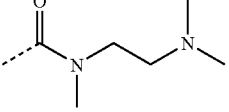 | H |
| 1-5-165 | 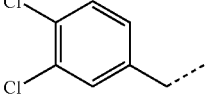 | H | H | H | H | 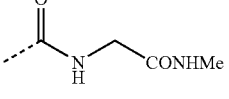 | H |
| 1-5-166 | 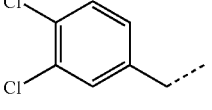 | H | H | H | H | 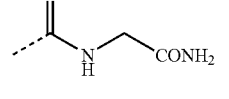 | H |
| 1-5-167 | 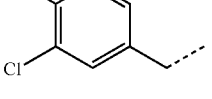 | H | H | H | H | 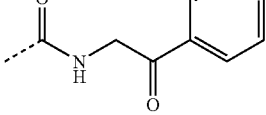 | H |
| 1-5-168 | 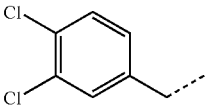 | H | H | H | H | 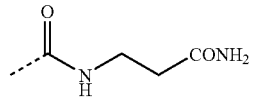 | H |
| 1-5-169 | 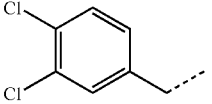 | H | H | H | H | 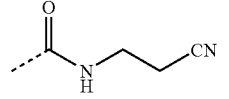 | H |
| 1-5-170 | 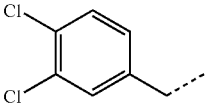 | H | H | H | H | 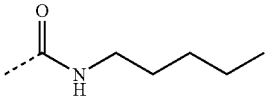 | H |
| 1-5-171 | 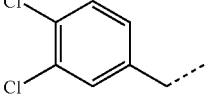 | H | H | H | H | 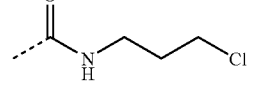 | H |
| 1-5-172 | 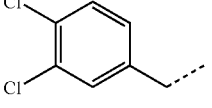 | H | H | H | H | 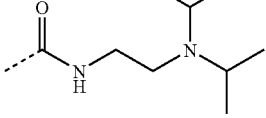 | H |
| 1-5-173 | 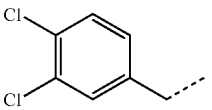 | H | H | H | H | 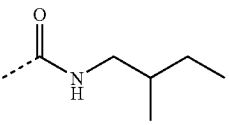 | H |

TABLE 1-5-continued

X = Single Bond, q = 0, r = 0, Y = —(R4)=C(R5)—

| Compound No. | R1—(CH2)p— | R2 | R3 | R4 | R5 | R6 | R7 |
|---|---|---|---|---|---|---|---|
| 1-5-174 | 3,4-dichlorobenzyl | H | H | H | H | —C(O)NH-(CH2)3-NHC(O)O-tBu | H |
| 1-5-175 | 3,4-dichlorobenzyl | H | H | H | H | —C(O)NH-(CH2)4-NHC(O)O-tBu | H |
| 1-5-176 | 3,4-dichlorobenzyl | H | H | H | H | —C(O)NH-CH2-(2-pyridyl) | H |
| 1-5-177 | 3,4-dichlorobenzyl | H | H | H | H | —C(O)NH-CH2-(3-pyridyl) | H |
| 1-5-178 | 3,4-dichlorobenzyl | H | H | H | H | —C(O)NH-CH2-(4-pyridyl) | H |
| 1-5-179 | 3,4-dichlorobenzyl | H | H | H | H | —C(O)N(CH3)-CH2CH2-OCH3 | H |
| 1-5-180 | 3,4-dichlorobenzyl | H | H | H | H | —C(O)NH-phenyl | H |
| 1-5-181 | 3,4-dichlorobenzyl | H | H | H | H | —C(O)NH-CH2-CH=CH-CH2-Cl | H |
| 1-5-182 | 3,4-dichlorobenzyl | H | H | H | H | —C(O)N(CH3)-CH2CH2CH3 | H |
| 1-5-183 | 3,4-dichlorobenzyl | H | H | H | H | —NH-C(O)-(4-methoxyphenyl) | H |

TABLE 1-5-continued

X = Single Bond, q = 0, r = 0, Y = —(R4)=C(R5)—

| Compound No. | R1—(CH2)p— | R2 | R3 | R4 | R5 | R6 | R7 |
|---|---|---|---|---|---|---|---|
| 1-5-184 | naphthalen-1-ylmethyl | H | H | H | H | -CH(CH3)OH | H |
| 1-5-185 | naphthalen-1-ylmethyl | H | H | H | H | -C(=O)H | H |
| 1-5-186 | naphthalen-1-ylmethyl | H | H | H | H | CN | H |
| 1-5-187 | naphthalen-1-ylmethyl | H | H | H | H | -CH(OH)CH2CH3 | H |
| 1-5-188 | naphthalen-1-ylmethyl | H | H | H | H | -C(OH)(CH3)CH2CH3 (shown as structure with OH) | H |
| 1-5-189 | naphthalen-1-ylmethyl | H | H | H | H | -C(=O)CH3 | H |
| 1-5-190 | naphthalen-1-ylmethyl | H | H | H | H | -C(=O)CH2CH3 | H |
| 1-5-191 | 3,4-dichlorobenzyl | H | H | H | H | -C(=O)NHCH2CH2SCH3 | H |
| 1-5-192 | 3,4-dichlorobenzyl | H | H | H | H | -C(=O)-N(4-methylpiperazin-1-yl) | H |

TABLE 1-5-continued

X = Single Bond, q = 0, r = 0, Y = —(R4)=C(R5)—

| Compound No. | R1—(CH2)p— | R2 | R3 | R4 | R5 | R6 | R7 |
|---|---|---|---|---|---|---|---|
| 1-5-193 | 3,4-diCl-benzyl | H | H | H | H | —C(O)N(Me)CH2CH2Ph | H |
| 1-5-194 | 3,4-diCl-benzyl | H | H | H | H | —C(O)NHCH2CH2(cyclohexenyl) | H |
| 1-5-195 | 3,4-diCl-benzyl | H | H | H | H | —C(O)N(Me)OMe | H |
| 1-5-196 | naphthalen-1-ylmethyl | H | H | H | H | —C(O)NHCH2COOEt | H |
| 1-5-197 | 5-Cl-2-OH-benzyl | H | H | H | H | —C(O)OMe | H |
| 1-5-198 | 3,5-diCl-2-OH-benzyl | H | H | H | H | —C(O)NHCH2CH2OMe | H |
| 1-5-199 | 3,5-diCl-2-OH-benzyl | H | H | H | H | —C(O)NHCH2CH2NMe2 | H |
| 1-5-200 | 3,5-diCl-2-OH-benzyl | H | H | H | H | —C(O)NHCH2CH2NHC(O)Me | H |
| 1-5-201 | 3,5-diCl-2-OH-benzyl | H | H | H | H | —C(O)NHCH2COOEt | H |
| 1-5-202 | 3,5-diCl-2-OH-benzyl | H | H | H | H | —C(O)NHCH2CH2COOMe | H |

TABLE 1-5-continued

X = Single Bond, q = 0, r = 0, Y = —(R4)=C(R5)—

| Compound No. | R1—(CH2)p— | R2 | R3 | R4 | R5 | R6 | R7 |
|---|---|---|---|---|---|---|---|
| 1-5-203 | 2,4-dichloro-6-(CH2)- phenol | H | H | H | H | -C(O)NH-propyl | H |
| 1-5-204 | 2,4-dichloro-6-(CH2)- phenol | H | H | H | H | -C(O)NH-benzyl | H |
| 1-5-205 | 4-bromo-2-(CH2)- phenol | H | H | H | H | -C(O)OMe | H |
| 1-5-206 | 4-bromo-2-(CH2)- phenol | H | H | H | H | -C(O)OEt | H |
| 1-5-207 | 4-bromo-2-(CH2)- phenol | H | H | H | H | -C(O)H | H |
| 1-5-208 | 4-bromo-2-(CH2)- phenol | H | H | H | H | -C(O)NH-CH2-CH=CH-CH2Cl | H |
| 1-5-209 | 4-bromo-2-(CH2)- phenol | H | H | H | H | -C(O)N(Me)(propyl) | H |
| 1-5-210 | 4-bromo-2-(CH2)- phenol | H | H | H | H | -C(O)N(Me)(CH2CH2Ph) | H |
| 1-5-211 | 4-bromo-2-(CH2)- phenol | H | H | H | H | -CH2OH | H |
| 1-5-212 | 4-bromo-2-(CH2)- phenol | H | H | H | H | -C(O)CH3 | H |
| 1-5-213 | 4-bromo-2-(CH2)- phenol | H | H | H | H | -CH(OH)CH2CH3 | H |

TABLE 1-5-continued

X = Single Bond, q = 0, r = 0, Y = —(R4)=C(R5)—

| Compound No. | R1—(CH2)p— | R2 | R3 | R4 | R5 | R6 | R7 |
|---|---|---|---|---|---|---|---|
| 1-5-214 | 4-bromo-2-hydroxyphenylmethyl | H | H | H | H | C(O)OMe | H |
| 1-5-215 | (1-methylindol-3-yl)methyl | H | H | H | H | C(O)OEt | H |
| 1-5-216 | (1-methylindol-3-yl)methyl | H | H | H | H | CHO | H |
| 1-5-217 | (1-methylindol-3-yl)methyl | H | H | H | H | C(O)NH-CH2-CH=CH-CH2Cl | H |
| 1-5-218 | (1-methylindol-3-yl)methyl | H | H | H | H | C(O)N(Me)CH2CH2Ph | H |
| 1-5-219 | (benzothiophen-3-yl)methyl | H | H | H | H | C(O)OMe | H |
| 1-5-220 | (benzothiophen-3-yl)methyl | H | H | H | H | CHO | H |
| 1-5-221 | (benzothiophen-3-yl)methyl | H | H | H | H | C(O)NH-CH2-CH=CH-CH2Cl | H |
| 1-5-222 | (benzothiophen-3-yl)methyl | H | H | H | H | C(O)N(Me)(n-Pr) | H |

TABLE 1-5-continued
X = Single Bond, q = 0, r = 0, Y = —(R4)=C(R5)—
| Compound No. | R1—(CH2)p— | R2 | R3 | R4 | R5 | R6 | R7 |
|---|---|---|---|---|---|---|---|
| 1-5-223 | 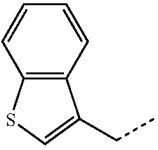 | H | H | H | H | 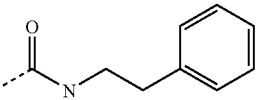 | H |
| 1-5-224 | 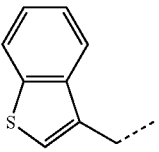 | H | H | H | H | 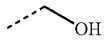 | H |
| 1-5-225 | 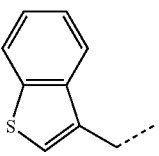 | H | H | H | H | 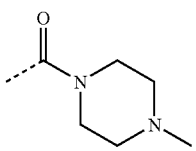 | H |
| 1-5-226 | 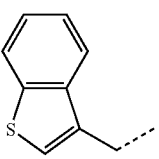 | H | H | H | H | 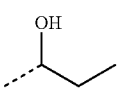 | H |
TABLE 1-6
X = Single Bond, q = 0, r = 0, Y = —(R4)C=C(R5)—
| Compound No. | R1—(CH2)p— | R2 | R3 | R4 | R5 | R6 | R7 |
|---|---|---|---|---|---|---|---|
| 1-6-1 | 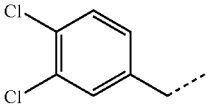 | H | Et | H | H | H | H |
| 1-6-2 | 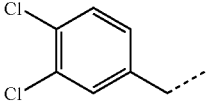 | Et | Et | H | H | H | H |
| 1-6-3 | 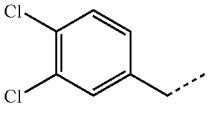 | CH2C6H5 | CH2C6H5 | H | H | H | H |
| 1-6-4 | 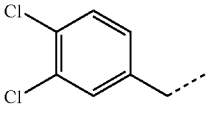 | H | CH2C6H5 | H | H | H | H |
| 1-6-5 | 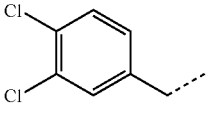 | (CH2)5CH3 | (CH2)5CH3 | H | H | H | H |

TABLE 1-6-continued
| | X = Single Bond, q = 0, r = 0, Y = —(R4)C=C(R5)— | | | | | | |
|---|---|---|---|---|---|---|---|
| Compound No. | R1—(CH2)p— | R2 | R3 | R4 | R5 | R6 | R7 |
| 1-6-6 | 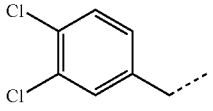 | H | (CH2)5CH3 | H | H | H | H |
| 1-6-7 | 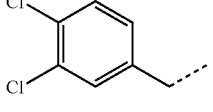 | (CH2)3C6H5 | (CH2)3C6H5 | H | H | H | H |
| 1-6-8 | 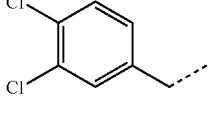 | H | (CH2)3C6H5 | H | H | H | H |
| 1-6-9 | 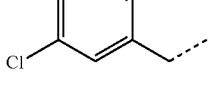 | H | CH2COOMe | H | H | H | H |
| 1-6-10 | 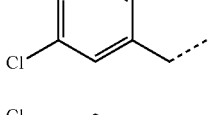 | H | (CH2)4COOEt | H | H | H | H |
| 1-6-11 | 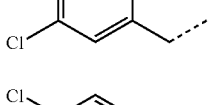 | H | (CH2)3NH2 | H | H | H | H |
| 1-6-12 | 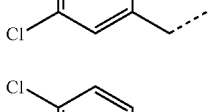 | H | (CH2)2CONH2 | H | H | H | H |
| 1-6-13 | 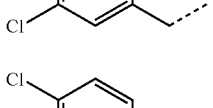 | H | (CH2)2COOH | H | H | H | H |
| 1-6-14 | 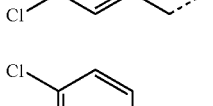 | H | (CH2)2CN | H | H | H | H |
| 1-6-15 | 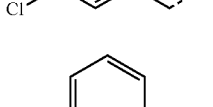 | H | (CH2)2COOEt | H | H | H | H |
| 1-6-16 | 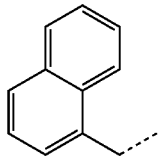 | H | Et | H | H | H | H |

TABLE 1-6-continued

X = Single Bond, q = 0, r = 0, Y = —(R4)C=C(R5)—

| Compound No. | R1—(CH2)p— | R2 | R3 | R4 | R5 | R6 | R7 |
|---|---|---|---|---|---|---|---|
| 1-6-17 | naphthyl-CH2 | Et | Et | H | H | H | H |
| 1-6-18 | naphthyl-CH2 | CH2C6H5 | CH2C6H5 | H | H | H | H |
| 1-6-19 | naphthyl-CH2 | H | CH2C6H5 | H | H | H | H |
| 1-6-20 | naphthyl-CH2 | (CH2)5CH3 | (CH2)5CH3 | H | H | H | H |
| 1-6-21 | naphthyl-CH2 | H | (CH2)5CH3 | H | H | H | H |
| 1-6-22 | naphthyl-CH2 | (CH2)3C6H5 | (CH2)3C6H5 | H | H | H | H |
| 1-6-23 | naphthyl-CH2 | H | (CH2)3C6H5 | H | H | H | H |
| 1-6-24 | naphthyl-CH2 | H | CH2COOMe | H | H | H | H |
| 1-6-25 | naphthyl-CH2 | H | (CH2)4COOEt | H | H | H | H |

TABLE 1-6-continued
X = Single Bond, q = 0, r = 0, Y = —(R4)C=C(R5)—
| Compound No. | R1—(CH2)p— | R2 | R3 | R4 | R5 | R6 | R7 |
|---|---|---|---|---|---|---|---|
| 1-6-26 | 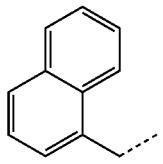 | H | (CH2)3NH2 | H | H | H | H |
| 1-6-27 | 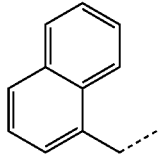 | H | (CH2)2CONH2 | H | H | H | H |
| 1-6-28 | 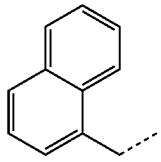 | H | (CH2)2COOH | H | H | H | H |
| 1-6-29 | 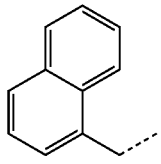 | H | (CH2)2CN | H | H | H | H |
| 1-6-30 | 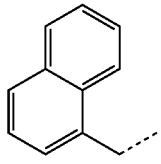 | H | (CH2)2COOEt | H | H | H | H |
| 1-6-31 | 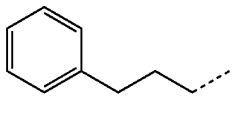 | H | Et | H | H | H | H |
| 1-6-32 | 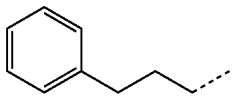 | Et | Et | H | H | H | H |
| 1-6-33 | 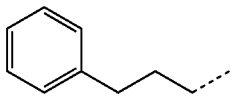 | CH2C6H5 | CH2C6H5 | H | H | H | H |
| 1-6-34 | 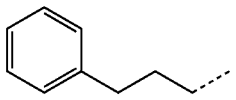 | H | CH2C6H5 | H | H | H | H |
| 1-6-35 | 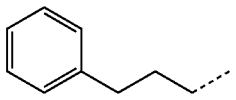 | (CH2)5CH3 | (CH2)5CH3 | H | H | H | H |
| 1-6-36 | 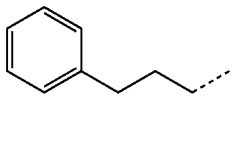 | H | (CH2)5CH3 | H | H | H | H |

TABLE 1-6-continued

X = Single Bond, q = 0, r = 0, Y = —(R4)C=C(R5)—

| Compound No. | R1—(CH2)p— | R2 | R3 | R4 | R5 | R6 | R7 |
|---|---|---|---|---|---|---|---|
| 1-6-37 | phenyl-(CH2)2- | (CH2)3C6H5 | (CH2)3C6H5 | H | H | H | H |
| 1-6-38 | phenyl-(CH2)2- | H | (CH2)3C6H5 | H | H | H | H |
| 1-6-39 | phenyl-(CH2)2- | H | CH2COOMe | H | H | H | H |
| 1-6-40 | phenyl-(CH2)2- | H | (CH2)4COOEt | H | H | H | H |
| 1-6-41 | phenyl-(CH2)2- | H | (CH2)3NH2 | H | H | H | H |
| 1-6-42 | phenyl-(CH2)2- | H | (CH2)2CONH2 | H | H | H | H |
| 1-6-43 | phenyl-(CH2)2- | H | (CH2)2COOH | H | H | H | H |
| 1-6-44 | phenyl-(CH2)2- | H | (CH2)2CN | H | H | H | H |
| 1-6-45 | phenyl-(CH2)2- | H | (CH2)2COOEt | H | H | H | H |
| 1-6-46 | 4-Cl-2-OH-C6H3-CH2- | H | Et | H | H | H | H |
| 1-6-47 | 4-Cl-2-OH-C6H3-CH2- | Et | Et | H | H | H | H |
| 1-6-48 | 4-Cl-2-OH-C6H3-CH2- | CH2C6H5 | CH2C6H5 | H | H | H | H |
| 1-6-49 | 4-Cl-2-OH-C6H3-CH2- | H | CH2C6H5 | H | H | H | H |

TABLE 1-6-continued

X = Single Bond, q = 0, r = 0, Y = —(R4)C═C(R5)—

| Compound No. | R1—(CH2)p— | R2 | R3 | R4 | R5 | R6 | R7 |
|---|---|---|---|---|---|---|---|
| 1-6-50 | 4-Cl, 2-OH phenyl-CH2- | (CH2)5CH3 | (CH2)5CH3 | H | H | H | H |
| 1-6-51 | 4-Cl, 2-OH phenyl-CH2- | H | (CH2)5CH3 | H | H | H | H |
| 1-6-52 | 4-Cl, 2-OH phenyl-CH2- | (CH2)3C6H5 | (CH2)3C6H5 | H | H | H | H |
| 1-6-53 | 4-Cl, 2-OH phenyl-CH2- | H | (CH2)3C6H5 | H | H | H | H |
| 1-6-54 | 4-Cl, 2-OH phenyl-CH2- | H | CH2COOMe | H | H | H | H |
| 1-6-55 | 4-Cl, 2-OH phenyl-CH2- | H | (CH2)4COOEt | H | H | H | H |
| 1-6-56 | 4-Cl, 2-OH phenyl-CH2- | H | (CH2)3NH2 | H | H | H | H |
| 1-6-57 | 4-Cl, 2-OH phenyl-CH2- | H | (CH2)2CONH2 | H | H | H | H |
| 1-6-58 | 4-Cl, 2-OH phenyl-CH2- | H | (CH2)2COOH | H | H | H | H |
| 1-6-59 | 4-Cl, 2-OH phenyl-CH2- | H | (CH2)2CN | H | H | H | H |
| 1-6-60 | 4-Cl, 2-OH phenyl-CH2- | H | (CH2)2COOEt | H | H | H | H |
| 1-6-61 | 2,4-diCl, 3-OH phenyl-CH2- | H | Et | H | H | H | H |

TABLE 1-6-continued
| | X = Single Bond, q = 0, r = 0, Y = —(R4)C=C(R5)— | | | | | | |
|---|---|---|---|---|---|---|---|
| Compound No. | R1—(CH2)p— | R2 | R3 | R4 | R5 | R6 | R7 |
| 1-6-62 | 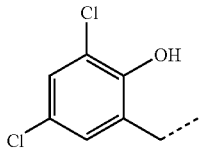 | Et | Et | H | H | H | H |
| 1-6-63 | 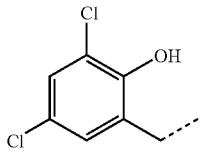 | CH2C6H5 | CH2C6H5 | H | H | H | H |
| 1-6-64 | 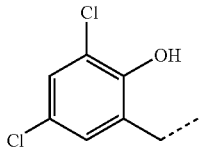 | H | CH2C6H5 | H | H | H | H |
| 1-6-65 | 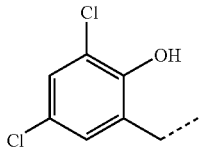 | (CH2)5CH3 | (CH2)5CH3 | H | H | H | H |
| 1-6-66 | 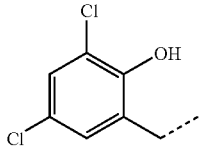 | H | (CH2)5CH3 | H | H | H | H |
| 1-6-67 | 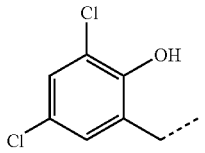 | (CH2)3C6H5 | (CH2)3C6H5 | H | H | H | H |
| 1-6-68 | 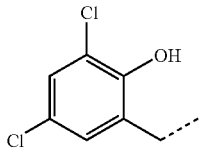 | H | (CH2)3C6H5 | H | H | H | H |
| 1-6-69 | 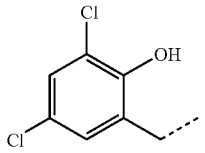 | H | CH2COOMe | H | H | H | H |
| 1-6-70 | 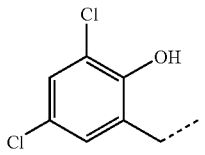 | H | (CH2)4COOEt | H | H | H | H |

TABLE 1-6-continued

| | X = Single Bond, q = 0, r = 0, Y = —(R4)C=C(R5)— | | | | | | |
|---|---|---|---|---|---|---|---|
| Compound No. | R1—(CH2)p— | R2 | R3 | R4 | R5 | R6 | R7 |
| 1-6-71 | 2,4-dichloro-6-hydroxybenzyl | H | (CH2)3NH2 | H | H | H | H |
| 1-6-72 | 2,4-dichloro-6-hydroxybenzyl | H | (CH2)2CONH2 | H | H | H | H |
| 1-6-73 | 2,4-dichloro-6-hydroxybenzyl | H | (CH2)2COOH | H | H | H | H |
| 1-6-74 | 2,4-dichloro-6-hydroxybenzyl | H | (CH2)2CN | H | H | H | H |
| 1-6-75 | 2,4-dichloro-6-hydroxybenzyl | H | (CH2)2COOEt | H | H | H | H |
| 1-6-76 | 4-bromo-2-hydroxybenzyl | H | Et | H | H | H | H |
| 1-6-77 | 4-bromo-2-hydroxybenzyl | Et | Et | H | H | H | H |
| 1-6-78 | 4-bromo-2-hydroxybenzyl | CH2C6H5 | CH2C6H5 | H | H | H | H |
| 1-6-79 | 4-bromo-2-hydroxybenzyl | H | CH2C6H5 | H | H | H | H |
| 1-6-80 | 4-bromo-2-hydroxybenzyl | (CH2)5CH3 | (CH2)5CH3 | H | H | H | H |

TABLE 1-6-continued

X = Single Bond, q = 0, r = 0, Y = —(R4)C=C(R5)—

| Compound No. | R1—(CH2)p— | R2 | R3 | R4 | R5 | R6 | R7 |
|---|---|---|---|---|---|---|---|
| 1-6-81 | 4-Br-2-(CH2—)-phenol | H | (CH2)5CH3 | H | H | H | H |
| 1-6-82 | 4-Br-2-(CH2—)-phenol | (CH2)3C6H5 | (CH2)3C6H5 | H | H | H | H |
| 1-6-83 | 4-Br-2-(CH2—)-phenol | H | (CH2)3C6H5 | H | H | H | H |
| 1-6-84 | 4-Br-2-(CH2—)-phenol | H | CH2COOMe | H | H | H | H |
| 1-6-85 | 4-Br-2-(CH2—)-phenol | H | (CH2)4COOEt | H | H | H | H |
| 1-6-86 | 4-Br-2-(CH2—)-phenol | H | (CH2)3NH2 | H | H | H | H |
| 1-6-87 | 4-Br-2-(CH2—)-phenol | H | (CH2)2CONH2 | H | H | H | H |
| 1-6-88 | 4-Br-2-(CH2—)-phenol | H | (CH2)2COOH | H | H | H | H |
| 1-6-89 | 4-Br-2-(CH2—)-phenol | H | (CH2)2CN | H | H | H | H |
| 1-6-90 | 4-Br-2-(CH2—)-phenol | H | (CH2)2COOEt | H | H | H | H |
| 1-6-91 | 1-Me-indol-3-yl-CH2— | H | Et | H | H | H | H |
| 1-6-92 | 1-Me-indol-3-yl-CH2— | Et | Et | H | H | H | H |

TABLE 1-6-continued

| | X = Single Bond, q = 0, r = 0, Y = —(R4)C=C(R5)— | | | | | | |
|---|---|---|---|---|---|---|---|
| Compound No. | R1—(CH2)p— | R2 | R3 | R4 | R5 | R6 | R7 |
| 1-6-93 | 3-(N-methylindolyl)methyl | CH2C6H5 | CH2C6H5 | H | H | H | H |
| 1-6-94 | 3-(N-methylindolyl)methyl | H | CH2C6H5 | H | H | H | H |
| 1-6-95 | 3-(N-methylindolyl)methyl | (CH2)5CH3 | (CH2)5CH3 | H | H | H | H |
| 1-6-96 | 3-(N-methylindolyl)methyl | H | (CH2)5CH3 | H | H | H | H |
| 1-6-97 | 3-(N-methylindolyl)methyl | (CH2)3C6H5 | (CH2)3C6H5 | H | H | H | H |
| 1-6-98 | 3-(N-methylindolyl)methyl | H | (CH2)3C6H5 | H | H | H | H |
| 1-6-99 | 3-(N-methylindolyl)methyl | H | CH2COOMe | H | H | H | H |
| 1-6-100 | 3-(N-methylindolyl)methyl | H | (CH2)4COOEt | H | H | H | H |
| 1-6-101 | 3-(N-methylindolyl)methyl | H | (CH2)3NH2 | H | H | H | H |

TABLE 1-6-continued

| | X = Single Bond, q = 0, r = 0, Y = —(R4)C=C(R5)— | | | | | | |
|---|---|---|---|---|---|---|---|
| Compound No. | R1—(CH2)p— | R2 | R3 | R4 | R5 | R6 | R7 |
| 1-6-102 | 3-(N-methylindolyl)methyl | H | (CH2)2CONH2 | H | H | H | H |
| 1-6-103 | 3-(N-methylindolyl)methyl | H | (CH2)2COOH | H | H | H | H |
| 1-6-104 | 3-(N-methylindolyl)methyl | H | (CH2)2CN | H | H | H | H |
| 1-6-105 | 3-(N-methylindolyl)methyl | H | (CH2)2COOEt | H | H | H | H |
| 1-6-106 | 3-benzothienylmethyl | H | Et | H | H | H | H |
| 1-6-107 | 3-benzothienylmethyl | Et | Et | H | H | H | H |
| 1-6-108 | 3-benzothienylmethyl | CH2C6H5 | CH2C6H5 | H | H | H | H |
| 1-6-109 | 3-benzothienylmethyl | H | CH2C6H5 | H | H | H | H |
| 1-6-110 | 3-benzothienylmethyl | (CH2)5CH3 | (CH2)5CH3 | H | H | H | H |

TABLE 1-6-continued
X = Single Bond, q = 0, r = 0, Y = —(R4)C=C(R5)—
| Compound No. | R1—(CH2)p— | R2 | R3 | R4 | R5 | R6 | R7 |
|---|---|---|---|---|---|---|---|
| 1-6-111 | 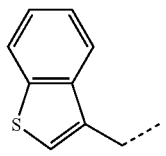 | H | (CH2)5CH3 | H | H | H | H |
| 1-6-112 | 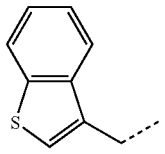 | (CH2)3C6H5 | (CH2)3C6H5 | H | H | H | H |
| 1-6-113 | 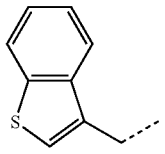 | H | (CH2)3C6H5 | H | H | H | H |
| 1-6-114 | 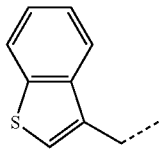 | H | CH2COOMe | H | H | H | H |
| 1-6-115 | 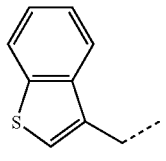 | H | (CH2)4COOEt | H | H | H | H |
| 1-6-116 | 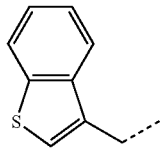 | H | (CH2)3NH2 | H | H | H | H |
| 1-6-117 | 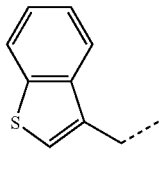 | H | (CH2)2CONH2 | H | H | H | H |
| 1-6-118 | 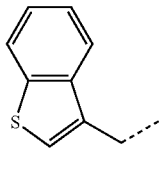 | H | (CH2)2COOH | H | H | H | H |
| 1-6-119 | 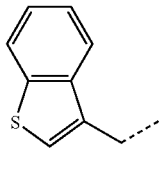 | H | (CH2)2CN | H | H | H | H |

TABLE 1-6-continued
| | X = Single Bond, q = 0, r = 0, Y = —(R4)C=C(R5)— | | | | | | |
|---|---|---|---|---|---|---|---|
| Compound No. | R1—(CH2)p— | R2 | R3 | R4 | R5 | R6 | R7 |
| 1-6-120 | 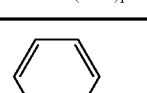 | H | (CH2)2COOEt | H | H | H | H |
TABLE 2
| | X = CO—, q = 0, r = 0, Y = (R4)C=(R5)— | | | | | | |
|---|---|---|---|---|---|---|---|
| Compound No. 2— | R1—(CH2)p— | R2 | R3 | R4 | R5 | R6 | R7 |
| 1 | 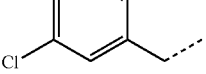 | H | H | H | H | H | H |
| 2 | 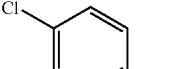 | H | H | H | Cl | H | H |
| 3 | 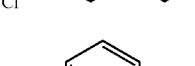 | H | H | H | H | H | H |
| 4 | 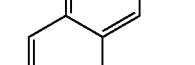 | H | H | H | Cl | H | H |
| 5 | 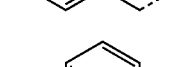 | H | H | H | H | H | H |
| 6 | 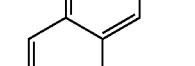 | H | H | H | H | H | H |
| 7 | 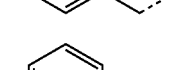 | H | H | H | H | H | H |
| 8 | 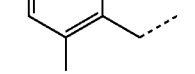 | H | H | H | H | H | H |

TABLE 2-continued
| | X = CO—, q = 0, r = 0, Y = (R4)C═(R5)— | | | | | | |
|---|---|---|---|---|---|---|---|
| Compound No. 2— | R1—(CH2)p— | R2 | R3 | R4 | R5 | R6 | R7 |
| 9 | 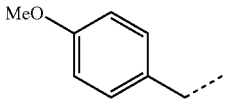 | H | H | H | H | H | H |
| 10 | 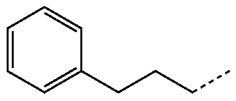 | H | H | H | H | H | H |
| 11 | 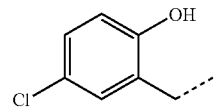 | H | H | H | H | H | H |
| 12 | 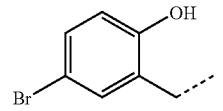 | H | H | H | H | H | H |
| 13 | 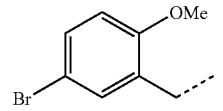 | H | H | H | H | H | H |
| 14 | 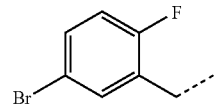 | H | H | H | H | H | H |
| 15 | 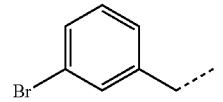 | H | H | H | H | H | H |
| 16 | 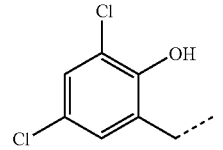 | H | H | H | H | H | H |
| 17 | 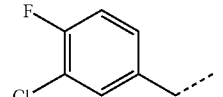 | H | H | H | H | H | H |
| 18 | 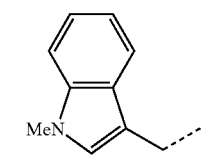 | H | H | H | H | H | H |
| 19 | 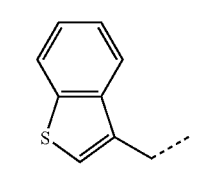 | H | H | H | H | H | H |

TABLE 2-continued
X = CO—, q = 0, r = 0, Y = (R4)C=(R5)—
| Compound No. 2— | R1—(CH2)p— | R2 | R3 | R4 | R5 | R6 | R7 |
|---|---|---|---|---|---|---|---|
| 20 | 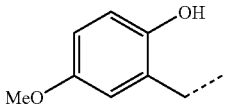 | H | H | H | H | H | H |
| 21 | 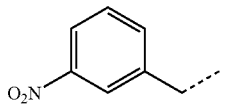 | H | H | H | H | H | H |
| 22 | 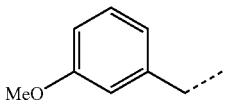 | H | H | H | H | H | H |
| 23 | 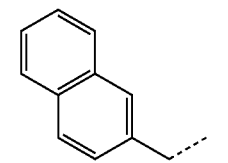 | H | H | H | H | H | H |
| 24 | 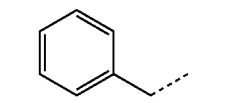 | H | H | H | H | H | H |
| 25 | 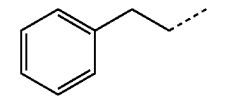 | H | H | H | H | H | H |
| 26 | 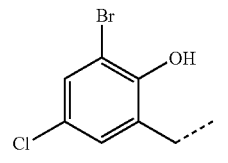 | H | H | H | H | H | H |
| 27 | 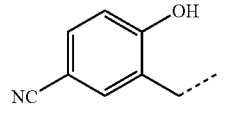 | H | H | H | H | H | H |
| 28 | 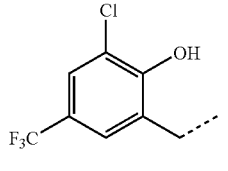 | H | H | H | H | H | H |
| 29 | 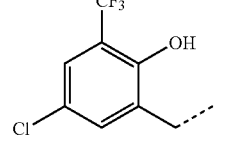 | H | H | H | H | H | H |
| 30 | 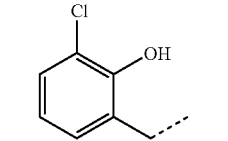 | H | H | H | H | H | H |

TABLE 2-continued

X = CO—, q = 0, r = 0, Y = (R4)C=(R5)—

| Compound No. 2— | R1—(CH2)p— | R2 | R3 | R4 | R5 | R6 | R7 |
|---|---|---|---|---|---|---|---|
| 31 | 4-methylbenzyl | H | H | H | H | H | H |
| 32 | 4-fluorobenzyl | H | H | H | H | H | H |
| 33 | 4-bromobenzyl | H | H | H | H | H | H |
| 34 | 4-trifluoromethylbenzyl | H | H | H | H | H | H |
| 35 | 4-hydroxybenzyl | H | H | H | H | H | H |
| 36 | 4-cyanobenzyl | H | H | H | H | H | H |
| 37 | 4-(methylsulfonyl)benzyl | H | H | H | H | H | H |
| 38 | 4-(methoxycarbonyl)benzyl | H | H | H | H | H | H |
| 39 | 4-(dimethylamino)benzyl | H | H | H | H | H | H |
| 40 | 4-methoxybenzyl | H | H | H | H | H | H |
| 41 | 4-ethoxybenzyl | H | H | H | H | H | H |
| 42 | 4-propoxybenzyl | H | H | H | H | H | H |

TABLE 2-continued
X = CO—, q = 0, r = 0, Y = (R4)C=(R5)—
| Compound No. 2— | R1—(CH2)p— | R2 | R3 | R4 | R5 | R6 | R7 |
|---|---|---|---|---|---|---|---|
| 43 | 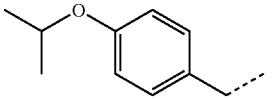 | H | H | H | H | H | H |
| 44 | 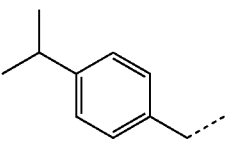 | H | H | H | H | H | H |
| 45 | 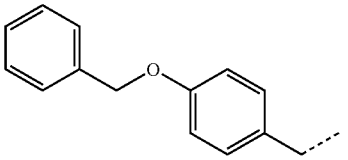 | H | H | H | H | H | H |
| 46 | 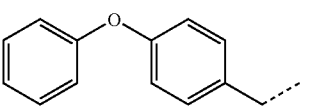 | H | H | H | H | H | H |
| 47 | 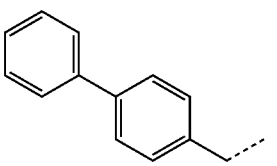 | H | H | H | H | H | H |
| 48 | 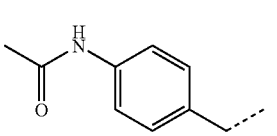 | H | H | H | H | H | H |
| 49 | 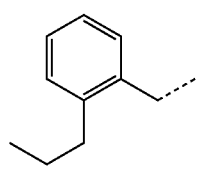 | H | H | H | H | H | H |
| 50 | 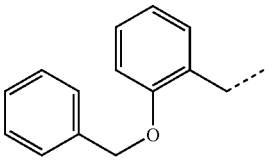 | H | H | H | H | H | H |
| 51 | 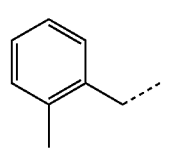 | H | H | H | H | H | H |
| 52 | 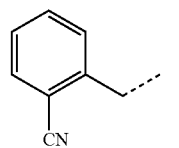 | H | H | H | H | H | H |

TABLE 2-continued
X = CO—, q = 0, r = 0, Y = (R4)C=(R5)—
| Compound No. 2— | R1—(CH2)p— | R2 | R3 | R4 | R5 | R6 | R7 |
|---|---|---|---|---|---|---|---|
| 53 | 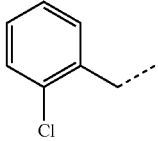 | H | H | H | H | H | H |
| 54 | 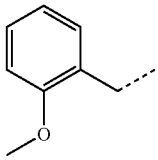 | H | H | H | H | H | H |
| 55 | 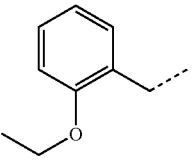 | H | H | H | H | H | H |
| 56 | 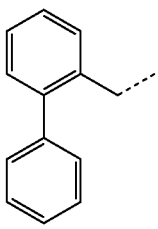 | H | H | H | H | H | H |
| 57 | 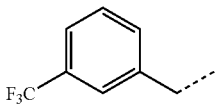 | H | H | H | H | H | H |
| 58 | 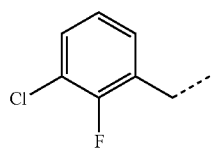 | H | H | H | H | H | H |
| 59 | 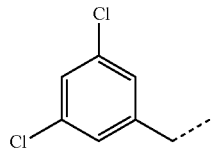 | H | H | H | H | H | H |
| 60 | 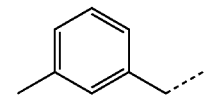 | H | H | H | H | H | H |
| 61 | 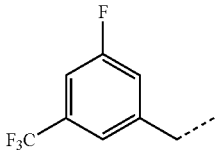 | H | H | H | H | H | H |

TABLE 2-continued

X = CO—, q = 0, r = 0, Y = (R4)C=(R5)—

| Compound No. 2— | R1—(CH2)p— | R2 | R3 | R4 | R5 | R6 | R7 |
|---|---|---|---|---|---|---|---|
| 62 | 3-(F₃CO)-C₆H₄-CH₂- | H | H | H | H | H | H |
| 63 | 2-F-5-MeO-C₆H₃-CH₂- | H | H | H | H | H | H |
| 64 | 2-F-5-(O₂N)-C₆H₃-CH₂- | H | H | H | H | H | H |
| 65 | 4-(O₂N)-C₆H₄-CH₂- | H | H | H | H | H | H |
| 66 | 3-F-2-Me-C₆H₃-CH₂- | H | H | H | H | H | H |
| 67 | 3-(F₃CS)-C₆H₄-CH₂- | H | H | H | H | H | H |
| 68 | 2,5-Cl₂-C₆H₃-CH₂- | H | H | H | H | H | H |
| 69 | 3-(F₂HC)-C₆H₄-CH₂- | H | H | H | H | H | H |
| 70 | 2-F-C₆H₄-CH₂- | H | H | H | H | H | H |
| 71 | 2-(NO₂)-C₆H₄-CH₂- | H | H | H | H | H | H |
| 72 | 2-(COOH)-C₆H₄-CH₂- | H | H | H | H | H | H |
| 73 | 2-OEt-4-Br-C₆H₃-CH₂- | H | H | H | H | H | H |

TABLE 2-continued

X = CO—, q = 0, r = 0, Y = (R4)C═(R5)—

| Compound No. 2— | R1—(CH2)p— | R2 | R3 | R4 | R5 | R6 | R7 |
|---|---|---|---|---|---|---|---|
| 74 | 2,3-dimethylphenyl-CH2- | H | H | H | H | H | H |
| 75 | 3-fluorophenyl-CH2- | H | H | H | H | H | H |
| 76 | 2,4-dichlorophenyl-CH2- | H | H | H | H | H | H |
| 77 | 3-cyanophenyl-CH2- | H | H | H | H | H | H |
| 78 | 3-hydroxyphenyl-CH2- | H | H | H | H | -H | H |
| 79 | 3-ethoxyphenyl-CH2- | H | H | H | H | H | H |
| 80 | 4-chloro-3-nitrophenyl-CH2- | H | H | H | H | H | H |
| 81 | 2,3-dichlorophenyl-CH2- | H | H | H | H | H | H |
| 82 | 2,3-difluoro-4-methylphenyl-CH2- | H | H | H | H | H | H |
| 83 | 3-bromo-4-fluorophenyl-CH2- | H | H | H | H | H | H |
| 84 | 2-fluoro-3-(trifluoromethyl)phenyl-CH2- | H | H | H | H | H | H |

TABLE 2-continued
X = CO—, q = 0, r = 0, Y = (R4)C=(R5)—
| Compound No. 2— | R1—(CH2)p— | R2 | R3 | R4 | R5 | R6 | R7 |
|---|---|---|---|---|---|---|---|
| 85 | 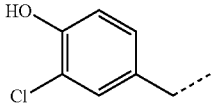 | H | H | H | H | H | H |
| 86 | 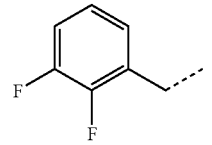 | H | H | H | H | H | H |
| 87 | 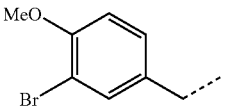 | H | H | H | H | H | H |
| 88 | 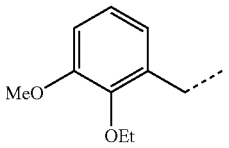 | H | H | H | H | H | H |
| 89 | 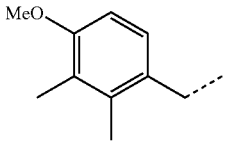 | H | H | H | H | H | H |
| 90 | 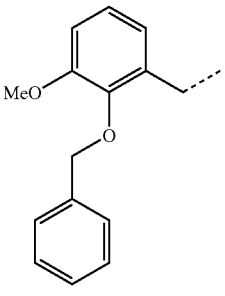 | H | H | H | H | H | H |
| 91 | 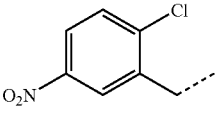 | H | H | H | H | H | H |
| 92 | 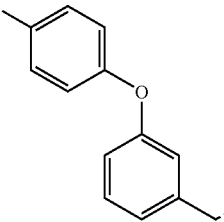 | H | H | H | H | H | H |

TABLE 2-continued

X = CO—, q = 0, r = 0, Y = (R4)C=(R5)—

| Compound No. 2— | R1—(CH2)p— | R2 | R3 | R4 | R5 | R6 | R7 |
|---|---|---|---|---|---|---|---|
| 93 | 4-methylphenoxy-3-phenyl- | H | H | H | H | H | H |
| 94 | 4-chlorophenoxy-3-phenyl- | H | H | H | H | H | H |
| 95 | 3-(benzyloxy)phenyl- | H | H | H | H | H | H |
| 96 | 3-phenoxyphenyl- | H | H | H | H | H | H |
| 97 | 4-methoxy-3-hydroxyphenyl- | H | H | H | H | H | H |
| 98 | 2-chloro-3-(trifluoromethyl)phenyl- | H | H | H | H | H | H |
| 99 | 4-hydroxy-3-nitrophenyl- | H | H | H | H | H | H |
| 100 | 2,3-dimethoxyphenyl- | H | H | H | H | H | H |
| 101 | 2,4-diethoxy-3-methylphenyl- | H | H | H | H | H | H |

TABLE 2-continued

X = CO—, q = 0, r = 0, Y = (R4)C=(R5)—

| Compound No. 2— | R1—(CH2)p— | R2 | R3 | R4 | R5 | R6 | R7 |
|---|---|---|---|---|---|---|---|
| 102 | 3-(2-hydroxyethoxy)benzyl | H | H | H | H | H | H |
| 103 | 2,3,4-trimethoxybenzyl | H | H | H | H | H | H |
| 104 | 4-fluoro-3-phenoxybenzyl | H | H | H | H | H | H |
| 105 | 2-carboxy-3,4-dimethoxybenzyl (OMe, MeO, COOH) | H | H | H | H | H | H |
| 106 | 5-chloro-2-nitrobenzyl | H | H | H | H | H | H |
| 107 | 3,5-dihydroxybenzyl | H | H | H | H | H | H |
| 108 | 3-benzyloxy-4-methoxybenzyl | H | H | H | H | H | H |
| 109 | 3,4-diethoxybenzyl | H | H | H | H | H | H |
| 110 | 3-carboxybenzyl | H | H | H | H | H | H |
| 111 | 3-hydroxy-4-methoxybenzyl | H | H | H | H | H | H |
| 112 | 3-hydroxy-4-nitrobenzyl | H | H | H | H | H | H |

TABLE 2-continued

| | X = CO—, q = 0, r = 0, Y = (R4)C═(R5)— | | | | | | |
|---|---|---|---|---|---|---|---|
| Compound No. 2— | R1—(CH2)p— | R2 | R3 | R4 | R5 | R6 | R7 |
| 113 | 3,5-bis(CF3)-benzyl | H | H | H | H | H | H |
| 114 | 2-OMe-3-NO2-benzyl | H | H | H | H | H | H |
| 115 | (4-methylnaphthalen-1-yl)methyl | H | H | H | H | H | H |
| 116 | (7-methyl-1-methyl-1H-indol-3-yl)methyl | H | H | H | H | H | H |
| 117 | (2-methoxynaphthalen-1-yl)methyl | H | H | H | H | H | H |
| 118 | benzofuran-2-ylmethyl | H | H | H | H | H | H |
| 119 | (1,2-dimethyl-1H-indol-3-yl)methyl | H | H | H | H | H | H |
| 120 | quinolin-8-ylmethyl | H | H | H | H | H | H |

TABLE 2-continued

| | X = CO—, q = 0, r = 0, Y = (R4)C═(R5)— | | | | | | |
|---|---|---|---|---|---|---|---|
| Compound No. 2— | R1—(CH2)p— | R2 | R3 | R4 | R5 | R6 | R7 |
| 121 | (2-hydroxynaphthalen-1-yl)methyl | H | H | H | H | H | H |
| 122 | (2-acetoxynaphthalen-1-yl)methyl | H | H | H | H | H | H |
| 123 | (1-hydroxynaphthalen-2-yl)methyl | H | H | H | H | H | H |
| 124 | (1H-indol-7-yl)methyl | H | H | H | H | H | H |
| 125 | (quinolin-4-yl)methyl | H | H | H | H | H | H |
| 126 | (1,5-dimethyl-1H-indol-3-yl)methyl | H | H | H | H | H | H |
| 127 | (anthracen-9-yl)methyl | H | H | H | H | H | H |

TABLE 2-continued
X = CO—, q = 0, r = 0, Y = (R4)C=(R5)—
| Compound No. 2— | R1—(CH2)p— | R2 | R3 | R4 | R5 | R6 | R7 |
|---|---|---|---|---|---|---|---|
| 128 | 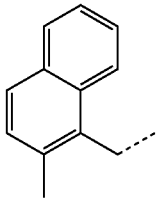 | H | H | H | H | H | H |
| 129 | 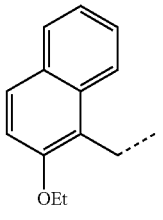 | H | H | H | H | H | H |
| 130 | 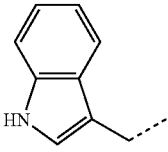 | H | H | H | H | H | H |
| 131 | 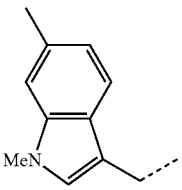 | H | H | H | H | H | H |
| 132 | 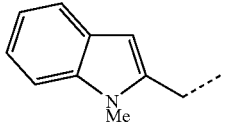 | H | H | H | H | H | H |
| 133 | 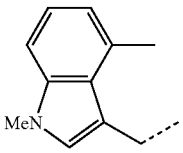 | H | H | H | H | H | H |
| 134 | 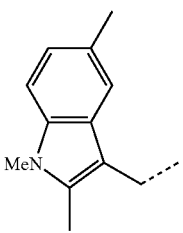 | H | H | H | H | H | H |
| 135 | 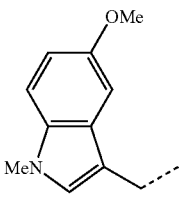 | H | H | H | H | H | H |

TABLE 2-continued

| | X = CO—, q = 0, r = 0, Y = (R4)C═(R5)— | | | | | | |
|---|---|---|---|---|---|---|---|
| Compound No. 2— | R1—(CH2)p— | R2 | R3 | R4 | R5 | R6 | R7 |
| 136 | 4-methylbenzothiophen-3-yl | H | H | H | H | H | H |
| 137 | 1-methylbenzimidazol-2-yl | H | H | H | H | H | H |
| 138 | 1-methyl-2-phenylindol-3-yl | H | H | H | H | H | H |
| 139 | 1-acetylindol-3-yl | H | H | H | H | H | H |
| 140 | quinolin-2-yl | H | H | H | H | H | H |
| 141 | 6-methoxy-1-methylindol-3-yl | H | H | H | H | H | H |
| 142 | 3-methylbenzothiophen-2-yl | H | H | H | H | H | H |
| 143 | 4-methoxynaphth-1-yl | H | H | H | H | H | H |

TABLE 2-continued
X = CO—, q = 0, r = 0, Y = (R4)C=(R5)—
| Compound No. 2— | R1—(CH2)p— | R2 | R3 | R4 | R5 | R6 | R7 |
|---|---|---|---|---|---|---|---|
| 144 | 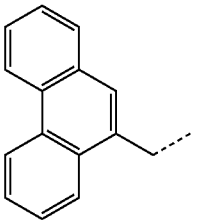 | H | H | H | H | H | H |
| 145 | 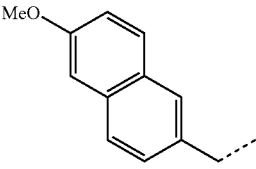 | H | H | H | H | H | H |
| 146 | 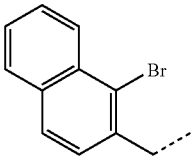 | H | H | H | H | H | H |
| 147 | 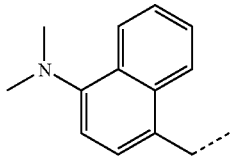 | H | H | H | H | H | H |
| 148 | 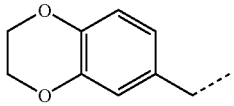 | H | H | H | H | H | H |
| 149 | 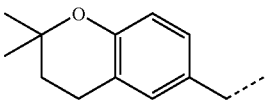 | H | H | H | H | H | H |
| 150 | 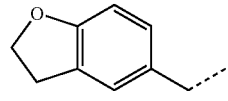 | H | H | H | H | H | H |
| 151 | 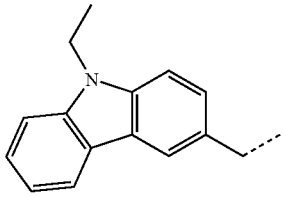 | H | H | H | H | H | H |
| 152 | 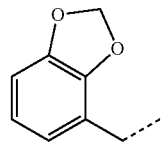 | H | H | H | H | H | H |

TABLE 2-continued
X = CO—, q = 0, r = 0, Y = (R4)C═(R5)—
| Compound No. 2— | R1—(CH2)p— | R2 | R3 | R4 | R5 | R6 | R7 |
|---|---|---|---|---|---|---|---|
| 153 | 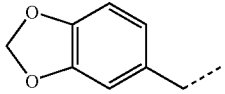 | H | H | H | H | H | H |
| 154 | 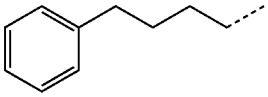 | H | H | H | H | H | H |
| 155 | 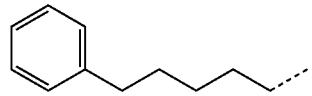 | H | H | H | H | H | H |
| 156 | 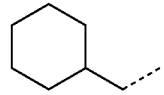 | H | H | H | H | H | H |
| 157 | 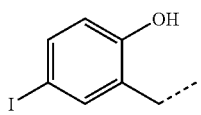 | H | H | H | H | H | H |
| 158 | 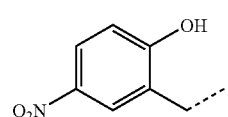 | H | H | H | H | H | H |
| 159 | 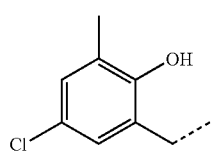 | H | H | H | H | H | H |
| 160 | 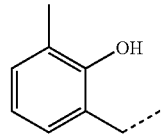 | H | H | H | H | H | H |
| 161 | 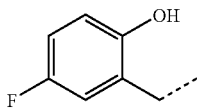 | H | H | H | H | H | H |
| 162 | 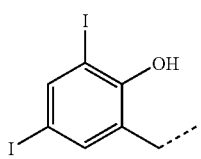 | H | H | H | H | H | H |
| 163 | 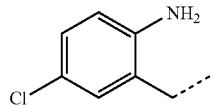 | H | H | H | H | H | H |
| 164 | 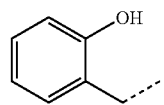 | H | H | H | H | H | H |

TABLE 2-continued

X = CO—, q = 0, r = 0, Y = (R4)C═(R5)—

| Compound No. 2— | R1—(CH2)p— | R2 | R3 | R4 | R5 | R6 | R7 |
|---|---|---|---|---|---|---|---|
| 165 | 2-aminobenzyl | H | H | H | H | H | H |
| 166 | 4-tert-butyl-2-hydroxybenzyl | H | H | H | H | H | H |
| 167 | 4-trifluoromethoxy-2-hydroxybenzyl | H | H | H | H | H | H |
| 168 | 3-methoxy-2-hydroxybenzyl | H | H | H | H | H | H |
| 169 | 2,3-dihydroxybenzyl | H | H | H | H | H | H |
| 170 | 3-ethoxy-2-hydroxybenzyl | H | H | H | H | H | H |
| 171 | 3-carboxy-2-hydroxybenzyl | H | H | H | H | H | H |
| 172 | 3-tert-butyl-2-hydroxybenzyl | H | H | H | H | H | H |
| 173 | furan-2-ylmethyl | H | H | H | H | H | H |
| 174 | oxazol-2-ylmethyl | H | H | H | H | H | H |

TABLE 2-continued
X = CO—, q = 0, r = 0, Y = (R4)C=(R5)—
| Compound No. 2— | R1—(CH2)p— | R2 | R3 | R4 | R5 | R6 | R7 |
|---|---|---|---|---|---|---|---|
| 175 | 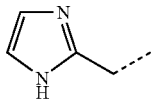 | H | H | H | H | H | H |
| 176 | 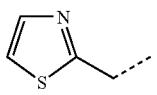 | H | H | H | H | H | H |
| 177 | 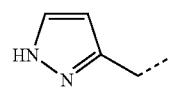 | H | H | H | H | H | H |
| 178 | 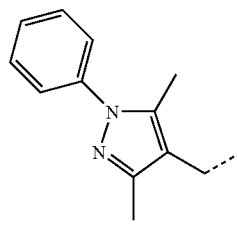 | H | H | H | H | H | H |
| 179 | 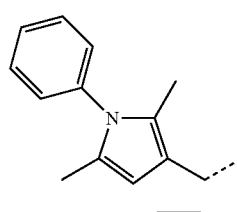 | H | H | H | H | H | H |
| 180 | 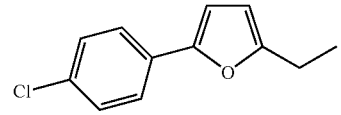 | H | H | H | H | H | H |
| 181 | 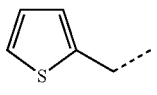 | H | H | H | H | H | H |
| 182 | 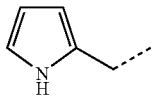 | H | H | H | H | H | H |
| 183 | 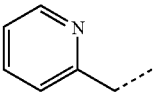 | H | H | H | H | H | H |
| 184 | 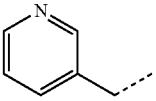 | H | H | H | H | H | H |
| 185 | 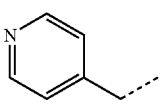 | H | H | H | H | H | H |
| 186 | 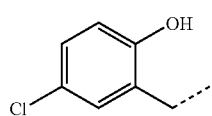 | H | H | H | Cl | H | H |

TABLE 2-continued

X = CO—, q = 0, r = 0, Y = (R4)C=(R5)—

| Compound No. 2— | R1—(CH2)p— | R2 | R3 | R4 | R5 | R6 | R7 |
|---|---|---|---|---|---|---|---|
| 187 | 2-hydroxy-5-nitrobenzyl | H | H | H | Cl | H | H |
| 188 | 2-hydroxy-5-methoxybenzyl | H | H | H | Cl | H | H |
| 189 | 3-chlorobenzyl | H | H | H | Cl | H | H |
| 190 | 3-bromobenzyl | H | H | H | Cl | H | H |
| 191 | 3-nitrobenzyl | H | H | H | Cl | H | H |
| 192 | 3-methoxybenzyl | H | H | H | Cl | H | H |
| 193 | 3,5-dichloro-2-hydroxybenzyl | H | H | H | Cl | H | H |
| 194 | (1-methylindol-3-yl)methyl | H | H | H | Cl | H | H |
| 195 | (benzothiophen-3-yl)methyl | H | H | H | Cl | H | H |
| 196 | benzyl | H | H | H | Cl | H | H |
| 197 | 3-phenylpropyl | H | H | H | Cl | H | H |

TABLE 2-continued

| | X = CO—, q = 0, r = 0, Y = (R4)C═(R5)— | | | | | | |
|---|---|---|---|---|---|---|---|
| Compound No. 2— | R1—(CH2)p— | R2 | R3 | R4 | R5 | R6 | R7 |
| 198 | 4-bromo-2-hydroxyphenyl-CH2 | H | H | H | Cl | H | H |
| 199 | naphthalen-2-yl-CH2 | H | H | H | Cl | H | H |
| 200 | phenyl-CH2CH2 | H | H | H | Cl | H | H |
| 201 | 3,5-dichloro-2-hydroxyphenyl-CH2 | H | H | Cl | H | H | H |
| 202 | 3,5-dichloro-2-hydroxyphenyl-CH2 | H | H | H | OMe | H | H |
| 203 | 3,5-dichloro-2-hydroxyphenyl-CH2 | H | H | H | COOMe | H | H |
| 204 | 3,5-dichloro-2-hydroxyphenyl-CH2 | H | H | H | H | Cl | H |
| 205 | 3,5-dichloro-2-hydroxyphenyl-CH2 | H | H | H | H | COOMe | H |
| 206 | 3,5-dichloro-2-hydroxyphenyl-CH2 | H | H | H | H | H | Cl |
| 207 | 3,5-dichloro-2-hydroxyphenyl-CH2 | H | H | H | OCF3 | H | H |

TABLE 2-continued
X = CO—, q = 0, r = 0, Y = (R4)C=(R5)—
| Compound No. 2— | R1—(CH2)p— | R2 | R3 | R4 | R5 | R6 | R7 |
|---|---|---|---|---|---|---|---|
| 208 | 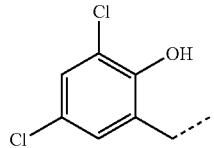 | H | H | COOMe | H | H | H |
| 209 | 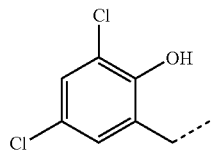 | H | H | H | CF3 | H | H |
| 210 | 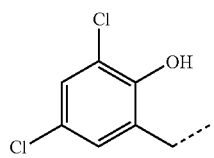 | H | H | H | Me | H | H |
| 211 | 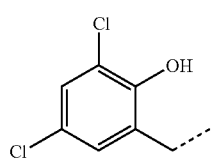 | H | H | H | F | H | H |
| 212 | 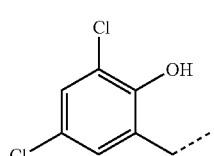 | H | H | H | OH | H | H |
| 213 | 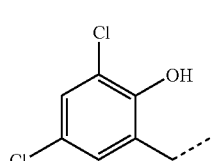 | H | H | H | NO2 | H | H |
| 214 | 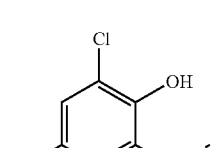 | H | H | H | F | F | H |
| 215 | 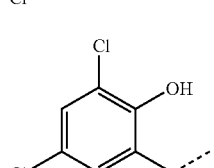 | H | H | F | H | H | H |
| 216 | 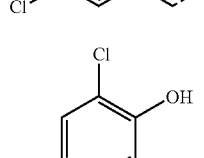 | H | H | Me | H | H | H |

TABLE 2-continued
X = CO—, q = 0, r = 0, Y = (R4)C=(R5)—
| Compound No. 2— | R1—(CH2)p— | R2 | R3 | R4 | R5 | R6 | R7 |
|---|---|---|---|---|---|---|---|
| 217 | 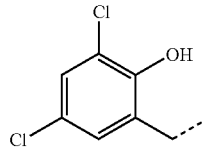 | H | H | H | CN | H | H |
| 218 | 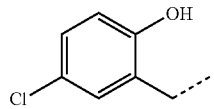 | H | H | Cl | H | H | H |
| 219 | 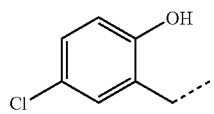 | H | H | H | OMe | H | H |
| 220 | 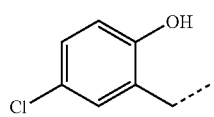 | H | H | H | COOMe | H | H |
| 221 | 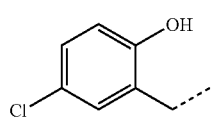 | H | H | H | H | Cl | H |
| 222 | 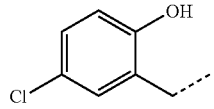 | H | H | H | H | COOMe | H |
| 223 | 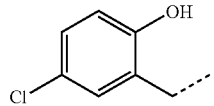 | H | H | H | H | H | Cl |
| 224 | 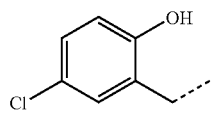 | H | H | H | OCF3 | H | H |
| 225 | 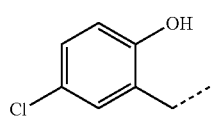 | H | H | COOMe | H | H | H |
| 226 | 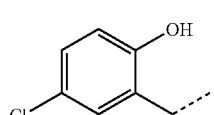 | H | H | H | CF3 | H | H |
| 227 | 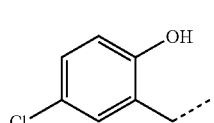 | H | H | H | Me | H | H |
| 228 | 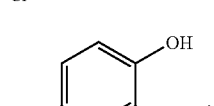 | H | H | H | F | H | H |

TABLE 2-continued

X = CO—, q = 0, r = 0, Y = (R4)C═(R5)—

| Compound No. 2— | R1—(CH2)p— | R2 | R3 | R4 | R5 | R6 | R7 |
|---|---|---|---|---|---|---|---|
| 229 | naphthyl-CH2 | H | H | Cl | H | H | H |
| 230 | naphthyl-CH2 | H | H | H | OMe | H | H |
| 231 | naphthyl-CH2 | H | H | H | COOMe | H | H |
| 232 | naphthyl-CH2 | H | H | H | H | Cl | H |
| 233 | naphthyl-CH2 | H | H | H | H | COOMe | H |
| 234 | naphthyl-CH2 | H | H | H | H | H | Cl |
| 235 | naphthyl-CH2 | H | H | H | OCF3 | H | H |
| 236 | naphthyl-CH2 | H | H | COOMe | H | H | H |

TABLE 2-continued

X = CO—, q = 0, r = 0, Y = (R4)C═(R5)—

| Compound No. 2— | R1—(CH2)p— | R2 | R3 | R4 | R5 | R6 | R7 |
|---|---|---|---|---|---|---|---|
| 237 | naphthyl-CH2 | H | H | H | CF3 | H | H |
| 238 | naphthyl-CH2 | H | H | H | Me | H | H |
| 239 | naphthyl-CH2 | H | H | H | F | H | H |
| 240 | phenyl-(CH2)2 | H | H | Cl | H | H | H |
| 241 | phenyl-(CH2)2 | H | H | H | OMe | H | H |
| 242 | phenyl-(CH2)2 | H | H | H | COOMe | H | H |
| 243 | phenyl-(CH2)2 | H | H | H | H | Cl | H |
| 244 | phenyl-(CH2)2 | H | H | H | H | COOMe | H |
| 245 | phenyl-(CH2)2 | H | H | H | H | H | Cl |
| 246 | phenyl-(CH2)2 | H | H | H | OCF3 | H | H |
| 247 | phenyl-(CH2)2 | H | H | COOMe | H | H | H |
| 248 | phenyl-(CH2)2 | H | H | H | CF3 | H | H |

TABLE 2-continued

| | X = CO—, q = 0, r = 0, Y = (R4)C═(R5)— | | | | | | |
|---|---|---|---|---|---|---|---|
| Compound No. 2— | R1—(CH2)p— | R2 | R3 | R4 | R5 | R6 | R7 |
| 249 | PhCH2CH2— | H | H | H | Me | H | H |
| 250 | PhCH2CH2— | H | H | H | F | H | H |
| 251 | 3,5-dichloro-2-hydroxybenzyl | H | H | H | H | H | COOMe |
| 252 | 3,5-dichloro-2-hydroxybenzyl | H | H | H | H | F | H |
| 253 | 3,5-dichloro-2-hydroxybenzyl | H | H | H | H | H | F |
| 254 | 3,5-dichloro-2-hydroxybenzyl | H | H | H | H | Me | H |
| 255 | 3,5-dichloro-2-hydroxybenzyl | H | H | H | H | H | Me |
| 256 | 3,5-dichloro-2-hydroxybenzyl | H | H | OMe | H | H | H |
| 257 | 3,5-dichloro-2-hydroxybenzyl | H | H | H | H | OMe | H |
| 258 | 3,5-dichloro-2-hydroxybenzyl | H | H | H | H | H | OMe |

TABLE 2-continued

| | X = CO—, q = 0, r = 0, Y = (R4)C═(R5)— | | | | | | |
|---|---|---|---|---|---|---|---|
| Compound No. 2— | R1—(CH2)p— | R2 | R3 | R4 | R5 | R6 | R7 |
| 259 | 2,4-dichloro-6-hydroxybenzyl | H | H | CF3 | H | H | H |
| 260 | 2,4-dichloro-6-hydroxybenzyl | H | H | H | H | CF3 | H |
| 261 | 2,4-dichloro-6-hydroxybenzyl | H | H | H | H | H | CF3 |
| 262 | 2,4-dichloro-6-hydroxybenzyl | H | H | OH | H | H | H |
| 263 | 2,4-dichloro-6-hydroxybenzyl | H | H | H | H | OH | H |
| 264 | 2,4-dichloro-6-hydroxybenzyl | H | H | H | H | H | OH |
| 265 | 2,4-dichloro-6-hydroxybenzyl | H | H | OCF3 | H | H | H |
| 266 | 2,4-dichloro-6-hydroxybenzyl | H | H | H | H | OCF3 | H |
| 267 | 2,4-dichloro-6-hydroxybenzyl | H | H | H | H | H | OCF3 |

TABLE 2-continued

| | X = CO—, q = 0, r = 0, Y = (R4)C═(R5)— | | | | | | |
|---|---|---|---|---|---|---|---|
| Compound No. 2— | R1—(CH2)p— | R2 | R3 | R4 | R5 | R6 | R7 |
| 268 | 2,4-dichloro-6-hydroxybenzyl | H | H | NO2 | H | H | H |
| 269 | 2,4-dichloro-6-hydroxybenzyl | H | H | H | H | NO2 | H |
| 270 | 2,4-dichloro-6-hydroxybenzyl | H | H | H | H | H | NO2 |
| 271 | 2,4-dichloro-6-hydroxybenzyl | H | H | CN | H | H | H |
| 272 | 2,4-dichloro-6-hydroxybenzyl | H | H | H | H | CN | H |
| 273 | 2,4-dichloro-6-hydroxybenzyl | H | H | H | H | H | CN |
| 274 | 2,4-dichloro-6-hydroxybenzyl | H | H | Br | H | H | H |
| 275 | 2,4-dichloro-6-hydroxybenzyl | H | H | H | Br | H | H |
| 276 | 2,4-dichloro-6-hydroxybenzyl | H | H | H | H | Br | H |

TABLE 2-continued

| | X = CO—, q = 0, r = 0, Y = (R4)C=(R5)— | | | | | | |
|---|---|---|---|---|---|---|---|
| Compound No. 2— | R1—(CH2)p— | R2 | R3 | R4 | R5 | R6 | R7 |
| 277 | 2,4-dichloro-6-hydroxybenzyl | H | H | H | H | H | Br |
| 278 | 2,4-dichloro-6-hydroxybenzyl | H | H | COOH | H | H | H |
| 279 | 2,4-dichloro-6-hydroxybenzyl | H | H | H | COOH | H | H |
| 280 | 2,4-dichloro-6-hydroxybenzyl | H | H | H | H | COOH | H |
| 281 | 2,4-dichloro-6-hydroxybenzyl | H | H | H | H | H | COOH |
| 282 | 2,4-dichloro-6-hydroxybenzyl | H | H | NHCOMe | H | H | H |
| 283 | 2,4-dichloro-6-hydroxybenzyl | H | H | H | NHCOMe | H | H |
| 284 | 2,4-dichloro-6-hydroxybenzyl | H | H | H | H | NHCOMe | H |
| 285 | 2,4-dichloro-6-hydroxybenzyl | H | H | H | H | H | NHCOMe |

TABLE 2-continued
| | X = CO—, q = 0, r = 0, Y = (R4)C═(R5)— | | | | | | |
|---|---|---|---|---|---|---|---|
| Compound No. 2— | R1—(CH2)p— | R2 | R3 | R4 | R5 | R6 | R7 |
| 286 | 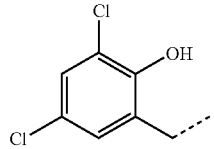 | H | H | SO2NH2 | H | H | H |
| 287 | 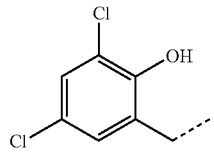 | H | H | H | SO2NH2 | H | H |
| 288 | 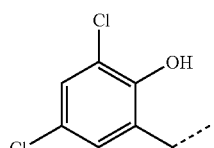 | H | H | H | H | SO2NH2 | H |
| 289 | 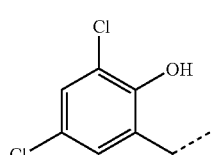 | H | H | H | H | H | SO2NH2 |
| 290 | 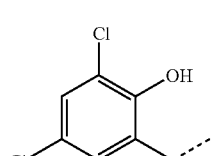 | H | H | Me | Me | H | H |
| 291 | 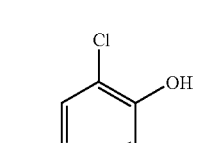 | H | H | Me | H | Me | H |
| 292 | 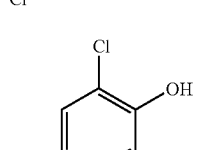 | H | H | H | Me | Me | H |
| 293 | 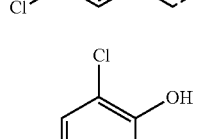 | H | H | F | F | H | H |
| 294 | 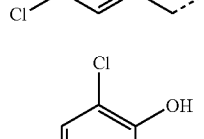 | H | H | F | H | F | H |

TABLE 2-continued

| | X = CO—, q = 0, r = 0, Y = (R4)C=(R5)— | | | | | | |
|---|---|---|---|---|---|---|---|
| Compound No. 2— | R1—(CH2)p— | R2 | R3 | R4 | R5 | R6 | R7 |
| 295 | 2,4-dichloro-6-hydroxybenzyl | H | H | H | F | F | H |
| 296 | 2,4-dichloro-6-hydroxybenzyl | H | H | Cl | Cl | H | H |
| 297 | 2,4-dichloro-6-hydroxybenzyl | H | H | Cl | H | Cl | H |
| 298 | 2,4-dichloro-6-hydroxybenzyl | H | H | H | Cl | Cl | H |
| 299 | 2,4-dichloro-6-hydroxybenzyl | H | H | Me | F | H | H |
| 300 | 2,4-dichloro-6-hydroxybenzyl | H | H | Me | Cl | H | H |
| 301 | 2,4-dichloro-6-hydroxybenzyl | H | H | Me | OH | H | H |
| 302 | 2,4-dichloro-6-hydroxybenzyl | H | H | Me | OMe | H | H |
| 303 | 2,4-dichloro-6-hydroxybenzyl | H | H | F | Me | H | H |

TABLE 2-continued
| | X = CO—, q = 0, r = 0, Y = (R4)C═(R5)— | | | | | | |
|---|---|---|---|---|---|---|---|
| Compound No. 2— | R1—(CH2)p— | R2 | R3 | R4 | R5 | R6 | R7 |
| 304 | 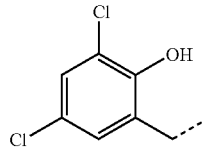 | H | H | F | Cl | H | H |
| 305 | 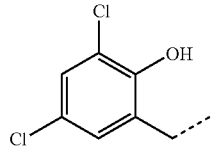 | H | H | F | OH | H | H |
| 306 | 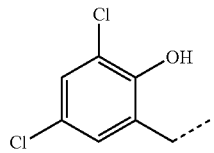 | H | H | F | OMe | H | H |
| 307 | 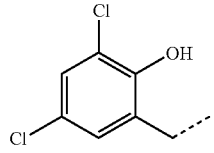 | H | H | Cl | Me | H | H |
| 308 | 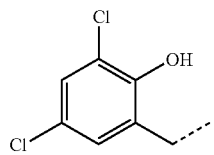 | H | H | Cl | F | H | H |
| 309 | 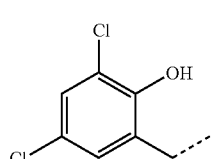 | H | H | Cl | OH | H | H |
| 310 | 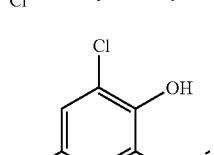 | H | H | Cl | OMe | H | H |
| 311 | 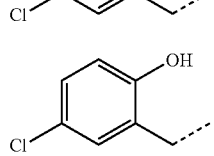 | H | H | H | H | H | COOMe |
| 312 | 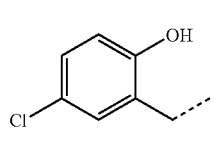 | H | H | F | H | H | H |
| 313 | 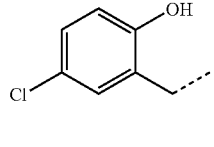 | H | H | H | H | F | H |

TABLE 2-continued

X = CO—, q = 0, r = 0, Y = (R4)C=(R5)—

| Compound No. 2— | R1—(CH2)p— | R2 | R3 | R4 | R5 | R6 | R7 |
|---|---|---|---|---|---|---|---|
| 314 | 4-Cl-2-(CH2)-phenol | H | H | H | H | H | F |
| 315 | 4-Cl-2-(CH2)-phenol | H | H | Me | H | H | H |
| 316 | 4-Cl-2-(CH2)-phenol | H | H | H | H | Me | H |
| 317 | 4-Cl-2-(CH2)-phenol | H | H | H | H | H | Me |
| 318 | 4-Cl-2-(CH2)-phenol | H | H | OMe | H | H | H |
| 319 | 4-Cl-2-(CH2)-phenol | H | H | H | H | OMe | H |
| 320 | 4-Cl-2-(CH2)-phenol | H | H | H | H | H | OMe |
| 321 | 4-Cl-2-(CH2)-phenol | H | H | CF3 | H | H | H |
| 322 | 4-Cl-2-(CH2)-phenol | H | H | H | H | CF3 | H |
| 323 | 4-Cl-2-(CH2)-phenol | H | H | H | H | H | CF3 |
| 324 | 4-Cl-2-(CH2)-phenol | H | H | OH | H | H | H |
| 325 | 4-Cl-2-(CH2)-phenol | H | H | H | OH | H | H |

TABLE 2-continued

| | X = CO—, q = 0, r = 0, Y = (R4)C=(R5)— | | | | | | |
|---|---|---|---|---|---|---|---|
| Compound No. 2— | R1—(CH2)p— | R2 | R3 | R4 | R5 | R6 | R7 |
| 326 | 4-Cl-2-OH-C6H3-CH2- | H | H | H | H | OH | H |
| 327 | 4-Cl-2-OH-C6H3-CH2- | H | H | H | H | H | OH |
| 328 | 4-Cl-2-OH-C6H3-CH2- | H | H | OCF3 | H | H | H |
| 329 | 4-Cl-2-OH-C6H3-CH2- | H | H | H | H | OCF3 | H |
| 330 | 4-Cl-2-OH-C6H3-CH2- | H | H | H | H | H | OCF3 |
| 331 | 4-Cl-2-OH-C6H3-CH2- | H | H | NO2 | H | H | H |
| 332 | 4-Cl-2-OH-C6H3-CH2- | H | H | H | NO2 | H | H |
| 333 | 4-Cl-2-OH-C6H3-CH2- | H | H | H | H | NO2 | H |
| 334 | 4-Cl-2-OH-C6H3-CH2- | H | H | H | H | H | NO2 |
| 335 | 4-Cl-2-OH-C6H3-CH2- | H | H | CN | H | H | H |
| 336 | 4-Cl-2-OH-C6H3-CH2- | H | H | H | CN | H | H |
| 337 | 4-Cl-2-OH-C6H3-CH2- | H | H | H | H | CN | H |

TABLE 2-continued
| | X = CO—, q = 0, r = 0, Y = (R4)C═(R5)— | | | | | | |
|---|---|---|---|---|---|---|---|
| Compound No. 2— | R1—(CH2)p— | R2 | R3 | R4 | R5 | R6 | R7 |
| 338 | 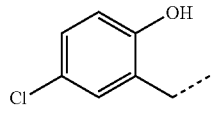 | H | H | H | H | H | CN |
| 339 | 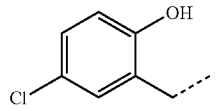 | H | H | Br | H | H | H |
| 340 | 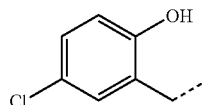 | H | H | H | Br | H | H |
| 341 | 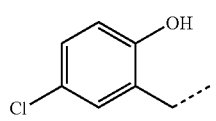 | H | H | H | H | Br | H |
| 342 | 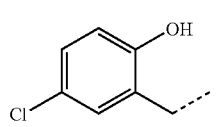 | H | H | H | H | H | Br |
| 343 | 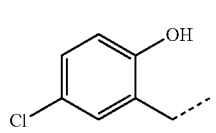 | H | H | COOH | H | H | H |
| 344 | 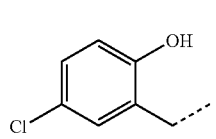 | H | H | H | COOH | H | H |
| 345 |  | H | H | H | H | COOH | H |
| 346 |  | H | H | H | H | H | COOH |
| 347 | 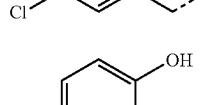 | H | H | NHCOMe | H | H | H |
| 348 |  | H | H | H | NHCOMe | H | H |
| 349 |  | H | H | H | H | NHOOMe | H |

TABLE 2-continued
| | X = CO—, q = 0, r = 0, Y = (R4)C=(R5)— | | | | | | |
|---|---|---|---|---|---|---|---|
| Compound No. 2— | R1—(CH2)p— | R2 | R3 | R4 | R5 | R6 | R7 |
| 350 | 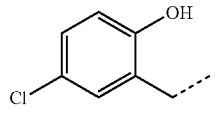 | H | H | H | H | H | NHCOMe |
| 351 | 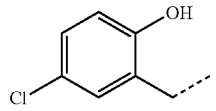 | H | H | SO2NH2 | H | H | H |
| 352 | 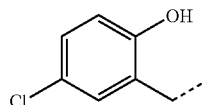 | H | H | H | SO2NH2 | H | H |
| 353 | 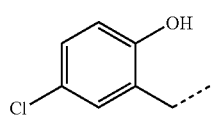 | H | H | H | H | SO2NH2 | H |
| 354 | 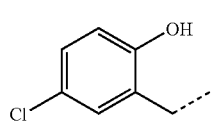 | H | H | H | H | H | SO2NH2 |
| 355 | 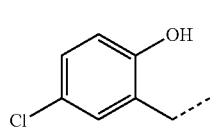 | H | H | Me | Me | H | H |
| 356 | 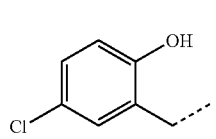 | H | H | Me | H | Me | H |
| 357 |  | H | H | H | Me | Me | H |
| 358 |  | H | H | F | F | H | H |
| 359 | 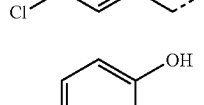 | H | H | F | H | F | H |
| 360 |  | H | H | H | F | F | H |
| 361 | 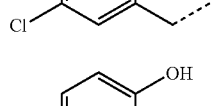 | H | H | Cl | Cl | H | H |

TABLE 2-continued

X = CO—, q = 0, r = 0, Y = (R4)C═(R5)—

| Compound No. 2— | R1—(CH2)p— | R2 | R3 | R4 | R5 | R6 | R7 |
|---|---|---|---|---|---|---|---|
| 362 | 4-Cl-2-OH-C6H3-CH2- | H | H | Cl | H | Cl | H |
| 363 | 4-Cl-2-OH-C6H3-CH2- | H | H | H | Cl | Cl | H |
| 364 | 4-Cl-2-OH-C6H3-CH2- | H | H | Me | F | H | H |
| 365 | 4-Cl-2-OH-C6H3-CH2- | H | H | Me | Cl | H | H |
| 366 | 4-Cl-2-OH-C6H3-CH2- | H | H | Me | OH | H | H |
| 367 | 4-Cl-2-OH-C6H3-CH2- | H | H | Me | OMe | H | H |
| 368 | 4-Cl-2-OH-C6H3-CH2- | H | H | F | Me | H | H |
| 369 | 4-Cl-2-OH-C6H3-CH2- | H | H | F | Cl | H | H |
| 370 | 4-Cl-2-OH-C6H3-CH2- | H | H | F | OH | H | H |
| 371 | 4-Cl-2-OH-C6H3-CH2- | H | H | F | OMe | H | H |
| 372 | 4-Cl-2-OH-C6H3-CH2- | H | H | Cl | Me | H | H |
| 373 | 4-Cl-2-OH-C6H3-CH2- | H | H | Cl | F | H | H |

TABLE 2-continued

X = CO—, q = 0, r = 0, Y = (R4)C=(R5)—

| Compound No. 2— | R1—(CH2)p— | R2 | R3 | R4 | R5 | R6 | R7 |
|---|---|---|---|---|---|---|---|
| 374 | 4-Cl-2-(CH2)-phenol | H | H | Cl | OH | H | H |
| 375 | 4-Cl-2-(CH2)-phenol | H | H | Cl | OMe | H | H |
| 376 | 1-naphthylmethyl | H | H | H | H | H | COOMe |
| 377 | 1-naphthylmethyl | H | H | F | H | H | H |
| 378 | 1-naphthylmethyl | H | H | H | H | F | H |
| 379 | 1-naphthylmethyl | H | H | H | H | H | F |
| 380 | 1-naphthylmethyl | H | H | Me | H | H | H |
| 381 | 1-naphthylmethyl | H | H | H | H | Me | H |
| 382 | 1-naphthylmethyl | H | H | H | H | H | Me |

TABLE 2-continued

X = CO—, q = 0, r = 0, Y = (R4)C═(R5)—

| Compound No. 2— | R1—(CH2)p— | R2 | R3 | R4 | R5 | R6 | R7 |
|---|---|---|---|---|---|---|---|
| 383 | naphthalen-1-ylmethyl | H | H | OMe | H | H | H |
| 384 | naphthalen-1-ylmethyl | H | H | H | H | OMe | H |
| 385 | naphthalen-1-ylmethyl | H | H | H | H | H | OMe |
| 386 | naphthalen-1-ylmethyl | H | H | CF3 | H | H | H |
| 387 | naphthalen-1-ylmethyl | H | H | H | H | CF3 | H |
| 388 | naphthalen-1-ylmethyl | H | H | H | H | H | CF3 |
| 389 | naphthalen-1-ylmethyl | H | H | OH | H | H | H |
| 390 | naphthalen-1-ylmethyl | H | H | H | OH | H | H |

TABLE 2-continued

X = CO—, q = 0, r = 0, Y = (R4)C═(R5)—

| Compound No. 2— | R1—(CH2)p— | R2 | R3 | R4 | R5 | R6 | R7 |
|---|---|---|---|---|---|---|---|
| 391 | naphthalen-1-ylmethyl | H | H | H | H | OH | H |
| 392 | naphthalen-1-ylmethyl | H | H | H | H | H | OH |
| 393 | naphthalen-1-ylmethyl | H | H | OCF3 | H | H | H |
| 394 | naphthalen-1-ylmethyl | H | H | H | H | OCF3 | H |
| 395 | naphthalen-1-ylmethyl | H | H | H | H | H | OCF3 |
| 396 | naphthalen-1-ylmethyl | H | H | NO2 | H | H | H |
| 397 | naphthalen-1-ylmethyl | H | H | H | NO2 | H | H |
| 398 | naphthalen-1-ylmethyl | H | H | H | H | NO2 | H |

TABLE 2-continued

X = CO—, q = 0, r = 0, Y = (R4)C=(R5)—

| Compound No. 2— | R1—(CH2)p— | R2 | R3 | R4 | R5 | R6 | R7 |
|---|---|---|---|---|---|---|---|
| 399 | 1-naphthylmethyl | H | H | H | H | H | NO2 |
| 400 | 1-naphthylmethyl | H | H | CN | H | H | H |
| 401 | 1-naphthylmethyl | H | H | H | CN | H | H |
| 402 | 1-naphthylmethyl | H | H | H | H | CN | H |
| 403 | 1-naphthylmethyl | H | H | H | H | H | CN |
| 404 | 1-naphthylmethyl | H | H | Br | H | H | H |
| 405 | 1-naphthylmethyl | H | H | H | Br | H | H |
| 406 | 1-naphthylmethyl | H | H | H | H | Br | H |

TABLE 2-continued

X = CO—, q = 0, r = 0, Y = (R4)C=(R5)—

| Compound No. 2— | R1—(CH2)p— | R2 | R3 | R4 | R5 | R6 | R7 |
|---|---|---|---|---|---|---|---|
| 407 | naphthyl-CH2 | H | H | H | H | H | Br |
| 408 | naphthyl-CH2 | H | H | COOH | H | H | H |
| 409 | naphthyl-CH2 | H | H | H | COOH | H | H |
| 410 | naphthyl-CH2 | H | H | H | H | COOH | H |
| 411 | naphthyl-CH2 | H | H | H | H | H | COOH |
| 412 | naphthyl-CH2 | H | H | NHCOMe | H | H | H |
| 413 | naphthyl-CH2 | H | H | H | NHCOMe | H | H |
| 414 | naphthyl-CH2 | H | H | H | H | NHCOMe | H |

TABLE 2-continued

X = CO—, q = 0, r = 0, Y = (R4)C=(R5)—

| Compound No. 2— | R1—(CH2)p— | R2 | R3 | R4 | R5 | R6 | R7 |
|---|---|---|---|---|---|---|---|
| 415 | 1-naphthylmethyl | H | H | H | H | H | NHOOMe |
| 416 | 1-naphthylmethyl | H | H | SO2NH2 | H | H | H |
| 417 | 1-naphthylmethyl | H | H | H | SO2NH2 | H | H |
| 418 | 1-naphthylmethyl | H | H | H | H | SO2NH2 | H |
| 419 | 1-naphthylmethyl | H | H | H | H | H | SO2NH2 |
| 420 | 1-naphthylmethyl | H | H | Me | Me | H | H |
| 421 | 1-naphthylmethyl | H | H | Me | H | Me | H |
| 422 | 1-naphthylmethyl | H | H | H | Me | Me | H |

TABLE 2-continued

| | X = CO—, q = 0, r = 0, Y = (R4)C═(R5)— | | | | | | |
|---|---|---|---|---|---|---|---|
| Compound No. 2— | R1—(CH2)p— | R2 | R3 | R4 | R5 | R6 | R7 |
| 423 | naphthalen-1-ylmethyl | H | H | F | F | H | H |
| 424 | naphthalen-1-ylmethyl | H | H | F | H | F | H |
| 425 | naphthalen-1-ylmethyl | H | H | H | F | F | H |
| 426 | naphthalen-1-ylmethyl | H | H | Cl | Cl | H | H |
| 427 | naphthalen-1-ylmethyl | H | H | Cl | H | Cl | H |
| 428 | naphthalen-1-ylmethyl | H | H | H | Cl | Cl | H |
| 429 | naphthalen-1-ylmethyl | H | H | Me | F | H | H |
| 430 | naphthalen-1-ylmethyl | H | H | Me | Cl | H | H |

TABLE 2-continued

X = CO—, q = 0, r = 0, Y = (R4)C=(R5)—

| Compound No. 2— | R1—(CH2)p— | R2 | R3 | R4 | R5 | R6 | R7 |
|---|---|---|---|---|---|---|---|
| 431 | naphthyl-CH2- | H | H | Me | OH | H | H |
| 432 | naphthyl-CH2- | H | H | Me | OMe | H | H |
| 433 | naphthyl-CH2- | H | H | F | Me | H | H |
| 434 | naphthyl-CH2- | H | H | F | Cl | H | H |
| 435 | naphthyl-CH2- | H | H | F | OH | H | H |
| 436 | naphthyl-CH2- | H | H | F | OMe | H | H |
| 437 | naphthyl-CH2- | H | H | Cl | Me | H | H |
| 438 | naphthyl-CH2- | H | H | Cl | F | H | H |

TABLE 2-continued

| | X = CO—, q = 0, r = 0, Y = (R4)C═(R5)— | | | | | | |
|---|---|---|---|---|---|---|---|
| Compound No. 2— | R1—(CH2)p— | R2 | R3 | R4 | R5 | R6 | R7 |
| 439 | naphthalen-1-ylmethyl | H | H | Cl | OH | H | H |
| 440 | naphthalen-1-ylmethyl | H | H | Cl | OMe | H | H |
| 441 | 5-bromo-2-hydroxybenzyl | H | H | Cl | H | H | H |
| 442 | 5-bromo-2-hydroxybenzyl | H | H | H | OMe | H | H |
| 443 | 5-bromo-2-hydroxybenzyl | H | H | H | COOMe | H | H |
| 444 | 5-bromo-2-hydroxybenzyl | H | H | H | H | Cl | H |
| 445 | 5-bromo-2-hydroxybenzyl | H | H | H | H | COOMe | H |
| 446 | 5-bromo-2-hydroxybenzyl | H | H | H | H | H | Cl |
| 447 | 5-bromo-2-hydroxybenzyl | H | H | H | OCF3 | H | H |
| 448 | 5-bromo-2-hydroxybenzyl | H | H | COOMe | H | H | H |
| 449 | 5-bromo-2-hydroxybenzyl | H | H | H | CF3 | H | H |

TABLE 2-continued

X = CO—, q = 0, r = 0, Y = (R4)C═(R5)—

| Compound No. 2— | R1—(CH2)p— | R2 | R3 | R4 | R5 | R6 | R7 |
|---|---|---|---|---|---|---|---|
| 450 | benzothiophen-3-ylmethyl | H | H | H | Me | H | H |
| 451 | 4-bromo-2-hydroxybenzyl | H | H | H | F | H | H |
| 452 | 4-bromo-2-hydroxybenzyl | H | H | H | OH | H | H |
| 453 | 4-bromo-2-hydroxybenzyl | H | H | H | NO2 | H | H |
| 454 | 4-bromo-2-hydroxybenzyl | H | H | H | F | F | H |
| 455 | 4-bromo-2-hydroxybenzyl | H | H | F | H | H | H |
| 456 | 4-bromo-2-hydroxybenzyl | H | H | Me | H | H | H |
| 457 | 4-bromo-2-hydroxybenzyl | H | H | H | CN | H | H |
| 458 | (1-methylindol-3-yl)methyl | H | H | Cl | H | H | H |
| 459 | (1-methylindol-3-yl)methyl | H | H | H | OMe | H | H |
| 460 | (1-methylindol-3-yl)methyl | H | H | H | COOMe | H | H |

TABLE 2-continued

| | X = CO—, q = 0, r = 0, Y = (R4)C=(R5)— | | | | | | |
|---|---|---|---|---|---|---|---|
| Compound No. 2— | R1—(CH2)p— | R2 | R3 | R4 | R5 | R6 | R7 |
| 461 | 1-methylindol-3-ylmethyl | H | H | H | H | Cl | H |
| 462 | 1-methylindol-3-ylmethyl | H | H | H | H | COOMe | H |
| 463 | 1-methylindol-3-ylmethyl | H | H | H | H | H | Cl |
| 464 | 1-methylindol-3-ylmethyl | H | H | H | OCF3 | H | H |
| 465 | 1-methylindol-3-ylmethyl | H | H | COOMe | H | H | H |
| 466 | 1-methylindol-3-ylmethyl | H | H | H | CF3 | H | H |
| 467 | 1-methylindol-3-ylmethyl | H | H | H | Me | H | H |
| 468 | 1-methylindol-3-ylmethyl | H | H | H | F | H | H |
| 469 | 1-methylindol-3-ylmethyl | H | H | H | OH | H | H |

TABLE 2-continued

X = CO—, q = 0, r = 0, Y = (R4)C=(R5)—

| Compound No. 2— | R1—(CH2)p— | R2 | R3 | R4 | R5 | R6 | R7 |
|---|---|---|---|---|---|---|---|
| 470 | 1-methylindol-3-ylmethyl | H | H | H | NO2 | H | H |
| 471 | 1-methylindol-3-ylmethyl | H | H | H | F | F | H |
| 472 | 1-methylindol-3-ylmethyl | H | H | F | H | H | H |
| 473 | 1-methylindol-3-ylmethyl | H | H | Me | H | H | H |
| 474 | 1-methylindol-3-ylmethyl | H | H | H | CN | H | H |
| 475 | benzothiophen-3-ylmethyl | H | H | Cl | H | H | H |
| 476 | benzothiophen-3-ylmethyl | H | H | H | OMe | H | H |
| 477 | benzothiophen-3-ylmethyl | H | H | H | COOMe | H | H |
| 478 | benzothiophen-3-ylmethyl | H | H | H | H | Cl | H |

TABLE 2-continued

X = CO—, q = 0, r = 0, Y = (R4)C=(R5)—

| Compound No. 2— | R1—(CH2)p— | R2 | R3 | R4 | R5 | R6 | R7 |
|---|---|---|---|---|---|---|---|
| 479 | benzothiophen-3-ylmethyl | H | H | H | H | COOMe | H |
| 480 | benzothiophen-3-ylmethyl | H | H | H | H | H | Cl |
| 481 | benzothiophen-3-ylmethyl | H | H | H | OCF3 | H | H |
| 482 | benzothiophen-3-ylmethyl | H | H | COOMe | H | H | H |
| 483 | benzothiophen-3-ylmethyl | H | H | H | CF3 | H | H |
| 484 | benzothiophen-3-ylmethyl | H | H | H | Me | H | H |
| 485 | benzothiophen-3-ylmethyl | H | H | H | F | H | H |
| 486 | benzothiophen-3-ylmethyl | H | H | H | OH | H | H |
| 487 | benzothiophen-3-ylmethyl | H | H | H | NO2 | H | H |

TABLE 2-continued

| | X = CO—, q = 0, r = 0, Y = (R4)C=(R5)— | | | | | | |
|---|---|---|---|---|---|---|---|
| Compound No. 2— | R1—(CH2)p— | R2 | R3 | R4 | R5 | R6 | R7 |
| 488 | benzothiophen-3-ylmethyl | H | H | H | F | F | H |
| 489 | benzothiophen-3-ylmethyl | H | H | F | H | H | H |
| 490 | benzothiophen-3-ylmethyl | H | H | Me | H | H | H |
| 491 | benzothiophen-3-ylmethyl | H | H | H | CN | H | H |
| 492 | 2,4-dichloro-6-hydroxybenzyl | H | Me | H | H | H | H |
| 493 | 4-chloro-2-hydroxybenzyl | H | Me | H | H | H | H |
| 494 | naphthalen-1-ylmethyl | H | Me | H | H | H | H |
| 495 | 3-phenylpropyl | H | Me | H | H | H | H |
| 496 | 4-chloro-2-fluoro-6-hydroxybenzyl | H | H | H | H | H | H |

TABLE 2-continued

| | X = CO—, q = 0, r = 0, Y = (R4)C═(R5)— | | | | | | |
|---|---|---|---|---|---|---|---|
| Compound No. 2— | R1—(CH2)p— | R2 | R3 | R4 | R5 | R6 | R7 |
| 497 | 4-Cl-2-F-6-OH-benzyl | H | H | F | H | H | H |
| 498 | 4-Cl-2-F-6-OH-benzyl | H | H | Cl | H | H | H |
| 499 | 4-Cl-2-F-6-OH-benzyl | H | H | Me | H | H | H |
| 500 | 4-Cl-2-F-6-OH-benzyl | H | H | Et | H | H | H |
| 501 | 4-Cl-2-F-6-OH-benzyl | H | H | OMe | H | H | H |
| 502 | 4-Cl-2-F-6-OH-benzyl | H | H | OEt | H | H | H |
| 503 | 4-Cl-2-F-6-OH-benzyl | H | H | CF3 | H | H | H |
| 504 | 4-Cl-2-F-6-OH-benzyl | H | H | OCF3 | H | H | H |
| 505 | 4-Cl-2-F-6-OH-benzyl | H | H | NO2 | H | H | H |

TABLE 2-continued

| | X = CO—, q = 0, r = 0, Y = (R4)C=(R5)— | | | | | | |
|---|---|---|---|---|---|---|---|
| Compound No. 2— | R1—(CH2)p— | R2 | R3 | R4 | R5 | R6 | R7 |
| 506 | 4-Cl-2-F-6-(OH)-benzyl | H | H | NH2 | H | H | H |
| 507 | 4-Cl-2-F-6-(OH)-benzyl | H | H | OH | H | H | H |
| 508 | 4-Cl-2-F-6-(OH)-benzyl | H | H | CN | H | H | H |
| 509 | 4-Cl-2-F-6-(OH)-benzyl | H | H | COMe | H | H | H |
| 510 | 4-Cl-2-F-6-(OH)-benzyl | H | H | COOMe | H | H | H |
| 511 | 4-Cl-2-F-6-(OH)-benzyl | H | H | H | F | H | H |
| 512 | 4-Cl-2-F-6-(OH)-benzyl | H | H | H | Cl | H | H |
| 513 | 4-Cl-2-F-6-(OH)-benzyl | H | H | H | Me | H | H |
| 514 | 4-Cl-2-F-6-(OH)-benzyl | H | H | H | Et | H | H |

TABLE 2-continued

| | X = CO—, q = 0, r = 0, Y = (R4)C=(R5)— | | | | | | |
|---|---|---|---|---|---|---|---|
| Compound No. 2— | R1—(CH2)p— | R2 | R3 | R4 | R5 | R6 | R7 |
| 515 | 4-Cl-2-F-6-(CH)-phenol | H | H | H | OMe | H | H |
| 516 | 4-Cl-2-F-6-(CH)-phenol | H | H | H | OEt | H | H |
| 517 | 4-Cl-2-F-6-(CH)-phenol | H | H | H | CF3 | H | H |
| 518 | 4-Cl-2-F-6-(CH)-phenol | H | H | H | OCF3 | H | H |
| 519 | 4-Cl-2-F-6-(CH)-phenol | H | H | NO2 | H | H | |
| 520 | 4-Cl-2-F-6-(CH)-phenol | H | H | H | NH2 | H | H |
| 521 | 4-Cl-2-F-6-(CH)-phenol | H | H | H | OH | H | H |
| 522 | 4-Cl-2-F-6-(CH)-phenol | H | H | H | CN | H | H |
| 523 | 4-Cl-2-F-6-(CH)-phenol | H | H | H | COMe | H | H |

TABLE 2-continued

| | X = CO—, q = 0, r = 0, Y = (R4)C=(R5)— | | | | | | |
|---|---|---|---|---|---|---|---|
| Compound No. 2— | R1—(CH2)p— | R2 | R3 | R4 | R5 | R6 | R7 |
| 524 | 4-Cl-2-F-6-OH-phenyl-CH2- | H | H | H | COOMe | H | H |
| 525 | 4-Cl-2-F-6-OH-phenyl-CH2- | H | H | F | F | H | H |
| 526 | 4-Cl-2-F-6-OH-phenyl-CH2- | H | H | F | Cl | H | H |
| 527 | 4-Cl-2-F-6-OH-phenyl-CH2- | H | H | F | Me | H | H |
| 528 | 4-Cl-2-F-6-OH-phenyl-CH2- | H | H | F | Et | H | H |
| 529 | 4-Cl-2-F-6-OH-phenyl-CH2- | H | H | F | OMe | H | H |
| 530 | 4-Cl-2-F-6-OH-phenyl-CH2- | H | H | F | OEt | H | H |
| 531 | 4-Cl-2-F-6-OH-phenyl-CH2- | H | H | F | CF3 | H | H |
| 532 | 4-Cl-2-F-6-OH-phenyl-CH2- | H | H | F | OCF3 | H | H |

TABLE 2-continued

| | X = CO—, q = 0, r = 0, Y = (R4)C=(R5)— | | | | | | |
|---|---|---|---|---|---|---|---|
| Compound No. 2— | R1—(CH2)p— | R2 | R3 | R4 | R5 | R6 | R7 |
| 533 | 2-F, 4-Cl, 6-OH-benzyl | H | H | Cl | F | H | H |
| 534 | 2-F, 4-Cl, 6-OH-benzyl | H | H | Cl | Cl | H | H |
| 535 | 2-F, 4-Cl, 6-OH-benzyl | H | H | Cl | Me | H | H |
| 536 | 2-F, 4-Cl, 6-OH-benzyl | H | H | Cl | Et | H | H |
| 537 | 2-F, 4-Cl, 6-OH-benzyl | H | H | Cl | OMe | H | H |
| 538 | 2-F, 4-Cl, 6-OH-benzyl | H | H | Cl | OEt | H | H |
| 539 | 2-F, 4-Cl, 6-OH-benzyl | H | H | Cl | CF3 | H | H |
| 540 | 2-F, 4-Cl, 6-OH-benzyl | H | H | Cl | OCF3 | H | H |
| 541 | 2-F, 4-Cl, 6-OH-benzyl | H | H | Me | F | H | H |

TABLE 2-continued

| | X = CO—, q = 0, r = 0, Y = (R4)C=(R5)— | | | | | | |
|---|---|---|---|---|---|---|---|
| Compound No. 2— | R1—(CH2)p— | R2 | R3 | R4 | R5 | R6 | R7 |
| 542 | 4-Cl, 2-F, 3-OH-benzyl | H | H | Me | Cl | H | H |
| 543 | 4-Cl, 2-F, 3-OH-benzyl | H | H | Me | Me | H | H |
| 544 | 4-Cl, 2-F, 3-OH-benzyl | H | H | Me | Et | H | H |
| 545 | 4-Cl, 2-F, 3-OH-benzyl | H | H | Me | OMe | H | H |
| 546 | 4-Cl, 2-F, 3-OH-benzyl | H | H | Me | OEt | H | H |
| 547 | 4-Cl, 2-F, 3-OH-benzyl | H | H | Me | CF3 | H | H |
| 548 | 4-Cl, 2-F, 3-OH-benzyl | H | H | Me | OCF3 | H | H |
| 549 | 4-Cl, 2-F, 3-OH-benzyl | H | H | OMe | F | H | H |
| 550 | 4-Cl, 2-F, 3-OH-benzyl | H | H | OMe | Cl | H | H |

TABLE 2-continued
| | X = CO—, q = 0, r = 0, Y = (R4)C=(R5)— | | | | | | |
|---|---|---|---|---|---|---|---|
| Compound No. 2— | R1—(CH2)p— | R2 | R3 | R4 | R5 | R6 | R7 |
| 551 | 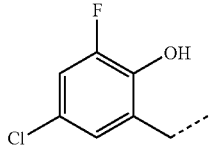 | H | H | OMe | Me | H | H |
| 552 | 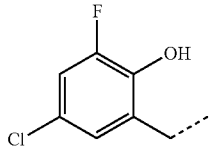 | H | H | OMe | Et | H | H |
| 553 | 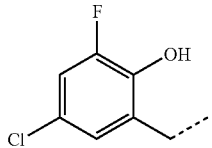 | H | H | OMe | OMe | H | H |
| 554 | 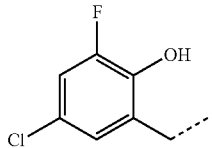 | H | H | OMe | OEt | H | H |
| 555 | 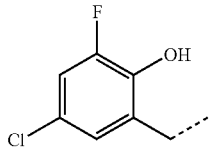 | H | H | OMe | CF3 | H | H |
| 556 | 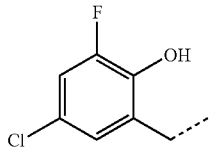 | H | H | OMe | OCF3 | H | H |
| 557 | 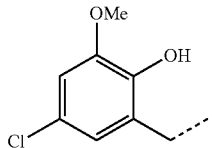 | H | H | H | H | H | H |
| 558 | 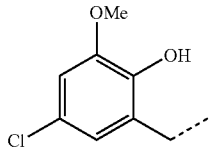 | H | H | F | H | H | H |
| 559 | 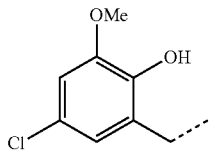 | H | H | Cl | H | H | H |

TABLE 2-continued
| | X = CO—, q = 0, r = 0, Y = (R4)C═(R5)— | | | | | | |
|---|---|---|---|---|---|---|---|
| Compound No. 2— | R1—(CH2)p— | R2 | R3 | R4 | R5 | R6 | R7 |
| 560 | 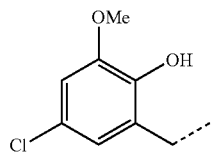 | H | H | Me | H | H | H |
| 561 | 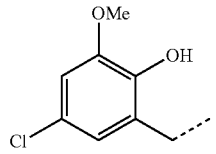 | H | H | Et | H | H | H |
| 562 | 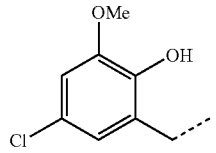 | H | H | OMe | H | H | H |
| 563 | 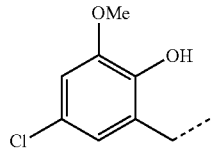 | H | H | H | F | H | H |
| 564 | 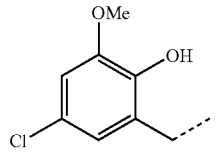 | H | H | H | Cl | H | H |
| 565 | 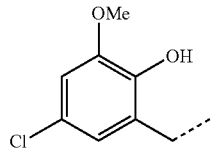 | H | H | H | Me | H | H |
| 566 | 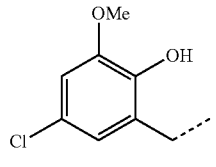 | H | H | H | Et | H | H |
| 567 | 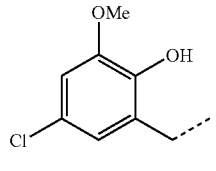 | H | H | H | OMe | H | H |
| 568 | 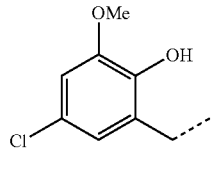 | H | H | F | F | H | H |

TABLE 2-continued

| | X = CO—, q = 0, r = 0, Y = (R4)C=(R5)— | | | | | | |
|---|---|---|---|---|---|---|---|
| Compound No. 2— | R1—(CH2)p— | R2 | R3 | R4 | R5 | R6 | R7 |
| 569 | 4-Cl, 2-OMe, 3-OH-benzyl | H | H | F | Cl | H | H |
| 570 | 4-Cl, 2-OMe, 3-OH-benzyl | H | H | F | Me | H | H |
| 571 | 4-Cl, 2-OMe, 3-OH-benzyl | H | H | F | Et | H | H |
| 572 | 4-Cl, 2-OMe, 3-OH-benzyl | H | H | F | OMe | H | H |
| 573 | 4-Cl, 2-OMe, 3-OH-benzyl | H | H | Cl | F | H | H |
| 574 | 4-Cl, 2-OMe, 3-OH-benzyl | H | H | Cl | Cl | H | H |
| 575 | 4-Cl, 2-OMe, 3-OH-benzyl | H | H | Cl | Me | H | H |
| 576 | 4-Cl, 2-OMe, 3-OH-benzyl | H | H | Cl | Et | H | H |
| 577 | 4-Cl, 2-OMe, 3-OH-benzyl | H | H | Cl | OMe | H | H |

TABLE 2-continued

| | X = CO—, q = 0, r = 0, Y = (R4)C=(R5)— | | | | | | |
|---|---|---|---|---|---|---|---|
| Compound No. 2— | R1—(CH2)p— | R2 | R3 | R4 | R5 | R6 | R7 |
| 578 | 4-Cl, 2-OMe, 3-OH-benzyl | H | H | Me | F | H | H |
| 579 | 4-Cl, 2-OMe, 3-OH-benzyl | H | H | Me | Cl | H | H |
| 580 | 4-Cl, 2-OMe, 3-OH-benzyl | H | H | Me | Me | H | H |
| 581 | 4-Cl, 2-OMe, 3-OH-benzyl | H | H | Me | Et | H | H |
| 582 | 4-Cl, 2-OMe, 3-OH-benzyl | H | H | Me | OMe | H | H |
| 583 | 4-Cl, 2-OMe, 3-OH-benzyl | H | H | Et | F | H | H |
| 584 | 4-Cl, 2-OMe, 3-OH-benzyl | H | H | Et | Cl | H | H |
| 585 | 4-Cl, 2-OMe, 3-OH-benzyl | H | H | Et | Me | H | H |
| 586 | 4-Cl, 2-OMe, 3-OH-benzyl | H | H | Et | Et | H | H |

TABLE 2-continued

| | X = CO—, q = 0, r = 0, Y = (R4)C=(R5)— | | | | | | |
|---|---|---|---|---|---|---|---|
| Compound No. 2— | R1—(CH2)p— | R2 | R3 | R4 | R5 | R6 | R7 |
| 587 | 4-Cl-2-OH-3-OMe-benzyl | H | H | Et | OMe | H | H |
| 588 | 4-Cl-2-OH-3-OMe-benzyl | H | H | OMe | F | H | H |
| 589 | 4-Cl-2-OH-3-OMe-benzyl | H | H | OMe | Cl | H | H |
| 590 | 4-Cl-2-OH-3-OMe-benzyl | H | H | OMe | Me | H | H |
| 591 | 4-Cl-2-OH-3-OMe-benzyl | H | H | OMe | Et | H | H |
| 592 | 4-Cl-2-OH-3-OMe-benzyl | H | H | OMe | OMe | H | H |
| 593 | 3,5-diCl-2-OH-benzyl | H | H | Me | CN | H | H |
| 594 | 3,5-diCl-2-OH-benzyl | H | H | H | CN | Me | H |
| 595 | 3,5-diCl-2-OH-benzyl | H | H | H | CN | H | Me |

TABLE 2-continued
X = CO—, q = 0, r = 0, Y = (R4)C=(R5)—
| Compound No. 2— | R1—(CH2)p— | R2 | R3 | R4 | R5 | R6 | R7 |
|---|---|---|---|---|---|---|---|
| 596 | 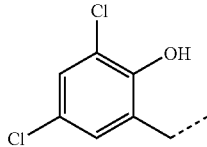 | H | H | Me | Br | H | H |
| 597 | 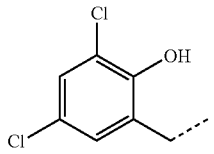 | H | H | H | Br | Me | H |
| 598 | 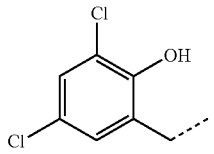 | H | H | H | Br | H | Me |
| 599 | 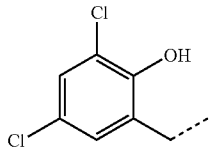 | H | H | Me | H | F | H |
| 600 | 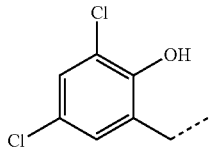 | H | H | Me | H | H | F |
| 601 | 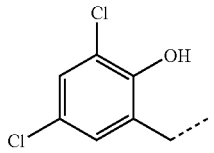 | H | H | F | H | Me | H |
| 602 | 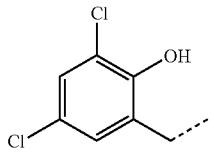 | H | H | F | H | H | Me |
| 603 | 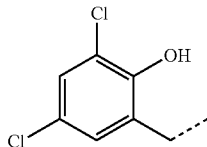 | H | H | Me | H | H | Me |
| 604 | 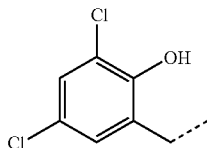 | H | H | H | OMe | Me | H |

TABLE 2-continued
| | X = CO—, q = 0, r = 0, Y = (R4)C=(R5)— | | | | | | |
|---|---|---|---|---|---|---|---|
| Compound No. 2— | R1—(CH2)p— | R2 | R3 | R4 | R5 | R6 | R7 |
| 605 | 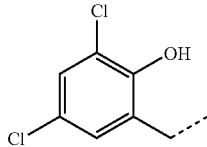 | H | H | H | OH | Me | H |
| 606 | 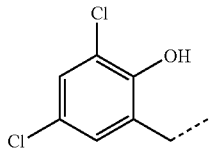 | H | H | NH2 | H | H | H |
| 607 | 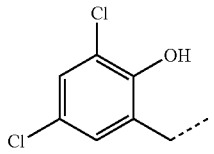 | H | H | H | NH2 | H | H |
| 608 | 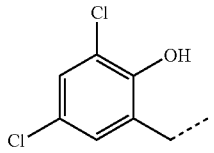 | H | H | H | H | NH2 | H |
| 609 | 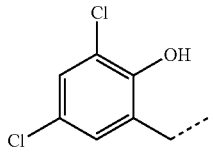 | H | H | Et | H | H | H |
| 610 | 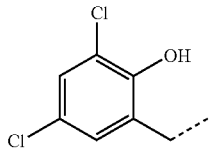 | H | H | H | Et | H | H |
| 611 | 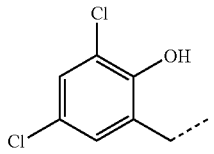 | H | H | H | H | Et | H |
| 612 | 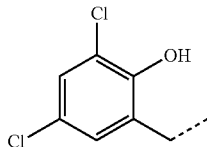 | H | H | iPr | H | H | H |
| 613 | 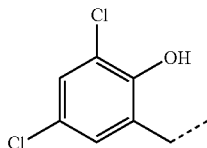 | H | H | H | iPr | H | H |

TABLE 2-continued
X = CO—, q = 0, r = 0, Y = (R4)C═(R5)—
| Compound No. 2— | R1—(CH2)p— | R2 | R3 | R4 | R5 | R6 | R7 |
|---|---|---|---|---|---|---|---|
| 614 | 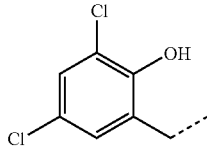 | H | H | H | H | iPr | H |
| 615 | 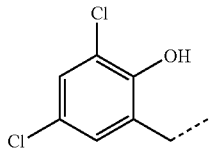 | H | H | Ph | H | H | H |
| 616 | 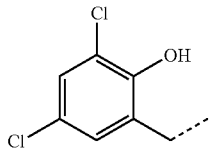 | H | H | H | Ph | H | H |
| 617 | 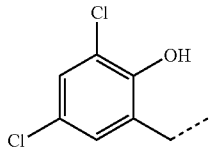 | H | H | H | H | Ph | H |
| 618 | 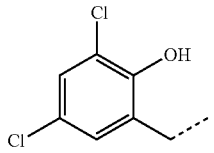 | H | H | OEt | H | H | H |
| 619 | 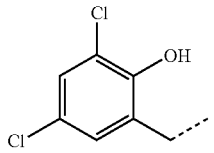 | H | H | H | OEt | H | H |
| 620 | 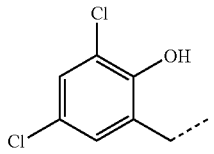 | H | H | H | H | OEt | H |
| 621 | 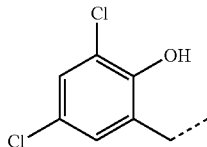 | H | H | OiPr | H | H | H |
| 622 | 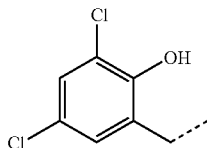 | H | H | H | OiPr | H | H |

TABLE 2-continued
| | X = CO—, q = 0, r = 0, Y = (R4)C═(R5)— | | | | | | |
|---|---|---|---|---|---|---|---|
| Compound No. 2— | R1—(CH2)p— | R2 | R3 | R4 | R5 | R6 | R7 |
| 623 | 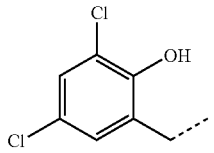 | H | H | H | H | OiPr | H |
| 624 | 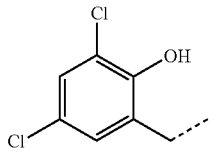 | H | H | OPh | H | H | H |
| 625 | 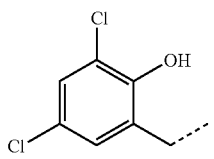 | H | H | H | OPh | H | H |
| 626 | 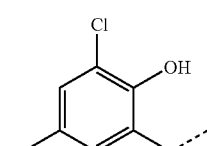 | H | H | H | H | OPh | H |
| 627 | 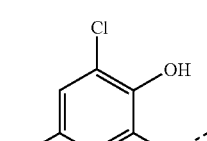 | H | H | SO2Me | H | H | H |
| 628 | 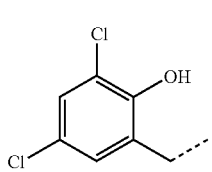 | H | H | H | SO2Me | H | H |
| 629 | 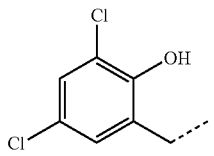 | H | H | H | H | SO2Me | H |
| 630 | 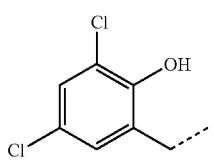 | H | H | SO2Et | H | H | H |
| 631 | 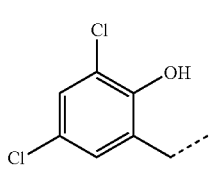 | H | H | H | SO2Et | H | H |

TABLE 2-continued
X = CO—, q = 0, r = 0, Y = (R4)C=(R5)—
| Compound No. 2— | R1—(CH2)p— | R2 | R3 | R4 | R5 | R6 | R7 |
|---|---|---|---|---|---|---|---|
| 632 | 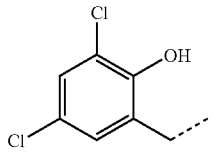 | H | H | H | H | SO2Et | H |
| 633 | 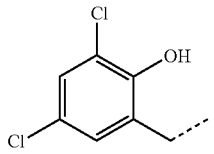 | H | H | SO2iPr | H | H | H |
| 634 | 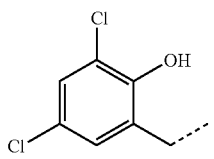 | H | H | H | SO2iPr | H | H |
| 635 | 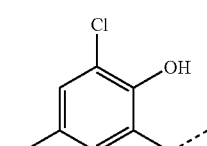 | H | H | H | H | SO2iPr | H |
| 636 | 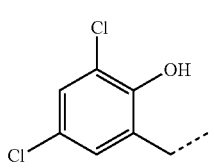 | H | H | SO2Ph | H | H | H |
| 637 | 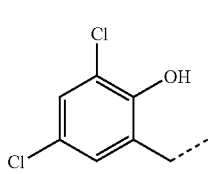 | H | H | H | SO2Ph | H | H |
| 638 | 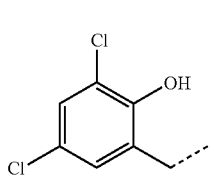 | H | H | H | H | SO2Ph | H |
| 639 |  | H | H | SO2Me | Me | H | H |
| 640 |  | H | H | SO2Me | H | Me | H |

TABLE 2-continued
| | X = CO—, q = 0, r = 0, Y = (R4)C═(R5)— | | | | | | |
|---|---|---|---|---|---|---|---|
| Compound No. 2— | R1—(CH2)p— | R2 | R3 | R4 | R5 | R6 | R7 |
| 641 | 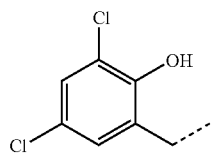 | H | H | Me | SO2Me | H | H |
| 642 | 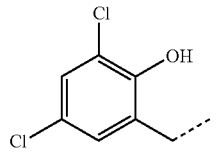 | H | H | H | SO2Me | Me | H |
| 643 | 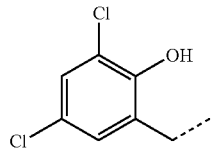 | H | H | SO2Me | F | H | H |
| 644 | 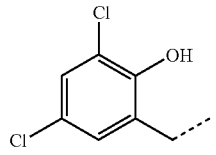 | H | H | SO2Me | H | F | H |
| 645 | 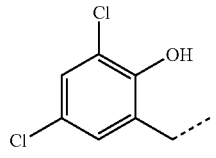 | H | H | F | SO2Me | H | H |
| 646 | 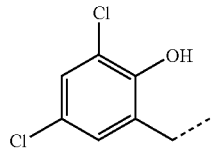 | H | H | H | SO2Me | F | H |
| 647 | 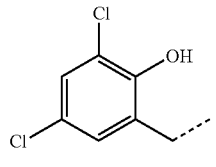 | H | H | SO2NMe2 | H | H | H |
| 648 | 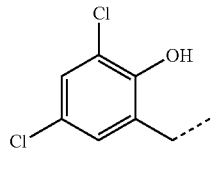 | H | H | H | SO2NMe2 | H | H |
| 649 | 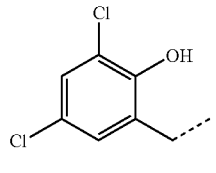 | H | H | H | H | SO2NMe2 | H |

TABLE 2-continued

X = CO—, q = 0, r = 0, Y = (R4)C═(R5)—

| Compound No. 2— | R1—(CH2)p— | R2 | R3 | R4 | R5 | R6 | R7 |
|---|---|---|---|---|---|---|---|
| 650 | 2,4-dichloro-6-hydroxybenzyl | H | H | SO2Et2 | H | H | H |
| 651 | 2,4-dichloro-6-hydroxybenzyl | H | H | H | SO2Et2 | H | |
| 652 | 2,4-dichloro-6-hydroxybenzyl | H | H | H | H | SO2Et2 | H |
| 653 | 2,4-dichloro-6-hydroxybenzyl | H | H | SO2NMe2 | Me | H | H |
| 654 | 2,4-dichloro-6-hydroxybenzyl | H | H | SO2NMe2 | H | Me | H |
| 655 | 2,4-dichloro-6-hydroxybenzyl | H | H | Me | SO2NMe2 | H | H |
| 656 | 2,4-dichloro-6-hydroxybenzyl | H | H | H | SO2NMe2 | Me | H |
| 657 | 2,4-dichloro-6-hydroxybenzyl | H | H | SO2NMe2 | F | H | H |
| 658 | 2,4-dichloro-6-hydroxybenzyl | H | H | SO2NMe2 | H | F | H |

TABLE 2-continued
X = CO—, q = 0, r = 0, Y = (R4)C=(R5)—
| Compound No. 2— | R1—(CH2)p— | R2 | R3 | R4 | R5 | R6 | R7 |
|---|---|---|---|---|---|---|---|
| 659 | 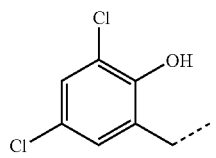 | H | H | F | SO2NMe2 | H | H |
| 660 | 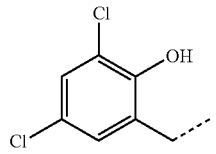 | H | H | H | SO2NMe2 | F | H |
| 661 | 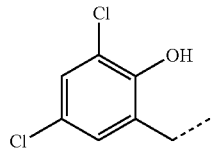 | H | H | NHCOEt | H | H | H |
| 662 | 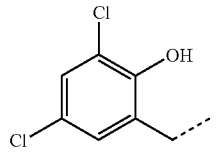 | H | H | H | NHOOEt | H | H |
| 663 | 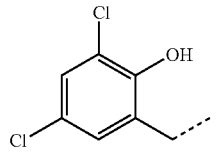 | H | H | H | NHOOEt | H | H |
| 664 | 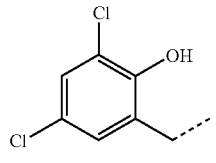 | H | H | NHCOiPr | H | H | H |
| 665 | 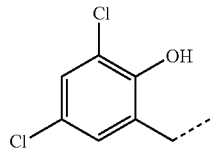 | H | H | H | NHCOiPr | H | H |
| 666 | 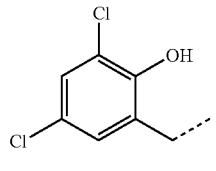 | H | H | H | H | NHCOiPr | H |
| 667 | 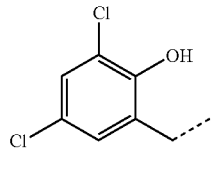 | H | H | Me | CN | H | H |

TABLE 2-continued

X = CO—, q = 0, r = 0, Y = (R4)C=(R5)—

| Compound No. 2— | R1—(CH2)p— | R2 | R3 | R4 | R5 | R6 | R7 |
|---|---|---|---|---|---|---|---|
| 668 | 4-Cl-2-F-6-OH-phenyl | H | H | H | CN | Me | H |
| 669 | 4-Cl-2-F-6-OH-phenyl | H | H | H | CN | H | Me |
| 670 | 4-Cl-2-F-6-OH-phenyl | H | H | H | Me | Br | H |
| 671 | 4-Cl-2-F-6-OH-phenyl | H | H | H | Br | Me | H |
| 672 | 4-Cl-2-F-6-OH-phenyl | H | H | H | Br | H | Me |
| 673 | 4-Cl-2-F-6-OH-phenyl | H | H | Me | H | F | H |
| 674 | 4-Cl-2-F-6-OH-phenyl | H | H | Me | H | H | F |
| 675 | 4-Cl-2-F-6-OH-phenyl | H | H | F | H | Me | H |
| 676 | 4-Cl-2-F-6-OH-phenyl | H | H | F | H | H | Me |

TABLE 2-continued

X = CO—, q = 0, r = 0, Y = (R4)C=(R5)—

| Compound No. 2— | R1—(CH2)p— | R2 | R3 | R4 | R5 | R6 | R7 |
|---|---|---|---|---|---|---|---|
| 677 | 4-Cl, 2-F, 6-OH-benzyl | H | H | Me | H | H | Me |
| 678 | 4-Cl, 2-F, 6-OH-benzyl | H | H | H | OMe | Me | H |
| 679 | 4-Cl, 2-F, 6-OH-benzyl | H | H | H | OH | Me | H |
| 680 | 4-Cl, 2-F, 6-OH-benzyl | H | H | NH2 | H | H | H |
| 681 | 4-Cl, 2-F, 6-OH-benzyl | H | H | H | NH2 | H | H |
| 682 | 4-Cl, 2-F, 6-OH-benzyl | H | H | H | H | NH2 | H |
| 683 | 4-Cl, 2-F, 6-OH-benzyl | H | H | Et | H | H | H |
| 684 | 4-Cl, 2-F, 6-OH-benzyl | H | H | H | Et | H | H |
| 685 | 4-Cl, 2-F, 6-OH-benzyl | H | H | H | H | Et | H |

TABLE 2-continued

| | X = CO—, q = 0, r = 0, Y = (R4)C=(R5)— | | | | | | |
|---|---|---|---|---|---|---|---|
| Compound No. 2— | R1—(CH2)p— | R2 | R3 | R4 | R5 | R6 | R7 |
| 686 | 4-Cl-2-F-6-OH-benzyl | H | H | iPr | H | H | H |
| 687 | 4-Cl-2-F-6-OH-benzyl | H | H | H | iPr | H | H |
| 688 | 4-Cl-2-F-6-OH-benzyl | H | H | H | H | iPr | H |
| 689 | 4-Cl-2-F-6-OH-benzyl | H | H | Ph | H | H | H |
| 690 | 4-Cl-2-F-6-OH-benzyl | H | H | H | Ph | H | H |
| 691 | 4-Cl-2-F-6-OH-benzyl | H | H | H | H | Ph | H |
| 692 | 4-Cl-2-F-6-OH-benzyl | H | H | OEt | H | H | H |
| 693 | 4-Cl-2-F-6-OH-benzyl | H | H | H | OEt | H | H |
| 694 | 4-Cl-2-F-6-OH-benzyl | H | H | H | H | OEt | H |

TABLE 2-continued

X = CO—, q = 0, r = 0, Y = (R4)C═(R5)—

| Compound No. 2— | R1—(CH2)p— | R2 | R3 | R4 | R5 | R6 | R7 |
|---|---|---|---|---|---|---|---|
| 695 | 4-Cl, 2-F, 3-OH-benzyl | H | H | OiPr | H | H | H |
| 696 | 4-Cl, 2-F, 3-OH-benzyl | H | H | H | OiPr | H | H |
| 697 | 4-Cl, 2-F, 3-OH-benzyl | H | H | H | H | OiPr | H |
| 698 | 4-Cl, 2-F, 3-OH-benzyl | H | H | OPh | H | H | H |
| 699 | 4-Cl, 2-F, 3-OH-benzyl | H | H | H | OPh | H | H |
| 700 | 4-Cl, 2-F, 3-OH-benzyl | H | H | H | H | OPh | H |
| 701 | 4-Cl, 2-F, 3-OH-benzyl | H | H | SO2Me | H | H | H |
| 702 | 4-Cl, 2-F, 3-OH-benzyl | H | H | H | SO2Me | H | H |
| 703 | 4-Cl, 2-F, 3-OH-benzyl | H | H | H | H | SO2Me | H |

TABLE 2-continued

| | X = CO—, q = 0, r = 0, Y = (R4)C═(R5)— | | | | | | |
|---|---|---|---|---|---|---|---|
| Compound No. 2— | R1—(CH2)p— | R2 | R3 | R4 | R5 | R6 | R7 |
| 704 | 4-Cl-2-F-6-OH-benzyl | H | H | SO2Et | H | H | H |
| 705 | 4-Cl-2-F-6-OH-benzyl | H | H | H | SO2Et | H | H |
| 706 | 4-Cl-2-F-6-OH-benzyl | H | H | H | H | SO2Et | H |
| 707 | 4-Cl-2-F-6-OH-benzyl | H | H | SO2iPr | H | H | H |
| 708 | 4-Cl-2-F-6-OH-benzyl | H | H | H | SO2iPr | H | H |
| 709 | 4-Cl-2-F-6-OH-benzyl | H | H | H | H | SO2iPr | H |
| 710 | 4-Cl-2-F-6-OH-benzyl | H | H | SO2Ph | H | H | H |
| 711 | 4-Cl-2-F-6-OH-benzyl | H | H | H | SO2Ph | H | H |
| 712 | 4-Cl-2-F-6-OH-benzyl | H | H | H | H | SO2Ph | H |

TABLE 2-continued

X = CO—, q = 0, r = 0, Y = (R4)C=(R5)—

| Compound No. 2— | R1—(CH2)p— | R2 | R3 | R4 | R5 | R6 | R7 |
|---|---|---|---|---|---|---|---|
| 713 | 4-Cl, 2-F, 6-OH-benzyl | H | H | SO2Me | Me | H | H |
| 714 | 4-Cl, 2-F, 6-OH-benzyl | H | H | SO2Me | H | Me | H |
| 715 | 4-Cl, 2-F, 6-OH-benzyl | H | H | Me | SO2Me | H | H |
| 716 | 4-Cl, 2-F, 6-OH-benzyl | H | H | H | SO2Me | Me | H |
| 717 | 4-Cl, 2-F, 6-OH-benzyl | H | H | SO2Me | F | H | H |
| 718 | 4-Cl, 2-F, 6-OH-benzyl | H | H | SO2Me | H | F | H |
| 719 | 4-Cl, 2-F, 6-OH-benzyl | H | H | F | SO2Me | H | H |
| 720 | 4-Cl, 2-F, 6-OH-benzyl | H | H | H | SO2Me | F | H |
| 721 | 4-Cl, 2-F, 6-OH-benzyl | H | H | SO2NMe2 | H | H | H |

TABLE 2-continued

| | X = CO—, q = 0, r = 0, Y = (R4)C═(R5)— | | | | | | |
|---|---|---|---|---|---|---|---|
| Compound No. 2— | R1—(CH2)p— | R2 | R3 | R4 | R5 | R6 | R7 |
| 722 | 4-Cl, 2-F, 6-OH-benzyl | H | H | H | SO2NMe2 | H | H |
| 723 | 4-Cl, 2-F, 6-OH-benzyl | H | H | H | H | SO2NMe2 | H |
| 724 | 4-Cl, 2-F, 6-OH-benzyl | H | H | SO2Et2 | H | H | H |
| 725 | 4-Cl, 2-F, 6-OH-benzyl | H | H | H | SO2Et2 | H | H |
| 726 | 4-Cl, 2-F, 6-OH-benzyl | H | H | H | H | SO2Et2 | H |
| 727 | 4-Cl, 2-F, 6-OH-benzyl | H | H | SO2NMe2 | Me | H | H |
| 728 | 4-Cl, 2-F, 6-OH-benzyl | H | H | SO2NMe2 | H | Me | H |
| 729 | 4-Cl, 2-F, 6-OH-benzyl | H | H | Me | SO2NMe2 | H | H |
| 730 | 4-Cl, 2-F, 6-OH-benzyl | H | H | H | SO2NMe2 | Me | H |

TABLE 2-continued

X = CO—, q = 0, r = 0, Y = (R4)C═(R5)—

| Compound No. 2— | R1—(CH2)p— | R2 | R3 | R4 | R5 | R6 | R7 |
|---|---|---|---|---|---|---|---|
| 731 | 4-Cl, 2-F, 6-OH-benzyl | H | H | SO2NMe2 | F | H | H |
| 732 | 4-Cl, 2-F, 6-OH-benzyl | H | H | SO2NMe2 | H | F | H |
| 733 | 4-Cl, 2-F, 6-OH-benzyl | H | H | F | SO2NMe2 | H | H |
| 734 | 4-Cl, 2-F, 6-OH-benzyl | H | H | H | SO2NMe2 | F | H |
| 735 | 4-Cl, 2-F, 6-OH-benzyl | H | H | NHOOEt | H | H | H |
| 736 | 4-Cl, 2-F, 6-OH-benzyl | H | H | H | NHCOEt | H | H |
| 737 | 4-Cl, 2-F, 6-OH-benzyl | H | H | H | H | NHCOEt | H |
| 738 | 4-Cl, 2-F, 6-OH-benzyl | H | H | NHCOiPr | H | H | H |
| 739 | 4-Cl, 2-F, 6-OH-benzyl | H | H | H | NHCOiPr | H | H |

TABLE 2-continued

X = CO—, q = 0, r = 0, Y = (R4)C=(R5)—

| Compound No. 2— | R1—(CH2)p— | R2 | R3 | R4 | R5 | R6 | R7 |
|---|---|---|---|---|---|---|---|
| 740 | 2-OH, 3-F, 5-Cl benzyl | H | H | H | H | NHCOiPr | H |
| 741 | 2-OH, 3-F, 5-Cl benzyl | H | H | F | H | H | F |
| 742 | 2-OH, 3-F, 5-Cl benzyl | H | H | F | H | H | F |

TABLE 3

X = —SO$_2$—, q = 0, r = 0, Y = —(R4)C=C(R5)—

| Compound No. 3- | R1—(CH2)p— | R2 | R3 | R4 | R5 | R6 | R7 |
|---|---|---|---|---|---|---|---|
| 1 | 2-OH, 3,5-diCl benzyl | H | H | H | H | H | H |
| 2 | 1-naphthylmethyl | H | H | H | H | H | H |
| 3 | 2-OH, 4-Cl benzyl | H | H | H | H | H | H |
| 4 | 3-phenylpropyl | H | H | H | H | H | H |
| 5 | 2-OH, 3,5-diCl benzyl | H | H | H | Me | H | H |
| 6 | 2-OH, 4-Cl benzyl | H | H | H | Me | H | H |

TABLE 3-continued

X = —SO₂—, q = 0, r = 0, Y = —(R4)C=C(R5)—

| Compound No. 3- | R1—(CH2)p— | R2 | R3 | R4 | R5 | R6 | R7 |
|---|---|---|---|---|---|---|---|
| 7 | 1-naphthylmethyl | H | H | H | Me | H | H |
| 8 | 2,4-dichloro-6-hydroxybenzyl | H | H | H | F | H | H |
| 9 | 4-chloro-2-hydroxybenzyl | H | H | H | F | H | H |
| 10 | 1-naphthylmethyl | H | H | H | F | H | H |
| 11 | 3,4-dichlorobenzyl | H | H | H | H | H | H |
| 12 | 3,4-dichlorobenzyl | H | H | H | Cl | H | H |
| 13 | 1-naphthylmethyl | H | H | H | Cl | H | H |
| 14 | 2-chlorobenzyl | H | H | H | H | H | H |
| 15 | 3-chlorobenzyl | H | H | H | H | H | H |
| 16 | 4-chlorobenzyl | H | H | H | H | H | H |

TABLE 3-continued

X = —SO$_2$—, q = 0, r = 0, Y = —(R4)C=C(R5)—

| Compound No. 3- | R1—(CH2)p— | R2 | R3 | R4 | R5 | R6 | R7 |
|---|---|---|---|---|---|---|---|
| 17 | 2-methoxybenzyl | H | H | H | H | H | H |
| 18 | 4-methoxybenzyl (MeO) | H | H | H | H | H | H |
| 19 | 5-bromo-2-hydroxybenzyl | H | H | H | H | H | H |
| 20 | 5-bromo-2-methoxybenzyl | H | H | H | H | H | H |
| 21 | 5-bromo-2-fluorobenzyl | H | H | H | H | H | H |
| 22 | 3-bromobenzyl | H | H | H | H | H | H |
| 23 | 3-chloro-4-fluorobenzyl | H | H | H | H | H | H |
| 24 | (1-methyl-1H-indol-3-yl)methyl | H | H | H | H | H | H |
| 25 | benzo[b]thiophen-3-ylmethyl | H | H | H | H | H | H |
| 26 | 2-hydroxy-4-methoxybenzyl | H | H | H | H | H | H |
| 27 | 3-nitrobenzyl | H | H | H | H | H | H |

TABLE 3-continued
X = —SO₂—, q = 0, r = 0, Y = —(R4)C=C(R5)—
| Compound No. 3- | R1—(CH2)p— | R2 | R3 | R4 | R5 | R6 | R7 |
|---|---|---|---|---|---|---|---|
| 28 | 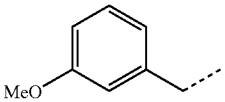 | H | H | H | H | H | H |
| 29 | 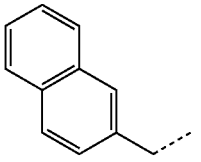 | H | H | H | H | H | H |
| 30 | 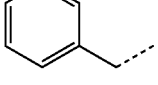 | H | H | H | H | H | H |
| 31 | 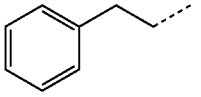 | H | H | H | H | H | H |
| 32 | 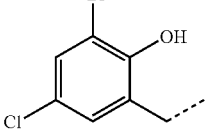 | H | H | H | H | H | H |
| 33 | 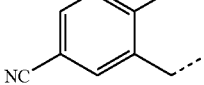 | H | H | H | H | H | H |
| 34 | 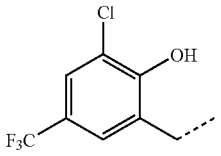 | H | H | H | H | H | H |
| 35 | 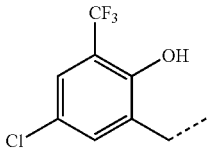 | H | H | H | H | H | H |
| 36 | 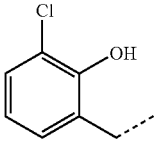 | H | H | H | H | H | H |
| 37 | 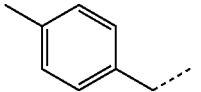 | H | H | H | H | H | H |
| 38 | 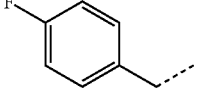 | H | H | H | H | H | H |

TABLE 3-continued

X = —SO₂—, q = 0, r = 0, Y = —(R4)C=C(R5)—

| Compound No. 3- | R1—(CH2)p— | R2 | R3 | R4 | R5 | R6 | R7 |
|---|---|---|---|---|---|---|---|
| 39 | 4-Br-C₆H₄-CH₂- | H | H | H | H | H | H |
| 40 | 4-F₃C-C₆H₄-CH₂- | H | H | H | H | H | H |
| 41 | 4-HO-C₆H₄-CH₂- | H | H | H | H | H | H |
| 42 | 4-NC-C₆H₄-CH₂- | H | H | H | H | H | H |
| 43 | 4-MeSO₂-C₆H₄-CH₂- | H | H | H | H | H | H |
| 44 | 4-MeOOC-C₆H₄-CH₂- | H | H | H | H | H | H |
| 45 | 4-Me₂N-C₆H₄-CH₂- | H | H | H | H | H | H |
| 46 | 4-MeO-C₆H₄-CH₂- | H | H | H | H | H | H |
| 47 | 4-EtO-C₆H₄-CH₂- | H | H | H | H | H | H |
| 48 | 4-nPrO-C₆H₄-CH₂- | H | H | H | H | H | H |
| 49 | 4-iPrO-C₆H₄-CH₂- | H | H | H | H | H | H |
| 50 | 4-iPr-C₆H₄-CH₂- | H | H | H | H | H | H |

TABLE 3-continued

X = —SO$_2$—, q = 0, r = 0, Y = —(R4)C=C(R5)—

| Compound No. 3- | R1—(CH2)p— | R2 | R3 | R4 | R5 | R6 | R7 |
|---|---|---|---|---|---|---|---|
| 51 | benzyloxy-phenyl | H | H | H | H | H | H |
| 52 | phenoxy-phenyl | H | H | H | H | H | H |
| 53 | biphenyl | H | H | H | H | H | H |
| 54 | 4-acetamidophenyl | H | H | H | H | H | H |
| 55 | 2-propylphenyl | H | H | H | H | H | H |
| 56 | 2-benzyloxyphenyl | H | H | H | H | H | H |
| 57 | 2-methylphenyl | H | H | H | H | H | H |
| 58 | 2-cyanophenyl | H | H | H | H | H | H |
| 59 | 2-chlorophenyl | H | H | H | H | H | H |

TABLE 3-continued

X = —SO$_2$—, q = 0, r = 0, Y = —(R4)C=C(R5)—

| Compound No. 3- | R1—(CH2)p— | R2 | R3 | R4 | R5 | R6 | R7 |
|---|---|---|---|---|---|---|---|
| 60 | 2-methoxybenzyl | H | H | H | H | H | H |
| 61 | 2-ethoxybenzyl | H | H | H | H | H | H |
| 62 | 2-phenylbenzyl (biphenyl-2-ylmethyl) | H | H | H | H | H | H |
| 63 | 3-(trifluoromethyl)benzyl | H | H | H | H | H | H |
| 64 | 3-chloro-2-fluorobenzyl | H | H | H | H | H | H |
| 65 | 3,5-dichlorobenzyl | H | H | H | H | H | H |
| 66 | 3-methylbenzyl | H | H | H | H | H | H |
| 67 | 3-fluoro-5-(trifluoromethyl)benzyl | H | H | H | H | H | H |
| 68 | 3-(trifluoromethoxy)benzyl | H | H | H | H | H | H |

TABLE 3-continued

X = —SO₂—, q = 0, r = 0, Y = —(R4)C=C(R5)—

| Compound No. 3- | R1—(CH2)p— | R2 | R3 | R4 | R5 | R6 | R7 |
|---|---|---|---|---|---|---|---|
| 69 | 4-F, 5-MeO-phenyl- | H | H | H | H | H | H |
| 70 | 4-F, 5-O₂N-phenyl- | H | H | H | H | H | H |
| 71 | 4-O₂N-phenyl- | H | H | H | H | H | H |
| 72 | 2-F, 3-Me-phenyl- | H | H | H | H | H | H |
| 73 | 3-F₃CS-phenyl- | H | H | H | H | H | H |
| 74 | 2,5-Cl₂-phenyl- | H | H | H | H | H | H |
| 75 | 3-F₂HC-phenyl- | H | H | H | H | H | H |
| 76 | 2-F-phenyl- | H | H | H | H | H | H |
| 77 | 2-NO₂-phenyl- | H | H | H | H | H | H |
| 78 | 2-COOH-phenyl- | H | H | H | H | H | H |
| 79 | 4-Br, 5-OEt-phenyl- | H | H | H | H | H | H |
| 80 | 2,3-diMe-phenyl- | H | H | H | H | H | H |

TABLE 3-continued

X = —SO$_2$—, q = 0, r = 0, Y = —(R4)C=C(R5)—

| Compound No. 3- | R1—(CH2)p— | R2 | R3 | R4 | R5 | R6 | R7 |
|---|---|---|---|---|---|---|---|
| 81 | 3-fluorobenzyl | H | H | H | H | H | H |
| 82 | 2,4-dichlorobenzyl | H | H | H | H | H | H |
| 83 | 3-cyanobenzyl | H | H | H | H | H | H |
| 84 | 3-hydroxybenzyl | H | H | H | H | H | H |
| 85 | 3-ethoxybenzyl | H | H | H | H | H | H |
| 86 | 4-chloro-3-nitrobenzyl | H | H | H | H | H | H |
| 87 | 2,3-dichlorobenzyl | H | H | H | H | H | H |
| 88 | 2,3-difluoro-4-methylbenzyl | H | H | H | H | H | H |
| 89 | 3-bromo-4-fluorobenzyl | H | H | H | H | H | H |
| 90 | 2-fluoro-3-(trifluoromethyl)benzyl | H | H | H | H | H | H |
| 91 | 3-chloro-4-hydroxybenzyl | H | H | H | H | H | H |

TABLE 3-continued
X = —SO₂—, q = 0, r = 0, Y = —(R4)C═C(R5)—
| Compound No. 3- | R1—(CH2)p— | R2 | R3 | R4 | R5 | R6 | R7 |
|---|---|---|---|---|---|---|---|
| 92 | 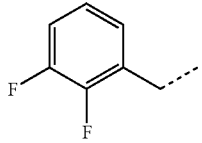 | H | H | H | H | H | H |
| 93 | 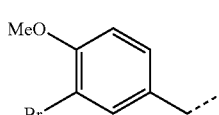 | H | H | H | H | H | H |
| 94 | 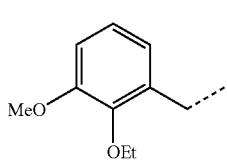 | H | H | H | H | H | H |
| 95 | 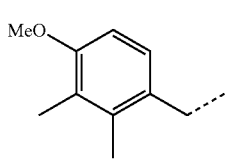 | H | H | H | H | H | H |
| 96 | 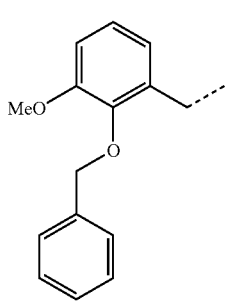 | H | H | H | H | H | H |
| 97 | 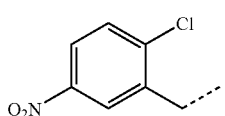 | H | H | H | H | H | H |
| 98 | 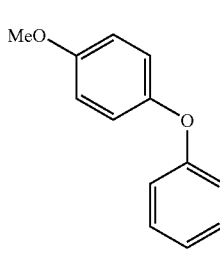 | H | H | H | H | H | H |
| 99 | 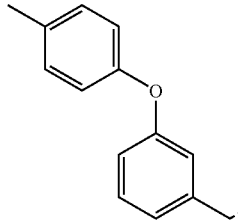 | H | H | H | H | H | H |

TABLE 3-continued
X = —SO₂—, q = 0, r = 0, Y = —(R4)C=C(R5)—
| Compound No. 3- | R1—(CH2)p— | R2 | R3 | R4 | R5 | R6 | R7 |
|---|---|---|---|---|---|---|---|
| 100 | 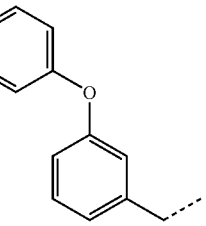 | H | H | H | H | H | H |
| 101 | 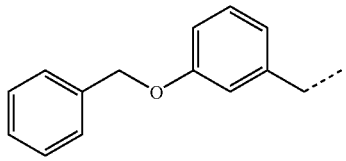 | H | H | H | H | H | H |
| 102 | 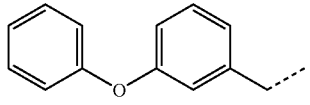 | H | H | H | H | H | H |
| 103 | 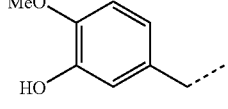 | H | H | H | H | H | H |
| 104 | 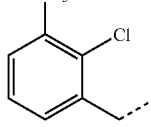 | H | H | H | H | H | H |
| 105 | 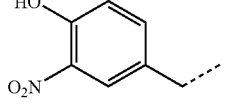 | H | H | H | H | H | H |
| 106 | 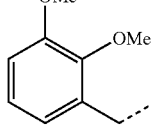 | H | H | H | H | H | H |
| 107 | 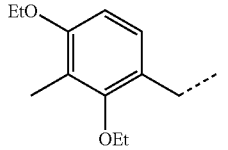 | H | H | H | H | H | H |
| 108 | 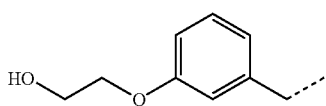 | H | H | H | H | H | H |

TABLE 3-continued

X = —SO₂—, q = 0, r = 0, Y = —(R4)C=C(R5)—

| Compound No. 3- | R1—(CH2)p— | R2 | R3 | R4 | R5 | R6 | R7 |
|---|---|---|---|---|---|---|---|
| 109 | 2,3,4-trimethoxybenzyl (MeO, OMe, OMe) | H | H | H | H | H | H |
| 110 | 2-fluoro-3-phenoxybenzyl | H | H | H | H | H | H |
| 111 | 2,3-dimethoxy-6-carboxybenzyl (MeO, OMe, COOH) | H | H | H | H | H | H |
| 112 | 5-chloro-2-nitrobenzyl | H | H | H | H | H | H |
| 113 | 3,5-dihydroxybenzyl | H | H | H | H | H | H |
| 114 | 3-benzyloxy-4-methoxybenzyl | H | H | H | H | H | H |
| 115 | 3,4-diethoxybenzyl | H | H | H | H | H | H |
| 116 | 3-carboxybenzyl | H | H | H | H | H | H |
| 117 | 3-hydroxy-4-methoxybenzyl | H | H | H | H | H | H |
| 118 | 3-hydroxy-4-nitrobenzyl | H | H | H | H | H | H |

TABLE 3-continued

| | X = —SO₂—, q = 0, r = 0, Y = —(R4)C=C(R5)— | | | | | | |
|---|---|---|---|---|---|---|---|
| Compound No. 3- | R1—(CH2)p— | R2 | R3 | R4 | R5 | R6 | R7 |
| 119 | 3,5-bis(trifluoromethyl)benzyl | H | H | H | H | H | H |
| 120 | 2-methoxy-3-nitrobenzyl | H | H | H | H | H | H |
| 121 | (4-methylnaphthalen-1-yl)methyl | H | H | H | H | H | H |
| 122 | (1,7-dimethyl-1H-indol-3-yl)methyl | H | H | H | H | H | H |
| 123 | (2-methoxynaphthalen-1-yl)methyl | H | H | H | H | H | H |
| 124 | benzofuran-2-ylmethyl | H | H | H | H | H | H |
| 125 | (1,2-dimethyl-1H-indol-3-yl)methyl | H | H | H | H | H | H |
| 126 | quinolin-8-ylmethyl | H | H | H | H | H | H |

TABLE 3-continued

X = —SO₂—, q = 0, r = 0, Y = —(R4)C=C(R5)—

| Compound No. 3- | R1—(CH2)p— | R2 | R3 | R4 | R5 | R6 | R7 |
|---|---|---|---|---|---|---|---|
| 127 | 2-hydroxynaphthalen-1-ylmethyl | H | H | H | H | H | H |
| 128 | 2-acetoxynaphthalen-1-ylmethyl | H | H | H | H | H | H |
| 129 | 1-hydroxynaphthalen-2-ylmethyl | H | H | H | H | H | H |
| 130 | 1H-indol-7-ylmethyl | H | H | H | H | H | H |
| 131 | quinolin-4-ylmethyl | H | H | H | H | H | H |
| 132 | 1-methyl-5-methyl-1H-indol-3-ylmethyl | H | H | H | H | H | H |
| 133 | anthracen-9-ylmethyl | H | H | H | H | H | H |

TABLE 3-continued

X = —SO₂—, q = 0, r = 0, Y = —(R4)C=C(R5)—

| Compound No. 3- | R1—(CH2)p— | R2 | R3 | R4 | R5 | R6 | R7 |
|---|---|---|---|---|---|---|---|
| 134 | 2-methylnaphthalen-1-ylmethyl | H | H | H | H | H | H |
| 135 | 2-ethoxynaphthalen-1-ylmethyl | H | H | H | H | H | H |
| 136 | 1H-indol-3-ylmethyl | H | H | H | H | H | H |
| 137 | 1,6-dimethyl-1H-indol-3-ylmethyl | H | H | H | H | H | H |
| 138 | 1-methyl-1H-indol-2-ylmethyl | H | H | H | H | H | H |
| 139 | 1,4-dimethyl-1H-indol-3-ylmethyl | H | H | H | H | H | H |
| 140 | 1,2,5-trimethyl-1H-indol-3-ylmethyl | H | H | H | H | H | H |

TABLE 3-continued

X = —SO₂—, q = 0, r = 0, Y = —(R4)C═C(R5)—

| Compound No. 3- | R1—(CH2)p— | R2 | R3 | R4 | R5 | R6 | R7 |
|---|---|---|---|---|---|---|---|
| 141 | 5-OMe, N-Me-indol-3-yl-methyl | H | H | H | H | H | H |
| 142 | 4-Me-benzothiophen-3-yl-methyl | H | H | H | H | H | H |
| 143 | 1-Me-benzimidazol-2-yl-methyl | H | H | H | H | H | H |
| 144 | N-Me, 2-phenyl-indol-3-yl-methyl | H | H | H | H | H | H |
| 145 | N-acetyl-indol-3-yl-methyl | H | H | H | H | H | H |
| 146 | quinolin-2-yl-methyl | H | H | H | H | H | H |
| 147 | 6-OMe, N-Me-indol-3-yl-methyl | H | H | H | H | H | H |
| 148 | 3-Me-benzothiophen-2-yl-methyl | H | H | H | H | H | H |

TABLE 3-continued

X = —SO₂—, q = 0, r = 0, Y = —(R4)C═C(R5)—

| Compound No. 3- | R1—(CH2)p— | R2 | R3 | R4 | R5 | R6 | R7 |
|---|---|---|---|---|---|---|---|
| 149 | 4-methoxynaphthalen-1-ylmethyl | H | H | H | H | H | H |
| 150 | phenanthren-9-ylmethyl | H | H | H | H | H | H |
| 151 | 6-methoxynaphthalen-2-ylmethyl | H | H | H | H | H | H |
| 152 | 1-bromonaphthalen-2-ylmethyl | H | H | H | H | H | H |
| 153 | 4-(dimethylamino)naphthalen-1-ylmethyl | H | H | H | H | H | H |
| 154 | 2,3-dihydro-1,4-benzodioxin-6-ylmethyl | H | H | H | H | H | H |
| 155 | 2,2-dimethylchroman-6-ylmethyl | H | H | H | H | H | H |
| 156 | 2,3-dihydrobenzofuran-5-ylmethyl | H | H | H | H | H | H |
| 157 | 9-ethylcarbazol-3-ylmethyl | H | H | H | H | H | H |

TABLE 3-continued
X = —SO₂—, q = 0, r = 0, Y = —(R4)C=C(R5)—
| Compound No. 3- | R1—(CH2)p— | R2 | R3 | R4 | R5 | R6 | R7 |
|---|---|---|---|---|---|---|---|
| 158 | 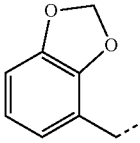 | H | H | H | H | H | H |
| 159 | 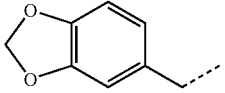 | H | H | H | H | H | H |
| 160 | 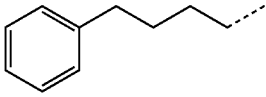 | H | H | H | H | H | H |
| 161 | 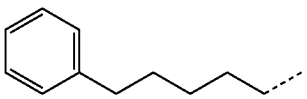 | H | H | H | H | H | H |
| 162 | 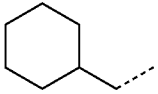 | H | H | H | H | H | H |
| 163 | 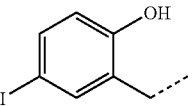 | H | H | H | H | H | H |
| 164 | 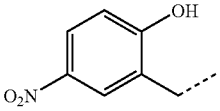 | H | H | H | H | H | H |
| 165 | 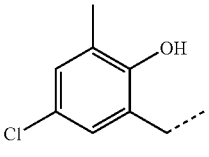 | H | H | H | H | H | H |
| 166 | 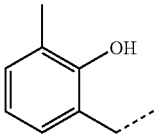 | H | H | H | H | H | H |
| 167 | 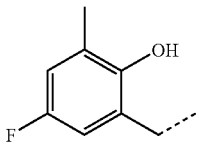 | H | H | H | H | H | H |
| 168 | 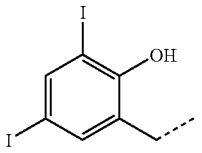 | H | H | H | H | H | H |

TABLE 3-continued

X = —SO$_2$—, q = 0, r = 0, Y = —(R4)C=C(R5)—

| Compound No. 3- | R1—(CH2)p— | R2 | R3 | R4 | R5 | R6 | R7 |
|---|---|---|---|---|---|---|---|
| 169 | 4-Cl-2-NH$_2$-benzyl | H | H | H | H | H | H |
| 170 | 2-OH-benzyl | H | H | H | H | H | H |
| 171 | 2-NH$_2$-benzyl | H | H | H | H | H | H |
| 172 | 4-tBu-2-OH-benzyl | H | H | H | H | H | H |
| 173 | 4-OCF$_3$-2-OH-benzyl | H | H | H | H | H | H |
| 174 | 3-OMe-2-OH-benzyl | H | H | H | H | H | H |
| 175 | 2,3-diOH-benzyl | H | H | H | H | H | H |
| 176 | 3-OEt-2-OH-benzyl | H | H | H | H | H | H |
| 177 | 3-COOH-2-OH-benzyl | H | H | H | H | H | H |
| 178 | 3-tBu-2-OH-benzyl | H | H | H | H | H | H |

TABLE 3-continued

X = —SO₂—, q = 0, r = 0, Y = —(R4)C═C(R5)—

| Compound No. 3- | R1—(CH2)p— | R2 | R3 | R4 | R5 | R6 | R7 |
|---|---|---|---|---|---|---|---|
| 179 | 2-furyl-CH₂- | H | H | H | H | H | H |
| 180 | oxazol-2-yl-CH₂- | H | H | H | H | H | H |
| 181 | imidazol-2-yl-CH₂- | H | H | H | H | H | H |
| 182 | thiazol-2-yl-CH₂- | H | H | H | H | H | H |
| 183 | pyrazol-3-yl-CH₂- | H | H | H | H | H | H |
| 184 | 1-phenyl-3,5-dimethyl-pyrazol-4-yl-CH₂- | H | H | H | H | H | H |
| 185 | 1-phenyl-2,5-dimethyl-pyrrol-3-yl-CH₂- | H | H | H | H | H | H |
| 186 | 5-(4-chlorophenyl)-furan-2-yl-CH₂- | H | H | H | H | H | H |
| 187 | thiophen-2-yl-CH₂- | H | H | H | H | H | H |
| 188 | pyrrol-2-yl-CH₂- | H | H | H | H | H | H |
| 189 | pyridin-2-yl-CH₂- | H | H | H | H | H | H |
| 190 | pyridin-3-yl-CH₂- | H | H | H | H | H | H |

TABLE 3-continued

X = —SO₂—, q = 0, r = 0, Y = —(R4)C=C(R5)—

| Compound No. 3- | R1—(CH2)p— | R2 | R3 | R4 | R5 | R6 | R7 |
|---|---|---|---|---|---|---|---|
| 191 | 4-pyridylmethyl | H | H | H | H | H | H |
| 192 | 5-chloro-2-hydroxybenzyl | H | H | H | Cl | H | H |
| 193 | 5-nitro-2-hydroxybenzyl | H | H | H | Cl | H | H |
| 194 | 5-methoxy-2-hydroxybenzyl | H | H | H | Cl | H | H |
| 195 | 3-chlorobenzyl | H | H | H | Cl | H | H |
| 196 | 3-bromobenzyl | H | H | H | Cl | H | H |
| 197 | 3-nitrobenzyl | H | H | H | Cl | H | H |
| 198 | 3-methoxybenzyl | H | H | H | Cl | H | H |
| 199 | 3,5-dichloro-2-hydroxybenzyl | H | H | H | Cl | H | H |
| 200 | 1-methylindol-3-ylmethyl | H | H | H | Cl | H | H |
| 201 | benzothiophen-3-ylmethyl | H | H | H | Cl | H | H |

TABLE 3-continued
X = —SO$_2$—, q = 0, r = 0, Y = —(R4)C=C(R5)—
| Compound No. 3- | R1—(CH2)p— | R2 | R3 | R4 | R5 | R6 | R7 |
|---|---|---|---|---|---|---|---|
| 202 | 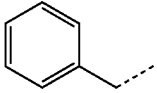 | H | H | H | Cl | H | H |
| 203 | 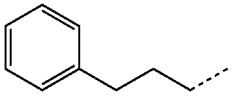 | H | H | H | Cl | H | H |
| 204 | 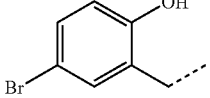 | H | H | H | Cl | H | H |
| 205 | 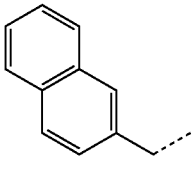 | H | H | H | Cl | H | H |
| 206 | 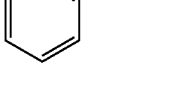 | H | H | H | Cl | H | H |
| 207 | 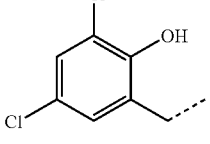 | H | H | Cl | H | H | H |
| 208 | 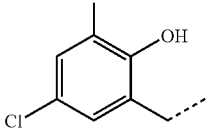 | H | H | H | OMe | H | H |
| 209 | 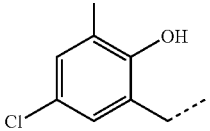 | H | H | H | COOMe | H | H |
| 210 | 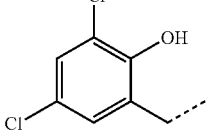 | H | H | H | H | Cl | H |
| 211 | 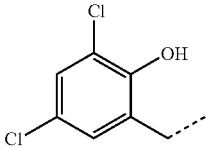 | H | H | H | H | COOMe | H |

TABLE 3-continued
X = —SO₂—, q = 0, r = 0, Y = —(R4)C=C(R5)—
| Compound No. 3- | R1—(CH2)p— | R2 | R3 | R4 | R5 | R6 | R7 |
|---|---|---|---|---|---|---|---|
| 212 | 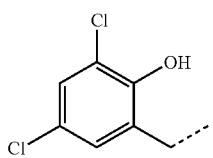 | H | H | H | H | H | Cl |
| 213 | 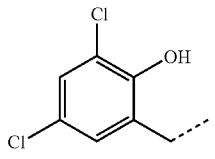 | H | H | H | OCF3 | H | H |
| 214 | 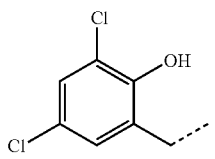 | H | H | COOMe | H | H | H |
| 215 | 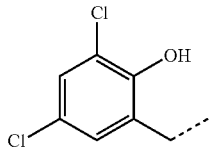 | H | H | H | CF3 | H | H |
| 216 | 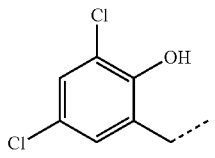 | H | H | H | OH | H | H |
| 217 | 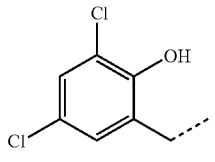 | H | H | H | NO2 | H | H |
| 218 | 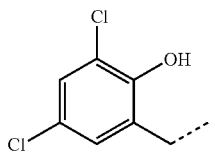 | H | H | H | F | F | H |
| 219 | 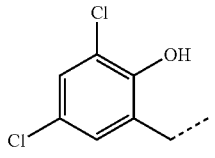 | H | H | F | H | H | H |
| 220 | 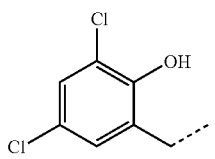 | H | H | Me | H | H | H |

TABLE 3-continued

X = —SO$_2$—, q = 0, r = 0, Y = —(R4)C=C(R5)—

| Compound No. 3- | R1—(CH2)p— | R2 | R3 | R4 | R5 | R6 | R7 |
|---|---|---|---|---|---|---|---|
| 221 | 2,4-dichloro-6-hydroxyphenyl-CH | H | H | H | CN | H | H |
| 222 | 2,4-dichloro-6-hydroxyphenyl-CH | H | H | Cl | H | H | H |
| 223 | 2,4-dichloro-6-hydroxyphenyl-CH | H | H | H | OMe | H | H |
| 224 | 2,4-dichloro-6-hydroxyphenyl-CH | H | H | H | COOMe | H | H |
| 225 | 2,4-dichloro-6-hydroxyphenyl-CH | H | H | H | H | Cl | H |
| 226 | 2,4-dichloro-6-hydroxyphenyl-CH | H | H | H | H | COOMe | H |
| 227 | 2,4-dichloro-6-hydroxyphenyl-CH | H | H | H | H | H | Cl |
| 228 | 2,4-dichloro-6-hydroxyphenyl-CH | H | H | H | OCF3 | H | H |
| 229 | 2,4-dichloro-6-hydroxyphenyl-CH | H | H | COOMe | H | H | H |

TABLE 3-continued

X = —SO₂—, q = 0, r = 0, Y = —(R4)C═C(R5)—

| Compound No. 3- | R1—(CH2)p— | R2 | R3 | R4 | R5 | R6 | R7 |
|---|---|---|---|---|---|---|---|
| 230 | 2,4-dichloro-6-(hydroxyphenyl)methyl | H | H | H | CF3 | H | H |
| 231 | 2,4-dichloro-6-(hydroxyphenyl)methyl | H | H | H | OH | H | H |
| 232 | 2,4-dichloro-6-(hydroxyphenyl)methyl | H | H | H | NO2 | H | H |
| 233 | 2,4-dichloro-6-(hydroxyphenyl)methyl | H | H | H | F | F | H |
| 234 | 2,4-dichloro-6-(hydroxyphenyl)methyl | H | H | F | H | H | H |
| 235 | 2,4-dichloro-6-(hydroxyphenyl)methyl | H | H | Me | H | H | H |
| 236 | 2,4-dichloro-6-(hydroxyphenyl)methyl | H | H | H | CN | H | H |
| 237 | 1-naphthylmethyl | H | H | Cl | H | H | H |
| 238 | 1-naphthylmethyl | H | H | H | OMe | H | H |

TABLE 3-continued

X = —SO₂—, q = 0, r = 0, Y = —(R4)C=C(R5)—

| Compound No. 3- | R1—(CH2)p— | R2 | R3 | R4 | R5 | R6 | R7 |
|---|---|---|---|---|---|---|---|
| 239 | naphthalen-1-ylmethyl | H | H | H | COOMe | H | H |
| 240 | naphthalen-1-ylmethyl | H | H | H | H | Cl | H |
| 241 | naphthalen-1-ylmethyl | H | H | H | H | COOMe | H |
| 242 | naphthalen-1-ylmethyl | H | H | H | H | H | Cl |
| 243 | naphthalen-1-ylmethyl | H | H | H | OCF3 | H | H |
| 244 | naphthalen-1-ylmethyl | H | H | COOMe | H | H | H |
| 245 | naphthalen-1-ylmethyl | H | H | H | CF3 | H | H |
| 246 | naphthalen-1-ylmethyl | H | H | H | OH | H | H |

TABLE 3-continued

X = —SO₂—, q = 0, r = 0, Y = —(R4)C=C(R5)—

| Compound No. 3- | R1—(CH2)p— | R2 | R3 | R4 | R5 | R6 | R7 |
|---|---|---|---|---|---|---|---|
| 247 | naphthyl-CH₂ | H | H | H | NO2 | H | H |
| 248 | naphthyl-CH₂ | H | H | H | F | F | H |
| 249 | naphthyl-CH₂ | H | H | F | H | H | H |
| 250 | naphthyl-CH₂ | H | H | Me | H | H | H |
| 251 | naphthyl-CH₂ | H | H | H | CN | H | H |
| 252 | Ph-(CH₂)₂— | H | H | Cl | H | H | H |
| 253 | Ph-(CH₂)₂— | H | H | H | OMe | H | H |
| 254 | Ph-(CH₂)₂— | H | H | H | COOMe | H | H |
| 255 | Ph-(CH₂)₂— | H | H | H | H | Cl | H |
| 256 | Ph-(CH₂)₂— | H | H | H | H | COOMe | H |
| 257 | Ph-(CH₂)₂— | H | H | H | H | H | Cl |

TABLE 3-continued

X = —SO₂—, q = 0, r = 0, Y = —(R4)C=C(R5)—

| Compound No. 3- | R1—(CH2)p— | R2 | R3 | R4 | R5 | R6 | R7 |
|---|---|---|---|---|---|---|---|
| 258 | phenyl-(CH2)2- | H | H | H | OCF3 | H | H |
| 259 | phenyl-(CH2)2- | H | H | COOMe | H | H | H |
| 260 | phenyl-(CH2)2- | H | H | H | CF3 | H | H |
| 261 | phenyl-(CH2)2- | H | H | H | Me | H | H |
| 262 | phenyl-(CH2)2- | H | H | H | F | H | H |
| 263 | phenyl-(CH2)2- | H | H | H | OH | H | H |
| 264 | phenyl-(CH2)2- | H | H | H | NO2 | H | H |
| 265 | phenyl-(CH2)2- | H | H | H | F | F | H |
| 266 | phenyl-(CH2)2- | H | H | F | H | H | H |
| 267 | phenyl-(CH2)2- | H | H | Me | H | H | H |
| 268 | phenyl-(CH2)2- | H | H | H | CN | H | H |
| 269 | 2,4-dichloro-6-hydroxyphenyl-CH2- | H | H | H | H | H | COOMe |

TABLE 3-continued

X = —SO₂—, q = 0, r = 0, Y = —(R4)C=C(R5)—

| Compound No. 3- | R1—(CH2)p— | R2 | R3 | R4 | R5 | R6 | R7 |
|---|---|---|---|---|---|---|---|
| 270 | 2,4-dichloro-6-hydroxyphenylmethyl | H | H | H | H | F | H |
| 271 | 2,4-dichloro-6-hydroxyphenylmethyl | H | H | H | H | H | F |
| 272 | 2,4-dichloro-6-hydroxyphenylmethyl | H | H | H | H | Me | H |
| 273 | 2,4-dichloro-6-hydroxyphenylmethyl | H | H | H | H | H | Me |
| 274 | 2,4-dichloro-6-hydroxyphenylmethyl | H | H | OMe | H | H | H |
| 275 | 2,4-dichloro-6-hydroxyphenylmethyl | H | H | H | H | OMe | H |
| 276 | 2,4-dichloro-6-hydroxyphenylmethyl | H | H | H | H | H | OMe |
| 277 | 2,4-dichloro-6-hydroxyphenylmethyl | H | H | CF3 | H | H | H |
| 278 | 2,4-dichloro-6-hydroxyphenylmethyl | H | H | H | H | CF3 | H |

TABLE 3-continued

X = —SO₂—, q = 0, r = 0, Y = —(R4)C=C(R5)—

| Compound No. 3- | R1—(CH2)p— | R2 | R3 | R4 | R5 | R6 | R7 |
|---|---|---|---|---|---|---|---|
| 279 | 2,4-dichloro-6-hydroxyphenyl | H | H | H | H | H | CF3 |
| 280 | 2,4-dichloro-6-hydroxyphenyl | H | H | OH | H | H | H |
| 281 | 2,4-dichloro-6-hydroxyphenyl | H | H | H | H | OH | H |
| 282 | 2,4-dichloro-6-hydroxyphenyl | H | H | H | H | H | OH |
| 283 | 2,4-dichloro-6-hydroxyphenyl | H | H | OCF3 | H | H | H |
| 284 | 2,4-dichloro-6-hydroxyphenyl | H | H | H | H | OCF3 | H |
| 285 | 2,4-dichloro-6-hydroxyphenyl | H | H | H | H | H | OCF3 |
| 286 | 2,4-dichloro-6-hydroxyphenyl | H | H | NO2 | H | H | H |
| 287 | 2,4-dichloro-6-hydroxyphenyl | H | H | H | H | NO2 | H |

TABLE 3-continued

X = —SO$_2$—, q = 0, r = 0, Y = —(R4)C=C(R5)—

| Compound No. 3- | R1—(CH2)p— | R2 | R3 | R4 | R5 | R6 | R7 |
|---|---|---|---|---|---|---|---|
| 288 | 2,4-dichloro-6-hydroxyphenyl | H | H | H | H | H | NO2 |
| 289 | 2,4-dichloro-6-hydroxyphenyl | H | H | CN | H | H | H |
| 290 | 2,4-dichloro-6-hydroxyphenyl | H | H | H | H | CN | H |
| 291 | 2,4-dichloro-6-hydroxyphenyl | H | H | H | H | H | CN |
| 292 | 2,4-dichloro-6-hydroxyphenyl | H | H | Br | H | H | H |
| 293 | 2,4-dichloro-6-hydroxyphenyl | H | H | H | Br | H | H |
| 294 | 2,4-dichloro-6-hydroxyphenyl | H | H | H | H | Br | H |
| 295 | 2,4-dichloro-6-hydroxyphenyl | H | H | H | H | H | Br |
| 296 | 2,4-dichloro-6-hydroxyphenyl | H | H | COOH | H | H | H |

TABLE 3-continued

X = —SO₂—, q = 0, r = 0, Y = —(R4)C=C(R5)—

| Compound No. 3- | R1—(CH2)p— | R2 | R3 | R4 | R5 | R6 | R7 |
|---|---|---|---|---|---|---|---|
| 297 | 2,4-dichloro-6-hydroxyphenyl-CH | H | H | H | COOH | H | H |
| 298 | 2,4-dichloro-6-hydroxyphenyl-CH | H | H | H | H | COOH | H |
| 299 | 2,4-dichloro-6-hydroxyphenyl-CH | H | H | H | H | H | COOH |
| 300 | 2,4-dichloro-6-hydroxyphenyl-CH | H | H | NHCOMe | H | H | H |
| 301 | 2,4-dichloro-6-hydroxyphenyl-CH | H | H | H | NHCOMe | H | H |
| 302 | 2,4-dichloro-6-hydroxyphenyl-CH | H | H | H | H | NHCOMe | H |
| 303 | 2,4-dichloro-6-hydroxyphenyl-CH | H | H | H | H | H | NHCOMe |
| 304 | 2,4-dichloro-6-hydroxyphenyl-CH | H | H | SO2NH2 | H | H | H |
| 305 | 2,4-dichloro-6-hydroxyphenyl-CH | H | H | H | SO2NH2 | H | H |

TABLE 3-continued
X = —SO$_2$—, q = 0, r = 0, Y = —(R4)C=C(R5)—
| Compound No. 3- | R1—(CH2)p— | R2 | R3 | R4 | R5 | R6 | R7 |
|---|---|---|---|---|---|---|---|
| 306 | 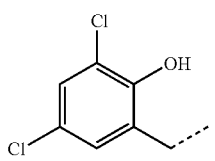 | H | H | H | H | SO2NH2 | H |
| 307 | 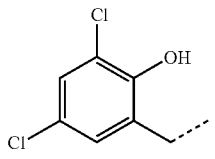 | H | H | H | H | H | SO2NH2 |
| 308 | 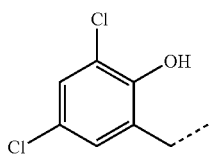 | H | H | Me | Me | H | H |
| 309 | 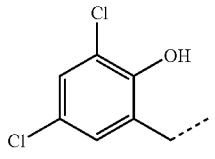 | H | H | Me | H | Me | H |
| 310 | 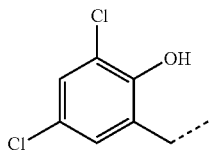 | H | H | H | Me | Me | H |
| 311 | 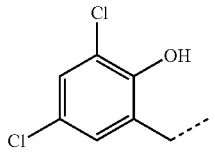 | H | H | F | F | H | H |
| 312 | 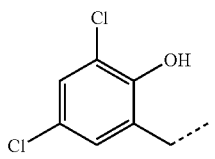 | H | H | F | H | F | H |
| 313 | 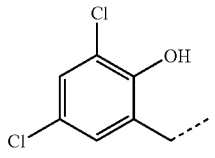 | H | H | H | F | F | H |
| 314 | 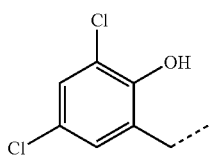 | H | H | Cl | Cl | H | H |

TABLE 3-continued
X = —SO$_2$—, q = 0, r = 0, Y = —(R4)C=C(R5)—
| Compound No. 3- | R1—(CH2)p— | R2 | R3 | R4 | R5 | R6 | R7 |
|---|---|---|---|---|---|---|---|
| 315 | 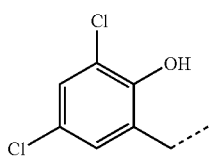 | H | H | Cl | H | Cl | H |
| 316 | 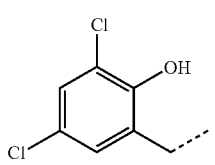 | H | H | H | Cl | Cl | H |
| 317 | 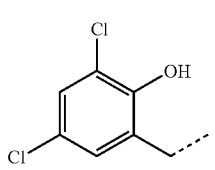 | H | H | Me | F | H | H |
| 318 | 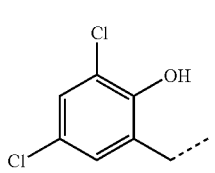 | H | H | Me | Cl | H | H |
| 319 | 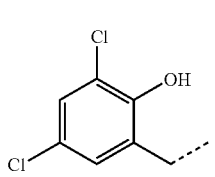 | H | H | Me | OH | H | H |
| 320 | 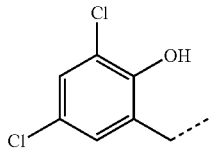 | H | H | Me | OMe | H | H |
| 321 | 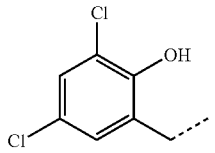 | H | H | F | Me | H | H |
| 322 |  | H | H | F | Cl | H | H |
| 323 |  | H | H | F | OH | H | H |

TABLE 3-continued
X = —SO₂—, q = 0, r = 0, Y = —(R4)C=C(R5)—
| Compound No. 3- | R1—(CH2)p— | R2 | R3 | R4 | R5 | R6 | R7 |
|---|---|---|---|---|---|---|---|
| 324 | 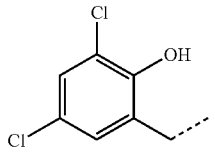 | H | H | F | OMe | H | H |
| 325 | 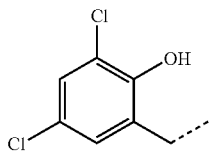 | H | H | Cl | Me | H | H |
| 326 | 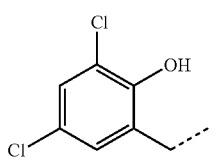 | H | H | Cl | F | H | H |
| 327 | 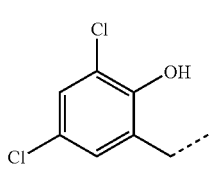 | H | H | Cl | OH | H | H |
| 328 | 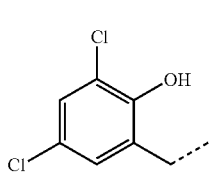 | H | H | Cl | OMe | H | H |
| 329 | 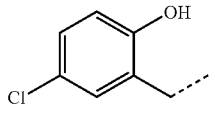 | H | H | H | H | H | COOMe |
| 330 | 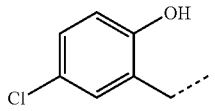 | H | H | H | H | F | H |
| 331 |  | H | H | H | H | H | F |
| 332 |  | H | H | H | H | Me | H |
| 333 |  | H | H | H | H | H | Me |

TABLE 3-continued
X = —SO₂—, q = 0, r = 0, Y = —(R4)C=C(R5)—
| Compound No. 3- | R1—(CH2)p— | R2 | R3 | R4 | R5 | R6 | R7 |
|---|---|---|---|---|---|---|---|
| 334 | 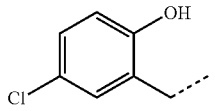 | H | H | OMe | H | H | H |
| 335 | 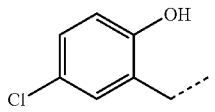 | H | H | H | H | OMe | H |
| 336 | 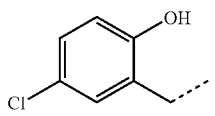 | H | H | H | H | H | OMe |
| 337 | 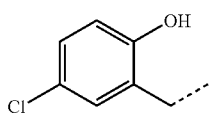 | H | H | CF3 | H | H | H |
| 338 | 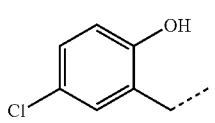 | H | H | H | H | CF3 | H |
| 339 | 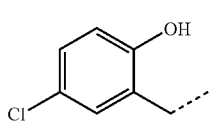 | H | H | H | H | H | CF3 |
| 340 | 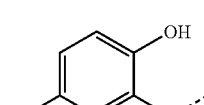 | H | H | OH | H | H | H |
| 341 | 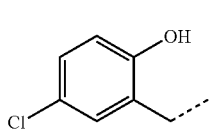 | H | H | H | H | OH | H |
| 342 | 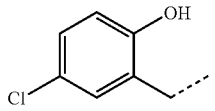 | H | H | H | H | H | OH |
| 343 | 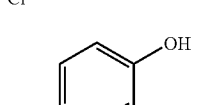 | H | H | OCF3 | H | H | H |
| 344 | 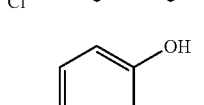 | H | H | H | H | OCF3 | H |
| 345 | 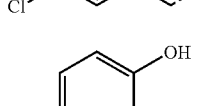 | H | H | H | H | H | OCF3 |

TABLE 3-continued
X = —SO$_2$—, q = 0, r = 0, Y = —(R4)C=C(R5)—
| Compound No. 3- | R1—(CH2)p— | R2 | R3 | R4 | R5 | R6 | R7 |
|---|---|---|---|---|---|---|---|
| 346 | 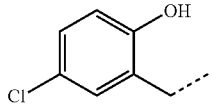 | H | H | NO2 | H | H | H |
| 347 | 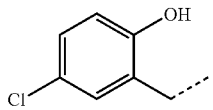 | H | H | H | H | NO2 | H |
| 348 | 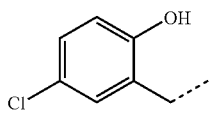 | H | H | H | H | H | NO2 |
| 349 | 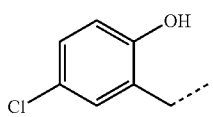 | H | H | CN | H | H | H |
| 350 | 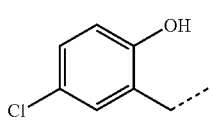 | H | H | H | H | CN | H |
| 351 | 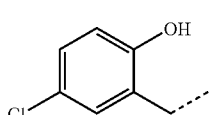 | H | H | H | H | H | CN |
| 352 | 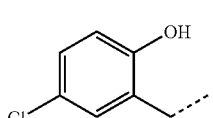 | H | H | Br | H | H | H |
| 353 | 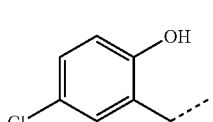 | H | H | H | Br | H | H |
| 354 | 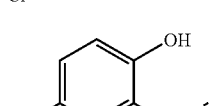 | H | H | H | H | Br | H |
| 355 | 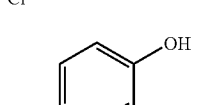 | H | H | H | H | H | Br |
| 356 | 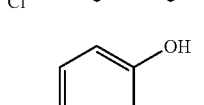 | H | H | COOH | H | H | H |
| 357 | 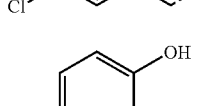 | H | H | H | COOH | H | H |

TABLE 3-continued
X = —SO₂—, q = 0, r = 0, Y = —(R4)C=C(R5)—
| Compound No. 3- | R1—(CH2)p— | R2 | R3 | R4 | R5 | R6 | R7 |
|---|---|---|---|---|---|---|---|
| 358 | 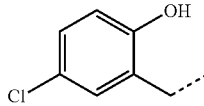 | H | H | H | H | COOH | H |
| 359 | 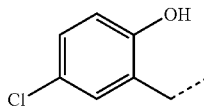 | H | H | H | H | H | COOH |
| 360 | 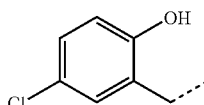 | H | H | NHCOMe | H | H | H |
| 361 | 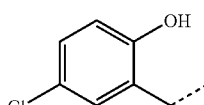 | H | H | H | NHCOMe | H | H |
| 362 | 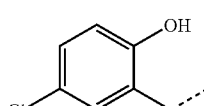 | H | H | H | H | NHCOMe | H |
| 363 | 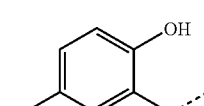 | H | H | H | H | H | NHCOMe |
| 364 | 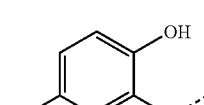 | H | H | SO2NH2 | H | H | H |
| 365 | 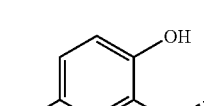 | H | H | H | SO2NH2 | H | H |
| 366 | 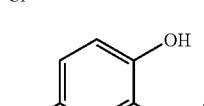 | H | H | H | H | SO2NH2 | H |
| 367 | 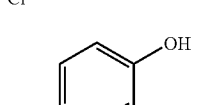 | H | H | H | H | H | SO2NH2 |
| 368 | 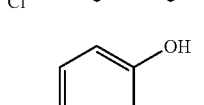 | H | H | Me | Me | H | H |
| 369 | 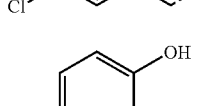 | H | H | Me | H | Me | H |

TABLE 3-continued

X = —SO$_2$—, q = 0, r = 0, Y = —(R4)C=C(R5)—

| Compound No. 3- | R1—(CH2)p— | R2 | R3 | R4 | R5 | R6 | R7 |
|---|---|---|---|---|---|---|---|
| 370 | 4-Cl, 2-OH-benzyl | H | H | H | Me | Me | H |
| 371 | 4-Cl, 2-OH-benzyl | H | H | F | F | H | H |
| 372 | 4-Cl, 2-OH-benzyl | H | H | F | H | F | H |
| 373 | 4-Cl, 2-OH-benzyl | H | H | H | F | F | H |
| 374 | 4-Cl, 2-OH-benzyl | H | H | Cl | Cl | H | H |
| 375 | 4-Cl, 2-OH-benzyl | H | H | Cl | H | Cl | H |
| 376 | 4-Cl, 2-OH-benzyl | H | H | H | Cl | Cl | H |
| 377 | 4-Cl, 2-OH-benzyl | H | H | Me | F | H | H |
| 378 | 4-Cl, 2-OH-benzyl | H | H | Me | Cl | H | H |
| 379 | 4-Cl, 2-OH-benzyl | H | H | Me | OH | H | H |
| 380 | 4-Cl, 2-OH-benzyl | H | H | Me | OMe | H | H |
| 381 | 4-Cl, 2-OH-benzyl | H | H | F | Me | H | H |

TABLE 3-continued
X = —SO$_2$—, q = 0, r = 0, Y = —(R4)C=C(R5)—
| Compound No. 3- | R1—(CH2)p— | R2 | R3 | R4 | R5 | R6 | R7 |
|---|---|---|---|---|---|---|---|
| 382 | 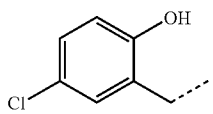 | H | H | F | Cl | H | H |
| 383 | 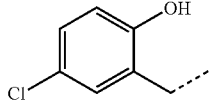 | H | H | F | OH | H | H |
| 384 | 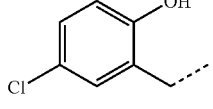 | H | H | F | OMe | H | H |
| 385 | 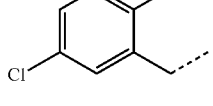 | H | H | Cl | Me | H | H |
| 386 | 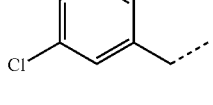 | H | H | Cl | F | H | H |
| 387 | 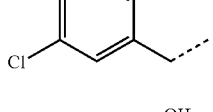 | H | H | Cl | OH | H | H |
| 388 | 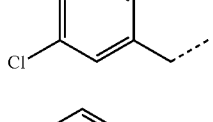 | H | H | Cl | OMe | H | H |
| 389 | 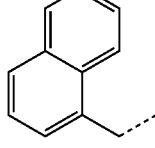 | H | H | H | H | H | COOMe |
| 390 | 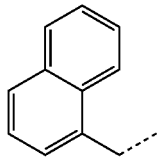 | H | H | H | H | F | H |
| 391 | 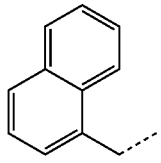 | H | H | H | H | H | F |

TABLE 3-continued
X = —SO₂—, q = 0, r = 0, Y = —(R4)C=C(R5)—
| Compound No. 3- | R1—(CH2)p— | R2 | R3 | R4 | R5 | R6 | R7 |
|---|---|---|---|---|---|---|---|
| 392 | 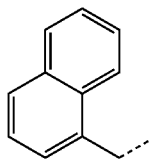 | H | H | H | H | Me | H |
| 393 | 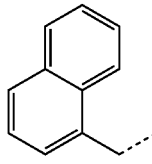 | H | H | H | H | H | Me |
| 394 | 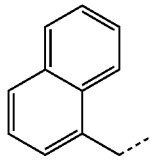 | H | H | OMe | H | H | H |
| 395 | 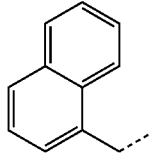 | H | H | H | H | OMe | H |
| 396 | 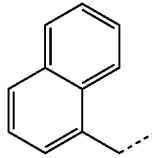 | H | H | H | H | H | OMe |
| 397 | 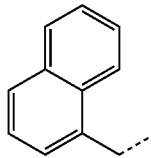 | H | H | CF3 | H | H | H |
| 398 | 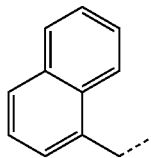 | H | H | H | H | CF3 | H |
| 399 | 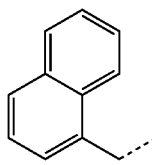 | H | H | H | H | H | CF3 |

TABLE 3-continued

X = —SO₂—, q = 0, r = 0, Y = —(R4)C═C(R5)—

| Compound No. 3- | R1—(CH2)p— | R2 | R3 | R4 | R5 | R6 | R7 |
|---|---|---|---|---|---|---|---|
| 400 | naphthyl-CH₂- | H | H | OH | H | H | H |
| 401 | naphthyl-CH₂- | H | H | H | H | OH | H |
| 402 | naphthyl-CH₂- | H | H | H | H | H | OH |
| 403 | naphthyl-CH₂- | H | H | OCF3 | H | H | H |
| 404 | naphthyl-CH₂- | H | H | H | H | OCF3 | H |
| 405 | naphthyl-CH₂- | H | H | H | H | H | OCF3 |
| 406 | naphthyl-CH₂- | H | H | NO2 | H | H | H |
| 407 | naphthyl-CH₂- | H | H | H | H | NO2 | H |

TABLE 3-continued

X = —SO₂—, q = 0, r = 0, Y = —(R4)C=C(R5)—

| Compound No. 3- | R1—(CH2)p— | R2 | R3 | R4 | R5 | R6 | R7 |
|---|---|---|---|---|---|---|---|
| 408 | naphthalen-1-ylmethyl | H | H | H | H | H | NO2 |
| 409 | naphthalen-1-ylmethyl | H | H | CN | H | H | H |
| 410 | naphthalen-1-ylmethyl | H | H | H | H | CN | H |
| 411 | naphthalen-1-ylmethyl | H | H | H | H | H | CN |
| 412 | naphthalen-1-ylmethyl | H | H | Br | H | H | H |
| 413 | naphthalen-1-ylmethyl | H | H | H | Br | H | H |
| 414 | naphthalen-1-ylmethyl | H | H | H | H | Br | H |
| 415 | naphthalen-1-ylmethyl | H | H | H | H | H | Br |

TABLE 3-continued
X = —SO₂—, q = 0, r = 0, Y = —(R4)C=C(R5)—
| Compound No. 3- | R1—(CH2)p— | R2 | R3 | R4 | R5 | R6 | R7 |
|---|---|---|---|---|---|---|---|
| 416 | 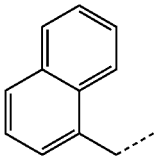 | H | H | COOH | H | H | H |
| 417 | 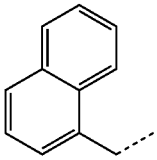 | H | H | H | COOH | H | H |
| 418 | 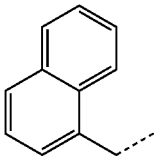 | H | H | H | H | COOH | H |
| 419 | 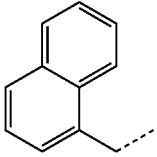 | H | H | H | H | H | COOH |
| 420 | 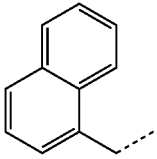 | H | H | NHCOMe | H | H | H |
| 421 | 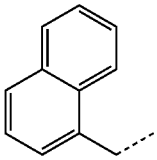 | H | H | H | NHCOMe | H | H |
| 422 | 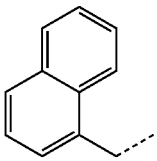 | H | H | H | H | NHCOMe | H |
| 423 | 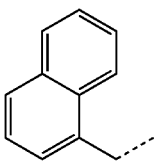 | H | H | H | H | H | NHCOMe |

TABLE 3-continued

X = —SO₂—, q = 0, r = 0, Y = —(R4)C=C(R5)—

| Compound No. 3- | R1—(CH2)p— | R2 | R3 | R4 | R5 | R6 | R7 |
|---|---|---|---|---|---|---|---|
| 424 | 1-naphthylmethyl | H | H | SO2NH2 | H | H | H |
| 425 | 1-naphthylmethyl | H | H | H | SO2NH2 | H | H |
| 426 | 1-naphthylmethyl | H | H | H | H | SO2NH2 | H |
| 427 | 1-naphthylmethyl | H | H | H | H | H | SO2NH2 |
| 428 | 1-naphthylmethyl | H | H | Me | Me | H | H |
| 429 | 1-naphthylmethyl | H | H | Me | H | Me | H |
| 430 | 1-naphthylmethyl | H | H | H | Me | Me | H |
| 431 | 1-naphthylmethyl | H | H | F | F | H | H |

TABLE 3-continued

X = —SO₂—, q = 0, r = 0, Y = —(R4)C=C(R5)—

| Compound No. 3- | R1—(CH2)p— | R2 | R3 | R4 | R5 | R6 | R7 |
|---|---|---|---|---|---|---|---|
| 432 | 1-naphthylmethyl | H | H | F | H | F | H |
| 433 | 1-naphthylmethyl | H | H | H | F | F | H |
| 434 | 1-naphthylmethyl | H | H | Cl | Cl | H | H |
| 435 | 1-naphthylmethyl | H | H | Cl | H | Cl | H |
| 436 | 1-naphthylmethyl | H | H | H | Cl | Cl | H |
| 437 | 1-naphthylmethyl | H | H | Me | F | H | H |
| 438 | 1-naphthylmethyl | H | H | Me | Cl | H | H |
| 439 | 1-naphthylmethyl | H | H | Me | OH | H | H |

TABLE 3-continued

X = —SO₂—, q = 0, r = 0, Y = —(R4)C=C(R5)—

| Compound No. 3- | R1—(CH2)p— | R2 | R3 | R4 | R5 | R6 | R7 |
|---|---|---|---|---|---|---|---|
| 440 | naphthyl-CH₂- | H | H | Me | OMe | H | H |
| 441 | naphthyl-CH₂- | H | H | F | Me | H | H |
| 442 | naphthyl-CH₂- | H | H | F | Cl | H | H |
| 443 | naphthyl-CH₂- | H | H | F | OH | H | H |
| 444 | naphthyl-CH₂- | H | H | F | OMe | H | H |
| 445 | naphthyl-CH₂- | H | H | Cl | Me | H | H |
| 446 | naphthyl-CH₂- | H | H | Cl | F | H | H |
| 447 | naphthyl-CH₂- | H | H | Cl | OH | H | H |

TABLE 3-continued

X = —SO₂—, q = 0, r = 0, Y = —(R4)C=C(R5)—

| Compound No. 3- | R1—(CH2)p— | R2 | R3 | R4 | R5 | R6 | R7 |
|---|---|---|---|---|---|---|---|
| 448 | naphthyl-CH₂- | H | H | Cl | OMe | H | H |
| 449 | 4-Br-2-(HO)-C₆H₃-CH₂- | H | H | Cl | H | H | H |
| 450 | 4-Br-2-(HO)-C₆H₃-CH₂- | H | H | H | OMe | H | H |
| 451 | 4-Br-2-(HO)-C₆H₃-CH₂- | H | H | H | COOMe | H | H |
| 452 | 4-Br-2-(HO)-C₆H₃-CH₂- | H | H | H | H | Cl | H |
| 453 | 4-Br-2-(HO)-C₆H₃-CH₂- | H | H | H | H | COOMe | H |
| 454 | 4-Br-2-(HO)-C₆H₃-CH₂- | H | H | H | H | H | Cl |
| 455 | 4-Br-2-(HO)-C₆H₃-CH₂- | H | H | H | OCF3 | H | H |
| 456 | 4-Br-2-(HO)-C₆H₃-CH₂- | H | H | COOMe | H | H | H |
| 457 | 4-Br-2-(HO)-C₆H₃-CH₂- | H | H | H | CF3 | H | H |
| 458 | 4-Br-2-(HO)-C₆H₃-CH₂- | H | H | H | Me | H | H |
| 459 | 4-Br-2-(HO)-C₆H₃-CH₂- | H | H | H | F | H | H |

TABLE 3-continued
X = —SO$_2$—, q = 0, r = 0, Y = —(R4)C=C(R5)—
| Compound No. 3- | R1—(CH2)p— | R2 | R3 | R4 | R5 | R6 | R7 |
|---|---|---|---|---|---|---|---|
| 460 | 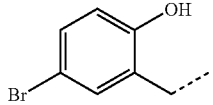 | H | H | H | OH | H | H |
| 461 | 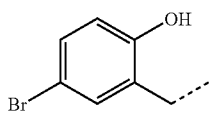 | H | H | H | NO2 | H | H |
| 462 | 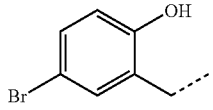 | H | H | H | F | F | H |
| 463 | 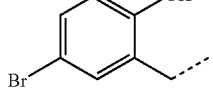 | H | H | F | H | H | H |
| 464 | 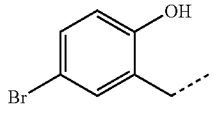 | H | H | Me | H | H | H |
| 465 | 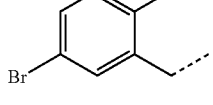 | H | H | H | CN | H | H |
| 466 | 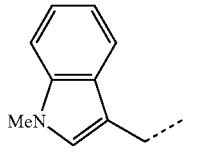 | H | H | Cl | H | H | H |
| 467 | 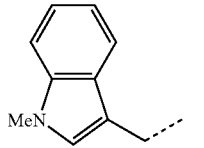 | H | H | H | OMe | H | H |
| 468 | 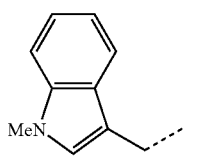 | H | H | H | COOMe | H | H |
| 469 | 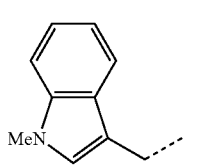 | H | H | H | H | Cl | H |

TABLE 3-continued
X = —SO$_2$—, q = 0, r = 0, Y = —(R4)C=C(R5)—
| Compound No. 3- | R1—(CH2)p— | R2 | R3 | R4 | R5 | R6 | R7 |
|---|---|---|---|---|---|---|---|
| 470 | 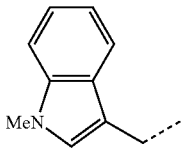 | H | H | H | H | COOMe | H |
| 471 | 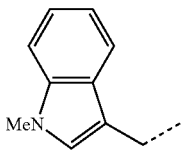 | H | H | H | H | H | Cl |
| 472 | 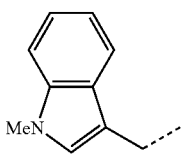 | H | H | H | OCF3 | H | H |
| 473 | 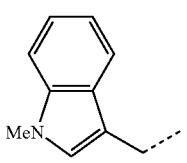 | H | H | COOMe | H | H | H |
| 474 | 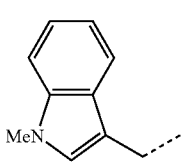 | H | H | H | CF3 | H | H |
| 475 | 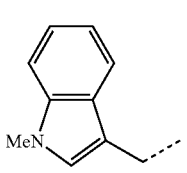 | H | H | H | Me | H | H |
| 476 | 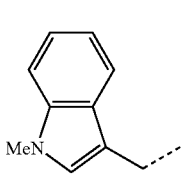 | H | H | H | F | H | H |
| 477 | 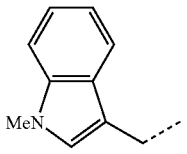 | H | H | H | OH | H | H |
| 478 | 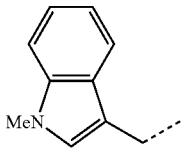 | H | H | H | NO2 | H | H |

TABLE 3-continued

X = —SO₂—, q = 0, r = 0, Y = —(R4)C=C(R5)—

| Compound No. 3- | R1—(CH2)p— | R2 | R3 | R4 | R5 | R6 | R7 |
|---|---|---|---|---|---|---|---|
| 479 | 1-methylindol-3-ylmethyl | H | H | H | F | F | H |
| 480 | 1-methylindol-3-ylmethyl | H | H | F | H | H | H |
| 481 | 1-methylindol-3-ylmethyl | H | H | Me | H | H | H |
| 482 | 1-methylindol-3-ylmethyl | H | H | H | CN | H | H |
| 483 | benzothiophen-3-ylmethyl | H | H | H | H | H | H |
| 484 | benzothiophen-3-ylmethyl | H | H | H | OMe | H | H |
| 485 | benzothiophen-3-ylmethyl | H | H | H | COOMe | H | H |
| 486 | benzothiophen-3-ylmethyl | H | H | H | H | Cl | H |
| 487 | benzothiophen-3-ylmethyl | H | H | H | H | COOMe | H |

TABLE 3-continued

X = —SO$_2$—, q = 0, r = 0, Y = —(R4)C=C(R5)—

| Compound No. 3- | R1—(CH2)p— | R2 | R3 | R4 | R5 | R6 | R7 |
|---|---|---|---|---|---|---|---|
| 488 | benzothiophen-3-ylmethyl | H | H | H | H | H | Cl |
| 489 | benzothiophen-3-ylmethyl | H | H | H | OCF3 | H | H |
| 490 | benzothiophen-3-ylmethyl | H | H | COOMe | H | H | H |
| 491 | benzothiophen-3-ylmethyl | H | H | H | CF3 | H | H |
| 492 | benzothiophen-3-ylmethyl | H | H | H | Me | H | H |
| 493 | benzothiophen-3-ylmethyl | H | H | H | F | H | H |
| 494 | benzothiophen-3-ylmethyl | H | H | H | OH | H | H |
| 495 | benzothiophen-3-ylmethyl | H | H | H | NO2 | H | H |
| 496 | benzothiophen-3-ylmethyl | H | H | H | F | F | H |

TABLE 3-continued

X = —SO$_2$—, q = 0, r = 0, Y = —(R4)C═C(R5)—

| Compound No. 3- | R1—(CH2)p— | R2 | R3 | R4 | R5 | R6 | R7 |
|---|---|---|---|---|---|---|---|
| 497 | benzothiophen-3-ylmethyl | H | H | F | H | H | H |
| 498 | benzothiophen-3-ylmethyl | H | H | Me | H | H | H |
| 499 | benzothiophen-3-ylmethyl | H | H | H | CN | H | H |
| 500 | 3,5-dichloro-2-hydroxybenzyl | H | Me | H | H | H | H |
| 501 | 5-chloro-2-hydroxybenzyl | H | Me | H | H | H | H |
| 502 | naphthalen-1-ylmethyl | H | Me | H | H | H | H |
| 503 | 3-phenylpropyl | H | Me | H | H | H | H |
| 504 | 3,5-dichloro-2-hydroxybenzyl | H | H | H | Et | H | H |
| 505 | 5-chloro-2-hydroxybenzyl | H | H | H | Et | H | H |
| 506 | naphthalen-1-ylmethyl | H | H | H | Et | H | H |

TABLE 3-continued

X = —SO₂—, q = 0, r = 0, Y = —(R4)C=C(R5)—

| Compound No. 3- | R1—(CH2)p— | R2 | R3 | R4 | R5 | R6 | R7 |
|---|---|---|---|---|---|---|---|
| 507 | phenyl-(CH2)3- | H | H | H | Et | H | H |
| 508 | 4-Cl-2-F-6-OH-benzyl | H | H | H | H | H | H |
| 509 | 4-Cl-2-F-6-OH-benzyl | H | H | F | H | H | H |
| 510 | 4-Cl-2-F-6-OH-benzyl | H | H | Cl | H | H | H |
| 511 | 4-Cl-2-F-6-OH-benzyl | H | H | Me | H | H | H |
| 512 | 4-Cl-2-F-6-OH-benzyl | H | H | Et | H | H | H |
| 513 | 4-Cl-2-F-6-OH-benzyl | H | H | OMe | H | H | H |
| 514 | 4-Cl-2-F-6-OH-benzyl | H | H | OEt | H | H | H |
| 515 | 4-Cl-2-F-6-OH-benzyl | H | H | CF3 | H | H | H |

TABLE 3-continued

X = —SO$_2$—, q = 0, r = 0, Y = —(R4)C=C(R5)—

| Compound No. 3- | R1—(CH2)p— | R2 | R3 | R4 | R5 | R6 | R7 |
|---|---|---|---|---|---|---|---|
| 516 | 4-Cl, 2-F, 6-OH-benzyl | H | H | OCF3 | H | H | H |
| 517 | 4-Cl, 2-F, 6-OH-benzyl | H | H | NO2 | H | H | H |
| 518 | 4-Cl, 2-F, 6-OH-benzyl | H | H | NH2 | H | H | H |
| 519 | 4-Cl, 2-F, 6-OH-benzyl | H | H | OH | H | H | H |
| 520 | 4-Cl, 2-F, 6-OH-benzyl | H | H | CN | H | H | H |
| 521 | 4-Cl, 2-F, 6-OH-benzyl | H | H | COMe | H | H | H |
| 522 | 4-Cl, 2-F, 6-OH-benzyl | H | H | COOMe | H | H | H |
| 523 | 4-Cl, 2-F, 6-OH-benzyl | H | H | H | F | H | H |
| 524 | 4-Cl, 2-F, 6-OH-benzyl | H | H | H | Cl | H | H |

TABLE 3-continued

X = —SO₂—, q = 0, r = 0, Y = —(R4)C═C(R5)—

| Compound No. 3- | R1—(CH2)p— | R2 | R3 | R4 | R5 | R6 | R7 |
|---|---|---|---|---|---|---|---|
| 525 | 4-Cl-2-F-6-OH-phenyl-CH₂- | H | H | H | Me | H | H |
| 526 | 4-Cl-2-F-6-OH-phenyl-CH₂- | H | H | H | Et | H | H |
| 527 | 4-Cl-2-F-6-OH-phenyl-CH₂- | H | H | H | OMe | H | H |
| 528 | 4-Cl-2-F-6-OH-phenyl-CH₂- | H | H | H | OEt | H | H |
| 529 | 4-Cl-2-F-6-OH-phenyl-CH₂- | H | H | H | CF3 | H | H |
| 530 | 4-Cl-2-F-6-OH-phenyl-CH₂- | H | H | H | OCF3 | H | H |
| 531 | 4-Cl-2-F-6-OH-phenyl-CH₂- | H | H | H | NO2 | H | H |
| 532 | 4-Cl-2-F-6-OH-phenyl-CH₂- | H | H | H | NH2 | H | H |
| 533 | 4-Cl-2-F-6-OH-phenyl-CH₂- | H | H | H | OH | H | H |

TABLE 3-continued

X = —SO₂—, q = 0, r = 0, Y = —(R4)C═C(R5)—

| Compound No. 3- | R1—(CH2)p— | R2 | R3 | R4 | R5 | R6 | R7 |
|---|---|---|---|---|---|---|---|
| 534 | 4-Cl, 2-F, 3-OH-benzyl | H | H | H | CN | H | H |
| 535 | 4-Cl, 2-F, 3-OH-benzyl | H | H | H | COMe | H | H |
| 536 | 4-Cl, 2-F, 3-OH-benzyl | H | H | H | COOMe | H | H |
| 537 | 4-Cl, 2-F, 3-OH-benzyl | H | H | F | F | H | H |
| 538 | 4-Cl, 2-F, 3-OH-benzyl | H | H | F | Cl | H | H |
| 539 | 4-Cl, 2-F, 3-OH-benzyl | H | H | F | Me | H | H |
| 540 | 4-Cl, 2-F, 3-OH-benzyl | H | H | F | Et | H | H |
| 541 | 4-Cl, 2-F, 3-OH-benzyl | H | H | F | OMe | H | H |
| 542 | 4-Cl, 2-F, 3-OH-benzyl | H | H | H | OEt | H | H |

TABLE 3-continued
X = —SO₂—, q = 0, r = 0, Y = —(R4)C=C(R5)—
| Compound No. 3- | R1—(CH2)p— | R2 | R3 | R4 | R5 | R6 | R7 |
|---|---|---|---|---|---|---|---|
| 543 | 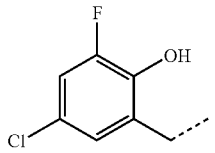 | H | H | F | CF3 | H | H |
| 544 | 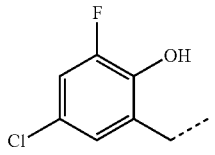 | H | H | F | OCF3 | H | H |
| 545 | 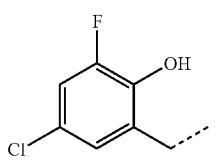 | H | H | Cl | F | H | H |
| 546 | 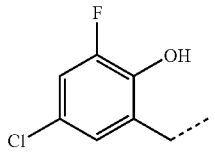 | H | H | Cl | Cl | H | H |
| 547 | 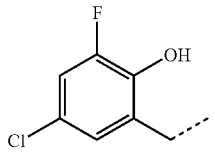 | H | H | Cl | Me | H | H |
| 548 | 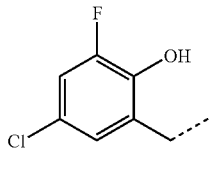 | H | H | Cl | Et | H | H |
| 549 | 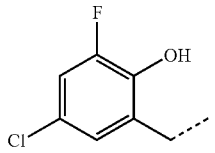 | H | H | Cl | OMe | H | H |
| 550 | 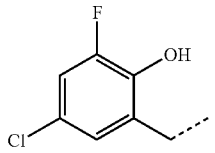 | H | H | Cl | OEt | H | H |
| 551 | 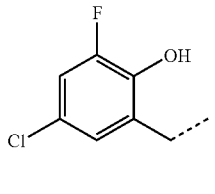 | H | H | Cl | CF3 | H | H |

TABLE 3-continued
X = —SO$_2$—, q = 0, r = 0, Y = —(R4)C=C(R5)—
| Compound No. 3- | R1—(CH2)p— | R2 | R3 | R4 | R5 | R6 | R7 |
|---|---|---|---|---|---|---|---|
| 552 | 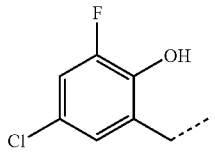 | H | H | Cl | OCF3 | H | H |
| 553 | 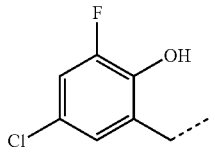 | H | H | Me | F | H | H |
| 554 | 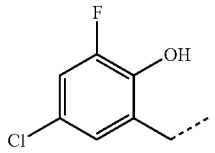 | H | H | Me | Cl | H | H |
| 555 | 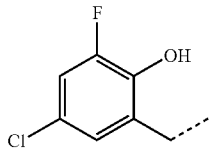 | H | H | Me | Me | H | H |
| 556 | 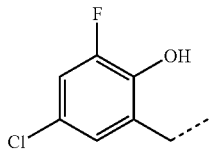 | H | H | Me | Et | H | H |
| 557 | 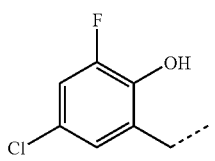 | H | H | Me | OMe | H | H |
| 558 | 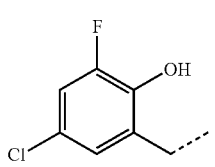 | H | H | Me | OEt | H | H |
| 559 | 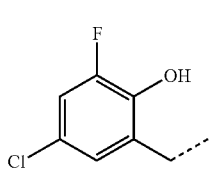 | H | H | Me | CF3 | H | H |
| 560 | 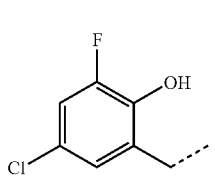 | H | H | Me | OCF3 | H | H |

TABLE 3-continued
X = —SO₂—, q = 0, r = 0, Y = —(R4)C═C(R5)—
| Compound No. 3- | R1—(CH2)p— | R2 | R3 | R4 | R5 | R6 | R7 |
|---|---|---|---|---|---|---|---|
| 561 | 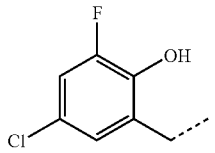 | H | H | OMe | F | H | H |
| 562 | 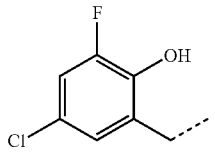 | H | H | OMe | Cl | H | H |
| 563 | 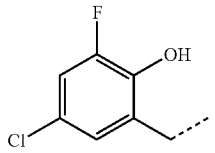 | H | H | OMe | Me | H | H |
| 564 | 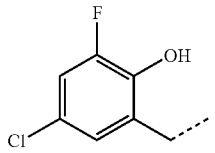 | H | H | OMe | Et | H | H |
| 565 | 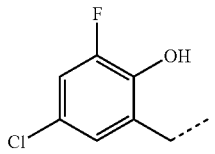 | H | H | OMe | OMe | H | H |
| 566 | 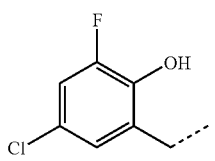 | H | H | OMe | OEt | H | H |
| 567 | 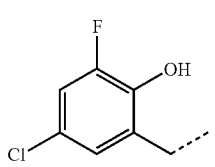 | H | H | OMe | CF3 | H | H |
| 568 | 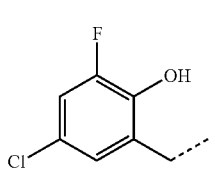 | H | H | OMe | OCF3 | H | H |
| 569 | 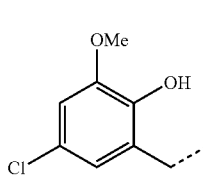 | H | H | H | H | H | H |

TABLE 3-continued

X = —SO₂—, q = 0, r = 0, Y = —(R4)C=C(R5)—

| Compound No. 3- | R1—(CH2)p— | R2 | R3 | R4 | R5 | R6 | R7 |
|---|---|---|---|---|---|---|---|
| 570 | 4-Cl-2-OH-3-OMe-benzyl | H | H | F | H | H | H |
| 571 | 4-Cl-2-OH-3-OMe-benzyl | H | H | Cl | H | H | H |
| 572 | 4-Cl-2-OH-3-OMe-benzyl | H | H | Me | H | H | H |
| 573 | 4-Cl-2-OH-3-OMe-benzyl | H | H | Et | H | H | H |
| 574 | 4-Cl-2-OH-3-OMe-benzyl | H | H | OMe | H | H | H |
| 575 | 4-Cl-2-OH-3-OMe-benzyl | H | H | H | F | H | H |
| 576 | 4-Cl-2-OH-3-OMe-benzyl | H | H | H | Cl | H | H |
| 577 | 4-Cl-2-OH-3-OMe-benzyl | H | H | H | Me | H | H |
| 578 | 4-Cl-2-OH-3-OMe-benzyl | H | H | H | Et | H | H |

TABLE 3-continued

X = —SO₂—, q = 0, r = 0, Y = —(R4)C═C(R5)—

| Compound No. 3- | R1—(CH2)p— | R2 | R3 | R4 | R5 | R6 | R7 |
|---|---|---|---|---|---|---|---|
| 579 | 4-Cl-2-OMe-6-OH-phenyl-CH₂- | H | H | H | OMe | H | H |
| 580 | 4-Cl-2-OMe-6-OH-phenyl-CH₂- | H | H | F | F | H | H |
| 581 | 4-Cl-2-OMe-6-OH-phenyl-CH₂- | H | H | F | Cl | H | H |
| 582 | 4-Cl-2-OMe-6-OH-phenyl-CH₂- | H | H | F | Me | H | H |
| 583 | 4-Cl-2-OMe-6-OH-phenyl-CH₂- | H | H | F | Et | H | H |
| 584 | 4-Cl-2-OMe-6-OH-phenyl-CH₂- | H | H | F | OMe | H | H |
| 585 | 4-Cl-2-OMe-6-OH-phenyl-CH₂- | H | H | Cl | F | H | H |
| 586 | 4-Cl-2-OMe-6-OH-phenyl-CH₂- | H | H | Cl | Cl | H | H |
| 587 | 4-Cl-2-OMe-6-OH-phenyl-CH₂- | H | H | Cl | Me | H | H |

TABLE 3-continued
X = —SO$_2$—, q = 0, r = 0, Y = —(R4)C=C(R5)—
| Compound No. 3- | R1—(CH2)p— | R2 | R3 | R4 | R5 | R6 | R7 |
|---|---|---|---|---|---|---|---|
| 588 | 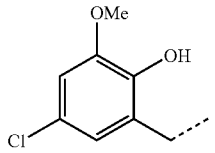 | H | H | Cl | Et | H | H |
| 589 | 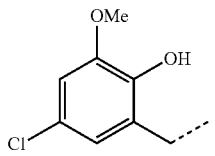 | H | H | Cl | OMe | H | H |
| 590 | 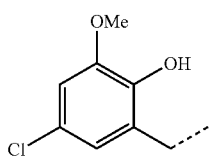 | H | H | Me | F | H | H |
| 591 | 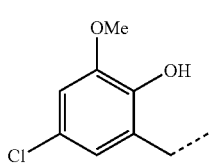 | H | H | Me | Cl | H | H |
| 592 | 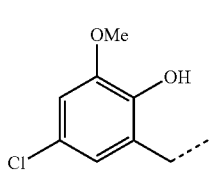 | H | H | Me | Me | H | H |
| 593 | 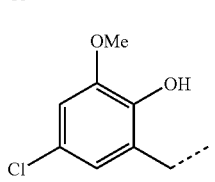 | H | H | Me | Et | H | H |
| 594 | 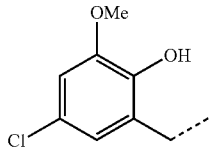 | H | H | Me | OMe | H | H |
| 595 | 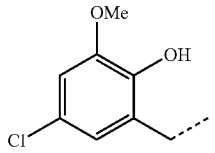 | H | H | Et | F | H | H |
| 596 | 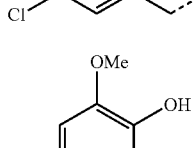 | H | H | Et | Cl | H | H |

TABLE 3-continued

X = —SO₂—, q = 0, r = 0, Y = —(R4)C=C(R5)—

| Compound No. 3- | R1—(CH2)p— | R2 | R3 | R4 | R5 | R6 | R7 |
|---|---|---|---|---|---|---|---|
| 597 | 4-Cl-2-OMe-6-OH-benzyl | H | H | Et | Me | H | H |
| 598 | 4-Cl-2-OMe-6-OH-benzyl | H | H | Et | Et | H | H |
| 599 | 4-Cl-2-OMe-6-OH-benzyl | H | H | Et | OMe | H | H |
| 600 | 4-Cl-2-OMe-6-OH-benzyl | H | H | OMe | F | H | H |
| 601 | 4-Cl-2-OMe-6-OH-benzyl | H | H | OMe | Cl | H | H |
| 602 | 4-Cl-2-OMe-6-OH-benzyl | H | H | OMe | Me | H | H |
| 603 | 4-Cl-2-OMe-6-OH-benzyl | H | H | OMe | Et | H | H |
| 604 | 4-Cl-2-OMe-6-OH-benzyl | H | H | OMe | OMe | H | H |
| 605 | 2,4-diCl-6-OH-benzyl | H | H | Me | CN | H | H |

TABLE 3-continued

X = —SO$_2$—, q = 0, r = 0, Y = —(R4)C═C(R5)—

| Compound No. 3- | R1—(CH2)p— | R2 | R3 | R4 | R5 | R6 | R7 |
|---|---|---|---|---|---|---|---|
| 606 | 2,4-dichloro-6-hydroxyphenyl-CH< | H | H | H | CN | Me | H |
| 607 | 2,4-dichloro-6-hydroxyphenyl-CH< | H | H | H | CN | H | Me |
| 608 | 2,4-dichloro-6-hydroxyphenyl-CH< | H | H | Me | Br | H | H |
| 609 | 2,4-dichloro-6-hydroxyphenyl-CH< | H | H | H | Br | Me | H |
| 610 | 2,4-dichloro-6-hydroxyphenyl-CH< | H | H | H | Br | H | Me |
| 611 | 2,4-dichloro-6-hydroxyphenyl-CH< | H | H | Me | H | F | H |
| 612 | 2,4-dichloro-6-hydroxyphenyl-CH< | H | H | Me | H | H | F |
| 613 | 2,4-dichloro-6-hydroxyphenyl-CH< | H | H | F | H | Me | H |
| 614 | 2,4-dichloro-6-hydroxyphenyl-CH< | H | H | F | H | H | Me |

TABLE 3-continued

X = —SO$_2$—, q = 0, r = 0, Y = —(R4)C=C(R5)—

| Compound No. 3- | R1—(CH2)p— | R2 | R3 | R4 | R5 | R6 | R7 |
|---|---|---|---|---|---|---|---|
| 615 | 2,4-dichloro-6-(...)phenol (OH, Cl, Cl) | H | H | Me | H | H | Me |
| 616 | 2,4-dichloro-6-(...)phenol | H | H | H | OMe | Me | H |
| 617 | 2,4-dichloro-6-(...)phenol | H | H | H | OH | Me | H |
| 618 | 2,4-dichloro-6-(...)phenol | H | H | NH2 | H | H | H |
| 619 | 2,4-dichloro-6-(...)phenol | H | H | H | NH2 | H | H |
| 620 | 2,4-dichloro-6-(...)phenol | H | H | H | H | NH2 | H |
| 621 | 2,4-dichloro-6-(...)phenol | H | H | Et | H | H | H |
| 622 | 2,4-dichloro-6-(...)phenol | H | H | H | Et | H | H |
| 623 | 2,4-dichloro-6-(...)phenol | H | H | H | H | Et | H |

TABLE 3-continued

X = —SO₂—, q = 0, r = 0, Y = —(R4)C═C(R5)—

| Compound No. 3- | R1—(CH2)p— | R2 | R3 | R4 | R5 | R6 | R7 |
|---|---|---|---|---|---|---|---|
| 624 | 2,4-dichloro-6-(CH)-phenol | H | H | iPr | H | H | H |
| 625 | 2,4-dichloro-6-(CH)-phenol | H | H | H | iPr | H | H |
| 626 | 2,4-dichloro-6-(CH)-phenol | H | H | H | H | iPr | H |
| 627 | 2,4-dichloro-6-(CH)-phenol | H | H | Ph | H | H | H |
| 628 | 2,4-dichloro-6-(CH)-phenol | H | H | H | Ph | H | H |
| 629 | 2,4-dichloro-6-(CH)-phenol | H | H | H | H | Ph | H |
| 630 | 2,4-dichloro-6-(CH)-phenol | H | H | OEt | H | H | H |
| 631 | 2,4-dichloro-6-(CH)-phenol | H | H | H | OEt | H | H |
| 632 | 2,4-dichloro-6-(CH)-phenol | H | H | H | H | OEt | H |

TABLE 3-continued
X = —SO$_2$—, q = 0, r = 0, Y = —(R4)C=C(R5)—
| Compound No. 3- | R1—(CH2)p— | R2 | R3 | R4 | R5 | R6 | R7 |
|---|---|---|---|---|---|---|---|
| 633 | 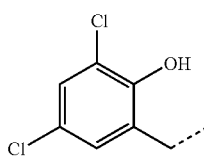 | H | H | OiPr | H | H | H |
| 634 | 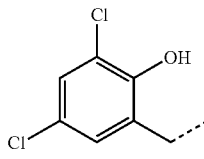 | H | H | H | OiPr | H | H |
| 635 | 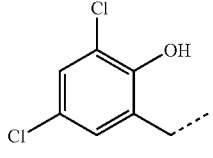 | H | H | H | H | OiPr | H |
| 636 | 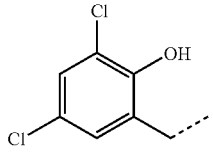 | H | H | OPh | H | H | H |
| 637 | 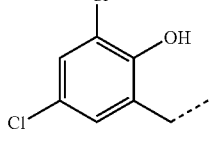 | H | H | H | OPh | H | H |
| 638 | 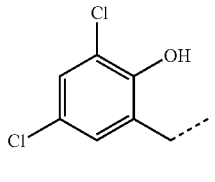 | H | H | H | H | OPh | H |
| 639 | 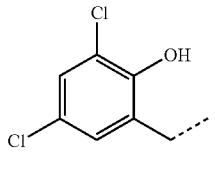 | H | H | SO2Me | H | H | H |
| 640 | 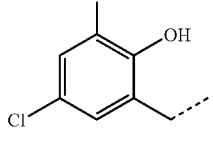 | H | H | H | SO2Me | H | H |
| 641 | 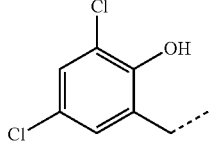 | H | H | H | H | SO2Me | H |

TABLE 3-continued

X = —SO₂—, q = 0, r = 0, Y = —(R4)C=C(R5)—

| Compound No. 3- | R1—(CH2)p— | R2 | R3 | R4 | R5 | R6 | R7 |
|---|---|---|---|---|---|---|---|
| 642 | 2,4-dichloro-6-hydroxyphenyl-CH2 | H | H | SO2Et | H | H | H |
| 643 | 2,4-dichloro-6-hydroxyphenyl-CH2 | H | H | H | SO2Et | H | H |
| 644 | 2,4-dichloro-6-hydroxyphenyl-CH2 | H | H | H | H | SO2Et | H |
| 645 | 2,4-dichloro-6-hydroxyphenyl-CH2 | H | H | SO2iPr | H | H | H |
| 646 | 2,4-dichloro-6-hydroxyphenyl-CH2 | H | H | H | SO2iPr | H | H |
| 647 | 2,4-dichloro-6-hydroxyphenyl-CH2 | H | H | H | H | SO2iPr | H |
| 648 | 2,4-dichloro-6-hydroxyphenyl-CH2 | H | H | SO2Ph | H | H | H |
| 649 | 2,4-dichloro-6-hydroxyphenyl-CH2 | H | H | H | SO2Ph | H | H |
| 650 | 2,4-dichloro-6-hydroxyphenyl-CH2 | H | H | H | H | SO2Ph | H |

TABLE 3-continued

X = —SO₂—, q = 0, r = 0, Y = —(R4)C=C(R5)—

| Compound No. 3- | R1—(CH2)p— | R2 | R3 | R4 | R5 | R6 | R7 |
|---|---|---|---|---|---|---|---|
| 651 | 2,4-dichloro-6-(OH) phenyl | H | H | SO2Me | Me | H | H |
| 652 | 2,4-dichloro-6-(OH) phenyl | H | H | SO2Me | H | Me | H |
| 653 | 2,4-dichloro-6-(OH) phenyl | H | H | Me | SO2Me | H | H |
| 654 | 2,4-dichloro-6-(OH) phenyl | H | H | H | SO2Me | Me | H |
| 655 | 2,4-dichloro-6-(OH) phenyl | H | H | SO2Me | F | H | H |
| 656 | 2,4-dichloro-6-(OH) phenyl | H | H | SO2Me | H | F | H |
| 657 | 2,4-dichloro-6-(OH) phenyl | H | H | F | SO2Me | H | H |
| 658 | 2,4-dichloro-6-(OH) phenyl | H | H | H | SO2Me | F | H |
| 659 | 2,4-dichloro-6-(OH) phenyl | H | H | SO2NMe2 | H | H | H |

TABLE 3-continued

X = —SO$_2$—, q = 0, r = 0, Y = —(R4)C═C(R5)—

| Compound No. 3- | R1—(CH2)p— | R2 | R3 | R4 | R5 | R6 | R7 |
|---|---|---|---|---|---|---|---|
| 660 | 2,4-dichloro-6-hydroxybenzyl | H | H | H | SO2NMe2 | H | H |
| 661 | 2,4-dichloro-6-hydroxybenzyl | H | H | H | H | SO2NMe2 | H |
| 662 | 2,4-dichloro-6-hydroxybenzyl | H | H | SO2Et2 | H | H | H |
| 663 | 2,4-dichloro-6-hydroxybenzyl | H | H | H | SO2Et2 | H | H |
| 664 | 2,4-dichloro-6-hydroxybenzyl | H | H | H | H | SO2Et2 | H |
| 665 | 2,4-dichloro-6-hydroxybenzyl | H | H | SO2NMe2 | Me | H | H |
| 666 | 2,4-dichloro-6-hydroxybenzyl | H | H | SO2NMe2 | H | Me | H |
| 667 | 2,4-dichloro-6-hydroxybenzyl | H | H | Me | SO2NMe2 | H | H |
| 668 | 2,4-dichloro-6-hydroxybenzyl | H | H | H | SO2NMe2 | Me | H |

TABLE 3-continued

X = —SO₂—, q = 0, r = 0, Y = —(R4)C=C(R5)—

| Compound No. 3- | R1—(CH2)p— | R2 | R3 | R4 | R5 | R6 | R7 |
|---|---|---|---|---|---|---|---|
| 669 | 2,4-diCl-phenol-CH | H | H | SO2NMe2 | F | H | H |
| 670 | 2,4-diCl-phenol-CH | H | H | SO2NMe2 | H | F | H |
| 671 | 2,4-diCl-phenol-CH | H | H | F | SO2NMe2 | H | H |
| 672 | 2,4-diCl-phenol-CH | H | H | H | SO2NMe2 | F | H |
| 673 | 2,4-diCl-phenol-CH | H | H | NHCOEt | H | H | H |
| 674 | 2,4-diCl-phenol-CH | H | H | H | NHCOEt | H | H |
| 675 | 2,4-diCl-phenol-CH | H | H | H | H | NHCOEt | H |
| 676 | 2,4-diCl-phenol-CH | H | H | NHCOiPr | H | H | H |
| 677 | 2,4-diCl-phenol-CH | H | H | H | NHCOiPr | H | H |

TABLE 3-continued

X = —SO$_2$—, q = 0, r = 0, Y = —(R4)C=C(R5)—

| Compound No. 3- | R1—(CH2)p— | R2 | R3 | R4 | R5 | R6 | R7 |
|---|---|---|---|---|---|---|---|
| 678 | 2,4-dichloro-6-hydroxyphenyl-CH | H | H | H | H | NHCOiPr | H |
| 679 | 4-chloro-2-fluoro-6-hydroxyphenyl-CH | H | H | Me | CN | H | H |
| 680 | 4-chloro-2-fluoro-6-hydroxyphenyl-CH | H | H | H | CN | Me | H |
| 681 | 4-chloro-2-fluoro-6-hydroxyphenyl-CH | H | H | H | CN | H | Me |
| 682 | 4-chloro-2-fluoro-6-hydroxyphenyl-CH | H | H | Me | Br | H | H |
| 683 | 4-chloro-2-fluoro-6-hydroxyphenyl-CH | H | H | H | Br | Me | H |
| 684 | 4-chloro-2-fluoro-6-hydroxyphenyl-CH | H | H | H | Br | H | Me |
| 685 | 4-chloro-2-fluoro-6-hydroxyphenyl-CH | H | H | Me | H | F | H |
| 686 | 4-chloro-2-fluoro-6-hydroxyphenyl-CH | H | H | Me | H | H | F |

TABLE 3-continued

X = —SO₂—, q = 0, r = 0, Y = —(R4)C=C(R5)—

| Compound No. 3- | R1—(CH2)p— | R2 | R3 | R4 | R5 | R6 | R7 |
|---|---|---|---|---|---|---|---|
| 687 | 4-Cl, 2-F, 3-OH-benzyl | H | H | F | H | Me | H |
| 688 | 4-Cl, 2-F, 3-OH-benzyl | H | H | F | H | H | Me |
| 689 | 4-Cl, 2-F, 3-OH-benzyl | H | H | Me | H | H | Me |
| 690 | 4-Cl, 2-F, 3-OH-benzyl | H | H | H | OMe | Me | H |
| 691 | 4-Cl, 2-F, 3-OH-benzyl | H | H | H | OH | Me | H |
| 692 | 4-Cl, 2-F, 3-OH-benzyl | H | H | NH2 | H | H | H |
| 693 | 4-Cl, 2-F, 3-OH-benzyl | H | H | H | NH2 | H | H |
| 694 | 4-Cl, 2-F, 3-OH-benzyl | H | H | H | H | NH2 | H |
| 695 | 4-Cl, 2-F, 3-OH-benzyl | H | H | Et | H | H | H |

TABLE 3-continued

X = —SO$_2$—, q = 0, r = 0, Y = —(R4)C═C(R5)—

| Compound No. 3- | R1—(CH2)p— | R2 | R3 | R4 | R5 | R6 | R7 |
|---|---|---|---|---|---|---|---|
| 696 | 4-Cl, 2-F, 3-OH-benzyl | H | H | H | Et | H | H |
| 697 | 4-Cl, 2-F, 3-OH-benzyl | H | H | H | H | Et | H |
| 698 | 4-Cl, 2-F, 3-OH-benzyl | H | H | iPr | H | H | H |
| 699 | 4-Cl, 2-F, 3-OH-benzyl | H | H | H | iPr | H | H |
| 700 | 4-Cl, 2-F, 3-OH-benzyl | H | H | H | H | iPr | H |
| 701 | 4-Cl, 2-F, 3-OH-benzyl | H | H | Ph | H | H | H |
| 702 | 4-Cl, 2-F, 3-OH-benzyl | H | H | H | Ph | H | H |
| 703 | 4-Cl, 2-F, 3-OH-benzyl | H | H | H | H | Ph | H |
| 704 | 4-Cl, 2-F, 3-OH-benzyl | H | H | OEt | H | H | H |

TABLE 3-continued

X = —SO$_2$—, q = 0, r = 0, Y = —(R4)C═C(R5)—

| Compound No. 3- | R1—(CH2)p— | R2 | R3 | R4 | R5 | R6 | R7 |
|---|---|---|---|---|---|---|---|
| 705 | 4-Cl, 2-F, 6-OH benzyl | H | H | H | OEt | H | H |
| 706 | 4-Cl, 2-F, 6-OH benzyl | H | H | H | H | OEt | H |
| 707 | 4-Cl, 2-F, 6-OH benzyl | H | H | OiPr | H | H | H |
| 708 | 4-Cl, 2-F, 6-OH benzyl | H | H | H | OiPr | H | H |
| 709 | 4-Cl, 2-F, 6-OH benzyl | H | H | H | H | OiPr | H |
| 710 | 4-Cl, 2-F, 6-OH benzyl | H | H | OPh | H | H | H |
| 711 | 4-Cl, 2-F, 6-OH benzyl | H | H | H | OPh | H | H |
| 712 | 4-Cl, 2-F, 6-OH benzyl | H | H | H | H | OPh | H |
| 713 | 4-Cl, 2-F, 6-OH benzyl | H | H | SO2Me | H | H | H |

TABLE 3-continued

X = —SO₂—, q = 0, r = 0, Y = —(R4)C═C(R5)—

| Compound No. 3- | R1—(CH2)p— | R2 | R3 | R4 | R5 | R6 | R7 |
|---|---|---|---|---|---|---|---|
| 714 | 4-Cl, 2-F, 6-OH-benzyl | H | H | H | SO2Me | H | H |
| 715 | 4-Cl, 2-F, 6-OH-benzyl | H | H | H | H | SO2Me | H |
| 716 | 4-Cl, 2-F, 6-OH-benzyl | H | H | SO2Et | H | H | H |
| 717 | 4-Cl, 2-F, 6-OH-benzyl | H | H | H | SO2Et | H | H |
| 718 | 4-Cl, 2-F, 6-OH-benzyl | H | H | H | H | SO2Et | H |
| 719 | 4-Cl, 2-F, 6-OH-benzyl | H | H | SO2iPr | H | H | H |
| 720 | 4-Cl, 2-F, 6-OH-benzyl | H | H | H | SO2iPr | H | H |
| 721 | 4-Cl, 2-F, 6-OH-benzyl | H | H | H | H | SO2iPr | H |
| 722 | 4-Cl, 2-F, 6-OH-benzyl | H | H | So2Ph | H | H | H |

TABLE 3-continued

X = —SO₂—, q = 0, r = 0, Y = —(R4)C=C(R5)—

| Compound No. 3- | R1—(CH2)p— | R2 | R3 | R4 | R5 | R6 | R7 |
|---|---|---|---|---|---|---|---|
| 723 | 4-Cl, 2-F, 6-OH-benzyl | H | H | H | SO2Ph | H | H |
| 724 | 4-Cl, 2-F, 6-OH-benzyl | H | H | H | H | SO2Ph | H |
| 725 | 4-Cl, 2-F, 6-OH-benzyl | H | H | SO2Me | Me | H | H |
| 726 | 4-Cl, 2-F, 6-OH-benzyl | H | H | SO2Me | H | Me | H |
| 727 | 4-Cl, 2-F, 6-OH-benzyl | H | H | Me | SO2Me | H | H |
| 728 | 4-Cl, 2-F, 6-OH-benzyl | H | H | H | SO2Me | Me | H |
| 729 | 4-Cl, 2-F, 6-OH-benzyl | H | H | SO2Me | F | H | H |
| 730 | 4-Cl, 2-F, 6-OH-benzyl | H | H | SO2Me | H | F | H |
| 731 | 4-Cl, 2-F, 6-OH-benzyl | H | H | F | SO2Me | H | H |

TABLE 3-continued

X = —SO₂—, q = 0, r = 0, Y = —(R4)C=C(R5)—

| Compound No. 3- | R1—(CH2)p— | R2 | R3 | R4 | R5 | R6 | R7 |
|---|---|---|---|---|---|---|---|
| 732 | 4-Cl, 2-F, 6-OH-benzyl | H | H | H | SO2Me | F | H |
| 733 | 4-Cl, 2-F, 6-OH-benzyl | H | H | SO2NMe2 | H | H | H |
| 734 | 4-Cl, 2-F, 6-OH-benzyl | H | H | H | SO2NMe2 | H | H |
| 735 | 4-Cl, 2-F, 6-OH-benzyl | H | H | H | H | SO2NMe2 | H |
| 736 | 4-Cl, 2-F, 6-OH-benzyl | H | H | SO2Et2 | H | H | H |
| 737 | 4-Cl, 2-F, 6-OH-benzyl | H | H | H | SO2Et2 | H | H |
| 738 | 4-Cl, 2-F, 6-OH-benzyl | H | H | H | H | SO2Et2 | H |
| 739 | 4-Cl, 2-F, 6-OH-benzyl | H | H | SO2NMe2 | Me | H | H |
| 740 | 4-Cl, 2-F, 6-OH-benzyl | H | H | SO2NMe2 | H | Me | H |

TABLE 3-continued

X = —SO₂—, q = 0, r = 0, Y = —(R4)C=C(R5)—

| Compound No. 3- | R1—(CH2)p— | R2 | R3 | R4 | R5 | R6 | R7 |
|---|---|---|---|---|---|---|---|
| 741 | F, OH, Cl-substituted benzyl | H | H | Me | SO2NMe2 | H | H |
| 742 | F, OH, Cl-substituted benzyl | H | H | H | SO2NMe2 | Me | H |
| 743 | F, OH, Cl-substituted benzyl | H | H | SO2NMe2 | F | H | H |
| 744 | F, OH, Cl-substituted benzyl | H | H | SO2NMe2 | H | F | H |
| 745 | F, OH, Cl-substituted benzyl | H | H | F | SO2NMe2 | H | H |
| 746 | F, OH, Cl-substituted benzyl | H | H | H | SO2NMe2 | F | H |
| 747 | F, OH, Cl-substituted benzyl | H | H | NHCOEt | H | H | H |
| 748 | F, OH, Cl-substituted benzyl | H | H | H | NHCOEt | H | H |
| 749 | F, OH, Cl-substituted benzyl | H | H | H | H | NHCOEt | H |

TABLE 3-continued

X = —SO$_2$—, q = 0, r = 0, Y = —(R4)C═C(R5)—

| Compound No. 3- | R1—(CH2)p— | R2 | R3 | R4 | R5 | R6 | R7 |
|---|---|---|---|---|---|---|---|
| 750 | 4-Cl, 2-F, 3-OH-benzyl | H | H | NHCOiPr | H | H | H |
| 751 | 4-Cl, 2-F, 3-OH-benzyl | H | H | H | NHCOiPr | H | H |
| 752 | 4-Cl, 2-F, 3-OH-benzyl | H | H | H | H | NHCOiPr | H |
| 753 | 4-Cl, 2-F, 3-OH-benzyl | H | H | F | H | H | F |
| 754 | 4-Cl, 2-F, 3-OH-benzyl | H | H | F | H | H | F |

TABLE 4

X = —CH2—, q = 0, r = 0, Y = —(R4)C═C(R5)—

| Compound No. 4- | R1—(CH2)p— | R2 | R3 | R4 | R5 | R6 | R7 |
|---|---|---|---|---|---|---|---|
| 1 | 3,4-dichlorobenzyl | H | H | H | H | H | H |
| 2 | 2,4-dichloro-6-OH-benzyl | H | H | H | H | H | H |
| 3 | 4-Cl, 2-OH-benzyl | H | H | H | H | H | H |

TABLE 4-continued

X = —CH2—, q = 0, r = 0, Y = —(R4)C=C(R5)—

| Compound No. 4- | R1—(CH2)p— | R2 | R3 | R4 | R5 | R6 | R7 |
|---|---|---|---|---|---|---|---|
| 4 | naphthalen-1-ylmethyl | H | H | H | H | H | H |
| 5 | 3-phenylpropyl | H | H | H | H | H | H |
| 6 | 3,5-dichloro-2-hydroxybenzyl | H | H | H | OCF3 | H | H |
| 7 | 3,5-dichloro-2-hydroxybenzyl | H | H | H | Cl | H | H |
| 8 | 3,5-dichloro-2-hydroxybenzyl | H | H | H | Me | H | H |
| 9 | 3,5-dichloro-2-hydroxybenzyl | H | H | H | F | H | H |
| 10 | 3,5-dichloro-2-hydroxybenzyl | H | H | Me | H | H | H |
| 11 | 3,5-dichloro-2-hydroxybenzyl | H | H | H | OH | H | H |
| 12 | 3,4-dichlorobenzyl | H | H | H | Cl | H | H |

TABLE 4-continued

X = —CH2—, q = 0, r = 0, Y = —(R4)C=C(R5)—

| Compound No. 4- | R1—(CH2)p— | R2 | R3 | R4 | R5 | R6 | R7 |
|---|---|---|---|---|---|---|---|
| 13 | naphthalen-1-ylmethyl | H | H | H | Cl | H | H |
| 14 | 2-chlorobenzyl | H | H | H | H | H | H |
| 15 | 3-chlorobenzyl | H | H | H | H | H | H |
| 16 | 4-chlorobenzyl | H | H | H | H | H | H |
| 17 | 2-methoxybenzyl | H | H | H | H | H | H |
| 18 | 4-methoxybenzyl | H | H | H | H | H | H |
| 19 | 5-bromo-2-hydroxybenzyl | H | H | H | H | H | H |
| 20 | 5-bromo-2-methoxybenzyl | H | H | H | H | H | H |
| 21 | 5-bromo-2-fluorobenzyl | H | H | H | H | H | H |
| 22 | 3-bromobenzyl | H | H | H | H | H | H |
| 23 | 3-chloro-4-fluorobenzyl | H | H | H | H | H | H |

TABLE 4-continued

X = —CH2—, q = 0, r = 0, Y = —(R4)C=C(R5)—

| Compound No. 4- | R1—(CH2)p— | R2 | R3 | R4 | R5 | R6 | R7 |
|---|---|---|---|---|---|---|---|
| 24 | 3-(N-methylindolyl)methyl | H | H | H | H | H | H |
| 25 | 3-benzothienylmethyl | H | H | H | H | H | H |
| 26 | 2-hydroxy-5-methoxybenzyl | H | H | H | H | H | H |
| 27 | 3-nitrobenzyl | H | H | H | H | H | H |
| 28 | 3-methoxybenzyl | H | H | H | H | H | H |
| 29 | 2-naphthylmethyl | H | H | H | H | H | H |
| 30 | benzyl | H | H | H | H | H | H |
| 31 | phenethyl | H | H | H | H | H | H |
| 32 | 3-bromo-5-chloro-2-hydroxybenzyl | H | H | H | H | H | H |
| 33 | 5-cyano-2-hydroxybenzyl | H | H | H | H | H | H |

TABLE 4-continued

X = —CH2—, q = 0, r = 0, Y = —(R4)C=C(R5)—

| Compound No. 4- | R1—(CH2)p— | R2 | R3 | R4 | R5 | R6 | R7 |
|---|---|---|---|---|---|---|---|
| 34 | 2-Cl, 4-CF3, 6-(CH2-), phenol | H | H | H | H | H | H |
| 35 | 2-CF3, 4-Cl, 6-(CH2-), phenol | H | H | H | H | H | H |
| 36 | 2-Cl, 6-(CH2-), phenol | H | H | H | H | H | H |
| 37 | 4-methylbenzyl | H | H | H | H | H | H |
| 38 | 4-fluorobenzyl | H | H | H | H | H | H |
| 39 | 4-bromobenzyl | H | H | H | H | H | H |
| 40 | 4-trifluoromethylbenzyl | H | H | H | H | H | H |
| 41 | 4-hydroxybenzyl | H | H | H | H | H | H |
| 42 | 4-cyanobenzyl | H | H | H | H | H | H |
| 43 | 4-methylsulfonylbenzyl | H | H | H | H | H | H |
| 44 | 4-(methoxycarbonyl)benzyl | H | H | H | H | H | H |

TABLE 4-continued

X = —CH2—, q = 0, r = 0, Y = —(R4)C=C(R5)—

| Compound No. 4- | R1—(CH2)p— | R2 | R3 | R4 | R5 | R6 | R7 |
|---|---|---|---|---|---|---|---|
| 45 | 4-(dimethylamino)phenyl-CH2— | H | H | H | H | H | H |
| 46 | 4-MeO-phenyl-CH2— | H | H | H | H | H | H |
| 47 | 4-EtO-phenyl-CH2— | H | H | H | H | H | H |
| 48 | 4-(n-PrO)-phenyl-CH2— | H | H | H | H | H | H |
| 49 | 4-(iPrO)-phenyl-CH2— | H | H | H | H | H | H |
| 50 | 4-iPr-phenyl-CH2— | H | H | H | H | H | H |
| 51 | 4-(PhCH2O)-phenyl-CH2— | H | H | H | H | H | H |
| 52 | 4-PhO-phenyl-CH2— | H | H | H | H | H | H |
| 53 | 4-biphenyl-CH2— | H | H | H | H | H | H |
| 54 | 4-(AcNH)-phenyl-CH2— | H | H | H | H | H | H |

TABLE 4-continued

X = —CH2—, q = 0, r = 0, Y = —(R4)C═C(R5)—

| Compound No. 4- | R1—(CH2)p— | R2 | R3 | R4 | R5 | R6 | R7 |
|---|---|---|---|---|---|---|---|
| 55 | 2-propylphenyl-CH2— | H | H | H | H | H | H |
| 56 | 2-(benzyloxy)phenyl-CH2— | H | H | H | H | H | H |
| 57 | 2-methylphenyl-CH2— | H | H | H | H | H | H |
| 58 | 2-cyanophenyl-CH2— | H | H | H | H | H | H |
| 59 | 2-chlorophenyl-CH2— | H | H | H | H | H | H |
| 60 | 2-methoxyphenyl-CH2— | H | H | H | H | H | H |
| 61 | 2-ethoxyphenyl-CH2— | H | H | H | H | H | H |
| 62 | 2-biphenyl-CH2— | H | H | H | H | H | H |
| 63 | 3-(trifluoromethyl)phenyl-CH2— | H | H | H | H | H | H |

TABLE 4-continued
X = —CH2—, q = 0, r = 0, Y = —(R4)C═C(R5)—
| Compound No. 4- | R1—(CH2)p— | R2 | R3 | R4 | R5 | R6 | R7 |
|---|---|---|---|---|---|---|---|
| 64 | 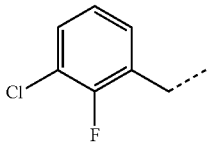 | H | H | H | H | H | H |
| 65 | 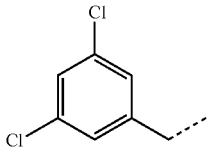 | H | H | H | H | H | H |
| 66 | 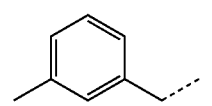 | H | H | H | H | H | H |
| 67 | 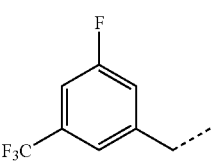 | H | H | H | H | H | H |
| 68 | 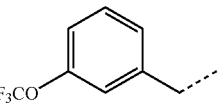 | H | H | H | H | H | H |
| 69 | 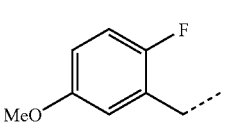 | H | H | H | H | H | H |
| 70 | 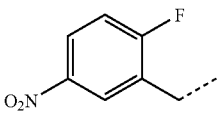 | H | H | H | H | H | H |
| 71 | 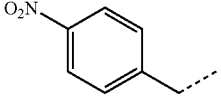 | H | H | H | H | H | H |
| 72 | 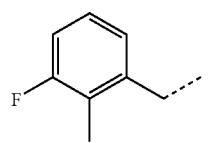 | H | H | H | H | H | H |
| 73 | 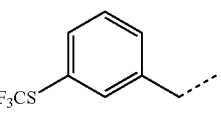 | H | H | H | H | H | H |
| 74 | 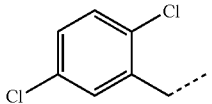 | H | H | H | H | H | H |

TABLE 4-continued

X = —CH2—, q = 0, r = 0, Y = —(R4)C=C(R5)—

| Compound No. 4- | R1—(CH2)p— | R2 | R3 | R4 | R5 | R6 | R7 |
|---|---|---|---|---|---|---|---|
| 75 | 3-(F₂HC)-C₆H₄-CH₂- | H | H | H | H | H | H |
| 76 | 2-F-C₆H₄-CH₂- | H | H | H | H | H | H |
| 77 | 2-NO₂-C₆H₄-CH₂- | H | H | H | H | H | H |
| 78 | 2-COOH-C₆H₄-CH₂- | H | H | H | H | H | H |
| 79 | 5-Br-2-OEt-C₆H₃-CH₂- | H | H | H | H | H | H |
| 80 | 2,3-(CH₃)₂-C₆H₃-CH₂- | H | H | H | H | H | H |
| 81 | 3-F-C₆H₄-CH₂- | H | H | H | H | H | H |
| 82 | 2,4-Cl₂-C₆H₃-CH₂- | H | H | H | H | H | H |
| 83 | 3-CN-C₆H₄-CH₂- | H | H | H | H | H | H |
| 84 | 3-HO-C₆H₄-CH₂- | H | H | H | H | H | H |
| 85 | 3-EtO-C₆H₄-CH₂- | H | H | H | H | H | H |
| 86 | 4-Cl-3-O₂N-C₆H₃-CH₂- | H | H | H | H | H | H |

TABLE 4-continued

X = —CH2—, q = 0, r = 0, Y = —(R4)C=C(R5)—

| Compound No. 4- | R1—(CH2)p— | R2 | R3 | R4 | R5 | R6 | R7 |
|---|---|---|---|---|---|---|---|
| 87 | 2,3-dichlorophenyl-CH2 | H | H | H | H | H | H |
| 88 | 4-methyl-2,3-difluorophenyl-CH2 | H | H | H | H | H | H |
| 89 | 4-fluoro-3-bromophenyl-CH2 | H | H | H | H | H | H |
| 90 | 3-trifluoromethyl-2-fluorophenyl-CH2 | H | H | H | H | H | H |
| 91 | 4-hydroxy-3-chlorophenyl-CH2 | H | H | H | H | H | H |
| 92 | 2,3-difluorophenyl-CH2 | H | H | H | H | H | H |
| 93 | 4-methoxy-3-bromophenyl-CH2 | H | H | H | H | H | H |
| 94 | 3-methoxy-2-ethoxyphenyl-CH2 | H | H | H | H | H | H |
| 95 | 4-methoxy-2,3-dimethylphenyl-CH2 | H | H | H | H | H | H |

TABLE 4-continued

X = —CH2—, q = 0, r = 0, Y = —(R4)C=C(R5)—

| Compound No. 4- | R1—(CH2)p— | R2 | R3 | R4 | R5 | R6 | R7 |
|---|---|---|---|---|---|---|---|
| 96 | 2-MeO, 3-(OBn) benzyl | H | H | H | H | H | H |
| 97 | 4-Cl, 3-nitro benzyl (O2N, Cl substituted) | H | H | H | H | H | H |
| 98 | 3-(4-MeO-phenoxy)benzyl | H | H | H | H | H | H |
| 99 | 3-(4-methylphenoxy)benzyl | H | H | H | H | H | H |
| 100 | 3-(4-Cl-phenoxy)benzyl | H | H | H | H | H | H |
| 101 | 3-(benzyloxy)benzyl | H | H | H | H | H | H |
| 102 | 3-phenoxybenzyl | H | H | H | H | H | H |

TABLE 4-continued

X = —CH2—, q = 0, r = 0, Y = —(R4)C═C(R5)—

| Compound No. 4- | R1—(CH2)p— | R2 | R3 | R4 | R5 | R6 | R7 |
|---|---|---|---|---|---|---|---|
| 103 | 3-hydroxy-4-methoxybenzyl | H | H | H | H | H | H |
| 104 | 2-chloro-3-(trifluoromethyl)benzyl | H | H | H | H | H | H |
| 105 | 4-hydroxy-3-nitrobenzyl | H | H | H | H | H | H |
| 104 | 2,3-dimethoxybenzyl | H | H | H | H | H | H |
| 105 | 4-ethoxy-2-ethoxy-3-methylbenzyl | H | H | H | H | H | H |
| 106 | 3-(2-hydroxyethoxy)benzyl | H | H | H | H | H | H |
| 107 | 4-ethoxy-2-ethoxy-3-methylbenzyl | H | H | H | H | H | H |
| 108 | 3-(2-hydroxyethoxy)benzyl | H | H | H | H | H | H |
| 109 | 2,3,4-trimethoxybenzyl | H | H | H | H | H | H |
| 110 | 4-fluoro-3-phenoxybenzyl | H | H | H | H | H | H |

TABLE 4-continued

X = —CH2—, q = 0, r = 0, Y = —(R4)C=C(R5)—

| Compound No. 4- | R1—(CH2)p— | R2 | R3 | R4 | R5 | R6 | R7 |
|---|---|---|---|---|---|---|---|
| 111 | 2-methoxy-3-(methoxy)-6-(COOH)-benzyl | H | H | H | H | H | H |
| 112 | 5-chloro-2-nitro-benzyl | H | H | H | H | H | H |
| 113 | 3,5-dihydroxy-benzyl | H | H | H | H | H | H |
| 114 | 4-methoxy-3-benzyloxy-benzyl | H | H | H | H | H | H |
| 115 | 3,4-diethoxy-benzyl | H | H | H | H | H | H |
| 116 | 3-carboxy-benzyl | H | H | H | H | H | H |
| 117 | 4-methoxy-3-hydroxy-benzyl (2-OMe, 5-OH) | H | H | H | H | H | H |
| 118 | 4-nitro-3-hydroxy-benzyl | H | H | H | H | H | H |
| 119 | 3,5-bis(trifluoromethyl)-benzyl | H | H | H | H | H | H |
| 120 | 3-methoxy-2-nitro-benzyl | H | H | H | H | H | H |

TABLE 4-continued

X = —CH2—, q = 0, r = 0, Y = —(R4)C=C(R5)—

| Compound No. 4- | R1—(CH2)p— | R2 | R3 | R4 | R5 | R6 | R7 |
|---|---|---|---|---|---|---|---|
| 121 | 4-methylnaphthalen-1-ylmethyl | H | H | H | H | H | H |
| 122 | 1-methyl-7-methyl-1H-indol-3-ylmethyl | H | H | H | H | H | H |
| 123 | 2-methoxynaphthalen-1-ylmethyl | H | H | H | H | H | H |
| 124 | benzofuran-2-ylmethyl | H | H | H | H | H | H |
| 125 | 1,2-dimethyl-1H-indol-3-ylmethyl | H | H | H | H | H | H |
| 126 | quinolin-8-ylmethyl | H | H | H | H | H | H |
| 127 | 2-hydroxynaphthalen-1-ylmethyl | H | H | H | H | H | H |
| 128 | 2-acetoxynaphthalen-1-ylmethyl | H | H | H | H | H | H |

TABLE 4-continued

X = —CH2—, q = 0, r = 0, Y = —(R4)C═C(R5)—

| Compound No. 4- | R1—(CH2)p— | R2 | R3 | R4 | R5 | R6 | R7 |
|---|---|---|---|---|---|---|---|
| 129 | naphthalen-2-yl with 1-OH | H | H | H | H | H | H |
| 130 | 1H-indol-7-yl | H | H | H | H | H | H |
| 131 | quinolin-4-yl | H | H | H | H | H | H |
| 132 | 1-methyl-5-methyl-1H-indol-3-yl | H | H | H | H | H | H |
| 133 | anthracen-9-yl | H | H | H | H | H | H |
| 134 | 2-methylnaphthalen-1-yl | H | H | H | H | H | H |
| 135 | 2-ethoxynaphthalen-1-yl | H | H | H | H | H | H |
| 136 | 1H-indol-3-yl | H | H | H | H | H | H |

TABLE 4-continued

X = —CH2—, q = 0, r = 0, Y = —(R4)C=C(R5)—

| Compound No. 4- | R1—(CH2)p— | R2 | R3 | R4 | R5 | R6 | R7 |
|---|---|---|---|---|---|---|---|
| 137 | 6-methyl-1-methylindol-3-yl | H | H | H | H | H | H |
| 138 | 1-methylindol-2-yl | H | H | H | H | H | H |
| 139 | 4-methyl-1-methylindol-3-yl | H | H | H | H | H | H |
| 140 | 2,5-dimethyl-1-methylindol-3-yl | H | H | H | H | H | H |
| 141 | 5-methoxy-1-methylindol-3-yl | H | H | H | H | H | H |
| 142 | 4-methylbenzothiophen-3-yl | H | H | H | H | H | H |
| 143 | 1-methylbenzimidazol-2-yl | H | H | H | H | H | H |

TABLE 4-continued

X = —CH2—, q = 0, r = 0, Y = —(R4)C=C(R5)—

| Compound No. 4- | R1—(CH2)p— | R2 | R3 | R4 | R5 | R6 | R7 |
|---|---|---|---|---|---|---|---|
| 144 | *N-methyl-2-phenylindol-3-yl* | H | H | H | H | H | H |
| 145 | *1-acetylindol-3-yl* | H | H | H | H | H | H |
| 146 | *quinolin-2-yl* | H | H | H | H | H | H |
| 147 | *6-methoxy-N-methylindol-3-yl* | H | H | H | H | H | H |
| 148 | *3-methylbenzothiophen-2-yl* | H | H | H | H | H | H |
| 149 | *4-methoxynaphthalen-1-yl* | H | H | H | H | H | H |
| 150 | *phenanthren-9-yl* | H | H | H | H | H | H |

TABLE 4-continued

X = —CH2—, q = 0, r = 0, Y = —(R4)C=C(R5)—

| Compound No. 4- | R1—(CH2)p— | R2 | R3 | R4 | R5 | R6 | R7 |
|---|---|---|---|---|---|---|---|
| 151 | 6-MeO-naphthalen-2-ylmethyl | H | H | H | H | H | H |
| 152 | 1-bromo-naphthalen-2-ylmethyl | H | H | H | H | H | H |
| 153 | 4-(dimethylamino)naphthalen-1-ylmethyl | H | H | H | H | H | H |
| 154 | 2,3-dihydro-1,4-benzodioxin-6-ylmethyl | H | H | H | H | H | H |
| 155 | 2,2-dimethylchroman-6-ylmethyl | H | H | H | H | H | H |
| 156 | 2,3-dihydrobenzofuran-5-ylmethyl | H | H | H | H | H | H |
| 157 | 9-ethyl-carbazol-3-ylmethyl | H | H | H | H | H | H |
| 158 | 1,3-benzodioxol-4-ylmethyl | H | H | H | H | H | H |
| 159 | 1,3-benzodioxol-5-ylmethyl | H | H | H | H | H | H |
| 160 | 4-phenylbutyl | H | H | H | H | H | H |

TABLE 4-continued
X = —CH2—, q = 0, r = 0, Y = —(R4)C=C(R5)—
| Compound No. 4- | R1—(CH2)p— | R2 | R3 | R4 | R5 | R6 | R7 |
|---|---|---|---|---|---|---|---|
| 161 | 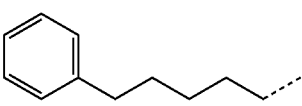 | H | H | H | H | H | H |
| 162 | 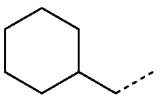 | H | H | H | H | H | H |
| 163 | 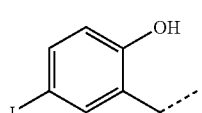 | H | H | H | H | H | H |
| 164 | 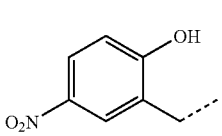 | H | H | H | H | H | H |
| 165 | 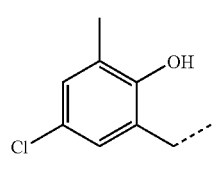 | H | H | H | H | H | H |
| 166 | 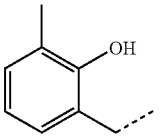 | H | H | H | H | H | H |
| 167 | 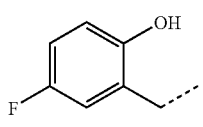 | H | H | H | H | H | H |
| 168 | 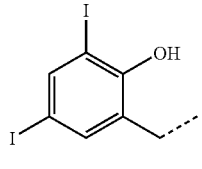 | H | H | H | H | H | H |
| 169 | 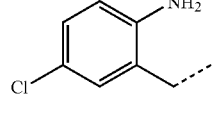 | H | H | H | H | H | H |
| 170 | 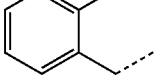 | H | H | H | H | H | H |
| 171 | 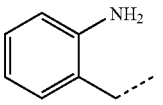 | H | H | H | H | H | H |

TABLE 4-continued

X = —CH2—, q = 0, r = 0, Y = —(R4)C═C(R5)—

| Compound No. 4- | R1—(CH2)p— | R2 | R3 | R4 | R5 | R6 | R7 |
|---|---|---|---|---|---|---|---|
| 172 | 4-tert-butyl-2-hydroxybenzyl | H | H | H | H | H | H |
| 173 | 2-hydroxy-5-(trifluoromethoxy)benzyl | H | H | H | H | H | H |
| 174 | 3-methoxy-2-hydroxybenzyl | H | H | H | H | H | H |
| 175 | 2,3-dihydroxybenzyl | H | H | H | H | H | H |
| 176 | 3-ethoxy-2-hydroxybenzyl | H | H | H | H | H | H |
| 177 | 3-carboxy-2-hydroxybenzyl | H | H | H | H | H | H |
| 178 | 3-tert-butyl-2-hydroxybenzyl | H | H | H | H | H | H |
| 179 | furan-2-ylmethyl | H | H | H | H | H | H |
| 180 | oxazol-2-ylmethyl | H | H | H | H | H | H |
| 181 | 1H-imidazol-2-ylmethyl | H | H | H | H | H | H |

TABLE 4-continued

X = —CH2—, q = 0, r = 0, Y = —(R4)C═C(R5)—

| Compound No. 4- | R1—(CH2)p— | R2 | R3 | R4 | R5 | R6 | R7 |
|---|---|---|---|---|---|---|---|
| 182 | thiazol-2-ylmethyl | H | H | H | H | H | H |
| 183 | 1H-pyrazol-3-ylmethyl | H | H | H | H | H | H |
| 184 | (1-phenyl-3,5-dimethyl-1H-pyrazol-4-yl)methyl | H | H | H | H | H | H |
| 185 | (1-phenyl-2,5-dimethyl-1H-pyrrol-3-yl)methyl | H | H | H | H | H | H |
| 186 | (5-(4-chlorophenyl)furan-2-yl)methyl | H | H | H | H | H | H |
| 187 | thiophen-2-ylmethyl | H | H | H | H | H | H |
| 188 | 1H-pyrrol-2-ylmethyl | H | H | H | H | H | H |
| 189 | pyridin-2-ylmethyl | H | H | H | H | H | H |
| 190 | pyridin-3-ylmethyl | H | H | H | H | H | H |
| 191 | pyridin-4-ylmethyl | H | H | H | H | H | H |
| 192 | (5-chloro-2-hydroxyphenyl)methyl | H | H | H | Cl | H | H |

TABLE 4-continued
X = —CH2—, q = 0, r = 0, Y = —(R4)C=C(R5)—
| Compound No. 4- | R1—(CH2)p— | R2 | R3 | R4 | R5 | R6 | R7 |
|---|---|---|---|---|---|---|---|
| 193 | 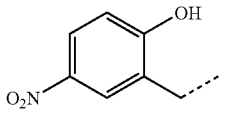 | H | H | H | Cl | H | H |
| 194 | 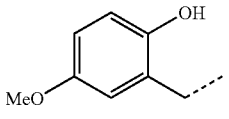 | H | H | H | Cl | H | H |
| 195 | 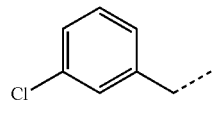 | H | H | H | Cl | H | H |
| 196 | 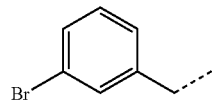 | H | H | H | Cl | H | H |
| 197 | 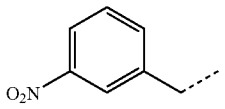 | H | H | H | Cl | H | H |
| 198 |  | H | H | H | Cl | H | H |
| 199 |  | H | H | H | Cl | H | H |
| 200 | 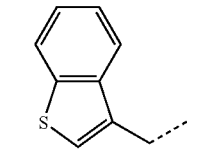 | H | H | H | Cl | H | H |
| 201 | 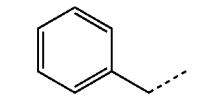 | H | H | H | Cl | H | H |
| 202 | 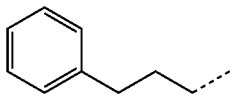 | H | H | H | Cl | H | H |
| 203 | 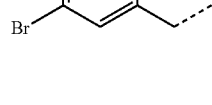 | H | H | H | Cl | H | H |

TABLE 4-continued

X = —CH2—, q = 0, r = 0, Y = —(R4)C=C(R5)—

| Compound No. 4- | R1—(CH2)p— | R2 | R3 | R4 | R5 | R6 | R7 |
|---|---|---|---|---|---|---|---|
| 204 | 2-naphthylmethyl | H | H | H | Cl | H | H |
| 205 | phenethyl | H | H | H | Cl | H | H |
| 206 | 3,5-dichloro-2-hydroxybenzyl | H | H | Cl | H | H | H |
| 207 | 3,5-dichloro-2-hydroxybenzyl | H | H | H | OMe | H | H |
| 208 | 3,5-dichloro-2-hydroxybenzyl | H | H | H | COOMe | H | H |
| 209 | 3,5-dichloro-2-hydroxybenzyl | H | H | H | H | Cl | H |
| 210 | 3,5-dichloro-2-hydroxybenzyl | H | H | H | H | COOMe | H |
| 211 | 3,5-dichloro-2-hydroxybenzyl | H | H | H | H | H | Cl |
| 212 | 3,5-dichloro-2-hydroxybenzyl | H | H | COOMe | H | H | H |

TABLE 4-continued
X = —CH2—, q = 0, r = 0, Y = —(R4)C=C(R5)—
| Compound No. 4- | R1—(CH2)p— | R2 | R3 | R4 | R5 | R6 | R7 |
|---|---|---|---|---|---|---|---|
| 213 | 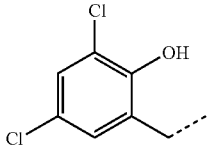 | H | H | H | CF3 | H | H |
| 214 | 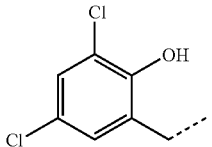 | H | H | H | NO2 | H | H |
| 215 | 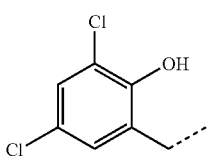 | H | H | H | F | F | H |
| 216 | 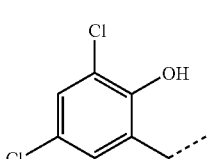 | H | H | F | H | H | H |
| 217 | 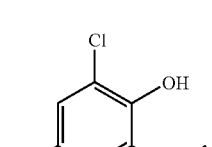 | H | H | H | CN | H | H |
| 218 | 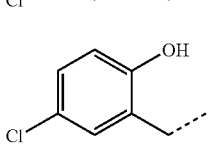 | H | H | Cl | H | H | H |
| 219 | 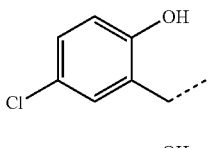 | H | H | H | OMe | H | H |
| 220 | 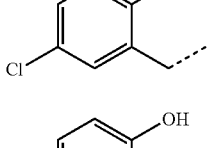 | H | H | H | COOMe | H | H |
| 221 | 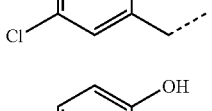 | H | H | H | H | Cl | H |
| 222 | 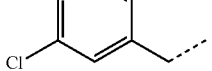 | H | H | H | H | COOMe | H |

TABLE 4-continued
X = —CH2—, q = 0, r = 0, Y = —(R4)C=C(R5)—
| Compound No. 4- | R1—(CH2)p— | R2 | R3 | R4 | R5 | R6 | R7 |
|---|---|---|---|---|---|---|---|
| 223 | 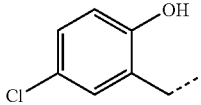 | H | H | H | H | H | Cl |
| 224 | 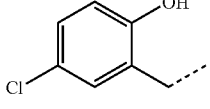 | H | H | H | OCF3 | H | H |
| 225 | 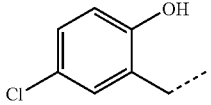 | H | H | COOMe | H | H | H |
| 226 | 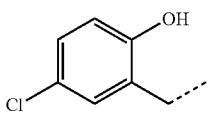 | H | H | H | CF3 | H | H |
| 227 | 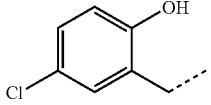 | H | H | H | Me | H | H |
| 228 | 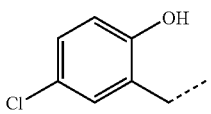 | H | H | H | F | H | H |
| 229 | 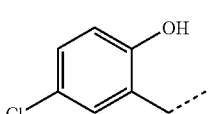 | H | H | H | OH | H | H |
| 230 | 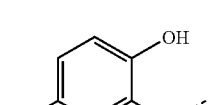 | H | H | H | NO2 | H | H |
| 231 | 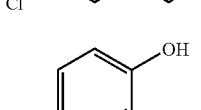 | H | H | H | F | F | H |
| 232 | 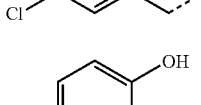 | H | H | F | H | H | H |
| 233 | 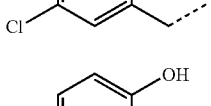 | H | H | Me | H | H | H |
| 234 | 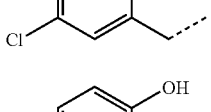 | H | H | H | CN | H | H |

TABLE 4-continued

X = —CH2—, q = 0, r = 0, Y = —(R4)C=C(R5)—

| Compound No. 4- | R1—(CH2)p— | R2 | R3 | R4 | R5 | R6 | R7 |
|---|---|---|---|---|---|---|---|
| 235 | naphthyl-CH2 | H | H | Cl | H | H | H |
| 236 | naphthyl-CH2 | H | H | H | OMe | H | H |
| 237 | naphthyl-CH2 | H | H | H | COOMe | H | H |
| 238 | naphthyl-CH2 | H | H | H | H | Cl | H |
| 239 | naphthyl-CH2 | H | H | H | H | COOMe | H |
| 240 | naphthyl-CH2 | H | H | H | H | H | Cl |
| 241 | naphthyl-CH2 | H | H | H | OCF3 | H | H |
| 242 | naphthyl-CH2 | H | H | COOMe | H | H | H |

TABLE 4-continued

X = —CH2—, q = 0, r = 0, Y = —(R4)C=C(R5)—

| Compound No. 4- | R1—(CH2)p— | R2 | R3 | R4 | R5 | R6 | R7 |
|---|---|---|---|---|---|---|---|
| 243 | naphthalen-1-ylmethyl | H | H | H | CF3 | H | H |
| 244 | naphthalen-1-ylmethyl | H | H | H | Me | H | H |
| 245 | naphthalen-1-ylmethyl | H | H | H | F | H | H |
| 246 | naphthalen-1-ylmethyl | H | H | H | OH | H | H |
| 247 | naphthalen-1-ylmethyl | H | H | H | NO2 | H | H |
| 248 | naphthalen-1-ylmethyl | H | H | H | F | F | H |
| 249 | naphthalen-1-ylmethyl | H | H | F | H | H | H |
| 250 | naphthalen-1-ylmethyl | H | H | Me | H | H | H |

TABLE 4-continued

X = —CH2—, q = 0, r = 0, Y = —(R4)C=C(R5)—

| Compound No. 4- | R1—(CH2)p— | R2 | R3 | R4 | R5 | R6 | R7 |
|---|---|---|---|---|---|---|---|
| 251 | naphthyl-CH2 | H | H | H | CN | H | H |
| 252 | Ph-CH2CH2- | H | H | Cl | H | H | H |
| 253 | Ph-CH2CH2- | H | H | H | OMe | H | H |
| 254 | Ph-CH2CH2- | H | H | H | COOMe | H | H |
| 255 | Ph-CH2CH2- | H | H | H | H | Cl | H |
| 256 | Ph-CH2CH2- | H | H | H | H | COOMe | H |
| 257 | Ph-CH2CH2- | H | H | H | H | H | Cl |
| 258 | Ph-CH2CH2- | H | H | H | OCF3 | H | H |
| 259 | Ph-CH2CH2- | H | H | COOMe | H | H | H |
| 260 | Ph-CH2CH2- | H | H | H | OCF3 | H | H |
| 261 | Ph-CH2CH2- | H | H | H | Me | H | H |
| 262 | Ph-CH2CH2- | H | H | H | F | H | H |
| 263 | Ph-CH2CH2- | H | H | H | OH | H | H |

TABLE 4-continued
X = —CH2—, q = 0, r = 0, Y = —(R4)C=C(R5)—
| Compound No. 4- | R1—(CH2)p— | R2 | R3 | R4 | R5 | R6 | R7 |
|---|---|---|---|---|---|---|---|
| 264 | 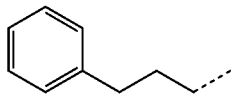 | H | H | H | NO2 | H | H |
| 265 | 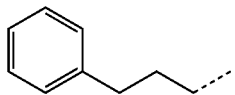 | H | H | H | F | F | H |
| 266 | 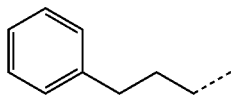 | H | H | F | H | H | H |
| 267 | 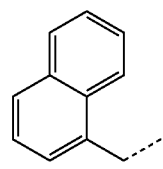 | H | H | Me | H | H | H |
| 268 | 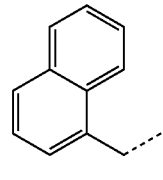 | H | H | H | CN | H | H |
| 269 | 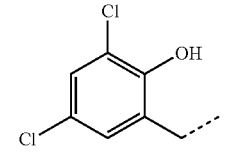 | H | H | H | H | H | COOMe |
| 270 | 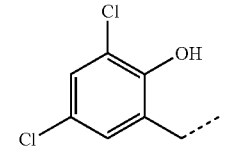 | H | H | H | H | F | H |
| 271 | 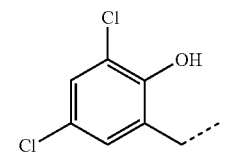 | H | H | H | H | H | F |
| 272 | 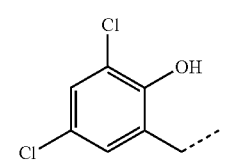 | H | H | H | H | Me | H |

TABLE 4-continued

X = —CH2—, q = 0, r = 0, Y = —(R4)C=C(R5)—

| Compound No. 4- | R1—(CH2)p— | R2 | R3 | R4 | R5 | R6 | R7 |
|---|---|---|---|---|---|---|---|
| 273 | 2,4-dichloro-6-hydroxyphenyl | H | H | H | H | H | Me |
| 274 | 2,4-dichloro-6-hydroxyphenyl | H | H | OMe | H | H | H |
| 275 | 2,4-dichloro-6-hydroxyphenyl | H | H | H | H | OMe | H |
| 276 | 2,4-dichloro-6-hydroxyphenyl | H | H | H | H | H | OMe |
| 277 | 2,4-dichloro-6-hydroxyphenyl | H | H | CF3 | H | H | H |
| 278 | 2,4-dichloro-6-hydroxyphenyl | H | H | Cl | H | CF3 | H |
| 279 | 2,4-dichloro-6-hydroxyphenyl | H | H | H | H | H | CF3 |
| 280 | 2,4-dichloro-6-hydroxyphenyl | H | H | OH | H | H | H |
| 281 | 2,4-dichloro-6-hydroxyphenyl | H | H | H | H | OH | H |

TABLE 4-continued
X = —CH2—, q = 0, r = 0, Y = —(R4)C=C(R5)—
| Compound No. 4- | R1—(CH2)p— | R2 | R3 | R4 | R5 | R6 | R7 |
|---|---|---|---|---|---|---|---|
| 282 | 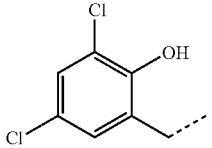 | H | H | H | H | H | OH |
| 283 | 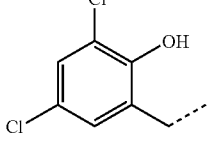 | H | H | OCF3 | H | H | H |
| 284 | 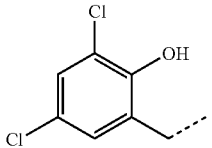 | H | H | H | H | OCF3 | H |
| 285 | 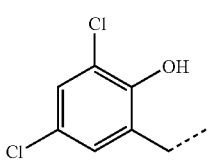 | H | H | H | H | H | OCF3 |
| 286 | 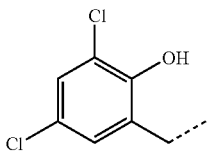 | H | H | NO2 | H | H | H |
| 287 | 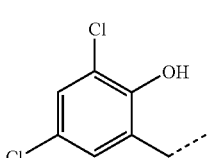 | H | H | H | H | NO2 | H |
| 288 | 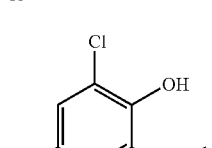 | H | H | H | H | H | NO2 |
| 289 | 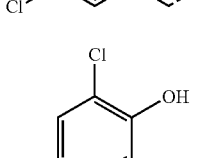 | H | H | CN | H | H | H |
| 290 | 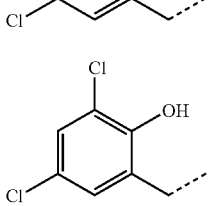 | H | H | H | H | CN | H |

TABLE 4-continued

X = —CH2—, q = 0, r = 0, Y = —(R4)C═C(R5)—

| Compound No. 4- | R1—(CH2)p— | R2 | R3 | R4 | R5 | R6 | R7 |
|---|---|---|---|---|---|---|---|
| 291 | 2,4-dichloro-6-hydroxybenzyl | H | H | H | H | H | CN |
| 292 | 2,4-dichloro-6-hydroxybenzyl | H | H | Br | H | H | H |
| 293 | 2,4-dichloro-6-hydroxybenzyl | H | H | H | Br | H | H |
| 294 | 2,4-dichloro-6-hydroxybenzyl | H | H | H | H | Br | H |
| 295 | 2,4-dichloro-6-hydroxybenzyl | H | H | H | H | H | Br |
| 296 | 2,4-dichloro-6-hydroxybenzyl | H | H | COOH | H | H | H |
| 297 | 2,4-dichloro-6-hydroxybenzyl | H | H | H | COOH | H | H |
| 298 | 2,4-dichloro-6-hydroxybenzyl | H | H | H | H | COOH | H |
| 299 | 2,4-dichloro-6-hydroxybenzyl | H | H | H | H | H | COOH |

TABLE 4-continued

X = —CH2—, q = 0, r = 0, Y = —(R4)C=C(R5)—

| Compound No. 4- | R1—(CH2)p— | R2 | R3 | R4 | R5 | R6 | R7 |
|---|---|---|---|---|---|---|---|
| 300 | 2,4-dichloro-6-hydroxyphenyl-CH2 | H | H | NHCOMe | H | H | H |
| 301 | 2,4-dichloro-6-hydroxyphenyl-CH2 | H | H | H | NHCOMe | H | H |
| 302 | 2,4-dichloro-6-hydroxyphenyl-CH2 | H | H | H | H | NHCOMe | H |
| 303 | 2,4-dichloro-6-hydroxyphenyl-CH2 | H | H | H | H | H | NHCOMe |
| 304 | 2,4-dichloro-6-hydroxyphenyl-CH2 | H | H | SO2NH2 | H | H | H |
| 305 | 2,4-dichloro-6-hydroxyphenyl-CH2 | H | H | H | SO2NH2 | H | H |
| 306 | 2,4-dichloro-6-hydroxyphenyl-CH2 | H | H | H | H | SO2NH2 | H |
| 307 | 2,4-dichloro-6-hydroxyphenyl-CH2 | H | H | H | H | H | SO2NH2 |
| 308 | 2,4-dichloro-6-hydroxyphenyl-CH2 | H | H | Me | Me | H | H |

TABLE 4-continued

X = —CH2—, q = 0, r = 0, Y = —(R4)C=C(R5)—

| Compound No. 4- | R1—(CH2)p— | R2 | R3 | R4 | R5 | R6 | R7 |
|---|---|---|---|---|---|---|---|
| 309 | 2,4-dichloro-6-hydroxyphenyl-CH2- | H | H | H | Me | H | Me |
| 310 | 2,4-dichloro-6-hydroxyphenyl-CH2- | H | H | H | Me | Me | H |
| 311 | 2,4-dichloro-6-hydroxyphenyl-CH2- | H | H | F | F | H | H |
| 312 | naphthalen-1-yl-CH2- | H | H | F | H | F | H |
| 313 | 2,4-dichloro-6-hydroxyphenyl-CH2- | H | H | H | F | F | H |
| 314 | 2,4-dichloro-6-hydroxyphenyl-CH2- | H | H | Cl | Cl | H | H |
| 315 | 2,4-dichloro-6-hydroxyphenyl-CH2- | H | H | Cl | H | Cl | H |
| 316 | 2,4-dichloro-6-hydroxyphenyl-CH2- | H | H | H | Cl | Cl | H |
| 317 | 2,4-dichloro-6-hydroxyphenyl-CH2- | H | H | Me | F | H | H |

TABLE 4-continued
X = —CH2—, q = 0, r = 0, Y = —(R4)C═C(R5)—
| Compound No. 4- | R1—(CH2)p— | R2 | R3 | R4 | R5 | R6 | R7 |
|---|---|---|---|---|---|---|---|
| 318 | 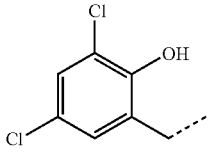 | H | H | Me | Cl | H | H |
| 319 | 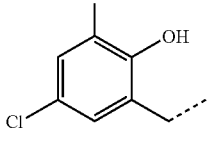 | H | H | Me | OH | H | H |
| 320 | 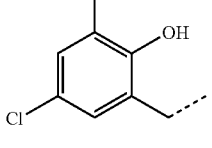 | H | H | Me | OMe | H | H |
| 321 | 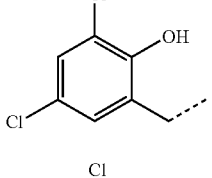 | H | H | F | Me | H | H |
| 322 | 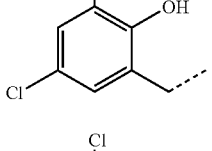 | H | H | F | Cl | H | H |
| 323 | 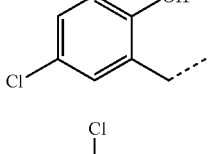 | H | H | F | OH | H | H |
| 324 | 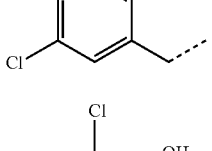 | H | H | F | OMe | H | H |
| 325 | 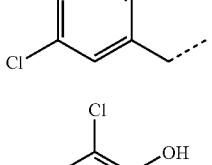 | H | H | Cl | Me | H | H |
| 326 | 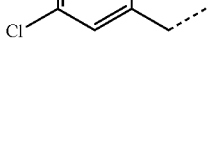 | H | H | Cl | F | H | H |

TABLE 4-continued

X = —CH2—, q = 0, r = 0, Y = —(R4)C=C(R5)—

| Compound No. 4- | R1—(CH2)p— | R2 | R3 | R4 | R5 | R6 | R7 |
|---|---|---|---|---|---|---|---|
| 327 | 2,4-dichloro-6-hydroxyphenyl-CH2 | H | H | Cl | OH | H | H |
| 328 | 2,4-dichloro-6-hydroxyphenyl-CH2 | H | H | Cl | OMe | H | H |
| 329 | 5-chloro-2-hydroxyphenyl-CH2 | H | H | H | H | H | COOMe |
| 330 | 5-chloro-2-hydroxyphenyl-CH2 | H | H | H | H | F | H |
| 331 | 5-chloro-2-hydroxyphenyl-CH2 | H | H | H | H | H | F |
| 332 | 5-chloro-2-hydroxyphenyl-CH2 | H | H | H | H | Me | H |
| 333 | 5-chloro-2-hydroxyphenyl-CH2 | H | H | H | H | H | Me |
| 334 | 5-chloro-2-hydroxyphenyl-CH2 | H | H | OMe | H | H | H |
| 335 | 5-chloro-2-hydroxyphenyl-CH2 | H | H | H | H | OMe | H |
| 336 | 5-chloro-2-hydroxyphenyl-CH2 | H | H | H | H | H | OMe |
| 337 | 5-chloro-2-hydroxyphenyl-CH2 | H | H | CF3 | H | H | H |

TABLE 4-continued
X = —CH2—, q = 0, r = 0, Y = —(R4)C=C(R5)—
| Compound No. 4- | R1—(CH2)p— | R2 | R3 | R4 | R5 | R6 | R7 |
|---|---|---|---|---|---|---|---|
| 338 | 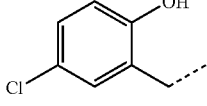 | H | H | H | H | CF3 | H |
| 339 | 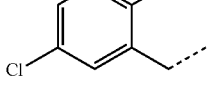 | H | H | H | H | H | CF3 |
| 340 | 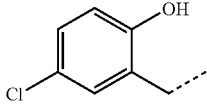 | H | H | OH | H | H | H |
| 341 | 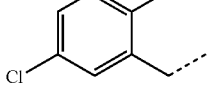 | H | H | H | H | OH | H |
| 342 | 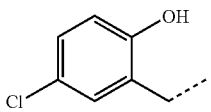 | H | H | H | H | H | OH |
| 343 | 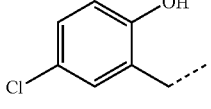 | H | H | OCF3 | H | H | H |
| 344 | 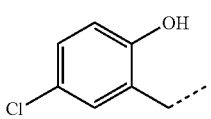 | H | H | H | H | OCF3 | H |
| 345 | 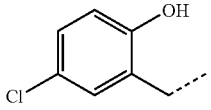 | H | H | H | H | H | OCF3 |
| 346 | 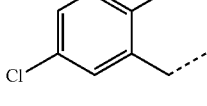 | H | H | NO2 | H | H | H |
| 347 | 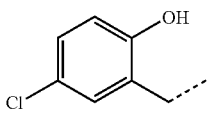 | H | H | H | H | NO2 | H |
| 348 | 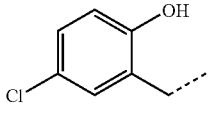 | H | H | H | H | H | NO2 |
| 349 | 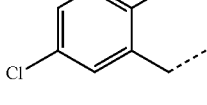 | H | H | CN | H | H | H |

TABLE 4-continued
X = —CH2—, q = 0, r = 0, Y = —(R4)C=C(R5)—
| Compound No. 4- | R1—(CH2)p— | R2 | R3 | R4 | R5 | R6 | R7 |
|---|---|---|---|---|---|---|---|
| 350 | 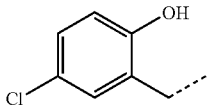 | H | H | H | H | CN | H |
| 351 | 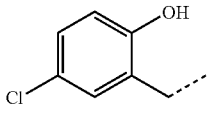 | H | H | H | H | H | CN |
| 352 | 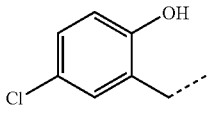 | H | H | Br | H | H | H |
| 353 | 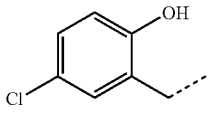 | H | H | H | Br | H | H |
| 354 | 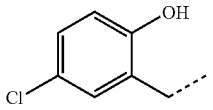 | H | H | H | H | Br | H |
| 355 |  | H | H | H | H | H | Br |
| 356 |  | H | H | COOH | H | H | H |
| 357 |  | H | H | H | COOH | H | H |
| 358 | 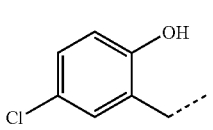 | H | H | H | H | COOH | H |
| 359 | 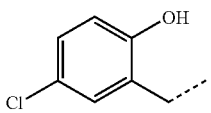 | H | H | H | H | H | COOH |
| 360 | 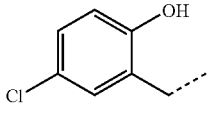 | H | H | NHCOMe | H | H | H |
| 361 |  | H | H | H | NHCOMe | H | H |

TABLE 4-continued
X = —CH2—, q = 0, r = 0, Y = —(R4)C=C(R5)—
| Compound No. 4- | R1—(CH2)p— | R2 | R3 | R4 | R5 | R6 | R7 |
|---|---|---|---|---|---|---|---|
| 362 | 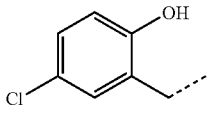 | H | H | H | H | NHCOMe | H |
| 363 | 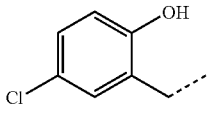 | H | H | H | H | H | NHCOMe |
| 364 | 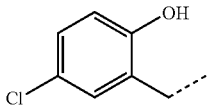 | H | H | SO2NH2 | H | H | H |
| 365 | 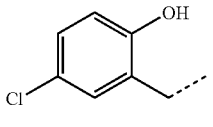 | H | H | H | SO2NH2 | H | H |
| 366 | 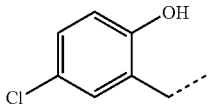 | H | H | H | H | SO2NH2 | H |
| 367 |  | H | H | H | H | H | SO2NH2 |
| 368 |  | H | H | Me | Me | H | H |
| 369 | 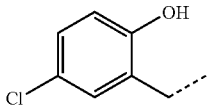 | H | H | Me | H | Me | H |
| 370 |  | H | H | H | Me | Me | H |
| 371 | 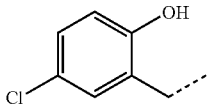 | H | H | F | F | H | H |
| 372 | 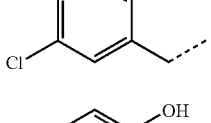 | H | H | F | H | F | H |
| 373 | 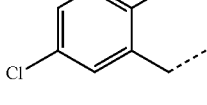 | H | H | H | F | F | H |

TABLE 4-continued
X = —CH2—, q = 0, r = 0, Y = —(R4)C=C(R5)—
| Compound No. 4- | R1—(CH2)p— | R2 | R3 | R4 | R5 | R6 | R7 |
|---|---|---|---|---|---|---|---|
| 374 | 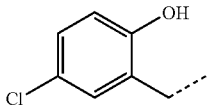 | H | H | Cl | Cl | H | H |
| 375 | 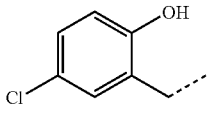 | H | H | Cl | H | Cl | H |
| 376 | 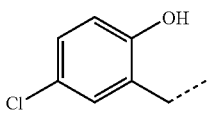 | H | H | H | Cl | Cl | H |
| 377 | 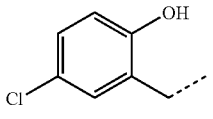 | H | H | Me | F | H | H |
| 378 | 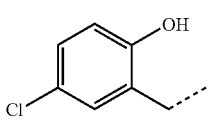 | H | H | Me | Cl | H | H |
| 379 | 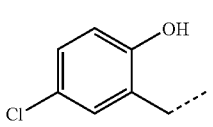 | H | H | Me | OH | H | H |
| 380 | 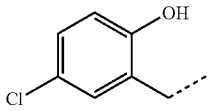 | H | H | Me | OMe | H | H |
| 381 | 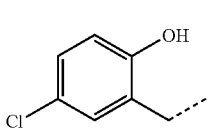 | H | H | F | Me | H | H |
| 382 | 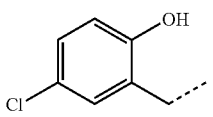 | H | H | F | Cl | H | H |
| 383 | 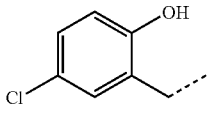 | H | H | F | OH | H | H |
| 384 | 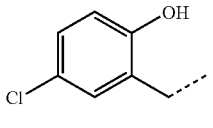 | H | H | F | OMe | H | H |
| 385 | 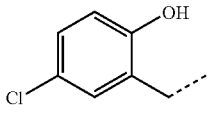 | H | H | Cl | Me | H | H |

TABLE 4-continued

X = —CH2—, q = 0, r = 0, Y = —(R4)C=C(R5)—

| Compound No. 4- | R1—(CH2)p— | R2 | R3 | R4 | R5 | R6 | R7 |
|---|---|---|---|---|---|---|---|
| 386 | 4-Cl, 2-OH-benzyl | H | H | Cl | F | H | H |
| 387 | 4-Cl, 2-OH-benzyl | H | H | Cl | OH | H | H |
| 388 | 4-Cl, 2-OH-benzyl | H | H | Cl | OMe | H | H |
| 389 | 1-naphthylmethyl | H | H | H | H | H | COOMe |
| 390 | 1-naphthylmethyl | H | H | H | H | F | H |
| 391 | 1-naphthylmethyl | H | H | H | H | H | F |
| 392 | 1-naphthylmethyl | H | H | H | H | Me | H |
| 393 | 1-naphthylmethyl | H | H | H | H | H | Me |
| 394 | 1-naphthylmethyl | H | H | OMe | H | H | H |

TABLE 4-continued

X = —CH2—, q = 0, r = 0, Y = —(R4)C=C(R5)—

| Compound No. 4- | R1—(CH2)p— | R2 | R3 | R4 | R5 | R6 | R7 |
|---|---|---|---|---|---|---|---|
| 395 | naphthyl-CH2 | H | H | H | H | OMe | H |
| 396 | naphthyl-CH2 | H | H | H | H | H | OMe |
| 397 | naphthyl-CH2 | H | H | CF3 | H | H | H |
| 398 | naphthyl-CH2 | H | H | H | H | CF3 | H |
| 399 | naphthyl-CH2 | H | H | H | H | H | CF3 |
| 400 | naphthyl-CH2 | H | H | OH | H | H | H |
| 401 | naphthyl-CH2 | H | H | H | H | OH | H |
| 402 | naphthyl-CH2 | H | H | H | H | H | OH |

TABLE 4-continued
X = —CH2—, q = 0, r = 0, Y = —(R4)C=C(R5)—
| Compound No. 4- | R1—(CH2)p— | R2 | R3 | R4 | R5 | R6 | R7 |
|---|---|---|---|---|---|---|---|
| 403 | 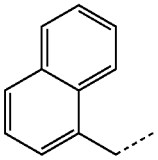 | H | H | OCF3 | H | H | H |
| 404 | 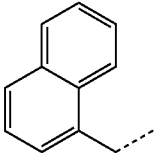 | H | H | H | H | OCF3 | H |
| 405 | 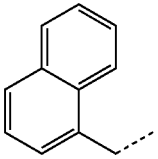 | H | H | H | H | H | OCF3 |
| 406 | 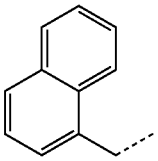 | H | H | NO2 | H | H | H |
| 407 | 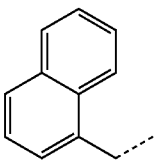 | H | H | H | H | NO2 | H |
| 408 | 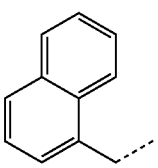 | H | H | H | H | H | NO2 |
| 409 | 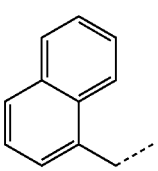 | H | H | CN | H | H | H |
| 410 | 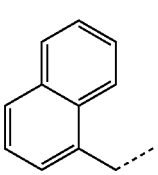 | H | H | H | H | CN | H |

TABLE 4-continued

X = —CH2—, q = 0, r = 0, Y = —(R4)C=C(R5)—

| Compound No. 4- | R1—(CH2)p— | R2 | R3 | R4 | R5 | R6 | R7 |
|---|---|---|---|---|---|---|---|
| 411 | naphthalen-1-ylmethyl | H | H | H | H | H | CN |
| 412 | naphthalen-1-ylmethyl | H | H | Br | H | H | H |
| 413 | naphthalen-1-ylmethyl | H | H | H | Br | H | H |
| 414 | naphthalen-1-ylmethyl | H | H | H | H | Br | H |
| 415 | naphthalen-1-ylmethyl | H | H | H | H | H | Br |
| 416 | naphthalen-1-ylmethyl | H | H | COOH | H | H | H |
| 417 | naphthalen-1-ylmethyl | H | H | H | COOH | H | H |
| 418 | naphthalen-1-ylmethyl | H | H | H | H | COOH | H |

TABLE 4-continued

X = —CH2—, q = 0, r = 0, Y = —(R4)C═C(R5)—

| Compound No. 4- | R1—(CH2)p— | R2 | R3 | R4 | R5 | R6 | R7 |
|---|---|---|---|---|---|---|---|
| 419 | naphthyl-CH2 | H | H | H | H | H | COOH |
| 420 | naphthyl-CH2 | H | H | NHCOMe | H | H | H |
| 421 | naphthyl-CH2 | H | H | H | NHCOMe | H | H |
| 422 | naphthyl-CH2 | H | H | H | H | NHCOMe | H |
| 423 | naphthyl-CH2 | H | H | H | H | H | NHCOMe |
| 424 | naphthyl-CH2 | H | H | SO2NH2 | H | H | H |
| 425 | naphthyl-CH2 | H | H | H | SO2NH2 | H | H |
| 426 | naphthyl-CH2 | H | H | H | H | SO2NH2 | H |

TABLE 4-continued

X = —CH2—, q = 0, r = 0, Y = —(R4)C═C(R5)—

| Compound No. 4- | R1—(CH2)p— | R2 | R3 | R4 | R5 | R6 | R7 |
|---|---|---|---|---|---|---|---|
| 427 | 1-naphthylmethyl | H | H | H | H | H | SO2NH2 |
| 428 | 1-naphthylmethyl | H | H | Me | Me | H | H |
| 429 | 1-naphthylmethyl | H | H | Me | H | Me | H |
| 430 | 1-naphthylmethyl | H | H | H | Me | Me | H |
| 431 | 1-naphthylmethyl | H | H | F | F | H | H |
| 432 | 1-naphthylmethyl | H | H | F | H | F | H |
| 433 | 1-naphthylmethyl | H | H | H | F | F | H |
| 434 | 1-naphthylmethyl | H | H | Cl | Cl | H | H |

TABLE 4-continued
X = —CH2—, q = 0, r = 0, Y = —(R4)C=C(R5)—
| Compound No. 4- | R1—(CH2)p— | R2 | R3 | R4 | R5 | R6 | R7 |
|---|---|---|---|---|---|---|---|
| 435 | 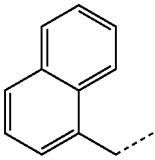 | H | H | Cl | H | Cl | H |
| 436 | 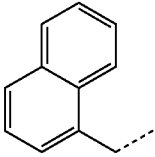 | H | H | H | Cl | Cl | H |
| 437 | 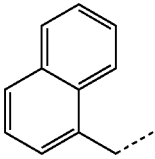 | H | H | Me | F | H | H |
| 438 | 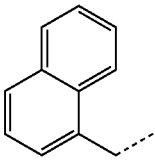 | H | H | Me | Cl | H | H |
| 439 | 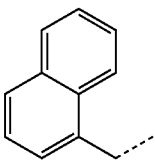 | H | H | Me | OH | H | H |
| 440 | 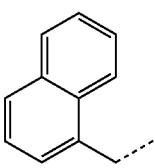 | H | H | Me | OMe | H | H |
| 441 | 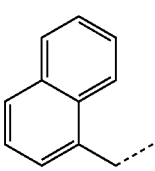 | H | H | F | Me | H | H |
| 442 | 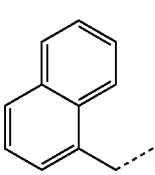 | H | H | F | Cl | H | H |

TABLE 4-continued

X = —CH2—, q = 0, r = 0, Y = —(R4)C=C(R5)—

| Compound No. 4- | R1—(CH2)p— | R2 | R3 | R4 | R5 | R6 | R7 |
|---|---|---|---|---|---|---|---|
| 443 | naphthalen-1-ylmethyl | H | H | F | OH | H | H |
| 444 | naphthalen-1-ylmethyl | H | H | F | OMe | H | H |
| 445 | naphthalen-1-ylmethyl | H | H | Cl | Me | H | H |
| 446 | naphthalen-1-ylmethyl | H | H | Cl | F | H | H |
| 447 | naphthalen-1-ylmethyl | H | H | Cl | OH | H | H |
| 448 | naphthalen-1-ylmethyl | H | H | Cl | OMe | H | H |
| 449 | 4-bromo-2-hydroxybenzyl | H | H | Cl | H | H | H |
| 450 | 4-bromo-2-hydroxybenzyl | H | H | H | OMe | H | H |
| 451 | 4-bromo-2-hydroxybenzyl | H | H | H | COOMe | H | H |

TABLE 4-continued

X = —CH2—, q = 0, r = 0, Y = —(R4)C=C(R5)—

| Compound No. 4- | R1—(CH2)p— | R2 | R3 | R4 | R5 | R6 | R7 |
|---|---|---|---|---|---|---|---|
| 452 | 4-Br, 2-CH2-, phenol | H | H | H | H | Cl | H |
| 453 | 4-Br, 2-CH2-, phenol | H | H | H | H | COOMe | H |
| 454 | 4-Br, 2-CH2-, phenol | H | H | H | H | H | Cl |
| 455 | 4-Br, 2-CH2-, phenol | H | H | H | OCF3 | H | H |
| 456 | 4-Br, 2-CH2-, phenol | H | H | COOMe | H | H | H |
| 457 | 4-Br, 2-CH2-, phenol | H | H | H | CF3 | H | H |
| 458 | 4-Br, 2-CH2-, phenol | H | H | H | Me | H | H |
| 459 | 4-Br, 2-CH2-, phenol | H | H | H | F | H | H |
| 460 | 4-Br, 2-CH2-, phenol | H | H | H | OH | H | H |
| 461 | 4-Br, 2-CH2-, phenol | H | H | H | NO2 | H | H |
| 462 | 4-Br, 2-CH2-, phenol | H | H | H | F | F | H |
| 463 | 4-Br, 2-CH2-, phenol | H | H | F | H | H | H |

TABLE 4-continued

X = —CH2—, q = 0, r = 0, Y = —(R4)C=C(R5)—

| Compound No. 4- | R1—(CH2)p— | R2 | R3 | R4 | R5 | R6 | R7 |
|---|---|---|---|---|---|---|---|
| 464 | 4-bromo-2-hydroxymethylphenyl (OH, Br) | H | H | Me | H | H | H |
| 465 | 4-bromo-2-hydroxymethylphenyl (OH, Br) | H | H | H | CN | H | H |
| 466 | 1-methylindol-3-ylmethyl | H | H | Cl | H | H | H |
| 467 | 1-methylindol-3-ylmethyl | H | H | H | OMe | H | H |
| 468 | 1-methylindol-3-ylmethyl | H | H | H | COOMe | H | H |
| 469 | 1-methylindol-3-ylmethyl | H | H | H | H | Cl | H |
| 470 | 1-methylindol-3-ylmethyl | H | H | H | H | COOMe | H |
| 471 | 1-methylindol-3-ylmethyl | H | H | H | H | H | Cl |
| 472 | 1-methylindol-3-ylmethyl | H | H | H | OCF3 | H | H |

TABLE 4-continued

X = —CH2—, q = 0, r = 0, Y = —(R4)C=C(R5)—

| Compound No. 4- | R1—(CH2)p— | R2 | R3 | R4 | R5 | R6 | R7 |
|---|---|---|---|---|---|---|---|
| 473 | N-methylindol-3-yl-CH2 | H | H | COOMe | H | H | H |
| 474 | N-methylindol-3-yl-CH2 | H | H | H | CF3 | H | H |
| 475 | N-methylindol-3-yl-CH2 | H | H | H | Me | H | H |
| 476 | N-methylindol-3-yl-CH2 | H | H | H | F | H | H |
| 477 | N-methylindol-3-yl-CH2 | H | H | H | OH | H | H |
| 478 | N-methylindol-3-yl-CH2 | H | H | H | NO2 | H | H |
| 479 | N-methylindol-3-yl-CH2 | H | H | H | F | F | H |
| 480 | N-methylindol-3-yl-CH2 | H | H | F | H | H | H |
| 481 | N-methylindol-3-yl-CH2 | H | H | Me | H | H | H |

TABLE 4-continued

X = —CH2—, q = 0, r = 0, Y = —(R4)C=C(R5)—

| Compound No. 4- | R1—(CH2)p— | R2 | R3 | R4 | R5 | R6 | R7 |
|---|---|---|---|---|---|---|---|
| 482 | 3-(N-methylindolyl)methyl | H | H | H | CN | H | H |
| 483 | 3-benzothienylmethyl | H | H | Cl | H | H | H |
| 484 | 3-benzothienylmethyl | H | H | H | OMe | H | H |
| 485 | 3-benzothienylmethyl | H | H | H | COOMe | H | H |
| 486 | 3-benzothienylmethyl | H | H | H | H | Cl | H |
| 487 | 3-benzothienylmethyl | H | H | H | H | COOMe | H |
| 488 | 3-benzothienylmethyl | H | H | H | H | H | Cl |
| 489 | 3-benzothienylmethyl | H | H | H | OCF3 | H | H |
| 490 | 3-benzothienylmethyl | H | H | COOMe | H | H | H |

TABLE 4-continued

X = —CH2—, q = 0, r = 0, Y = —(R4)C=C(R5)—

| Compound No. 4- | R1—(CH2)p— | R2 | R3 | R4 | R5 | R6 | R7 |
|---|---|---|---|---|---|---|---|
| 491 | benzothiophen-3-yl | H | H | H | CF3 | H | H |
| 492 | benzothiophen-3-yl | H | H | H | Me | H | H |
| 493 | benzothiophen-3-yl | H | H | H | F | H | H |
| 494 | benzothiophen-3-yl | H | H | H | OH | H | H |
| 495 | benzothiophen-3-yl | H | H | H | NO2 | H | H |
| 496 | benzothiophen-3-yl | H | H | H | F | F | H |
| 497 | benzothiophen-3-yl | H | H | F | H | H | H |
| 498 | benzothiophen-3-yl | H | H | Me | H | H | H |
| 499 | benzothiophen-3-yl | H | H | H | CN | H | H |

TABLE 4-continued
X = —CH2—, q = 0, r = 0, Y = —(R4)C═C(R5)—
| Compound No. 4- | R1—(CH2)p— | R2 | R3 | R4 | R5 | R6 | R7 |
|---|---|---|---|---|---|---|---|
| 500 | 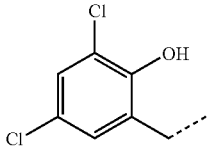 | H | Me | H | H | H | H |
| 501 | 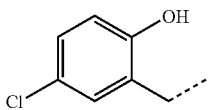 | H | Me | H | H | H | H |
| 502 | 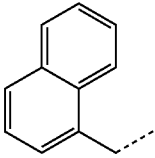 | H | Me | H | H | H | H |
| 503 | 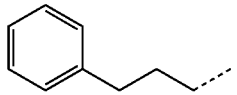 | H | Me | H | H | H | H |
| 504 | 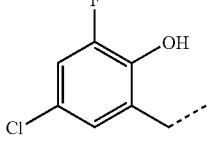 | H | H | H | H | H | H |
| 505 | 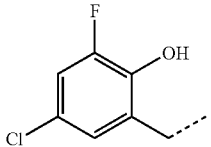 | H | H | F | H | H | H |
| 506 | 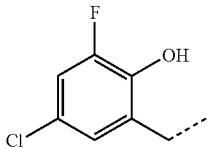 | H | H | Cl | H | H | H |
| 507 | 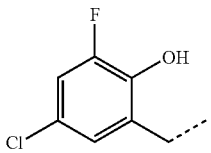 | H | H | Me | H | H | H |
| 508 | 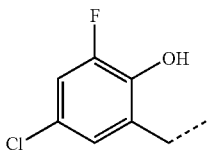 | H | H | Et | H | H | H |

TABLE 4-continued

X = —CH2—, q = 0, r = 0, Y = —(R4)C=C(R5)—

| Compound No. 4- | R1—(CH2)p— | R2 | R3 | R4 | R5 | R6 | R7 |
|---|---|---|---|---|---|---|---|
| 509 | 4-Cl, 2-F, 6-OH benzyl | H | H | OMe | H | H | H |
| 510 | 4-Cl, 2-F, 6-OH benzyl | H | H | OEt | H | H | H |
| 511 | 4-Cl, 2-F, 6-OH benzyl | H | H | CF3 | H | H | H |
| 512 | 4-Cl, 2-F, 6-OH benzyl | H | H | OCF3 | H | H | H |
| 513 | 4-Cl, 2-F, 6-OH benzyl | H | H | NO2 | H | H | H |
| 514 | 4-Cl, 2-F, 6-OH benzyl | H | H | NH2 | H | H | H |
| 515 | 4-Cl, 2-F, 6-OH benzyl | H | H | OH | H | H | H |
| 516 | 4-Cl, 2-F, 6-OH benzyl | H | H | CN | H | H | H |
| 517 | 4-Cl, 2-F, 6-OH benzyl | H | H | COMe | H | H | H |

TABLE 4-continued

X = —CH2—, q = 0, r = 0, Y = —(R4)C=C(R5)—

| Compound No. 4- | R1—(CH2)p— | R2 | R3 | R4 | R5 | R6 | R7 |
|---|---|---|---|---|---|---|---|
| 518 | 4-Cl, 2-F, 6-OH benzyl | H | H | COOMe | H | H | H |
| 519 | 4-Cl, 2-F, 6-OH benzyl | H | H | H | F | H | H |
| 520 | 4-Cl, 2-F, 6-OH benzyl | H | H | H | Cl | H | H |
| 521 | 4-Cl, 2-F, 6-OH benzyl | H | H | H | Me | H | H |
| 522 | 4-Cl, 2-F, 6-OH benzyl | H | H | H | Et | H | H |
| 523 | 4-Cl, 2-F, 6-OH benzyl | H | H | H | OMe | H | H |
| 524 | 4-Cl, 2-F, 6-OH benzyl | H | H | H | OEt | H | H |
| 525 | 4-Cl, 2-F, 6-OH benzyl | H | H | H | CF3 | H | H |
| 526 | 4-Cl, 2-F, 6-OH benzyl | H | H | H | OCF3 | H | H |

TABLE 4-continued

X = —CH2—, q = 0, r = 0, Y = —(R4)C=C(R5)—

| Compound No. 4- | R1—(CH2)p— | R2 | R3 | R4 | R5 | R6 | R7 |
|---|---|---|---|---|---|---|---|
| 527 | 4-Cl, 2-F, 6-OH-benzyl | H | H | H | NO2 | H | H |
| 528 | 4-Cl, 2-F, 6-OH-benzyl | H | H | H | NH2 | H | H |
| 529 | 4-Cl, 2-F, 6-OH-benzyl | H | H | H | OH | H | H |
| 530 | 4-Cl, 2-F, 6-OH-benzyl | H | H | H | OH | H | H |
| 531 | 4-Cl, 2-F, 6-OH-benzyl | H | H | H | COMe | H | H |
| 532 | 4-Cl, 2-F, 6-OH-benzyl | H | H | H | COOMe | H | H |
| 533 | 4-Cl, 2-F, 6-OH-benzyl | H | H | F | F | H | H |
| 534 | 4-Cl, 2-F, 6-OH-benzyl | H | H | F | Cl | H | H |
| 535 | 4-Cl, 2-F, 6-OH-benzyl | H | H | F | Me | H | H |

TABLE 4-continued

X = —CH2—, q = 0, r = 0, Y = —(R4)C=C(R5)—

| Compound No. 4- | R1—(CH2)p— | R2 | R3 | R4 | R5 | R6 | R7 |
|---|---|---|---|---|---|---|---|
| 536 | 4-Cl, 2-F, 6-OH phenyl | H | H | F | Et | H | H |
| 537 | 4-Cl, 2-F, 6-OH phenyl | H | H | F | OMe | H | H |
| 538 | 4-Cl, 2-F, 6-OH phenyl | H | H | F | OEt | H | H |
| 539 | 4-Cl, 2-F, 6-OH phenyl | H | H | F | CF3 | H | H |
| 540 | 4-Cl, 2-F, 6-OH phenyl | H | H | F | OCF3 | H | H |
| 541 | 4-Cl, 2-F, 6-OH phenyl | H | H | Cl | F | H | H |
| 542 | 4-Cl, 2-F, 6-OH phenyl | H | H | Cl | Cl | H | H |
| 543 | 4-Cl, 2-F, 6-OH phenyl | H | H | Cl | Me | H | H |
| 544 | 4-Cl, 2-F, 6-OH phenyl | H | H | Cl | Et | H | H |

TABLE 4-continued

X = —CH2—, q = 0, r = 0, Y = —(R4)C=C(R5)—

| Compound No. 4- | R1—(CH2)p— | R2 | R3 | R4 | R5 | R6 | R7 |
|---|---|---|---|---|---|---|---|
| 545 | 4-Cl, 2-F, 6-OH-phenyl | H | H | Cl | OMe | H | H |
| 546 | 4-Cl, 2-F, 6-OH-phenyl | H | H | Cl | OEt | H | H |
| 547 | 4-Cl, 2-F, 6-OH-phenyl | H | H | Cl | CF3 | H | H |
| 548 | 4-Cl, 2-F, 6-OH-phenyl | H | H | Cl | OCF3 | H | H |
| 549 | 4-Cl, 2-F, 6-OH-phenyl | H | H | Me | F | H | H |
| 550 | 4-Cl, 2-F, 6-OH-phenyl | H | H | Me | Cl | H | H |
| 551 | 4-Cl, 2-F, 6-OH-phenyl | H | H | Me | Me | H | H |
| 552 | 4-Cl, 2-F, 6-OH-phenyl | H | H | Me | Et | H | H |
| 553 | 4-Cl, 2-F, 6-OH-phenyl | H | H | Me | OMe | H | H |

TABLE 4-continued

X = —CH2—, q = 0, r = 0, Y = —(R4)C=C(R5)—

| Compound No. 4- | R1—(CH2)p— | R2 | R3 | R4 | R5 | R6 | R7 |
|---|---|---|---|---|---|---|---|
| 554 | 4-Cl, 2-F, 6-(OH) benzyl | H | H | Me | OEt | H | H |
| 555 | 4-Cl, 2-F, 6-(OH) benzyl | H | H | Me | CF3 | H | H |
| 556 | 4-Cl, 2-F, 6-(OH) benzyl | H | H | Me | OCF3 | H | H |
| 557 | 4-Cl, 2-F, 6-(OH) benzyl | H | H | OMe | F | H | H |
| 558 | 4-Cl, 2-F, 6-(OH) benzyl | H | H | OMe | Cl | H | H |
| 559 | 4-Cl, 2-F, 6-(OH) benzyl | H | H | OMe | Me | H | H |
| 560 | 4-Cl, 2-F, 6-(OH) benzyl | H | H | OMe | Et | H | H |
| 561 | 4-Cl, 2-F, 6-(OH) benzyl | H | H | OMe | OMe | H | H |
| 562 | 4-Cl, 2-F, 6-(OH) benzyl | H | H | OMe | OEt | H | H |

TABLE 4-continued

X = —CH2—, q = 0, r = 0, Y = —(R4)C=C(R5)—

| Compound No. 4- | R1—(CH2)p— | R2 | R3 | R4 | R5 | R6 | R7 |
|---|---|---|---|---|---|---|---|
| 563 | 4-chloro-2-fluoro-6-(...)phenol (F, OH, Cl) | H | H | OMe | CF3 | H | H |
| 564 | 4-chloro-2-fluoro-6-(...)phenol (F, OH, Cl) | H | H | OMe | OCF3 | H | H |

TABLE 5

X = —CO—, q = 0, r = 0, Y = —S—

| Compound No. 5- | R1—(CH2)p— | R2 | R3 | R6 | R7 |
|---|---|---|---|---|---|
| 1 | 2,4-dichloro-6-(...)phenol | H | H | H | H |
| 2 | 3,4-dichlorophenyl | H | H | H | H |
| 3 | 3,4-dichlorophenyl | H | H | H | H |
| 4 | naphth-1-yl | H | H | H | H |
| 5 | naphth-1-yl | H | H | H | H |
| 6 | 2-chlorophenyl | H | H | H | H |
| 7 | 3-chlorophenyl | H | H | H | H |

TABLE 5-continued
| | X = —CO—, q = 0, r = 0, Y = —S— | | | | |
|---|---|---|---|---|---|
| Compound No. 5- | R1—(CH2)p— | R2 | R3 | R6 | R7 |
| 8 | 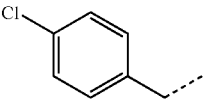 | H | H | H | H |
| 9 | 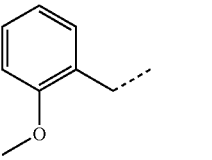 | H | H | H | H |
| 10 | 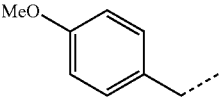 | H | H | H | H |
| 11 | 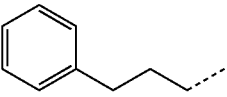 | H | H | H | H |
| 12 | 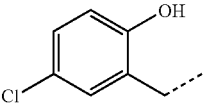 | H | H | H | H |
| 13 | 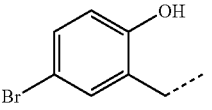 | H | H | H | H |
| 14 | 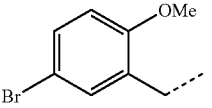 | H | H | H | H |
| 15 | 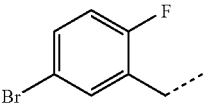 | H | H | H | H |
| 16 | 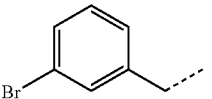 | H | H | H | H |
| 17 | 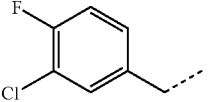 | H | H | H | H |
| 18 | 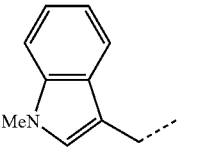 | H | H | H | H |

TABLE 5-continued

X = —CO—, q = 0, r = 0, Y = —S—

| Compound No. 5- | R1—(CH2)p— | R2 | R3 | R6 | R7 |
|---|---|---|---|---|---|
| 19 | benzothiophen-3-ylmethyl | H | H | H | H |
| 20 | 2-hydroxy-5-methoxybenzyl | H | H | H | H |
| 21 | 3-nitrobenzyl | H | H | H | H |
| 22 | 3-methoxybenzyl | H | H | H | H |
| 23 | naphthalen-2-ylmethyl | H | H | H | H |
| 24 | benzyl | H | H | H | H |
| 25 | phenethyl | H | H | H | H |
| 26 | 3-bromo-5-chloro-2-hydroxybenzyl | H | H | H | H |
| 27 | 4-cyano-2-hydroxybenzyl | H | H | H | H |
| 28 | 3-chloro-2-hydroxy-5-(trifluoromethyl)benzyl | H | H | H | H |
| 29 | 5-chloro-2-hydroxy-3-(trifluoromethyl)benzyl | H | H | H | H |

TABLE 5-continued

X = —CO—, q = 0, r = 0, Y = —S—

| Compound No. 5- | R1—(CH2)p— | R2 | R3 | R6 | R7 |
|---|---|---|---|---|---|
| 30 | 3-Cl, 2-OH-phenyl-CH2- | H | H | H | H |
| 31 | 4-Me-phenyl-CH2- | H | H | H | H |
| 32 | 4-F-phenyl-CH2- | H | H | H | H |
| 33 | 4-Br-phenyl-CH2- | H | H | H | H |
| 34 | 4-F3C-phenyl-CH2- | H | H | H | H |
| 35 | 4-HO-phenyl-CH2- | H | H | H | H |
| 36 | 4-NC-phenyl-CH2- | H | H | H | H |
| 37 | 4-MeSO2-phenyl-CH2- | H | H | H | H |
| 38 | 4-MeOOC-phenyl-CH2- | H | H | H | H |
| 39 | 4-Me2N-phenyl-CH2- | H | H | H | H |
| 40 | 4-MeO-phenyl-CH2- | H | H | H | H |
| 41 | 4-EtO-phenyl-CH2- | H | H | H | H |

TABLE 5-continued

X = —CO—, q = 0, r = 0, Y = —S—

| Compound No. 5- | R1—(CH2)p— | R2 | R3 | R6 | R7 |
|---|---|---|---|---|---|
| 42 | (propoxy-phenyl-methyl) | H | H | H | H |
| 43 | (isopropoxy-phenyl-methyl) | H | H | H | H |
| 44 | (isopropyl-phenyl-methyl) | H | H | H | H |
| 45 | (benzyloxy-phenyl-methyl) | H | H | H | H |
| 46 | (phenoxy-phenyl-methyl) | H | H | H | H |
| 47 | (biphenyl-methyl) | H | H | H | H |
| 48 | (acetamido-phenyl-methyl) | H | H | H | H |
| 49 | (2-propyl-phenyl-methyl) | H | H | H | H |
| 50 | (2-benzyloxy-phenyl-methyl) | H | H | H | H |
| 51 | (2-methyl-phenyl-methyl) | H | H | H | H |

TABLE 5-continued

| | X = —CO—, q = 0, r = 0, Y = —S— | | | | |
|---|---|---|---|---|---|
| Compound No. 5- | R1—(CH2)p— | R2 | R3 | R6 | R7 |
| 52 | 2-CN-C6H4-CH2- | H | H | H | H |
| 53 | 2-Cl-C6H4-CH2- | H | H | H | H |
| 54 | 2-OMe-C6H4-CH2- | H | H | H | H |
| 55 | 2-OEt-C6H4-CH2- | H | H | H | H |
| 56 | 2-Ph-C6H4-CH2- | H | H | H | H |
| 57 | 3-CF3-C6H4-CH2- | H | H | H | H |
| 58 | 3-Cl-2-F-C6H3-CH2- | H | H | H | H |
| 59 | 3,5-diCl-C6H3-CH2- | H | H | H | H |
| 60 | 3-Me-C6H4-CH2- | H | H | H | H |

TABLE 5-continued

X = —CO—, q = 0, r = 0, Y = —S—

| Compound No. 5- | R1—(CH2)p— | R2 | R3 | R6 | R7 |
|---|---|---|---|---|---|
| 61 | 3-F, 5-CF3-benzyl | H | H | H | H |
| 62 | 3-F3CO-benzyl | H | H | H | H |
| 63 | 2-F, 5-MeO-benzyl | H | H | H | H |
| 64 | 2-F, 5-O2N-benzyl | H | H | H | H |
| 65 | 4-O2N-benzyl | H | H | H | H |
| 66 | 3-F, 2-Me-benzyl | H | H | H | H |
| 67 | 3-F3CS-benzyl | H | H | H | H |
| 68 | 2,5-diCl-benzyl | H | H | H | H |
| 69 | 3-F2HC-benzyl | H | H | H | H |
| 70 | 2-F-benzyl | H | H | H | H |
| 71 | 2-NO2-benzyl | H | H | H | H |
| 72 | 2-COOH-benzyl | H | H | H | H |

TABLE 5-continued

X = —CO—, q = 0, r = 0, Y = —S—

| Compound No. 5- | R1—(CH2)p— | R2 | R3 | R6 | R7 |
|---|---|---|---|---|---|
| 73 | 4-Br, 2-(CH2—), 1-OEt phenyl | H | H | H | H |
| 74 | 2,3-dimethylphenyl-CH2— | H | H | H | H |
| 75 | 3-F-phenyl-CH2— | H | H | H | H |
| 76 | 2,4-diCl-phenyl-CH2— | H | H | H | H |
| 77 | 3-CN-phenyl-CH2— | H | H | H | H |
| 78 | 3-OH-phenyl-CH2— | H | H | H | H |
| 79 | 3-OEt-phenyl-CH2— | H | H | H | H |
| 80 | 4-Cl, 3-NO2-phenyl-CH2— | H | H | H | H |
| 81 | 2,3-diCl-phenyl-CH2— | H | H | H | H |
| 82 | 4-methyl, 2,3-diF-phenyl-CH2— | H | H | H | H |
| 83 | 4-F, 2-Br-phenyl-CH2— | H | H | H | H |

TABLE 5-continued

X = —CO—, q = 0, r = 0, Y = —S—

| Compound No. 5- | R1—(CH2)p— | R2 | R3 | R6 | R7 |
|---|---|---|---|---|---|
| 84 | 2-F, 3-CF3-benzyl | H | H | H | H |
| 85 | 3-Cl, 4-OH-benzyl | H | H | H | H |
| 86 | 2,3-diF-benzyl | H | H | H | H |
| 87 | 3-Br, 4-MeO-benzyl | H | H | H | H |
| 88 | 2-OEt, 3-MeO-benzyl | H | H | H | H |
| 89 | 2,3-diMe, 4-MeO-benzyl | H | H | H | H |
| 90 | 2-OBn, 3-MeO-benzyl | H | H | H | H |
| 91 | 4-Cl, 3-NO2-benzyl | H | H | H | H |
| 92 | 3-(4-MeO-phenoxy)-benzyl | H | H | H | H |

TABLE 5-continued

X = —CO—, q = 0, r = 0, Y = —S—

| Compound No. 5- | R1—(CH2)p— | R2 | R3 | R6 | R7 |
|---|---|---|---|---|---|
| 93 | 4-methylphenyl-O-(3-phenyl)-CH2– | H | H | H | H |
| 94 | 4-chlorophenyl-O-(3-phenyl)-CH2– | H | H | H | H |
| 95 | benzyl-O-(3-phenyl)-CH2– | H | H | H | H |
| 96 | phenyl-O-(3-phenyl)-CH2– | H | H | H | H |
| 97 | 4-MeO-3-HO-phenyl-CH2– | H | H | H | H |
| 98 | 3-CF3-2-Cl-phenyl-CH2– | H | H | H | H |
| 99 | 4-HO-3-O2N-phenyl-CH2– | H | H | H | H |
| 100 | 2,3-diOMe-phenyl-CH2– | H | H | H | H |
| 101 | 4-EtO-3-Me-2-OEt-phenyl-CH2– | H | H | H | H |

TABLE 5-continued

X = —CO—, q = 0, r = 0, Y = —S—

| Compound No. 5- | R1—(CH2)p— | R2 | R3 | R6 | R7 |
|---|---|---|---|---|---|
| 102 | HO-CH2CH2-O-(3-phenyl)-CH2- | H | H | H | H |
| 103 | 2,3,4-trimethoxyphenyl-CH2- (MeO, OMe, OMe) | H | H | H | H |
| 104 | 2-fluoro-3-phenoxyphenyl-CH2- | H | H | H | H |
| 105 | 2,3-dimethoxy-6-(COOH)phenyl-CH2- | H | H | H | H |
| 106 | 5-chloro-2-nitrophenyl-CH2- | H | H | H | H |
| 107 | 3,5-dihydroxyphenyl-CH2- | H | H | H | H |
| 108 | 3-benzyloxy-4-methoxyphenyl-CH2- | H | H | H | H |
| 109 | 3,4-diethoxyphenyl-CH2- | H | H | H | H |
| 110 | 3-carboxyphenyl-CH2- | H | H | H | H |
| 111 | 4-methoxy-3-hydroxyphenyl-CH2- (OMe, HO) | H | H | H | H |
| 112 | 2-nitro-3-hydroxyphenyl-CH2- (O2N, HO) | H | H | H | H |

TABLE 5-continued

| | X = —CO—, q = 0, r = 0, Y = —S— | | | | |
|---|---|---|---|---|---|
| Compound No. 5- | R1—(CH2)p— | R2 | R3 | R6 | R7 |
| 113 | 3,5-bis(trifluoromethyl)benzyl | H | H | H | H |
| 114 | 2-methoxy-3-nitrobenzyl | H | H | H | H |
| 115 | (4-methylnaphthalen-1-yl)methyl | H | H | H | H |
| 116 | (1-methyl-7-methylindol-3-yl)methyl | H | H | H | H |
| 117 | (2-methoxynaphthalen-1-yl)methyl | H | H | H | H |
| 118 | benzofuran-2-ylmethyl | H | H | H | H |
| 119 | (1,2-dimethylindol-3-yl)methyl | H | H | H | H |
| 120 | quinolin-8-ylmethyl | H | H | H | H |

TABLE 5-continued

| | X = —CO—, q = 0, r = 0, Y = —S— | | | | |
|---|---|---|---|---|---|
| Compound No. 5- | R1—(CH2)p— | R2 | R3 | R6 | R7 |
| 121 | 2-hydroxynaphthalen-1-ylmethyl | H | H | H | H |
| 122 | 2-acetoxynaphthalen-1-ylmethyl | H | H | H | H |
| 123 | 1-hydroxynaphthalen-2-ylmethyl | H | H | H | H |
| 124 | 1H-indol-7-ylmethyl | H | H | H | H |
| 125 | quinolin-4-ylmethyl | H | H | H | H |
| 126 | 1,5-dimethyl-1H-indol-3-ylmethyl | H | H | H | H |
| 127 | anthracen-9-ylmethyl | H | H | H | H |

TABLE 5-continued

X = —CO—, q = 0, r = 0, Y = —S—

| Compound No. 5- | R1—(CH2)p— | R2 | R3 | R6 | R7 |
|---|---|---|---|---|---|
| 128 | 2-methylnaphthalen-1-ylmethyl | H | H | H | H |
| 129 | 2-ethoxynaphthalen-1-ylmethyl | H | H | H | H |
| 130 | 1H-indol-3-ylmethyl | H | H | H | H |
| 131 | 6-methyl-1-methylindol-3-ylmethyl | H | H | H | H |
| 132 | 1-methylindol-2-ylmethyl | H | H | H | H |
| 133 | 4-methyl-1-methylindol-3-ylmethyl | H | H | H | H |
| 134 | 2,5-dimethyl-1-methylindol-3-ylmethyl | H | H | H | H |
| 135 | 5-methoxy-1-methylindol-3-ylmethyl | H | H | H | H |

TABLE 5-continued

X = —CO—, q = 0, r = 0, Y = —S—

| Compound No. 5- | R1—(CH2)p— | R2 | R3 | R6 | R7 |
|---|---|---|---|---|---|
| 136 | 4-methylbenzothiophen-3-yl | H | H | H | H |
| 137 | 1-methylbenzimidazol-2-yl | H | H | H | H |
| 138 | 1-methyl-2-phenylindol-3-yl | H | H | H | H |
| 139 | 1-acetylindol-3-yl | H | H | H | H |
| 140 | quinolin-2-yl | H | H | H | H |
| 141 | 6-methoxy-1-methylindol-3-yl | H | H | H | H |
| 142 | 3-methylbenzothiophen-2-yl | H | H | H | H |
| 143 | 4-methoxynaphthalen-1-yl | H | H | H | H |

TABLE 5-continued

| | X = —CO—, q = 0, r = 0, Y = —S— | | | | |
|---|---|---|---|---|---|
| Compound No. 5- | R1—(CH2)p— | R2 | R3 | R6 | R7 |
| 144 | (phenanthrenyl-CH2) | H | H | H | H |
| 145 | (6-methoxy-naphth-2-yl-CH2) | H | H | H | H |
| 146 | (1-bromo-naphth-2-yl-CH2) | H | H | H | H |
| 147 | (4-dimethylamino-naphth-1-yl-CH2) | H | H | H | H |
| 148 | (2,3-dihydro-1,4-benzodioxin-6-yl-CH2) | H | H | H | H |
| 149 | (2,2-dimethyl-chroman-6-yl-CH2) | H | H | H | H |
| 150 | (2,3-dihydrobenzofuran-5-yl-CH2) | H | H | H | H |
| 151 | (9-ethyl-carbazol-3-yl-CH2) | H | H | H | H |
| 152 | (1,3-benzodioxol-4-yl-CH2) | H | H | H | H |

TABLE 5-continued
X = —CO—, q = 0, r = 0, Y = —S—
| Compound No. 5- | R1—(CH2)p— | R2 | R3 | R6 | R7 |
|---|---|---|---|---|---|
| 153 | 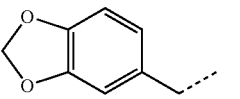 | H | H | H | H |
| 154 | 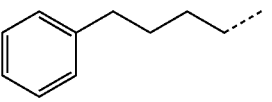 | H | H | H | H |
| 155 | 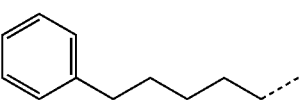 | H | H | H | H |
| 156 | 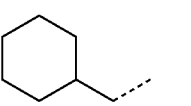 | H | H | H | H |
| 157 | 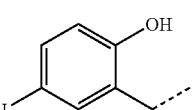 | H | H | H | H |
| 158 | 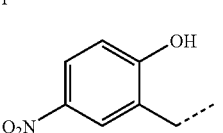 | H | H | H | H |
| 159 | 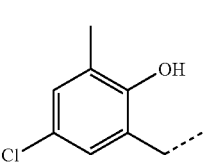 | H | H | H | H |
| 160 | 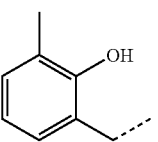 | H | H | H | H |
| 161 | 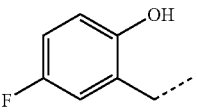 | H | H | H | H |
| 162 | 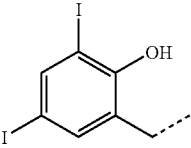 | H | H | H | H |
| 163 | 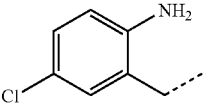 | H | H | H | H |
| 164 | 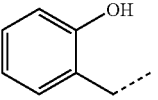 | H | H | H | H |

TABLE 5-continued
X = —CO—, q = 0, r = 0, Y = —S—
| Compound No. 5- | R1—(CH2)p— | R2 | R3 | R6 | R7 |
|---|---|---|---|---|---|
| 165 | 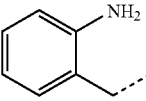 | H | H | H | H |
| 166 | 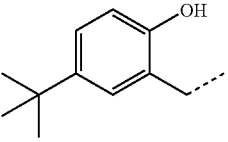 | H | H | H | H |
| 167 | 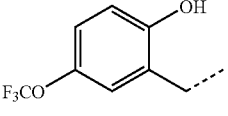 | H | H | H | H |
| 168 | 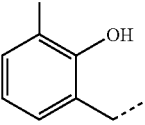 | H | H | H | H |
| 169 | 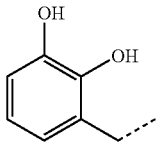 | H | H | H | H |
| 170 | 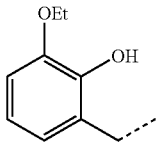 | H | H | H | H |
| 171 | 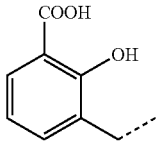 | H | H | H | H |
| 172 | 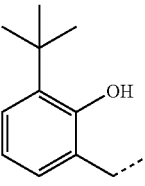 | H | H | H | H |
| 173 | 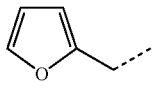 | H | H | H | H |
| 174 | 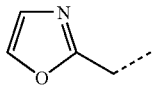 | H | H | H | H |
| 175 | 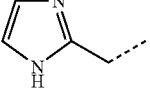 | H | H | H | H |

TABLE 5-continued
| | X = —CO—, q = 0, r = 0, Y = —S— | | | | |
|---|---|---|---|---|---|
| Compound No. 5- | R1—(CH2)p— | R2 | R3 | R6 | R7 |
| 176 | 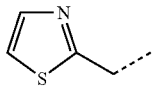 | H | H | H | H |
| 177 | 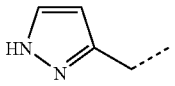 | H | H | H | H |
| 178 | 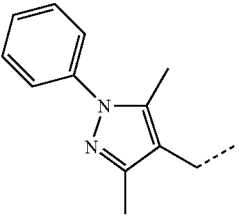 | H | H | H | H |
| 179 | 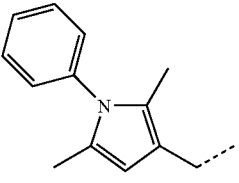 | H | H | H | H |
| 180 | 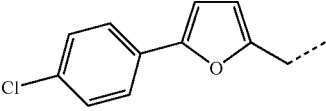 | H | H | H | H |
| 181 | 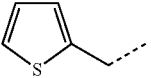 | H | H | H | H |
| 182 | 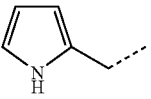 | H | H | H | H |
| 183 | 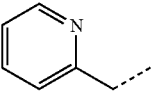 | H | H | H | H |
| 184 | 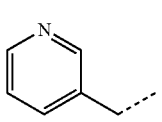 | H | H | H | H |
| 185 | 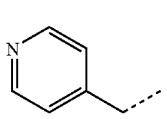 | H | H | H | H |
| 186 | 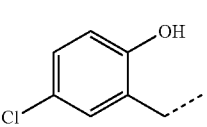 | H | H | H | H |

TABLE 5-continued
X = —CO—, q = 0, r = 0, Y = —S—
| Compound No. 5- | R1—(CH2)p— | R2 | R3 | R6 | R7 |
|---|---|---|---|---|---|
| 187 | 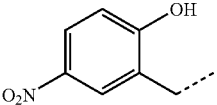 | H | H | H | H |
| 188 | 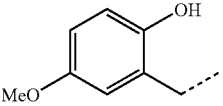 | H | H | H | H |
| 189 | 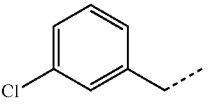 | H | H | H | H |
| 190 | 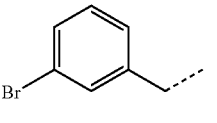 | H | H | H | H |
| 191 | 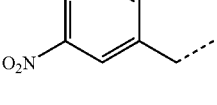 | H | H | H | H |
| 192 | 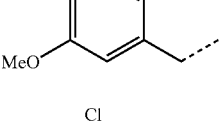 | H | H | H | H |
| 193 | 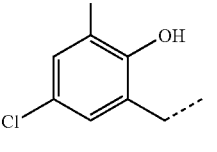 | H | H | H | H |
| 194 | 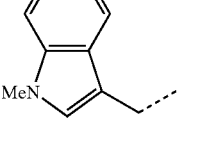 | H | H | H | H |
| 195 | 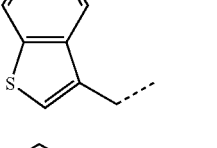 | H | H | H | H |
| 196 | 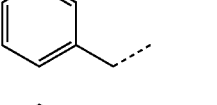 | H | H | H | H |
| 197 | 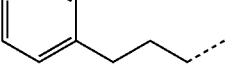 | H | H | H | H |

TABLE 5-continued

| | X = —CO—, q = 0, r = 0, Y = —S— | | | | |
|---|---|---|---|---|---|
| Compound No. 5- | R1—(CH2)p— | R2 | R3 | R6 | R7 |
| 198 | 4-Br, 2-(CH2)-phenol | H | H | H | H |
| 199 | naphthalen-2-ylmethyl | H | H | H | H |
| 200 | phenethyl | H | H | H | H |
| 201 | 3,5-dichloro-2-hydroxybenzyl | H | H | Cl | H |
| 202 | 3,5-dichloro-2-hydroxybenzyl | H | H | COOMe | H |
| 203 | 3,5-dichloro-2-hydroxybenzyl | H | H | OMe | H |
| 204 | 3,5-dichloro-2-hydroxybenzyl | H | H | OCF3 | H |
| 205 | 3,5-dichloro-2-hydroxybenzyl | H | H | CF3 | H |
| 206 | 3,5-dichloro-2-hydroxybenzyl | H | H | Me | H |

TABLE 5-continued

X = —CO—, q = 0, r = 0, Y = —S—

| Compound No. 5- | R1—(CH2)p— | R2 | R3 | R6 | R7 |
|---|---|---|---|---|---|
| 207 | 2,4-dichloro-6-hydroxybenzyl | H | H | F | H |
| 208 | 2,4-dichloro-6-hydroxybenzyl | H | H | NO2 | H |
| 209 | 2,4-dichloro-6-hydroxybenzyl | H | H | CN | H |
| 210 | 2,4-dichloro-6-hydroxybenzyl | H | H | OH | H |
| 211 | 4-chloro-2-hydroxybenzyl | H | H | H | H |
| 212 | 4-chloro-2-hydroxybenzyl | H | H | Cl | H |
| 213 | 4-chloro-2-hydroxybenzyl | H | H | COOMe | H |
| 214 | 4-chloro-2-hydroxybenzyl | H | H | OMe | H |
| 215 | 4-chloro-2-hydroxybenzyl | H | H | OCF3 | H |
| 216 | 4-chloro-2-hydroxybenzyl | H | H | CF3 | H |
| 217 | 4-chloro-2-hydroxybenzyl | H | H | Me | H |

TABLE 5-continued
X = —CO—, q = 0, r = 0, Y = —S—
| Compound No. 5- | R1—(CH2)p— | R2 | R3 | R6 | R7 |
|---|---|---|---|---|---|
| 218 | 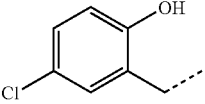 | H | H | F | H |
| 219 | 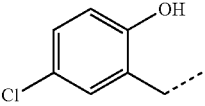 | H | H | NO2 | H |
| 220 | 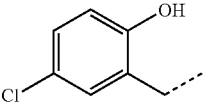 | H | H | CN | H |
| 221 | 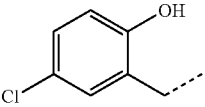 | H | H | OH | H |
| 222 | 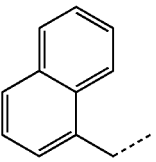 | H | H | H | H |
| 223 | 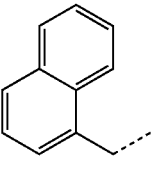 | H | H | Cl | H |
| 224 | 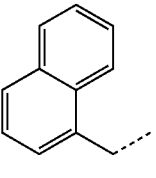 | H | H | COOMe | H |
| 225 | 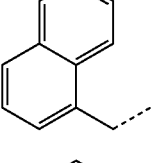 | H | H | OMe | H |
| 226 | 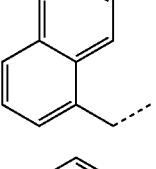 | H | H | OCF3 | H |
| 227 | 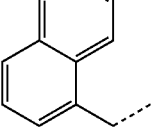 | H | H | CF3 | H |

TABLE 5-continued

X = —CO—, q = 0, r = 0, Y = —S—

| Compound No. 5- | R1—(CH2)p— | R2 | R3 | R6 | R7 |
|---|---|---|---|---|---|
| 228 | 1-naphthylmethyl | H | H | Me | H |
| 229 | 1-naphthylmethyl | H | H | F | H |
| 230 | 1-naphthylmethyl | H | H | NO2 | H |
| 231 | 1-naphthylmethyl | H | H | CN | H |
| 232 | 1-naphthylmethyl | H | H | OH | H |
| 233 | phenylpropyl | H | H | H | H |
| 234 | phenylpropyl | H | H | Cl | H |
| 235 | phenylpropyl | H | H | COOMe | H |
| 236 | phenylpropyl | H | H | OMe | H |
| 237 | phenylpropyl | H | H | OCF3 | H |
| 238 | phenylpropyl | H | H | CF3 | H |

TABLE 5-continued

| | X = —CO—, q = 0, r = 0, Y = —S— | | | | |
|---|---|---|---|---|---|
| Compound No. 5- | R1—(CH2)p— | R2 | R3 | R6 | R7 |
| 239 | 3-phenylpropyl | H | H | Me | H |
| 240 | 3-phenylpropyl | H | H | F | H |
| 241 | 3-phenylpropyl | H | H | NO2 | H |
| 242 | 3-phenylpropyl | H | H | CN | H |
| 243 | 3-phenylpropyl | H | H | OH | H |
| 244 | 5-bromo-2-hydroxybenzyl | H | H | H | H |
| 245 | 5-bromo-2-hydroxybenzyl | H | H | Cl | H |
| 246 | 5-bromo-2-hydroxybenzyl | H | H | COOMe | H |
| 247 | 5-bromo-2-hydroxybenzyl | H | H | OMe | H |
| 248 | 5-bromo-2-hydroxybenzyl | H | H | OCF3 | H |
| 249 | 5-bromo-2-hydroxybenzyl | H | H | CF3 | H |
| 250 | 5-bromo-2-hydroxybenzyl | H | H | Me | H |

TABLE 5-continued

X = —CO—, q = 0, r = 0, Y = —S—

| Compound No. 5- | R1—(CH2)p— | R2 | R3 | R6 | R7 |
|---|---|---|---|---|---|
| 251 | 4-Br, 2-OH-phenyl-CH2- | H | H | F | H |
| 252 | 4-Br, 2-OH-phenyl-CH2- | H | H | NO2 | H |
| 253 | 4-Br, 2-OH-phenyl-CH2- | H | H | CN | H |
| 254 | 4-Br, 2-OH-phenyl-CH2- | H | H | OH | H |
| 255 | (1-Me-indol-3-yl)-CH2- | H | H | H | H |
| 256 | (1-Me-indol-3-yl)-CH2- | H | H | Cl | H |
| 257 | (1-Me-indol-3-yl)-CH2- | H | H | COOMe | H |
| 258 | (1-Me-indol-3-yl)-CH2- | H | H | OMe | H |
| 259 | (1-Me-indol-3-yl)-CH2- | H | H | OCF3 | H |
| 260 | (1-Me-indol-3-yl)-CH2- | H | H | CF3 | H |

TABLE 5-continued

X = —CO—, q = 0, r = 0, Y = —S—

| Compound No. 5- | R1—(CH2)p— | R2 | R3 | R6 | R7 |
|---|---|---|---|---|---|
| 261 | 3-(1-methylindolyl)methyl | H | H | Me | H |
| 262 | 3-(1-methylindolyl)methyl | H | H | F | H |
| 263 | 3-(1-methylindolyl)methyl | H | H | NO2 | H |
| 264 | 3-(1-methylindolyl)methyl | H | H | CN | H |
| 265 | 3-(1-methylindolyl)methyl | H | H | OH | H |
| 266 | 3-benzothienylmethyl | H | H | H | H |
| 267 | 3-benzothienylmethyl | H | H | Cl | H |
| 268 | 3-benzothienylmethyl | H | H | COOMe | H |
| 269 | 3-benzothienylmethyl | H | H | OMe | H |

TABLE 5-continued
| | X = —CO—, q = 0, r = 0, Y = —S— | | | | |
|---|---|---|---|---|---|
| Compound No. 5- | R1—(CH2)p— | R2 | R3 | R6 | R7 |
| 270 | 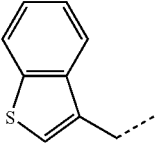 | H | H | OCF3 | H |
| 271 | 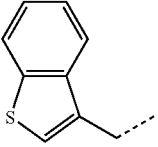 | H | H | CF3 | H |
| 272 | 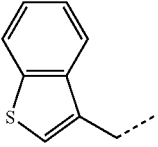 | H | H | Me | H |
| 273 | 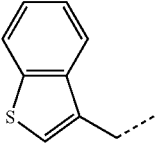 | H | H | F | H |
| 274 | 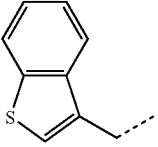 | H | H | NO2 | H |
| 275 | 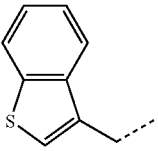 | H | H | CN | H |
| 276 | 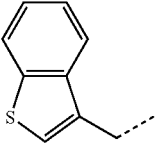 | H | H | OH | H |
TABLE 6
| | X = —CO—, q = 0, r = 0, Y = —N(R8)— | | | | | |
|---|---|---|---|---|---|---|
| Compound No. 6 | R1—(CH2)p— | R2 | R3 | R6 | R7 | R8 |
| 1 | 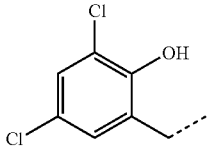 | H | H | H | H | Me |

TABLE 6-continued
X = —CO—, q = 0, r = 0, Y = —N(R8)—
| Compound No. 6 | R1—(CH2)$_p$— | R2 | R3 | R6 | R7 | R8 |
|---|---|---|---|---|---|---|
| 2 | 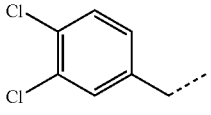 | H | H | H | H | Me |
| 3 | 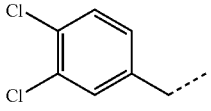 | H | H | H | H | Me |
| 4 | 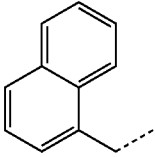 | H | H | H | H | Me |
| 5 | 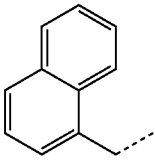 | H | H | H | H | Me |
| 6 | 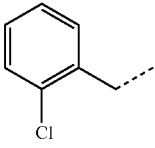 | H | H | H | H | Me |
| 7 | 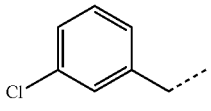 | H | H | H | H | Me |
| 8 | 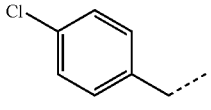 | H | H | H | H | Me |
| 9 | 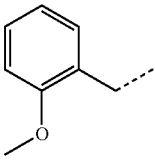 | H | H | H | H | Me |
| 10 | 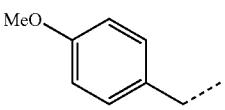 | H | H | H | H | Me |
| 11 | 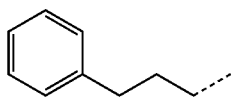 | H | H | H | H | Me |
| 12 | 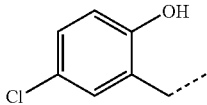 | H | H | H | H | Me |

TABLE 6-continued

X = —CO—, q = 0, r = 0, Y = —N(R8)—

| Compound No. 6 | R1—(CH2)$_p$— | R2 | R3 | R6 | R7 | R8 |
|---|---|---|---|---|---|---|
| 13 | 4-Br, 2-(CH2)-phenol | H | H | H | H | Me |
| 14 | 4-Br, 2-(CH2)-anisole | H | H | H | H | Me |
| 15 | 4-Br, 2-(CH2)-fluorobenzene | H | H | H | H | Me |
| 16 | 3-Br-benzyl | H | H | H | H | Me |
| 17 | 3-Cl, 4-F-benzyl | H | H | H | H | Me |
| 18 | (1-Me-indol-3-yl)methyl | H | H | H | H | Me |
| 19 | (benzothiophen-3-yl)methyl | H | H | H | H | Me |
| 20 | 4-MeO, 2-(CH2)-phenol | H | H | H | H | Me |
| 21 | 3-NO2-benzyl | H | H | H | H | Me |
| 22 | 3-MeO-benzyl | H | H | H | H | Me |
| 23 | (naphthalen-2-yl)methyl | H | H | H | H | Me |

TABLE 6-continued

X = —CO—, q = 0, r = 0, Y = —N(R8)—

| Compound No. 6 | R1—(CH2)$_p$— | R2 | R3 | R6 | R7 | R8 |
|---|---|---|---|---|---|---|
| 24 | benzyl | H | H | H | H | Me |
| 25 | phenethyl | H | H | H | H | Me |
| 26 | 3-Br-5-Cl-2-OH-benzyl | H | H | H | H | Me |
| 27 | 4-OH-3-(CH2)-5-CN-phenyl (NC, OH) | H | H | H | H | Me |
| 28 | 3-Cl-5-CF3-2-OH-benzyl | H | H | H | H | Me |
| 29 | 3-CF3-5-Cl-2-OH-benzyl | H | H | H | H | Me |
| 30 | 3-Cl-2-OH-benzyl | H | H | H | H | Me |
| 31 | 4-Me-benzyl | H | H | H | H | Me |
| 32 | 4-F-benzyl | H | H | H | H | Me |
| 33 | 4-Br-benzyl | H | H | H | H | Me |
| 34 | 4-CF3-benzyl | H | H | H | H | Me |

TABLE 6-continued
X = —CO—, q = 0, r = 0, Y = —N(R8)—
| Compound No. 6 | R1—(CH2)p— | R2 | R3 | R6 | R7 | R8 |
|---|---|---|---|---|---|---|
| 35 | 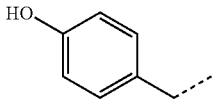 | H | H | H | H | Me |
| 36 | 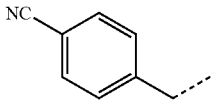 | H | H | H | H | Me |
| 37 | 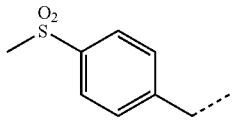 | H | H | H | H | Me |
| 38 | 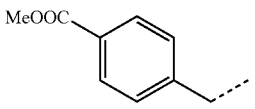 | H | H | H | H | Me |
| 39 | 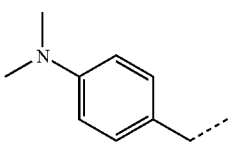 | H | H | H | H | Me |
| 40 | 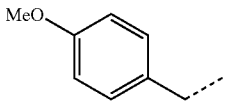 | H | H | H | H | Me |
| 41 | 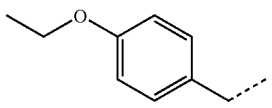 | H | H | H | H | Me |
| 42 | 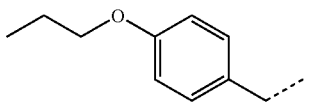 | H | H | H | H | Me |
| 43 | 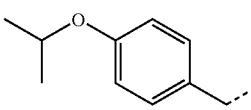 | H | H | H | H | Me |
| 44 | 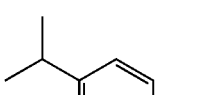 | H | H | H | H | Me |
| 45 | 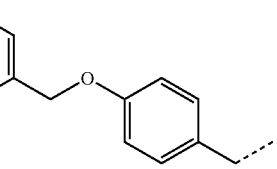 | H | H | H | H | Me |

TABLE 6-continued

X = —CO—, q = 0, r = 0, Y = —N(R8)—

| Compound No. 6 | R1—(CH2)$_p$— | R2 | R3 | R6 | R7 | R8 |
|---|---|---|---|---|---|---|
| 46 | 4-phenoxybenzyl | H | H | H | H | Me |
| 47 | 4-biphenylmethyl | H | H | H | H | Me |
| 48 | 4-acetamidobenzyl | H | H | H | H | Me |
| 49 | 2-propylbenzyl | H | H | H | H | Me |
| 50 | 2-benzyloxybenzyl | H | H | H | H | Me |
| 51 | 2-methylbenzyl | H | H | H | H | Me |
| 52 | 2-cyanobenzyl | H | H | H | H | Me |
| 53 | 2-chlorobenzyl | H | H | H | H | Me |
| 54 | 2-methoxybenzyl | H | H | H | H | Me |

TABLE 6-continued

X = —CO—, q = 0, r = 0, Y = —N(R8)—

| Compound No. 6 | R1—(CH2)$_p$— | R2 | R3 | R6 | R7 | R8 |
|---|---|---|---|---|---|---|
| 55 | 2-ethoxybenzyl | H | H | H | H | Me |
| 56 | 2-phenylbenzyl (biphenyl-2-ylmethyl) | H | H | H | H | Me |
| 57 | 3-(trifluoromethyl)benzyl | H | H | H | H | Me |
| 58 | 3-chloro-2-fluorobenzyl | H | H | H | H | Me |
| 59 | 3,5-dichlorobenzyl | H | H | H | H | Me |
| 60 | 3-methylbenzyl | H | H | H | H | Me |
| 61 | 3-fluoro-5-(trifluoromethyl)benzyl | H | H | H | H | Me |
| 62 | 3-(trifluoromethoxy)benzyl | H | H | H | H | Me |
| 63 | 5-methoxy-2-fluorobenzyl | H | H | H | H | Me |
| 64 | 5-nitro-2-fluorobenzyl | H | H | H | H | Me |

TABLE 6-continued
X = —CO—, q = 0, r = 0, Y = —N(R8)—
| Compound No. 6 | R1—(CH2)$_p$— | R2 | R3 | R6 | R7 | R8 |
|---|---|---|---|---|---|---|
| 65 | 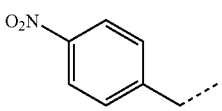 | H | H | H | H | Me |
| 66 | 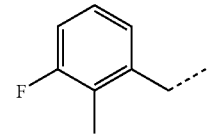 | H | H | H | H | Me |
| 67 | 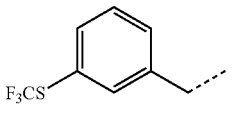 | H | H | H | H | Me |
| 68 | 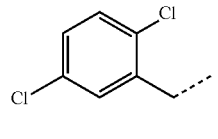 | H | H | H | H | Me |
| 69 | 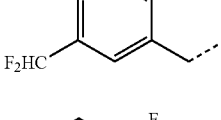 | H | H | H | H | Me |
| 70 | 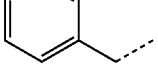 | H | H | H | H | Me |
| 71 | 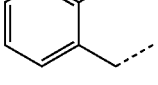 | H | H | H | H | Me |
| 72 | 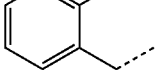 | H | H | H | H | Me |
| 73 | 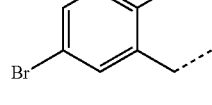 | H | H | H | H | Me |
| 74 | 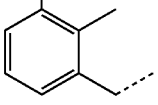 | H | H | H | H | Me |
| 75 | 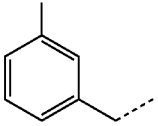 | H | H | H | H | Me |

TABLE 6-continued
X = —CO—, q = 0, r = 0, Y = —N(R8)—
| Compound No. 6 | R1—(CH2)$_p$— | R2 | R3 | R6 | R7 | R8 |
|---|---|---|---|---|---|---|
| 76 | 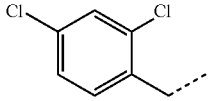 | H | H | H | H | Me |
| 77 | 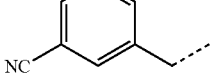 | H | H | H | H | Me |
| 78 | 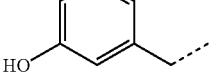 | H | H | H | H | Me |
| 79 | 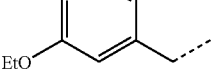 | H | H | H | H | Me |
| 80 | 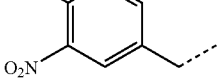 | H | H | H | H | Me |
| 81 | 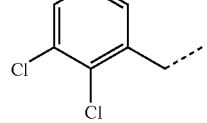 | H | H | H | H | Me |
| 82 | 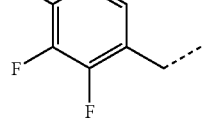 | H | H | H | H | Me |
| 83 | 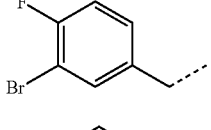 | H | H | H | H | Me |
| 84 | 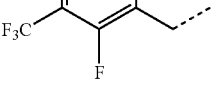 | H | H | H | H | Me |
| 85 | 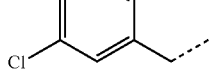 | H | H | H | H | Me |
| 86 | 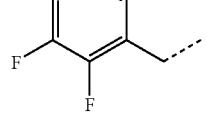 | H | H | H | H | Me |

TABLE 6-continued

X = —CO—, q = 0, r = 0, Y = —N(R8)—

| Compound No. 6 | R1—(CH2)$_p$— | R2 | R3 | R6 | R7 | R8 |
|---|---|---|---|---|---|---|
| 87 | 4-MeO, 3-Br-phenyl | H | H | H | H | Me |
| 88 | 2-OEt, 3-MeO-phenyl | H | H | H | H | Me |
| 89 | 4-MeO, 2,3-diMe-phenyl | H | H | H | H | Me |
| 90 | 3-MeO, 2-OBn-phenyl | H | H | H | H | Me |
| 91 | 2-Cl, 5-NO$_2$-phenyl | H | H | H | H | Me |
| 92 | 3-(4-MeO-phenoxy)-phenyl | H | H | H | H | Me |
| 93 | 3-(4-Me-phenoxy)-phenyl | H | H | H | H | Me |

TABLE 6-continued

X = —CO—, q = 0, r = 0, Y = —N(R8)—

| Compound No. 6 | R1—(CH2)$_p$— | R2 | R3 | R6 | R7 | R8 |
|---|---|---|---|---|---|---|
| 94 | 4-Cl-phenyl-O-(3-phenyl-CH2-) | H | H | H | H | Me |
| 95 | phenyl-CH2-O-(3-phenyl-CH2-) | H | H | H | H | Me |
| 96 | phenyl-O-(3-phenyl-CH2-) | H | H | H | H | Me |
| 97 | 3-MeO-4-HO-phenyl-CH2- | H | H | H | H | Me |
| 98 | 2-CF3-3-Cl-phenyl-CH2- | H | H | H | H | Me |
| 99 | 4-HO-3-O2N-phenyl-CH2- | H | H | H | H | Me |
| 100 | 2,3-(OMe)2-phenyl-CH2- | H | H | H | H | Me |
| 101 | 2-EtO-3-Me-4-EtO-phenyl-CH2- | H | H | H | H | Me |
| 102 | 3-(HO-CH2CH2-O)-phenyl-CH2- | H | H | H | H | Me |

TABLE 6-continued

X = —CO—, q = 0, r = 0, Y = —N(R8)—

| Compound No. 6 | R1—(CH2)$_p$— | R2 | R3 | R6 | R7 | R8 |
|---|---|---|---|---|---|---|
| 103 | 2,3,4-trimethoxybenzyl (MeO, OMe, OMe) | H | H | H | H | Me |
| 104 | 3-phenoxy-4-fluorobenzyl | H | H | H | H | Me |
| 105 | 2-methoxy-3-methoxy-6-carboxybenzyl (OMe, MeO, COOH) | H | H | H | H | Me |
| 106 | 5-chloro-2-nitrobenzyl | H | H | H | H | Me |
| 107 | 3,5-dihydroxybenzyl | H | H | H | H | Me |
| 108 | 3-benzyloxy-4-methoxybenzyl | H | H | H | H | Me |
| 109 | 3,4-diethoxybenzyl | H | H | H | H | Me |
| 110 | 3-carboxybenzyl | H | H | H | H | Me |
| 111 | 3-hydroxy-4-methoxybenzyl | H | H | H | H | Me |
| 112 | 3-hydroxy-4-nitrobenzyl | H | H | H | H | Me |

TABLE 6-continued

X = —CO—, q = 0, r = 0, Y = —N(R8)—

| Compound No. 6 | R1—(CH2)$_p$— | R2 | R3 | R6 | R7 | R8 |
|---|---|---|---|---|---|---|
| 113 | 3,5-bis(trifluoromethyl)benzyl | H | H | H | H | Me |
| 114 | 2-methoxy-3-nitrobenzyl | H | H | H | H | Me |
| 115 | (4-methylnaphthalen-1-yl)methyl | H | H | H | H | Me |
| 116 | (1,7-dimethyl-1H-indol-3-yl)methyl | H | H | H | H | Me |
| 117 | (2-methoxynaphthalen-1-yl)methyl | H | H | H | H | Me |
| 118 | benzofuran-2-ylmethyl | H | H | H | H | Me |
| 119 | (1,2-dimethyl-1H-indol-3-yl)methyl | H | H | H | H | Me |
| 120 | quinolin-8-ylmethyl | H | H | H | H | Me |

TABLE 6-continued

X = —CO—, q = 0, r = 0, Y = —N(R8)—

| Compound No. 6 | R1—(CH2)$_p$— | R2 | R3 | R6 | R7 | R8 |
|---|---|---|---|---|---|---|
| 121 | 2-hydroxy-1-naphthylmethyl | H | H | H | H | Me |
| 122 | 2-acetoxy-1-naphthylmethyl | H | H | H | H | Me |
| 123 | 1-hydroxy-2-naphthylmethyl | H | H | H | H | Me |
| 124 | indol-7-ylmethyl | H | H | H | H | Me |
| 125 | quinolin-4-ylmethyl | H | H | H | H | Me |
| 126 | (5-methyl-1-methylindol-3-yl)methyl | H | H | H | H | Me |
| 127 | anthracen-9-ylmethyl | H | H | H | H | Me |

TABLE 6-continued

X = —CO—, q = 0, r = 0, Y = —N(R8)—

| Compound No. 6 | R1—(CH2)$_p$— | R2 | R3 | R6 | R7 | R8 |
|---|---|---|---|---|---|---|
| 128 | 2-methyl-naphthalen-1-yl-methyl | H | H | H | H | Me |
| 129 | 2-ethoxy-naphthalen-1-yl-methyl | H | H | H | H | Me |
| 130 | 1H-indol-3-yl-methyl | H | H | H | H | Me |
| 131 | 1,6-dimethyl-1H-indol-3-yl-methyl | H | H | H | H | Me |
| 132 | 1-methyl-1H-indol-2-yl-methyl | H | H | H | H | Me |
| 133 | 1,4-dimethyl-1H-indol-3-yl-methyl | H | H | H | H | Me |
| 134 | 1,2,5-trimethyl-1H-indol-3-yl-methyl | H | H | H | H | Me |

TABLE 6-continued

X = —CO—, q = 0, r = 0, Y = —N(R8)—

| Compound No. 6 | R1—(CH2)$_p$— | R2 | R3 | R6 | R7 | R8 |
|---|---|---|---|---|---|---|
| 135 | 5-OMe-1-Me-indol-3-yl | H | H | H | H | Me |
| 136 | 4-Me-benzothiophen-3-yl | H | H | H | H | Me |
| 137 | 1-Me-benzimidazol-2-yl | H | H | H | H | Me |
| 138 | 1-Me-2-phenyl-indol-3-yl | H | H | H | H | Me |
| 139 | 1-acetyl-indol-3-yl | H | H | H | H | Me |
| 140 | quinolin-2-yl | H | H | H | H | Me |
| 141 | 6-OMe-1-Me-indol-3-yl | H | H | H | H | Me |
| 142 | 3-Me-benzothiophen-2-yl | H | H | H | H | Me |

TABLE 6-continued

X = —CO—, q = 0, r = 0, Y = —N(R8)—

| Compound No. 6 | R1—(CH2)$_p$— | R2 | R3 | R6 | R7 | R8 |
|---|---|---|---|---|---|---|
| 143 | 4-methoxynaphthalen-1-ylmethyl | H | H | H | H | Me |
| 144 | phenanthren-9-ylmethyl | H | H | H | H | Me |
| 145 | 6-methoxynaphthalen-2-ylmethyl | H | H | H | H | Me |
| 146 | 1-bromonaphthalen-2-ylmethyl | H | H | H | H | Me |
| 147 | 4-(dimethylamino)naphthalen-1-ylmethyl | H | H | H | H | Me |
| 148 | 2,3-dihydro-1,4-benzodioxin-6-ylmethyl | H | H | H | H | Me |
| 149 | 2,2-dimethylchroman-6-ylmethyl | H | H | H | H | Me |
| 150 | 2,3-dihydrobenzofuran-5-ylmethyl | H | H | H | H | Me |
| 151 | 9-ethylcarbazol-3-ylmethyl | H | H | H | H | Me |

TABLE 6-continued
X = —CO—, q = 0, r = 0, Y = —N(R8)—
| Compound No. 6 | R1—(CH2)p— | R2 | R3 | R6 | R7 | R8 |
|---|---|---|---|---|---|---|
| 152 | 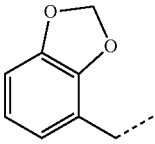 | H | H | H | H | Me |
| 153 | 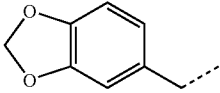 | H | H | H | H | Me |
| 154 | 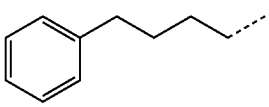 | H | H | H | H | Me |
| 155 | 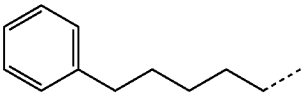 | H | H | H | H | Me |
| 156 | 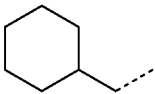 | H | H | H | H | Me |
| 157 | 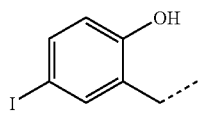 | H | H | H | H | Me |
| 158 | 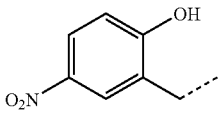 | H | H | H | H | Me |
| 159 | 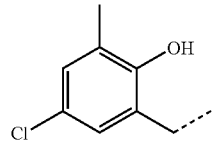 | H | H | H | H | Me |
| 160 | 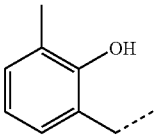 | H | H | H | H | Me |
| 161 | 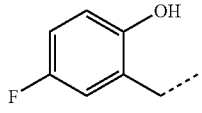 | H | H | H | H | Me |
| 162 | 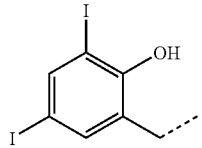 | H | H | H | H | Me |

TABLE 6-continued

X = —CO—, q = 0, r = 0, Y = —N(R8)—

| Compound No. 6 | R1—(CH2)p— | R2 | R3 | R6 | R7 | R8 |
|---|---|---|---|---|---|---|
| 163 | 2-NH2, 5-Cl-benzyl | H | H | H | H | Me |
| 164 | 2-OH-benzyl | H | H | H | H | Me |
| 165 | 2-NH2-benzyl | H | H | H | H | Me |
| 166 | 2-OH, 5-tBu-benzyl | H | H | H | H | Me |
| 167 | 2-OH, 5-OCF3-benzyl | H | H | H | H | Me |
| 168 | 2-OH, 3-OMe-benzyl | H | H | H | H | Me |
| 169 | 2,3-diOH-benzyl | H | H | H | H | Me |
| 170 | 2-OH, 3-OEt-benzyl | H | H | H | H | Me |
| 171 | 2-OH, 3-COOH-benzyl | H | H | H | H | Me |
| 172 | 2-OH, 3-tBu-benzyl | H | H | H | H | Me |

TABLE 6-continued
X = —CO—, q = 0, r = 0, Y = —N(R8)—
| Compound No. 6 | R1—(CH2)$_p$— | R2 | R3 | R6 | R7 | R8 |
|---|---|---|---|---|---|---|
| 173 | 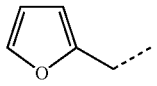 | H | H | H | H | Me |
| 174 | 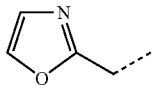 | H | H | H | H | Me |
| 175 | 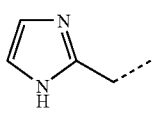 | H | H | H | H | Me |
| 176 | 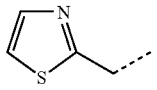 | H | H | H | H | Me |
| 177 | 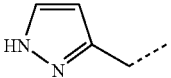 | H | H | H | H | Me |
| 178 | 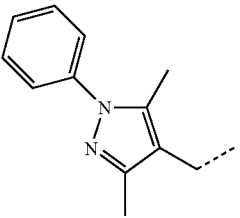 | H | H | H | H | Me |
| 179 | 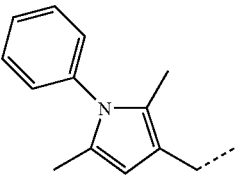 | H | H | H | H | Me |
| 180 | 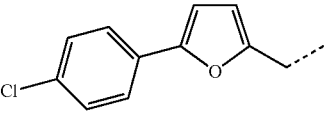 | H | H | H | H | Me |
| 181 | 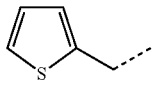 | H | H | H | H | Me |
| 182 | 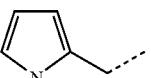 | H | H | H | H | Me |
| 183 | 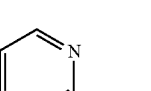 | H | H | H | H | Me |
| 184 | 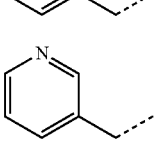 | H | H | H | H | Me |

TABLE 6-continued
X = —CO—, q = 0, r = 0, Y = —N(R8)—
| Compound No. 6 | R1—(CH2)$_p$— | R2 | R3 | R6 | R7 | R8 |
|---|---|---|---|---|---|---|
| 185 | 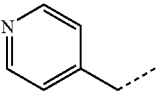 | H | H | H | H | Me |
| 186 | 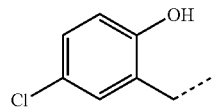 | H | H | H | H | Me |
| 187 | 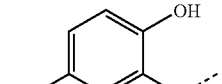 | H | H | H | H | Me |
| 188 | 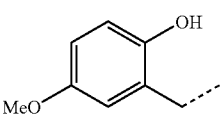 | H | H | H | H | Me |
| 189 | 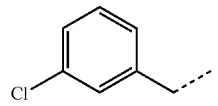 | H | H | H | H | Me |
| 190 | 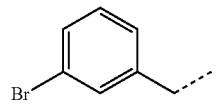 | H | H | H | H | Me |
| 191 | 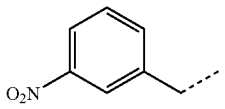 | H | H | H | H | Me |
| 192 | 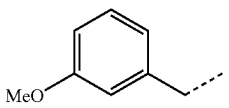 | H | H | H | H | Me |
| 193 | 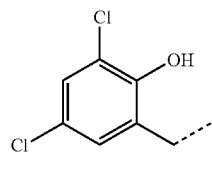 | H | H | H | H | Me |
| 194 | 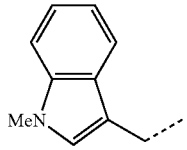 | H | H | H | H | Me |
| 195 | 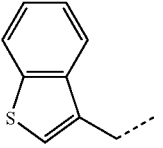 | H | H | H | H | Me |

TABLE 6-continued
| X = —CO—, q = 0, r = 0, Y = —N(R8)— | | | | | | |
|---|---|---|---|---|---|---|
| Compound No. 6 | R1—(CH2)$_p$— | R2 | R3 | R6 | R7 | R8 |
| 196 | 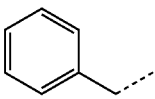 | H | H | H | H | Me |
| 197 | 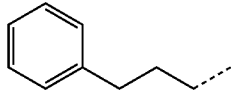 | H | H | H | H | Me |
| 198 | 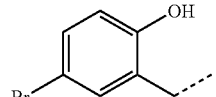 | H | H | H | H | Me |
| 199 | 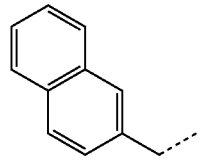 | H | H | H | H | Me |
| 200 | 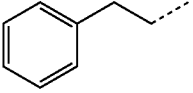 | H | H | H | H | Me |
| 201 | 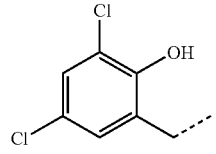 | H | H | Cl | H | Me |
| 202 | 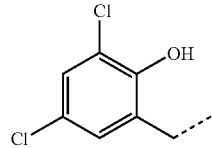 | H | H | COOMe | H | Me |
| 203 | 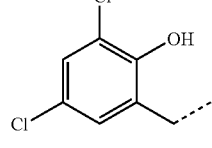 | H | H | OMe | H | Me |
| 204 | 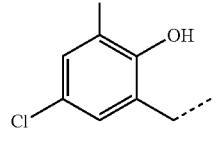 | H | H | OCF3 | H | Me |
| 205 | 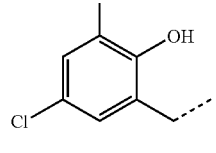 | H | H | CF3 | H | Me |

TABLE 6-continued

X = —CO—, q = 0, r = 0, Y = —N(R8)—

| Compound No. 6 | R1—(CH2)$_p$— | R2 | R3 | R6 | R7 | R8 |
|---|---|---|---|---|---|---|
| 206 | 2,4-dichloro-6-hydroxybenzyl | H | H | Me | H | Me |
| 207 | 2,4-dichloro-6-hydroxybenzyl | H | H | F | H | Me |
| 208 | 2,4-dichloro-6-hydroxybenzyl | H | H | NO2 | H | Me |
| 209 | 2,4-dichloro-6-hydroxybenzyl | H | H | CN | H | Me |
| 210 | 2,4-dichloro-6-hydroxybenzyl | H | H | OH | H | Me |
| 211 | 4-chloro-2-hydroxybenzyl | H | H | H | H | Me |
| 212 | 4-chloro-2-hydroxybenzyl | H | H | Cl | H | Me |
| 213 | 4-chloro-2-hydroxybenzyl | H | H | COOMe | H | Me |
| 214 | 4-chloro-2-hydroxybenzyl | H | H | OMe | H | Me |
| 215 | 4-chloro-2-hydroxybenzyl | H | H | OCF3 | H | Me |

TABLE 6-continued

X = —CO—, q = 0, r = 0, Y = —N(R8)—

| Compound No. 6 | R1—(CH2)p— | R2 | R3 | R6 | R7 | R8 |
|---|---|---|---|---|---|---|
| 216 | 4-Cl-2-hydroxyphenyl-CH2- | H | H | CF3 | H | Me |
| 217 | 4-Cl-2-hydroxyphenyl-CH2- | H | H | Me | H | Me |
| 218 | 4-Cl-2-hydroxyphenyl-CH2- | H | H | F | H | Me |
| 219 | 4-Cl-2-hydroxyphenyl-CH2- | H | H | NO2 | H | Me |
| 220 | 4-Cl-2-hydroxyphenyl-CH2- | H | H | CN | H | Me |
| 221 | 4-Cl-2-hydroxyphenyl-CH2- | H | H | OH | H | Me |
| 222 | naphthalen-1-yl-CH2- | H | H | H | H | Me |
| 223 | naphthalen-1-yl-CH2- | H | H | Cl | H | Me |
| 224 | naphthalen-1-yl-CH2- | H | H | COOMe | H | Me |
| 225 | naphthalen-1-yl-CH2- | H | H | OMe | H | Me |

TABLE 6-continued

X = —CO—, q = 0, r = 0, Y = —N(R8)—

| Compound No. 6 | R1—(CH2)$_p$— | R2 | R3 | R6 | R7 | R8 |
|---|---|---|---|---|---|---|
| 226 | 1-naphthylmethyl | H | H | OCF3 | H | Me |
| 227 | 1-naphthylmethyl | H | H | CF3 | H | Me |
| 228 | 1-naphthylmethyl | H | H | Me | H | Me |
| 229 | 1-naphthylmethyl | H | H | F | H | Me |
| 230 | 1-naphthylmethyl | H | H | NO2 | H | Me |
| 231 | 1-naphthylmethyl | H | H | CN | H | Me |
| 232 | 1-naphthylmethyl | H | H | OH | H | Me |
| 233 | phenylpropyl | H | H | H | H | Me |
| 234 | phenylpropyl | H | H | Cl | H | Me |

TABLE 6-continued

X = —CO—, q = 0, r = 0, Y = —N(R8)—

| Compound No. 6 | R1—(CH2)ₚ— | R2 | R3 | R6 | R7 | R8 |
|---|---|---|---|---|---|---|
| 235 | PhCH₂CH₂— | H | H | COOMe | H | Me |
| 236 | PhCH₂CH₂— | H | H | OMe | H | Me |
| 237 | PhCH₂CH₂— | H | H | OCF3 | H | Me |
| 238 | PhCH₂CH₂— | H | H | CF3 | H | Me |
| 239 | PhCH₂CH₂— | H | H | Me | H | Me |
| 240 | PhCH₂CH₂— | H | H | F | H | Me |
| 241 | PhCH₂CH₂— | H | H | NO2 | H | Me |
| 242 | PhCH₂CH₂— | H | H | CN | H | Me |
| 243 | PhCH₂CH₂— | H | H | OH | H | Me |
| 244 | 4-Br-2-OH-C₆H₃CH₂— | H | H | H | H | Me |
| 245 | 4-Br-2-OH-C₆H₃CH₂— | H | H | Cl | H | Me |
| 246 | 4-Br-2-OH-C₆H₃CH₂— | H | H | COOMe | H | Me |
| 247 | 4-Br-2-OH-C₆H₃CH₂— | H | H | OMe | H | Me |

TABLE 6-continued

X = —CO—, q = 0, r = 0, Y = —N(R8)—

| Compound No. 6 | R1—(CH2)p— | R2 | R3 | R6 | R7 | R8 |
|---|---|---|---|---|---|---|
| 248 | 4-Br-2-(CH2)-phenol | H | H | OCF3 | H | Me |
| 249 | 4-Br-2-(CH2)-phenol | H | H | CF3 | H | Me |
| 250 | 6-Br-2-(CH2)-phenol | H | H | Me | H | Me |
| 251 | 4-Br-2-(CH2)-phenol | H | H | F | H | Me |
| 252 | 4-Br-2-(CH2)-phenol | H | H | NO2 | H | Me |
| 253 | 4-Br-2-(CH2)-phenol | H | H | CN | H | Me |
| 254 | 4-Br-2-(CH2)-phenol | H | H | OH | H | Me |
| 255 | 1,2-diMe-indol-3-yl-CH2— | H | H | H | H | Me |
| 256 | 1,2-diMe-indol-3-yl-CH2— | H | H | Cl | H | Me |
| 257 | 1,2-diMe-indol-3-yl-CH2— | H | H | COOMe | H | Me |

TABLE 6-continued

X = —CO—, q = 0, r = 0, Y = —N(R8)—

| Compound No. 6 | R1—(CH2)$_p$— | R2 | R3 | R6 | R7 | R8 |
|---|---|---|---|---|---|---|
| 258 | 2-Me,1-Me-indol-3-yl-CH2 | H | H | OMe | H | Me |
| 259 | 2-Me,1-Me-indol-3-yl-CH2 | H | H | OCF3 | H | Me |
| 260 | 2-Me,1-Me-indol-3-yl-CH2 | H | H | CF3 | H | Me |
| 261 | 2-Me,1-Me-indol-3-yl-CH2 | H | H | Me | H | Me |
| 262 | 2-Me,1-Me-indol-3-yl-CH2 | H | H | F | H | Me |
| 263 | 2-Me,1-Me-indol-3-yl-CH2 | H | H | NO2 | H | Me |
| 264 | 2-Me,1-Me-indol-3-yl-CH2 | H | H | CN | H | Me |

TABLE 6-continued

X = —CO—, q = 0, r = 0, Y = —N(R8)—

| Compound No. 6 | R1—(CH2)$_p$— | R2 | R3 | R6 | R7 | R8 |
|---|---|---|---|---|---|---|
| 265 | 2-methyl-1-methylindol-3-yl | H | H | OH | H | Me |
| 266 | benzothiophen-3-yl | H | H | H | H | Me |
| 267 | benzothiophen-3-yl | H | H | Cl | H | Me |
| 268 | benzothiophen-3-yl | H | H | COOMe | H | Me |
| 269 | benzothiophen-3-yl | H | H | OMe | H | Me |
| 270 | benzothiophen-3-yl | H | H | OCF3 | H | Me |
| 271 | benzothiophen-3-yl | H | H | CF3 | H | Me |
| 272 | benzothiophen-3-yl | H | H | Me | H | Me |
| 273 | benzothiophen-3-yl | H | H | F | H | Me |

TABLE 6-continued

X = —CO—, q = 0, r = 0, Y = —N(R8)—

| Compound No. 6 | R1—(CH2)$_p$— | R2 | R3 | R6 | R7 | R8 |
|---|---|---|---|---|---|---|
| 274 | 4-methylbenzo[b]thiophen-3-ylmethyl | H | H | NO2 | H | Me |
| 275 | 4-methylbenzo[b]thiophen-3-ylmethyl | H | H | CN | H | Me |
| 276 | 4-methylbenzo[b]thiophen-3-ylmethyl | H | H | OH | H | Me |

TABLE 7

X = —CO—, q = 1, R = 0, Y = —(R4)C=C(R5)—

| Compound No. 7 | R1—(CH2)p— | R2 | R3 | R4 | R5 | R6 | R7 |
|---|---|---|---|---|---|---|---|
| 1 | 3,4-dichlorobenzyl | H | H | H | H | H | H |
| 2 | 3,4-dichlorobenzyl | H | H | H | Cl | H | H |
| 3 | naphthalen-1-ylmethyl | H | H | H | H | H | H |
| 4 | naphthalen-1-ylmethyl | H | H | H | Cl | H | H |
| 5 | 2-chlorobenzyl | H | H | H | H | H | H |

TABLE 7-continued
X = —CO—, q = 1, R = 0, Y = —(R4)C=C(R5)—
| Compound No. 7 | R1—(CH2)p— | R2 | R3 | R4 | R5 | R6 | R7 |
|---|---|---|---|---|---|---|---|
| 6 | 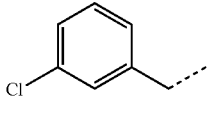 | H | H | H | H | H | H |
| 7 | 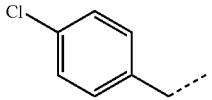 | H | H | H | H | H | H |
| 8 | 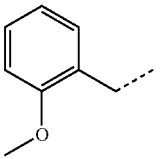 | H | H | H | H | H | H |
| 9 | 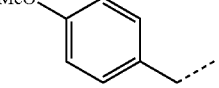 | H | H | H | H | H | H |
| 10 | 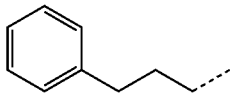 | H | H | H | H | H | H |
| 11 | 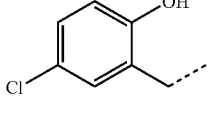 | H | H | H | H | H | H |
| 12 | 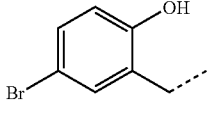 | H | H | H | H | H | H |
| 13 | 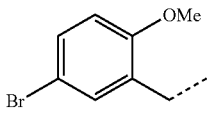 | H | H | H | H | H | H |
| 14 | 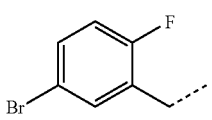 | H | H | H | H | H | H |
| 15 | 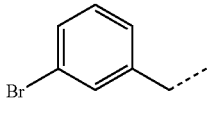 | H | H | H | H | H | H |
| 16 | 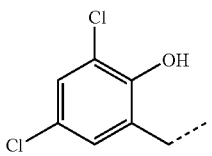 | H | H | H | H | H | H |
| 17 | 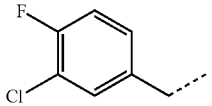 | H | H | H | H | H | H |

TABLE 7-continued

X = —CO—, q = 1, R = 0, Y = —(R4)C=C(R5)—

| Compound No. 7 | R1—(CH2)p— | R2 | R3 | R4 | R5 | R6 | R7 |
|---|---|---|---|---|---|---|---|
| 18 | 3-(N-methylindolyl)methyl | H | H | H | H | H | H |
| 19 | 3-benzothienylmethyl | H | H | H | H | H | H |
| 20 | 2-hydroxy-5-methoxybenzyl | H | H | H | H | H | H |
| 21 | 3-nitrobenzyl | H | H | H | H | H | H |
| 22 | 3-methoxybenzyl | H | H | H | H | H | H |
| 23 | 2-naphthylmethyl | H | H | H | H | H | H |
| 24 | benzyl | H | H | H | H | H | H |
| 25 | phenethyl | H | H | H | H | H | H |
| 26 | 3-bromo-5-chloro-2-hydroxybenzyl | H | H | H | H | H | H |
| 27 | 5-cyano-2-hydroxybenzyl | H | H | H | H | H | H |

TABLE 7-continued

X = —CO—, q = 1, R = 0, Y = —(R4)C═C(R5)—

| Compound No. 7 | R1—(CH2)p— | R2 | R3 | R4 | R5 | R6 | R7 |
|---|---|---|---|---|---|---|---|
| 28 | 2-chloro-6-(CH2)-4-(trifluoromethyl)phenol | H | H | H | H | H | H |
| 29 | 4-chloro-2-(CH2)-6-(trifluoromethyl)phenol | H | H | H | H | H | H |
| 30 | 2-chloro-6-(CH2)phenol | H | H | H | H | H | H |
| 31 | 4-methylbenzyl | H | H | H | H | H | H |
| 32 | 4-fluorobenzyl | H | H | H | H | H | H |
| 33 | 4-bromobenzyl | H | H | H | H | H | H |
| 34 | 4-(trifluoromethyl)benzyl | H | H | H | H | H | H |
| 35 | 4-hydroxybenzyl | H | H | H | H | H | H |
| 36 | 4-cyanobenzyl | H | H | H | H | H | H |
| 37 | 4-(methylsulfonyl)benzyl | H | H | H | H | H | H |
| 38 | 4-(methoxycarbonyl)benzyl | H | H | H | H | H | H |

TABLE 7-continued

X = —CO—, q = 1, R = 0, Y = —(R4)C=C(R5)—

| Compound No. 7 | R1—(CH2)p— | R2 | R3 | R4 | R5 | R6 | R7 |
|---|---|---|---|---|---|---|---|
| 39 | 4-(dimethylamino)benzyl | H | H | H | H | H | H |
| 40 | 4-methoxybenzyl | H | H | H | H | H | H |
| 41 | 4-ethoxybenzyl | H | H | H | H | H | H |
| 42 | 4-propoxybenzyl | H | H | H | H | H | H |
| 43 | 4-isopropoxybenzyl | H | H | H | H | H | H |
| 44 | 4-isopropylbenzyl | H | H | H | H | H | H |
| 45 | 4-(benzyloxy)benzyl | H | H | H | H | H | H |
| 46 | 4-phenoxybenzyl | H | H | H | H | H | H |
| 47 | biphenyl-4-ylmethyl | H | H | H | H | H | H |
| 48 | 4-acetamidobenzyl | H | H | H | H | H | H |

TABLE 7-continued

X = —CO—, q = 1, R = 0, Y = —(R4)C=C(R5)—

| Compound No. 7 | R1—(CH2)p— | R2 | R3 | R4 | R5 | R6 | R7 |
|---|---|---|---|---|---|---|---|
| 49 | 2-propylphenyl-CH2— | H | H | H | H | H | H |
| 50 | 2-benzyloxyphenyl-CH2— | H | H | H | H | H | H |
| 51 | 2-methylphenyl-CH2— | H | H | H | H | H | H |
| 52 | 2-cyanophenyl-CH2— | H | H | H | H | H | H |
| 53 | 2-chlorophenyl-CH2— | H | H | H | H | H | H |
| 54 | 2-methoxyphenyl-CH2— | H | H | H | H | H | H |
| 55 | 2-ethoxyphenyl-CH2— | H | H | H | H | H | H |
| 56 | 2-phenylphenyl-CH2— | H | H | H | H | H | H |
| 57 | 3-trifluoromethylphenyl-CH2— | H | H | H | H | H | H |

TABLE 7-continued
X = —CO—, q = 1, R = 0, Y = —(R4)C=C(R5)—
| Compound No. 7 | R1—(CH2)p— | R2 | R3 | R4 | R5 | R6 | R7 |
|---|---|---|---|---|---|---|---|
| 58 | 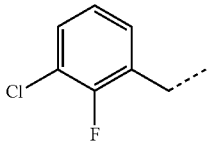 | H | H | H | H | H | H |
| 59 | 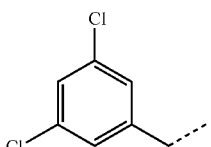 | H | H | H | H | H | H |
| 60 | 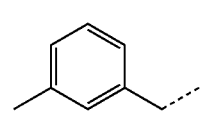 | H | H | H | H | H | H |
| 61 | 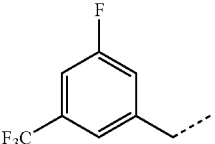 | H | H | H | H | H | H |
| 62 | 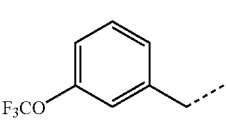 | H | H | H | H | H | H |
| 63 | 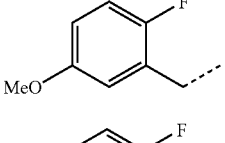 | H | H | H | H | H | H |
| 64 | 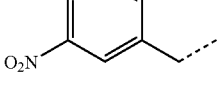 | H | H | H | H | H | H |
| 65 | 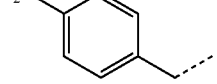 | H | H | H | H | H | H |
| 66 | 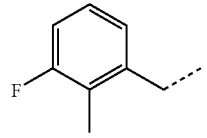 | H | H | H | H | H | H |
| 67 | 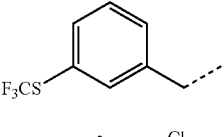 | H | H | H | H | H | H |
| 68 | 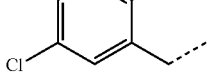 | H | H | H | H | H | H |

TABLE 7-continued

X = —CO—, q = 1, R = 0, Y = —(R4)C=C(R5)—

| Compound No. 7 | R1—(CH2)p— | R2 | R3 | R4 | R5 | R6 | R7 |
|---|---|---|---|---|---|---|---|
| 69 | 3-(F₂HC)-C₆H₄-CH₂- | H | H | H | H | H | H |
| 70 | 2-F-C₆H₄-CH₂- | H | H | H | H | H | H |
| 71 | 2-NO₂-C₆H₄-CH₂- | H | H | H | H | H | H |
| 72 | 2-COOH-C₆H₄-CH₂- | H | H | H | H | H | H |
| 73 | 5-Br-2-OEt-C₆H₃-CH₂- | H | H | H | H | H | H |
| 74 | 2,3-diMe-C₆H₃-CH₂- | H | H | H | H | H | H |
| 75 | 3-F-C₆H₄-CH₂- | H | H | H | H | H | H |
| 76 | 2,4-diCl-C₆H₃-CH₂- | H | H | H | H | H | H |
| 77 | 3-NC-C₆H₄-CH₂- | H | H | H | H | H | H |
| 78 | 3-HO-C₆H₄-CH₂- | H | H | H | H | H | H |
| 79 | 3-EtO-C₆H₄-CH₂- | H | H | H | H | H | H |
| 80 | 4-Cl-3-O₂N-C₆H₃-CH₂- | H | H | H | H | H | H |

TABLE 7-continued

X = —CO—, q = 1, R = 0, Y = —(R4)C=C(R5)—

| Compound No. 7 | R1—(CH2)p— | R2 | R3 | R4 | R5 | R6 | R7 |
|---|---|---|---|---|---|---|---|
| 81 | 2,3-dichlorobenzyl | H | H | H | H | H | H |
| 82 | 2,3-difluoro-4-methylbenzyl | H | H | H | H | H | H |
| 83 | 3-bromo-4-fluorobenzyl | H | H | H | H | H | H |
| 84 | 2-fluoro-3-(trifluoromethyl)benzyl | H | H | H | H | H | H |
| 85 | 3-chloro-4-hydroxybenzyl | H | H | H | H | H | H |
| 86 | 2,3-difluorobenzyl | H | H | H | H | H | H |
| 87 | 3-bromo-4-methoxybenzyl | H | H | H | H | H | H |
| 88 | 2-ethoxy-3-methoxybenzyl | H | H | H | H | H | H |
| 89 | 4-methoxy-2,3-dimethylbenzyl | H | H | H | H | H | H |

TABLE 7-continued

X = —CO—, q = 1, R = 0, Y = —(R4)C=C(R5)—

| Compound No. 7 | R1—(CH2)p— | R2 | R3 | R4 | R5 | R6 | R7 |
|---|---|---|---|---|---|---|---|
| 90 | 2-MeO, 3-(OBn) benzyl | H | H | H | H | H | H |
| 91 | 4-Cl, 2-NO2 benzyl (O2N-, Cl-substituted) | H | H | H | H | H | H |
| 92 | 3-(4-methoxyphenoxy)phenyl | H | H | H | H | H | H |
| 93 | 3-(4-methylphenoxy)phenyl | H | H | H | H | H | H |
| 94 | 3-(4-chlorophenoxy)phenyl | H | H | H | H | H | H |
| 95 | 3-(benzyloxy)phenyl | H | H | H | H | H | H |
| 96 | 3-phenoxyphenyl | H | H | H | H | H | H |

TABLE 7-continued

X = —CO—, q = 1, R = 0, Y = —(R4)C═C(R5)—

| Compound No. 7 | R1—(CH2)p— | R2 | R3 | R4 | R5 | R6 | R7 |
|---|---|---|---|---|---|---|---|
| 97 | 3-hydroxy-4-methoxybenzyl | H | H | H | H | H | H |
| 98 | 2-chloro-3-(trifluoromethyl)benzyl | H | H | H | H | H | H |
| 99 | 4-hydroxy-3-nitrobenzyl | H | H | H | H | H | H |
| 100 | 2,3-dimethoxybenzyl | H | H | H | H | H | H |
| 101 | 2,4-diethoxy-3-methylbenzyl | H | H | H | H | H | H |
| 102 | 3-(2-hydroxyethoxy)benzyl | H | H | H | H | H | H |
| 103 | 2,3,4-trimethoxybenzyl | H | H | H | H | H | H |
| 104 | 4-fluoro-3-phenoxybenzyl | H | H | H | H | H | H |
| 105 | 2-carboxy-3,4-dimethoxybenzyl | H | H | H | H | H | H |
| 106 | 4-chloro-2-nitrobenzyl | H | H | H | H | H | H |

TABLE 7-continued
X = —CO—, q = 1, R = 0, Y = —(R4)C=C(R5)—
| Compound No. 7 | R1—(CH2)p— | R2 | R3 | R4 | R5 | R6 | R7 |
|---|---|---|---|---|---|---|---|
| 107 | 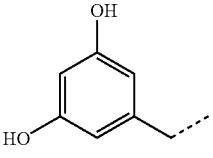 | H | H | H | H | H | H |
| 108 | 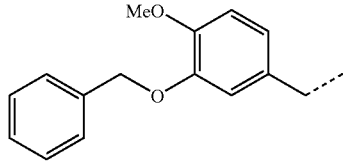 | H | H | H | H | H | H |
| 109 | 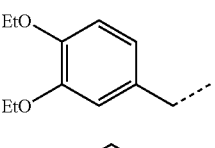 | H | H | H | H | H | H |
| 110 | 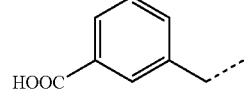 | H | H | H | H | H | H |
| 111 | 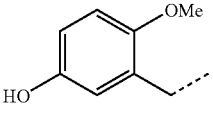 | H | H | H | H | H | H |
| 112 | 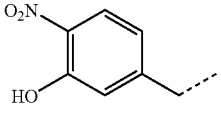 | H | H | H | H | H | H |
| 113 | 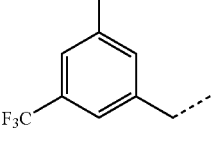 | H | H | H | H | H | H |
| 114 | 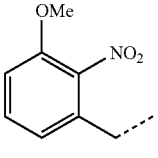 | H | H | H | H | H | H |
| 115 | 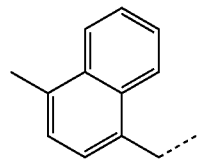 | H | H | H | H | H | H |
| 116 | 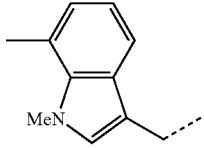 | H | H | H | H | H | H |

TABLE 7-continued

X = —CO—, q = 1, R = 0, Y = —(R4)C=C(R5)—

| Compound No. 7 | R1—(CH2)p— | R2 | R3 | R4 | R5 | R6 | R7 |
|---|---|---|---|---|---|---|---|
| 117 | 1-(2-methoxynaphthyl)methyl | H | H | H | H | H | H |
| 118 | benzofuran-2-ylmethyl | H | H | H | H | H | H |
| 119 | (1-methyl-2-methylindol-3-yl)methyl | H | H | H | H | H | H |
| 120 | quinolin-8-ylmethyl | H | H | H | H | H | H |
| 121 | 1-(2-hydroxynaphthyl)methyl | H | H | H | H | H | H |
| 122 | 1-(2-acetoxynaphthyl)methyl | H | H | H | H | H | H |
| 123 | 2-(1-hydroxynaphthyl)methyl | H | H | H | H | H | H |
| 124 | (1H-indol-7-yl)methyl | H | H | H | H | H | H |

TABLE 7-continued

X = —CO—, q = 1, R = 0, Y = —(R4)C=C(R5)—

| Compound No. 7 | R1—(CH2)p— | R2 | R3 | R4 | R5 | R6 | R7 |
|---|---|---|---|---|---|---|---|
| 125 | 4-quinolinyl-CH2— | H | H | H | H | H | H |
| 126 | (5-methyl-1-methylindol-3-yl)-CH2— | H | H | H | H | H | H |
| 127 | (anthracen-9-yl)-CH2— | H | H | H | H | H | H |
| 128 | (2-methylnaphthalen-1-yl)-CH2— | H | H | H | H | H | H |
| 129 | (2-ethoxynaphthalen-1-yl)-CH2— | H | H | H | H | H | H |
| 130 | (1H-indol-3-yl)-CH2— | H | H | H | H | H | H |
| 131 | (6-methyl-1-methylindol-3-yl)-CH2— | H | H | H | H | H | H |

TABLE 7-continued
X = —CO—, q = 1, R = 0, Y = —(R4)C═C(R5)—
| Compound No. 7 | R1—(CH2)p— | R2 | R3 | R4 | R5 | R6 | R7 |
|---|---|---|---|---|---|---|---|
| 132 | 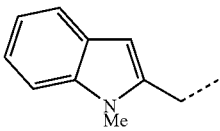 | H | H | H | H | H | H |
| 133 | 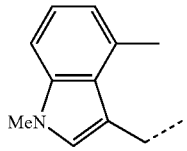 | H | H | H | H | H | H |
| 134 | 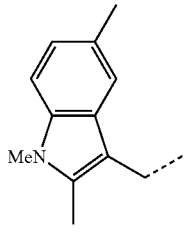 | H | H | H | H | H | H |
| 135 | 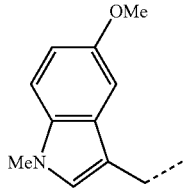 | H | H | H | H | H | H |
| 136 | 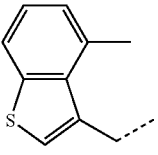 | H | H | H | H | H | H |
| 137 | 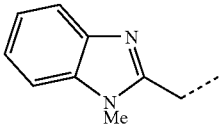 | H | H | H | H | H | H |
| 138 | 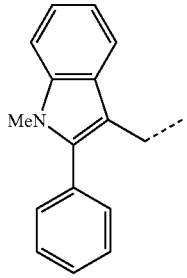 | H | H | H | H | H | H |

TABLE 7-continued

X = —CO—, q = 1, R = 0, Y = —(R4)C=C(R5)—

| Compound No. 7 | R1—(CH2)p— | R2 | R3 | R4 | R5 | R6 | R7 |
|---|---|---|---|---|---|---|---|
| 139 | 1-acetyl-indol-3-yl | H | H | H | H | H | H |
| 140 | quinolin-2-yl | H | H | H | H | H | H |
| 141 | 6-methoxy-1-methyl-indol-3-yl | H | H | H | H | H | H |
| 142 | 3-methyl-benzothiophen-2-yl | H | H | H | H | H | H |
| 143 | 4-methoxy-naphth-1-yl | H | H | H | H | H | H |
| 144 | phenanthren-9-yl | H | H | H | H | H | H |
| 145 | 6-methoxy-naphth-2-yl | H | H | H | H | H | H |
| 146 | 1-bromo-naphth-2-yl | H | H | H | H | H | H |

TABLE 7-continued

X = —CO—, q = 1, R = 0, Y = —(R4)C═C(R5)—

| Compound No. 7 | R1—(CH2)p— | R2 | R3 | R4 | R5 | R6 | R7 |
|---|---|---|---|---|---|---|---|
| 147 | (4-dimethylamino-naphth-1-yl)methyl | H | H | H | H | H | H |
| 148 | (2,3-dihydro-1,4-benzodioxin-6-yl)methyl | H | H | H | H | H | H |
| 149 | (2,2-dimethylchroman-6-yl)methyl | H | H | H | H | H | H |
| 150 | (2,3-dihydrobenzofuran-5-yl)methyl | H | H | H | H | H | H |
| 151 | (9-ethylcarbazol-3-yl)methyl | H | H | H | H | H | H |
| 152 | (1,3-benzodioxol-4-yl)methyl | H | H | H | H | H | H |
| 153 | (1,3-benzodioxol-5-yl)methyl | H | H | H | H | H | H |
| 154 | 3-phenylpropyl | H | H | H | H | H | H |
| 155 | 4-phenylbutyl | H | H | H | H | H | H |
| 156 | cyclohexylmethyl | H | H | H | H | H | H |
| 157 | (5-iodo-2-hydroxyphenyl)methyl | H | H | H | H | H | H |

TABLE 7-continued
X = —CO—, q = 1, R = 0, Y = —(R4)C=C(R5)—
| Compound No. 7 | R1—(CH2)p— | R2 | R3 | R4 | R5 | R6 | R7 |
|---|---|---|---|---|---|---|---|
| 158 | 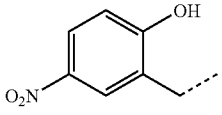 | H | H | H | H | H | H |
| 159 | 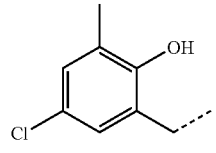 | H | H | H | H | H | H |
| 160 | 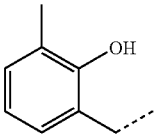 | H | H | H | H | H | H |
| 161 | 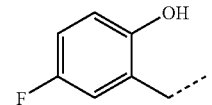 | H | H | H | H | H | H |
| 162 | 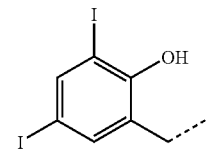 | H | H | H | H | H | H |
| 163 | 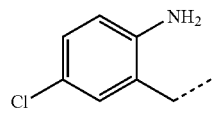 | H | H | H | H | H | H |
| 164 | 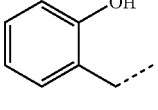 | H | H | H | H | H | H |
| 165 | 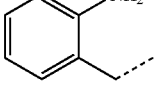 | H | H | H | H | H | H |
| 166 | 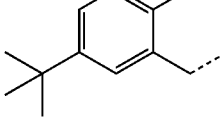 | H | H | H | H | H | H |
| 167 | 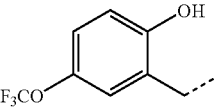 | H | H | H | H | H | H |
| 168 | 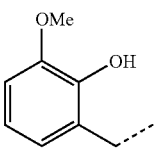 | H | H | H | H | H | H |

TABLE 7-continued
X = —CO—, q = 1, R = 0, Y = —(R4)C═C(R5)—
| Compound No. 7 | R1—(CH2)p— | R2 | R3 | R4 | R5 | R6 | R7 |
|---|---|---|---|---|---|---|---|
| 169 | 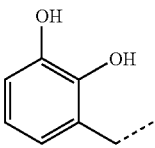 | H | H | H | H | H | H |
| 170 | 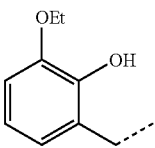 | H | H | H | H | H | H |
| 171 | 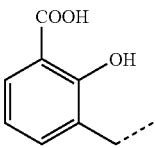 | H | H | H | H | H | H |
| 172 | 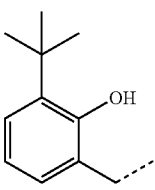 | H | H | H | H | H | H |
| 173 | 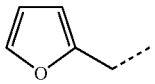 | H | H | H | H | H | H |
| 174 | 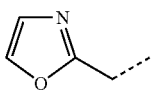 | H | H | H | H | H | H |
| 175 | 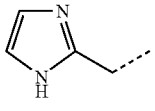 | H | H | H | H | H | H |
| 176 | 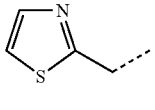 | H | H | H | H | H | H |
| 177 | 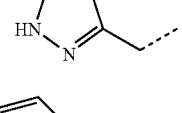 | H | H | H | H | H | H |
| 178 | 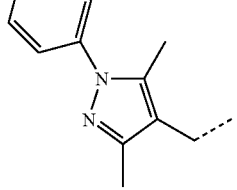 | H | H | H | H | H | H |

TABLE 7-continued
X = —CO—, q = 1, R = 0, Y = —(R4)C=C(R5)—
| Compound No. 7 | R1—(CH2)p— | R2 | R3 | R4 | R5 | R6 | R7 |
|---|---|---|---|---|---|---|---|
| 179 | 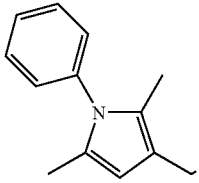 | H | H | H | H | H | H |
| 180 | 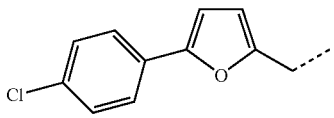 | H | H | H | H | H | H |
| 181 | 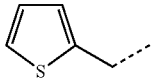 | H | H | H | H | H | H |
| 182 | 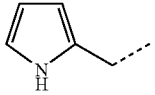 | H | H | H | H | H | H |
| 183 | 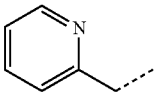 | H | H | H | H | H | H |
| 184 | 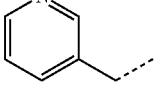 | H | H | H | H | H | H |
| 185 | 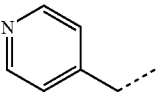 | H | H | H | H | H | H |
| 186 | 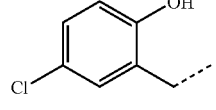 | H | H | H | Cl | H | H |
| 187 | 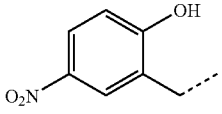 | H | H | H | Cl | H | H |
| 188 | 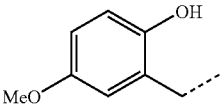 | H | H | H | Cl | H | H |
| 189 | 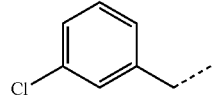 | H | H | H | Cl | H | H |
| 190 | 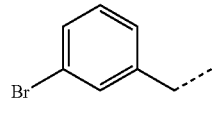 | H | H | H | Cl | H | H |

TABLE 7-continued

X = —CO—, q = 1, R = 0, Y = —(R4)C=C(R5)—

| Compound No. 7 | R1—(CH2)p— | R2 | R3 | R4 | R5 | R6 | R7 |
|---|---|---|---|---|---|---|---|
| 191 | 3-nitrobenzyl | H | H | H | Cl | H | H |
| 192 | 3-methoxybenzyl | H | H | H | Cl | H | H |
| 193 | 3,5-dichloro-2-hydroxybenzyl | H | H | H | Cl | H | H |
| 194 | (1-methylindol-3-yl)methyl | H | H | H | Cl | H | H |
| 195 | (benzothiophen-3-yl)methyl | H | H | H | Cl | H | H |
| 196 | benzyl | H | H | H | Cl | H | H |
| 197 | 3-phenylpropyl | H | H | H | Cl | H | H |
| 198 | 5-bromo-2-hydroxybenzyl | H | H | H | Cl | H | H |
| 199 | (naphthalen-2-yl)methyl | H | H | H | Cl | H | H |
| 200 | 2-phenylethyl | H | H | H | Cl | H | H |
| 201 | 3,5-dichloro-2-hydroxybenzyl | H | H | Cl | H | H | H |

TABLE 7-continued
X = —CO—, q = 1, R = 0, Y = —(R4)C═C(R5)—
| Compound No. 7 | R1—(CH2)p— | R2 | R3 | R4 | R5 | R6 | R7 |
|---|---|---|---|---|---|---|---|
| 202 | 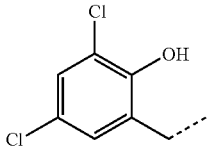 | H | H | H | OMe | H | H |
| 203 | 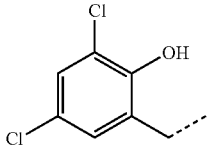 | H | H | H | COOMe | H | H |
| 204 | 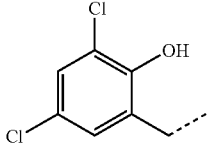 | H | H | H | H | Cl | H |
| 205 | 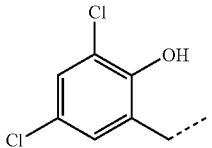 | H | H | H | H | COOMe | H |
| 206 | 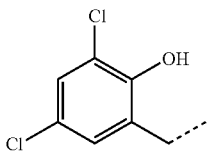 | H | H | H | H | H | Cl |
| 207 | 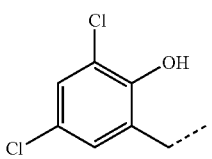 | H | H | H | OCF3 | H | H |
| 208 | 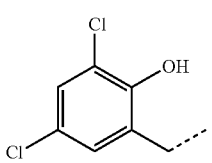 | H | H | COOMe | H | H | H |
| 209 | 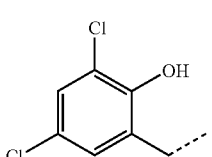 | H | H | H | CF3 | H | H |
| 210 | 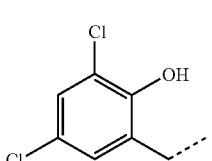 | H | H | H | Me | H | H |

TABLE 7-continued
X = —CO—, q = 1, R = 0, Y = —(R4)C=C(R5)—
| Compound No. 7 | R1—(CH2)p— | R2 | R3 | R4 | R5 | R6 | R7 |
|---|---|---|---|---|---|---|---|
| 211 | 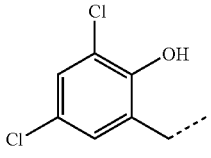 | H | H | H | F | H | H |
| 212 | 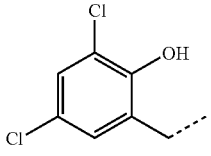 | H | H | H | OH | H | H |
| 213 | 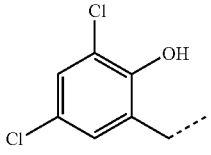 | H | H | H | NO2 | H | H |
| 214 | 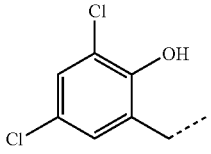 | H | H | H | F | F | H |
| 215 | 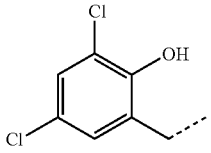 | H | H | F | H | H | H |
| 216 | 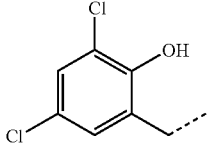 | H | H | Me | H | H | H |
| 217 | 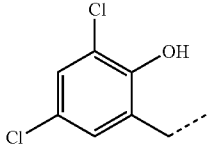 | H | H | H | CN | H | H |
| 218 | 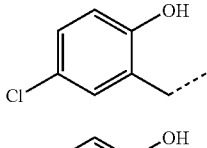 | H | H | Cl | H | H | H |
| 219 | 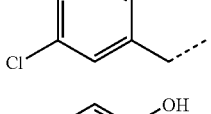 | H | H | H | OMe | H | H |
| 220 | 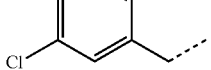 | H | H | H | COOMe | H | H |

TABLE 7-continued
X = —CO—, q = 1, R = 0, Y = —(R4)C═C(R5)—
| Compound No. 7 | R1—(CH2)p— | R2 | R3 | R4 | R5 | R6 | R7 |
|---|---|---|---|---|---|---|---|
| 221 | 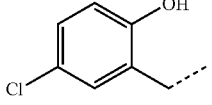 | H | H | H | H | Cl | H |
| 222 | 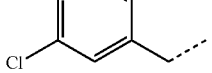 | H | H | H | H | COOMe | H |
| 223 | 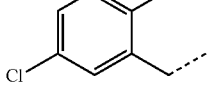 | H | H | H | H | H | Cl |
| 224 | 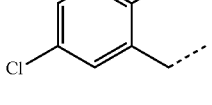 | H | H | H | OCF3 | H | H |
| 225 | 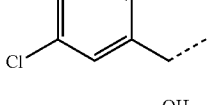 | H | H | COOMe | H | H | H |
| 226 | 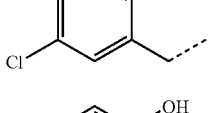 | H | H | H | CF3 | H | H |
| 227 | 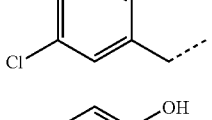 | H | H | H | Me | H | H |
| 228 | 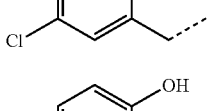 | H | H | H | F | H | H |
| 229 | 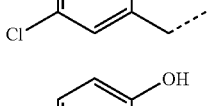 | H | H | H | OH | H | H |
| 230 | 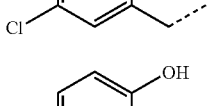 | H | H | H | NO2 | H | H |
| 231 | 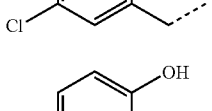 | H | H | H | F | F | H |
| 232 | 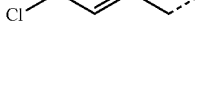 | H | H | F | H | H | H |

TABLE 7-continued

X = —CO—, q = 1, R = 0, Y = —(R4)C=C(R5)—

| Compound No. 7 | R1—(CH2)p— | R2 | R3 | R4 | R5 | R6 | R7 |
|---|---|---|---|---|---|---|---|
| 233 | 4-Cl, 2-OH-phenyl-CH2— | H | H | Me | H | H | H |
| 234 | 4-Cl, 2-OH-phenyl-CH2— | H | H | H | CN | H | H |
| 235 | naphthalen-1-yl-CH2— | H | H | Cl | H | H | H |
| 236 | naphthalen-1-yl-CH2— | H | H | H | OMe | H | H |
| 237 | naphthalen-1-yl-CH2— | H | H | H | COOMe | H | H |
| 238 | naphthalen-1-yl-CH2— | H | H | H | H | Cl | H |
| 239 | naphthalen-1-yl-CH2— | H | H | H | H | COOMe | H |
| 240 | naphthalen-1-yl-CH2— | H | H | H | H | H | Cl |
| 241 | naphthalen-1-yl-CH2— | H | H | H | OCF3 | H | H |

TABLE 7-continued

X = —CO—, q = 1, R = 0, Y = —(R4)C═C(R5)—

| Compound No. 7 | R1—(CH2)p— | R2 | R3 | R4 | R5 | R6 | R7 |
|---|---|---|---|---|---|---|---|
| 242 | naphthalen-1-ylmethyl | H | H | COOMe | H | H | H |
| 243 | naphthalen-1-ylmethyl | H | H | H | CF3 | H | H |
| 244 | naphthalen-1-ylmethyl | H | H | H | Me | H | H |
| 245 | naphthalen-1-ylmethyl | H | H | H | F | H | H |
| 246 | naphthalen-1-ylmethyl | H | H | H | OH | H | H |
| 247 | naphthalen-1-ylmethyl | H | H | H | NO2 | H | H |
| 248 | naphthalen-1-ylmethyl | H | H | H | F | F | H |
| 249 | naphthalen-1-ylmethyl | H | H | F | H | H | H |

TABLE 7-continued
X = —CO—, q = 1, R = 0, Y = —(R4)C═C(R5)—
| Compound No. 7 | R1—(CH2)p— | R2 | R3 | R4 | R5 | R6 | R7 |
|---|---|---|---|---|---|---|---|
| 250 | 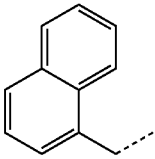 | H | H | Me | H | H | H |
| 251 | 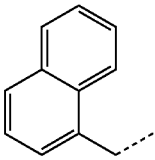 | H | H | H | CN | H | H |
| 252 | 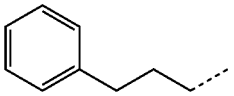 | H | H | Cl | H | H | H |
| 253 | 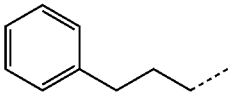 | H | H | H | OMe | H | H |
| 254 | 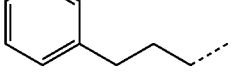 | H | H | H | COOMe | H | H |
| 255 | 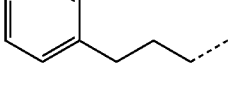 | H | H | H | H | Cl | H |
| 256 | 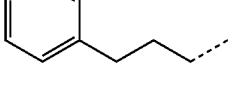 | H | H | H | H | COOMe | H |
| 257 | 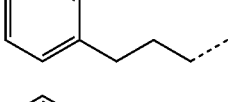 | H | H | H | H | H | Cl |
| 258 | 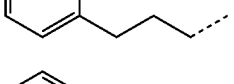 | H | H | H | OCF3 | H | H |
| 259 | 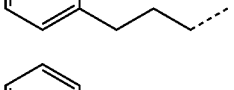 | H | H | COOMe | H | H | H |
| 260 | 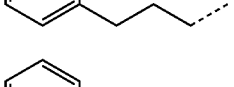 | H | H | H | CF3 | H | H |
| 261 | 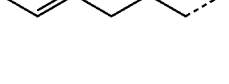 | H | H | H | Me | H | H |

TABLE 7-continued
X = —CO—, q = 1, R = 0, Y = —(R4)C=C(R5)—
| Compound No. 7 | R1—(CH2)p— | R2 | R3 | R4 | R5 | R6 | R7 |
|---|---|---|---|---|---|---|---|
| 262 | 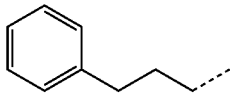 | H | H | H | F | H | H |
| 263 | 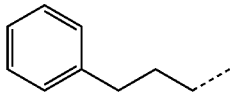 | H | H | H | OH | H | H |
| 264 | 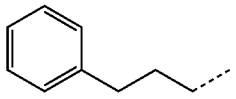 | H | H | H | NO2 | H | H |
| 265 | 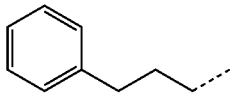 | H | H | H | F | F | H |
| 266 | 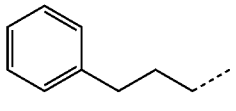 | H | H | F | H | H | H |
| 267 | 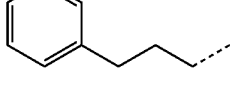 | H | H | Me | H | H | H |
| 268 | 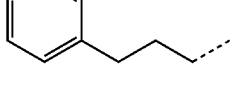 | H | H | H | CN | H | H |
| 269 | 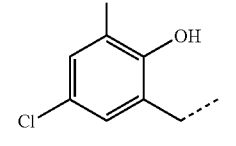 | H | H | H | H | H | COOMe |
| 270 | 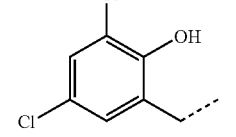 | H | H | H | H | F | H |
| 271 | 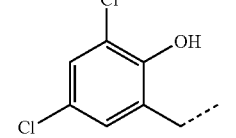 | H | H | H | H | H | F |
| 272 | 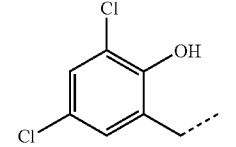 | H | H | H | H | Me | H |

TABLE 7-continued
X = —CO—, q = 1, R = 0, Y = —(R4)C=C(R5)—
| Compound No. 7 | R1—(CH2)p— | R2 | R3 | R4 | R5 | R6 | R7 |
|---|---|---|---|---|---|---|---|
| 273 | 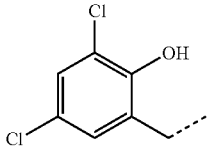 | H | H | H | H | H | Me |
| 274 | 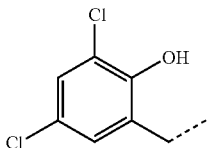 | H | H | OMe | H | H | H |
| 275 | 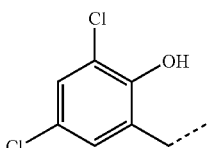 | H | H | H | H | OMe | H |
| 276 | 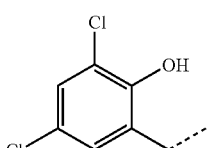 | H | H | H | H | H | OMe |
| 277 | 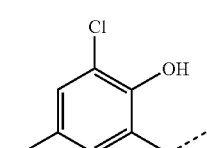 | H | H | CF3 | H | H | H |
| 278 | 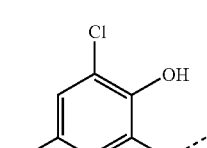 | H | H | H | H | CF3 | H |
| 279 | 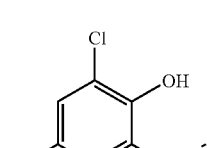 | H | H | H | H | H | CF3 |
| 280 | 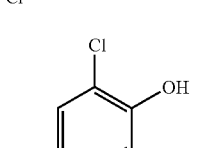 | H | H | OH | H | H | H |
| 281 | 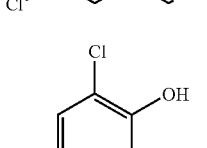 | H | H | H | H | OH | H |

TABLE 7-continued
X = —CO—, q = 1, R = 0, Y = —(R4)C=C(R5)—
| Compound No. 7 | R1—(CH2)p— | R2 | R3 | R4 | R5 | R6 | R7 |
|---|---|---|---|---|---|---|---|
| 282 | 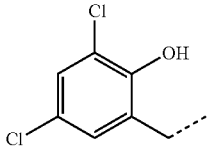 | H | H | H | H | H | OH |
| 283 | 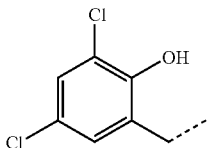 | H | H | OCF3 | H | H | H |
| 284 | 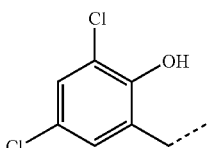 | H | H | H | H | OCF3 | H |
| 285 | 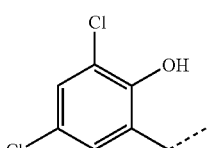 | H | H | H | H | H | OCF3 |
| 286 | 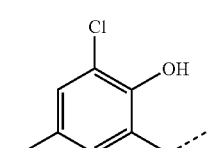 | H | H | NO2 | H | H | H |
| 287 | 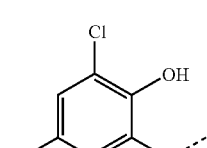 | H | H | H | H | NO2 | H |
| 288 | 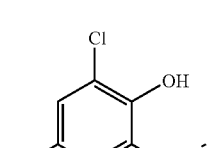 | H | H | H | H | H | NO2 |
| 289 | 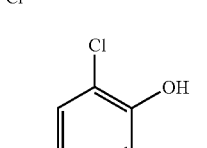 | H | H | CN | H | H | H |
| 290 | 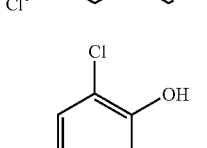 | H | H | H | H | CN | H |

TABLE 7-continued
X = —CO—, q = 1, R = 0, Y = —(R4)C=C(R5)—
| Compound No. 7 | R1—(CH2)p— | R2 | R3 | R4 | R5 | R6 | R7 |
|---|---|---|---|---|---|---|---|
| 291 | 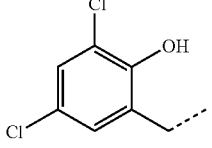 | H | H | H | H | H | CN |
| 292 | 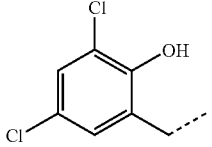 | H | H | Br | H | H | H |
| 293 | 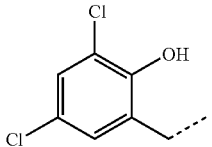 | H | H | H | Br | H | H |
| 294 | 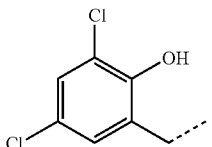 | H | H | H | H | Br | H |
| 295 | 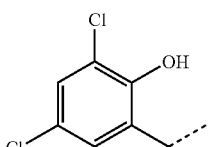 | H | H | H | H | H | Br |
| 296 | 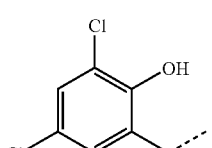 | H | H | COOH | H | H | H |
| 297 | 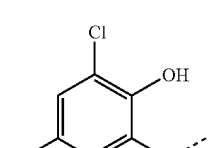 | H | H | H | COOH | H | H |
| 298 | 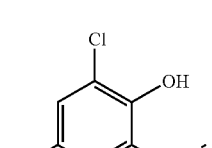 | H | H | H | H | COOH | H |
| 299 | 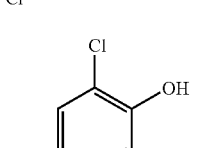 | H | H | H | H | H | COOH |

TABLE 7-continued
X = —CO—, q = 1, R = 0, Y = —(R4)C=C(R5)—
| Compound No. 7 | R1—(CH2)p— | R2 | R3 | R4 | R5 | R6 | R7 |
|---|---|---|---|---|---|---|---|
| 300 | 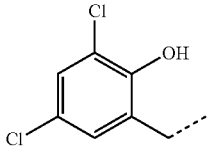 | H | H | NHCOMe | H | H | H |
| 301 | 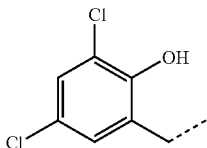 | H | H | H | NHCOMe | H | H |
| 302 | 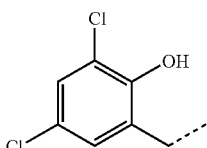 | H | H | H | H | NHCOMe | H |
| 303 | 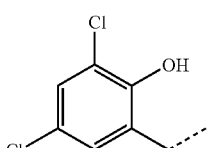 | H | H | H | H | H | NHCOMe |
| 304 | 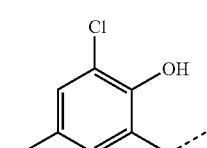 | H | H | SO2NH2 | H | H | H |
| 305 | 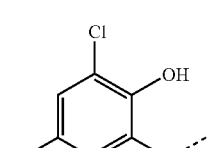 | H | H | H | SO2NH2 | H | H |
| 306 | 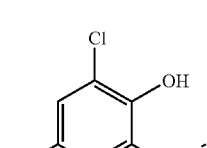 | H | H | H | H | SO2NH2 | H |
| 307 | 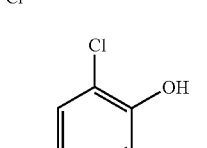 | H | H | H | H | H | SO2NH2 |
| 308 | 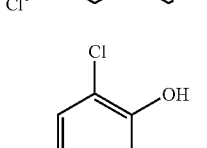 | H | H | Me | Me | H | H |

TABLE 7-continued
X = —CO—, q = 1, R = 0, Y = —(R4)C=C(R5)—
| Compound No. 7 | R1—(CH2)p— | R2 | R3 | R4 | R5 | R6 | R7 |
|---|---|---|---|---|---|---|---|
| 309 | 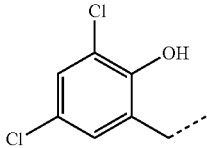 | H | H | Me | H | Me | H |
| 310 | 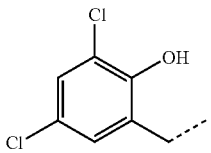 | H | H | H | Me | Me | H |
| 311 | 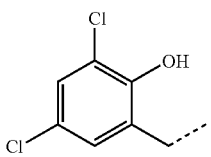 | H | H | F | F | H | H |
| 312 | 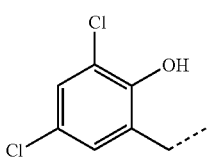 | H | H | F | H | F | H |
| 313 | 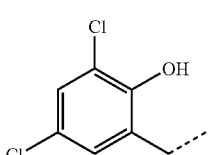 | H | H | H | F | F | H |
| 314 | 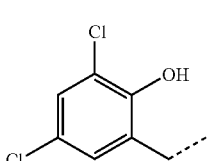 | H | H | Cl | Cl | H | H |
| 315 | 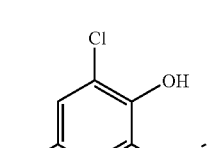 | H | H | Cl | H | Cl | H |
| 316 | 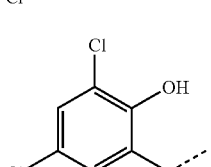 | H | H | H | Cl | Cl | H |
| 317 | 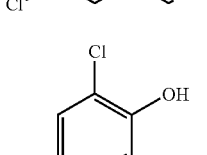 | H | H | Me | F | H | H |

TABLE 7-continued
X = —CO—, q = 1, R = 0, Y = —(R4)C=C(R5)—
| Compound No. 7 | R1—(CH2)p— | R2 | R3 | R4 | R5 | R6 | R7 |
|---|---|---|---|---|---|---|---|
| 318 | 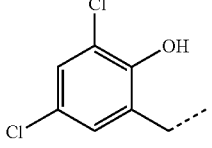 | H | H | Me | Cl | H | H |
| 319 | 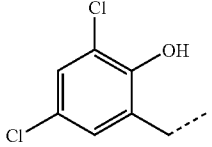 | H | H | Me | OH | H | H |
| 320 | 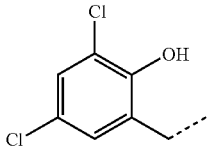 | H | H | Me | OMe | H | H |
| 321 | 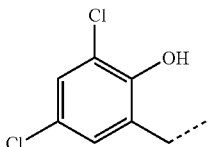 | H | H | F | Me | H | H |
| 322 | 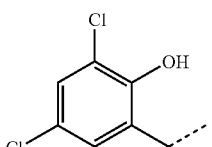 | H | H | F | Cl | H | H |
| 323 | 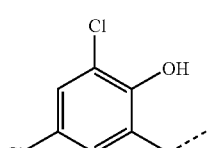 | H | H | F | OH | H | H |
| 324 | 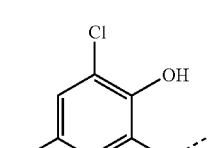 | H | H | F | OMe | H | H |
| 325 | 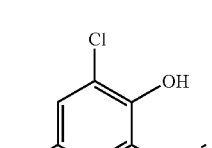 | H | H | Cl | Me | H | H |
| 326 | 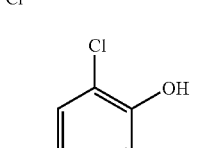 | H | H | Cl | F | H | H |

TABLE 7-continued
X = —CO—, q = 1, R = 0, Y = —(R4)C=C(R5)—
| Compound No. 7 | R1—(CH2)p— | R2 | R3 | R4 | R5 | R6 | R7 |
|---|---|---|---|---|---|---|---|
| 327 | 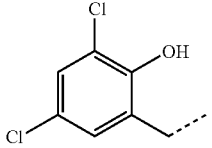 | H | H | Cl | OH | H | H |
| 328 | 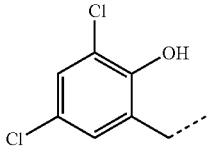 | H | H | Cl | OMe | H | H |
| 329 | 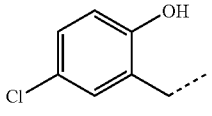 | H | H | H | H | H | COOMe |
| 330 | 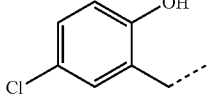 | H | H | H | H | F | H |
| 331 | 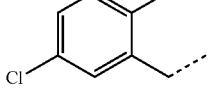 | H | H | H | H | H | F |
| 332 | 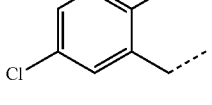 | H | H | H | H | Me | H |
| 333 | 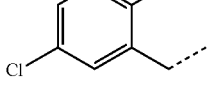 | H | H | H | H | H | Me |
| 334 | 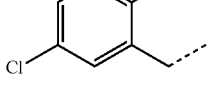 | H | H | OMe | H | H | H |
| 335 | 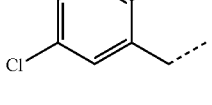 | H | H | H | H | OMe | H |
| 336 | 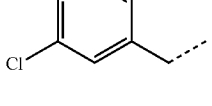 | H | H | H | H | H | OMe |
| 337 | 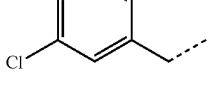 | H | H | CF3 | H | H | H |

TABLE 7-continued
X = —CO—, q = 1, R = 0, Y = —(R4)C=C(R5)—
| Compound No. 7 | R1—(CH2)p— | R2 | R3 | R4 | R5 | R6 | R7 |
|---|---|---|---|---|---|---|---|
| 338 | 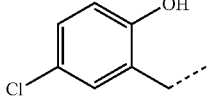 | H | H | H | H | CF3 | H |
| 339 | 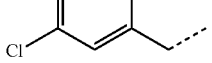 | H | H | H | H | H | CF3 |
| 340 | 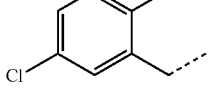 | H | H | OH | H | H | H |
| 341 | 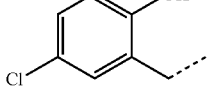 | H | H | H | H | OH | H |
| 342 | 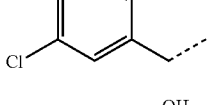 | H | H | H | H | H | OH |
| 343 | 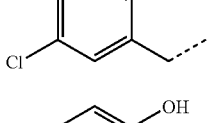 | H | H | OCF3 | H | H | H |
| 344 | 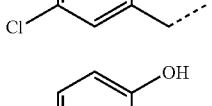 | H | H | H | H | OCF3 | H |
| 345 | 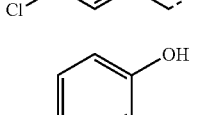 | H | H | H | H | H | OCF3 |
| 346 | 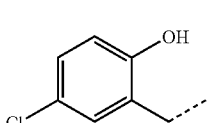 | H | H | NO2 | H | H | H |
| 347 | 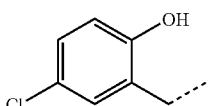 | H | H | H | H | NO2 | H |
| 348 | 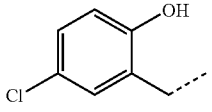 | H | H | H | H | H | NO2 |
| 349 |  | H | H | CN | H | H | H |

TABLE 7-continued
X = —CO—, q = 1, R = 0, Y = —(R4)C═C(R5)—
| Compound No. 7 | R1—(CH2)p— | R2 | R3 | R4 | R5 | R6 | R7 |
|---|---|---|---|---|---|---|---|
| 350 | 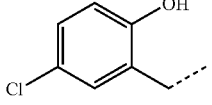 | H | H | H | H | CN | H |
| 351 | 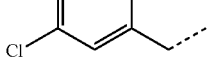 | H | H | H | H | H | CN |
| 352 | 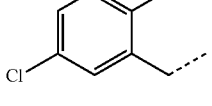 | H | H | Br | H | H | H |
| 353 | 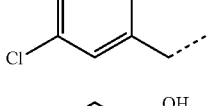 | H | H | H | Br | H | H |
| 354 | 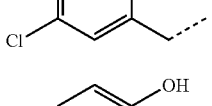 | H | H | H | H | Br | H |
| 355 | 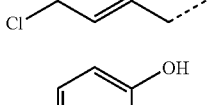 | H | H | H | H | H | Br |
| 356 | 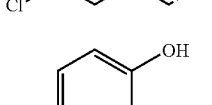 | H | H | COOH | H | H | H |
| 357 | 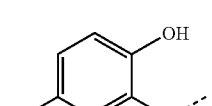 | H | H | H | COOH | H | H |
| 358 | 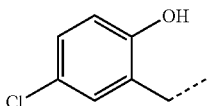 | H | H | H | H | COOH | H |
| 359 | 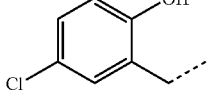 | H | H | H | H | H | COOH |
| 360 | 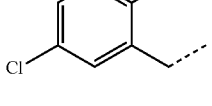 | H | H | NHCOMe | H | H | H |
| 361 |  | H | H | H | MHCOMe | H | H |

TABLE 7-continued
X = —CO—, q = 1, R = 0, Y = —(R4)C=C(R5)—
| Compound No. 7 | R1—(CH2)p— | R2 | R3 | R4 | R5 | R6 | R7 |
|---|---|---|---|---|---|---|---|
| 362 | 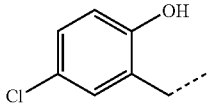 | H | H | H | H | NHCOMe | H |
| 363 | 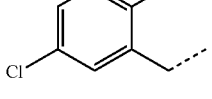 | H | H | H | H | H | NHCOMe |
| 364 | 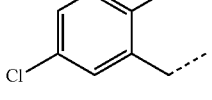 | H | H | SO2NH2 | H | H | H |
| 365 | 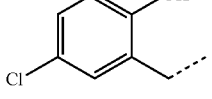 | H | H | H | SO2NH2 | H | H |
| 366 | 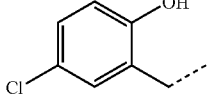 | H | H | H | H | SO2NH2 | H |
| 367 | 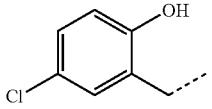 | H | H | H | H | H | SO2NH2 |
| 368 | 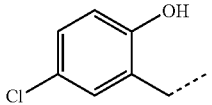 | H | H | Me | Me | H | H |
| 369 | 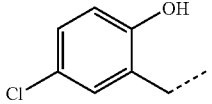 | H | H | Me | H | Me | H |
| 370 | 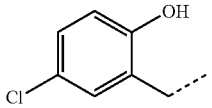 | H | H | H | Me | Me | H |
| 371 | 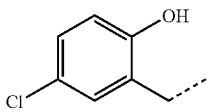 | H | H | F | F | H | H |
| 372 | 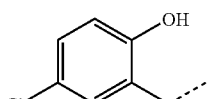 | H | H | F | H | F | H |
| 373 | 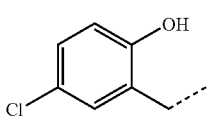 | H | H | H | F | F | H |

TABLE 7-continued
X = —CO—, q = 1, R = 0, Y = —(R4)C=C(R5)—
| Compound No. 7 | R1—(CH2)p— | R2 | R3 | R4 | R5 | R6 | R7 |
|---|---|---|---|---|---|---|---|
| 374 | 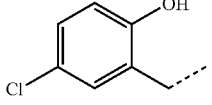 | H | H | Cl | Cl | H | H |
| 375 | 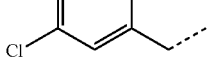 | H | H | Cl | H | Cl | H |
| 376 | 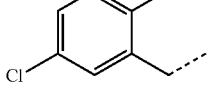 | H | H | H | Cl | Cl | H |
| 377 | 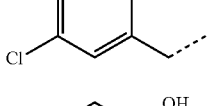 | H | H | Me | F | H | H |
| 378 | 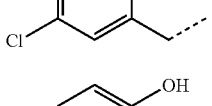 | H | H | Me | Cl | H | H |
| 379 | 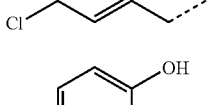 | H | H | Me | OH | H | H |
| 380 | 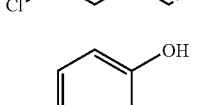 | H | H | Me | OMe | H | H |
| 381 | 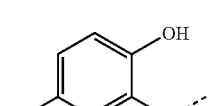 | H | H | F | Me | H | H |
| 382 | 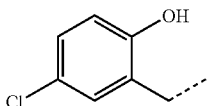 | H | H | F | Cl | H | H |
| 383 | 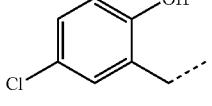 | H | H | F | OH | H | H |
| 384 | 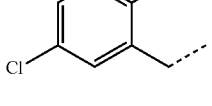 | H | H | F | OMe | H | H |
| 385 |  | H | H | Cl | Me | H | H |

TABLE 7-continued
X = —CO—, q = 1, R = 0, Y = —(R4)C=C(R5)—
| Compound No. 7 | R1—(CH2)p— | R2 | R3 | R4 | R5 | R6 | R7 |
|---|---|---|---|---|---|---|---|
| 386 | 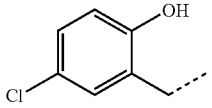 | H | H | Cl | F | H | H |
| 387 | 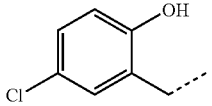 | H | H | Cl | OH | H | H |
| 388 | 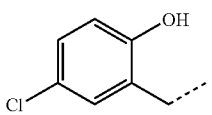 | H | H | Cl | OMe | H | H |
| 389 | 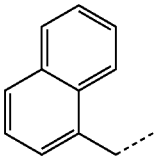 | H | H | H | H | H | COOMe |
| 390 | 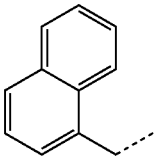 | H | H | H | H | F | H |
| 391 | 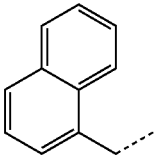 | H | H | H | H | H | F |
| 392 | 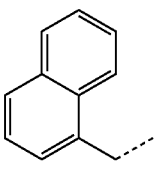 | H | H | H | H | Me | H |
| 393 | 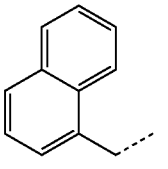 | H | H | H | H | H | Me |
| 394 | 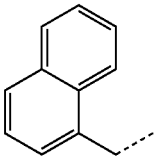 | H | H | OMe | H | H | H |

TABLE 7-continued

X = —CO—, q = 1, R = 0, Y = —(R4)C═C(R5)—

| Compound No. 7 | R1—(CH2)p— | R2 | R3 | R4 | R5 | R6 | R7 |
|---|---|---|---|---|---|---|---|
| 395 | 1-naphthylmethyl | H | H | H | H | OMe | H |
| 396 | 1-naphthylmethyl | H | H | H | H | H | OMe |
| 397 | 1-naphthylmethyl | H | H | CF3 | H | H | H |
| 398 | 1-naphthylmethyl | H | H | H | H | CF3 | H |
| 399 | 1-naphthylmethyl | H | H | H | H | H | CF3 |
| 400 | 1-naphthylmethyl | H | H | OH | H | H | H |
| 401 | 1-naphthylmethyl | H | H | H | H | OH | H |
| 402 | 1-naphthylmethyl | H | H | H | H | H | OH |

TABLE 7-continued
X = —CO—, q = 1, R = 0, Y = —(R4)C=C(R5)—
| Compound No. 7 | R1—(CH2)p— | R2 | R3 | R4 | R5 | R6 | R7 |
|---|---|---|---|---|---|---|---|
| 403 | 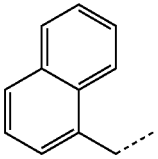 | H | H | OCF3 | H | H | H |
| 404 | 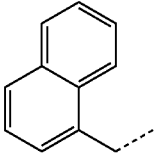 | H | H | H | H | OCF3 | H |
| 405 | 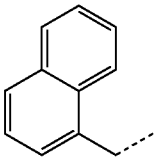 | H | H | H | H | H | OCF3 |
| 406 | 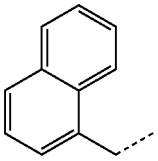 | H | H | NO2 | H | H | H |
| 407 | 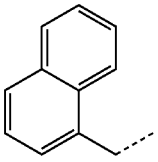 | H | H | H | H | NO2 | H |
| 408 | 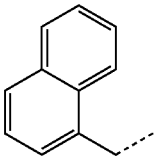 | H | H | H | H | H | NO2 |
| 409 | 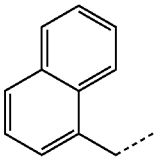 | H | H | CN | H | H | H |
| 410 | 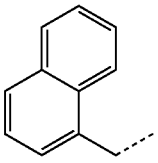 | H | H | H | H | CN | H |

TABLE 7-continued

X = —CO—, q = 1, R = 0, Y = —(R4)C═C(R5)—

| Compound No. 7 | R1—(CH2)p— | R2 | R3 | R4 | R5 | R6 | R7 |
|---|---|---|---|---|---|---|---|
| 411 | naphthyl-CH₂— | H | H | H | H | H | CN |
| 412 | naphthyl-CH₂— | H | H | Br | H | H | H |
| 413 | naphthyl-CH₂— | H | H | H | Br | H | H |
| 414 | naphthyl-CH₂— | H | H | H | H | Br | H |
| 415 | naphthyl-CH₂— | H | H | H | H | H | Br |
| 416 | naphthyl-CH₂— | H | H | COOH | H | H | H |
| 417 | naphthyl-CH₂— | H | H | H | COOH | H | H |
| 418 | naphthyl-CH₂— | H | H | H | H | COOH | H |

TABLE 7-continued

X = —CO—, q = 1, R = 0, Y = —(R4)C=C(R5)—

| Compound No. 7 | R1—(CH2)p— | R2 | R3 | R4 | R5 | R6 | R7 |
|---|---|---|---|---|---|---|---|
| 419 | naphthyl-CH2— | H | H | H | H | H | COOH |
| 420 | naphthyl-CH2— | H | H | NHCOMe | H | H | H |
| 421 | naphthyl-CH2— | H | H | H | NHCOMe | H | H |
| 422 | naphthyl-CH2— | H | H | H | H | NHCOMe | H |
| 423 | naphthyl-CH2— | H | H | H | H | H | NHCOMe |
| 424 | naphthyl-CH2— | H | H | SO2NH2 | H | H | H |
| 425 | naphthyl-CH2— | H | H | H | SO2NH2 | H | H |
| 426 | naphthyl-CH2— | H | H | H | H | SO2NH2 | H |

TABLE 7-continued

X = —CO—, q = 1, R = 0, Y = —(R4)C═C(R5)—

| Compound No. 7 | R1—(CH2)p— | R2 | R3 | R4 | R5 | R6 | R7 |
|---|---|---|---|---|---|---|---|
| 427 | naphthalen-1-ylmethyl | H | H | H | H | H | SO2NH2 |
| 428 | naphthalen-1-ylmethyl | H | H | Me | Me | H | H |
| 429 | naphthalen-1-ylmethyl | H | H | Me | H | Me | H |
| 430 | naphthalen-1-ylmethyl | H | H | H | Me | Me | H |
| 431 | naphthalen-1-ylmethyl | H | H | F | F | H | H |
| 432 | naphthalen-1-ylmethyl | H | H | F | H | F | H |
| 433 | naphthalen-1-ylmethyl | H | H | H | F | F | H |
| 434 | naphthalen-1-ylmethyl | H | H | Cl | Cl | H | H |

TABLE 7-continued

X = —CO—, q = 1, R = 0, Y = —(R4)C=C(R5)—

| Compound No. 7 | R1—(CH2)p— | R2 | R3 | R4 | R5 | R6 | R7 |
|---|---|---|---|---|---|---|---|
| 435 | 1-naphthylmethyl | H | H | Cl | H | Cl | H |
| 436 | 1-naphthylmethyl | H | H | H | Cl | Cl | H |
| 437 | 1-naphthylmethyl | H | H | Me | F | H | H |
| 438 | 1-naphthylmethyl | H | H | Me | Cl | H | H |
| 439 | 1-naphthylmethyl | H | H | Me | OH | H | H |
| 440 | 1-naphthylmethyl | H | H | Me | OMe | H | H |
| 441 | 1-naphthylmethyl | H | H | F | Me | H | H |
| 442 | 1-naphthylmethyl | H | H | F | Cl | H | H |

TABLE 7-continued
X = —CO—, q = 1, R = 0, Y = —(R4)C=C(R5)—
| Compound No. 7 | R1—(CH2)p— | R2 | R3 | R4 | R5 | R6 | R7 |
|---|---|---|---|---|---|---|---|
| 443 | 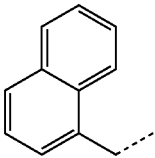 | H | H | F | OH | H | H |
| 444 | 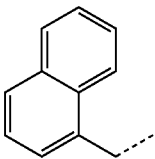 | H | H | F | OMe | H | H |
| 445 | 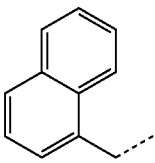 | H | H | Cl | Me | H | H |
| 446 | 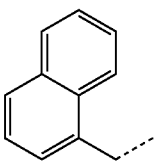 | H | H | Cl | F | H | H |
| 447 | 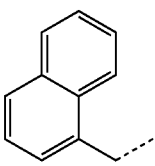 | H | H | Cl | OH | H | H |
| 448 | 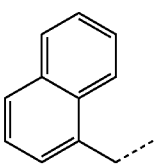 | H | H | Cl | OMe | H | H |
| 449 | 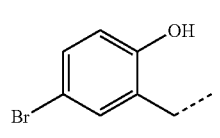 | H | H | Cl | H | H | H |
| 450 | 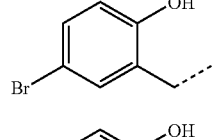 | H | H | H | OMe | H | H |
| 451 | 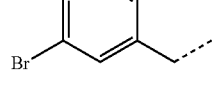 | H | H | H | COOMe | H | H |
| 452 | 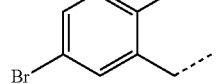 | H | H | H | H | Cl | H |

TABLE 7-continued

X = —CO—, q = 1, R = 0, Y = —(R4)C=C(R5)—

| Compound No. 7 | R1—(CH2)p— | R2 | R3 | R4 | R5 | R6 | R7 |
|---|---|---|---|---|---|---|---|
| 453 | 4-Br, 2-(CH2)-phenol | H | H | H | H | COOMe | H |
| 454 | 4-Br, 2-(CH2)-phenol | H | H | H | H | H | Cl |
| 455 | 4-Br, 2-(CH2)-phenol | H | H | H | OCF3 | H | H |
| 456 | 4-Br, 2-(CH2)-phenol | H | H | COOMe | H | H | H |
| 457 | 4-Br, 2-(CH2)-phenol | H | H | H | CF3 | H | H |
| 458 | 4-Br, 2-(CH2)-phenol | H | H | H | Me | H | H |
| 459 | 4-Br, 2-(CH2)-phenol | H | H | H | F | H | H |
| 460 | 4-Br, 2-(CH2)-phenol | H | H | H | OH | H | H |
| 461 | 4-Br, 2-(CH2)-phenol | H | H | H | NO2 | H | H |
| 462 | 4-Br, 2-(CH2)-phenol | H | H | H | F | F | H |
| 463 | 4-Br, 2-(CH2)-phenol | H | H | F | H | H | H |
| 464 | 4-Br, 2-(CH2)-phenol | H | H | Me | H | H | H |

TABLE 7-continued

X = —CO—, q = 1, R = 0, Y = —(R4)C=C(R5)—

| Compound No. 7 | R1—(CH2)p— | R2 | R3 | R4 | R5 | R6 | R7 |
|---|---|---|---|---|---|---|---|
| 465 | 4-bromo-2-hydroxyphenyl-CH2— (Br, OH on phenyl) | H | H | H | CN | H | H |
| 466 | 1-methylindol-3-yl-CH2— | H | H | Cl | H | H | H |
| 467 | 1-methylindol-3-yl-CH2— | H | H | H | OMe | H | H |
| 468 | 1-methylindol-3-yl-CH2— | H | H | H | COOMe | H | H |
| 469 | 1-methylindol-3-yl-CH2— | H | H | H | H | Cl | H |
| 470 | 1-methylindol-3-yl-CH2— | H | H | H | H | COOMe | H |
| 471 | 1-methylindol-3-yl-CH2— | H | H | H | H | H | Cl |
| 472 | 1-methylindol-3-yl-CH2— | H | H | H | OCF3 | H | H |
| 473 | 1-methylindol-3-yl-CH2— | H | H | COOMe | H | H | H |

TABLE 7-continued

X = —CO—, q = 1, R = 0, Y = —(R4)C=C(R5)—

| Compound No. 7 | R1—(CH2)p— | R2 | R3 | R4 | R5 | R6 | R7 |
|---|---|---|---|---|---|---|---|
| 474 | 1-methylindol-3-ylmethyl | H | H | H | CF3 | H | H |
| 475 | 1-methylindol-3-ylmethyl | H | H | H | Me | H | H |
| 476 | 1-methylindol-3-ylmethyl | H | H | H | F | H | H |
| 477 | 1-methylindol-3-ylmethyl | H | H | H | OH | H | H |
| 478 | 1-methylindol-3-ylmethyl | H | H | H | NO2 | H | H |
| 479 | 1-methylindol-3-ylmethyl | H | H | H | F | F | H |
| 480 | 1-methylindol-3-ylmethyl | H | H | F | H | H | H |
| 481 | 1-methylindol-3-ylmethyl | H | H | Me | H | H | H |
| 482 | 1-methylindol-3-ylmethyl | H | H | H | CN | H | H |

TABLE 7-continued

X = —CO—, q = 1, R = 0, Y = —(R4)C=C(R5)—

| Compound No. 7 | R1—(CH2)p— | R2 | R3 | R4 | R5 | R6 | R7 |
|---|---|---|---|---|---|---|---|
| 483 | benzothiophene | H | H | Cl | H | H | H |
| 484 | benzothiophene | H | H | H | OMe | H | H |
| 485 | benzothiophene | H | H | H | COOMe | H | H |
| 486 | benzothiophene | H | H | H | H | Cl | H |
| 487 | benzothiophene | H | H | H | H | COOMe | H |
| 488 | benzothiophene | H | H | H | H | H | Cl |
| 489 | benzothiophene | H | H | H | OCF3 | H | H |
| 490 | benzothiophene | H | H | COOMe | H | H | H |
| 491 | benzothiophene | H | H | H | CF3 | H | H |

TABLE 7-continued

X = —CO—, q = 1, R = 0, Y = —(R4)C=C(R5)—

| Compound No. 7 | R1—(CH2)p— | R2 | R3 | R4 | R5 | R6 | R7 |
|---|---|---|---|---|---|---|---|
| 492 | 4-methylbenzothiophen-3-yl | H | H | H | Me | H | H |
| 493 | 4-methylbenzothiophen-3-yl | H | H | H | F | H | H |
| 494 | 4-methylbenzothiophen-3-yl | H | H | H | OH | H | H |
| 495 | 4-methylbenzothiophen-3-yl | H | H | H | NO2 | H | H |
| 496 | 4-methylbenzothiophen-3-yl | H | H | H | F | F | H |
| 497 | 4-methylbenzothiophen-3-yl | H | H | F | H | H | H |
| 498 | 4-methylbenzothiophen-3-yl | H | H | Me | H | H | H |
| 499 | 4-methylbenzothiophen-3-yl | H | H | H | CN | H | H |
| 500 | 2,4-dichloro-6-hydroxyphenyl-CH2 | H | Me | H | H | H | H |

TABLE 7-continued

X = —CO—, q = 1, R = 0, Y = —(R4)C=C(R5)—

| Compound No. 7 | R1—(CH2)p— | R2 | R3 | R4 | R5 | R6 | R7 |
|---|---|---|---|---|---|---|---|
| 501 | 4-chloro-2-hydroxyphenylmethyl (with OH, Cl) | H | Me | H | H | H | H |
| 502 | naphthalen-1-ylmethyl | H | Me | H | H | H | H |
| 503 | 3-phenylpropyl | H | Me | H | H | H | H |
| 504 | 4-chloro-2-fluoro-6-hydroxyphenylmethyl | H | H | H | H | H | H |
| 505 | 4-chloro-2-fluoro-6-hydroxyphenylmethyl | H | H | F | H | H | H |
| 506 | 4-chloro-2-fluoro-6-hydroxyphenylmethyl | H | H | Cl | H | H | H |
| 507 | 4-chloro-2-fluoro-6-hydroxyphenylmethyl | H | H | Me | H | H | H |
| 508 | 4-chloro-2-fluoro-6-hydroxyphenylmethyl | H | H | Et | H | H | H |
| 509 | 4-chloro-2-fluoro-6-hydroxyphenylmethyl | H | H | OMe | H | H | H |

TABLE 7-continued
X = —CO—, q = 1, R = 0, Y = —(R4)C=C(R5)—
| Compound No. 7 | R1—(CH2)p— | R2 | R3 | R4 | R5 | R6 | R7 |
|---|---|---|---|---|---|---|---|
| 510 | 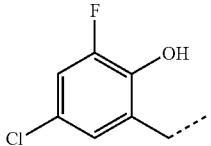 | H | H | OEt | H | H | H |
| 511 | 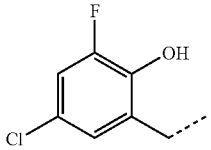 | H | H | CF3 | H | H | H |
| 512 | 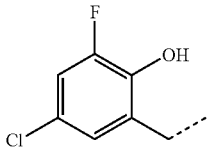 | H | H | OCF3 | H | H | H |
| 513 | 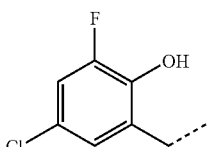 | H | H | NO2 | H | H | H |
| 514 | 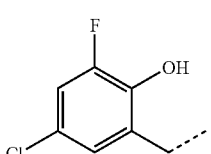 | H | H | NH2 | H | H | H |
| 515 | 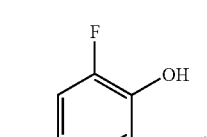 | H | H | OH | H | H | H |
| 516 | 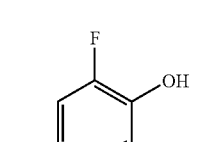 | H | H | CN | H | H | H |
| 517 | 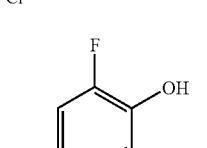 | H | H | COMe | H | H | H |
| 518 | 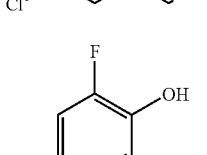 | H | H | COOMe | H | H | H |

TABLE 7-continued
X = —CO—, q = 1, R = 0, Y = —(R4)C=C(R5)—
| Compound No. 7 | R1—(CH2)p— | R2 | R3 | R4 | R5 | R6 | R7 |
|---|---|---|---|---|---|---|---|
| 519 | 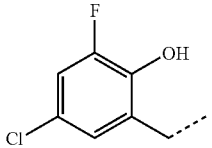 | H | H | H | F | H | H |
| 520 | 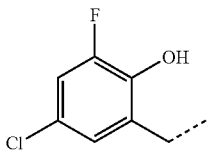 | H | H | H | Cl | H | H |
| 521 | 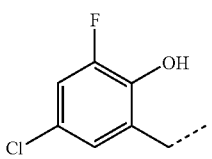 | H | H | H | Me | H | H |
| 522 | 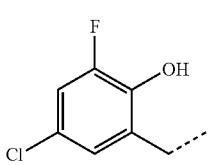 | H | H | H | Et | H | H |
| 523 | 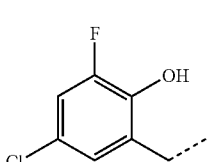 | H | H | H | OMe | H | H |
| 524 | 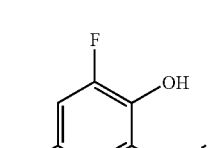 | H | H | H | OEt | H | H |
| 525 | 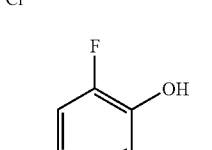 | H | H | H | CF3 | H | H |
| 526 | 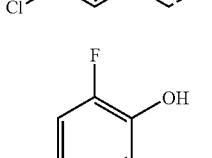 | H | H | H | OCF3 | H | H |
| 527 | 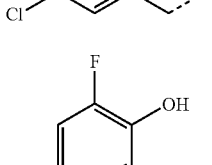 | H | H | H | NO2 | H | H |

TABLE 7-continued

X = —CO—, q = 1, R = 0, Y = —(R4)C═C(R5)—

| Compound No. 7 | R1—(CH2)p— | R2 | R3 | R4 | R5 | R6 | R7 |
|---|---|---|---|---|---|---|---|
| 528 | 4-Cl-2-F-6-OH-benzyl | H | H | H | NH2 | H | H |
| 529 | 4-Cl-2-F-6-OH-benzyl | H | H | H | OH | H | H |
| 530 | 4-Cl-2-F-6-OH-benzyl | H | H | H | CN | H | H |
| 531 | 4-Cl-2-F-6-OH-benzyl | H | H | H | COMe | H | H |
| 532 | 4-Cl-2-F-6-OH-benzyl | H | H | H | COOMe | H | H |
| 533 | 4-Cl-2-F-6-OH-benzyl | H | H | F | F | H | H |
| 534 | 4-Cl-2-F-6-OH-benzyl | H | H | F | Cl | H | H |
| 535 | 4-Cl-2-F-6-OH-benzyl | H | H | F | Me | H | H |
| 536 | 4-Cl-2-F-6-OH-benzyl | H | H | F | Et | H | H |

TABLE 7-continued

X = —CO—, q = 1, R = 0, Y = —(R4)C=C(R5)—

| Compound No. 7 | R1—(CH2)p— | R2 | R3 | R4 | R5 | R6 | R7 |
|---|---|---|---|---|---|---|---|
| 537 | 4-Cl, 2-F, 6-OH-benzyl | H | H | F | OMe | H | H |
| 538 | 4-Cl, 2-F, 6-OH-benzyl | H | H | F | OEt | H | H |
| 539 | 4-Cl, 2-F, 6-OH-benzyl | H | H | F | CF3 | H | H |
| 540 | 4-Cl, 2-F, 6-OH-benzyl | H | H | F | OCF3 | H | H |
| 541 | 4-Cl, 2-F, 6-OH-benzyl | H | H | Cl | F | H | H |
| 542 | 4-Cl, 2-F, 6-OH-benzyl | H | H | Cl | Cl | H | H |
| 543 | 4-Cl, 2-F, 6-OH-benzyl | H | H | Cl | Me | H | H |
| 544 | 4-Cl, 2-F, 6-OH-benzyl | H | H | Cl | Et | H | H |
| 545 | 4-Cl, 2-F, 6-OH-benzyl | H | H | Cl | OMe | H | H |

TABLE 7-continued

X = —CO—, q = 1, R = 0, Y = —(R4)C=C(R5)—

| Compound No. 7 | R1—(CH2)p— | R2 | R3 | R4 | R5 | R6 | R7 |
|---|---|---|---|---|---|---|---|
| 546 | 4-Cl-2-F-6-OH-benzyl | H | H | Cl | OEt | H | H |
| 547 | 4-Cl-2-F-6-OH-benzyl | H | H | Cl | CF3 | H | H |
| 548 | 4-Cl-2-F-6-OH-benzyl | H | H | Cl | OCF3 | H | H |
| 549 | 4-Cl-2-F-6-OH-benzyl | H | H | Me | F | H | H |
| 550 | 4-Cl-2-F-6-OH-benzyl | H | H | Me | Cl | H | H |
| 551 | 4-Cl-2-F-6-OH-benzyl | H | H | Me | Me | H | H |
| 552 | 4-Cl-2-F-6-OH-benzyl | H | H | Me | Et | H | H |
| 553 | 4-Cl-2-F-6-OH-benzyl | H | H | Me | OMe | H | H |
| 554 | 4-Cl-2-F-6-OH-benzyl | H | H | Me | OEt | H | H |

TABLE 7-continued

X = —CO—, q = 1, R = 0, Y = —(R4)C=C(R5)—

| Compound No. 7 | R1—(CH2)p— | R2 | R3 | R4 | R5 | R6 | R7 |
|---|---|---|---|---|---|---|---|
| 555 | 4-Cl-2-F-6-(CH2)-phenol | H | H | Me | CF3 | H | H |
| 556 | 4-Cl-2-F-6-(CH2)-phenol | H | H | Me | OCF3 | H | H |
| 557 | 4-Cl-2-F-6-(CH2)-phenol | H | H | OMe | F | H | H |
| 558 | 4-Cl-2-F-6-(CH2)-phenol | H | H | OMe | Cl | H | H |
| 559 | 4-Cl-2-F-6-(CH2)-phenol | H | H | OMe | Me | H | H |
| 560 | 4-Cl-2-F-6-(CH2)-phenol | H | H | OMe | Et | H | H |
| 561 | 4-Cl-2-F-6-(CH2)-phenol | H | H | OMe | OMe | H | H |
| 562 | 4-Cl-2-F-6-(CH2)-phenol | H | H | OMe | OEt | H | H |
| 563 | 4-Cl-2-F-6-(CH2)-phenol | H | H | OMe | CF3 | H | H |

TABLE 7-continued

X = —CO—, q = 1, R = 0, Y = —(R4)C=C(R5)—

| Compound No. 7 | R1—(CH2)p— | R2 | R3 | R4 | R5 | R6 | R7 |
|---|---|---|---|---|---|---|---|
| 564 | (2-fluoro-4-chloro-6-hydroxybenzyl) | H | H | OMe | OCF3 | H | H |

TABLE 8

X = —CS—, q = 0, r = 0, Y = —(R4)C=C(R5)—

| Compound No. 8- | R1—(CH2)p— | R2 | R3 | R4 | R5 | R6 | R7 |
|---|---|---|---|---|---|---|---|
| 1 | 3,4-dichlorobenzyl | H | H | H | H | H | H |
| 2 | 3,4-dichlorobenzyl | H | H | H | Cl | H | H |
| 3 | 1-naphthylmethyl | H | H | H | H | H | H |
| 4 | 1-naphthylmethyl | H | H | H | Cl | H | H |
| 5 | 2-chlorobenzyl | H | H | H | H | H | H |
| 6 | 3-chlorobenzyl | H | H | H | H | H | H |
| 7 | 4-chlorobenzyl | H | H | H | H | H | H |
| 8 | 2-methoxybenzyl | H | H | H | H | H | H |

TABLE 8-continued

X = —CS—, q = 0, r = 0, Y = —(R4)C═C(R5)—

| Compound No. 8- | R1—(CH2)p— | R2 | R3 | R4 | R5 | R6 | R7 |
|---|---|---|---|---|---|---|---|
| 9 | 4-MeO-C6H4-CH2- | H | H | H | H | H | H |
| 10 | Ph-CH2CH2CH2- | H | H | H | H | H | H |
| 11 | 4-Cl-2-OH-C6H3-CH2- | H | H | H | H | H | H |
| 12 | 4-Br-2-OH-C6H3-CH2- | H | H | H | H | H | H |
| 13 | 4-Br-2-OMe-C6H3-CH2- | H | H | H | H | H | H |
| 14 | 4-Br-2-F-C6H3-CH2- | H | H | H | H | H | H |
| 15 | 3-Br-C6H4-CH2- | H | H | H | H | H | H |
| 16 | 2,4-diCl-6-OH-C6H2-CH2- | H | H | H | H | H | H |
| 17 | 3-Cl-4-F-C6H3-CH2- | H | H | H | H | H | H |
| 18 | (1-Me-indol-3-yl)-CH2- | H | H | H | H | H | H |
| 19 | (benzothiophen-3-yl)-CH2- | H | H | H | H | H | H |

TABLE 8-continued
X = —CS—, q = 0, r = 0, Y = —(R4)C=C(R5)—
| Compound No. 8- | R1—(CH2)p— | R2 | R3 | R4 | R5 | R6 | R7 |
|---|---|---|---|---|---|---|---|
| 20 | 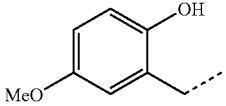 | H | H | H | H | H | H |
| 21 | 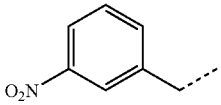 | H | H | H | H | H | H |
| 22 | 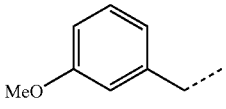 | H | H | H | H | H | H |
| 23 | 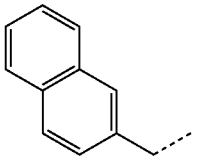 | H | H | H | H | H | H |
| 24 | 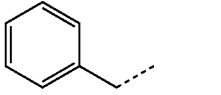 | H | H | H | H | H | H |
| 25 | 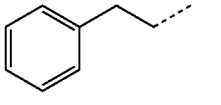 | H | H | H | H | H | H |
| 26 | 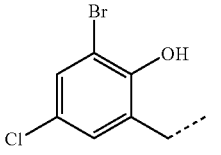 | H | H | H | H | H | H |
| 27 | 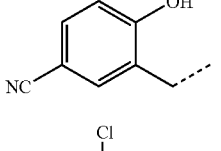 | H | H | H | H | H | H |
| 28 | 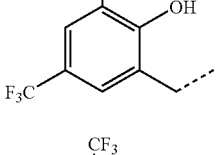 | H | H | H | H | H | H |
| 29 | 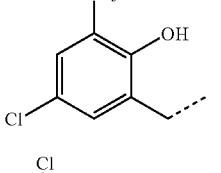 | H | H | H | H | H | H |
| 30 | 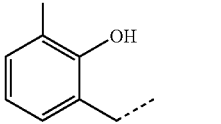 | H | H | H | H | H | H |

TABLE 8-continued
| | X = —CS—, q = 0, r = 0, Y = —(R4)C=C(R5)— | | | | | | |
|---|---|---|---|---|---|---|---|
| Compound No. 8- | R1—(CH2)p— | R2 | R3 | R4 | R5 | R6 | R7 |
| 31 | 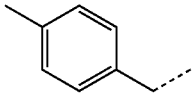 | H | H | H | H | H | H |
| 32 | 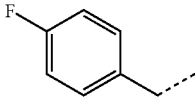 | H | H | H | H | H | H |
| 33 | 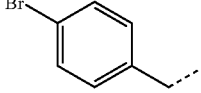 | H | H | H | H | H | H |
| 34 | 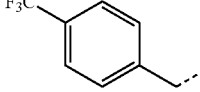 | H | H | H | H | H | H |
| 35 | 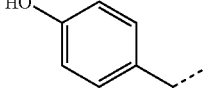 | H | H | H | H | H | H |
| 36 | 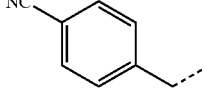 | H | H | H | H | H | H |
| 37 | 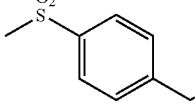 | H | H | H | H | H | H |
| 38 | 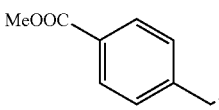 | H | H | H | H | H | H |
| 39 | 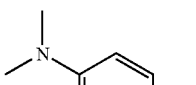 | H | H | H | H | H | H |
| 40 | 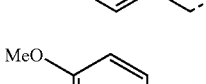 | H | H | H | H | H | H |
| 41 | 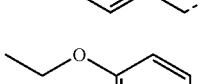 | H | H | H | H | H | H |
| 42 | 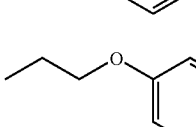 | H | H | H | H | H | H |

TABLE 8-continued

X = —CS—, q = 0, r = 0, Y = —(R4)C=C(R5)—

| Compound No. 8- | R1—(CH2)p— | R2 | R3 | R4 | R5 | R6 | R7 |
|---|---|---|---|---|---|---|---|
| 43 | 4-isopropoxybenzyl | H | H | H | H | H | H |
| 44 | 4-isopropylbenzyl | H | H | H | H | H | H |
| 45 | 4-benzyloxybenzyl | H | H | H | H | H | H |
| 46 | 4-phenoxybenzyl | H | H | H | H | H | H |
| 47 | 4-phenylbenzyl (biphenyl-4-ylmethyl) | H | H | H | H | H | H |
| 48 | 4-acetamidobenzyl | H | H | H | H | H | H |
| 49 | 2-propylbenzyl | H | H | H | H | H | H |
| 50 | 2-benzyloxybenzyl | H | H | H | H | H | H |
| 51 | 2-methylbenzyl | H | H | H | H | H | H |
| 52 | 2-cyanobenzyl | H | H | H | H | H | H |

TABLE 8-continued

X = —CS—, q = 0, r = 0, Y = —(R4)C═C(R5)—

| Compound No. 8- | R1—(CH2)p— | R2 | R3 | R4 | R5 | R6 | R7 |
|---|---|---|---|---|---|---|---|
| 53 | 2-chlorobenzyl | H | H | H | H | H | H |
| 54 | 2-methoxybenzyl | H | H | H | H | H | H |
| 55 | 2-ethoxybenzyl | H | H | H | H | H | H |
| 56 | 2-phenylbenzyl | H | H | H | H | H | H |
| 57 | 3-trifluoromethylbenzyl | H | H | H | H | H | H |
| 58 | 3-chloro-2-fluorobenzyl | H | H | H | H | H | H |
| 59 | 3,5-dichlorobenzyl | H | H | H | H | H | H |
| 60 | 3-methylbenzyl | H | H | H | H | H | H |
| 61 | 3-fluoro-5-trifluoromethylbenzyl | H | H | H | H | H | H |

TABLE 8-continued

X = —CS—, q = 0, r = 0, Y = —(R4)C=C(R5)—

| Compound No. 8- | R1—(CH2)p— | R2 | R3 | R4 | R5 | R6 | R7 |
|---|---|---|---|---|---|---|---|
| 62 | 3-F₃CO-C₆H₄-CH₂- | H | H | H | H | H | H |
| 63 | 2-F,5-MeO-C₆H₃-CH₂- | H | H | H | H | H | H |
| 64 | 2-F,5-O₂N-C₆H₃-CH₂- | H | H | H | H | H | H |
| 65 | 4-O₂N-C₆H₄-CH₂- | H | H | H | H | H | H |
| 66 | 2-F,6-methyl (on ring)-C₆H₃-CH₂- | H | H | H | H | H | H |
| 67 | 3-F₃CS-C₆H₄-CH₂- | H | H | H | H | H | H |
| 68 | 2,5-Cl₂-C₆H₃-CH₂- | H | H | H | H | H | H |
| 69 | 3-F₂HC-C₆H₄-CH₂- | H | H | H | H | H | H |
| 70 | 2-F-C₆H₄-CH₂- | H | H | H | H | H | H |
| 71 | 2-NO₂-C₆H₄-CH₂- | H | H | H | H | H | H |
| 72 | 2-COOH-C₆H₄-CH₂- | H | H | H | H | H | H |
| 73 | 2-OEt,4-Br-C₆H₃-CH₂- | H | H | H | H | H | H |

TABLE 8-continued

X = —CS—, q = 0, r = 0, Y = —(R4)C=C(R5)—

| Compound No. 8- | R1—(CH2)p— | R2 | R3 | R4 | R5 | R6 | R7 |
|---|---|---|---|---|---|---|---|
| 74 | 2,3-dimethylphenyl-CH2— | H | H | H | H | H | H |
| 75 | 3-fluorophenyl-CH2— | H | H | H | H | H | H |
| 76 | 2,4-dichlorophenyl-CH2— | H | H | H | H | H | H |
| 77 | 3-cyanophenyl-CH2— | H | H | H | H | H | H |
| 78 | 3-hydroxyphenyl-CH2— | H | H | H | H | H | H |
| 79 | 3-ethoxyphenyl-CH2— | H | H | H | H | H | H |
| 80 | 4-chloro-3-nitrophenyl-CH2— | H | H | H | H | H | H |
| 81 | 2,3-dichlorophenyl-CH2— | H | H | H | H | H | H |
| 82 | 2,3-difluoro-4-methylphenyl-CH2— | H | H | H | H | H | H |
| 83 | 3-bromo-4-fluorophenyl-CH2— | H | H | H | H | H | H |
| 84 | 2-fluoro-3-(trifluoromethyl)phenyl-CH2— | H | H | H | H | H | H |

TABLE 8-continued

| X = —CS—, q = 0, r = 0, Y = —(R4)C=C(R5)— | | | | | | | |
|---|---|---|---|---|---|---|---|
| Compound No. 8- | R1—(CH2)p— | R2 | R3 | R4 | R5 | R6 | R7 |
| 85 | 2-chloro-4-(hydroxymethyl)phenol group | H | H | H | H | H | H |
| 86 | 2,3-difluorobenzyl group | H | H | H | H | H | H |
| 87 | 3-bromo-4-methoxybenzyl group | H | H | H | H | H | H |
| 88 | 2-ethoxy-3-methoxybenzyl group | H | H | H | H | H | H |
| 89 | 4-methoxy-2,3-dimethylbenzyl group | H | H | H | H | H | H |
| 90 | 2-(benzyloxy)-3-methoxybenzyl group | H | H | H | H | H | H |
| 91 | 4-chloro-3-nitrobenzyl group | H | H | H | H | H | H |
| 92 | 3-(4-methoxyphenoxy)benzyl group | H | H | H | H | H | H |

TABLE 8-continued

X = —CS—, q = 0, r = 0, Y = —(R4)C=C(R5)—

| Compound No. 8- R1—(CH2)p— | R2 | R3 | R4 | R5 | R6 | R7 |
|---|---|---|---|---|---|---|
| 93 (4-methylphenoxy-phenyl-methyl) | H | H | H | H | H | H |
| 94 (4-chlorophenoxy-phenyl-methyl) | H | H | H | H | H | H |
| 95 (benzyloxy-phenyl-methyl) | H | H | H | H | H | H |
| 96 (phenoxy-phenyl-methyl) | H | H | H | H | H | H |
| 97 (2-MeO, 3-HO-phenyl-methyl) | H | H | H | H | H | H |
| 98 (2-Cl, 3-CF3-phenyl-methyl) | H | H | H | H | H | H |
| 99 (4-HO, 3-O2N-phenyl-methyl) | H | H | H | H | H | H |
| 100 (2,3-diOMe-phenyl-methyl) | H | H | H | H | H | H |
| 101 (2,4-diOEt, 3-Me-phenyl-methyl) | H | H | H | H | H | H |

TABLE 8-continued

X = —CS—, q = 0, r = 0, Y = —(R4)C=C(R5)—

| Compound No. 8- | R1—(CH2)p— | R2 | R3 | R4 | R5 | R6 | R7 |
|---|---|---|---|---|---|---|---|
| 102 | 3-(2-hydroxyethoxy)benzyl | H | H | H | H | H | H |
| 103 | 2,3,4-trimethoxybenzyl | H | H | H | H | H | H |
| 104 | 4-fluoro-3-phenoxybenzyl | H | H | H | H | H | H |
| 105 | 6-carboxy-2,3-dimethoxybenzyl | H | H | H | H | H | H |
| 106 | 5-chloro-2-nitrobenzyl | H | H | H | H | H | H |
| 107 | 3,5-dihydroxybenzyl | H | H | H | H | H | H |
| 108 | 3-benzyloxy-4-methoxybenzyl | H | H | H | H | H | H |
| 109 | 3,4-diethoxybenzyl | H | H | H | H | H | H |
| 110 | 3-carboxybenzyl | H | H | H | H | H | H |
| 111 | 4-hydroxy-2-methoxybenzyl | H | H | H | H | H | H |
| 112 | 3-hydroxy-4-nitrobenzyl | H | H | H | H | H | H |

TABLE 8-continued
| | X = —CS—, q = 0, r = 0, Y = —(R4)C=C(R5)— | | | | | | |
|---|---|---|---|---|---|---|---|
| Compound No. 8- | R1—(CH2)p— | R2 | R3 | R4 | R5 | R6 | R7 |
| 113 | 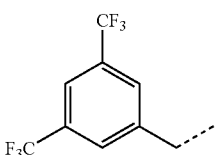 | H | H | H | H | H | H |
| 114 | 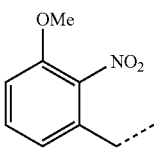 | H | H | H | H | H | H |
| 115 | 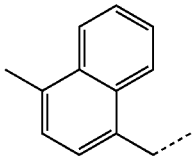 | H | H | H | H | H | H |
| 116 | 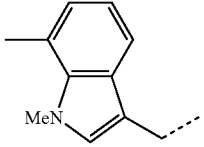 | H | H | H | H | H | H |
| 117 | 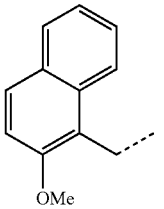 | H | H | H | H | H | H |
| 118 | 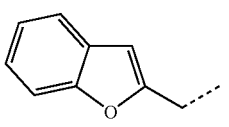 | H | H | H | H | H | H |
| 119 | 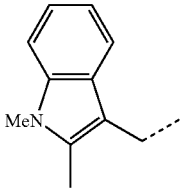 | H | H | H | H | H | H |
| 120 | 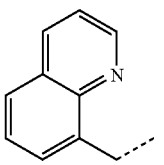 | H | H | H | H | H | H |

TABLE 8-continued

| | X = —CS—, q = 0, r = 0, Y = —(R4)C=C(R5)— | | | | | | |
|---|---|---|---|---|---|---|---|
| Compound No. 8- R1—(CH2)p— | | R2 | R3 | R4 | R5 | R6 | R7 |
| 121 | 2-hydroxy-1-naphthylmethyl | H | H | H | H | H | H |
| 122 | 2-acetoxy-1-naphthylmethyl | H | H | H | H | H | H |
| 123 | 1-hydroxy-2-naphthylmethyl | H | H | H | H | H | H |
| 124 | 7-indolylmethyl | H | H | H | H | H | H |
| 125 | 4-quinolylmethyl | H | H | H | H | H | H |
| 126 | 1-methyl-5-methylindol-3-ylmethyl | H | H | H | H | H | H |
| 127 | 9-anthrylmethyl | H | H | H | H | H | H |

TABLE 8-continued

X = —CS—, q = 0, r = 0, Y = —(R4)C=C(R5)—

| Compound No. 8- | R1—(CH2)p— | R2 | R3 | R4 | R5 | R6 | R7 |
|---|---|---|---|---|---|---|---|
| 128 | 1-methylnaphthalen-2-ylmethyl | H | H | H | H | H | H |
| 129 | 2-ethoxynaphthalen-1-ylmethyl | H | H | H | H | H | H |
| 130 | 1H-indol-3-ylmethyl | H | H | H | H | H | H |
| 131 | 6-methyl-1-methyl-1H-indol-3-ylmethyl | H | H | H | H | H | H |
| 132 | 1-methyl-1H-indol-2-ylmethyl | H | H | H | H | H | H |
| 133 | 4-methyl-1-methyl-1H-indol-3-ylmethyl | H | H | H | H | H | H |
| 134 | 2,5-dimethyl-1-methyl-1H-indol-3-ylmethyl | H | H | H | H | H | H |
| 135 | 5-methoxy-1-methyl-1H-indol-3-ylmethyl | H | H | H | H | H | H |

TABLE 8-continued

X = —CS—, q = 0, r = 0, Y = —(R4)C═C(R5)—

| Compound No. 8- R1—(CH2)p— | R2 | R3 | R4 | R5 | R6 | R7 |
|---|---|---|---|---|---|---|
| 136 (4-methylbenzothiophen-3-yl) | H | H | H | H | H | H |
| 137 (1-methylbenzimidazol-2-yl) | H | H | H | H | H | H |
| 138 (1-methyl-2-phenylindol-3-yl) | H | H | H | H | H | H |
| 139 (1-acetylindol-3-yl) | H | H | H | H | H | H |
| 140 (quinolin-2-yl) | H | H | H | H | H | H |
| 141 (6-methoxy-1-methylindol-3-yl) | H | H | H | H | H | H |
| 142 (3-methylbenzothiophen-2-yl) | H | H | H | H | H | H |
| 143 (4-methoxynaphthalen-1-yl) | H | H | H | H | H | H |

TABLE 8-continued

X = —CS—, q = 0, r = 0, Y = —(R4)C=C(R5)—

| Compound No. 8- R1—(CH2)p— | | R2 | R3 | R4 | R5 | R6 | R7 |
|---|---|---|---|---|---|---|---|
| 144 | [phenanthrenyl-CH2] | H | H | H | H | H | H |
| 145 | [6-methoxynaphthalen-2-yl-CH2] | H | H | H | H | H | H |
| 146 | [1-bromonaphthalen-2-yl-CH2] | H | H | H | H | H | H |
| 147 | [4-(dimethylamino)naphthalen-1-yl-CH2] | H | H | H | H | H | H |
| 148 | [2,3-dihydro-1,4-benzodioxin-6-yl-CH2] | H | H | H | H | H | H |
| 149 | [2,2-dimethylchroman-6-yl-CH2] | H | H | H | H | H | H |
| 150 | [2,3-dihydrobenzofuran-5-yl-CH2] | H | H | H | H | H | H |
| 151 | [9-ethylcarbazol-3-yl-CH2] | H | H | H | H | H | H |
| 152 | [1,3-benzodioxol-4-yl-CH2] | H | H | H | H | H | H |

TABLE 8-continued
X = —CS—, q = 0, r = 0, Y = —(R4)C═C(R5)—
| Compound No. 8- | R1—(CH2)p— | R2 | R3 | R4 | R5 | R6 | R7 |
|---|---|---|---|---|---|---|---|
| 153 | 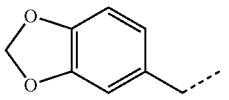 | H | H | H | H | H | H |
| 154 | 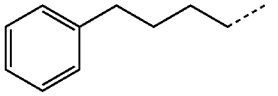 | H | H | H | H | H | H |
| 155 | 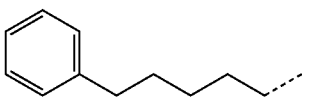 | H | H | H | H | H | H |
| 156 | 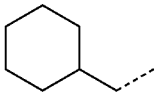 | H | H | H | H | H | H |
| 157 | 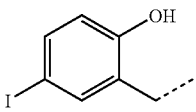 | H | H | H | H | H | H |
| 158 | 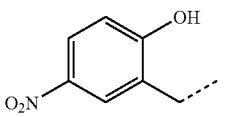 | H | H | H | H | H | H |
| 159 | 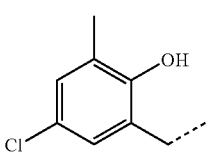 | H | H | H | H | H | H |
| 160 | 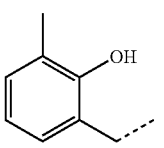 | H | H | H | H | H | H |
| 161 | 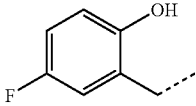 | H | H | H | H | H | H |
| 162 | 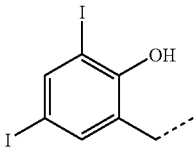 | H | H | H | H | H | H |
| 163 | 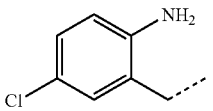 | H | H | H | H | H | H |
| 164 | 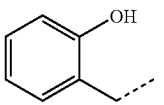 | H | H | H | H | H | H |

TABLE 8-continued

X = —CS—, q = 0, r = 0, Y = —(R4)C=C(R5)—

| Compound No. 8- | R1—(CH2)p— | R2 | R3 | R4 | R5 | R6 | R7 |
|---|---|---|---|---|---|---|---|
| 165 | 2-aminobenzyl | H | H | H | H | H | H |
| 166 | 5-tert-butyl-2-hydroxybenzyl | H | H | H | H | H | H |
| 167 | 2-hydroxy-5-trifluoromethoxybenzyl | H | H | H | H | H | H |
| 168 | 3-methoxy-2-hydroxybenzyl | H | H | H | H | H | H |
| 169 | 2,3-dihydroxybenzyl | H | H | H | H | H | H |
| 170 | 3-ethoxy-2-hydroxybenzyl | H | H | H | H | H | H |
| 171 | 3-carboxy-2-hydroxybenzyl | H | H | H | H | H | H |
| 172 | 3-tert-butyl-2-hydroxybenzyl | H | H | H | H | H | H |
| 173 | furan-2-ylmethyl | H | H | H | H | H | H |
| 174 | oxazol-2-ylmethyl | H | H | H | H | H | H |
| 175 | 1H-imidazol-2-ylmethyl | H | H | H | H | H | H |

TABLE 8-continued
X = —CS—, q = 0, r = 0, Y = —(R4)C=C(R5)—
| Compound No. 8- | R1—(CH2)p— | R2 | R3 | R4 | R5 | R6 | R7 |
|---|---|---|---|---|---|---|---|
| 176 | 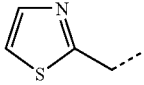 | H | H | H | H | H | H |
| 177 | 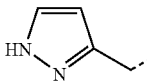 | H | H | H | H | H | H |
| 178 | 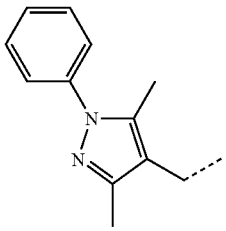 | H | H | H | H | H | H |
| 179 | 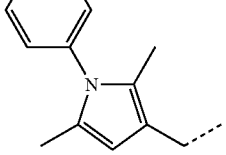 | H | H | H | H | H | H |
| 180 | 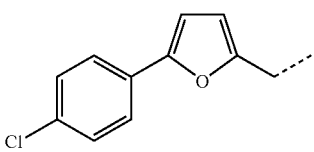 | H | H | H | H | H | H |
| 181 | 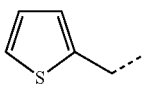 | H | H | H | H | H | H |
| 182 | 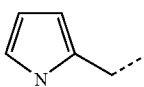 | H | H | H | H | H | H |
| 183 | 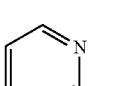 | H | H | H | H | H | H |
| 184 | 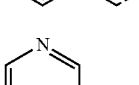 | H | H | H | H | H | H |
| 185 | 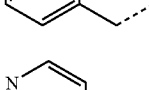 | H | H | H | H | H | H |
| 186 | 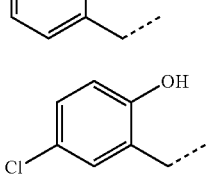 | H | H | H | Cl | H | H |

TABLE 8-continued
X = —CS—, q = 0, r = 0, Y = —(R4)C=C(R5)—
| Compound No. 8- | R1—(CH2)p— | R2 | R3 | R4 | R5 | R6 | R7 |
|---|---|---|---|---|---|---|---|
| 187 | 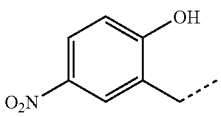 | H | H | H | Cl | H | H |
| 188 | 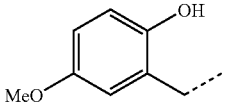 | H | H | H | Cl | H | H |
| 189 | 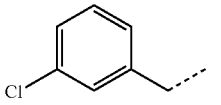 | H | H | H | Cl | H | H |
| 190 | 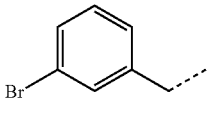 | H | H | H | Cl | H | H |
| 191 | 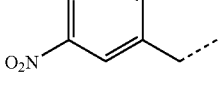 | H | H | H | Cl | H | H |
| 192 | 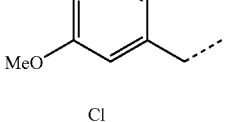 | H | H | H | Cl | H | H |
| 193 | 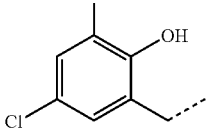 | H | H | H | Cl | H | H |
| 194 | 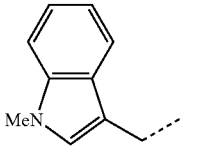 | H | H | H | Cl | H | H |
| 195 | 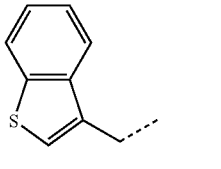 | H | H | H | Cl | H | H |
| 196 | 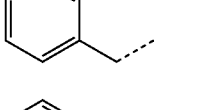 | H | H | H | Cl | H | H |
| 197 | 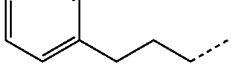 | H | H | H | Cl | H | H |

TABLE 8-continued

X = —CS—, q = 0, r = 0, Y = —(R4)C═C(R5)—

| Compound No. 8- R1—(CH2)p— | R2 | R3 | R4 | R5 | R6 | R7 |
|---|---|---|---|---|---|---|
| 198 (4-Br, 2-OH-phenyl) | H | H | H | Cl | H | H |
| 199 (naphthyl) | H | H | H | Cl | H | H |
| 200 (phenyl-CH2) | H | H | H | Cl | H | H |
| 201 (3,5-diCl, 2-OH-phenyl) | H | H | Cl | H | H | H |
| 202 (3,5-diCl, 2-OH-phenyl) | H | H | H | OMe | H | H |
| 203 (3,5-diCl, 2-OH-phenyl) | H | H | H | COOMe | H | H |
| 204 (3,5-diCl, 2-OH-phenyl) | H | H | H | H | Cl | H |
| 205 (3,5-diCl, 2-OH-phenyl) | H | H | H | H | COOMe | H |
| 206 (3,5-diCl, 2-OH-phenyl) | H | H | H | H | H | Cl |
| 207 (3,5-diCl, 2-OH-phenyl) | H | H | H | OCF3 | H | H |

TABLE 8-continued
X = —CS—, q = 0, r = 0, Y = —(R4)C=C(R5)—
| Compound No. 8- R1—(CH2)p— | R2 | R3 | R4 | R5 | R6 | R7 |
|---|---|---|---|---|---|---|
| 208 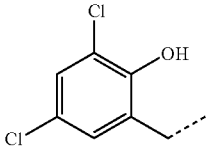 | H | H | COOMe | H | H | H |
| 209 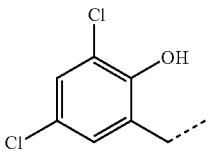 | H | H | H | CF3 | H | H |
| 210 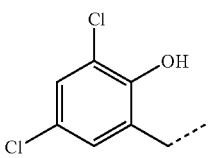 | H | H | H | Me | H | H |
| 211 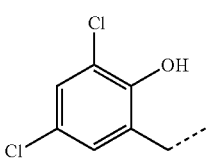 | H | H | H | F | H | H |
| 212 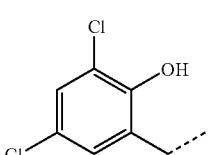 | H | H | H | OH | H | H |
| 213 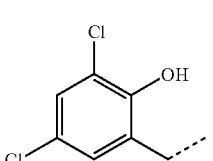 | H | H | H | NO2 | H | H |
| 214 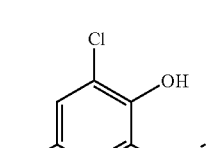 | H | H | H | F | F | H |
| 215 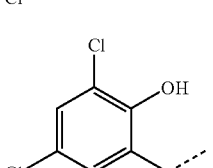 | H | H | F | H | H | H |
| 216 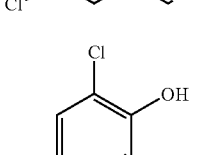 | H | H | Me | H | H | H |

TABLE 8-continued

X = —CS—, q = 0, r = 0, Y = —(R4)C=C(R5)—

| Compound No. 8- | R1—(CH2)p— | R2 | R3 | R4 | R5 | R6 | R7 |
|---|---|---|---|---|---|---|---|
| 217 | 2,4-dichloro-6-(OH)phenyl-CH2 | H | H | H | CN | H | H |
| 218 | 4-chloro-2-(OH)phenyl-CH2 | H | H | Cl | H | H | H |
| 219 | 4-chloro-2-(OH)phenyl-CH2 | H | H | H | OMe | H | H |
| 220 | 4-chloro-2-(OH)phenyl-CH2 | H | H | H | COOMe | H | H |
| 221 | 4-chloro-2-(OH)phenyl-CH2 | H | H | H | H | Cl | H |
| 222 | 4-chloro-2-(OH)phenyl-CH2 | H | H | H | H | COOMe | H |
| 223 | 4-chloro-2-(OH)phenyl-CH2 | H | H | H | H | H | Cl |
| 224 | 4-chloro-2-(OH)phenyl-CH2 | H | H | H | OCF3 | H | H |
| 225 | 4-chloro-2-(OH)phenyl-CH2 | H | H | COOMe | H | H | H |
| 226 | 4-chloro-2-(OH)phenyl-CH2 | H | H | H | CF3 | H | H |
| 227 | 4-chloro-2-(OH)phenyl-CH2 | H | H | H | Me | H | H |
| 228 | 4-chloro-2-(OH)phenyl-CH2 | H | H | H | F | H | H |

TABLE 8-continued

X = —CS—, q = 0, r = 0, Y = —(R4)C=C(R5)—

| Compound No. 8- R1—(CH2)p— | R2 | R3 | R4 | R5 | R6 | R7 |
|---|---|---|---|---|---|---|
| 229 4-Cl-2-hydroxybenzyl | H | H | H | OH | H | H |
| 230 4-Cl-2-hydroxybenzyl | H | H | H | NO2 | H | H |
| 231 4-Cl-2-hydroxybenzyl | H | H | H | F | F | H |
| 232 4-Cl-2-hydroxybenzyl | H | H | F | H | H | H |
| 233 4-Cl-2-hydroxybenzyl | H | H | Me | H | H | H |
| 234 4-Cl-2-hydroxybenzyl | H | H | H | CN | H | H |
| 235 naphthalen-1-ylmethyl | H | H | Cl | H | H | H |
| 236 naphthalen-1-ylmethyl | H | H | H | OMe | H | H |
| 237 naphthalen-1-ylmethyl | H | H | H | COOMe | H | H |
| 238 naphthalen-1-ylmethyl | H | H | H | H | Cl | H |

TABLE 8-continued

X = —CS—, q = 0, r = 0, Y = —(R4)C═C(R5)—

| Compound No. 8- R1—(CH2)p— | | R2 | R3 | R4 | R5 | R6 | R7 |
|---|---|---|---|---|---|---|---|
| 239 | naphthyl-CH2 | H | H | H | H | COOMe | H |
| 240 | naphthyl-CH2 | H | H | H | H | H | Cl |
| 241 | naphthyl-CH2 | H | H | H | OCF3 | H | H |
| 242 | naphthyl-CH2 | H | H | COOMe | H | H | H |
| 243 | naphthyl-CH2 | H | H | H | CF3 | H | H |
| 244 | naphthyl-CH2 | H | H | H | Me | H | H |
| 245 | naphthyl-CH2 | H | H | H | F | H | H |
| 246 | naphthyl-CH2 | H | H | H | OH | H | H |
| 247 | naphthyl-CH2 | H | H | H | NO2 | H | H |

TABLE 8-continued
| | X = —CS—, q = 0, r = 0, Y = —(R4)C═C(R5)— | | | | | | |
|---|---|---|---|---|---|---|---|
| Compound No. 8- R1—(CH2)p— | | R2 | R3 | R4 | R5 | R6 | R7 |
| 248 | 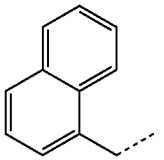 | H | H | H | F | F | H |
| 249 | 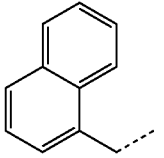 | H | H | F | H | H | H |
| 250 | 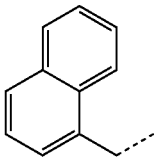 | H | H | Me | H | H | H |
| 251 | 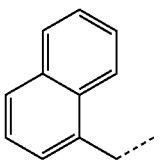 | H | H | H | CN | H | H |
| 252 | 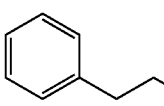 | H | H | Cl | H | H | H |
| 253 | 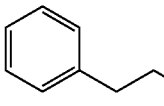 | H | H | H | OMe | H | H |
| 254 | 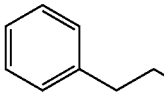 | H | H | H | COOMe | H | H |
| 255 | 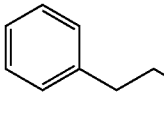 | H | H | H | H | Cl | H |
| 256 | 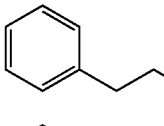 | H | H | H | H | COOMe | H |
| 257 | 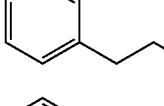 | H | H | H | H | H | Cl |
| 258 | 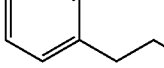 | H | H | H | OCF3 | H | H |

TABLE 8-continued

X = —CS—, q = 0, r = 0, Y = —(R4)C=C(R5)—

| Compound No. 8- | R1—(CH2)p— | R2 | R3 | R4 | R5 | R6 | R7 |
|---|---|---|---|---|---|---|---|
| 259 | phenyl-(CH2)2- | H | H | COOMe | H | H | H |
| 260 | phenyl-(CH2)2- | H | H | H | CF3 | H | H |
| 261 | phenyl-(CH2)2- | H | H | H | Me | H | H |
| 262 | phenyl-(CH2)2- | H | H | H | F | H | H |
| 263 | phenyl-(CH2)2- | H | H | H | OH | H | H |
| 264 | phenyl-(CH2)2- | H | H | H | NO2 | H | H |
| 265 | phenyl-(CH2)2- | H | H | H | F | F | H |
| 266 | phenyl-(CH2)2- | H | H | F | H | H | H |
| 267 | phenyl-(CH2)2- | H | H | Me | H | H | H |
| 268 | phenyl-(CH2)2- | H | H | H | CN | H | H |
| 269 | 3,5-dichloro-2-hydroxybenzyl | H | H | H | H | H | COOMe |
| 270 | 3,5-dichloro-2-hydroxybenzyl | H | H | H | H | F | H |

TABLE 8-continued
X = —CS—, q = 0, r = 0, Y = —(R4)C=C(R5)—
| Compound No. 8- R1—(CH2)p— | | R2 | R3 | R4 | R5 | R6 | R7 |
|---|---|---|---|---|---|---|---|
| 271 | 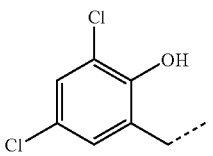 | H | H | H | H | H | F |
| 272 | 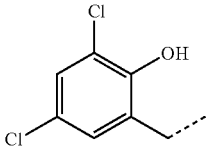 | H | H | H | H | Me | H |
| 273 | 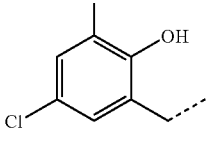 | H | H | H | H | H | Me |
| 274 | 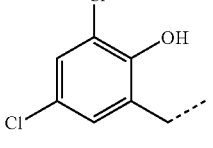 | H | H | OMe | H | H | H |
| 275 | 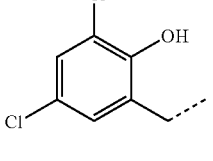 | H | H | H | H | OMe | H |
| 276 | 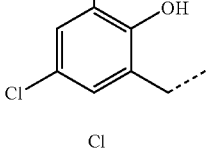 | H | H | H | H | H | OMe |
| 277 | 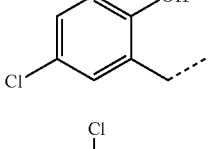 | H | H | CF3 | H | H | H |
| 278 | 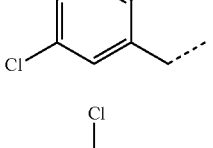 | H | H | H | H | CF3 | H |
| 279 | 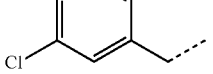 | H | H | H | H | H | CF3 |

TABLE 8-continued
X = —CS—, q = 0, r = 0, Y = —(R4)C=C(R5)—
| Compound No. 8- R1—(CH2)p— | | R2 | R3 | R4 | R5 | R6 | R7 |
|---|---|---|---|---|---|---|---|
| 280 | 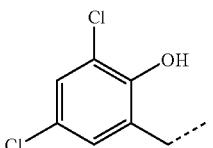 | H | H | OH | H | H | H |
| 281 | 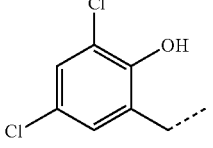 | H | H | H | H | OH | H |
| 282 | 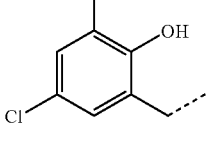 | H | H | H | H | H | OH |
| 283 | 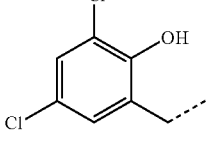 | H | H | OCF3 | H | H | H |
| 284 | 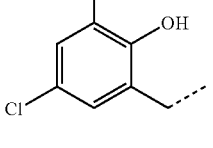 | H | H | H | H | OCF3 | H |
| 285 | 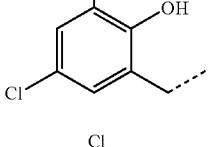 | H | H | H | H | H | OCF3 |
| 286 | 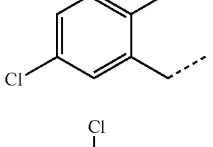 | H | H | NO2 | H | H | H |
| 287 | 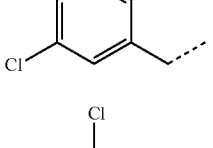 | H | H | H | H | NO2 | H |
| 288 | 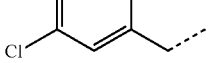 | H | H | H | H | H | NO2 |

TABLE 8-continued
X = —CS—, q = 0, r = 0, Y = —(R4)C═C(R5)—
| Compound No. 8- R1—(CH2)p— | | R2 | R3 | R4 | R5 | R6 | R7 |
|---|---|---|---|---|---|---|---|
| 289 | 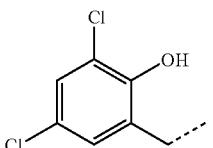 | H | H | CN | H | H | H |
| 290 | 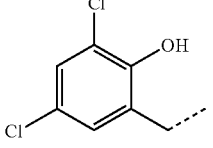 | H | H | H | H | CN | H |
| 291 | 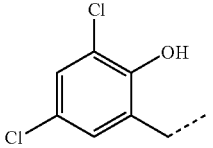 | H | H | H | H | H | CN |
| 292 | 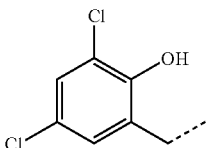 | H | H | Br | H | H | H |
| 293 | 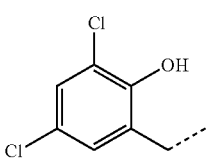 | H | H | H | Br | H | H |
| 294 | 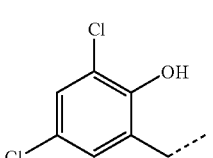 | H | H | H | H | Br | H |
| 295 | 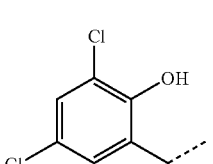 | H | H | H | H | H | Br |
| 296 | 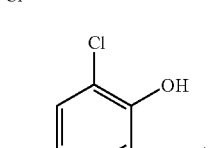 | H | H | COOH | H | H | H |
| 297 | 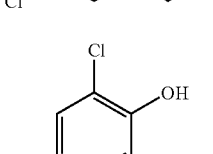 | H | H | H | COOH | H | H |

TABLE 8-continued
X = —CS—, q = 0, r = 0, Y = —(R4)C=C(R5)—
| Compound No. 8- R1—(CH2)p— | | R2 | R3 | R4 | R5 | R6 | R7 |
|---|---|---|---|---|---|---|---|
| 298 | 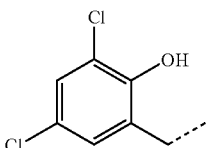 | H | H | H | H | COOH | H |
| 299 | 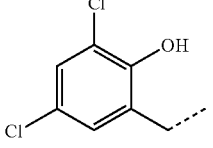 | H | H | H | H | H | COOH |
| 300 | 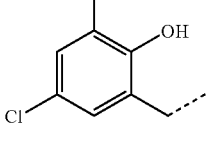 | H | H | NHCOMe | H | H | H |
| 301 | 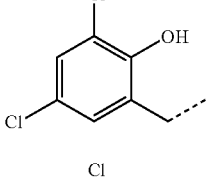 | H | H | H | NHCOMe | H | H |
| 302 | 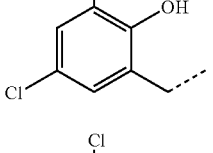 | H | H | H | H | NHCOMe | H |
| 303 | 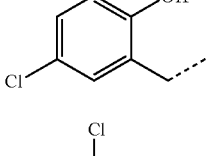 | H | H | H | H | H | NHCOMe |
| 304 | 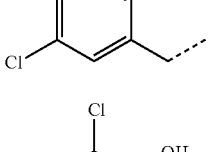 | H | H | SO2NH2 | H | H | H |
| 305 | 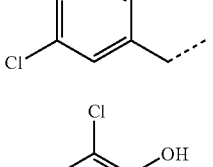 | H | H | H | SO2NH2 | H | H |
| 306 | 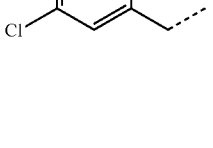 | H | H | H | H | SO2NH2 | H |

TABLE 8-continued
X = —CS—, q = 0, r = 0, Y = —(R4)C═C(R5)—
| Compound No. 8- R1—(CH2)p— | | R2 | R3 | R4 | R5 | R6 | R7 |
|---|---|---|---|---|---|---|---|
| 307 | 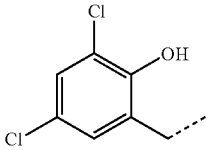 | H | H | H | H | H | SO2NH2 |
| 308 | 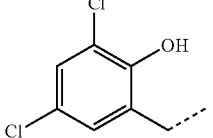 | H | H | Me | Me | H | H |
| 309 | 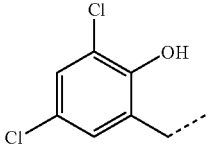 | H | H | Me | H | Me | H |
| 310 | 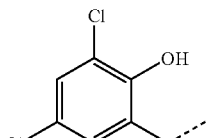 | H | H | H | Me | Me | H |
| 311 | 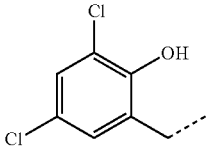 | H | H | F | F | H | H |
| 312 | 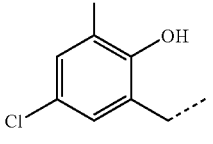 | H | H | F | H | F | H |
| 313 | 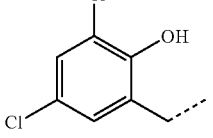 | H | H | H | F | F | H |
| 314 | 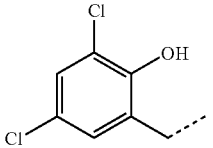 | H | H | Cl | Cl | H | H |
| 315 | 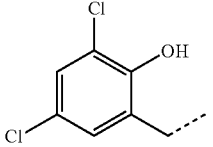 | H | H | Cl | H | Cl | H |

TABLE 8-continued
X = —CS—, q = 0, r = 0, Y = —(R4)C=C(R5)—
| Compound No. 8- R1—(CH2)p— | | R2 | R3 | R4 | R5 | R6 | R7 |
|---|---|---|---|---|---|---|---|
| 316 | 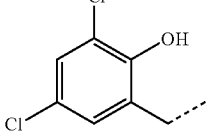 | H | H | H | Cl | Cl | H |
| 317 | 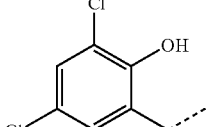 | H | H | Me | F | H | H |
| 318 | 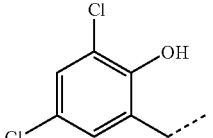 | H | H | Me | Cl | H | H |
| 319 | 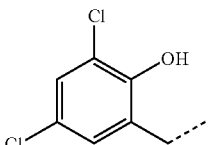 | H | H | Me | OH | H | H |
| 320 | 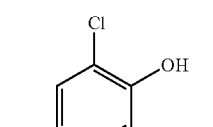 | H | H | Me | OMe | H | H |
| 321 | 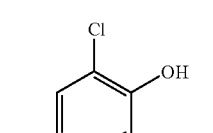 | H | H | F | Me | H | H |
| 322 | 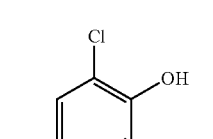 | H | H | F | Cl | H | H |
| 323 | 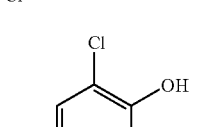 | H | H | F | OH | H | H |
| 324 | 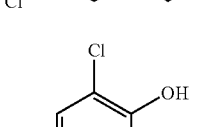 | H | H | FH | OMe | H | H |

TABLE 8-continued

X = —CS—, q = 0, r = 0, Y = —(R4)C=C(R5)—

| Compound No. 8- | R1—(CH2)p— | R2 | R3 | R4 | R5 | R6 | R7 |
|---|---|---|---|---|---|---|---|
| 325 | 2,4-dichloro-6-hydroxyphenyl-CH2— | H | H | Cl | Me | H | H |
| 326 | 2,4-dichloro-6-hydroxyphenyl-CH2— | H | H | Cl | F | H | H |
| 327 | 2,4-dichloro-6-hydroxyphenyl-CH2— | H | H | Cl | OH | H | H |
| 328 | 2,4-dichloro-6-hydroxyphenyl-CH2— | H | H | Cl | OMe | H | H |
| 329 | 4-chloro-2-hydroxyphenyl-CH2— | H | H | H | H | H | COOMe |
| 330 | 4-chloro-2-hydroxyphenyl-CH2— | H | H | H | H | F | H |
| 331 | 4-chloro-2-hydroxyphenyl-CH2— | H | H | H | H | H | F |
| 332 | 4-chloro-2-hydroxyphenyl-CH2— | H | H | H | H | Me | H |
| 333 | 4-chloro-2-hydroxyphenyl-CH2— | H | H | H | H | H | Me |
| 334 | 4-chloro-2-hydroxyphenyl-CH2— | H | H | OMe | H | H | H |
| 335 | 4-chloro-2-hydroxyphenyl-CH2— | H | H | H | H | OMe | H |

TABLE 8-continued
X = —CS—, q = 0, r = 0, Y = —(R4)C═C(R5)—
| Compound No. 8- | R1—(CH2)p— | R2 | R3 | R4 | R5 | R6 | R7 |
|---|---|---|---|---|---|---|---|
| 336 | 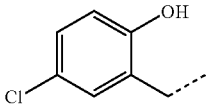 | H | H | H | H | H | OMe |
| 337 | 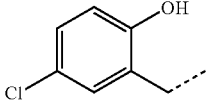 | H | H | CF3 | H | H | H |
| 338 | 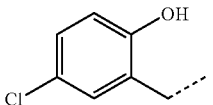 | H | H | H | H | CF3 | H |
| 339 | 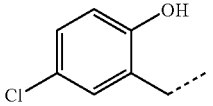 | H | H | H | H | H | CF3 |
| 340 | 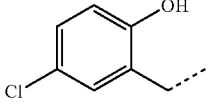 | H | H | OH | H | H | H |
| 341 | 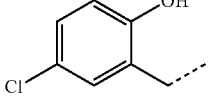 | H | H | H | H | OH | H |
| 342 | 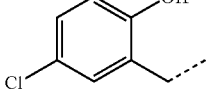 | H | H | H | H | H | OH |
| 343 | 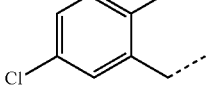 | H | H | OCF3 | H | H | H |
| 344 | 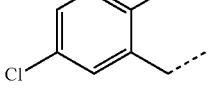 | H | H | H | H | OCF3 | H |
| 345 | 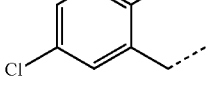 | H | H | H | H | H | OCF3 |
| 346 | 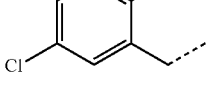 | H | H | NO2 | H | H | H |
| 347 | 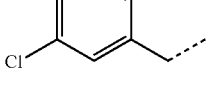 | H | H | H | H | NO2 | H |

TABLE 8-continued

X = —CS—, q = 0, r = 0, Y = —(R4)C=C(R5)—

| Compound No. 8- | R1—(CH2)p— | R2 | R3 | R4 | R5 | R6 | R7 |
|---|---|---|---|---|---|---|---|
| 348 | 4-Cl, 2-OH-benzyl | H | H | H | H | H | NO2 |
| 349 | 4-Cl, 2-OH-benzyl | H | H | CN | H | H | H |
| 350 | 4-Cl, 2-OH-benzyl | H | H | H | H | CN | H |
| 351 | 4-Cl, 2-OH-benzyl | H | H | H | H | H | CN |
| 352 | 4-Cl, 2-OH-benzyl | H | H | Br | H | H | H |
| 353 | 4-Cl, 2-OH-benzyl | H | H | H | Br | H | H |
| 354 | 4-Cl, 2-OH-benzyl | H | H | H | H | Br | H |
| 355 | 4-Cl, 2-OH-benzyl | H | H | H | H | H | Br |
| 356 | 4-Cl, 2-OH-benzyl | H | H | COOH | H | H | H |
| 357 | 4-Cl, 2-OH-benzyl | H | H | H | COOH | H | H |
| 358 | 4-Cl, 2-OH-benzyl | H | H | H | H | COOH | H |
| 359 | 4-Cl, 2-OH-benzyl | H | H | H | H | H | COOH |

TABLE 8-continued
X = —CS—, q = 0, r = 0, Y = —(R4)C=C(R5)—
| Compound No. 8- | R1—(CH2)p— | R2 | R3 | R4 | R5 | R6 | R7 |
|---|---|---|---|---|---|---|---|
| 360 | 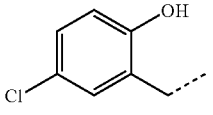 | H | H | NHCOMe | H | H | H |
| 361 | 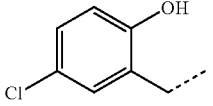 | H | H | H | NHCOMe | H | H |
| 362 | 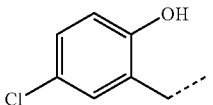 | H | H | H | H | NHCOMe | H |
| 363 | 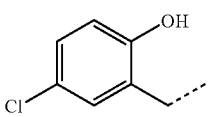 | H | H | H | H | H | NHCOMe |
| 364 | 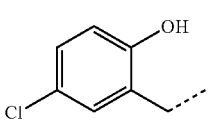 | H | H | SO2NH2 | H | H | H |
| 365 | 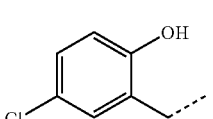 | H | H | H | SO2NH2 | H | H |
| 366 | 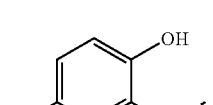 | H | H | H | H | SO2NH2 | H |
| 367 | 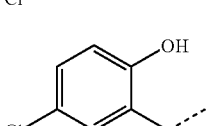 | H | H | H | H | H | SO2NH2 |
| 368 | 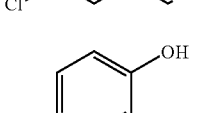 | H | H | Me | Me | H | H |
| 369 | 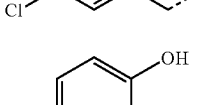 | H | H | Me | H | Me | H |
| 370 | 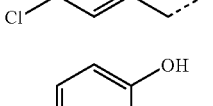 | H | H | H | Me | Me | H |
| 371 | 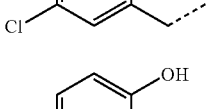 | H | H | F | F | H | H |

TABLE 8-continued
X = —CS—, q = 0, r = 0, Y = —(R4)C=C(R5)—
| Compound No. 8- | R1—(CH2)p— | R2 | R3 | R4 | R5 | R6 | R7 |
|---|---|---|---|---|---|---|---|
| 372 | 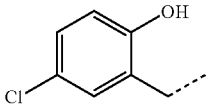 | H | H | F | H | F | H |
| 373 | 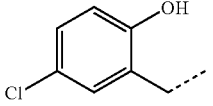 | H | H | H | F | F | H |
| 374 | 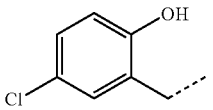 | H | H | Cl | Cl | H | H |
| 375 | 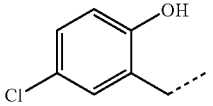 | H | H | Cl | H | Cl | H |
| 376 | 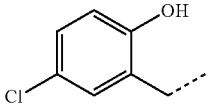 | H | H | H | Cl | Cl | H |
| 377 | 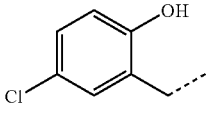 | H | H | Me | F | H | H |
| 378 | 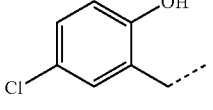 | H | H | Me | Cl | H | H |
| 379 | 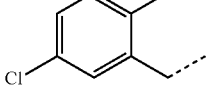 | H | H | Me | OH | H | H |
| 380 | 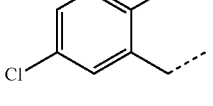 | H | H | Me | OMe | H | H |
| 381 | 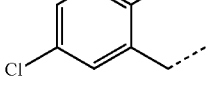 | H | H | F | Me | H | H |
| 382 | 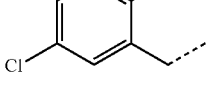 | H | H | F | Cl | H | H |
| 383 | 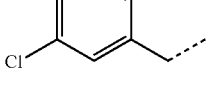 | H | H | F | OH | H | H |

TABLE 8-continued
X = —CS—, q = 0, r = 0, Y = —(R4)C=C(R5)—
| Compound No. 8- R1—(CH2)p— | | R2 | R3 | R4 | R5 | R6 | R7 |
|---|---|---|---|---|---|---|---|
| 384 | 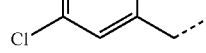 | H | H | F | OMe | H | H |
| 385 | 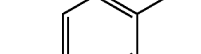 | H | H | Cl | Me | H | H |
| 386 | 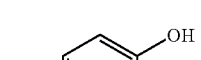 | H | H | Cl | F | H | H |
| 387 | 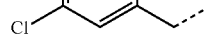 | H | H | Cl | OH | H | H |
| 388 |  | H | H | Cl | OMe | H | H |
| 389 | 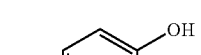 | H | H | H | H | H | COOMe |
| 390 | 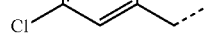 | H | H | H | H | F | H |
| 391 | 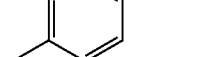 | H | H | H | H | H | F |
| 392 | 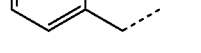 | H | H | H | H | Me | H |
| 393 | 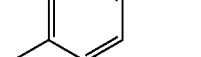 | H | H | H | H | H | Me |

TABLE 8-continued
X = —CS—, q = 0, r = 0, Y = —(R4)C=C(R5)—
| Compound No. 8- R1—(CH2)p— | | R2 | R3 | R4 | R5 | R6 | R7 |
|---|---|---|---|---|---|---|---|
| 394 | 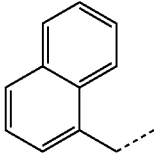 | H | H | OMe | H | H | H |
| 395 | 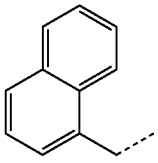 | H | H | H | H | OMe | H |
| 396 | 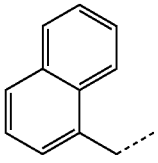 | H | H | H | H | H | OMe |
| 397 | 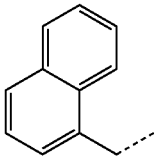 | H | H | CF3 | H | H | H |
| 398 | 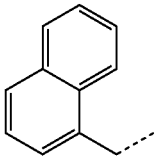 | H | H | H | H | CF3 | H |
| 399 | 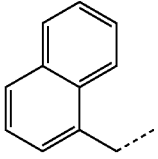 | H | H | H | H | H | CF3 |
| 400 | 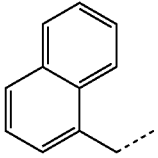 | H | H | OH | H | H | H |
| 401 | 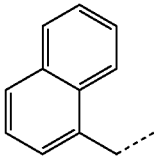 | H | H | H | H | OH | H |
| 402 | 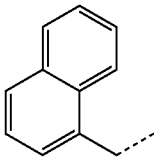 | H | H | H | H | H | OH |

TABLE 8-continued

X = —CS—, q = 0, r = 0, Y = —(R4)C=C(R5)—

| Compound No. 8- R1—(CH2)p— | | R2 | R3 | R4 | R5 | R6 | R7 |
|---|---|---|---|---|---|---|---|
| 403 | naphthyl-CH2 | H | H | OCF3 | H | H | H |
| 404 | naphthyl-CH2 | H | H | H | H | OCF3 | H |
| 405 | naphthyl-CH2 | H | H | H | H | H | OCF3 |
| 406 | naphthyl-CH2 | H | H | NO2 | H | H | H |
| 407 | naphthyl-CH2 | H | H | H | H | NO2 | H |
| 408 | naphthyl-CH2 | H | H | H | H | H | NO2 |
| 409 | naphthyl-CH2 | H | H | CN | H | H | H |
| 410 | naphthyl-CH2 | H | H | H | H | CN | H |

TABLE 8-continued

X = —CS—, q = 0, r = 0, Y = —(R4)C=C(R5)—

| Compound No. 8- | R1—(CH2)p— | R2 | R3 | R4 | R5 | R6 | R7 |
|---|---|---|---|---|---|---|---|
| 411 | naphthyl-CH2- | H | H | H | H | H | CN |
| 412 | naphthyl-CH2- | H | H | Br | H | H | H |
| 413 | naphthyl-CH2- | H | H | H | Br | H | H |
| 414 | naphthyl-CH2- | H | H | H | H | Br | H |
| 415 | naphthyl-CH2- | H | H | H | H | H | Br |
| 416 | naphthyl-CH2- | H | H | COOH | H | H | H |
| 417 | naphthyl-CH2- | H | H | H | COOH | H | H |
| 418 | naphthyl-CH2- | H | H | H | H | COOH | H |
| 419 | naphthyl-CH2- | H | H | H | H | H | COOH |

TABLE 8-continued

X = —CS—, q = 0, r = 0, Y = —(R4)C═C(R5)—

| Compound No. 8- R1—(CH2)p— | R2 | R3 | R4 | R5 | R6 | R7 |
|---|---|---|---|---|---|---|
| 420 (naphthalen-1-ylmethyl) | H | H | NHCOMe | H | H | H |
| 421 (naphthalen-1-ylmethyl) | H | H | H | NHCOMe | H | H |
| 422 (naphthalen-1-ylmethyl) | H | H | H | H | NHCOMe | H |
| 423 (naphthalen-1-ylmethyl) | H | H | H | H | H | NHCOMe |
| 424 (naphthalen-1-ylmethyl) | H | H | SO2NH2 | H | H | H |
| 425 (naphthalen-1-ylmethyl) | H | H | H | SO2NH2 | H | H |
| 426 (naphthalen-1-ylmethyl) | H | H | H | H | SO2NH2 | H |
| 427 (naphthalen-1-ylmethyl) | H | H | H | H | H | SO2NH2 |

TABLE 8-continued
X = —CS—, q = 0, r = 0, Y = —(R4)C=C(R5)—
| Compound No. 8- | R1—(CH2)p— | R2 | R3 | R4 | R5 | R6 | R7 |
|---|---|---|---|---|---|---|---|
| 428 | 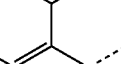 | H | H | Me | Me | H | H |
| 429 | 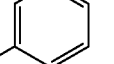 | H | H | Me | H | Me | H |
| 430 | 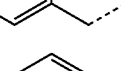 | H | H | H | Me | Me | H |
| 431 |  | H | H | F | F | H | H |
| 432 | 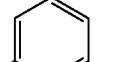 | H | H | F | H | F | H |
| 433 | 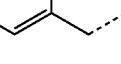 | H | H | H | F | F | H |
| 434 | 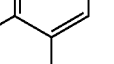 | H | H | Cl | Cl | H | H |
| 435 | 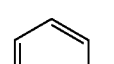 | H | H | Cl | H | Cl | H |
| 436 | 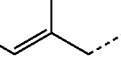 | H | H | H | Cl | Cl | H |

TABLE 8-continued

X = —CS—, q = 0, r = 0, Y = —(R4)C=C(R5)—

| Compound No. 8- R1—(CH2)p— | R2 | R3 | R4 | R5 | R6 | R7 |
|---|---|---|---|---|---|---|
| 437 naphthalen-1-ylmethyl | H | H | Me | F | H | H |
| 438 naphthalen-1-ylmethyl | H | H | Me | Cl | H | H |
| 439 naphthalen-1-ylmethyl | H | H | Me | OH | H | H |
| 440 naphthalen-1-ylmethyl | H | H | Me | OMe | H | H |
| 441 naphthalen-1-ylmethyl | H | H | F | Me | H | H |
| 442 naphthalen-1-ylmethyl | H | H | F | Cl | H | H |
| 443 naphthalen-1-ylmethyl | H | H | F | OH | H | H |
| 444 naphthalen-1-ylmethyl | H | H | F | OMe | H | H |

TABLE 8-continued

X = —CS—, q = 0, r = 0, Y = —(R4)C=C(R5)—

| Compound No. 8- | R1—(CH2)p— | R2 | R3 | R4 | R5 | R6 | R7 |
|---|---|---|---|---|---|---|---|
| 445 | 1-naphthylmethyl | H | H | Cl | Me | H | H |
| 446 | 1-naphthylmethyl | H | H | Cl | F | H | H |
| 447 | 1-naphthylmethyl | H | H | Cl | OH | H | H |
| 448 | 1-naphthylmethyl | H | H | Cl | OMe | H | H |
| 449 | 4-Br-2-OH-benzyl | H | H | Cl | H | H | H |
| 450 | 4-Br-2-OH-benzyl | H | H | H | OMe | H | H |
| 451 | 4-Br-2-OH-benzyl | H | H | H | COOMe | H | H |
| 452 | 4-Br-2-OH-benzyl | H | H | H | H | Cl | H |
| 453 | 4-Br-2-OH-benzyl | H | H | H | H | COOMe | H |
| 454 | 4-Br-2-OH-benzyl | H | H | H | H | H | Cl |
| 455 | 4-Br-2-OH-benzyl | H | H | H | OCF3 | H | H |

TABLE 8-continued
X = —CS—, q = 0, r = 0, Y = —(R4)C=C(R5)—
| Compound No. 8- | R1—(CH2)p— | R2 | R3 | R4 | R5 | R6 | R7 |
|---|---|---|---|---|---|---|---|
| 456 | 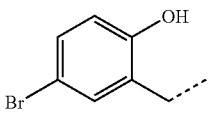 | H | H | COOMe | H | H | H |
| 457 | 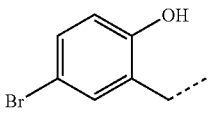 | H | H | H | CF3 | H | H |
| 458 | 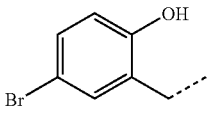 | H | H | H | Me | H | H |
| 459 | 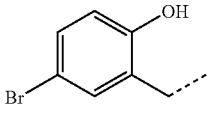 | H | H | H | F | H | H |
| 460 | 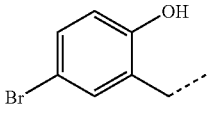 | H | H | H | OH | H | H |
| 461 | 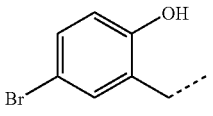 | H | H | H | NO2 | H | H |
| 462 | 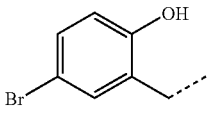 | H | H | H | F | F | H |
| 463 | 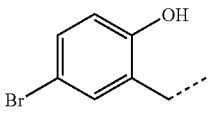 | H | H | F | H | H | H |
| 464 | 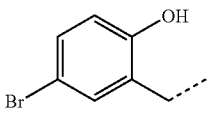 | H | H | Me | H | H | H |
| 465 | 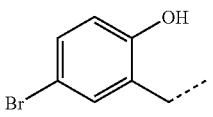 | H | H | H | OH | H | H |
| 466 | 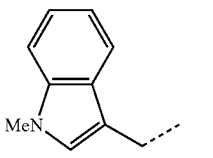 | H | H | Cl | H | H | H |

TABLE 8-continued

X = —CS—, q = 0, r = 0, Y = —(R4)C=C(R5)—

| Compound No. 8- | R1—(CH2)p— | R2 | R3 | R4 | R5 | R6 | R7 |
|---|---|---|---|---|---|---|---|
| 467 | 1-Me-indol-3-yl-CH2 | H | H | H | OMe | H | H |
| 468 | 1-Me-indol-3-yl-CH2 | H | H | H | COOMe | H | H |
| 469 | 1-Me-indol-3-yl-CH2 | H | H | H | H | Cl | H |
| 470 | 1-Me-indol-3-yl-CH2 | H | H | H | H | COOMe | H |
| 471 | 1-Me-indol-3-yl-CH2 | H | H | H | H | H | Cl |
| 472 | 1-Me-indol-3-yl-CH2 | H | H | H | OCF3 | H | H |
| 473 | 1-Me-indol-3-yl-CH2 | H | H | COOMe | H | H | H |
| 474 | 1-Me-indol-3-yl-CH2 | H | H | H | CF3 | H | H |
| 475 | 1-Me-indol-3-yl-CH2 | H | H | H | Me | H | H |

TABLE 8-continued
| | X = —CS—, q = 0, r = 0, Y = —(R4)C=C(R5)— | | | | | | |
|---|---|---|---|---|---|---|---|
| Compound No. 8- | R1—(CH2)p— | R2 | R3 | R4 | R5 | R6 | R7 |
| 476 | 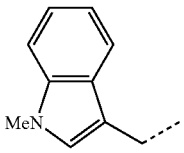 | H | H | H | F | H | H |
| 477 | 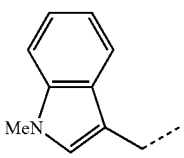 | H | H | H | OH | H | H |
| 478 | 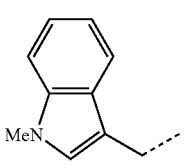 | H | H | H | NO2 | H | H |
| 479 | 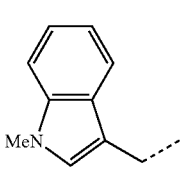 | H | H | H | F | F | H |
| 480 | 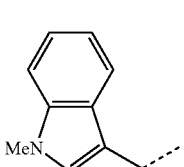 | H | H | F | H | H | H |
| 481 | 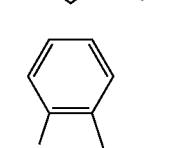 | H | H | Me | H | H | H |
| 482 | 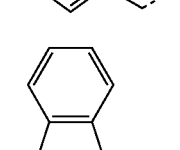 | H | H | H | CN | H | H |
| 483 | 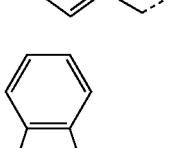 | H | H | Cl | H | H | H |
| 484 | 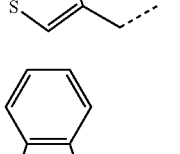 | H | H | H | OMe | H | H |

TABLE 8-continued
X = —CS—, q = 0, r = 0, Y = —(R4)C=C(R5)—
| Compound No. 8- R1—(CH2)p— | | R2 | R3 | R4 | R5 | R6 | R7 |
|---|---|---|---|---|---|---|---|
| 485 | 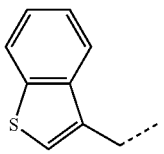 | H | H | H | COOMe | H | H |
| 486 | 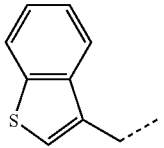 | H | H | H | H | Cl | H |
| 487 | 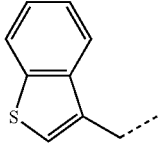 | H | H | H | H | COOMe | H |
| 488 | 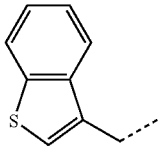 | H | H | H | H | H | Cl |
| 489 | 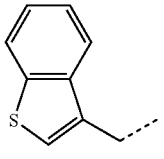 | H | H | H | OCF3 | H | H |
| 490 | 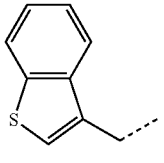 | H | H | COOMe | H | H | H |
| 491 | 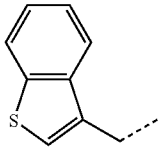 | H | H | H | CF3 | H | H |
| 492 | 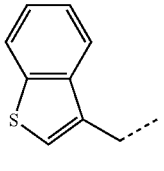 | H | H | H | Me | H | H |
| 493 | 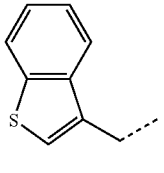 | H | H | H | F | H | H |

TABLE 8-continued
X = —CS—, q = 0, r = 0, Y = —(R4)C═C(R5)—
| Compound No. 8- | R1—(CH2)p— | R2 | R3 | R4 | R5 | R6 | R7 |
|---|---|---|---|---|---|---|---|
| 494 | 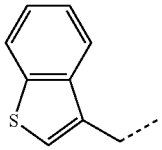 | H | H | H | OH | H | H |
| 495 | 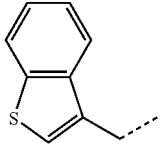 | H | H | H | NO2 | H | H |
| 496 | 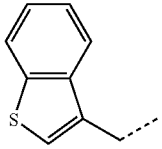 | H | H | H | F | F | H |
| 497 | 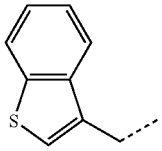 | H | H | F | H | H | H |
| 498 | 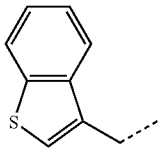 | H | H | Me | H | H | H |
| 499 | 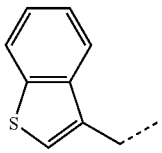 | H | H | H | CN | H | H |
| 500 | 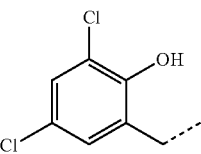 | H | Me | H | H | H | H |
| 501 | 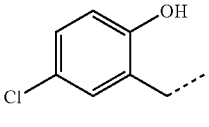 | H | Me | H | H | H | H |
| 502 | 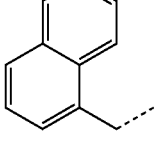 | H | Me | H | H | H | H |
| 503 | 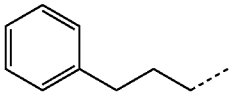 | H | Me | H | H | H | H |

TABLE 8-continued

X = —CS—, q = 0, r = 0, Y = —(R4)C=C(R5)—

| Compound No. 8- R1—(CH2)p— | R2 | R3 | R4 | R5 | R6 | R7 |
|---|---|---|---|---|---|---|
| 504  4-Cl-2-F-6-OH-benzyl | H | H | H | H | H | H |
| 505  4-Cl-2-F-6-OH-benzyl | H | H | F | H | H | H |
| 506  4-Cl-2-F-6-OH-benzyl | H | H | Cl | H | H | H |
| 507  4-Cl-2-F-6-OH-benzyl | H | H | Me | H | H | H |
| 508  4-Cl-2-F-6-OH-benzyl | H | H | Et | H | H | H |
| 509  4-Cl-2-F-6-OH-benzyl | H | H | OMe | H | H | H |
| 510  4-Cl-2-F-6-OH-benzyl | H | H | OEt | H | H | H |
| 511  4-Cl-2-F-6-OH-benzyl | H | H | CF3 | H | H | H |
| 512  4-Cl-2-F-6-OH-benzyl | H | H | OCF3 | H | H | H |

TABLE 8-continued
X = —CS—, q = 0, r = 0, Y = —(R4)C=C(R5)—
| Compound No. 8- R1—(CH2)p— | | R2 | R3 | R4 | R5 | R6 | R7 |
|---|---|---|---|---|---|---|---|
| 513 | 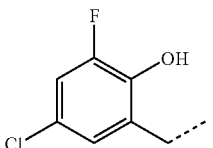 | H | H | NO2 | H | H | H |
| 514 | 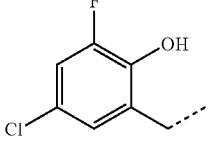 | H | H | NH2 | H | H | H |
| 515 | 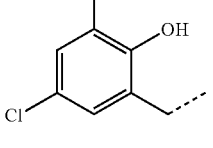 | H | H | OH | H | H | H |
| 516 | 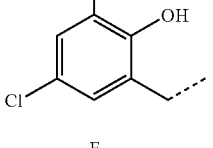 | H | H | CN | H | H | H |
| 517 | 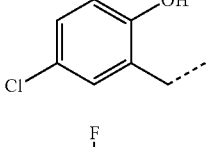 | H | H | COMe | H | H | H |
| 518 | 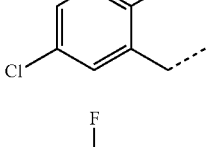 | H | H | COOMe | H | H | H |
| 519 | 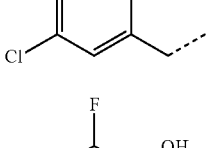 | H | H | H | F | H | H |
| 520 | 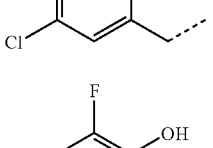 | H | H | H | Cl | H | H |
| 521 | 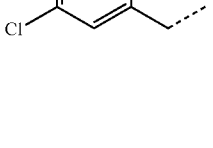 | H | H | H | Me | H | H |

TABLE 8-continued

X = —CS—, q = 0, r = 0, Y = —(R4)C═C(R5)—

| Compound No. 8- R1—(CH2)p— | R2 | R3 | R4 | R5 | R6 | R7 |
|---|---|---|---|---|---|---|
| 522 4-Cl-2-F-6-OH-benzyl | H | H | H | Et | H | H |
| 523 4-Cl-2-F-6-OH-benzyl | H | H | H | OMe | H | H |
| 524 4-Cl-2-F-6-OH-benzyl | H | H | H | OEt | H | H |
| 525 4-Cl-2-F-6-OH-benzyl | H | H | H | CF3 | H | H |
| 526 4-Cl-2-F-6-OH-benzyl | H | H | H | OCF3 | H | H |
| 527 4-Cl-2-F-6-OH-benzyl | H | H | H | NO2 | H | H |
| 528 4-Cl-2-F-6-OH-benzyl | H | H | H | NH2 | H | H |
| 529 4-Cl-2-F-6-OH-benzyl | H | H | H | OH | H | H |
| 530 4-Cl-2-F-6-OH-benzyl | H | H | H | CN | H | H |

TABLE 8-continued

X = —CS—, q = 0, r = 0, Y = —(R4)C=C(R5)—

| Compound No. 8- R1—(CH2)p— | R2 | R3 | R4 | R5 | R6 | R7 |
|---|---|---|---|---|---|---|
| 531 4-Cl-2-F-6-OH-benzyl | H | H | H | COMe | H | H |
| 532 4-Cl-2-F-6-OH-benzyl | H | H | H | COOMe | H | H |
| 533 4-Cl-2-F-6-OH-benzyl | H | H | F | F | H | H |
| 534 4-Cl-2-F-6-OH-benzyl | H | H | F | Cl | H | H |
| 535 4-Cl-2-F-6-OH-benzyl | H | H | F | Me | H | H |
| 536 4-Cl-2-F-6-OH-benzyl | H | H | F | Et | H | H |
| 537 4-Cl-2-F-6-OH-benzyl | H | H | F | OMe | H | H |
| 538 4-Cl-2-F-6-OH-benzyl | H | H | F | OEt | H | H |
| 539 4-Cl-2-F-6-OH-benzyl | H | H | F | CF3 | H | H |

TABLE 8-continued
X = —CS—, q = 0, r = 0, Y = —(R4)C=C(R5)—
| Compound No. 8- R1—(CH2)p— | | R2 | R3 | R4 | R5 | R6 | R7 |
|---|---|---|---|---|---|---|---|
| 540 | 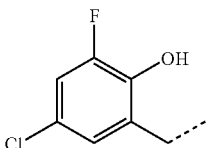 | H | H | F | OCF3 | H | H |
| 541 | 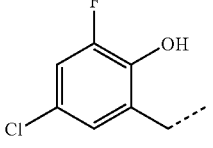 | H | H | Cl | F | H | H |
| 542 | 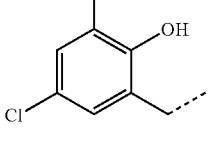 | H | H | Cl | Cl | H | H |
| 543 | 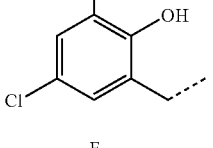 | H | H | Cl | Me | H | H |
| 544 | 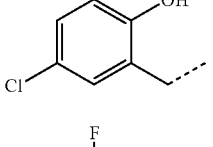 | H | H | Cl | Et | H | H |
| 545 | 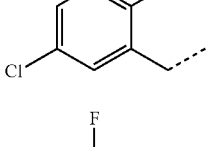 | H | H | Cl | OMe | H | H |
| 546 | 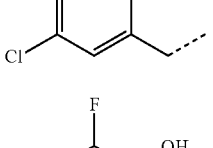 | H | H | Cl | OEt | H | H |
| 547 | 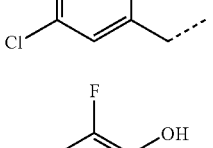 | H | H | Cl | CF3 | H | H |
| 548 | 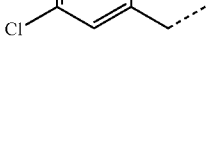 | H | H | Cl | OCF3 | H | H |

TABLE 8-continued

| | X = —CS—, q = 0, r = 0, Y = —(R4)C=C(R5)— | | | | | | |
|---|---|---|---|---|---|---|---|
| Compound No. 8- | R1—(CH2)p— | R2 | R3 | R4 | R5 | R6 | R7 |
| 549 | 4-Cl, 2-F, 3-OH-benzyl (F, OH, Cl substituted) | H | H | Me | F | H | H |
| 550 | 4-Cl, 2-F, 3-OH-benzyl | H | H | Me | Cl | H | H |
| 551 | 4-Cl, 2-F, 3-OH-benzyl | H | H | Me | Me | H | H |
| 552 | 4-Cl, 2-F, 3-OH-benzyl | H | H | Me | Et | H | H |
| 553 | 4-Cl, 2-F, 3-OH-benzyl | H | H | Me | OMe | H | H |
| 554 | 4-Cl, 2-F, 3-OH-benzyl | H | H | Me | OEt | H | H |
| 555 | 4-Cl, 2-F, 3-OH-benzyl | H | H | Me | CF3 | H | H |
| 556 | 4-Cl, 2-F, 3-OH-benzyl | H | H | Me | OCF3 | H | H |
| 557 | 4-Cl, 2-F, 3-OH-benzyl | H | H | OMe | F | H | H |

TABLE 8-continued

X = —CS—, q = 0, r = 0, Y = —(R4)C=C(R5)—

| Compound No. 8- R1—(CH2)p— | R2 | R3 | R4 | R5 | R6 | R7 |
|---|---|---|---|---|---|---|
| 558 (2-OH, 3-F, 5-Cl benzyl) | H | H | OMe | Cl | H | H |
| 559 (2-OH, 3-F, 5-Cl benzyl) | H | H | OMe | Me | H | H |
| 560 (2-OH, 3-F, 5-Cl benzyl) | H | H | OMe | Et | H | H |
| 561 (2-OH, 3-F, 5-Cl benzyl) | H | H | OMe | OMe | H | H |
| 562 (2-OH, 3-F, 5-Cl benzyl) | H | H | OMe | OEt | H | H |
| 563 (2-OH, 3-F, 5-Cl benzyl) | H | H | OMe | CF3 | H | H |
| 564 (2-OH, 3-F, 5-Cl benzyl) | H | H | OMe | OCF3 | H | H |

The present invention also encompasses pharmaceutically acceptable acid adducts of the aforementioned piperidine compounds. As examples of suitable acids there may be mentioned inorganic acids such as hydrochloric acid, hydrobromic acid, sulfuric acid, phosphoric acid and carbonic acid, or organic acids such as maleic acid, citric acid, malic acid, tartaric acid, fumaric acid, methanesulfonic acid, trifluoroacetic acid and formic acid.

The invention further encompasses $C_1$-$C_6$ alkyl adducts of cyclic amine compounds such as, for example, 1-(4-chlorobenzyl)-1-methyl-4-[{2-benzimidazolyl}aminomethyl]piperidinium iodide. As preferred examples of alkyl groups for $C_1$-$C_6$ alkyl adducts there may be mentioned methyl, ethyl, n-propyl, n-butyl, n-pentyl, n-hexyl, n-heptyl, n-octyl, isopropyl, isobutyl, sec-butyl, tert-butyl, isopentyl, neopentyl, tert-pentyl, 2-methylpentyl and 1-ethylbutyl, among which methyl and ethyl are especially preferred. As preferred examples of counter anions to the ammonium cation there may be mentioned halide anions such as fluoride, chloride, bromide and iodide.

The compounds represented by formula (I) of the invention may contain optically active carbons, and therefore include racemic forms and all possible optically active forms.

When $R^3$ of the compound represented by formula (I) is hydrogen, the structure represented by formula (I) will be indistinguishable from the structure represented by formula (II) below, and formulas (I) and (II) will represent the same compound. When $R^3$ is hydrogen, therefore, the invention includes both the structures of formula (I) and formula (II).

(where $R^1$ and p have the same respective definitions as in formula (I))

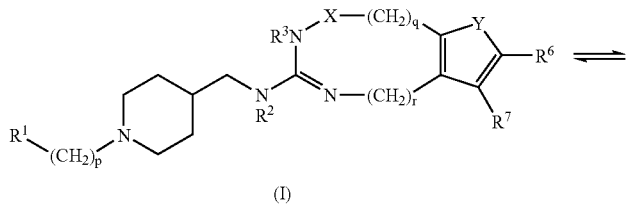

(I)

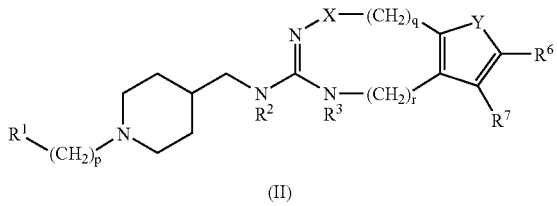

(II)

The compounds represented by formula (I) may be produced by any of the general production processes described below.

<Production Process 1>

One equivalent of a compound represented by the following formula (III):

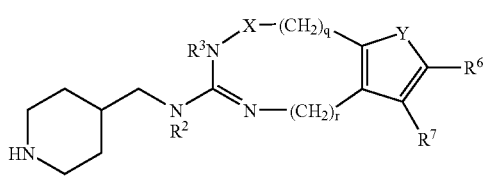

(III)

(wherein $R^2$, $R^3$, X, q, r, Y, $R^6$ and $R^7$ have the same definitions as in formula (I))

is treated with 0.1-10 equivalents of an alkylating reagent represented by the following formula (IV):

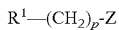

$R^1$—$(CH_2)_p$-Z     (IV)

(wherein $R^1$ and p have the same definitions as in formula (I), and Z represents a halogen, alkylsulfonyloxy or arylsulfonyloxy)

in the presence or in the absence of a solvent, to produce a compound represented by formula (I).

The reaction of Production Process 1 may be smoothly carried out using a base containing an inorganic salt such as potassium carbonate, calcium carbonate or sodium hydrogen carbonate, an amine such as triethylamine, diisopropylethylamine or pyridine, or a polymer supporting base such as (piperidinomethyl)polystyrene, (morpholinomethyl)polystyrene, (diethylaminomethyl)polystyrene or poly(4-vinylpyridine).

The reaction of Production Process 1 will sometimes be accelerated by addition of an iodide such as potassium iodide or sodium iodide.

The compounds of formula (III) may be synthesized by known processes described in the relevant literature.

<Production Process 2>

One equivalent of an aldehyde represented by the following formula (V):

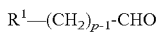

$R^1$—$(CH_2)_{p-1}$-CHO     (V)

is treated with 0.1-10 equivalents of a compound represented by formula (III), in the presence or in the absence of a solvent, to produce a compound represented by formula (I).

The reaction of Production Process 2 is generally referred to as reductive amination, and the reaction may be conducted under conditions with a catalyst containing a metal such as palladium, platinum, nickel or rhodium, a hydride complex such as aluminum lithium hydride, sodium borohydride, sodium cyanoborohydride or sodium triacetoxyborohydride, catalytic hydrogenation with borane, or electrolytic reduction.

<Production Process 3>

One equivalent of a compound represented by the following formula (VI):

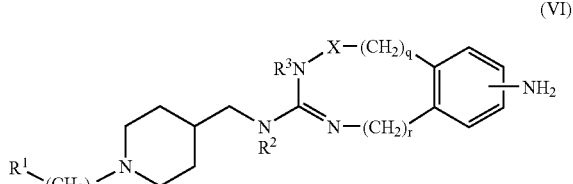

(VI)

(wherein $R^1$, p, $R^2$, $R^3$, X, q and r have the same definitions as in formula (I))

is treated with 0.1-10 equivalents of a carboxylic acid or its reactive derivative, in the presence or in the absence of a solvent, to produce a compound represented by formula (I).

Reactive derivatives of carboxylic acids include highly reactive carboxylic acid derivatives ordinarily used in organic synthetic chemistry, such as, for example, acid halides, acid anhydrides or mixed anhydrides.

The reaction of Production Process 3 may be smoothly carried out using an appropriate amount of a dehydrating agent such as molecular sieve and a condensation agent such as dicyclohexylcarbodiimide (DCC), N-ethyl-N'-(3-dimethylaminopropyl)carbodiimide (EDCI or WSC), carbodiimidazole (CDI), N-hydroxysuccinimide (HOSu), N-hydroxybenzotriazole (HOBT), benzotriazol-1-yloxytris (pyrrolidino)phosphonium, hexafluorophosphate (PyBOP), 2-(1H-benzotriazol-1-yl)-1,1,3,3-tetramethyluronium hexafluorophosphate (HBTU), 2-(1H-benzotriazol-1-yl)-1, 1,3,3-tetramethyluronium tetrafluoroborate (TBTU), 2-(5-norbornane-2,3-dicarboxyimide)-1,1,3,3-tetramethyluronium tetrafluoroborate (TNTU), O—(N-succinimidyl)-1,1,3, 3-tetramethyluronium tetrafluoroborate (TSTU) or bromotris (pyrrolidino)phosphonium hexafluorophosphate (PyBrop).

The reaction of Production Process 3 may be smoothly carried out using a base indicated for Production Process 1.

The compounds of formula (VI) may be synthesized by known processes described in the relevant literature.

<Production Process 4>

One equivalent of a compound represented by the following formula (VII):

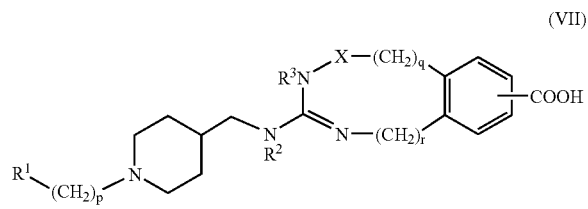

(VII)

(wherein $R^1$, p, $R^2$, $R^3$, X, q and r have the same definitions as in formula (I))

is treated with 0.1-10 equivalents of an amine, in the presence or in the absence of a solvent, to produce a compound represented by formula (I).

The reaction of Production Process 4 can proceed smoothly by using appropriate amounts of the same dehydrating agents, condensation agents or bases used in Production Process 3.

The compounds of formula (VII) may be synthesized by known processes described in the relevant literature.

<Production Process 5>

One equivalent of a compound represented by the following formula (VIII):

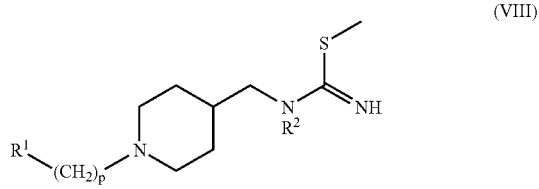

(VIII)

(wherein $R^1$, $R^2$ and p have the same definitions as in formula (I))

is treated with 0.1-10 equivalents of an acid anhydride represented by the following formula (IX):

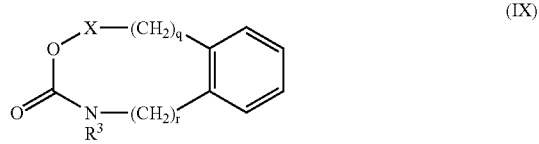

(IX)

(wherein $R^3$, q and r have the same definitions as in formula (I), and X represents CO)

in the presence or in the absence of a solvent, to produce a compound represented by formula (I).

The reaction of Production Process 5 may be smoothly carried out using a base indicated for Production Process 1.

The compounds of formula (VIII) and (IX) may be synthesized by known processes described in the relevant literature.

<Production Process 6>

One equivalent of a compound represented by the following formula (X):

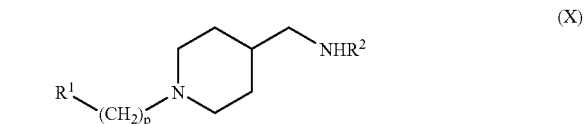

(X)

(wherein $R^1$, $R^2$ and p have the same definitions as in formula (I))

is treated with 0.1-10 equivalents of a sulfanyl or sulfinyl compound represented by the following formula (XI):

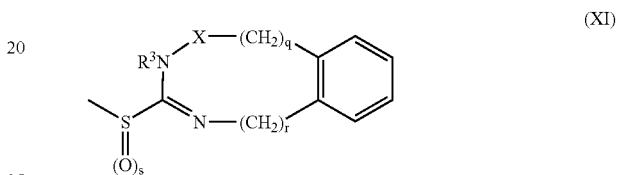

(XI)

(wherein $R^3$, X, q and r have the same definitions as in formula (I), and s represents 0 or 1), in the presence or in the absence of a solvent, to produce a compound represented by formula (I).

The reaction of Production Process 6 may be smoothly carried out using a base indicated for Production Process 1, or a suitable acid (hydrochloric acid, sulfuric acid, acetic acid, benzoic acid, toluenesulfonic acid, methanesulfonic acid or the like).

The compounds of formula (X) and (XI) may be synthesized by known processes described in the relevant literature.

When the compounds of each of Production Processes 1-6 contain functional groups which react with the substrates used under the respective reaction conditions or functional groups which generally can adversely affect reactions in organic synthetic chemistry, such functional groups may be protected with appropriate known protective groups, and then subjected to the reaction of the production processes and subsequently deprotected using known steps, to obtain the compounds of formula (I).

The compounds of the invention may also be produced by utilizing known reactions ordinarily employed in organic synthetic chemistry, such as alkylation, acylation or reduction, for further conversion of (one or more of) the substituents of the compounds produced by Production Processes 1-6.

In each of Production Processes 1-6, the reaction may be conducted using a halogenated carbon compound such as dichloromethane or chloroform, an aromatic hydrocarbon such as benzene or toluene, an ether such as diethyl ether or tetrahydrofuran, an ester such as ethyl acetate, an aprotic polar solvent such as dimethylformamide, dimethylsulfoxide or acetonitrile, or an alcohol such as methanol, ethanol or isopropyl alcohol.

In each of Production Processes 1-6 the reaction temperature is in the range of −78° C. and +150° C., and preferably between 0° C. and 100° C. Upon completion of the reaction, ordinary separation and purification procedures such as concentration, filtration, extraction, solid phase extraction, recrystallization or chromatography may be employed to isolate the piperidine derivatives represented by formula (I). These may then be converted to pharmaceutically acceptable acid adducts or $C_1$-$C_6$ alkyl adducts by ordinary methods.

The compounds represented by formula (I), their pharmaceutically acceptable acid adducts or their pharmaceutically acceptable $C_1$-$C_6$ alkyl adducts may be used in therapeutically effective doses together with pharmaceutically acceptable carriers and/or diluents for preparation of pharmaceutical compositions, as drugs for inhibiting binding of CCR3 ligands such as eotaxins to CCR3 on target cells, as drugs with activity of inhibiting the physiological effects of binding of CCR3 ligands such as eotaxins to their target cells, and as therapeutic and/or prophylactic agents for diseases believed to be associated with CCR3. Specifically, the 4,4-piperidine derivatives represented by formula (I), their pharmaceutically acceptable acid adducts or their pharmaceutically acceptable $C_1$-$C_6$ alkyl adducts may be administered orally or parenterally, such as intravenously, subcutaneously, intramuscularly, percutaneously or intrarectally.

The dosage form for oral administration may be, for example, tablets, pills, granules, powder, a solution, a suspension, capsules or the like.

Tablets may be molded by an ordinary method using, for example, an excipient such as lactose, starch or microcrystalline cellulose, a binder such as carboxymethyl cellulose, methyl cellulose or polyvinylpyrrolidone and a disintegrator such as sodium alginate, sodium hydrogen carbonate or lauryl sodium sulfate.

Pills, powders or granules may also be molded by ordinary methods using the aforementioned excipients and the like. Solutions and suspensions may be formed by ordinary methods using, for example, glycerin esters such as tricaprylin or triacetin and/or alcohols such as ethanol. Capsules may be prepared by filling capsules made of gelatin or the like with granules, powders and/or solutions.

Dosage forms for subcutaneous, intramuscular or intravenous administration include injections in the form of aqueous or non-aqueous solutions. Aqueous solutions may employ, for example, physiological saline. Non-aqueous solutions may employ, for example, propylene glycol, polyethylene glycol, olive oil or ethyl oleate, with addition of antiseptic agents and/or stabilizers or the like as necessary. Injections are sterilized by appropriate filtration through a bacteria-capturing filter or treatment with addition of a sterilizing agent.

As examples of dosage forms for percutaneous administration there may be mentioned ointments and creams, among which ointments may be formed using fats and oils such as castor oil or olive oil, or vaseline, and creams may be formed by ordinary methods using emulsifying agents such as fatty oils or diethylene glycol or sorbitan monofatty acid esters.

For intrarectal administration there may be used ordinary suppositories such as gelatin soft capsules.

The dosage of a piperidine derivative of the invention, its pharmaceutically acceptable acid adduct or its pharmaceutically acceptable $C_1$-$C_6$ alkyl adduct will differ depending on the type of disease, the route of administration, the age and gender of the patient and the severity of the disease, but it will normally be 1-500 mg/day per adult.

EXAMPLES

The present invention will now be explained in greater detail through the following examples. The invention, however, is not limited to these examples. The compound numbers referred to in the examples are those assigned to the compounds listed as preferred examples in the tables. The example numbers correspond to the compound numbers of the compounds produced in those examples.

Reference Example 1-1-1

Synthesis of C-[1-(3,4-dichloro-benzyl)-piperidin-4-yl]-methylamine

After dissolving 4-aminomethyl-piperidine (10 g) in acetonitrile (250 ml), 3,4-dichlorobenzyl chloride (5.8 g) and potassium carbonate (5 g) were added at room temperature, and the mixture was stirred at 60° C. overnight. The reaction mixture was filtered, the solvent was removed under reduced pressure, and the obtained residue was purified by thin-layer silica gel chromatography (dichloromethane/methanol/triethylamine=85/7/7) to obtain C-[1-(3,4-dichloro-benzyl)-piperidin-4-yl]-methylamine. The compound was identified by LC-MS.

Yield: 6 g (75%), Purity: 100%, Found: ESI/MS m/e 273.2.

Reference Example 1-1-2

Synthesis of 1-(2-amino-phenyl-3-[1-(3,4-dichloro-benzyl)-piperidin-4-ylmethyl]-thiourea After dissolving C-[1-(3,4-dichloro-benzyl)-piperidin-4-yl]-methylamine (80 mg) in acetonitrile (2 ml), thiocarbonyldiimidazole (80 mg) and imidazole (6 mg) were added at 0° C. The mixture was stirred at room temperature for 2 hours and 30 minutes, and then 3-nitro-1,2-phenylenediamine (66 mg) was added and the temperature was raised to 50° C. prior to stirring for 12 hours. The reaction mixture was filtered, the solvent was removed under reduced pressure, and the obtained residue was purified by thin-layer silica gel chromatography (hexane/ethyl acetate/dichloromethane/methanol=60/25/10/5) to obtain 1-(2-amino-phenyl-3-[1-(3,4-dichloro-benzyl)-piperidin-4-ylmethyl]-thiourea. The compound was identified by LC-MS.

Yield: 75 mg (61%), Purity: 100%, Found: ESI/MS m/e 423.1.

Example 1-1-1

Synthesis of (1H-benzoimidazol-2-yl)-[1-(3,4-dichloro-benzyl)-piperidin-4-ylmethyl]-amine After adding ethanol (1 ml) to 1-(2-amino-phenyl-3-[1-(3,4-dichloro-benzyl)-piperidin-4-ylmethyl]-thiourea (11 mg, 0.025 mmol), mercury (II) oxide red (16 mg, 0.074 mmol) and sulfur (0.3 mg, 0.0094 mmol) were added at room temperature, and the mixture was refluxed for 7 hours. The mercury was filtered with celite, and the solvent was removed under reduced pressure. The residue was purified by silica gel column chromatography (hexane/dichloromethane/methanol/triethylamine=40/25/20/10/5) to obtain (1H-benzoimidazol-2-yl)-[1-(3,4-dichloro-benzyl)-piperidin-4-ylmethyl]-amine. The compound was identified by LC-MS.

Yield: 8 mg (83%), Purity: 100%, Found: ESI/MS m/e 389.1.

Example 1-1-2 to Example 1-1-11

Compound Nos. 1-1-2 to 1-1-11 were synthesized in the same manner as Reference Example 1-1-1, Reference Example 1-1-2 and Example 1-1-1, using the corresponding starting materials. The results are shown in Table 9.

TABLE 9

| Compound No. 1-1- | Yield (mg) | Yield (%) | MW | M + 1 |
|---|---|---|---|---|
| 1 | 8 | 83 | 389.3 | 389.1 |
| 2 | 30 | 68 | 434.3 | 434.2 |
| 3 | 13 | 32 | 403.4 | 403.2 |
| 4 | 5 | 12 | 423.8 | 423.1 |
| 5 | 7 | 16 | 407.3 | 407.1 |
| 6 | 13 | 28 | 457.3 | 457.2 |
| 7 | 4 | 9 | 433.3 | 433.2 |
| 8 | 23 | 50 | 458.2 | 458.9 |
| 9 | 4 | 10 | 403.4 | 403.1 |
| 10 | 13 | 32 | 419.4 | 419.0 |
| 11 | 9 | 21 | 434.3 | 434.1 |

Reference Example 1-2-1

Synthesis of 4-aminomethyl-piperidine-1-carboxylic acid tert-butyl ester

After dissolving 4-aminomethylpiperidine (5.00 g, 43.8 mmol) in toluene (90 mL), benzaldehyde (4.45 mL, 43.8 mmol) was added, a Dean-Stark trap was fitted, and the mixture was heated to reflux for 2 hours. The reaction mixture was cooled to room temperature, di-t-butyl dicarbonate (11.5 mL, 43.8 mmol) was added in 5 divided portions, and the mixture was stirred at room temperature for 4 hours. After concentrating the reaction mixture under reduced pressure, an aqueous potassium hydrogen sulfate solution (1.0 M, 70 mL, 70 mmol) was added in an ice bath, and the mixture was vigorously stirred for 1 hour. It was then washed with diethyl ether (30 mL×2 times), and 2N aqueous sodium hydroxide was added to the aqueous layer to adjust the pH to approximately 7. The aqueous solution was adjusted to a pH of approximately 7 and then washed with ethyl acetate (30 mL×3 times), and 2N sodium hydroxide was added to the aqueous layer to adjust the pH to approximately 12. The aqueous solution was then adjusted to a pH of approximately 12 and extracted with ethyl acetate (50 mL×4 times), after which the obtained organic layer was dried over anhydrous magnesium sulfate. It was then concentrated under reduced pressure to obtain 4-aminomethyl-piperidine-1-carboxylic acid tert-butyl ester.

Yield: 6.49 g (70%).

Reference Example 1-2-2

Synthesis of 4-[(1H-benzimidazol-2-ylamino)-methyl]-piperidine-1-carboxylic acid tert-butyl ester After dissolving 4-aminomethyl-piperidine-1-carboxylic acid tert-butyl ester (3.18 g, 14.8 mmol) in acetonitrile (20 mL), a suspension of thiocarbonyldiimidazole (3.17 g, 17.8 mmol) and imidazole (302 mg, 4.45 mmol) in acetonitrile (30 mL) was added dropwise thereto in an ice bath. The temperature was raised to room temperature, the mixture was stirred for 90 minutes, o-phenylenediamine (1.93 g, 17.8 mmol) was added thereto, and the mixture was stirred at 50° C. for 2 hours. Diisopropylcarbodiimide (3.4 mL, 22.2 mmol) was further added, and the mixture was stirred at 80° C. for 3 hours. The mixture was cooled, concentrated under reduced pressure, and then dissolved in ethyl acetate (200 mL) and washed with water (100 mL×2 times) and brine (100 mL). It was then dried over anhydrous magnesium sulfate and concentrated under reduced pressure. The concentrated residue was purified by silica gel column chromatography (dichloromethane/methanol=19/1 dichloromethane/methanol/triethylamine=10/1/1) to obtain 4-[(1H-benzimidazol-2-ylamino)-methyl]-piperidine-1-carboxylic acid tert-butyl ester.

Yield: 4.33 g (89%).

Reference Example 1-2-3

Synthesis of (1H-benzimidazol-2-yl)-piperidin-4-ylmethyl-amine

After dissolving 4-[(1H-benzimidazol-2-ylamino)-methyl]-piperidine-1-carboxylic acid tert-butyl ester (4.33 g, 13.1 mmol) in methanol (10 mL), a 4N hydrogen chloride-1,4-dioxane solution (33 mL, 131 mmol) was added in small portions at a time in an ice bath, and the mixture was stirred at room temperature for 3 hours. The reaction mixture was cooled on ice, 2N aqueous sodium hydroxide was added to adjust the pH to approximately 11. Salt was added to the aqueous solution to saturation, and the organic layer obtained by extraction with 1-butanol (100 mL×3 times) was washed with saturated brine and then dried over anhydrous sodium sulfate. The dried 1-butanol was concentrated under reduced pressure to obtain (1H-benzimidazol-2-yl)-piperidin-4-ylmethyl-amine.

Yield: 3.0 g (100%).

Example 1-2-1

Synthesis of (1H-benzimidazol-2-yl)-[1-(1-methyl-1H-indol-2-ylmethyl)-piperidin-4-ylmethyl]-amine After adding 1-methyl-1H-indole-2-carboaldehyde (0.26 mmol) and sodium triacetoxyborohydride (0.26 mmol) to a solution of (1H-benzimidazol-2-yl)-piperidin-4-ylmethyl-amine (20.0 mg, 0.09 mmol) in dimethylformamide-acetic acid (10:1) (1.0 ml), the mixture was stirred at room temperature overnight. Methanol (1.0 ml) was added to the reaction mixture to suspend the reaction, and after stirring for 1 hour, the solution was passed through SCX (Bond Elute SCX500MG: cationic ion-exchange resin, Varian). The SCX was washed with methanol and then with a mixed solution of chloroform/methanol (1/1), and elution was performed with a 2N ammonia-methanol solution. The solvent was distilled off under reduced pressure to obtain (1H-benzimidazol-2-yl)-[1-(1-methyl-1H-indol-2-ylmethyl)-piperidin-4-ylmethyl]-amine. The compound was identified by LC-MS.

Yield: 18 mg (54%), Purity: 86%, Found: ESI/MS m/e 374.2 (M+1).

Example 1-2-2 to Example 1-2-169

Compound Nos. 1-2-2 to 1-2-169 were synthesized in the same manner as Example 1-2-1, using the corresponding starting materials. The results are shown in Table 10.

Reference Example 1-2-4

Synthesis of 4-phenylbutylaldehyde

After adding molecular sieves MS4A (desiccant, trade name of Wako Pure Chemical Industries) (451.5 mg) to a solution of pyridinium dichromate (451.5 mg, 1.20 mmol) in dichloromethane (3.33 ml), the mixture was stirred for 1 hour.

Next, 4-phenylbutanol (154 μl, 1.00 mmol) was added to the suspension and the mixture was stirred at room temperature for 1.5 hours. The reaction suspension was filtered with silica gel, and the filtrate was concentrated under reduced pressure to obtain 4-phenylbutylaldehyde.

Yield: 38.45 mg (26%).

Example 1-2-170

Synthesis of (1H-benzimidazol-2-yl)-[1-(4-phenyl-butyl)-piperidin-4-ylmethyl]-amine After adding acetic acid (28.6 μl) and sodium triacetoxyborohydride (52.99 mg, 0.25 mmol) to a mixed solution of (1H-benzimidazol-2-yl)-piperidin-4-ylmethyl-amine (30.32 mg, 0.10 mmol) and a mixed solution of the obtained 4-phenylbutylaldehyde (38.45 mg) in dichloroethane (1.0 ml) and dimethylformamide (0.5 ml), the mixture was stirred at room temperature overnight. The reaction suspension was passed through SCX (Bond Elute SCX500MG), and the SCX was washed with a mixed solution of chloroform-methanol (1:1). This was followed by elution with a 2N ammonia-methanol solution, and the solvent was then distilled off under reduced pressure to obtain a residue. The residue was purified by preparative HPLC to obtain (1H-benzimidazol-2-yl)-[1-(4-phenyl-butyl)-piperidin-4-ylmethyl]-amine. The compound was identified by LC-MS.

Yield: 19.44 mg (54%), Purity: 89.8%, Found: ESI/MS m/e 363.2 (M+1).

Example 1-2-171

Compound No. 1-2-171 was synthesized in the same manner as Example 1-2-170, using an aldehyde starting material synthesized according to Reference Example 1-2-4. The results are shown in Table 10.

Example 1-2-172

Synthesis of (1H-benzimidazol-2-yl)-[1-(6-methoxy-1-methyl-1H-indol-3-ylmethyl)-piperidin-4-ylmethyl]-amine After adding anhydrous acetonitrile (2 ml) to a mixture of (1H-benzimidazol-2-yl)-piperidin-4-ylmethyl-amine (20 mg, 0.09 mmol), (6-methoxy-1-methyl-1H-indol-3-ylmethyl)-trimethylammonium iodide (0.1 mmol) and anhydrous potassium carbonate (5 mg, 0.11 mmol), the mixture was stirred at 50° C. for 12 hours. The mixture was cooled to room temperature and then passed through a silica gel short column and purified by preparative HPLC to obtain (1H-benzimidazol-2-yl)-[1-(6-methoxy-1-methyl-1H-indol-3-ylmethyl)-piperidin-4-ylmethyl]-amine. The compound was identified by LC-MS.

Yield: 5.66 mg (13%), Purity: 96.3%, Found: ESI/MS m/e 404.4 (M+1).

Example 1-2-173 to Example 1-2-180

Compound Nos. 1-2-173 to 1-2-180 were synthesized according to Example 1-2-172, from the corresponding halides or quaternary ammonium halides. The results are shown in Table 10.

TABLE 10

| Compound No. 1-2- | Yield (mg) | Yield (%) | MW | M + 1 |
|---|---|---|---|---|
| 1 | 18 | 54 | 373.5 | 374.2 |
| 2 | 29 | 54 | 370.5 | 371.2 |
| 3 | 11 | 41 | 320.4 | 321.2 |
| 4 | 23 | 76 | 354.9 | 355.2 |
| 5 | 9 | 29 | 334.5 | 335.2 |
| 6 | 28 | 82 | 388.4 | 389.2 |
| 7 | 23 | 74 | 362.5 | 363.2 |
| 8 | 21 | 71 | 345.4 | 346.2 |
| 9 | 33 | 96 | 398.5 | 399.2 |
| 10 | 16 | 48 | 378.5 | 379.2 |
| 11 | 21 | 68 | 350.5 | 351.2 |
| 12 | 16 | 82 | 326.5 | 327.2 |
| 13 | 8 | 40 | 334.5 | 335.2 |
| 14 | 19 | 91 | 348.5 | 349.3 |
| 15 | 25 | 78 | 359.5 | 360.2 |
| 16 | 18 | 54 | 373.5 | 374.2 |
| 17 | 12 | 42 | 310.4 | 311.2 |
| 18 | 21 | 70 | 326.5 | 327.1 |
| 19 | 22 | 62 | 390.6 | 391.2 |
| 20 | 14 | 48 | 321.4 | 322.2 |
| 21 | 15 | 53 | 321.4 | 322.2 |
| 22 | 15 | 46 | 371.5 | 372.2 |
| 23 | 14 | 41 | 371.5 | 372.2 |
| 24 | 17 | 57 | 327.5 | 328.1 |
| 25 | 21 | 75 | 310.4 | 311.2 |
| 26 | 22 | 79 | 310.4 | 311.2 |
| 27 | 24 | 65 | 414.6 | 415.2 |
| 28 | 6 | 17 | 413.6 | 414.2 |
| 29 | 23 | 69 | 374.5 | 375.2 |
| 30 | 20 | 70 | 334.5 | 335.6 |
| 31 | 15 | 50 | 345.4 | 346.5 |
| 32 | 22 | 63 | 396.5 | 397.2 |
| 33 | 21 | 68 | 350.5 | 351.2 |
| 34 | 18 | 58 | 354.9 | 355.3 |
| 35 | 15 | 43 | 389.3 | 389.4 |
| 36 | 21 | 68 | 354.9 | 355.3 |
| 37 | 16 | 51 | 365.4 | 366.3 |
| 38 | 15 | 45 | 388.4 | 389.4 |
| 39 | 15 | 43 | 399.3 | 399.1 |
| 40 | 16 | 54 | 334.5 | 335.4 |
| 41 | 15 | 53 | 336.4 | 337.2 |
| 42 | 22 | 74 | 336.4 | 337.2 |
| 43 | 13 | 41 | 363.5 | 364.2 |
| 44 | 18 | 54 | 377.5 | 378.2 |
| 45 | 21 | 68 | 364.5 | 365.2 |
| 46 | 11 | 33 | 378.5 | 379.2 |
| 47 | 15 | 46 | 378.5 | 379.2 |
| 48 | 17 | 45 | 426.6 | 427.2 |
| 49 | 23 | 63 | 426.6 | 427.2 |
| 50 | 22 | 69 | 370.5 | 371.4 |
| 51 | 21 | 66 | 364.5 | 365.3 |
| 52 | 18 | 57 | 360.5 | 361.2 |
| 53 | 21 | 57 | 420.9 | 421.5 |
| 54 | 21 | 55 | 396.5 | 397.4 |
| 55 | 7 | 20 | 388.5 | 389.3 |
| 56 | 10 | 41 | 403.5 | 404.2 |
| 57 | 3 | 13 | 387.5 | 388.2 |
| 58 | 22 | 100 | 338.4 | 339.2 |
| 59 | 22 | 67 | 321.4 | 322.2 |
| 60 | 19 | 56 | 338.4 | 339.1 |
| 61 | 24 | 68 | 350.5 | 351.2 |
| 62 | 23 | 100 | 378.5 | 379.2 |
| 63 | 30 | 100 | 412.5 | 413.2 |
| 64 | 17 | 70 | 404.4 | 405.1 |
| 65 | 28 | 100 | 389.3 | 389.1 |
| 66 | 14 | 57 | 406.4 | 407.1 |
| 67 | 30 | 83 | 364.5 | 365.1 |
| 68 | 20 | 43 | 456.4 | 457.1 |
| 69 | 28 | 78 | 352.4 | 353.2 |
| 70 | 29 | 69 | 412.5 | 413.2 |
| 71 | 33 | 78 | 426.6 | 427.2 |
| 72 | 34 | 86 | 399.3 | 400.1 |
| 73 | 28 | 82 | 345.4 | 346.2 |
| 74 | 24 | 54 | 442.6 | 443.2 |
| 75 | 25 | 68 | 365.4 | 366.2 |
| 76 | 35 | 81 | 426.6 | 427.2 |

TABLE 10-continued

| Compound No. 1-2- | Yield (mg) | Yield (%) | MW | M + 1 |
|---|---|---|---|---|
| 77 | 26 | 57 | 447.0 | 447.2 |
| 78 | 28 | 72 | 380.5 | 381.2 |
| 79 | 22 | 58 | 380.5 | 381.2 |
| 80 | 17 | 78 | 362.5 | 363.2 |
| 81 | 20 | 90 | 370.9 | 371.1 |
| 82 | 20 | 90 | 372.9 | 373.1 |
| 83 | 19 | 69 | 456.6 | 457.2 |
| 84 | 8 | 32 | 417.3 | 417.1 |
| 85 | 12 | 47 | 429.4 | 429.2 |
| 86 | 17 | 69 | 408.5 | 409.3 |
| 87 | 18 | 79 | 381.4 | 382.2 |
| 88 | 20 | 87 | 381.4 | 382.2 |
| 89 | 11 | 46 | 399.9 | 400.1 |
| 90 | 20 | 88 | 378.5 | 379.2 |
| 91 | 16 | 73 | 364.4 | 365.2 |
| 92 | 15 | 58 | 430.5 | 431.3 |
| 93 | 16 | 67 | 400.5 | 401.3 |
| 94 | 20 | 81 | 413.6 | 414.3 |
| 95 | 12 | 50 | 400.5 | 401.3 |
| 96 | 13 | 52 | 414.6 | 415.3 |
| 97 | 19 | 78 | 408.5 | 409.3 |
| 98 | 22 | 62 | 350.5 | 351.5 |
| 99 | 10 | 27 | 380.4 | 381.2 |
| 100 | 29 | 80 | 366.5 | 367.1 |
| 101 | 3 | 6 | 456.6 | 457.3 |
| 102 | 13 | 37 | 352.4 | 353.2 |
| 103 | 15 | 40 | 366.5 | 367.2 |
| 104 | 15 | 56 | 449.4 | 450.2 |
| 105 | 15 | 61 | 410.5 | 411.3 |
| 106 | 16 | 69 | 389.3 | 389.2 |
| 107 | 11 | 51 | 356.4 | 357.2 |
| 108 | 10 | 39 | 422.9 | 423.2 |
| 109 | 10 | 41 | 406.4 | 407.2 |
| 110 | 2 | 8 | 392.5 | 393.7 |
| 111 | 4 | 15 | 395.5 | 396.3 |
| 112 | 6 | 27 | 359.5 | 360.3 |
| 113 | 16 | 47 | 376.5 | 377.3 |
| 114 | 19 | 50 | 420.6 | 421.4 |
| 115 | 4 | 11 | 420.6 | 421.4 |
| 116 | 14 | 40 | 401.5 | 402.4 |
| 117 | 17 | 54 | 370.9 | 371.2 |
| 118 | 14 | 39 | 415.3 | 417.1(Br) |
| 119 | 8 | 25 | 381.4 | 382.2 |
| 120 | 7 | 21 | 383.4 | 384.2 |
| 121 | 10 | 32 | 354.4 | 355.2 |
| 122 | 6 | 17 | 392.5 | 393.3 |
| 123 | 18 | 56 | 368.5 | 369.2 |
| 124 | 22 | 61 | 417.3 | 419.1(Br) |
| 125 | 26 | 69 | 429.4 | 429.2 |
| 126 | 21 | 67 | 366.5 | 367.3 |
| 127 | 27 | 85 | 443.4 | 445.2(Br) |
| 128 | 23 | 66 | 399.9 | 400.2 |
| 129 | 31 | 91 | 394.5 | 395.3 |
| 130 | 20 | 61 | 370.4 | 371.2 |
| 131 | 30 | 91 | 372.9 | 373.2 |
| 132 | 22 | 60 | 422.6 | 423.2 |
| 133 | 22 | 70 | 364.5 | 365.2 |
| 134 | 22 | 72 | 352.5 | 353.2 |
| 135 | 19 | 57 | 399.9 | 400.1 |
| 136 | 24 | 74 | 378.5 | 379.2 |
| 137 | 3 | 91 | 420.4 | 421.3 |
| 138 | 11 | 35 | 348.5 | 349.3 |
| 139 | 10 | 28 | 424.5 | 425.3 |
| 140 | 8 | 25 | 380.5 | 381.2 |
| 141 | 20 | 51 | 455.6 | 456.3 |
| 142 | 13 | 37 | 404.6 | 405.3 |
| 143 | 13 | 38 | 389.3 | 389.1 |
| 144 | 17 | 43 | 450.5 | 451.3 |
| 145 | 20 | 58 | 400.5 | 401.3 |
| 146 | 24 | 63 | 437.6 | 438.3 |
| 147 | 21 | 61 | 390.6 | 391.2 |
| 148 | 5 | 17 | 336.4 | 337.1 |
| 149 | 11 | 33 | 364.4 | 365.1 |
| 150 | 7 | 19 | 405.3 | 405.1 |
| 151 | 2 | 6 | 386.5 | 387.1 |
| 152 | 5 | 14 | 386.5 | 387.1 |
| 153 | 1 | 4 | 428.5 | 429.2 |
| 154 | 8 | 8 | 369.9 | 370.1 |
| 155 | 6 | 20 | 365.4 | 366.1 |
| 156 | 5 | 16 | 365.4 | 366.1 |
| 157 | 6 | 20 | 338.4 | 366.1 |
| 158 | 10 | 12 | 335.5 | 336.1 |
| 159 | 11 | 29 | 420.5 | 421.1 |
| 160 | 9 | 23 | 462.3 | 463.1 |
| 161 | 17 | 53 | 364.4 | 365.1 |
| 162 | 10 | 26 | 449.8 | 451.0(Br) |
| 163 | 23 | 23 | 371.5 | 372.1 |
| 164 | 17 | 17 | 386.4 | 387.1 |
| 165 | 7 | 20 | 384.9 | 385.1 |
| 166 | 5 | 10 | 588.2 | 589.0 |
| 167 | 14 | 38 | 438.9 | 439.2 |
| 168 | 9 | 23 | 438.9 | 439.1 |
| 169 | 15 | 46 | 370.9 | 371.1 |
| 170 | 19 | 54 | 362.5 | 363.2 |
| 171 | 31 | 82 | 376.5 | 377.3 |
| 172 | 6 | 13 | 403.5 | 404.4 |
| 173 | 3 | 8 | 387.5 | 388.3 |
| 174 | 6 | 18 | 387.5 | 388.2 |
| 175 | 23 | 70 | 384.5 | 385.2 |
| 176 | 9 | 27 | 384.5 | 385.2 |
| 177 | 8 | 22 | 401.6 | 402.3 |
| 178 | 5 | 13 | 387.5 | 388.2 |
| 179 | 7 | 20 | 387.5 | 388.4 |
| 180 | 2 | 5 | 449.6 | 450.5 |

Reference Example 1-3-1

Synthesis of 4-[(4-nitro-1H-benzimidazol-2-ylamino)-methyl]-piperidine-1-carboxylic acid tert-butyl ester After dissolving 4-aminomethyl-piperidine-1-carboxylic acid tert-butyl ester (2 g) in acetonitrile (100 ml), thiocarbonyldiimidazole (2 g) and imidazole (0.2 g) were added at 0° C. The mixture was stirred at room temperature for 2 hours and 30 minutes, 3-nitro-1,2-phenylenediamine (2.1 g) was added, the temperature was raised to 50° C., and the mixture was stirred for 12 hours. Diisopropylcarbodiimide (2.4 g) was added, the mixture was refluxed for 3 hours and 30 minutes, and then the solvent was removed under reduced pressure and the obtained residue was purified by silica gel chromatography (dichloromethane/hexane=7/3→1/0) to obtain 4-[(4-nitro-1H-benzimidazol-2-ylamino)-methyl]-piperidine-1-carboxylic acid tert-butyl ester. The compound was identified by LC-MS.

Yield: 3.5 g (100%), Purity: 95%, Found: ESI/MS m/e 376.4 (M+1).

Reference Example 1-3-2

Synthesis of (4-nitro-1H-benzimidazol-2-yl)-piperidin-4-ylmethyl-amine

After dissolving 4-[(4-nitro-1H-benzimidazol-2-ylamino)-methyl]-piperidine-1-carboxylic acid tert-butyl ester (13 mg) in methanol (1 ml), a 4N hydrogen chloride-1,4-dioxane solution (1 ml) was added and the mixture was stirred at 60° C. for 1 hour. The solvent was distilled off under reduced pressure, aqueous sodium hydroxide and dichloromethane were added to the obtained residue, and extraction was performed with dichloromethane. The solvent was distilled off under reduced pressure to obtain (4-nitro-1H-benzimidazol-2-yl)-piperidin-4-ylmethyl-amine. The compound was identified by LC-MS.

Yield: 8 mg (83%), Purity: 100%, Found: ESI/MS m/e 276.1 (M+1).

Reference Example 1-3-3

Synthesis of (1-naphthalen-1-ylmethyl-piperidin-4-ylmethyl)-(4-nitro-1H-benzimidazol-2-yl)-amine After adding 1-naphthoaldehyde (3 mmol) and sodium triacetoxyborohydride (3 mmol) to a solution of (4-nitro-1H-benzimidazol-2-yl)-piperidin-4-ylmethyl-amine (450 mg, 1 mmol) in dimethylformamide-acetic acid (10:1) (7 mL), the mixture was stirred at room temperature overnight. Water and dichloromethane were added, and extraction was performed with dichloromethane. The solvent was removed under reduced pressure, and the residue was purified by silica gel column chromatography (ethyl acetate/triethylamine=100/0→98/2) to obtain (1-naphthalen-1-ylmethyl-piperidin-4-ylmethyl)-(4-nitro-1H-benzimidazol-2-yl)-amine. The compound was identified by LC-MS.

Yield: 500 mg (100%), Purity: 100%, Found: ESI/MS m/e 394.0 (M+1).

Reference Example 1-3-4

Synthesis of 4-amino-2-[(1-naphthalen-1-ylmethyl-piperidin-4-ylmethyl)-amino]-benzimidazole-1-carboxylic acid tert-butyl ester After dissolving (1-naphthalen-1-ylmethyl-piperidin-4-ylmethyl)-(4-nitro-1H-benzimidazol-2-yl)-amine (500 mg) in 1,4-dioxane (15 ml), di-t-butyl dicarbonate (1 g) was added and the mixture was stirred at 50° C. for 2 hours. The solvent was removed under reduced pressure, and the obtained residue was washed with hexane (5 ml×5 times). The residue was dissolved in tetrahydrofuran (10 ml), Raney nickel (500 mg) was added, and the mixture was stirred at room temperature overnight under a hydrogen stream. The reaction mixture was filtered with celite, and then the solvent was distilled off under reduced pressure to obtain 4-amino-2-[(1-naphthalen-1-ylmethyl-piperidin-4-ylmethyl)-amino]-benzimidazole-1-carboxylic acid tert-butyl ester.

The compound was identified by LC-MS.

Yield: 200 mg (39%), Purity: 100%, Found: ESI/MS m/e 464.3 (M+1).

Example 1-3-1

Synthesis of 3-acetylamino-N-{2-[(1-naphthalen-1-ylmethyl-piperidin-4-ylmethyl)-amino]-1H-benzimidazol-4-yl}-propionamide After dissolving 4-amino-2-[(1-naphthalen-1-ylmethyl-piperidin-4-ylmethyl)-amino]-benzimidazole-1-carboxylic acid tert-butyl ester (0.02 mmol) in tetrahydrofuran (1 ml), diisopropylcarbodiimide (0.05 mmol), 1-hydroxybenzotriazole monohydrate (0.05 mmol) and 3-acetylaminopropionic acid (0.05 mmol) were added and the mixture was stirred at room temperature overnight. After adding a 4N hydrogen chloride-1,4-dioxane solution (1 ml) to the reaction mixture, it was stirred at 50° C. for 1 hour, the solvent was removed under reduced pressure, and then dichloromethane and 5N aqueous sodium hydroxide were added to the obtained residue prior to stirring. The organic layer was passed through SCX (Bond Elute SCX500MG), and after washing the SCX with methanol, elution was performed with a 2N ammonia-methanol solution. The solvent was distilled off under reduced pressure to obtain 3-acetylamino-N-{2-[(1-naphthalen-1-ylmethyl-piperidin-4-ylmethyl)-amino]-1H-benzimidazol-4-yl}-propionamide. The compound was identified by LC-MS.

Yield: 0.4 mg (4%), Purity: 100%, Found: ESI/MS m/e 499.3 (M+1).

Example 1-3-2 to Example 1-3-8

Compound Nos. 1-3-2 to 1-3-8 were synthesized in the same manner as Reference Examples 1-3-1 to 1-3-4 and Example 1-3-1, using the corresponding starting materials. The results are shown in Table 11.

Example 1-3-9

Synthesis of N-(2-{[1-(3,4-dichlorobenzyl)-piperidin-4-ylmethyl]-amino}-1H-benzimidazol-4-yl)-butylamide After dissolving 4-amino-2-{[1-(3,4-dichlorobenzyl)-piperidin-4-ylmethyl]-amino}-benzimidazole-1-carboxylic acid tert-butyl ester (10 mg, 0.02 mmol) in tetrahydrofuran (1 ml), triethylamine (5.6 µl, 0.04 mmol) and butyryl chloride (8.3 µl, 0.08 mmol) were added and the mixture was stirred at room temperature for 1 hour and 30 minutes. After adding a 4N hydrogen chloride-1,4-dioxane solution (1 ml) to the reaction mixture, it was stirred at 50° C. for 2 hours. The solvent was removed under reduced pressure, dichloromethane and 5N aqueous sodium hydroxide were added to the obtained residue, and after stirring, the organic layer was passed through SCX (Bond Elute SCX500MG). The SCX was washed with methanol and elution was performed with a 2N ammonia-methanol solution. The solvent was distilled off under reduced pressure to obtain N-(2-{[1-(3,4-dichlorobenzyl)-piperidin-4-ylmethyl]-amino}-1H-benzimidazol-4-yl)-butylamide. The compound was identified by LC-MS.

Yield: 4.9 mg (52%), Purity: 100%, Found: ESI/MS m/e 474.0 (M+1).

The 4-amino-2-{[1-(3,4-dichlorobenzyl)-piperidin-4-ylmethyl]-amino}-benzimidazole-1-carboxylic acid tert-butyl ester starting material was synthesized in the same manner as Reference Examples 1-3-1 to 1-3-4, using the corresponding starting materials.

Example 1-3-10 to Example 1-3-56

Compound Nos. 1-3-10 to 1-3-56 were synthesized in the same manner as Example 1-3-9, using the corresponding starting materials. The results are shown in Table 11.

Example 1-3-57

Synthesis of propane-1-sulfonic acid (2-{[1-(3,4-dichloro-benzyl)-piperidin-4-ylmethyl]-amino}-1H-benzimidazol-4-yl)-amide After dissolving 4-amino-2-{[1-(3,4-dichloro-benzyl)-piperidin-4-ylmethyl]-amino}-benzimidazole-1-carboxylic acid tert-butyl ester (10 mg, 0.02 mmol) in tetrahydrofuran (1 ml), triethylamine (0.04 mmol) and propane-1-sulfonyl chloride (0.08 mmol) were added and the mixture was stirred at room temperature overnight. After adding a 4N hydrogen chloride-1,4-dioxane solution (1 ml) to the reaction mixture, it was stirred at 50° C. for 1 hour. The solvent was removed under reduced pressure, dichloromethane and 5N aqueous sodium hydroxide were added to the obtained residue, and after stirring, the organic layer was passed through SCX (Bond Elute SCX500MG). The SCX was washed with methanol and elution was performed with a 2N ammonia-methanol solution. The solvent was distilled off under reduced pressure to obtain propane-1-sulfonic acid (2-{[1-(3,4-dichloro-benzyl)-piperidin-4-ylmethyl]-amino}-1H-benzimidazol-4-yl)-amide. The compound was identified by LC-MS.

Yield: 0.8 mg (8%), Purity: 100%, Found: ESI/MS m/e 510.1 (M+1).

Example 1-3-58

Compound No. 1-3-58 was synthesized in the same manner as Example 1-3-57, using the corresponding starting materials. The results are shown in Table 11.

Example 1-3-59

Synthesis of 1-(2-{[1-(3,4-dichloro-benzyl)-piperidin-4-ylmethyl]-amino}-1H-benzimidazol-4-yl)-3-ethyl-urea After dissolving 4-amino-2-{[1-(3,4-dichloro-benzyl)-piperidin-4-ylmethyl]-amino}-benzimidazole-1-carboxylic acid tert-butyl ester (10 mg, 0.02 mmol) in acetonitrile (1 ml), ethyl isocyanate (0.08 mmol) was added and the mixture was stirred at room temperature overnight. After adding a 4N hydrogen chloride-1,4-dioxane solution (1 ml) to the reaction mixture, it was stirred at 50° C. for 1 hour and then the reaction mixture was passed through SCX (Bond Elute SCX500MG). The SCX was washed with methanol and elution was performed with a 2N ammonia-methanol solution. The solvent was distilled off under reduced pressure to obtain 1-(2-{[1-(3,4-dichloro-benzyl)-piperidin-4-ylmethyl]-amino}-1H-benzimidazol-4-yl)-3-ethyl-urea. The compound was identified by LC-MS.

Yield: 1.6 mg (17%), Purity: 96%, Found: ESI/MS m/e 475.1 (M+1).

Example 1-3-60

Compound No. 1-3-60 was synthesized in the same manner as Example 1-3-59, using the corresponding starting materials. The results are shown in Table 11.

Example 1-3-61

Synthesis of N2-[1-(3,4-dichlorobenzyl)-piperidin-4-ylmethyl]-1H-benzimidazole-2,4-diamine After dissolving 4-amino-2-{[1-(3,4-dichloro-benzyl)-piperidin-4-ylmethyl]-amino}-benzimidazole-1-carboxylic acid tert-butyl ester (10 mg, 0.02 mmol) in methanol (1 ml), a 4N hydrogen chloride-1,4-dioxane solution (1 ml) was added and the mixture was stirred at 50° C. for 1 hour. The reaction mixture was passed through SCX (Bond Elute SCX500MG), the SCX was washed with methanol, and then elution was performed with a 2N ammonia-methanol solution. The solvent was distilled off under reduced pressure to obtain N2-[1-(3,4-dichlorobenzyl)-piperidin-4-ylmethyl]-1H-benzimidazole-2,4-diamine. The compound was identified by LC-MS.

Yield: 6.5 mg (80%), Purity: 100%, Found: ESI/MS m/e 404.1 (M+1).

Example 1-3-62

Compound No. 1-3-62 was synthesized in the same manner as Example 1-3-61, using the corresponding starting materials. The results are shown in Table 11.

TABLE 11

| Compound No. 1-3- | Yield (mg) | Yield (%) | MW | M + 1 |
| --- | --- | --- | --- | --- |
| 1 | 0.4 | 4 | 498.6 | 499.3 |
| 2 | 2 | 24 | 490.4 | 489.9 |
| 3 | 4 | 39 | 462.6 | 463.3 |
| 4 | 5 | 50 | 476.6 | 477.1 |
| 5 | 1 | 12 | 484.6 | 485.4 |
| 6 | 2 | 23 | 499.0 | 499.1 |
| 7 | 3 | 29 | 490.4 | 490.1 |
| 8 | 3 | 30 | 475.4 | 475.1 |
| 9 | 5 | 52 | 474.4 | 474.0 |
| 10 | 4 | 16 | 488.5 | 488.4 |
| 11 | 4 | 12 | 565.5 | 565.4 |
| 12 | 4 | 14 | 557.5 | 557.5 |
| 13 | 24 | 92 | 520.5 | 520.4 |
| 14 | 1 | 3 | 551.5 | 551.5 |
| 15 | 39 | 100 | 514.5 | 514.4 |
| 16 | 2 | 8 | 499.4 | 499.4 |
| 17 | 28 | 100 | 509.4 | 509.5 |
| 18 | 30 | 100 | 506.5 | 506.4 |
| 19 | 3 | 11 | 488.5 | 488.4 |
| 20 | 1 | 4 | 546.5 | 546.4 |
| 21 | 30 | 100 | 509.4 | 509.5 |
| 22 | 31 | 100 | 509.4 | 509.5 |
| 23 | 29 | 100 | 552.5 | 552.4 |
| 24 | 1 | 4 | 553.4 | 553.4 |
| 25 | 14 | 53 | 528.5 | 528.4 |
| 26 | 17 | 67 | 514.5 | 514.4 |
| 27 | 2 | 8 | 498.4 | 498.4 |
| 28 | 19 | 73 | 514.5 | 514.4 |
| 29 | 15 | 57 | 528.5 | 528.4 |
| 30 | 17 | 68 | 500.5 | 500.5 |
| 31 | 4 | 15 | 486.4 | 486.4 |
| 32 | 21 | 89 | 472.4 | 472.4 |
| 33 | 20 | 86 | 460.4 | 460.4 |
| 34 | 40 | 100 | 458.4 | 458.4 |
| 35 | 16 | 66 | 476.4 | 476.3 |
| 36 | 19 | 69 | 552.5 | 538.4 |
| 37 | 19 | 80 | 474.4 | 474.2 |
| 38 | 19 | 76 | 488.5 | 488.3 |
| 39 | 19 | 71 | 522.5 | 522.5 |
| 40 | 1 | 4 | 538.5 | 538.4 |
| 41 | 3 | 11 | 542.9 | 542.4 |
| 42 | 17 | 65 | 508.5 | 508.4 |
| 43 | 5 | 22 | 446.4 | 446.1 |
| 44 | 7 | 68 | 518.4 | 518.0 |
| 45 | 8 | 76 | 522.5 | 522.0 |
| 46 | 9 | 88 | 536.5 | 536.3 |
| 47 | 2 | 6 | 504.4 | 504.0 |
| 48 | 2 | 7 | 503.4 | 503.3 |
| 49 | 3 | 10 | 476.4 | 476.0 |
| 50 | 2 | 6 | 475.4 | 475.2 |
| 51 | 5 | 19 | 517.5 | 517.1 |
| 52 | 6 | 67 | 446.4 | 446.1 |
| 53 | 6 | 55 | 536.5 | 536.3 |
| 54 | 5 | 47 | 474.4 | 474.0 |
| 55 | 2 | 23 | 522.5 | 522.0 |
| 56 | 1 | 10 | 504.4 | 503.9 |
| 57 | 1 | 8 | 510.5 | 510.1 |
| 58 | 4 | 37 | 510.5 | 510.2 |
| 59 | 2 | 17 | 475.4 | 475.1 |

TABLE 11-continued

| Compound No. 1-3- | Yield (mg) | Yield (%) | MW | M + 1 |
|---|---|---|---|---|
| 60 | 2 | 17 | 475.4 | 475.0 |
| 61 | 7 | 80 | 404.3 | 404.1 |
| 62 | 9 | 72 | 404.3 | 404.1 |

Reference Example 1-4-1

Synthesis of 3-nitrophthalic acid 4-nitroisobenzofuran-1,3-dione (20.0 g, 0.104 mol) was added in small portions at a time to an aqueous ammonia solution (28%, 28 ml) heated to 50° C. After stirring for 30 minutes, the reaction mixture was cooled on ice, and the precipitate was filtered out and dried to obtain an ammonium salt. The salt was suspended in water (40 ml), and then concentrated hydrochloric acid was added dropwise to adjust the pH to approximately 2. The precipitated solid was filtered and dried to obtain 3-nitrophthalic acid. The compound was identified by NMR.

Yield: 12.3 g (56%).
$^1$H-NMR (270 MHz, CD$_3$OD): δ8.28(1H, dd, J=7.6, 1.2 Hz), 8.25 (1H, dd, J=7.8, 1.2 Hz), 7.72(1H, dd, J=7.8, 7.6 Hz) ppm.

Reference Example 1-4-2

Synthesis of 2-amino-3-nitrobenzoic acid

Potassium hydroxide (4.27 g, 76.2 mmol) was dissolved in water (22 ml), and bromine (0.463 ml, 9.50 mmol) was added dropwise while cooling on ice. After adding 3-nitrophthalic acid (2.00 g, 9.52 mmol) to thorough dissolution, the mixture was stirred at 60° C. for 3 hours, and stirring was continued overnight at room temperature. The reaction mixture was cooled on ice, and an orange precipitate was filtered out. It was then dissolved in 20 ml of water, and concentrated hydrochloric acid was added dropwise to adjust the pH to 4. After cooling on ice, the yellow precipitate was filtered out and dried to obtain 2-amino-3-nitrobenzoic acid. The compound was identified by NMR.

Yield: 1.03 g (59%).
$^1$H-NMR (270 MHz, CD$_3$OD): δ8.33(1H, dd, J=8.4, 1.7 Hz), 8.27(1H, dd, J=7.6, 1.7 Hz), 6.67(1H, dd, J=8.7, 7.6 Hz) ppm.

Reference Example 1-4-3

Synthesis of 2-amino-3-nitrobenzoic acid methyl ester

After dissolving 2-amino-3-nitrobenzoic acid (1.00 g, 5.49 mmol) in methanol (40 ml), sulfuric acid (0.50 ml) was added and the mixture was heated to reflux for 2 days. The reaction mixture was cooled to room temperature, and then the pH was adjusted to approximately 9 with saturated aqueous sodium bicarbonate and the mixture was concentrated under reduced pressure to approximately 10 ml. Water (20 ml) was added, the mixture was extracted with ethyl acetate (10 ml×3 times), and the obtained organic layer was dried over anhydrous magnesium sulfate. It was then concentrated under reduced pressure, and the produced crystals were dried to obtain 2-amino-3-nitrobenzoic acid methyl ester. The compound was identified by NMR.

Yield: 661.4 mg (61%).
$^1$H-NMR (270 MHz, CDCl$_3$): δ8.50(br), 8.37(1H, dd, J=8.6, 1.4 Hz), 8.23(1H, dd, J=7.6, 1.4 Hz), 6.65(1H, dd, J=8.6, 7.6 Hz), 3.92(3H, s) ppm.

Reference Example 1-4-4

Synthesis of 2,3-diaminobenzoic acid methyl ester

After dissolving 2-amino-3-nitrobenzoic acid methyl ester (661 mg, 3.37 mmol) in methanol (30 ml), 10% palladium-carbon powder (5 mol %) was added under a nitrogen stream, and the mixture was stirred for 1 hour under a hydrogen atmosphere. The reaction mixture was filtered through celite, and the obtained filtrate was concentrated under reduced pressure. The residue was purified by silica gel column chromatography (n-hexane/ethyl acetate=2/1) to obtain 2,3-diaminobenzoic acid methyl ester. The compound was identified by NMR.

Yield: 517.2 mg (92%).
$^1$H-NMR (270 MHz, CDCl$_3$): δ7.46(1H, dd, J=8.2 Hz, 1.5 Hz), 6.85(1H, dd, J=8.2 Hz, 1.5 Hz), 6.60(1H, t, J=8.2 Hz), 5.53(br), 3.87(3H, s), 3.35(br) ppm.

Reference Example 1-4-5

Synthesis of 2-[(1-tert-butoxycarbonyl-piperidin-4-ylmethyl)-amino]-1H-benzimidazole-4-carboxylic acid methyl ester After dissolving 4-aminomethyl-piperidine-1-carboxylic acid tert-butyl ester (3.29 g, 15.4 mmol) in acetonitrile (40 ml), the mixture was cooled in an ice bath. A solution of 1,1-thiocarbonyldiimidazole (3.28 g, 18.4 mmol) and imidazole (314 mg, 4.6 mmol) in acetonitrile (30 ml) was added dropwise thereto, and the mixture was stirred for 2 hours while raising the temperature to room temperature. After adding 2,3-diaminobenzoic acid methyl ester (3.07 g, 18.5 mmol) to the reaction mixture, it was stirred at 50° C. overnight. Diisopropylcarbodiimide (2.84 ml, 18.5 mmol) was then added and the mixture was stirred at 80° C. for 2 hours. The residue obtained by concentrating the reaction mixture under reduced pressure was purified by silica gel column chromatography (n-hexane/ethyl acetate=3/2→ethyl acetate/methanol/triethylamine=10/1/0.1) to obtain 2-[(1-tert-butoxycarbonyl-piperidin-4-ylmethyl)-amino]-1H-benzimidazole-4-carboxylic acid methyl ester. The compound was identified by LC-MS.

Yield: 5.47 g (91.4%), [M+1]=389.2.

Reference Example 1-4-6

Synthesis of 2-[(piperidin-4-ylmethyl)-amino]-1H-benzimidazole-4-carboxylic acid methyl ester After dissolving 2-[(1-tert-butoxycarbonyl-piperidin-4-ylmethyl)-amino]-1H-benzimidazole-4-carboxylic acid methyl ester (2.28 g, 5.87 mmol) in methanol (3 ml), a 4N hydrogen chloride-1,4-dioxane solution (10 ml, 40 mmol) was added and the mixture was stirred at room temperature overnight. The precipitated crystals were filtered out, washed with ethyl acetate and then dried to obtain 2-[(piperidin-4- ylmethyl)-amino]-1H-benzimidazole-4-carboxylic acid methyl ester. The compound was identified by LC-MS.

Yield: 1.19 g (56.1%), [M+1]=289.2.

Example 1-4-1

Synthesis of 2-{[1-(3,5-dichloro-2-hydroxy-benzyl)-piperidin-4-ylmethyl]-amino}-1H-benzimidazole-4-carboxylic acid methyl ester After dissolving 2-[(piperidin-4-ylmethyl)-amino]-1H-benzimidazole-4-carboxylic acid methyl ester (20 mg, 0.055 mmol) in dimethylsulfoxide-acetic acid (10:1), 2-hydroxy-3,5-dichlorobenzaldehyde (32.0 mg, 0.166 mmol) and sodium triacetoxyborohydride (35.0 mg, 0.166 mg) were added and the mixture was stirred at 50° C. for 2 days. Methanol (1 ml) was added to the reaction mixture, and then after stirring for 1 minute, it was purified by SCX solid phase extraction (Bond Elute SCX500MG). The product was further purified by preparative HPLC to obtain 2-{[1-(3,5-dichloro-2-hydroxy-benzyl)-piperidin-4-ylmethyl]-amino}-1H-benzimidazole-4-carboxylic acid methyl ester. The compound was identified by LC-MS.

Yield: 10.1 mg (39.3%), Purity: 94.0%, [M+1]=463.1

Example 1-4-2 to Example 1-4-9

Compound Nos. 1-4-2 to 1-4-9 were synthesized in the same manner as Example 1-4-1, using the corresponding starting materials. The results are shown in Table 12.

Reference Example 1-4-7

Synthesis of 2-[(1-tert-butoxycarbonyl-piperidin-4-ylmethyl)-amino]-1H-benzimidazole-4-carboxylic acid After dissolving 2-[(1-tert-butoxycarbonyl-piperidin-4-ylmethyl)-amino]-1H-benzimidazole-4-carboxylic acid methyl ester (5.47 g, 14.1 mmol) in methanol (60 ml), an aqueous lithium hydroxide solution (4 mol/L, 20 ml, 80 mmol) was added and the mixture was stirred at 50° C. overnight. The reaction mixture was cooled in an ice bath, and 6N hydrochloric acid (5 ml) was added dropwise. Stirring was continued for 1 hour in an ice bath while gradually adding 1N hydrochloric acid to adjust the pH to approximately 7.5. The precipitate was filtered out and washed with ethyl acetate and water. It was then dried under reduced pressure to obtain 2-[(1-tert-butoxycarbonyl-piperidin-4-ylmethlyl)-amino]-1H-benzimidazole-4-carboxylic acid. The compound was identified by LC-MS.

Yield: 3.68 g (69.7%), [M+1]=375.2.

Reference Example 1-4-8

Synthesis of 4-{[4-(2-methoxy-ethylcarbamoyl)-1H-benzimidazol-2-ylamino]-methyl}-piperidine-1-carboxylic acid tert-butyl ester After suspending 2-[(1-tert-butoxycarbonyl-piperidin-4-ylmethyl)-amino]-1H-benzimidazole-4-carboxylic acid (1.20 g, 3.20 mmol) in a mixed solvent of dimethylformamide and tetrahydrofuran (1:1, 20 ml), 1-hydroxybenzotriazole monohydrate (737 mg, 4.81 mmol) and 2-methoxyethylamine (0.42 ml, 4.8 mmol) were added. 1-Ethyl-3-(3-dimethylaminopropyl)carbodiimide hydrochloride (1.90 g, 6.40 mmol) was further added, and then the mixture was stirred at room temperature for 4 hours. Water (100 ml) was added to the reaction mixture, extraction was preferred with ethyl acetate (150 ml×3 times), and the organic layer was washed with saturated brine (100 ml) and then dried over anhydrous magnesium sulfate. The residue obtained by concentrating this under reduced pressure was purified by silica gel column chromatography (ethyl acetate/methanol=30/1) to obtain 4-{[4-(2-methoxy-ethylcarbamoyl)-1H-benzimidazol-2-ylamino)-methyl}-piperidine-1-carboxylic acid tert-butyl ester. The compound was identified by LC-MS.

Yield: 1.30 g (94.1%), Purity: [M+1]=432.2.

Reference Example 1-4-9

Synthesis of 2-[(piperidin-4-ylmethyl)-amino]-1H-benzimidazole-4-carboxylic acid (2-methoxy-ethyl)-amide After dissolving 4-{[4-(2-methoxy-ethylcarbamoyl)-1H-benzimidazol-2-ylamino]-methyl}-piperidine-1-carboxylic acid tert-butyl ester (1.30 g, 3.01 mmol) in methanol (1 ml), a 4N hydrogen chloride-1,4-dioxane solution (7.0 ml, 28.0 mmol) was added and the mixture was stirred at 50° C. for 1 hour. The reaction mixture was concentrated under reduced pressure and vacuum dried to obtain 2-[(piperidin-4-ylmethyl)-amino]-1H-benzimidazole-4-carboxylic acid (2-methoxy-ethyl)-amide. The compound was identified by LC-MS.

Yield: 1.23 g (100%), Purity: [M+1]=332.2.

Example 1-4-10

Synthesis of 2-{[1-(5-chloro-2-hydroxy-benzyl)-piperidin-4-ylmethyl]-amino}-1H-benzimidazole-4-carboxylic acid (2-methoxy-ethyl)-amide After dissolving 2-[(piperidin-4-ylmethyl)-amino]-1H-benzimidazole-4-carboxylic acid (2-methoxy-ethyl)-amide (20 mg, 0.049 mmol) in dimethylsulfoxide-acetic acid (10:1, 0.50 ml), 2-hydroxy-5-chlorobenzaldehyde (23 mg, 0.15 mmol) and sodium triacetoxyborohydride (31 mg, 0.15 mg) were added and the mixture was stirred at 50° C. for 2 days. Methanol (1 ml) was added to the reaction mixture, and after stirring for 1 minute, the mixture was purified by SCX solid phase extraction (Bond Elute SCX500MG). The product was further purified by preparative HPLC to obtain 2-{[1-(5-chloro-2-hydroxy-benzyl)-piperidin-4-ylmethyl]-amino}-1H-benzimidazole-4-carboxylic acid (2-methoxy-ethyl)-amide. The compound was identified by LC-MS.

Yield: 9.4 mg (40.6%), Purity: 94.0%, [M+1]=472.2.

Example 1-4-11 to Example 1-4-17

Compound Nos. 1-4-11 to 1-4-17 were synthesized in the same manner as Example 1-4-10, using the corresponding starting materials. The results are shown in Table 12.

Reference Example 1-4-10

Synthesis of 2-{[1-(3,5-dichloro-2-hydroxy-benzyl)-piperidin-4-ylmethyl]-amino}-1H-benzimidazole-4-carboxylic acid After suspending 2-{[1-(3,5-dichloro-2-hydroxy-benzyl)-piperidin-4-ylmethyl]-amino}-1H-benzimidazole-4-carboxylic acid methyl ester (993 mg, 2.14 mmol) in methanol (10 ml), an aqueous lithium hydroxide solution (4M, 5.4 ml, 21.4 mmol) was added. The reaction mixture was stirred at 50° C. for 2 hours and then cooled to room temperature. 1N hydrochloric acid was added dropwise to adjust the pH to approximately 6.0. Ethyl acetate (1 ml) was then added and the mixture was stirred for 3 hours, after which the precipitate was filtered out to obtain 2-{[1-(3,5-dichloro-2-hydroxy-benzyl)-piperidin-4-ylmethyl]-amino}-1H-benzimidazole-4-carboxylic acid. The compound was identified by LC-MS.

Yield: 802.6 mg (83.5%), [M+1]=449.1.

Example 1-4-18

Synthesis of 2-{[1-(3,5-dichloro-2-hydroxy-benzyl)-piperidin-4-ylmethyl]-amino}-1H-benzimidazole-4-carboxylic acid isopropylamide 2-{[1-(3,5-Dichloro-2-hydroxy-benzyl)-piperidin-4-ylmethyl]-amino}-1H-benzimidazole-4-carboxylic acid (30.0 mg, 0.0668 mmol) was suspended in dimethylformamide (0.50 ml). After adding 1-hydroxybenzotriazole monohydrate (30.6 mg, 0.200 mmol), isopropylamine (11.8 mg, 0.200 mmol) and diisopropylcarbodiimide (30.8 μl, 0.200 mmol) thereto, the mixture was stirred at 40° C. overnight. Methanol (2 ml) was added to the reaction mixture, and after stirring for 10 minutes, the reaction mixture was passed through SCX (Bond Elute SCX500MG) and the SCX was washed with methanol. After elution with a 2N ammonia-methanol solution, the solvent was distilled off under reduced pressure to obtain a residue. The residue was purified by preparative HPLC to obtain 2-{[1-(3,5-dichloro-2-hydroxy-benzyl)-piperidin-4-ylmethyl]-amino}-1H-benzimidazole-4-carboxylic acid isopropylamide. The compound was identified by LC-MS.

Yield: 25.6 mg (78.1%), Purity: 97.3%, [M+1]=490.1

Example 1-4-19 to Example 1-4-30

Compound Nos. 1-4-19 to 1-4-30 were synthesized in the same manner as Example 1-4-18, using the corresponding starting materials. The results are shown in Table 12.

TABLE 12

| Compound No. 1-4- | Yield (mg) | Yield (%) | MW | M + 1 |
|---|---|---|---|---|
| 1 | 10 | 39 | 463.4 | 463.1 |
| 2 | 19 | 80 | 428.9 | 429.1 |
| 3 | 28 | 100 | 473.4 | 473.1 |
| 4 | 18 | 74 | 439.5 | 440.1 |
| 5 | 26 | 100 | 428.5 | 429.2 |
| 6 | 28 | 100 | 431.5 | 432.2 |
| 7 | 28 | 100 | 434.6 | 435.1 |
| 8 | 24 | 98 | 406.5 | 407.2 |
| 9 | 294 | 44 | 447.4 | 447.1 |
| 10 | 9 | 41 | 472.0 | 472.2 |
| 11 | 11 | 42 | 516.4 | 518.1(Br) |
| 12 | 17 | 74 | 482.5 | 483.2 |
| 13 | 12 | 49 | 506.4 | 506.1 |
| 14 | 6 | 27 | 471.6 | 472.2 |
| 15 | 10 | 43 | 474.6 | 475.2 |
| 16 | 14 | 59 | 477.6 | 478.2 |
| 17 | 22 | 96 | 449.6 | 450.2 |
| 18 | 26 | 78 | 490.4 | 490.1 |
| 19 | 18 | 56 | 476.4 | 476.1 |
| 20 | 24 | 68 | 520.5 | 520.2 |
| 21 | 23 | 66 | 518.4 | 518.1 |
| 22 | 4 | 22 | 517.5 | 517.3 |
| 23 | 9 | 51 | 503.5 | 503.3 |
| 24 | 13 | 67 | 575.5 | 575.3 |
| 25 | 2 | 12 | 518.4 | 518.3 |
| 26 | 21 | 116 | 518.4 | 518.3 |
| 27 | 11 | 62 | 490.4 | 490.2 |
| 28 | 11 | 61 | 522.5 | 522.3 |
| 29 | 13 | 69 | 536.5 | 536.3 |
| 30 | 7 | 84 | 475.4 | 475.2 |

Reference Example 1-5-1

Synthesis of 3,4-diaminobenzoic acid ethyl ester 3,4-Diaminobenzoic acid (2.003 g, 13.17 mmol) and triphenylphosphine (4.248 g, 16.20 mmol) were suspended in toluene (20 ml) and tetrahydrofuran (10 ml). Ethanol (2 ml) was then added, diisopropyl azodicarboxylate (2.5 ml, 9.96 mmol) was added dropwise to the obtained light brown suspension, and the mixture was stirred at room temperature for 3.5 hours. Isopropyl azodicarboxylate (1.5 ml, 5.98 mmol) was further added dropwise, the mixture was stirred at room temperature for 1 hour, and the obtained reaction mixture was extracted with 1N hydrochloric acid (100 ml×2 times), after which the aqueous layer was washed with 50 ml of ethyl acetate. After adding 2N aqueous sodium hydroxide to the aqueous layer to raise the pH to 11 or higher, the precipitate was extracted with ethyl acetate (100 ml×2 times). The organic layer was washed with saturated brine (50 ml) and dried overnight over anhydrous sodium sulfate. The desiccant was filtered out and the filtrate was concentrated to obtain 3,4-diaminobenzoic acid ethyl ester as a faint yellow solid. The compound was identified by LC-MS.

Yield: 1.547 g (65%), Found: ESI/MS m/e 181.1(M+1).

The following compounds were also synthesized in the same manner as Reference Example 1-5-1, using the corresponding starting materials.

3,4-Diaminobenzoic acid isopropyl ester: Yield=1.302 g (49%)

3,4-Diaminobenzoic acid isobutyl ester: Yield=2.014 g (72%)

3,4-Diaminobenzoic acid benzyl ester: Yield=0.331 g (10%)

3,4-Diaminobenzoic acid cyclohexyl ester: Yield=0.245 g (8%)

Reference Example 1-5-2

Synthesis of 2-[(1-tert-butoxycarbonyl-piperidin-4-ylmethyl)-amino]-1H-benzimidazole-5-carboxylic acid ethyl ester 4-Aminomethyl-piperidine-1-carboxylic acid tert-butyl ester (0.394 g, 1.84 mmol) was dissolved in acetonitrile (3 ml). A solution of thiocarbonyldiimidazole (0.340 g, 1.91 mmol) and imidazole (0.052 g, 0.77 mmol) in acetonitrile (6 ml) was added dropwise over 3 minutes, at 0° C. The mixture was stirred at room temperature for 1 hour, 3,4-diaminobenzoic acid ethyl ester (0.371 g, 2.06 mmol) was added to the reaction mixture, and the mixture was stirred at 50° C. for 5.5 hours. Diisopropylcarbodiimide (0.32 ml) was further added, and the mixture was stirred overnight at 50° C. Saturated brine was then added to the obtained reaction mixture, extraction was performed with ethyl acetate (100 ml), and the organic layer was dried overnight over anhydrous sodium sulfate. After filtering out the desiccant and concentrating the filtrate, the obtained light brown oil was purified by silica gel column chromatography (dichloromethane/methanol=49/1 →19/1) to obtain 2-[(1-tert-butoxycarbonyl-piperidin-4-ylmethyl)-amino]-1H-benzimidazole-5-carboxylic acid ethyl ester as a yellow amorphous solid.

Yield: 0.838 g (%), Found: ESI/MS m/e 403.2(M+1).

Reference Example 1-5-3

Synthesis of 2-[(piperidin-4-ylmethyl)-amino]-1H-benzimidazole-5-carboxylic acid ethyl ester After dissolving the 2-[(1-tert-butoxycarbonyl-piperidin-4-ylmethyl)-amino]-1H-benzimidazole-5-carboxylic acid ethyl ester in tetrahydrofuran (2 ml), a 4N hydrogen chloride/1,4-dioxane solution (3 ml) was added. Since a precipitate was produced, ethanol (5 ml) was added to dissolve it and the solution was stirred at room temperature overnight. The reaction mixture was concentrated to obtain 2-[(piperidin-4-ylmethyl)-amino]-1H-benzimidazole-5-carboxylic acid ethyl ester as a red amorphous solid. The compound was identified by LC-MS.

Yield: 0.942 g (100%), Found: ESI/MS m/e 303.1(M+1).

Example 1-5-1

Synthesis of 2-{[1-(3,5-dichloro-2-hydroxybenzyl)-piperidin-4-ylmethyl]-amino}-1H-benzimidazole-5-carboxylic acid ethyl ester After adding 3,5-dichloro-2-hydroxybenzaldehyde (0.3 mmol) and sodium triacetoxyborohydride (0.3 mmol) to a solution of 2-[(piperidin-4-ylmethyl)-amino]-1H-benzimidazole-5-carboxylic acid ethyl ester (0.1 mmol) in dimethylformamide-acetic acid (10:1) (1.0 ml), the mixture was stirred at room temperature overnight. Methanol (1.0 ml) was added to the reaction mixture to suspend the reaction, and after stirring for 1 hour, the solution was passed through SCX (Bond Elute SCX500MG). The SCX was washed with methanol and then with a mixed solution of chloroform/methanol (1/1), and elution was performed with a 0.5N ammonia-dioxane solution. The solvent was distilled off under reduced pressure, and the obtained residue was subjected to preparative HPLC to obtain 2-{[1-(3,5-dichloro-2-hydroxybenzyl)-piperidin-4-ylmethyl]-amino}-1H-benzimidazole-5-carboxylic acid ethyl ester. The compound was identified by LC-MS.

Yield: 1.6 mg (3.4%), Purity: 98%, Found: ESI/MS m/e 477.1 (M+1).

Example 1-5-2 to Example 1-5-8

Compound Nos. 1-5-2 to 1-5-8 were synthesized in the same manner as Reference Examples 1-5-1 to 1-5-3 and Example 1-5-1, using the corresponding starting materials. The results are shown in Table 13.

Reference Example 1-5-4

Synthesis of 3,4-diaminobenzoic acid methyl ester

Thionyl chloride (13.0 ml, 180 mmol) was slowly added dropwise at 0° C. to a solution of 3,4-diaminobenzoic acid (25.0 g, 164 mmol) in methanol (164 ml). After stirring the mixture at room temperature overnight, it was further stirred at 80° C. overnight. The reaction mixture was cooled to room temperature, and the precipitated solid was filtered out and washed with methanol. The filtrate was concentrated under reduced pressure and the obtained solid was filtered out and washed with methanol. All of the obtained solid was dried under reduced pressure at 60° C. to obtain 3,4-diaminobenzoic acid methyl ester. The compound was identified by NMR.

Yield: 31.16 g (79%).
$^1$H-NMR (270 MHz, CDCl$_3$): 3.76(s, 3H), 6.85(d, 1H, J=8.6 Hz), 7.63(dd, 1H, J=1.9, 8.6 Hz), 7.78(d, 1H, J=1.9 Hz).

Example 1-5-9 to Example 1-5-13

Compound Nos. 1-5-9 to 1-5-13 were synthesized in the same manner as Reference Example 1-5-4, Reference Example 1-5-2, Reference Example 1-5-3 and Example 1-5-1, using the corresponding starting materials. The results are shown in Table 13.

Reference Example 1-5-5

Synthesis of 4-methylamino-3-nitrobenzoic acid methyl ester

After dissolving 4-fluoro-3-nitrobenzoic acid methyl ester (507.3 mg, 2.55 mmol) in tetrahydrofuran (1 ml), methylamine (2.0 M tetrahydrofuran solution, 2.55 ml, 5.09 mmol) was added in an ice bath, and the mixture was stirred at room temperature overnight; The reaction mixture was concentrated under reduced pressure and dissolved in ethyl acetate (20 ml), and after washing in saturated aqueous sodium bicarbonate and brine, it was dried over anhydrous magnesium sulfate. It was then concentrated under reduced pressure, the obtained residue was dissolved in a methylamine-tetrahydrofuran solution (2.0 M, 3 ml), and upon sealing, the solution was stirred at 50° C. for 5 hours. The reaction mixture was concentrated under reduced pressure and dissolved in ethyl acetate (30 ml), and the solution was washed with saturated aqueous sodium bicarbonate and brine and then dried over anhydrous magnesium sulfate. The dried product was concentrated under reduced pressure to obtain 4-methylamino-3-nitro-benzoic acid methyl ester. The compound was identified by LC-MS.

Yield: 540 mg (100%), [M+1]=211.1.

Reference Example 1-5-6

Synthesis of 3-amino-4-methylaminobenzoic acid methyl ester

After dissolving 4-methylamino-3-nitrobenzoic acid methyl ester (540 mg, 2.5 mmol) in ethyl acetate-methanol (2:1) (20 ml), 10% palladium-carbon powder (5 mol %) was added thereto under a nitrogen atmosphere. The mixture was stirred for 4 hours under a hydrogen atmosphere, and then the reaction mixture was filtered through celite. The filtrate was concentrated under reduced pressure to obtain 3-amino-4-methylaminobenzoic acid methyl ester. The compound was identified by LC-MS.

Yield: 441 mg (100%), [M+1]=181.1.

Example 1-5-14 to Example 1-5-16

Compound Nos. 1-5-14 to 1-5-16 were synthesized in the same manner as Reference Example 1-5-5, Reference Example 1-5-6, Reference Example 1-5-2, Reference Example 1-5-3 and Example 1-5-1, using the corresponding starting materials. The results are shown in Table 13.

Reference Example 1-5-7

Synthesis of 4-tert-butoxycarbonylamino-3-nitrobenzoic acid methyl ester

After dissolving 4-amino-3-nitrobenzoic acid methyl ester (1.03 g, 5.25 mmol) in tetrahydrofuran (50 ml), sodium bis(trimethylsilyl)amide (1.0 M tetrahydrofuran solution, 10.5 ml, 10.5 mmol) was added and the mixture was stirred at room temperature for 15 minutes. A solution of dibutyl dicarbonate (1.44 ml, 6.30 mmol) in tetrahydrofuran (10 ml) was added dropwise thereto, and the mixture was stirred at room temperature for 1 hour. The reaction mixture was concentrated under reduced pressure, and 1N hydrochloric acid was added to the residue to adjust the pH to approximately 6. The mixture was then extracted with ethyl acetate (100 ml×3 times), and the obtained organic layer was washed with saturated brine and then dried over anhydrous magnesium sulfate. The residue obtained by concentration under reduced pressure was purified by silica gel column chromatography (n-hexane/ethyl acetate=9/1) to obtain 4-tert-butoxycarbonylamino-3-nitrobenzoic acid methyl ester. The compound was identified by LC-MS.

Yield: 1.11 g (71.4%), [M+1]=297.1.

Reference Example 1-5-8

Synthesis of 3-amino-4-tert-butoxycarbonylaminobenzoic acid methyl ester 4-tert-Butoxycarbonylamino-3-nitrobenzoic acid methyl ester (1.11 g, 3.75 mmol) was dissolved in ethyl acetate-methanol (1:1) (30 ml). Next, 10% palladium-carbon powder (200 mg, 5 mol %) was added to the aqueous solution under a nitrogen atmosphere, and the mixture was stirred overnight under a hydrogen atmosphere. The reaction mixture was filtered with celite, and the filtrate was concentrated under reduced pressure to obtain 3-amino-4-tert-butoxycarbonylaminobenzoic acid methyl ester. The compound was identified by LC-MS.

Yield: 924.1 mg (92.3%), [M+1]=267.3.

Reference Example 1-5-9

Synthesis of 4-tert-butoxycarbonylamino-3-(2-nitro-benzenesulfonylamino)-benzoic acid methyl ester After dissolving 3-amino-4-tert-butoxycarbonylaminobenzoic acid methyl ester (817.3 mg, 3.07 mmol) in dichloromethane (10 ml), pyridine (0.373 ml, 4.60 mmol) and 2-nitrobenzenesulfonyl chloride (815 mg, 3.68 mmol) were added in an ice bath, and the mixture was stirred at room temperature for 4 hours. Pyridine (0.050 ml) and 2-nitrobenzenesulfonyl chloride (135 mg) were added, and stirring was continued for 2 hours. The reaction mixture was concentrated under reduced pressure, water (30 ml) was added, and then extraction was performed with ethyl acetate (20 ml×3 times). The obtained organic layer was washed with saturated brine and then dried over anhydrous magnesium sulfate. After concentration under reduced pressure, the crystallized residue was suspended in n-hexane-ethyl acetate (4:1), filtered, and dried to obtain 4-tert-butoxycarbonylamino-3-(2-nitro-benzenesulfonylamino)-benzoic acid methyl ester. The compound was identified by LC-MS.

Yield: 1.23 g (88.7%).

Reference Example 1-5-10

Synthesis of 4-tert-butoxycarbonylamino-3-[methyl-(2-nitro-benzenesulfonyl)-amino]-benzoic acid methyl ester After dissolving 4-tert-butoxycarbonylamino-3-(2-nitro-benzenesulfonylamino)-benzoic acid methyl ester (1.23 g, 2.73 mmol) in dimethylformamide (10 ml), potassium carbonate (1.13 g, 8.16 mmol) and methyl iodide (0.254 ml, 4.09 mmol) were added in an ice bath, and the mixture was stirred at room temperature for 2 hours. Water (100 ml) was added to the reaction mixture, and extraction was performed with ethyl acetate (40 ml×4 times). The obtained organic layer was washed with saturated brine and then dried over anhydrous magnesium sulfate. After concentration under reduced pressure, the crystallized residue was dried to obtain 4-tert-butoxycarbonylamino-3-[methyl-(2-nitro-benzenesulfonyl)-amino]-benzoic acid methyl ester. The compound was identified by LC-MS.

Yield: 1.41 g (100%).

Reference Example 1-5-11

Synthesis of 4-tert-butoxycarbonylamino-3-methylamino-benzoic acid methyl ester

After dissolving 4-tert-butoxycarbonylamino-3-[methyl-(2-nitro-benzenesulfonyl)-amino]-benzoic acid methyl ester (1.41 g, 2.73 mmol) in dimethylformamide (10 ml), potassium carbonate (1.13 g, 8.16 mmol) and thiophenol (0.307 ml, 2.99 mmol) were added in an ice bath, and the mixture was stirred at room temperature for 1 hour. Water (100 ml) was added to the reaction mixture, and extraction was performed with ethyl acetate (40 ml×3 times). The obtained organic layer was washed with saturated brine and then dried over anhydrous magnesium sulfate. The residue obtained by concentration under reduced pressure was purified by silica gel column chromatography (n-hexane/ethyl acetate=85/15) to obtain 4-tert-butoxycarbonylamino-3-methylamino-benzoic acid methyl ester. The compound was identified by LC-MS. Yield: 794.3 mg (62.7%), [M+1]=281.1.

Reference Example 1-5-12

Synthesis of 4-amino-3-methylaminobenzoic acid methyl ester

After dissolving 4-tert-butoxycarbonylamino-3-methylaminobenzoic acid methyl ester (794.3 mg, 2.83 mmol) in methanol (7.0 ml), a 4N hydrogen chloride-1,4-dioxane solution (3.54 ml, 14.3 mmol) was added in an ice bath, and the mixture was stirred at room temperature for 30 minutes. An equivalent amount of the 4N hydrogen chloride-1,4-dioxane solution was further added, and the mixture was stirred at 40° C. for 30 minutes. The reaction mixture was poured into ice-cooled saturated aqueous sodium bicarbonate, and was extracted with ethyl acetate (30 ml×3). The obtained organic layer was washed with saturated brine and dried over anhydrous magnesium sulfate. The residue obtained by concentration under reduced pressure was purified by silica gel column chromatography (n-hexane/ethyl acetate=4/1→3/2→1/1) to obtain 4-amino-3-methylaminobenzoic acid methyl ester. The compound was identified by LC-MS.

Yield: 342.7 mg (67.2%), [M+1]=181.1.

Example 1-5-17 to Example 1-5-19

Compound Nos. 1-5-17 to 1-5-19 were synthesized in the same manner as Reference Examples 1-5-7 to 1-5-12, Reference Example 1-5-2, Reference Example 1-5-3 and Example 1-5-1, using the corresponding starting materials. The results are shown in Table 13.

Example 1-5-20

Synthesis of 2-{[1-(3-phenyl-propyl)-piperidin-4-ylmethyl]-amino}-1H-benzimidazole-5-carboxylic acid After suspending 2-{[1-(3-phenyl-propyl)-piperidin-4-ylmethyl]-amino}-1H-benzimidazole-5-carboxylic acid methyl ester (3.2 mmol) in methanol (10 ml), a 4N lithium hydroxide aqueous solution (5.4 ml, 21.4 mmol) was added. The reaction mixture was stirred at 50° C. for 2 hours and then cooled to room temperature. Next, 1N hydrochloric acid was added dropwise to adjust the pH to approximately 6.0. Ethyl acetate (1 ml) was added to the aqueous solution and the mixture was stirred for 3 hours, and then the precipitate was filtered out to obtain 2-{[1-(3-phenyl-propyl)-piperidin-4-ylmethyl]-amino}-1H-benzimidazole-5-carboxylic acid. The compound was identified by LC-MS.

Yield: 1.01 g (79.9%), Purity: 98.5%, [M+1]=393.1.

Example 1-5-21 to Example 1-5-22

Compound Nos. 1-5-21 to 1-5-22 were synthesized in the same manner as Example 1-5-20, using the corresponding starting materials. The results are shown in Table 13.

Example 1-5-23

Synthesis of 2-[(1-naphthalen-1-ylmethyl-piperidin-4-ylmethyl)-amino]-1H-benzimidazole-5-carboxylic acid (2-dimethyl)-amide 2-[(1-Naphthalen-1-ylmethyl-piperidin-4-ylmethyl)-amino]-1H-benzimidazole-5-carboxylic acid (20.0 mg, 0.0480 mmol) and 1-hydroxybenzotriazole monohydrate (22.0 mg, 0.145 mmol) were dissolved in tetrahydrofuran-dimethylformamide (1:1, 0.500 ml). After then adding N,N-dimethylethylenediamine (0.0160 ml, 0.145 mmol) and N,N-diisopropylcarbodiimide (0.0220 ml, 0.145 mmol) thereto, the mixture was stirred at room temperature overnight. Water (2 ml) was added to the reaction mixture, and after stirring for 10 minutes, extraction was performed with ethyl acetate (1 ml×3 times). The obtained ethyl acetate layer was purified by SCX solid phase extraction and then purified by preparative HPLC to obtain 2-[(1-naphthalen-1-ylmethyl-piperidin-4-ylmethyl)-amino]-1H-benzimidazole-5-carboxylic acid (2-dimethyl)-amide. The compound was identified by LC-MS.

Yield: 10.5 mg (45.1%), Purity: 100%, [M+1]=485.4

Example 1-5-24 to Example 1-5-190

Compound Nos. 1-5-24 to 1-5-190 were synthesized in the same manner as Example 1-5-23, using the corresponding starting materials. The results are shown in Table 13.

Reference Example 1-5-13

Synthesis of 2-[(1-naphthalen-1-ylmethyl-piperidin-4-ylmethyl)-amino]-benzimidazole-1,5-dicarboxylic acid 1-tert-butyl ester 5-methyl ester After dissolving 2-[(1-naphthalen-1-ylmethyl-piperidin-4-ylmethyl)-amino]-1H-benzimidazole-5-carboxylic acid methyl ester (1 g, 2.33 mmol) in 1,4-dioxane (25 ml), di-t-butyl dicarbonate (1017 mg, 4.66 mmol) was added and the mixture was stirred at 80° C. for 11 hours. The solvent was distilled off under reduced pressure, and the obtained residue was purified by silica gel column chromatography (dichloromethane/methanol/TEA=85/10/5) to obtain 2-[(1-naphthalen-1-ylmethyl-piperidin-4-ylmethyl)-amino]-benzimidazole-1,5-dicarboxylic acid 1-tert-butyl ester 5-methyl ester. The compound was identified by LC-MS.

Yield: 1.1 g (96%), LC-MS (529.2 m/z M+1).

Example 1-5-191

Synthesis of {2-[(1-naphthalen-1-ylmethyl-piperidin-4-ylmethyl)-amino]-1H-benzimidazol-5-yl}-methanol After dissolving 2-[(1-naphthalen-1-ylmethyl-piperidin-4-ylmethyl)-amino]-benzimidazole-1,5-dicarboxylic acid 1-tert-butyl ester 5-methyl ester (940 mg, 1.78 mmol) in dry tetrahydrofuran (18 ml) under a nitrogen stream, aluminum lithium hydride (135 mg, 3.56 mmol) was added at 0° C., and the mixture was stirred for 3 hours. Saturated aqueous sodium sulfate was added, and then the solvent was distilled off under reduced pressure. Since the residue contained water, it was dissolved in ethyl acetate and washed with saturated brine, and the solvent was then distilled off under reduced pressure to obtain a residue. The residue was purified by silica gel column chromatography (dichloromethane/methanol/TEA=90/5/5) to obtain {2-[(1-naphthalen-1-ylmethyl-piperidin-4-ylmethyl)-amino]-1H-benzimidazol-5-yl-}-methanol.

Yield: 822 mg (91%), Purity: 89.3%, LC-MS (401.2 m/z M+1).

Example 1-5-192

Synthesis of 2-[(1-naphthalen-1-ylmethyl-piperidin-4-ylmethyl)-amino]-1H-benzimidazole-5-carboaldehyde A solution of 1-hydroxy-1-oxo-1H-1$\lambda^5$-benzo[d][1,2]iodoxol-3-one (846 mg, 3.02 mmol) in dimethylsulfoxide (10 ml) was added to a solution of {2-[(1-naphthalen-1-ylmethyl-piperidin-4-ylmethyl)-amino]-1H-benzimidazol-5-yl}- methanol (807 mg, 2.01 mmol) in dimethylsulfoxide (10 ml), and the mixture was stirred at room temperature for 9 hours. The reaction mixture was poured into ice water (200 ml) and stirred at room temperature for 30 minutes, after which ethyl acetate was added and stirring was continued vigorously for 10 minutes for extraction. After washing with saturated aqueous sodium bicarbonate and saturated brine, the mixture was dried over anhydrous sodium sulfate, the solvent was distilled off under reduced pressure, and the obtained residue was purified by silica gel column chromatography (ethyl acetate/methanol=9/1). This was further purified by preparative HPLC to obtain 2-[(1-naphthalen-1-ylmethyl-piperidin-4-ylmethyl)-amino]-1H-benzimidazole-5-carboaldehyde.

Yield: 34 mg (4%), Purity: 100%, LC-MS (399.2 m/z M+1).

Example 1-5-193

Synthesis of 2-[(1-naphthalen-1-ylmethyl-piperidin-4-ylmethyl)-amino]-1H-benzimidazole-5-carbonitrile After dissolving 2-[(1-naphthalen-1-ylmethyl-piperidin-4-ylmethyl)-amino]-1H-benzimidazole-5-carboaldehyde (2.7 mg, 0.0570 mmol) in anhydrous dimethylformamide (1 ml) under a nitrogen stream, hydroxylamine hydrochloride (8 mg, 0.115 mmol) and one drop of 6N hydrochloric acid were added and the mixture was stirred at 80° C. for 2 hours and 30 minutes. Two drops of 5N aqueous sodium hydroxide were then added, and after extraction with ethyl acetate, extraction was repeated with dichloromethane. The organic layer was washed with saturated brine and then dried over anhydrous sodium sulfate, and the solvent was distilled off under reduced pressure to obtain a residue. Anhydrous dimethylformamide (1 ml) and nine drops of a 4N hydrogen chloride/1, 4-dioxane solution were added to the residue, and the mixture was stirred at 100° C. for 12 hours. After neutralization with 5N aqueous sodium hydroxide, the same extraction procedure was carried out and the obtained residue was purified by thin-layer silica gel chromatography (dichloromethane/methanol/triethylamine=85/10/5) to obtain 2-[(1-naphthalen-1-ylmethyl-piperidin-4-ylmethyl)-amino]-1H-benzimidazole-5-carbonitrile.

Yield: 29%, Purity: 99.3%, Yield: 6.6 mg. LC-MS (396.3 m/z M+1).

Reference Example 1-5-14

Synthesis of 2-[(1-naphthalen-1-ylmethyl-piperidin-4-ylmethyl)-(2-trimethylsilanyl-ethoxymethyl)-amino]-1-(2-trimethylsilanyl-ethoxymethyl)-1H-benzimidazole-5-carboxylic acid methyl ester After dissolving 2-[(1-naphthalen-1-ylmethyl-piperidin-4-ylmethyl)-amino]-1H-benzimidazole-5-carboxylic acid methyl ester (1 g, 2.33 mmol) in anhydrous tetrahydrofuran (30 ml) under a nitrogen stream, the mixture was cooled to 0° C. Next, 60% sodium hydride (187 mg, 4.89 mmol) was added and the mixture was stirred at 0° C. for 72 minutes. 2-(Trimethylsilyl)ethoxymethyl chloride (815.8 mg, 4.89 mmol) was further added, the mixture was stirred at 0° C. for 30 minutes, and then water was added. The solution was extracted with ethyl acetate and then with dichloromethane, and each extract was washed with saturated brine and then combined and dried over anhydrous sodium sulfate. The solvent was distilled off under reduced pressure, and the obtained residue was purified by silica gel column chromatography (ethyl acetate/hexane=2/3→3/2→1/0) to obtain 2-[(1-naphthalen-1-ylmethyl-piperidin-4-ylmethyl)-(2-trimethylsilanyl-ethoxymethyl)-amino]-1-(2-trimethylsilanyl-ethoxymethyl)-1H-benzimidazole-5-carboxylic acid methyl ester. The compound was identified by LC-MS.

Yield: 624 mg (39%), Purity: 95.1%, LC-MS (689.3 m/z M+1).

Reference Example 1-5-15

Synthesis of [2-[(1-naphthalen-1-ylmethyl-piperidin-4-ylmethyl)-(2-trimethylsilanyl-ethoxymethyl)-amino]-1-(2-trimethylsilanyl-ethoxymethyl)-1H-benzimidazol-5-yl]-methanol After dissolving 2-[(1-naphthalen-1-ylmethyl-piperidin-4-ylmethyl)-(2-trimethylsilanyl-ethoxymethyl)-amino]-1-(2-trimethylsilanyl-ethoxymethyl)-1H-benzimidazole-5-carboxylic acid methyl ester (624 mg, 0.91 mmol) in anhydrous tetrahydrofuran (10 ml) under a nitrogen stream, aluminum lithium hydride (72.4 mg, 1.82 mmol) was added at 0° C., and the mixture was stirred for 2 hours. After then adding a saturated aqueous sodium sulfate solution, extraction was performed with ethyl acetate and then with dichloromethane. Each extract was washed with saturated brine, and then combined and dried over anhydrous sodium sulfate. The solvent was distilled off under reduced pressure to obtain [2-[(1-naphthalen-1-ylmethyl-piperidin -4-ylmethyl)-(2-trimethylsilanyl-ethoxymethyl)-amino]-1-(2-trimethylsilanyl-ethoxymethyl)-1H-benzimidazol-5-yl]-methanol. The compound was identified by LC-MS.

Yield: 568 mg (95%), Purity: 89.4%, LC-MS (661.4 m/z M+1).

Reference Example 1-5-16

Synthesis of 2-[(1-naphthalen-1-ylmethyl-piperidin-4-ylmethyl)-(2-trimethylsilanyl-ethoxymethyl)-amino]-1-(2-trimethylsilanyl-ethoxymethyl)-1H-benzimidazole-5-carboaldehyde A solution of [2-[(1-naphthalen-1-ylmethyl-piperidin-4-ylmethyl)-(2-trimethylsilanyl-ethoxymethyl)-amino]-1-(2-trimethylsilanyl-ethoxymethyl)-1H-benzimidazol-5-yl]-methanol (467 mg, 0.71 mmol) in dimethylsulfoxide (5 ml) was added to a solution of 297 mg of 1-hydroxy-1-oxo-1H-1$\lambda^5$-benzo[d][1,2]iodoxol-3-one (1.06 mmol) in dimethylsulfoxide (5 ml), and the mixture was stirred at room temperature for 18 hours. The reaction mixture was poured into ice water (200 ml) and stirred at room temperature for 30 minutes, after which ethyl acetate was added and stirring was continued vigorously for 10 minutes for extraction. After washing with saturated aqueous sodium bicarbonate and then with saturated brine, the mixture was dried over anhydrous sodium sulfate, and then the solvent was distilled off under reduced pressure to obtain 2-[(1-naphthalen-1-ylmethyl-piperidin-4-ylmethyl)-(2-trimethylsilanyl-ethoxymethyl)-amino]-1-(2-trimethylsilanyl-ethoxymethyl)-1H-benzimidazole-5-carboaldehyde.

Yield: 475 mg (100%), Purity: 83.2%, LC-MS (659.3 m/z M+1).

Reference Example 1-5-17

Synthesis of 1-[2-[(1-naphthalen-1-ylmethyl-piperidin-4-ylmethyl)-(2-trimethylsilanyl-ethoxymethyl)-amino]-1-(2-trimethylsilanyl-ethoxymethyl)-1H-benzimidazol-5-yl]-propan-1-ol After dissolving 2-[(1-naphthalen-1-ylmethyl-piperidin-4-ylmethyl)-(2-trimethylsilanyl-ethoxymethyl)-amino]-1-(2-trimethylsilanyl-ethoxymethyl)-1H-benzimidazole-5-carboaldehyde (86 mg, 0.131 mmol) in anhydrous tetrahydrofuran (1.2 ml) under a nitrogen stream, ethylmagnesium bromide (0.26 ml, 1M tetrahydrofuran solution) was added at 0° C., and the mixture was stirred at room temperature for 13 minutes. Saturated aqueous ammonium chloride was added, and extraction was performed with ethyl acetate. The organic layer was washed with saturated brine and then dried over sodium sulfate, and the solvent was distilled off under reduced pressure to obtain 1-[2-[(1-naphthalen-1-ylmethyl-piperidin-4-ylmethyl)-(2-trimethylsilanyl-ethoxymethyl)-amino]-1-(2-trimethylsilanyl-ethoxymethyl)-1H-benzimidazol-5-yl]-propan-1-ol.

Yield: 92.5 mg (100%), Purity: 88%, LC-MS (689.3 m/z M+1).

Example 1-5-194

Synthesis of 1-{2-[(1-naphthalen-1-ylmethyl-piperidin-4-ylmethyl)-amino]-1H-benzimidazol-5-yl}-propan-1-ol After dissolving 1-[2-[(1-naphthalen-1-ylmethyl-piperidin-4-ylmethyl)-(2-trimethylsilanyl-ethoxymethyl)-amino]-1-(2-trimethylsilanyl-ethoxymethyl)-1H-benzimidazol-5-yl]-propan-1-ol (50 mg, 0.073 mmol) in anhydrous dimethylformamide (2 ml), tetrabutylammonium fluoride (0.5 ml, 1.0 M tetrahydrofuran solution) was added and the mixture was stirred at 100° C. for 13 hours. Ethyl acetate and water were added, after which the aqueous layer was adjusted to pH 11 and extracted with ethyl acetate. The organic layer was washed with saturated brine and then dried over anhydrous sodium sulfate, the solvent was distilled off under reduced pressure, and the obtained residue was purified by thin-layer silica gel chromatography (ethyl acetate/methanol=4/1). The purified product was further purified by preparative HPLC to obtain 1-{2-[(1-naphthalen-1-ylmethyl-piperidin-4-ylmethyl)-amino]-1H-benzimidazol-5-yl}-propan-1-ol.

Yield: 1.08 mg (3%), Purity: 100%, LC-MS (429.2 m/z M+1).

Reference Example 1-5-18

Synthesis of 1-[2-[(1-naphthalen-1-ylmethyl-piperidin-4-ylmethyl)-(2-trimethylsilanyl-ethoxymethyl)-amino]-[(2-trimethylsilanyl-ethoxymethyl)-1H-benzimidazol-5-yl]-propan-1-one A solution of 1-[2-[(1-naphthalen-1-ylmethyl-piperidin-4-ylmethyl)-(2-trimethylsilanyl-ethoxymethyl)-amino]-1-(2-trimethylsilanyl-ethoxymethyl)-1H-benzimidazol-5-yl]-propan-1-ol (72 mg, 0.10 mmol) in dimethylsulfoxide (1 ml) was added to a solution of 1-hydroxy-1-oxo-1H-1$\lambda^5$-benzo[d][1,2]iodoxol-3-one (44 mg, 0.157 mmol) in dimethylsulfoxide (1 ml), and the mixture was stirred at room temperature for 18 hours. The reaction mixture was poured into ice water (50 ml) and stirred at room temperature for 30 minutes, after which ethyl acetate was added and stirring was continued vigorously for 10 minutes for extraction. After washing with saturated aqueous sodium bicarbonate and then with saturated brine, the mixture was dried over anhydrous sodium sulfate, and the solvent was distilled off under reduced pressure to obtain 1-[2-[(1-naphthalen-1-ylmethyl-piperidin-4-ylmethyl)-(2-trimethylsilanyl-ethoxymethyl)-amino]-1-(2-trimethylsilanyl-ethoxymethyl)-1H-benzimidazol-5-yl]-propan-1-one.

Yield: 64 mg (89%), Purity: 92.8%, LC-MS (687.4 m/z M+1)

Example 1-5-195

Synthesis of 1-{2-[(1-naphthalen-1-ylmethyl-piperidin-4-ylmethyl)-amino]-1H-benzimidazol-5-yl}-propan-1-one After dissolving 1-[2-[(1-naphthalen-1-ylmethyl-piperidin-4-ylmethyl)-(2-trimethylsilanyl-ethoxymethyl)-amino]-1-(2-trimethylsilanyl-ethoxymethyl)-1H-benzimidazol-5-yl]-propan-1-one (32 mg, 0.047 mmol) in anhydrous dimethylformamide (1 ml), tetrabutylammonium fluoride (0.8 ml, 1.0 M tetrahydrofuran solution) and water (5 μl) were added, and the mixture was stirred at 100° C. for 2 hours and 30 minutes. Water and ethyl acetate were added, and extraction was performed with ethyl acetate. The organic layer was washed with saturated brine and then dried over anhydrous sodium sulfate, the solvent was distilled off under reduced pressure, and the obtained residue was purified by thin-layer silica gel chromatography (dichloromethane/methanol/TEA=85/10/1). The purified product was further purified by preparative HPLC and thin-layer silica gel chromatography (dichloromethane/methanol=8/2) to obtain 1-{2-[(1-naphthalen-1-ylmethyl-piperidin-4-ylmethyl)-amino]-1H-benzimidazol-5-yl}-propan-1-one.

Yield: 2.04 mg (10%), Purity: 100%, LC-MS (427.2 m/z M+1).

Example 1-5-196 and Example 1-5-197

Compound Nos. 1-5-196 and 1-5-197 were synthesized in the same manner as Example 1-5-195, using the corresponding starting materials. The results are shown in Table 13.

TABLE 13

| Compound No. 1-5- | Yield (mg) | Yield (%) | MW | M + 1 |
|---|---|---|---|---|
| 1 | 2 | 3 | 477.4 | 477.1 |
| 2 | 14 | 31 | 442.9 | 443.1 |
| 3 | 15 | 35 | 442.6 | 443.2 |
| 4 | 12 | 29 | 420.6 | 421.2 |
| 5 | 1 | 2 | 491.4 | 491.2 |
| 6 | 4 | 9 | 457.0 | 457.2 |
| 7 | 11 | 26 | 456.6 | 457.2 |
| 8 | 21 | 52 | 434.6 | 435.2 |
| 9 | 48 | 92 | 428.5 | 429.1 |
| 10 | 51 | 100 | 406.5 | 407.2 |
| 11 | 8 | 20 | 463.4 | 463.1 |
| 12 | 13 | 36 | 439.5 | 440.1 |
| 13 | 500 | 58 | 434.6 | 435.1 |
| 14 | 19 | 28 | 477.4 | 477.1 |
| 15 | 41 | 100 | 442.6 | 443.2 |
| 16 | 45 | 100 | 420.6 | 421.2 |
| 17 | 6 | 24 | 477.4 | 477.1 |
| 18 | 23 | 99 | 442.6 | 443.2 |
| 19 | 24 | 100 | 420.6 | 421.2 |
| 20 | 1010 | 80 | 392.5 | 393.1 |

TABLE 13-continued

| Compound No. 1-5- | Yield (mg) | Yield (%) | MW | M + 1 |
|---|---|---|---|---|
| 21 | 994 | 93 | 417.5 | 418.1 |
| 22 | 458 | 67 | 459.3 | 459.4 |
| 23 | 11 | 45 | 484.6 | 485.4 |
| 24 | 10 | 43 | 498.6 | 499.4 |
| 25 | 39 | 100 | 556.7 | 557.5 |
| 26 | 13 | 53 | 499.6 | 500.3 |
| 27 | 13 | 57 | 471.6 | 472.3 |
| 28 | 12 | 51 | 503.6 | 504.4 |
| 29 | 4 | 16 | 517.7 | 518.4 |
| 30 | 17 | 51 | 455.6 | 456.4 |
| 31 | 12 | 35 | 469.6 | 470.3 |
| 32 | 8 | 23 | 483.7 | 484.4 |
| 33 | 3 | 10 | 469.6 | 470.4 |
| 34 | 7 | 18 | 499.6 | 500.4 |
| 35 | 17 | 52 | 457.6 | 458.4 |
| 36 | 15 | 43 | 471.6 | 472.3 |
| 37 | 6 | 19 | 456.6 | 457.4 |
| 38 | 25 | 100 | 433.6 | 434.2 |
| 39 | 10 | 43 | 462.6 | 463.2 |
| 40 | 4 | 16 | 476.6 | 477.2 |
| 41 | 7 | 27 | 534.7 | 535.3 |
| 42 | 9 | 36 | 477.6 | 478.2 |
| 43 | 8 | 36 | 435.6 | 436.2 |
| 44 | 29 | 100 | 477.6 | 478.2 |
| 45 | 27 | 100 | 449.6 | 450.2 |
| 46 | 29 | 100 | 481.6 | 482.3 |
| 47 | 29 | 100 | 495.7 | 496.3 |
| 48 | 14 | 61 | 458.6 | 459.2 |
| 49 | 9 | 39 | 487.7 | 488.3 |
| 50 | 11 | 47 | 502.6 | 503.3 |
| 51 | 10 | 42 | 474.6 | 475.2 |
| 52 | 9 | 39 | 506.7 | 507.2 |
| 53 | 10 | 38 | 520.7 | 521.3 |
| 54 | 11 | 24 | 456.6 | 456.2 |
| 55 | 13 | 27 | 485.0 | 485.2 |
| 56 | 8 | 16 | 499.0 | 499.2 |
| 57 | 9 | 16 | 557.1 | 557.2 |
| 58 | 16 | 32 | 500.0 | 500.1 |
| 59 | 10 | 20 | 500.0 | 500.2 |
| 60 | 15 | 32 | 472.0 | 472.2 |
| 61 | 17 | 34 | 504.0 | 504.1 |
| 62 | 19 | 37 | 518.1 | 518.2 |
| 63 | 21 | 48 | 440.0 | 440.2 |
| 64 | 8 | 17 | 469.0 | 469.1 |
| 65 | 23 | 48 | 483.0 | 483.2 |
| 66 | 19 | 35 | 541.1 | 541.2 |
| 67 | 9 | 19 | 484.0 | 484.2 |
| 68 | 2 | 5 | 442.0 | 442.1 |
| 69 | 11 | 23 | 484.0 | 484.1 |
| 70 | 26 | 53 | 488.0 | 488.2 |
| 71 | 29 | 58 | 502.1 | 502.2 |
| 72 | 21 | 46 | 456.0 | 456.1 |
| 73 | 14 | 31 | 457.6 | 458.2 |
| 74 | 15 | 34 | 435.6 | 436.2 |
| 75 | 5 | 11 | 460.6 | 461.2 |
| 76 | 14 | 31 | 458.0 | 458.1 |
| 77 | 11 | 25 | 442.0 | 442.1 |
| 78 | 14 | 32 | 441.6 | 442.2 |
| 79 | 12 | 29 | 419.6 | 420.2 |
| 80 | 10 | 22 | 444.6 | 445.2 |
| 81 | 15 | 34 | 442.0 | 442.2 |
| 82 | 10 | 23 | 426.0 | 426.1 |
| 83 | 9 | 21 | 427.5 | 428.2 |
| 84 | 10 | 25 | 405.5 | 406.2 |
| 85 | 2 | 5 | 430.6 | 431.2 |
| 86 | 10 | 23 | 427.9 | 428.1 |
| 87 | 23 | 56 | 411.9 | 412.2 |
| 88 | 12 | 45 | 522.5 | 522.0 |
| 89 | 13 | 52 | 518.4 | 518.1 |
| 90 | 6 | 29 | 474.4 | 474.0 |
| 91 | 11 | 47 | 503.5 | 503.1 |
| 92 | 10 | 41 | 517.5 | 517.1 |
| 93 | 6 | 26 | 518.4 | 518.1 |
| 94 | 5 | 20 | 490.4 | 490.0 |
| 95 | 11 | 42 | 575.5 | 575.1 |
| 96 | 9 | 37 | 536.5 | 536.0 |

TABLE 13-continued

| Compound No. 1-5- | Yield (mg) | Yield (%) | MW | M + 1 |
|---|---|---|---|---|
| 97 | 18 | 60 | 475.4 | 475.2 |
| 98 | 24 | 92 | 490.4 | 490.0 |
| 99 | 12 | 28 | 476.4 | 476.0 |
| 100 | 8 | 15 | 557.5 | 557.3 |
| 101 | 5 | 10 | 543.5 | 543.3 |
| 102 | 5 | 9 | 526.5 | 526.3 |
| 103 | 5 | 8 | 538.5 | 538.1 |
| 104 | 5 | 10 | 516.5 | 516.3 |
| 105 | 5 | 10 | 542.6 | 542.3 |
| 106 | 8 | 16 | 514.4 | 514.2 |
| 107 | 2 | 5 | 486.4 | 486.2 |
| 108 | 4 | 9 | 478.4 | 484.3 |
| 109 | 4 | 7 | 544.5 | 544.2 |
| 110 | 11 | 20 | 546.5 | 546.3 |
| 111 | 3 | 5 | 560.5 | 560.3 |
| 112 | 10 | 20 | 517.5 | 517.2 |
| 113 | 12 | 22 | 530.5 | 531.3 |
| 114 | 10 | 21 | 471.4 | 471.1 |
| 115 | 3 | 5 | 532.5 | 532.3 |
| 116 | 7 | 14 | 472.4 | 473.3 |
| 117 | 10 | 18 | 516.5 | 516.3 |
| 118 | 9 | 18 | 502.5 | 502.0 |
| 119 | 7 | 14 | 543.5 | 543.3 |
| 120 | 3 | 6 | 486.4 | 486.3 |
| 121 | 4 | 8 | 502.5 | 502.3 |
| 122 | 10 | 19 | 528.5 | 528.2 |
| 123 | 7 | 14 | 502.5 | 502.0 |
| 124 | 9 | 18 | 488.5 | 488.2 |
| 125 | 7 | 13 | 570.6 | 570.2 |
| 126 | 33 | 70 | 472.4 | 473.3 |
| 127 | 20 | 38 | 542.6 | 543.3 |
| 128 | 33 | 60 | 545.6 | 545.3 |
| 129 | 24 | 47 | 516.5 | 517.3 |
| 130 | 31 | 56 | 545.6 | 545.4 |
| 131 | 28 | 55 | 502.5 | 503.3 |
| 132 | 32 | 70 | 460.4 | 461.2 |
| 133 | 23 | 45 | 518.5 | 519.3 |
| 134 | 25 | 48 | 530.5 | 531.3 |
| 135 | 23 | 45 | 502.5 | 503.3 |
| 136 | 23 | 44 | 518.5 | 519.3 |
| 137 | 19 | 37 | 520.5 | 521.3 |
| 138 | 16 | 30 | 528.5 | 529.3 |
| 139 | 19 | 36 | 528.5 | 529.3 |
| 140 | 33 | 70 | 470.4 | 471.3 |
| 141 | 19 | 34 | 556.6 | 557.4 |
| 142 | 15 | 30 | 517.5 | 517.3 |
| 143 | 17 | 34 | 488.5 | 489.3 |
| 144 | 20 | 41 | 488.5 | 489.3 |
| 145 | 20 | 41 | 488.5 | 489.3 |
| 146 | 7 | 14 | 516.5 | 517.3 |
| 147 | 22 | 41 | 531.5 | 529.3 |
| 148 | 17 | 30 | 559.5 | 559.3 |
| 149 | 16 | 34 | 474.4 | 475.2 |
| 150 | 21 | 41 | 500.5 | 501.3 |
| 151 | 15 | 29 | 514.5 | 515.3 |
| 152 | 9 | 18 | 504.5 | 505.3 |
| 153 | 34 | 58 | 573.6 | 573.4 |
| 154 | 28 | 56 | 504.5 | 504.3 |
| 155 | 35 | 61 | 571.6 | 571.4 |
| 156 | 31 | 59 | 529.5 | 529.3 |
| 157 | 28 | 48 | 587.6 | 587.4 |
| 158 | 20 | 36 | 546.5 | 547.3 |
| 159 | 3 | 6 | 500.5 | 500.2 |
| 160 | 2 | 3 | 502.4 | 502.3 |
| 161 | 2 | 4 | 528.5 | 528.2 |
| 162 | 1 | 2 | 516.5 | 516.3 |
| 163 | 1 | 2 | 532.5 | 532.3 |
| 164 | 2 | 4 | 517.5 | 517.3 |
| 165 | 36 | 71 | 503.4 | 503.3 |
| 166 | 19 | 38 | 489.4 | 489.2 |
| 167 | 6 | 10 | 550.5 | 550.3 |
| 168 | 3 | 6 | 503.4 | 503.3 |
| 169 | 2 | 4 | 485.4 | 485.2 |
| 170 | 1 | 2 | 502.5 | 502.1 |
| 171 | 2 | 3 | 508.9 | 508.1 |
| 172 | 4 | 6 | 559.6 | 559.3 |

TABLE 13-continued

| Compound No. 1-5- | Yield (mg) | Yield (%) | MW | M + 1 |
|---|---|---|---|---|
| 173 | 3 | 6 | 502.5 | 502.0 |
| 174 | 22 | 37 | 589.6 | 589.4 |
| 175 | 21 | 35 | 603.6 | 603.3 |
| 176 | 5 | 10 | 523.5 | 523.2 |
| 177 | 6 | 12 | 523.5 | 523.2 |
| 178 | 5 | 10 | 523.5 | 523.2 |
| 179 | 5 | 11 | 504.5 | 504.3 |
| 180 | 7 | 14 | 508.5 | 508.2 |
| 181 | 2 | 3 | 520.9 | 520.2 |
| 182 | 2 | 3 | 488.5 | 488.2 |
| 183 | 4 | 7 | 538.5 | 538.1 |
| 184 | 821 | 100 | 400.5 | 401.2 |
| 185 | 34 | 4 | 398.5 | 399.2 |
| 186 | 7 | 29 | 395.5 | 396.3 |
| 187 | 1 | 3 | 428.6 | 429.2 |
| 188 | 2 | 9 | 426.6 | 427.2 |
| 189 | 4 | 1 | 412.5 | 413.2 |
| 190 | 3 | 1 | 440.6 | 441.2 |
| 191 | 822 | 91 | 400.5 | 401.2 |
| 192 | 34 | 4 | 398.6 | 399.2 |
| 193 | 7 | 29 | 395.6 | 396.3 |
| 194 | 1 | 3 | 428.5 | 429.2 |
| 195 | 2 | 10 | 426.6 | 427.2 |
| 196 | 7 | 18 | 499.0 | 500.4 |
| 197 | 871 | 41 | 428.0 | 429.2 |

Example 1-6-1

Synthesis of [1-(3,4-dichloro-benzyl)-piperidin-4-ylmethyl]-(1-ethyl-1H-benzimidazol-2-yl)-amine After dissolving (1H-benzimidazol-2-yl)-[1-(3,4-dichloro-benzyl)-piperidin-4-ylmethyl]-amine (20 mg, 0.05 mmol) in dimethylformamide (1 ml), ethyl bromide (0.075 mmol) and sodium hydride (0.1 mmol) were added, and the mixture was stirred at room temperature for 3 hours and 30 minutes. Ice and diluted hydrochloric acid were added to the reaction mixture to suspend the reaction, and the solution was passed through SCX (Bond Elute SCX500MG). The SCX was washed with methanol and elution was performed with a 2N ammonia-methanol solution, after which the obtained eluate was distilled off under reduced pressure. The residue was purified by thin-layer silica gel chromatography (hexane/ethyl acetate/dichloromethane/methanol=60/25/10/5) to obtain [1-(3,4-dichloro-benzyl)-piperidin-4-ylmethyl]-(1-ethyl-1H-benzimidazol-2-yl)-amine and [1-(3,4-dichloro-benzyl)-piperidin-4-ylmethyl]-ethyl-(1-ethyl-1H-benzimidazol-2-yl)-amine. The compounds were identified by LC-MS.

Yield: 5.8 mg (28%), Purity: 100%, Found: ESI/MS m/e 417.0 (M+1).

Example 1-6-2

Compound No. 1-6-2, [1-(3,4-dichloro-benzyl)-piperidin-4-ylmethyl]-ethyl-(1-ethyl-1H-benzimidazol-2-yl)-amine, was synthesized in the same manner as Example 1-6-1, using the corresponding starting materials.

Yield: 7.7 mg (35%), Purity: 100%, Found: ESI/MS m/e 445.1 (M+1).

Example 1-6-3 to Example 1-6-15

Compound Nos. 1-6-3 to 1-6-15 were synthesized in the same manner as Example 1-6-1, using the corresponding starting materials. The results are shown in Table 14.

TABLE 14

| Compound No. 1-6- | Yield (mg) | Yield (%) | MW | M + 1 |
|---|---|---|---|---|
| 1 | 6 | 28 | 417.4 | 417.0 |
| 2 | 8 | 35 | 445.4 | 445.1 |
| 3 | 15 | 52 | 569.6 | 569.3 |
| 4 | 6 | 23 | 479.5 | 479.3 |
| 5 | 6 | 20 | 557.6 | 557.2 |
| 6 | 6 | 26 | 473.5 | 473.1 |
| 7 | 1 | 3 | 625.7 | 625.4 |
| 8 | 9 | 34 | 507.5 | 507.3 |
| 9 | 2 | 7 | 461.4 | 461.2 |
| 10 | 6 | 24 | 517.5 | 517.2 |
| 11 | 3 | 13 | 446.4 | 446.2 |
| 12 | 3 | 15 | 460.4 | 460.1 |
| 13 | 8 | 33 | 461.4 | 461.2 |
| 14 | 4 | 20 | 442.4 | 443.1 |
| 15 | 6 | 24 | 489.4 | 489.2 |

Synthesis of Quinazolinone Derivatives (1)

Reference Example 2-1

Synthesis of {1-[(3,4-dichlorophenyl)methyl]-4-piperidyl}methylamine

After dissolving 4-aminomethylpiperidine (13.7 g, 120 mmol) in acetonitrile (200 ml), potassium carbonate (11.057 g, 80 mmol) and 3,4-dichlorobenzyl chloride (7.818 g, 40 mmol) were added and the mixture was stirred at 60° C. overnight. After completion of the reaction, the reaction mixture was filtered and the solvent was distilled off. Purification was performed by silica gel column chromatography (dichloromethane/methanol/triethylamine=90/5/5) to obtain {1-[(3,4-dichlorophenyl)methyl]-4-piperidyl}methylamine. The compound was identified by LC-MS.

Yield: 10.8 g (quantitative, M+1=273.1.

Reference Example 2-2

Synthesis of N-{[({1-[(3,4-dichlorophenyl)methyl](4-piperidyl)}methyl)amino]thioxomethyl}(fluoren-9-ylmethoxy)carboxamide After dissolving {1-[(3,4-dichlorophenyl)methyl]-4-piperidyl}methylamine (1325 mg, 4.84 mmol) in tetrahydrofuran (20 ml), FmocNCS (9-fluorenylmethoxycarbonyl isothiocyanate) (1498 mg, 5.32 mmol) was added, and the mixture was stirred at room temperature overnight. After completion of the reaction, the reaction mixture was concentrated and purified by silica gel column chromatography (hexane/ethyl acetate=85/15) to obtain N-{[({1-[(3,4-dichlorophenyl)methyl](4-piperidyl)}methyl)amino]thioxomethyl}(fluoren-9-ylmethoxy)carboxamide. The compound was identified by LC-MS.

Yield: 2624 mg (98%), M+1=554.1.

Reference Example 2-3

Synthesis of amino[({1-[(3,4-dichlorophenyl)methyl](4-piperidyl)}methyl)amino]methane-1-thione After dissolving N-{[({1-[(3,4-dichlorophenyl)methyl](4-piperidyl)}methyl)amino]thioxomethyl}(fluoren-9-ylmethoxy)carboxamide (553 mg, 1 mmol) in DMF (4 ml), piperidine (0.989 ml, 10 mmol) was added and the mixture was stirred at room temperature overnight. Upon completion of the reaction, water (20 ml) was added and extraction was performed with ethyl acetate (20 ml×3 times). The extracted organic layer was washed with water (100 ml×2 times) and then with saturated brine, dried over anhydrous sodium sulfate, and then filtered and concentrated. Purification was performed by silica gel column chromatography (ethyl acetate/methanol=1/0→4/1) to obtain amino[({1-[(3,4-dichlorophenyl)methyl](4-piperidyl)}methyl)amino]methane-1-thione. The compound was identified by LC-MS.

Yield: 284 mg (86%), M+1=332.0.

Reference Example 2-4

Synthesis of ({1-[(3,4-dichlorophenyl)methyl](4-piperidyl)}methyl)(iminomethylthiomethyl)amine After dissolving amino [({1-[(3,4-dichlorophenyl)methyl](4-piperidyl)}methyl)amino]methane-1-thione (148 mg, 0.446 mmol) in tetrahydrofuran (5 ml), methyl iodide (71 mg, 0.491 mmol) was added and the mixture was stirred at room temperature overnight. Upon completion of the reaction, the mixture was concentrated and dried under reduced pressure in a desiccator to obtain ({1-[(3,4-dichlorophenyl)methyl](4-piperidyl)}methyl) (iminomethylthiomethyl)amine. The compound was identified by LC-MS.

Yield: 211 mg (quantitative), M+1=346.1.

Example 2-1

Synthesis of 2-[({1-[(3,4-dichlorophenyl)methyl]-4-piperidyl}methyl)amino]hydroquinazolin-4-one After dissolving ({1-[(3,4-dichlorophenyl)methyl](4-piperidyl)}methyl)(iminomethylthiomethyl)amine (70 mg, 0.148 mmol) and isatoic anhydride (27 mg, 0.163 mmol) in DMF (1.5 ml), the mixture was stirred at 80° C. for 2 hours. A 2N aqueous sodium hydroxide solution (1 ml) was added to suspend the reaction. Water (15 ml) was added, and extraction was performed with ethyl acetate (15 ml×3 times). The extracted organic layer was washed with water (50 ml×2 times) and then with saturated brine, dried over anhydrous sodium sulfate, and then filtered and concentrated. Purification was performed by silica gel column chromatography (ethyl acetate/methanol=1/0→4/1) to obtain 2-[({1-[(3,4-dichlorophenyl)methyl]-4-piperidyl}methyl)amino]hydroquinazolin-4-one. The compound was identified by LC-MS.

Yield: 27 mg (44%), M+1=417.1.

Examples 2-2 and 2-3

Compound Nos. 2-2 and 2-3 were synthesized by the same method as Example 2-1, using the corresponding reactants. The results are shown in Table 15.

Synthesis of Quinazolinone Derivatives (2)

Reference Example 2-5

Synthesis of 2-methylthiohydroquinazolin-4-one

After dissolving 2-mercapto-4(3H)quinazolinone (25 mmol, 4.45 g) in a mixed aqueous solution of water (100 ml) and 2N NaOH (1.1 eq, 14 ml), MeI (1.1 eq, 1.72 ml) was added and the mixture was stirred at room temperature for 2 hours and 30 minutes. Upon completion of the reaction, the mixture was filtered, 180 ml of water was added for washing, and drying was performed in a desiccator for 4 hours. The compound was identified by LC-MS.

quantitative yield, Yield: 5.5 g, M+1=192.9.

Example 2-4

Synthesis of 2-({[1-(naphthylmethyl)-4-piperidyl]methyl}amino)hydroquinazolin-4-one After dissolving [1-(naphthylmethyl)-4-piperidyl]methylamine (4.4 mmol, 1122 mg) in DMA (15 ml), NEt₃ (1.5 eq, 920 μL) and 2-methylthiohydroquinazolin-4-one (2 eq; 1690 mg) were added. The mixture was stirred at 100° C. overnight, and upon completion of the reaction, it was extracted with ethyl acetate (50 ml×3 times), washed with water (150 ml×2 times), and dried over sodium sulfate. After concentration, purification was performed by column chromatography (Hex/AcOEt=1/9, AcOEt×2). The compound was identified by LC-MS.

Yield: 159 mg (10%), M+1=399.3.

Synthesis of quinazolinone derivatives (3)

Synthesis of [2-[(4-piperidylmethyl)amino]hydroquinazolin-4-one hydrochloride

Reference Example 2-6

Preparation of 1-Boc-4-aminomethylpiperidine

After dissolving 4-aminomethylpiperidine (10.0 g, 87.6 mmol) in toluene (175 mL), benzaldehyde (8.90 mL, 87.6 mmol) was added, a Dean-Stark trap was fitted, and the mixture was heated to reflux for 1 hour. The reaction mixture was cooled to room temperature, and then di-t-butyl dicarbonate (20.1 mL, 87.6 mmol) was added in 4 portions over a period of one hour, and the mixture was stirred overnight. The reaction mixture was concentrated under reduced pressure, and then aqueous potassium hydrogen sulfate (1.0 M, 140 mL, 140 mmol) was added to the resulting residue in an ice bath and the mixture was stirred for 2 hours. The aqueous solution was washed with diethyl ether (100 mL), and 1N aqueous sodium hydroxide was added to adjust the pH to approximately 7. This aqueous solution was washed with ethyl acetate (200 mL), and then a 1N aqueous sodium hydroxide solution was added to adjust the pH to approximately 12 and extraction was performed with ethyl acetate (100 mL×3 times). The obtained organic layer was washed with saturated brine and then dried over anhydrous sodium sulfate. It was then concentrated under reduced pressure, and vacuum dried. The compound was identified by LC-MS.

Yield: 16.04 g (85%), M+23=237.1.

Reference Example 2-7

Synthesis of [({[fluoren-9-ylmethoxy]carbonylamino}thioxomethyl)amino]methyl]piperidinecarboxylic acid tert-butyl ester After dissolving 1-Boc-4-aminomethylpiperidine (2140 mg, 10 mmol) in tetrahydrofuran (25 ml), FmocNCS (3091 mg, 11 mmol) was added and the mixture was stirred at room temperature overnight. Upon completion of the reaction, the reaction mixture was concentrated, and then purified by silica gel column chromatography (hexane/ethyl acetate=85/15→4/1) to obtain [({[fluoren-9-ylmethoxy]carbonylamino}thioxomethyl)amino]methyl]piperidinecarboxylic acid tert-butyl ester. The compound was identified by LC-MS.

Yield: 4445 mg (90%), M+1=496.2.

Reference Example 2-8

Synthesis of 4-{[(aminothioxomethyl)amino]methyl}piperidinecarboxylic acid tert-butyl ester After dissolving ({[fluoren-9-ylmethoxy]carbonylamino}thioxomethyl)amino]methyl]piperidinecarboxylic acid tert-butyl ester (2000 mg, 4.04 mmol) in DMF (20 ml), piperidine (7.99 ml, 80.8 mmol) was added and the mixture was stirred at room temperature overnight. Upon completion of the reaction, water (100 ml) was added and extraction was performed with ethyl acetate (100 ml×3 times). The extracted organic layer was washed with water (300 ml×2 times) and saturated brine, and then dried over anhydrous sodium sulfate, filtered out and concentrated. Purification was performed by silica gel column chromatography (hexane/ethyl acetate=1/1→ethyl acetate) to obtain 4-{[(aminothioxomethyl)amino]methyl}piperidinecarboxylic acid tert-butyl ester. The compound was identified by LC-MS.

Yield: 1075 mg (98%), M+1=274.1.

Reference Example 2-9

Synthesis of 4-{[(iminomethylthiomethyl)amino]methyl}piperidinecarboxylic acid tert-butyl ester hydroiodide After dissolving 4-{[(aminothioxomethyl)amino]methyl}piperidinecarboxylic acid tert-butyl ester (1075 mg, 3.94 mmol) in tetrahydrofuran (30 ml), methyl iodide (616 mg, 4.33 mmol) was added and the mixture was stirred at room temperature overnight. Upon completion of the reaction, the mixture was concentrated and dried under reduced pressure in a desiccator to obtain 4-{[(iminomethylthiomethyl)amino]methyl}piperidinecarboxylic acid tert-butyl ester hydroiodide. The compound was identified by LC-MS.

Yield: 1597 mg (98%), M+1=288.1.

Reference Example 2-10

Synthesis of 4-{[(4-oxohydroquinazolin-2-yl)amino]methyl}piperidinecarboxylic acid tert-butyl ester After dissolving 4-{[(iminomethylthiomethyl)amino]methyl}piperidinecarboxylic acid tert-butyl ester hydroiodide (1722 mg, 4.15 mmol) in DMF (20 ml), triethylamine (0.868 ml, 6.23 mmol) and isatoic anhydride (2029 mg, 12.45 mmol) were added, and the mixture was stirred at 80° C. for 2 hours. A 2N aqueous sodium hydroxide solution (10 ml) was added to suspend the reaction. Water (100 ml) was then added, and extraction was performed with ethyl acetate (100 ml×3 times). The extracted organic layer was washed with water (100 ml×2 times) and then with saturated brine, and was then dried over anhydrous sodium sulfate, filtered and concentrated. Purification was performed by silica gel column chromatography (hexane/ethyl acetate=1/1→1/2) to obtain 4-{[(4-oxohydroquinazolin-2-yl)amino]methyl}piperidinecarboxylic acid tert-butyl ester. The compound was identified by LC-MS.

Yield: 685 mg (46%), M+1=359.1.

Reference Example 2-11

Synthesis of 2-[(4-piperidylmethyl)amino]hydroquinazolin-4-one hydrochloride

After dissolving 4-{[(4-oxohydroquinazolin-2-yl)amino]methyl}piperidinecarboxylic acid tert-butyl ester (685 mg, 1.91 mmol) in methanol (5 ml), 4N hydrochloric acid dioxane (5 ml) was added and the mixture was stirred at room temperature overnight. Upon completion of the reaction, the mixture was concentrated and dried under reduced pressure in a desiccator to obtain 2-[(4-piperidylmethyl)amino]hydroquinazolin-4-one hydrochloride. The compound was identified by LC-MS.

Yield: 581 mg (quantitative), M+1=259.1.

Synthesis of [2-[(4-piperidylmethyl)amino]hydroquinazolin-4-one

Reference Example 2-12

Synthesis of (1-benzyl-4-piperidyl)methylamine

After dissolving 4-aminomethylpiperidine (5.754 ml, 50 mmol) in acetonitrile (200 ml), potassium carbonate (13.82 g, 100 mmol) and benzyl chloride (17.13 g, 150 mmol) were added and the mixture was stirred at 60° C. overnight. Upon completion of the reaction, the reaction mixture was filtered and the solvent was distilled off. A developing solvent (CH$_2$Cl$_2$/MeOH/NEt$_3$ 90/5/5) was used for purification by silica gel column chromatography to obtain (1-benzyl-4-piperidyl)methylamine. The compound was identified by LC-MS.

Yield: 9.277 g (91%), M+1=205.2.

Reference Example 2-13

Synthesis of 2-({[1-benzyl-4-piperidyl]methyl}amino)hydroquinazolin-4-one

The (1-benzyl-4-piperidyl)methylamine was used to synthesize 2-({[1-benzyl-4-piperidyl]methyl}amino)hydroquinazolin-4-one in the same manner as Reference Examples 2-7 (Yield: 84%), 2-8 (Yield: 73%), 2-9 (quantitative yield) and 2-10 (Yield: 73%).

Reference Example 2-14

Synthesis of 2-[(4-piperidylmethyl)amino]hydroquinazolin-4-one

After dissolving 2-({[1-benzyl-4-piperidyl]methyl}amino)hydroquinazolin-4-one (880 mg, 2.53 mmol) in methanol (80 mL), nitrogen substitution was carried out. Palladium hydroxide (100 mg) was added and the mixture was stirred at 60° C. for 4 hours under a hydrogen atmosphere. The reaction mixture was cooled to room temperature, nitrogen substitution was carried out, and filtration was performed through celite. The filtrate was concentrated under reduced pressure to obtain 2-[(4-piperidylmethyl)amino]hydroquinazolin-4-one. The compound was identified by LC-MS.

Yield: 588 mg (86%), M+1=259.1.

Example 2-5

Synthesis of 2-[({1-[(2-chlorophenyl)methyl]-4-piperidyl}methyl)amino]hydroquinazolin-4-one After dissolving 2-[(4-piperidylmethyl)amino]hydroquinazolin-4-one hydrochloride (0.1 mmol, 33 mg, Reference Example 2-11) or 2-[(4-piperidylmethyl)amino]hydroquinazolin-4-one (0.1 mmol) in DMF/acetic acid (10/1, 1 ml), 2-chlorobenzaldehyde (0.3 mmol, 0.034 ml) and NaBH(OAc)$_3$ (0.3 mmol, 64 mg) were added and the mixture was stirred at room temperature overnight. Next, 1 ml of MeOH was added to suspend the reaction. The reaction mixture was then poured into SCX (Bond Elute SCX500MG). After washing with CHCl$_3$/MeOH (=1/1, 5 ml×2 times), elution was performed with 5 ml of a 2N NH$_3$/MeOH solution. A centrifugal concentrator was used for distilling off of the solvent to obtain 2-[({1-[(2-chlorophenyl)methyl]-4-piperidyl}methyl)amino]hydroquinazolin-4-one.

Yield: 15 mg (39%), Purity: 92-96% M+1=383.1.

Examples 2-6 to 2-30, Examples 2-186 to 2-200]

Compound Nos. 2-6 to 2-30 and Compound Nos. 2-186 to 2-200 were synthesized by the same method as Example 2-5, using the corresponding reactants. The results are shown in Table 15.

Synthesis of
[2-[(4-piperidylmethyl)amino]hydroquinazolin-4-one
hydrochloride analogs Reference Example 2-15

Synthesis of 2-amino-5-(methoxycarbonyl)benzoic acid

After dissolving 2-amino-5-iodobenzoic acid (4 mmol, 1052 mg) in DMF (10 ml) and MeOH (5 ml), NEt$_3$ (3 eq, 1.67 ml) was added. Next, palladium acetate (0.1 eq, 90 mg) and dppp (0.1 eq, 165 mg) were added, carbon monoxide substitution was carried out, and the mixture was stirred at 80° C. for 5 hours. Upon completion of the reaction, acetic acid (2.5 ml) was added to suspend the reaction. Water (50 ml) was added, and extraction was performed with ethyl acetate (50 ml×3 times). The organic layer was washed with water (100 ml×2 times) and then dried over sodium sulfate. After concentration, a developing solvent (Hex/AcOEt=4/1→1/1) was used for purification by silica gel chromatography to obtain 2-amino-5-(methoxycarbonyl)benzoic acid. The compound was identified by LC-MS.

Yield: 618 mg (79%), M+1=196.0.

Synthesis of Substituted Isatoic Anhydrides (1)

Reference Example 2-16

Synthesis of 2-(Boc)amino-6-chlorobenzoic acid

After dissolving 2-amino-6-chlorobenzoic acid (1.13 g, 6.59 mmol) in tetrahydrofuran (5.0 mL), a solution of sodium bistrimethylsilylamide/1.0 M in THF (19.8 mL, 19.8 mmol) was added dropwise. After stirring this mixture for 15 minutes, a solution of (Boc)$_2$O (1.82 mL, 7.91 mmol) in tetrahydrofuran (2.0 mL) was added dropwise, and the mixture was stirred for 3 hours. Water (20 mL) and 1N hydrochloric acid (about 25 mL) were added to the reaction mixture to adjust the pH to approximately 4. It was then extracted with ethyl acetate (40 mL×3 times), and the obtained organic layer was washed with water (50 mL×2 times) and saturated brine (50 mL), and then dried over anhydrous magnesium sulfate. The dried product was concentrated under reduced pressure to obtain a concentrated residue, which was then purified by silica gel column chromatography (methylene chloride:methanol:acetic acid=95:5:1) to obtain 2-(Boc)amino-6-chlorobenzoic acid. The compound was identified by LC-MS and NMR.

Yield: 1.62 g (90%), M+23=294.0.
$^1$H-NMR (270 MHz, CDCl$_3$): δ8.40(1H, s), 8.04(1H, d, J=8.2 Hz), 7.35(1H, t, J=8.2 Hz), 7.13(1H, d, J=8.2 Hz), 1.52(9H, s) ppm.

The following intermediates were synthesized by the same method as Reference Example 2-16, using the corresponding reactants.

2-(Boc)amino-3-chlorobenzoic acid: Yield=3.58 g (70%), M+23=294.0.

2-(Boc)amino-5-methoxycarbonylbenzoic acid: Yield=988 mg (49%), M+1=296.1.

Reference Example 2-17]

Synthesis of 5-chloroisatoic anhydride

After suspending 2-(Boc)amino-6-chlorobenzoic acid (1.51 g, 5.56 mmol) in toluene (20 mL), the mixture was heated to reflux. Oxalyl chloride (0.572 mL, 6.67 mmol) was added dropwise thereto, and the mixture was vigorously stirred for 10 minutes. After cooling the reaction mixture on ice, the precipitated crystals were filtered out, washed with n-hexane and dried in a desiccator to obtain 5-chloroisatoic anhydride.

Yield: 769 mg (70%), M+1=198.0.
$^1$H-NMR (270 MHz, DMSO-d6): δ11.8(1H, s), 7.65(1H, t, J=8.2 Hz), 7.30(1H, d, J=8.2 Hz), 7.10(1H, d, J=8.2 Hz) ppm.

The following intermediates were synthesized by the same method as Reference Example 2-17, using the corresponding reactants.

8-Chloroisatoic anhydride: Yield=1.42 g (55%), M+1=197.9.

6-Methoxycarbonylisatoic anhydride: Yield=397 mg (57%), M+1=222.0.

6-Trifluoromethylisatoic anhydride: Yield=1.52 g (50%), M+1=232.0.

Synthesis of Substituted Isatoic Anhydrides (2)

Reference Example 2-18

Synthesis of 6-(trifluoromethoxy)isatoic anhydride

After dissolving 5-(trifluoromethoxy)anthranilic acid (2.221 g, 10.04 mmol) in THF (25 mL), triphosgene (1.08 g) was added and the mixture was stirred at room temperature overnight. Upon completion of the reaction, the solvent was removed and the residue was dried under reduced pressure. It was then washed with acetone and hexane, and subsequently dried under reduced pressure in a desiccator to obtain 6-(trifluoromethoxy)isatoic anhydride. The compound was identified by LC-MS.

Yield: 1.516 g (61%), M+1=248.0.

The following intermediates were synthesized in the same manner as Reference Example 2-18 using the corresponding reactants.

6-Nitroisatoic anhydride: Yield=0.889 g (43%), M+1=208.9.

6-Methylisatoic anhydride: Yield=1.251 g (70%), M+1–178.0.

5-Carboxylisatoic anhydride: Yield=1.352 g (65%), M+1=208.0.

6-Fluoroisatoic anhydride: M+1=182.0.

6-Hydroxyisatoic anhydride: M+1=180.0.

6-Methoxyisatoic anhydride: M+1=194.0.

5-Methylisatoic anhydride: M+1=178.0.

6-Acetamideisatoic anhydride: Yield=0.4 g (9%),
$^1$H-NMR (200 MHz, DMSO): δ2.05(s, 3H), 7.05(d, 1H), 7.85(dd, 1H), 8.25(d, 1H), 10.15(s, 1H).

Synthesis of Substituted Isatoic Anhydrides (3)

Reference Example 2-19

Synthesis of N-(3,4-dimethylphenyl)-2-hydroxyimino-acetamide

To a mixed solution comprising a solution of chloral (73.8 g, 0.41 mol) and sodium sulfate (1066 g) in water (2.5 ml) and a solution of 3,4-dimethylamine (50 g, 0.41 mol) and concentrated hydrochloric acid (35.4 ml) in water (600 ml) there was added a solution of hydroxylamine (90 g, 0.41 mmol) in water (500 ml), and the mixture was stirred for one hour while heating to reflux. The obtained hot solution was filtered, and the obtained precipitate was washed with water and dichloromethane to obtain N-(3,4-dimethylphenyl)-2-hydroxyimino-acetamide.

Yield: 63 g (80%).

Reference Example 2-20

Synthesis of 4,5-dimethyl-1H-indole-2,3-dione

To a solution of concentrated sulfuric acid (85 ml) in water (17 ml) there was slowly added N-(3,4-dimethylphenyl)-2-hydroxyimino-acetamide (30 g, 0.156 mmol), and the mixture was stirred at 85° C. for 2 hours. The obtained solution was poured into ice water, and the precipitated orange solid was filtered out. The obtained solid was dissolved in 10% aqueous sodium hydroxide, active carbon was added, and the mixture was stirred. The obtained solution was filtered, and acetic acid was used for acidification to obtain 4,5-dimethyl-1H-indole-2,3-dione as crystals.

Yield: 9:8 g (30%)
$^1$H-NMR (200 MHz, DMSO-d6): 2.25(s, 3H), 2.55(s, 3H), 6.95(d, 2H), 7.50(d, 2H), 10.55(bs, 1H)

Reference Example 2-21

Synthesis of 6-amino-2,3-dimethylbenzoic acid

A solution of 4,5-dimethyl-1H-indole-2,3-dione (9.8 g, 0.056 mmol) and sodium hydroxide (8.1 g, 0.2 mol) in water (80 ml) was heated to 85° C., and then 10% aqueous hydrogen peroxide (43 ml) was slowly added. The obtained solution was stirred at 85° C. for 2 hours and then cooled to room temperature and filtered. Sulfuric acid was used for acidification of the filtrate to obtain 6-amino-2,3-dimethylbenzoic acid as crystals.

Yield: 3.6 g (38%)
$^1$H-NMR (200 MHz, DMSO-d6): 2.05(s, 3H), 2.15(s, 3H), 6.50(d, 2H), 6.92(d, 2H)

Reference Example 2-22

Synthesis of 5,6-dimethylisatoic anhydride 5,6-Dimethylisatoic anhydride was synthesized by the same method as Reference Example 2-18 using 6-amino-2,3-dimethylbenzoic acid (1 g, 6 mmol).

Yield: 500 mg (92%)
$^1$H-NMR (200, DMSO): 2.25(s, 3H), 2.55(s, 3H), 6.92(d, 2H), 7.50(d, 2H), 10.65(bs, 1H)

The following isatoic anhydrides were synthesized by the same method as Reference Examples 2-19 to –22, using the corresponding reactants.

5-Methyl-6-fluoroisatoic anhydride:

$^1$H-NMR (200 MHz, DMSO-d6): 2.45(s, 3H), 6.75(dd, 1H), 7.45(dd, 1H), 11.0(bs, 1H)

5-Methyl-6-bromoisatoic anhydride:

$^1$H-NMR (200, DMSO): 2.75(s, 3H), 6.85(d, 1H), 7.95(d, 1H), 10.75(bs, 1H)

6-(N,N-dimethylaminosulfonyl)isatoic anhydride:

$^1$H-NMR (200 MHz, DMSO-d6): 2.65(s, 6H), 7.35(d, 1H), 8.05(s, 1H), 8.15(d, 1H), 11.2(bs, 1H)

6-Methoxy-7-methylisatoic anhydride:

M+1=208.0

5-Methyl-6-methoxyisatoic anhydride:

$M$+1=208.0

6,7-Dimethylisatoic anhydride:

$^1$H-NMR (200, DMSO): 2.24(s, 3H), 2.29(s, 3H), 6.91(s, 1H), 7.66(s, 1H), 10.60(bs, 1H).

5,7-Dimethylisatoic anhydride:

$^1$H-NMR (200 MHz, DMSO-d6): 6.91(s, 1H), 6.79(s, 1H), 2.56(s, 3H), 2.32(s, 3H)

6-Ethylisatoic anhydride:

$^1$H-NMR (200, DMSO): 7.73(s, 1H), 7.65(d, 1H), 7.09(d, 1H), 2.64(q, 2H), 1.18(t, 3H)

6-Ethoxyisatoic anhydride:

$^1$H-NMR (200 MHz, DMSO-d6): 1.35(t, 3H), 4.05(q, 2H), 7.05(d, 1H), 7.35(d, 1H), 7.45(dd, 1H), 10.5(bs, 1H)

5-Methyl-8-fluoroisatoic anhydride:

$^1$H-NMR (200 MHz, DMSO-d6): 2.56(s, 3H), 7.05(dd, 1H), 7.55(dd, 1H)

5,8-Dimethylisatoic anhydride:

$^1$H-NMR (200 MHz, DMSO-d6): 2.27(s, 3H), 2.56(s, 3H), 7.00(d, 1H), 7.45(d, 1H)

6-Isopropylisatoic anhydride:

$^1$H-NMR (200, DMSO): 7.73(s, 1H), 7.65(d, 1H), 7.10(d, 1H), 2.95(h, 1H), 1.20(d, 6H)

6-Sulfonylphenylisatoic anhydride:

$^1$H-NMR (200 MHz, DMSO-d6): 7.35(d, 1H), 7.65(m, 3H), 8.00(m, 2H), 8.25(dd, 1H), 8.35(d, 1H), 11.30(s, 1H)

Synthesis of Substituted Isatoic Anhydrides (4)

Reference Example 2-23

Synthesis of 2-amino-5-methylsulfanylbenzoic acid

A 4N aqueous sodium hydroxide solution (42 m) was added to an aqueous solution (500 ml) containing 5-chloro-2-nitrobenzoic acid (50 g, 0.25 mmol). After adding a solution of Na$_2$S (66 g, 0.8 mol) in water (150 ml) to the obtained solution, the mixture was stirred at 55° C. for 2.5 hours. Next, a 20% aqueous sodium hydroxide solution (50 ml) and dimethylsulfuric acid (63 ml, 0.66 mmol) were added to the solution, and the mixture was stirred at 80° C. for 1 hour. Hydrochloric acid was added to the resulting solution, and the separated precipitate was filtered out and washed with ether to obtain 2-amino-5-methylsulfanylbenzoic acid.

Yield: 14 g (26%)

Reference Example 2-24

Synthesis of 2-amino-5-methylsulfonylbenzoic acid m-Chloroperbenzoic acid (42.7 g, 0.165 mmol) was added to a solution of 2-amino-5-methylsulfanylbenzoic acid (12 g, 0.055 mol) in dichloromethane and acetone, and the mixture was stirred at room temperature for 3 hours. The precipitated solid was filtered out and washed with ether and dichloromethane to obtain 2-amino-5-methylsulfonylbenzoic acid.

Yield: 4 g (30%)

$^1$H-NMR (200 MHz, DMSO-d6): 3.15(s, 3H), 6.95(dd, 1H), 7.55(bs, 2H), 7.77(dd, 1H), 8.25(d, 1H)

Reference Example 2-25

Synthesis of 6-methanesulfonylisatoic anhydride

6-Methanesulfonylisatoic anhydride was synthesized by the same method as Reference Example 11 using 2-amino-5-methylsulfonylbenzoic acid (2 g, 9.6 mmol).

Yield: 1500 mg (66%)

$^1$H-NMR (200 MHz, DMSO-d6): 3.35(s, 3H), 7.35(d, 1H), 8.25(dd, 1H), 8.35(d, 1H), 9.90(s, 1H)

Reference Example 2-26

Synthesis of 2-[(4-piperidylmethyl)amino]hydroquinazolin-4-one hydrochloride analogs The following intermediates were synthesized in the same manner as Reference Example 2-10 and Reference Example 2-11, for the isatoic anhydrous synthesized by Reference Example 2-17 or 2-18.

5-Chloro-2-[(4-piperidylmethyl)amino]hydroquinazolin-4-one hydrochloride.

8-Chloro-2-[(4-piperidylmethyl)amino]hydroquinazolin-4-one hydrochloride.

6-Methoxycarbonyl-2-[(4-piperidylmethyl)amino]hydroquinazolin-4-one hydrochloride.

6-Trifluoromethyl-2-[(4-piperidylmethyl)amino]hydroquinazolin-4-one hydrochloride.

6-Trifluoromethoxy-2-[(4-piperidylmethyl)amino]hydroquinazolin-4-one hydrochloride.

6-Nitro-2-[(4-piperidylmethyl)amino]hydroquinazolin-4-one hydrochloride.

6-Methyl-2-[(4-piperidylmethyl)amino]hydroquinazolin-4-one hydrochloride.

5-Methoxycarbonyl-2-[(4-piperidylmethyl)amino]hydroquinazolin-4-one hydrochloride.

6-Fluoro-2-[(4-piperidylmethyl)amino]hydroquinazolin-4-one hydrochloride.

6-Hydroxy-2-[(4-piperidylmethyl)amino]hydroquinazolin-4-one hydrochloride.

6-Methoxy-2-[(4-piperidylmethyl)amino]hydroquinazolin-4-one hydrochloride.

5-Methyl-2-[(4-piperidylmethyl)amino]hydroquinazolin-4-one hydrochloride.

Examples 2-201 to 2-250, 499, 511, 513, 565

Compound Nos. 2-201 to 2-250, 499, 511, 513 and 565 were synthesized by the same method as Example 2-5, using the corresponding synthesized 2-[(4-piperidylmethyl)amino] hydroquinazolin-4-one hydrochloride analogs and reactants of Reference Examples 2-15 to 2-19. The results are shown in Table 15.

Synthesis of 3-N-alkylquinazolinone derivatives

Reference Example 2-27

Synthesis of 4-({[(methylamino)thioxomethyl]amino}methyl) piperidine carboxylic acid tert-butyl ester After dissolving 1-Boc-4-aminomethylpiperidine (642 mg, 3 mmol) in THF (8 ml), methyl isothiocyanate (241 mg, 3.3 mmol) was added and the mixture was stirred at room temperature overnight. Upon completion of the reaction, purification was performed by silica gel column chromatography (Hex/AcOEt=1/4) to obtain 4-({[(methylamino)thioxomethyl]amino}methyl)piperidine carboxylic acid tert-butyl ester. The compound was identified by LC-MS.

Yield: 839 mg (98%), M+1=288.1.

Reference Example 2-28

Synthesis of 3-methyl-2-[(4-piperidylmethyl)amino]-3-hydroquinazolin-4-one hydrochloride 3-Methyl-2-[(4-piperidylmethyl)amino]-3-hydroquinazolin-4-one hydrochloride was synthesized in the same manner as Reference Example 2-9 (Yield: 1171 mg (94%)), Refer ence Example 2-10 (Yield: 331 mg (33%)) and Reference Example 2-11 (Yield: 116 mg, quantitative).

Yield: 116 mg (quantitative), M+1=273.1.

Examples 2-492 to 2-495

Compound Nos. 2-492 to 2-495 were synthesized by the same method as Example 2-5, using the corresponding reactants for the compounds synthesized by Reference Examples 2-20 and 2-21. The results are shown in Table 15.

TABLE 15

| Compound No. 2- | Yield (mg) | Yield (%) | MW | M + 1 |
|---|---|---|---|---|
| 1 | 27.0 | 44 | 416.1 | 417.1 |
| 2 | 25.0 | 38 | 450.1 | 453.2(Cl × 3) |
| 3 | 4.1 | 6 | 432.2 | 433.2 |
| 4 | 159.0 | 10 | 398.2 | 399.3 |
| 5 | 15.0 | 39 | 382.1 | 383.1 |
| 6 | 21.0 | 55 | 382.1 | 383.1 |
| 7 | 25.0 | 65 | 382.1 | 383.1 |
| 8 | 23.3 | 92 | 378.2 | 379.1 |
| 9 | 36.0 | 100 | 378.2 | 379.1 |
| 10 | 22.6 | 97 | 376.2 | 377.2 |
| 11 | 23.2 | 97 | 398.2 | 399.1 |
| 12 | 25.3 | 95 | 442.1 | 443.0 |
| 13 | 27.7 | 100 | 456.1 | 458.1(Br) |
| 14 | 19.3 | 72 | 444.1 | 445.0 |
| 15 | 24.8 | 97 | 426.1 | 427.1 |
| 16 | 23.3 | 90 | 432.1 | 433.1 |
| 17 | 23.3 | 97 | 400.1 | 401.1 |
| 18 | 24.3 | 90 | 401.2 | 402.2 |
| 19 | 29.1 | 100 | 404.2 | 405.2 |
| 20 | 11.9 | 50 | 394.2 | 395.2 |
| 21 | 13.1 | 55 | 393.2 | 394.2 |
| 22 | 12.1 | 53 | 378.2 | 379.2 |
| 23 | 17.0 | 71 | 398.2 | 399.2 |
| 24 | 12.5 | 60 | 348.2 | 349.2 |
| 25 | 7.6 | 35 | 362.2 | 363.2 |
| 26 | 1.6 | 3 | 476.0 | 479.0(Br) |
| 27 | 6.0 | 15 | 389.2 | 390.2 |
| 28 | 12.0 | 30 | 466.1 | 467.2 |
| 29 | 12.0 | 28 | 466.1 | 467.1 |
| 30 | 14.0 | 40 | 398.2 | 399.2 |
| 186 | 15.0 | 57 | 432.1 | 433.0 |
| 187 | 25.8 | 95 | 443.1 | 444.1 |
| 188 | 25.0 | 96 | 428.2 | 429.1 |
| 189 | 21.6 | 85 | 416.1 | 417.1 |
| 190 | 22.6 | 80 | 460.1 | 463.0(Br, Cl) |
| 191 | 24.4 | 93 | 427.1 | 428.1 |
| 192 | 26.6 | 96 | 412.2 | 413.1 |
| 193 | 21.3 | 75 | 466.1 | 467.1 |
| 194 | 17.2 | 65 | 435.2 | 436.2 |
| 195 | 24.2 | 90 | 438.1 | 439.1 |
| 196 | 21.4 | 92 | 382.2 | 383.1 |
| 197 | 22.5 | 90 | 410.2 | 411.1 |
| 198 | 16.5 | 57 | 476.1 | 479(Br, Cl) |
| 199 | 7.8 | 30 | 432.2 | 433.1 |
| 200 | 6.3 | 26 | 396.2 | 397.1 |
| 201 | 1.0 | 5 | 466.1 | 469.1(Cl × 3) |
| 202 | 4.7 | 34 | 462.1 | 463.0 |
| 203 | 4.0 | 21 | 490.1 | 491.1 |
| 204 | 4.8 | 34 | 466.1 | 469.1(Cl × 3) |
| 205 | 2.0 | 41 | 490.1 | 491.0 |
| 206 | 2.5 | 14 | 466.1 | 467.0 |
| 207 | 2.8 | 14 | 516.1 | 517.1 |
| 208 | 2.9 | 15 | 490.1 | 491.1 |
| 209 | 3.9 | 19 | 500.1 | 501.1 |
| 210 | 2.4 | 12 | 446.1 | 447.1 |
| 211 | 5.0 | 26 | 450.1 | 451.1 |
| 212 | 2.5 | 13 | 448.1 | 449.0 |
| 213 | 4.0 | 9 | 477.1 | 478.0 |
| 214 | 20.0 | 37 | 468.1 | 469.1 |
| 215 | 7.0 | 13 | 450.1 | 451.0 |
| 216 | 2.8 | 6 | 446.1 | 447.1 |
| 217 | 3.0 | 8 | 457.1 | 458.1 |
| 218 | 2.2 | 13 | 432.1 | 433.0 |

TABLE 15-continued

| Compound No. 2- | Yield (mg) | Yield (%) | MW | M + 1 |
|---|---|---|---|---|
| 219 | 9.5 | 74 | 428.2 | 429.3 |
| 220 | 5.5 | 31 | 456.2 | 457.1 |
| 221 | 5.2 | 40 | 432.1 | 433.1 |
| 222 | 3.1 | 68 | 456.2 | 457.2 |
| 223 | 6.7 | 40 | 432.1 | 433.1 |
| 224 | 5.0 | 27 | 482.1 | 483.1 |
| 225 | 3.5 | 20 | 456.2 | 457.2 |
| 226 | 3.4 | 18 | 466.1 | 467.1 |
| 227 | 3.0 | 17 | 412.2 | 413.1 |
| 228 | 5.9 | 33 | 416.1 | 417.0 |
| 229 | 4.0 | 23 | 432.2 | 433.1 |
| 230 | 2.0 | 23 | 428.2 | 429.2 |
| 231 | 1.0 | 6 | 456.2 | 457.2 |
| 232 | 1.6 | 9 | 432.2 | 433.2 |
| 233 | 1.7 | 9 | 456.2 | 457.3 |
| 234 | 7.2 | 43 | 432.2 | 433.1 |
| 235 | 8.5 | 46 | 482.2 | 483.1 |
| 236 | 2.6 | 15 | 456.2 | 457.2 |
| 237 | 2.0 | 11 | 466.2 | 467.2 |
| 238 | 3.7 | 21 | 412.2 | 413.2 |
| 239 | 5.3 | 30 | 416.2 | 417.1 |
| 240 | 6.3 | 38 | 410.2 | 411.2 |
| 241 | 2.9 | 36 | 406.2 | 407.3 |
| 242 | 9.2 | 55 | 434.2 | 435.2 |
| 243 | 10.2 | 62 | 410.2 | 411.2 |
| 244 | 21.1 | 121 | 434.2 | 435.2 |
| 245 | 10.0 | 63 | 410.2 | 411.1 |
| 246 | 15.7 | 89 | 460.2 | 461.2 |
| 247 | 2.1 | 13 | 434.2 | 435.2 |
| 248 | 5.8 | 33 | 444.2 | 445.2 |
| 249 | 4.4 | 26 | 390.2 | 391.2 |
| 250 | 7.6 | 45 | 394.2 | 395.1 |
| 492 | 5.0 | 17 | 446.1 | 447.1 |
| 493 | 9.0 | 31 | 412.2 | 413.2 |
| 494 | 16.0 | 55 | 412.2 | 413.2 |
| 495 | 15.0 | 52 | 390.2 | 391.2 |
| 499 | 12.0 | 38 | 430.9 | 431.1 |
| 511 | 10.0 | 32 | 434.9 | 435.1 |
| 513 | 6.0 | 16 | 430.9 | 431.1 |
| 565 | 9.2 | 26 | 442.9 | 443.1 |

Synthesis of Benzothiadiazine Derivatives

Reference Example 3-1

Synthesis of 7-fluoro-2H,4H-benzo[e]1,2,4-thiadiazine-1,1,3-trione

After dissolving chlorosulfonyl isocyanate (3.29 mL, 37.8 mmol) in nitroethane (45 mL), the mixture was cooled to −80° C. A solution of 4-fluoroaniline (3.50 g, 31.5 mmol) in nitromethane (5 mL) was then added dropwise thereto over a period of 10 minutes. The reaction mixture was heated to 0° C., and aluminum chloride (5.33 g, 40.0 mmol) was added. After heating to reflux for 30 minutes, the reaction mixture was cooled to room temperature and then poured into ice water (120 mL). The precipitated crystals were filtered out and dried to obtain 7-fluoro-2H,4H-benzo[e]1,2,4-thiadiazine-1,1,3-trione.

Yield: 3.72 g (55%), M+1=217.0.

7-Methyl-2H,4H-benzo[e]1,2,4-thiadiazine-1,1,3-trione (4.24 g, 67%), 7-ethyl-2H,4H-benzo[e]1,2,4-thiadiazine-1,1,3-trione (2.6 g, 37%) and 7-methoxy-2H,4H-benzo[e]1,2,4- thiadiazine-1,1,3-trione (1.09 g, 16%) were synthesized in the same manner as Reference Example 3-1.

Reference Example 3-2

Synthesis of 2-amino-5-fluorobenzenesulfonamide

After suspending 7-fluoro-2H,4H-benzo[e]1,2,4-thiadiazine-1,1,3-trione (3.00 g, 13.9 mmol) in 50% sulfuric acid (90 mL), the mixture was stirred at 130° C. for 1 hour. The reaction mixture was cooled in an ice bath while adding 40% aqueous sodium hydroxide for neutralization. The aqueous solution was concentrated under reduced pressure to 200 mL, and the precipitate was filtered out. It was then suspended in ethyl acetate (100 mL), and the insoluble portion was filtered out. The filtrate was concentrated under reduced pressure and dried to obtain 2-amino-5-fluorobenzenesulfonamide.

Yield: 2.27 g (86%), M+1=191.0.

2-Amino-5-methylbenzenesulfonamide (Yield: 958 mg (55%)), 2-amino-5-ethylbenzenesulfonamide (Yield: 1.4 g (64%)) and 2-amino-5-methoxybenzenesulfonamide (Yield: 696 mg (72%)) were synthesized in the same manner as Reference Example 3-2.

Reference Example 3-3

Synthesis of 2-bromo-4,5-dimethylnitrobenzene

After measuring out 10.02 g of 4,5-dimethyl-2-nitroaniline (60.3 mmol) into a 300 mL round-bottomed flask equipped with a magnetic stirrer, 30 mL of 48% aqueous hydrobromic acid and 30 mL of water were added, and the mixture was vigorously stirred. The suspension became orange. The orange suspension was directly cooled on an ice water-salt bath, and then an aqueous solution of 4.422 g (64.1 mmol) of sodium nitrite in 24 mL of water was added dropwise to the orange suspension while keeping the liquid temperature from exceeding 5° C. Completion of the dropwise addition resulted in conversion of the reaction mixture to a light brown solution. The light brown solution was stirred on the ice water bath.

Next, 30 mL of 48% aqueous hydrobromic acid and 11.85 (82.6 mmol) g of copper (I) bromide were placed in a 1 L Erlenmeyer flask equipped with a magnetic stirrer, and the previously obtained light brown solution was added dropwise over a period of 5 minutes while cooling and stirring on an ice water bath. After completion of the dropwise addition, the mixture was stirred for 20 minutes on the ice-water bath, and then heated on a 80° C. oil bath while vigorously stirring.

Heating was terminated after 1 hour, and upon stirring overnight at room temperature, the reaction mixture was extracted with ethyl acetate (300 mL×2 times), and the organic layers were combined and washed with 5N hydrochloric acid, saturated sodium bicarbonate water and saturated brine in that order. The organic layer was dried over anhydrous sodium sulfate, and then the desiccant was removed by filtration under reduced pressure and the filtrate was concentrated to obtain a yellowish brown solid. The yellowish brown solid was purified by silica gel column chromatography (Hex:EtOAc=10:1) to obtain light brown needle-like crystals. The light brown needle-like crystals were recrystallized from hexane to obtain 2-bromo-4,5-dimethylnitrobenzene as yellow needle-like crystals.

Yield: 6.637 g (47.9%)

$^1$H-NMR (270 MHz, CDCl$_3$): δ2.29(3H, s), 2.31(3H, s), 7.49 (1H, s), 7.69(1H, s).

Reference Example 3-4

Synthesis of 2-bromo-4,5-dimethylaniline

After measuring out 1.006 g (4.375 mmol) of 2-bromo-4,5-dimethylnitrobenzene into a 100 mL round-bottomed flask equipped with a magnetic stirrer, 10 mL of 2-methoxyethanol and 10 mL of water were added and the mixture was stirred to create a suspension. After adding 2.799 g (10.07 mmol) of sodium hydrosulfite thereto, it was heated on a 100° C. oil bath while vigorously stirring. After 2.5 hours, the resulting faint yellow suspension was heated and stirred, while adding 10 mL of water until the insoluble portion disappeared to produce a faint yellow solution. To the faint yellow solution there was added dropwise 10 mL of concentrated hydrochloric acid over a period of 5 minutes, after which the mixture was refluxed for 20 minutes.

Next, the temperature of the reaction mixture was lowered to room temperature, and upon adding sodium carbonate in powder form to neutralize the reaction mixture, a faint brownish white precipitate separated at approximately pH 7-8. The collected precipitate was dried to obtain 2-bromo-4,5-dimethylaniline as a white solid.

Yield: 0.832 g (95.0%).

$^1$H-NMR (270 MHz, CDCl$_3$): δ2.13(6H, s), 6.59 (1H, s), 7.16(1H, s).

Reference Example 3-5

Synthesis of 5-bromo-7,8-dimethyl-2H,4H-benzo[e]1,2,4-thiadiazine-1,1,3-trione

The title compound was obtained in the same manner as Reference Example 3-1.

Yield: 5.27 g (83%), M+1=304.9.

$^1$H-NMR (270 MHz, CD$_3$OD): δ7.69(1H, s), 2.55(3H, s), 2.31(3H, s)

Reference Example 3-6

Synthesis of 7,8-dimethyl-2H,4H-benzo[e]1,2,4-thiadiazine-1,1,3-trione

5-Bromo-7,8-dimethyl-2H,4H-benzo[e]1,2,4-thiadiazine-1,1,3-trione (5.27 g, 17.3 mmol) was suspended in methanol (60 mL), and then ammonium formate (5.45 g, 86.5 mmol, 5 eq) was added and nitrogen substitution was performed. Next, 10% palladium-carbon powder (1.84 g, 1.73 mmol, 10 mol %) was added and the mixture was heated to reflux for 4 hours. The reaction mixture was cooled to room temperature and filtered through celite. The filtrate was cooled on ice and the precipitated crystals were filtered out and dried to obtain 7,8-dimethyl-2H, 4H-benzo[e]1,2,4-thiadiazine-1,1,3-trione.

Yield: 3.66 g (94%), M+1=227.0.

$^1$H-NMR (270 MHz, CD$_3$OD): δ7.19(1H, d, J=8.3 Hz), 6.78 (1H, d, J=8.3 Hz), 2.57(3H, s), 2.26(3H, s).

Reference Example 3-7

Synthesis of 2-amino-5,6-dimethylbenzenesulfonamide

The title compound was obtained in the same manner as Reference Example 3-2.

Yield: 1.98 g (61%), M+1=201.1.

¹H-NMR (270 MHz, DMSO-d6): δ7.20(2H, s), 6.98(1H, d, J=8.4 Hz), 6.55(1H, d, J=8.4 Hz), 5.98(2H, s), 2.39(3H, s), 2.10(3H, s)

2-Amino-6-methylbenzenesulfonamide was synthesized in the same manner as Reference Examples 3-3 to 3-7, using 4-methyl-2-nitroaniline as the starting material.

Yield: 555 mg (45%).

¹H-NMR (270 MHz, DMSO): δ2.48(3H, s), 6.12(2H, s), 6.40(1H, d, J=7.0 Hz), 6.62(1H, d, J=8.1 Hz), 6.99-7.04(1H, dd, J=8.1 Hz, J=7.0 Hz), 7.19(2H, s)

Reference Example 3-8

Synthesis of 4-{[(7-fluoro-1,1-dioxo-4H-benzo[e]1,2,4-thiadiazin-3-yl)amino]methyl}piperidine carboxylic acid tert-butyl ester After dissolving 1-N-Boc-4-aminomethylpiperidine (1.08 g, 5.04 mmol) in acetonitrile (8.0 mL), the mixture was cooled to 0° C. A solution of 1,1'-thiocarbonyldiimidazole (988 mg, 5.54 mmol) and imidazole (103 mg, 1.51 mmol) in acetonitrile (10 mL) was added dropwise thereto, and the mixture was stirred at room temperature for 2 hours. Next, 2-amino-5-fluorobenzenesulfonamide (1.25 g, 6.55 mmol) and dimethylaminopyridine (739 mg, 6.05 mmol) were added to the reaction mixture, which was then stirred at 80° C. overnight. Diisopropylcarbodiimide (0.233 mL, 1.51 mmol) was added thereto, and the mixture was stirred for 1 hour. The reaction mixture was cooled to room temperature and then concentrated under reduced-pressure, and the residue was dissolved in ethyl acetate (50 mL). This was washed with water (20 mL) and saturated brine (20 mL), and then dried over anhydrous sodium sulfate. The residue obtained by concentration under reduced pressure was purified by silica gel column chromatography (n-hexane:ethyl acetate=3:2→2:3) to obtain 4-{[(7-fluoro-1,1-dioxo-4H-benzo[e]1,2,4-thiadiazin-3-yl)amino]methyl}piperidine carboxylic acid tert-butyl ester.

Yield: 1.66 g (80%), M-Boc+2H=313.1.

The following compounds were synthesized in the same manner as Reference Example 3-8.

4-7{[(1,1-Dioxo-4H-benzo[e]1,2,4-thiadiazin-3-yl)amino]methyl}piperidine carboxylic acid tert-butyl ester: Yield=132 mg (67%).

4-{[(7-Methyl-1,1-dioxo-4H-benzo[e]1,2,4-thiadiazin-3-yl)amino]methyl}piperidine carboxylic acid tert-butyl ester: Yield=681 mg (49%).

4-{[(7-Methoxy-1,1-dioxo-4H-benzo[e]1,2,4-thiadiazin-3-yl)amino]methyl}piperidine carboxylic acid tert-butyl ester: Yield=766 mg (63%).

4-{[(7-Ethyl-1,1-dioxo-4H-benzo[e]1,2,4-thiadiazin-3-yl)amino]methyl}piperidine carboxylic acid tert-butyl ester: Yield=525 mg (36%).

4-{[(8-Methyl-1,1-dioxo-4H-benzo[e]1,2,4-thiadiazin-3-yl)amino]methyl}piperidine carboxylic acid tert-butyl ester: Yield=203 mg (44%).

4-{[(7,8-Dimethyl-1,1-dioxo-4H-benzo[e]1,2,4-thiadiazin-3-yl)amino]methyl}piperidine carboxylic acid tert-butyl ester: Yield=175 mg (30%).

Reference Example 3-9

Synthesis of 7-fluoro-3-[(4-piperidylmethyl)amino]-4H-benzo[e]1,2,4-thiadiazine-1,1-dione hydrochloride 7-fluoro-3-[(4-piperidylmethyl)amino]-4H-benzo[e]1,2,4-thiadiazine-1,1-dione was obtained in the same manner as Reference Example 2-11. Yield: 497 mg (90%), M+1=313.1.

The following compounds were synthesized in the same manner as Reference Example 3-9.

7-Methyl-3-[(4-piperidylmethyl)amino]-4H-benzo[e]1,2,4-thiadiazine-1,1-dione hydrochloride: Yield=691 mg (quantitative).

3-[(4-Piperidylmethyl)amino]-4H-benzo[e]1,2,4-thiadiazine-1,1-dione hydrochloride: quantitative yield, Yield=116 mg, M+1=295.1.

7-Methoxy-3-[(4-piperidylmethyl)amino]-4H-benzo[e]1,2,4-thiadiazine-1,1-dione hydrochloride: Yield=505 mg (79%), M+1=325.0.

7-Ethyl-3-[(4-piperidylmethyl)amino]-4H-benzo[e]1,2,4-thiadiazine-1,1-dione hydrochloride: Yield=470 mg (quantitative, M+1=323.1).

8-Methyl-3-[(4-piperidylmethyl)amino]-4H-benzo[e]1,2,4-thiadiazine-1,1-dione hydrochloride: Yield=97 mg (63%), M+1=309.1.

7,8-Dimethyl-3-[(4-piperidylmethyl)amino]-4H-benzo[e]1,2,4-thiadiazine-1,1-dione hydrochloride: Yield=44 mg (89%), M+1=323.1.

Examples 3-1 to 3-10, 3-208, 220, 223, 235, 238, 368, 504, 505, 511, 523, 525 to 527, 555, 577

Compound Nos. 3-1 to 3-10, 3-208, 220, 223, 235, 238, 368, 504, 505, 511, 523, 525 to 527, 555 and 577 were synthesized in the same manner as Example 2-5, using the corresponding reactants for the compounds synthesized in Reference Examples 3-1 to 3-9. The results are shown in Table 16.

TABLE 16

| Compound No. 3- | Yield (mg) | Yield (%) | MW | M + 1 |
|---|---|---|---|---|
| 1 | 10.0 | 35 | 468.0 | 469.0 |
| 2 | 7.0 | 26 | 434.1 | 435.1 |
| 3 | 9.0 | 34 | 434.1 | 435.0 |
| 4 | 13.0 | 52 | 412.1 | 413.1 |
| 5 | 25.2 | 66.2 | 482.1 | 483.0 |
| 6 | 20.8 | 58.9 | 448.1 | 449.1 |
| 7 | 25.4 | 71.9 | 448.2 | 449.2 |
| 8 | 9.9 | 26.1 | 486.1 | 487.0 |
| 9 | 20.5 | 58.1 | 452.1 | 453.1 |
| 10 | 38.3 | 100 | 452.2 | 453.1 |
| 208 | 20.4 | 54 | 499.4 | 499.0 |
| 220 | 4.7 | 11 | 483.4 | 483.0 |
| 223 | 28.7 | 81 | 465.0 | 465.1 |
| 235 | 8.1 | 21 | 449.0 | 449.1 |
| 238 | 34.1 | 97 | 464.6 | 465.2 |
| 368 | 4.5 | 12 | 463.0 | 463.1 |
| 504 | 4.0 | 13 | 497.4 | 497.1 |
| 505 | 10.0 | 35 | 463.0 | 463.1 |

TABLE 16-continued

| Compound No. 3- | Yield (mg) | Yield (%) | MW | M + 1 |
|---|---|---|---|---|
| 511 | 9.8 | 24 | 467.0 | 467.0 |
| 523 | 15.0 | 50 | 470.9 | 471.1 |
| 525 | 5.4 | 13 | 467.0 | 467.1 |
| 526 | 8.0 | 27 | 481.0 | 481.1 |
| 527 | 18.0 | 60 | 483.0 | 483.1 |
| 555 | 17.2 | 37 | 481.0 | 481.1 |
| 577 | 9.4 | 25 | 479.1 | 479.0 |

Synthesis of Dihydroquinazoline Derivatives

Reference Example 4-1

Synthesis of 4-(dihydroquinazoline-2-aminomethyl)piperidine hydrochloride

After dissolving 1-Boc-4-(aminomethyl)piperidine (350 mg, 1.6 mmol) in $CH_3CN$ (15 ml), thiocarbonyldiimidazole (350 mg, 1.9 mmol) was added and the mixture was stirred at room temperature for 1 hour. 2-Aminobenzylamine (240 mg, 1.9 mmol) was added to the reaction mixture, which was then stirred at room temperature for one hour. The solvent was distilled off under reduced pressure to obtain 1-Boc-4-(2-aminobenzylthioureamethyl)piperidine. The compound was identified by LC-MS.

M+1=379.2.

After dissolving the 1-Boc-4-(2-aminobenzylthioureamethyl)piperidine in EtOH (30 ml), mercury oxide (800 mg) was added and the mixture was refluxed for 1 hour. The solvent was distilled off under reduced pressure to obtain 1-Boc-4-(dihydroquinazoline-2-aminomethyl)piperidine. The compound was identified by LC-MS.

M+1=345.2.

After dissolving the 1-Boc-4-(dihydroquinazoline-2-aminomethyl)piperidine in methanol (10 ml), a 4N hydrogen chloride/1,4-dioxane solution (16 ml) was added and the mixture was stirred at 50° C. for 90 minutes. The solvent was distilled off under reduced pressure to obtain 4-(dihydroquinazoline-2-aminomethyl)piperidine hydrochloride. The compound was identified by LC-MS.

Yield: 449 mg (89%), M+1=245.1.

Examples 4-1 to 4-5

Compound Nos. 4-1 to 4-5 were synthesized in the same manner as Example 2-5, using the corresponding reactants. The results are shown in Table 17.

Example 4-7

Synthesis of 2,4-dichloro-6-[(4-{[(6-chloro(1,4-dihydroquinazolin-2-yl))amino]methyl}piperidyl)methyl]phenol After dissolving Compound No. 2-193 (2.5 mg, 0.028 mmol) in THF (0.5 mL), a 1N $BH_3$/THF solution (0.56 ml, 0.56 mmol) was added and the mixture was stirred at 80° C. for 24 hours. A 5N NaOH aqueous solution (0.5 mL) was added to the obtained solution, and the mixture was stirred at 80° C. for 5 hours. The obtained solution was extracted with ethyl acetate (2 mL×2 times), transferred to Sep-Pak-Dry (trade name of Varian, sodium sulfate cartridge) for drying, and then transferred to SCX (Bond Elute SCX500MG). The SCX was washed with a $CHCl_3$/MeOH (1/1) mixed solution (5 mL) and then eluted with a 2N $NH_3$/MeOH solution (5 mL). The eluate was concentrated and purified with a preparative HPLC system to obtain 2,4-dichloro-6-[(4-{[(6-chloro(1,4-dihydroquinazolin-2-yl))amino]methyl}piperidyl) methyl]phenol.

Yield: 2.3 mg (19%), M+1=453.0.

Examples 4-6, 4-8 to 4-11

Compound Nos. 4-6 and 4-8 to 4-11 were synthesized in the same manner as Example 4-2, using the corresponding reactants. The results are shown in Table 17.

TABLE 17

| Compound No. 4- | Yield (mg) | Yield (%) | MW | M + 1 |
|---|---|---|---|---|
| 1 | 3.6 | 10 | 402.2 | 403.2 |
| 2 | 2.7 | 16 | 418.1 | 419.0 |
| 3 | 7.7 | 50 | 384.1 | 385.1 |
| 4 | 1.0 | 7 | 384.1 | 385.1 |
| 5 | 6.6 | 61 | 362.2 | 363.2 |
| 6 | 2.6 | 25 | 502.1 | 503.1 |
| 7 | 2.3 | 19 | 452.1 | 453.0 |
| 8 | 1.4 | 3 | 432.2 | 433.1 |
| 9 | 6.3 | 12 | 436.1 | 437.1 |
| 10 | 2.1 | 4 | 432.2 | 433.1 |
| 11 | 2.8 | 6 | 434.1 | 435.1 |

Synthesis of 2-[(4-piperidinylmethyl)amino]hydrothiopheno[3,2,d]pyrimidin-4-one derivatives Reference Example 5-1

Synthesis of 3-{[(phenylcarbonylamino)thioxomethyl]amino}thiophene-2-carboxylic acid methyl ester A solution of benzoyl isothiocyanate (1038 mg, 6.36 mmol) in acetone (3 mL) was added to absolution of 3-aminothiophene-2-carboxylic acid methyl ester (500 mg, 3.18 mmol) in acetone (3 mL). The mixture was stirred at room temperature for 10 hours and then concentrated, and the residue was purified by silica gel chromatography (Hex/EtOAc=10/1) to obtain 3-{[(phenylcarbonylamino)thioxomethyl]amino}thiophene-2-carboxylic acid methyl ester.

Yield: 866 mg (85%), M+1=321.0.

Reference Example 5-2

Synthesis of potassium hydrothiopheno[3,2,d]pyrimidin-4-one-2-thiolate

A solution of 3-{[(phenylcarbonylamino)thioxomethyl]amino}thiophene-2-carboxylic acid methyl ester (866 mg, 2.7 mmol) in EtOH (3 mL) was added to a solution of KOH (303 mg, 5.4 mmol) in EtOH (10 mL). The mixture was stirred for 3 hours while heating to reflux, and the separated white precipitate was filtered out. It was then washed with EtOH (5 mL×2 times) and dried under reduced pressure to obtain potassium hydrothiopheno[3,2,d]pyrimidin-4-one-2-thiolate.

Yield: 476 mg (79%).

NMR (DMSO-$d_6$): δH 6.85(m, 1H), 7.22(m, 1H), 10.41 (br, 1H)

Reference Example 5-3

Synthesis of 2-methylthiohydrothiopheno[3,2,d]pyrimidin-4-one

MeI (133 μL, 2.14 mmol) was added to an aqueous solution (10 mL) of potassium hydrothiopheno[3,2,d]pyrimidin-4-one-2-thiolate (476 mg, 2.14 mmol). The mixture was stirred at room temperature for 3 hours, and the separated white precipitate was filtered out. It was then washed with water (5 mL×2 times) and dried under reduced pressure to obtain 2-methylthiohydrothiopheno[3,2,d]pyrimidin-4-one.

Yield: 337 mg (79%).

NMR (DMSO-$d_6$): δH 2.49(s, 1H), 7.26(d, J=5.4, 1H), 8.08(d, J=5.4, 1H).

Reference Example 5-4

Synthesis of 2-[(1-Boc-4-piperidinylmethyl)amino]hydrothiopheno[3,2,d]pyrimidin-4-one After adding 287 mg of 60% 3-chloroperbenzoic acid (1.0 mmol) to a solution of 200 mg (1.0 mmol) of 2-methylthiohydrothiopheno[3,2,d]pyrimidin-4-one in chloroform (5 mL) while cooling on ice, the mixture was stirred at room temperature for 2 hours. The obtained solution was concentrated, and then 235 mg (1.1 mmol) of the compound 1-Boc-4-aminomethylpiperidine, 0.2 mL (1.5 mmol) of triethylamine and diglyme (diethyleneglycol dimethyl ether) (5 mL) were added. The obtained solution was stirred at 180° C. for 10 hours, and then water (10 mL) was added, and the mixture was extracted with ethyl acetate (5 mL×2 times) and dried over magnesium sulfate. After filtration, the filtrate was concentrated and the residue was purified by silica gel chromatography (Hex/EtOAc=1/1→0/1) to obtain 2-[(1-Boc-4-piperidinylmethyl)amino]hydrothiopheno[3,2,d]pyrimidin-4-one.

Yield: 160 mg (44%).

LC/MS (LC/MSD): (M+H)+=365.1 (Found:) M=364.16 (calculated).

Reference Example 5-5

Synthesis of 2-[(4-piperidinylmethyl)amino]hydrothiopheno[3,2,d]pyrimidin-4-one

The compound was synthesized in the same manner as Reference Example 2-11.

Yield: 135 mg (90%), M+1=265.1.

Example 5-1

Compound No. 5-1 was synthesized by the same method as Example 2-5, using the compounds synthesized by Reference Examples 5-1 to 5-5. The results are shown in Table 18.

TABLE 18

| Compound No. 5- | Yield (mg) | Yield (%) | MW | M + 1 |
| --- | --- | --- | --- | --- |
| 1 | 17.0 | 42 | 438.0 | 439.0 |

Synthesis of 5-methyl-2-[(4-piperidinylmethyl)amino]hydropyrrolo[3,2,d]pyrimidin-4-one derivatives Reference Example 6-1

Synthesis of 5-methyl-2-[(4-piperidinylmethyl)amino]hydropyrrolo[3,2,d]pyrimidin-4-one The title compound was obtained by synthesis in the same manner as Reference Examples 5-1 to 5-5, using 3-amino-1-methylpyrrolo-2-carboxylic acid ethyl ester as the starting material.

Yield: 245 mg (92%), M+1=262.1 (Found:) M=261.1 (calculated).

Example 6-1

Compound No. 6-1 was synthesized by the same method as Example 2-5, using the compound synthesized by Reference Example 6-1. The results are shown in Table 19.

TABLE 19

| Compound No. 6- | Yield (mg) | Yield (%) | MW | M + 1 |
| --- | --- | --- | --- | --- |
| 1 | 4.0 | 11 | 436.3 | 436.1 |

Synthesis of 2-[(4-piperidinylmethyl)amino]-1H,5H-benzo[f]1,3-diazepin-4-one derivatives Reference Example 7-1

Synthesis of 4-{[({[2-(carbamoylmethyl)phenyl]amino}thioxomethyl)amino]methyl}piperidine carboxylic acid tert-butyl ester After dissolving 1-N-Boc-4-aminomethylpiperidine (869 mg, 4.06 mmol) in acetonitrile (10 mL), a solution of thiocarbonyldiimidazole (794 mg, 4.46 mmol) and imidazole (82.9 mg, 1.22 mmol) in acetonitrile (15 mL) was added dropwise in an ice bath, and the mixture was stirred at room temperature for 4 hours. After then adding 2-(2-aminophenyl)acetamide (670 mg, 4.46 mmol) thereto, the mixture was stirred overnight at 60° C. The reaction mixture was concentrated under reduced pressure and the obtained residue was purified by silica gel column chromatography (methylene chloride/methanol=65:1→49:1) to obtain the title compound.

Yield: 1.41 g (85%), M+1=407.2 (found), M=406.2 (calculated).

Reference Example 7-2

Synthesis of 4-{[(4-oxo-1H, 5H-benzo[f]1,3-diazepin-2-yl)amino]methyl}piperidine carboxylic acid tert-butyl ester After dissolving 4-{[({[2-(carbamoylmethyl)phenyl]amino}thioxomethyl)amino]methyl}piperidine carboxylic acid tert-butyl ester (410 mg, 1.01 mmol) in tetrahydrofuran (15 mL), N,N'-dicyclohexylcarbodiimide (208 mg, 1.01 mmol) was added and the mixture was stirred at room temperature for 6 hours. The filtrate obtained by filtering the insoluble portion was concentrated under reduced pressure, and the concentrate was suspended in a solution of n-hexane:ethyl acetate=1:2 (3 mL). The insoluble portion was refiltered, and the residue obtained by concentrating the filtrate under reduced pressure was purified by silica gel column chromatography (n-hexane/ethyl acetate=2/3→1/2) to obtain the title compound. Yield: 193 mg (51%).

$^{13}$C-NMR (100 MHz, CDCl$_3$): δ=156.6, 155.0, 136.1, 129.6, 129.2, 126.6, 126.2, 117.9, 79.7, 45.6, 36.7, 29.7, 28.5, 20.5

$^1$H-NMR (400 MHz, CDCl$_3$): δ=7.38(1H, d, J=7.3 Hz), 7.18-7.32(3H, m), 7.14(1H, s), 5.43(1H, s), 4.07(2H, s), 3.71(2H, s), 3.06(1H, s), 2.65(2H, m), 1.61(3H, m), 1.48(9H, s), 1.05 (2H, m)

Reference Example 7-3

Synthesis of 2-[(4-piperidinylmethyl)amino]-1H,5H-benzo[f]1,3-diazepin-4-one

The title compound was synthesized in the same manner as Reference Example 2-11, using 4-{[(4-oxo-1H, 5H-benzo[f]1,3-diazepin-2-yl)amino]methyl}piperidine carboxylic acid tert-butyl ester as the starting material.

Yield: 218 mg (quantitative, M+1=273.1 (Found:) M=272.2 (calculated).

Example 7-1

Compound Nos. 7-16 and 7-504 were synthesized by the same method as Example 2-5, using reactants for the compounds synthesized by Reference Examples 7-1 to 7-3. The results are shown in Table 20.

TABLE 20

| Compound No. 7- | Yield (mg) | Yield (%) | MW | M + 1 |
|---|---|---|---|---|
| 16 | 4.0 | 10 | 447.4 | 447.1 |
| 504 | 6.0 | 16 | 430.9 | 431.1 |

Synthesis of [2-[(4-piperidylmethyl)amino]hydroquinazolin-4-one derivatives

Example 8-16

Synthesis of 2-[({1-[(3,5-dichloro-2-hydroxy-phenyl)methyl]-4-piperidyl}methyl)amino]hydroquinazoline-4-thione After placing 5.7 mg (0.0132 mol) of Compound No. 2-16 in a 15 mL round-bottomed flask equipped with a magnetic stirrer, it was dissolved in 1 g of phosphorous oxychloride and the solution was stirred for one hour at a bath temperature of 120° C. The phosphorus oxychloride was distilled off by concentration under reduced pressure, and then 84.2 mg (1.106 mmol) of thiourea and 4 mL of 1,4-dioxane were added and the mixture was refluxed for 1 hour. After distilling off the solvent, the residue was suspended in methanol, solid phase extraction was performed with an SCX column, and the eluate obtained by elution with a 2 M ammonia/methanol solution was concentrated and purified by preparative HPLC. The fraction containing the target substance was concentrated to obtain 2-[({1-[(3,5-dichloro-2-hydroxy-phenyl)methyl]-4-piperidyl}methyl)amino]hydroquinazoline-4-thione as a colorless powder. The results are shown in Table 21.

TABLE 21

| Compound No. 8- | Yield (mg) | Yield (%) | MW | M + 1 |
|---|---|---|---|---|
| 16 | 0.6 | 10 | 449.4 | 449.1 |

Example 9

Measurement of Inhibiting Power of Test Compounds Against Eotaxin-Induced Intracellular Calcium Concentration Increase in CCR3-Expressing Cells K562 cells stably expressing CCR3 receptor were used in the following method for measurement of the inhibiting power of compounds of the invention against intracellular calcium concentration increase.

The CCR3-expressing K562 cells were suspended in HBSS solution (Hanks' Balanced Salt Solution, Gibco BRL) containing 10 mM HEPES (N-[2-hydroxyethyl]piperazine-N'-[2-ethanesulfonic acid], Gibco BRL), and then 1 mM Fura-2 acetoxymethyl ester (product of Dojin Kagaku) was added to a final concentration of 1 μM and the mixture was incubated at 37° C. for 30 minutes. After rinsing the cells, they were added simultaneously with the test compound into a 96-well white plate (Falcon), the agonist was added after 5 minutes, the mixture was excited at 340 nm and 380 nm, and the 340/380 ratio was monitored to measure the intracellular calcium concentration. Human eotaxin (product of Genzyme Techne) (0.5 μg/ml) was used as an agonist. The inhibiting power of the test compound was determined by measuring the intracellular calcium concentration upon treatment of the CCR3-expressing K562 cells with the test compound 5 minutes before eotaxin stimulation, and calculating the suppression by the following formula.

Suppression (%)={1−(A−B)/(C−B)}×100

(A: Intracellular calcium concentration upon stimulation with eotaxin after treatment with test compound, B: Intracellular calcium concentration without stimulation, C: Intracellular calcium concentration upon stimulation with eotaxin without treatment with test compound)

The inhibiting power of piperidine derivatives of the invention was measured, and for example, the compounds having the Compound Nos. listed below demonstrated inhibiting power of 20-50%, 50-80% or 80% or greater, at 10 μM or 2 μM concentrations of the compounds.

The following compounds exhibited 20-50% inhibition at 10 μM concentration:

Compound No. 1-: 1-7, 1-9, 2-5, 2-6, 2-8, 2-12, 2-13, 2-15, 2-16, 2-18, 2-21, 2-22, 2-24, 2-29, 2-31, 2-35, 2-43, 2-45, 2-48, 2-56, 2-70, 2-71, 2-77, 2-85, 2-96, 2-100 to 2-103, 2-107, 2-108, 2-116, 2-128, 2-129, 2-136, 2-141, 2-146, 2-147, 2-176 to 2-180, 3-8, 3-55, 3-56, 3-58, 5-37, 5-98, 5-104, 5-113, 5-118, 5-122, 5-125, 5-127, 5-141, 6-4 to 6-6, 6-8.

The following compounds exhibited 50-80%-inhibition at 10 μM concentration:

Compound No. 1-: 1-3 to 1-6, 1-10, 1-11, 2-2 to 2-4, 2-23, 2-30, 2-33, 2-34, 2-39, 2-41, 2-42, 2-47, 2-49, 2-51, 2-54, 2-57, 2-60, 2-61, 2-64 to 2-66, 2-73, 2-80 to 2-82, 2-84, 2-89 to 2-91, 2-95, 2-106, 2-109, 2-112, 2-113, 2-115, 2-120, 2-122, 2-123, 2-127, 2-130, 2-133, 2-134, 2-137, 2-138, 2-142, 2-142, 2-170, 2-173 to 2-175, 3-7, 3-9, 4-29, 5-20, 5-21, 5-30, 5-36, 5-39, 5-40, 5-42 to 5-45, 5-49, 5-65, 5-72, 5-96, 5-97, 5-99, 5-101 to 5-103, 5-108, 5-109, 5-111, 5-115, 5-117, 5-119, 5-121, 5-128 to 5-130, 5-134, 5-135, 5-137 to 5-139, 5-142, 5-147, 5-148, 5-154 to 5-158, 5-167, 5-168, 5-174, 5-175, 5-180, 5-181, 5-183

Compound No. 2-: 2 to 4

The following compounds exhibited ≧80% inhibition at 10 μM concentration:
Compound No. 1-: 1-1, 1-8, 2-1, 2-14, 2-36 to 2-38, 2-40, 2-50, 2-52, 2-72, 2-75, 2-98, 2-117 to 2-119, 2-121, 2-124 to 2-126, 2-131, 2-149 to 2-151, 2-153, 2-154, 3-2, 3-13, 3-15, 3-17, 3-18, 3-21 to 3-23, 3-25, 3-26, 3-28 to 3-30, 3-32 to 3-38, 3-42 to 3-52, 3-59, 3-61, 3-62, 5-22 to 5-29, 5-31 to 5-35, 5-38, 5-41, 5-46 to 5-48, 5-50 to 5-64, 5-66 to 5-71, 5-88 to 5-93, 5-95, 5-107, 5-110, 5-114, 5-116, 5-120, 5-123, 5-124, 5-126, 5-131 to 5-133, 5-136, 5-140, 5-143 to 5-146, 5-149 to 5-153, 5-159 to 5-166, 5-169 to 5-173, 5-176 to 5-179, 5-182, 6-7, 6-9, 6-11 to 6-13, 6-15

Compound No. 2-: 1

Compound No. 4-: 1

The following compounds exhibited 20-50% inhibition at 2 μM concentration:

Compound No. 1-: 2-156 to 2-159, 2-163, 2-164, 3-14, 3-24, 3-27, 3-40, 4-1, 4-3, 4-4, 4-6, 5-15, 5-16, 5-74, 5-75, 5-77, 5-79, 5-82, 5-84, 5-85

Compound No. 2-: 5, 7, 8, 13, 22, 24, 200, 232, 243, 245, 247,

The following compounds exhibited 50-80% inhibition at 2 μM concentration:

Compound No. 1-: 2-166, 2-168, 2-169, 3-4, 3-11, 3-16, 3-31, 4-12, 4-15 to 4-17, 5-7, 5-8, 5-14, 5-19, 5-73, 5-76, 5-78, 5-80, 5-81, 5-83, 5-86, 5-188

Compound No. 2-: 6, 10, 14, 16, 17, 20, 21, 23, 29, 196, 205, 221, 223, 224, 234, 237, 244, 495

Compound No. 4-: 5

Compound No. 7-: 504

The following compounds exhibited ≧80% inhibition at 2 μM concentration:

Compound No. 1-: 2-160, 2-162, 2-165, 2-167, 3-1, 3-3, 3-5, 3-6, 4-10, 4-11, 4-13, 4-14, 4-18 to 4-21, 5-1 to 5-6, 5-9 to 5-13, 5-17, 5-18, 5-184 to 5-187, 5-189, 5-190

Compound No. 2-: 11, 12, 15, 18, 19, 26 to 28, 30, 186 to 195, 197 to 199, 201 to 204, 206 to 220, 225 to 231, 235, 236, 238 to 242, 246, 248 to 250, 499, 511, 513, 565

Compound No. 3-: 1-10, 208, 220, 223, 235, 238, 368, 504, 505, 511, 523, 525, 526, 527, 555, 577

Compound No. 4-: 2 to 4, 6 to 11

Compound No. 6-: 1

Compound No. 7-: 16, 504

Compound No. 8-: 16

Example 10

Measurement of Inhibiting Power Against Eotaxin Binding to CCR3-Expressing Cells Human CCR3-expressing L1.2 cells were suspended in assay buffer [RPMI1640 (phenol red free), 25 mM HEPES (pH 7.4), 0.1% $NaN_3$, 0.1% gelatin, 0.08% CHAPS] to prepare a $5 \times 10^5$/mL whole cell suspension. A solution of the test compound diluted with assay buffer was prepared as the test compound solution. A solution of $[^{125}I]$-labeled human eotaxin (Amersham) diluted with assay buffer to 1 μCi/mL was prepared as the labeled ligand solution. After dispensing 25 μL of the test compound solution, 25 μL of the labeled ligand solution and 50 μL of the whole cell suspension in that order into each well of a 96-well microplate (Falcon) covered with 0.5% BSA and stirring (100 μL of reaction solution), incubation was performed at 25° C. for 90 minutes.

After completion of the reaction, a 96-well filter plate (Millipore) containing filters immersed in 0.5% polyethyleneimine solution was used for filter filtration of the reaction mixture, with washing of the filters four times with 150 μL of cold washing buffer (assay buffer+0.5 M NaCl) (filtering was performed after adding 150 μL of cold washing buffer). The filters were blow-dried, and then 25 μL of liquid scintillator (MicroScient-O, Packard) was added to each well and the radioactivity incorporated in each membrane fraction on the filter was measured by a Top Count (Packard).

The count upon addition of 100 ng of unlabeled human eotaxin instead of the test compound was subtracted as the non-specific adsorption, to calculate the inhibiting power of the test compound against binding of human eotaxin to the CCR3 expressing cells, with 100% as the count with no addition of the test compound.

$$\text{Inhibiting power (\%)} = \{1 - (A-B)/(C-B)\} \times 100$$

(A: Count upon addition of test compound, B: Count upon addition of 100 ng of unlabeled human eotaxin, C: Count upon addition of $[^{125}I]$-labeled human eotaxin alone)

Example 11

Measurement of Inhibiting Power of Test Compounds on Eotaxin-Induced Cell Migration of CCR3-Expressing Cells L1.2 cells stably expressing CCR3 receptor were used to measure the inhibiting power of compounds of the invention against cell migration, by the following method.

The test compound was suspended in 0.5% BSA-containing RPMI1640 (Gibco BRL) solution and human eotaxin (product of Genzyme Techne) (20 ng/mL) was added as an agonist, and then the mixture was placed in the lower compartment of a 96-well chemotaxis chamber (Neuro Probe, Inc.) and a special chemotaxis chamber filter was inserted in the upper compartment. After adding the same test compound and CCR3-expressing L1.2 cells to the upper compartment, incubation was performed at 37° C. for 2 hours.

Upon completion of the reaction, the special filter was stained with a screening blood staining solution (Diff-Quick, Kokusai Shiyaku Co., Ltd.), the absorbance at 550 nm was measured, and the suppression (%) was calculated according to the following formula.

$$\text{Suppression (\%)} = \{1-(A-B)/(C-B)\} \times 100$$

(A: Cell migration upon eotaxin stimulation of CCR3-expressing L1.2 cells treated with test compound, B: cell migration without stimulation, C: cell migration upon eotaxin stimulation without treatment with test compound)

Upon measurement of several of the compounds of the invention as test compounds in Examples 10 and 11, the inhibiting power was found to be essentially the same as in Example 9.

INDUSTRIAL APPLICABILITY

The compounds represented by formula (I) of the present invention exhibit activity which inhibits binding of CCR3 ligands such as eotaxins to their target cells and activity of inhibiting the physiological effects of binding of CCR3 ligands such as eotaxins to their target cells, and can therefore be utilized as CCR3 antagonists.

The invention claimed is:
1. A compound represented by the following formula (I):

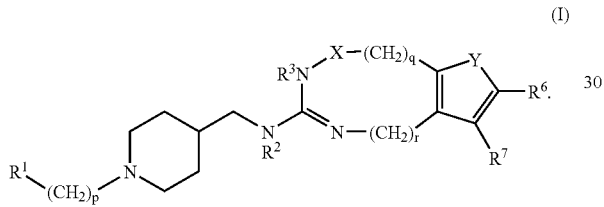

wherein $R^1$ represents phenyl, $C_3$-$C_8$ cycloalkyl or an aromatic heterocyclic group having 1-3 atoms selected from the group consisting of oxygen, sulfur and nitrogen as hetero atoms, the phenyl or aromatic heterocyclic group of $R^1$ may optionally fuse with a benzene ring or aromatic heterocyclic group having 1-3 atoms selected from the group consisting of oxygen, sulfur and nitrogen as hetero atoms to form a fused ring, the phenyl, $C_3$-$C_8$ cycloalkyl or aromatic heterocyclic group, or fused ring, in $R^1$ may be unsubstituted, or substituted with one or more substituents selected from the group consisting of halogens, hydroxy, cyano, nitro, carboxyl, $C_1$-$C_6$ alkyl, $C_3$-$C_8$ cycloalkyl, $C_2$-$C_6$ alkenyl, $C_1$-$C_6$ alkoxy, $C_1$-$C_6$ alkylthio, $C_3$-$C_5$ alkylene, $C_2$-$C_4$ alkyleneoxy, $C_1$-$C_3$ alkylenedioxy, phenyl, phenoxy, phenylthio, benzyl, benzyloxy, benzoylamino, formyl, $C_2$-$C_7$ alkanoyl, $C_2$-$C_7$ alkoxycarbonyl, $C_2$-$C_7$ alkanoyloxy, $C_2$-$C_7$ alkanoylamino, $C_1$-$C_6$ alkylsulfonyl, $C_3$-$C_8$ (alkoxycarbonyl)methyl, amino, mono($C_1$-$C_6$ alkyl)amino, di($C_1$-$C_6$ alkyl)amino, carbamoyl, $C_2$-$C_7$ N-alkylcarbamoyl, $C_4$-$C_9$ N-cycloalkylcarbamoyl, N-phenylcarbamoyl, piperidylcarbonyl, morpholinylcarbonyl, pyrrolidinylcarbonyl, piperazinylcarbonyl, N-methoxycarbamoyl, (formyl)amino and ureido, and the substituent of the phenyl, $C_3$-$C_8$ cycloalkyl or aromatic heterocyclic group, or fused ring, of $R^1$ may be unsubstituted, or substituted with one or more substituents selected from the group consisting of $C_1$-$C_6$ alkyl, $C_2$-$C_6$ alkenyl, $C_2$-$C_6$ alkynyl, phenyl, $C_3$-$C_5$ alkylene, $C_3$-$C_8$ cycloalkyl, $C_3$-$C_8$ cycloalkenyl, $C_1$-$C_6$ alkoxy, $C_1$-$C_6$ alkylthio, amino, mono($C_1$-$C_6$ alkyl)amino, di($C_1$-$C_6$ alkyl)amino, pyrrolidinyl, piperidyl, $C_3$-$C_7$ lactam, carbamoyl, $C_2$-$C_7$ N-alkylcarbamoyl, $C_2$-$C_7$ alkoxycarbonyl, carboxyl, hydroxy, benzoyl, cyano, trifluoromethyl, halogen and tert-butoxycarbonylamino, provided that when $R^1$ is $C_3$-$C_8$ cycloalkyl, the substituent does not include amino, mono($C_1$-$C_6$ alkyl)amino or di($C_1$-$C_6$ alkyl)amino;

p represents an integer of 1-6;

$R^2$ and $R^3$ may be the same or different and each independently represents hydrogen, $C_1$-$C_6$ alkyl or phenyl, where the $C_1$-$C_6$ alkyl or phenyl group of $R^2$ and $R^3$ may be unsubstituted, or substituted with one or more substituents selected from the group consisting of halogens, hydroxy, $C_1$-$C_6$ alkyl, $C_2$-$C_7$ alkoxycarbonyl, amino, carbamoyl, carboxyl, cyano and $C_1$-$C_6$ alkoxy;

X represents —CO—, —SO$_2$—, —CH$_2$—, —CS— or a single bond;

q represents 0 or 1;

r represents 0 or 1;

Y represents —($R^4$)C=C($R^5$)—, —S— or —NR$^8$—;

$R^4$, $R^5$, $R^6$ and $R^7$ may be the same or different, and each independently represents hydrogen, a halogen, hydroxy, cyano, nitro, carboxyl, $C_1$-$C_6$ alkyl, $C_3$-$C_8$ cycloalkyl, $C_2$-$C_6$ alkenyl, $C_1$-$C_6$ alkoxy, $C_1$-$C_6$ alkylthio, $C_3$-$C_5$ alkylene, $C_2$-$C_4$ alkyleneoxy, $C_1$-$C_3$ alkylenedioxy, phenyl, phenoxy, phenylthio, phenylsulfonyl, benzyl, benzyloxy, benzoylamino, formyl, $C_2$-$C_7$ alkanoyl, $C_2$-$C_7$ alkoxycarbonyl, $C_2$-$C_7$ alkanoyloxy, $C_2$-$C_7$ alkanoylamino, $C_4$-$C_{10}$ cycloalkanoylamino, $C_3$-$C_7$ alkenoylamino, $C_1$-$C_6$ alkylsulfonyl, $C_1$-$C_6$ alkylsulfonylamino, $C_3$-$C_8$ (alkoxycarbonyl)methyl, amino, mono($C_1$-$C_6$ alkyl)amino, di($C_1$-$C_6$ alkyl)amino, carbamoyl, $C_2$-$C_7$ N-alkylcarbamoyl, $C_4$-$C_9$ N-cycloalkylcarbamoyl, N-phenylcarbamoyl, N—($C_7$-$C_{12}$ phenylalkyl)carbamoyl, piperidylcarbonyl, morpholinylcarbonyl, pyrrolidinylcarbonyl, piperazinylcarbonyl, N-methoxycarbamoyl, sulfamoyl, $C_1$-$C_6$ N-alkylsulfamoyl, (formyl)amino, (thioformyl)amino, ureido or thioureido, where the aforementioned groups of $R^4$, $R^5$, $R^6$ and $R^7$ each may be independently unsubstituted, or substituted with one or more substituents selected from the group consisting of $C_1$-$C_6$ alkyl, $C_2$-$C_6$ alkenyl, $C_2$-$C_6$ alkynyl, phenyl, $C_3$-$C_5$ alkylene, $C_3$-$C_8$ cycloalkyl, $C_3$-$C_8$ cycloalkenyl, $C_1$-$C_6$ alkoxy, ($C_1$-$C_6$ alkoxy) ($C_1$-$C_6$ alkoxy), phenyl($C_1$-$C_6$ alkoxy), $C_1$-$C_6$ alkylthio, amino, mono($C_1$-$C_6$ alkyl)amino, di($C_1$-$C_6$ alkyl) amino, pyrrolidinyl, piperidyl, ($C_2$-$C_7$ alkanoyl)piperidyl, $C_3$-$C_7$ lactam, carbamoyl, $C_2$-$C_7$ N-alkylcarbamoyl, $C_4$-$C_9$ N-cycloalkylcarbamoyl, N-phenylcarbamoyl, N-($C_7$-$C_{12}$ phenylalkyl)carbamoyl, $C_2$-$C_7$ alkanoylamino, $C_2$-$C_7$ alkoxycarbonyl, carboxyl, hydroxy, benzoyl, cyano, trifluoromethyl, halogens, tert-butoxycarbonylamino, $C_1$-$C_6$ alkylsulfonyl and heterocycles or aromatic heterocycles (where a heterocycle or aromatic heterocycle has 1-3 atoms selected from the group consisting of oxygen, sulfur and nitrogen as hetero atoms, and may be substituted with $C_1$-$C_6$ alkyl); and $R^8$ represents hydrogen or $C_1$-$C_6$ alkyl, where the $C_1$-$C_6$ alkyl group of $R^8$ may be unsubstituted, or substituted with one or more substituents selected from the group consisting of halogens, hydroxy, cyano, nitro, carboxyl, carbamoyl, mercapto, guanidino, $C_3$-$C_8$ cycloalkyl, $C_1$-$C_6$ alkoxy, $C_1$-$C_6$ alkylthio, phenyl (where phenyl may be substituted, or substituted with one or more substituents selected from the group consisting of halogens, hydroxy, $C_1$-$C_6$ alkyl, $C_1$-$C_6$ alkoxy and benzyloxy), phenoxy, benzyloxy, benzyloxycarbonyl, $C_2$-$C_7$ alkanoyl, $C_2$-$C_7$ alkoxycarbonyl, $C_2$-$C_7$ alkanoyloxy, $C_2$-$C_7$ alkanoylamino, $C_2$-$C_7$ N-alkylcarbamoyl, $C_2$-$C_6$ alkylsulfonyl, amino, mono($C_1$-$C_6$ alkyl)amino, di($C_1$-$C_6$ alkyl)amino and ureido, a pharmaceutically acceptable acid adduct thereof, or a pharmaceutically acceptable $C_1$-$C_6$ alkyl adduct thereof.

2. A compound according to claim 1, a pharmaceutically acceptable acid adduct thereof, or a pharmaceutically acceptable $C_1$-$C_6$ alkyl adduct thereof, wherein X in formula (I) is —$SO_2$—.

3. A compound according to claim 1, a pharmaceutically acceptable acid adduct thereof, or a pharmaceutically acceptable $C_1$-$C_6$ alkyl adduct thereof, wherein X in formula (I) is —CO—.

4. A compound according to claim 1, a pharmaceutically acceptable acid adduct thereof, or a pharmaceutically acceptable $C_1$-$C_6$ alkyl adduct thereof, wherein X in formula (I) is —$CH_2$—.

5. A compound according to claim 1, a pharmaceutically acceptable acid adduct thereof, or a pharmaceutically acceptable $C_1$-$C_6$ alkyl adduct thereof, wherein X in formula (I) is —CS—.

6. A compound according to claim 1, a pharmaceutically acceptable acid adduct thereof, or a pharmaceutically acceptable $C_1$-$C_6$ alkyl adduct thereof, wherein X in formula (I) is a single bond.

7. A compound according to any one of claims 1 to 6, a pharmaceutically acceptable acid adduct thereof, or a pharmaceutically acceptable $C_1$-$C_6$ alkyl adduct thereof, wherein Y in formula (I) is —($R^4$)C=C($R^5$)—.

8. A compound according to any one of claims 1 to 6, a pharmaceutically acceptable acid adduct thereof, or a pharmaceutically acceptable $C_1$-$C_6$ alkyl adduct thereof, wherein Y in formula (I) is —S—.

9. A compound according to any one of claims 1 to 6, a pharmaceutically acceptable acid adduct thereof, or a pharmaceutically acceptable $C_1$-$C_6$ alkyl adduct thereof, wherein Y in formula (I) is —$NR^8$—.

10. A compound according to any one of claims 1 to 9, a pharmaceutically acceptable acid adduct thereof, or a pharmaceutically acceptable $C_1$-$C_6$ alkyl adduct thereof, wherein $R^1$ in formula (I) is substituted or unsubstituted phenyl.

11. A compound according to any one of claims 1 to 10, a pharmaceutically acceptable acid adduct thereof, or a pharmaceutically acceptable $C_1$-$C_6$ alkyl adduct thereof, wherein $R^2$ in formula (I) is hydrogen.

12. A compound according to any one of claims 1 to 11, a pharmaceutically acceptable acid adduct thereof, or a pharmaceutically acceptable $C_1$-$C_6$ alkyl adduct thereof, wherein $R^3$ in formula (I) is hydrogen.

13. A compound according to any one of claims 1 to 12, a pharmaceutically acceptable acid adduct thereof, or a pharmaceutically acceptable $C_1$-$C_6$ alkyl adduct thereof, wherein q=0 and r=0 in formula (I).

14. A compound according to any one of claims 1 to 6, a pharmaceutically acceptable acid adduct thereof, or a pharmaceutically acceptable $C_1$-$C_6$ alkyl adduct thereof, wherein q=1 and r=0 in formula (I).

15. A compound according to any one of claims 1 to 12, a pharmaceutically acceptable acid adduct thereof, or a pharmaceutically acceptable $C_1$-$C_6$ alkyl adduct thereof, wherein q=0 and r=1 in formula (I).

16. A compound according to any one of claims 1 to 15, a pharmaceutically acceptable acid adduct thereof, or a pharmaceutically acceptable $C_1$-$C_6$ alkyl adduct thereof, wherein p=1 in formula (I).

17. A compound according to claim 2, a pharmaceutically acceptable acid adduct thereof, or a pharmaceutically acceptable $C_1$-$C_6$ alkyl adduct thereof, wherein Y is —($R^4$)C=C($R^5$)—, $R^1$ is substituted or unsubstituted phenyl, $R^2$ is hydrogen, $R^3$ is hydrogen, q=0, r=0 and p=1 in formula (I).

18. A compound according to claim 3, a pharmaceutically acceptable acid adduct thereof, or a pharmaceutically acceptable $C_1$-$C_6$ alkyl adduct thereof, wherein Y is —($R^4$) C=C($R^5$)—, $R^1$ is substituted or unsubstituted phenyl, $R^2$ is hydrogen, $R^3$ is hydrogen, q=0, r=0 and p=1 in formula (I).

19. A compound according to claim 4, a pharmaceutically acceptable acid adduct thereof, or a pharmaceutically acceptable $C_1$-$C_6$ alkyl adduct thereof, wherein Y is —($R^4$)C=C($R^5$)—, $R^1$ is substituted or unsubstituted phenyl, $R^2$ is hydrogen, $R^3$ is hydrogen, q=0, r=0 and p=1 in formula (I).

20. A compound according to claim 6, a pharmaceutically acceptable acid adduct thereof, or a pharmaceutically acceptable $C_1$-$C_6$ alkyl adduct thereof, wherein Y is —($R^4$) C=C($R^5$)—, $R^1$ is substituted or unsubstituted phenyl, $R^2$ is hydrogen, $R^3$ is hydrogen, q=0, r=0 and p=1 in formula (I).

21. A compound according to any one of claims 17 to 20, a pharmaceutically acceptable acid adduct thereof, or a pharmaceutically acceptable $C_1$-$C_6$ alkyl adduct thereof, wherein $R^4$ and $R^5$ in formula (I) may be the same or different and each is independently hydrogen, a halogen, hydroxy, cyano, nitro, carboxyl, $C_1$-$C_6$ alkyl, $C_1$-$C_6$ alkoxy, $C_2$-$C_7$ alkoxycarbonyl, $C_2$-$C_7$ alkanoylamino, $C_1$-$C_6$ alkylsulfonyl, amino, carbamoyl, $C_2$-$C_7$ N-alkylcarbamoyl, sulfamoyl or $C_1$-$C_6$ N-alkylsulfamoyl.

22. A compound according to any one of claims 17 to 20, a pharmaceutically acceptable acid adduct thereof, or a pharmaceutically acceptable $C_1$-$C_6$ alkyl adduct thereof, wherein $R^4$ and $R^5$ in formula (I) may be the same or different and each is independently a halogen, hydroxy, cyano, nitro, $C_1$-$C_6$ alkyl, $C_1$-$C_6$ alkoxy, $C_2$-$C_7$ alkoxycarbonyl, $C_1$-$C_6$ alkylsulfonyl or $C_1$-$C_6$ N-alkylsulfamoyl.

23. A compound according to any one of claims 17 to 22, a pharmaceutically acceptable acid adduct thereof, or a pharmaceutically acceptable $C_1$-$C_6$ alkyl adduct thereof, wherein each $R^1$ in formula (I) above may be the same or different and is independently hydrogen, a halogen, hydroxy, cyano, nitro, $C_1$-$C_6$ alkyl or $C_1$-$C_6$ alkoxy.

24. A pharmaceutical composition with CCR3 antagonism, which comprises as an effective ingredient thereof a compound represented by formula (I) above according to any one of claims 1 to 23, a pharmaceutically acceptable acid adduct thereof or a pharmaceutically acceptable $C_1$-$C_6$ alkyl adduct thereof; and a pharmaceutically acceptable carrier.

25. A method for treatment of a disease or condition selected from the group consisting of bronchial asthma, allergic rhinitis, atopic dermatitis, urticaria, contact dermatitis, alleriric coniunctivitis, inflammatory bowel disease. Acquired Immuno Deficiency Syndrome, eosinqphilia, eosinophilic gastroenteritis, eosinophilic enteropathy, eosinonhilic fasciitis, eosinophilic granuloma, eosinophilic pustular folliculitis, eosinophilic pneumonia and eosinophilic leukemia comorising administering an effective amount of a compound represented by formula (I) according to any one of claims 1 to 6, a pharmaceutically acceptable acid adduct thereof or a pharmaceutically acceptable C1-C6 alkyl adduct thereof.

* * * * *